US011484032B2

(12) United States Patent
Zwiebel et al.

(10) Patent No.: US 11,484,032 B2
(45) Date of Patent: *Nov. 1, 2022

(54) COMPOSITIONS FOR INHIBITION OF INSECT SENSING

(71) Applicant: Vanderbilt University, Nashville, TN (US)

(72) Inventors: Laurence Zwiebel, Nashville, TN (US); Gregory M. Pask, Nashville, TN (US); David C. Rinker, Nashville, TN (US); Ian M. Romaine, Goodlettsville, TN (US); Gary A. Sulikowski, Brentwood, TN (US); Paul R. Reid, Durham, NC (US); Alex G. Waterson, Murfreesboro, TN (US); Kwangho Kim, Nashville, TN (US); Patrick L. Jones, Danvers, MA (US); Robert W. Taylor, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 15 days.

This patent is subject to a terminal disclaimer.

(21) Appl. No.: 16/945,369

(22) Filed: Jul. 31, 2020

(65) Prior Publication Data

US 2021/0219551 A1   Jul. 22, 2021

Related U.S. Application Data

(63) Continuation of application No. 16/186,106, filed on Nov. 9, 2018, now Pat. No. 10,813,355, which is a continuation of application No. 15/443,340, filed on Feb. 27, 2017, now Pat. No. 10,188,105, which is a continuation-in-part of application No. 14/115,553, filed as application No. PCT/US2012/034847 on Apr. 25, 2012, now Pat. No. 9,578,881.

(Continued)

(51) Int. Cl.

| A01N 43/653 | (2006.01) |
|---|---|
| A01N 43/82 | (2006.01) |
| A01N 43/78 | (2006.01) |
| A01N 43/90 | (2006.01) |
| A01N 25/08 | (2006.01) |
| A01N 47/16 | (2006.01) |
| A01N 47/18 | (2006.01) |
| A01N 53/00 | (2006.01) |
| C07D 249/12 | (2006.01) |
| C07D 401/04 | (2006.01) |
| C07D 401/14 | (2006.01) |
| C07D 403/04 | (2006.01) |
| C07D 405/04 | (2006.01) |
| C07D 405/06 | (2006.01) |
| C07D 405/14 | (2006.01) |
| C07D 409/04 | (2006.01) |
| C07D 409/14 | (2006.01) |
| C07D 413/14 | (2006.01) |
| C07D 471/04 | (2006.01) |

(Continued)

(52) U.S. Cl.
CPC ........... *A01N 43/653* (2013.01); *A01N 25/08* (2013.01); *A01N 43/78* (2013.01); *A01N 43/82* (2013.01); *A01N 43/90* (2013.01); *A01N 47/16* (2013.01); *A01N 47/18* (2013.01); *A01N 53/00* (2013.01); *C07D 249/12* (2013.01); *C07D 401/04* (2013.01); *C07D 401/14* (2013.01); *C07D 403/04* (2013.01); *C07D 405/04* (2013.01); *C07D 405/06* (2013.01); *C07D 405/14* (2013.01); *C07D 409/04* (2013.01); *C07D 409/14* (2013.01); *C07D 413/14* (2013.01); *C07D 471/04* (2013.01); *C07D 491/048* (2013.01); *C07D 491/052* (2013.01); *C07D 491/056* (2013.01); *C07D 513/04* (2013.01)

(58) Field of Classification Search
CPC ...... A01N 43/653; A01N 25/08; A01N 43/78; A01N 43/82; A01N 43/90; A01N 47/16; A01N 47/18; A01N 53/00; C07D 249/12; C07D 401/04; C07D 401/14; C07D 403/04; C07D 405/04; C07D 405/06; C07D 405/14; C07D 409/04; C07D 413/14; C07D 471/04; C07D 491/048; C07D 491/052; C07D 491/056; C07D 513/04

See application file for complete search history.

(56) References Cited

U.S. PATENT DOCUMENTS

| 2,798,053 A | 7/1957 | Brown |
|---|---|---|
| 3,755,560 A | 8/1973 | Dickert et al. |

(Continued)

FOREIGN PATENT DOCUMENTS

| AU | 2012254032 A1 | 11/2013 |
|---|---|---|
| CA | 2835328 A1 | 11/2012 |

(Continued)

OTHER PUBLICATIONS

U.S. Appl. No. 61/406,368, filed Oct. 25, 2010, Zwiebel (Vanderbilt University).

(Continued)

*Primary Examiner* — Blessing M Fubara
(74) *Attorney, Agent, or Firm* — Ballard Spahr LLP

(57) ABSTRACT

In one aspect, the invention relates to chemical modulators of insect olfactory receptors. In particular, compounds and compositions are provided that can inhibit sensory (e.g., host targeting) functions in airborne insects such as mosquitos. Methods of employing such agents, and articles incorporating the same, are also provided. This abstract is intended as a scanning tool for purposes of searching in the particular art and is not intended to be limiting of the present invention.

20 Claims, 67 Drawing Sheets

Related U.S. Application Data

(60) Provisional application No. 61/625,602, filed on Apr. 17, 2012, provisional application No. 61/586,492, filed on Jan. 13, 2012, provisional application No. 61/540,929, filed on Sep. 29, 2011, provisional application No. 61/483,857, filed on May 9, 2011, provisional application No. 61/483,440, filed on May 6, 2011.

(51) Int. Cl.
*C07D 491/048* (2006.01)
*C07D 491/052* (2006.01)
*C07D 491/056* (2006.01)
*C07D 513/04* (2006.01)

(56) References Cited

U.S. PATENT DOCUMENTS

| | | | |
|---|---|---|---|
| 4,418,534 A | 12/1983 | Dufft | |
| 4,421,769 A | 12/1983 | Dixon et al. | |
| 4,509,949 A | 4/1985 | Huang et al. | |
| 4,599,379 A | 7/1986 | Flesher et al. | |
| 4,628,078 A | 12/1986 | Glover et al. | |
| 4,835,206 A | 5/1989 | Farrar et al. | |
| 4,849,484 A | 7/1989 | Heard | |
| 5,011,681 A | 4/1991 | Ciotti et al. | |
| 5,087,445 A | 2/1992 | Haffey et al. | |
| 5,100,660 A | 3/1992 | Hawe et al. | |
| 5,567,430 A | 10/1996 | Levy | |
| 5,698,210 A | 12/1997 | Levy | |
| 5,824,328 A | 10/1998 | Levy | |
| 5,846,553 A | 12/1998 | Levy | |
| 5,858,384 A | 1/1999 | Levy | |
| 5,858,386 A | 1/1999 | Levy | |
| 5,885,605 A | 3/1999 | Levy | |
| 5,902,596 A | 5/1999 | Levy | |
| 5,939,462 A | 8/1999 | Connell et al. | |
| 5,983,390 A | 11/1999 | Desy | |
| 6,001,382 A | 12/1999 | Levy | |
| 6,335,027 B1 | 1/2002 | Levy | |
| 6,337,078 B1 | 1/2002 | Levy | |
| 6,346,262 B1 | 2/2002 | Levy | |
| 6,350,461 B1 | 2/2002 | Levy | |
| 6,387,386 B1 | 5/2002 | Levy | |
| 6,391,328 B1 | 5/2002 | Levy | |
| 6,663,838 B1 | 12/2003 | Soller et al. | |
| 7,090,147 B2 | 8/2006 | Lovett | |
| 7,306,167 B2 | 12/2007 | Colarusso et al. | |
| 7,314,723 B2 | 1/2008 | Zwiebel | |
| 9,332,757 B2 | 5/2016 | Zwiebel et al. | |
| 9,578,881 B2 * | 2/2017 | Zwiebel | A01N 47/18 |
| 10,091,997 B2 | 10/2018 | Zwiebel et al. | |
| 10,188,105 B2 * | 1/2019 | Zwiebel | C07D 401/14 |
| 10,813,355 B2 * | 10/2020 | Zwiebel | C07D 401/04 |
| 2002/0013326 A1 | 1/2002 | Tiebes et al. | |
| 2003/0165879 A1 | 9/2003 | Woods et al. | |
| 2003/0166850 A1 | 9/2003 | Jones et al. | |
| 2006/0260183 A1 | 11/2006 | Hockaday | |
| 2007/0160637 A1 | 7/2007 | Schilling et al. | |
| 2008/0095813 A1 | 4/2008 | Kiec | |
| 2009/0099135 A1 | 4/2009 | Enan | |
| 2009/0136968 A1 | 5/2009 | Sallman | |
| 2009/0163545 A1 | 6/2009 | Goldfarb | |
| 2009/0226422 A1 | 9/2009 | Chaudhary et al. | |
| 2009/0232918 A1 | 9/2009 | Enan | |
| 2009/0253763 A1 | 10/2009 | Ohshita et al. | |
| 2010/0226949 A1 | 9/2010 | Ray et al. | |
| 2011/0139894 A1 | 6/2011 | Masterson et al. | |
| 2011/0257211 A1 | 10/2011 | Chand et al. | |
| 2012/0082639 A1 | 4/2012 | Hassanali et al. | |
| 2014/0045690 A1 | 2/2014 | Defieber et al. | |
| 2014/0242135 A1 | 8/2014 | Zwiebel et al. | |
| 2016/0286807 A1 | 10/2016 | Zwiebel et al. | |
| 2017/0208809 A1 | 7/2017 | Zwiebel et al. | |

FOREIGN PATENT DOCUMENTS

| | | | |
|---|---|---|---|
| CN | 1030298 A | 1/1989 | |
| CN | 2180054 Y | 10/1994 | |
| CN | 101237777 A | 8/2008 | |
| CN | 101616914 A | 12/2009 | |
| CN | 102396496 A | 4/2012 | |
| CN | 103402988 B | 11/2015 | |
| EP | 0036711 A2 | 9/1981 | |
| EP | 0036711 B1 | 12/1985 | |
| EP | 2632257 A2 | 9/2013 | |
| EP | 2704575 A2 | 3/2014 | |
| GB | 2057884 A | 4/1981 | |
| KR | 20080105463 A | 12/2008 | |
| WO | WO-95/17091 A1 | 6/1995 | |
| WO | WO-98/35944 A1 | 8/1998 | |
| WO | WO-98/57969 A1 | 12/1998 | |
| WO | WO-00/35285 A1 | 6/2000 | |
| WO | WO-02/43483 A2 | 6/2002 | |
| WO | WO-2004/001058 A2 | 12/2003 | |
| WO | WO-2004/030611 A2 | 4/2004 | |
| WO | WO-2004/041209 A2 | 5/2004 | |
| WO | WO-2004/089367 A1 | 10/2004 | |
| WO | WO-2004/089416 A2 | 10/2004 | |
| WO | WO-2005/087750 A1 | 9/2005 | |
| WO | WO-2006/076009 A2 | 7/2006 | |
| WO | WO-2006/131230 A2 | 12/2006 | |
| WO | WO-2007/121512 A1 | 11/2007 | |
| WO | WO-2009/030996 A1 | 3/2009 | |
| WO | WO-2009030996 A1 * | 3/2009 | ......... A61K 31/4196 |
| WO | WO-2009/051801 A2 | 4/2009 | |
| WO | WO-2009/086303 A2 | 7/2009 | |
| WO | WO-2010/003877 A1 | 1/2010 | |
| WO | WO-2010/060151 A1 | 6/2010 | |
| WO | WO-2010/139966 A1 | 12/2010 | |
| WO | WO-2011/163198 A2 | 12/2011 | |
| WO | WO-2012/061039 A2 | 5/2012 | |
| WO | WO-2012/154403 A2 | 11/2012 | |
| WO | WO-2016/154471 A1 | 9/2016 | |
| WO | WO-2017/011466 A1 | 1/2017 | |
| ZA | 2013/09154 | 11/2012 | |

OTHER PUBLICATIONS

U.S. Appl. No. 61/406,786, filed Oct. 26, 2010, Zwiebel (Vanderbilt University).
U.S. Appl. No. 61/483,440, filed May 6, 2011, Zwiebel (Vanderbilt University).
U.S. Appl. No. 61/483,857, filed May 9, 2011, Zwiebel (Vanderbilt University).
U.S. Appl. No. 61/540,929, filed Sep. 29, 2011, Zwiebel (Vanderbilt University).
U.S. Appl. No. 61/586,492, filed Jan. 13, 2012, Zwiebel (Vanderbilt University).
U.S. Appl. No. 13/881,638 (U.S. Pat. No. 9,332,757), filed Oct. 16, 2013 (May 10, 2016), Zwiebel (Vanderbilt University).
U.S. Appl. No. 15/093,593 (U.S. Pat. No. 10,091,997), filed Apr. 7, 2016 (Oct. 9, 2018), Zwiebel (Vanderbilt University).
U.S. Appl. No. 16/145,996 (U.S. Pat. No. 10,701,938), filed Sep. 28, 2018 (Jul. 7, 2020), Zwiebel (Vanderbilt University).
U.S. Appl. No. 61/625,602, filed Apr. 17, 2012, Zwiebel (Vanderbilt University).
U.S. Appl. No. 14/115,553 (U.S. Pat. No. 9,578,881), filed Apr. 25, 2012 (Feb. 28, 2017), Zwiebel (Vanderbilt University).
U.S. Appl. No. 15/443,340 (U.S. Pat. No. 10,188,105), filed Feb. 27, 2017 (Jan. 29, 2019), Zwiebel (Vanderbilt University).
U.S. Appl. No. 16/186,106 (U.S. Pat. No. 10,813,355), filed Nov. 9, 2018 (Oct. 27, 2020), Zwiebel (Vanderbilt University).
U.S. Appl. No. 62/191,960, filed Jul. 13, 2015, Zwiebel (Vanderbilt University).
U.S. Appl. No. 15/741,999 (2018/0192651), filed Jan. 4, 2018 (Jul. 12, 2018), Zwiebel (Vanderbilt University).
U.S. Appl. No. 62/138,348, filed Mar. 25, 2015, Zwiebel (Vanderbilt University).
U.S. Appl. No. 15/561,427 (U.S. Pat. No. 10,791,739), filed Sep. 25, 2017 (Oct. 6, 2020), Zwiebel (Vanderbilt University).

(56) References Cited

OTHER PUBLICATIONS

U.S. Appl. No. 17/003,327, filed Aug. 26, 2020, Zwiebel (Vanderbilt University).
CN, 20118062303.0 (103402988A), filed Oct. 21, 2011 (Nov. 25, 2015), Zwiebel (Vancerbilt University).
CN, 2015106834069 (105394046), filed Oct. 20, 2015 (Mar. 16, 2016), Zwiebel (Vanderbilt University).
EP, 118384619 (2632257), filed Oct. 21, 2011 (Sep. 4, 2013), Zwiebel (Vanderbilt University).
PCT, PCT/US2011/057246 (WO 2012/061039), filed Oct. 21, 2011 (May 10, 2012), Zwiebel (Vanderbilt University).
AU, 2012254032 (2012254032), filed Nov. 6, 2013 (Jun. 8, 2017), Zwiebel (Vanderbilt University).
AU, 2017202652 filed Apr. 21, 2017, Zwiebel (Vanderbilt University).
AU, 2019203549, filed Apr. 25, 2012, Zwiebel (Vanderbilt University).
CA, 2835328, filed Apr. 25, 2012, Zwiebel (Vanderbilt University).
EP, 1278194.6 (2704575), filed Apr. 25, 2012 (Mar. 12, 2014), Zwiebel (Vanderbilt University).
PCT, PCT/US2012/034847 (WO 2012/154403), filed Apr. 25, 2012 (Nov. 15, 2012), Zwiebel (Vanderbilt University).
ZA, 2013/09154 (2013/09154), filed Dec. 5, 2013 (May 25, 2016), Zwiebel (Vanderbilt University).
CN, 2016800506646 (CN 107920523 A), filed Jul. 12, 2016 (Apr. 17, 2018), Zwiebel (Vanderbilt University).
IL, 256780, filed Jul. 12, 2016, Zwiebel (Vanderbilt University).
PCT, PCT/US2016/041918 (WO 2017/011466), filed Jul. 12, 2016 (Jan. 19, 2017), Zwiebel (Vanderbilt University).
AU, 2016238305, filed Oct. 17, 2017 (Nov. 9, 2017), Zwiebel (Vanderbilt University).
BR, BR1120170204401, filed Sep. 25, 2017, Zwiebel (Vanderbilt University).
CA, 3018974, filed Sep. 25, 2018, Zwiebel (Vanderbilt University).
CN, 2016800234726 (107529746), filed Oct. 23, 2017 (Jan. 2, 2018), Zwiebel (Vanderbilt University).
EP, 16769719.2 (3273779), filed Oct. 24, 2017 (Jan. 31, 2018), Zwiebel (Vanderbilt University).
IL, 254686, filed Sep. 25, 2017, Zwiebel (Vanderbilt University).
PCT, PCT/US2016/024076 (WO 2016/154471), filed Mar. 24, 2016 (Sep. 29, 2016), Zwiebel (Vanderbilt University).
SG, 11201707879Q, filed Sep. 25, 2017 (Oct. 30, 2017), Zwiebel (Vanderbilt University).
ZA, 2017/06575, filed Sep. 29, 2017, Zwiebel (Vanderbilt University).
Acree et al., L-Lactic Acid: A Mosquito Attractant Isolated from Humans. Science. 1968; 161:1346-7.
Antonny et al., The mechanism of aluminum-independent G-protein activation by fluoride and magnesium. 31P NMR spectroscopy and fluorescence kinetic studies. J Biol Chem. 1993; 268:2393-402.
Baumann et al., Primary structure and functional expression of a Drosophila cyclic nucleotide-gated channel present in eyes and antennae. Embo J. 1994; 13:5040-50.
Benton et al., Variant ionotropic glutamate receptors as chemosensory receptors in Drosophila. Cell. 2009; 136:149-62.
Benton et al., Atypical membrane topology and heteromeric function of Drosophila odorant receptors in vivo. PLoS Biol. 2006; 4(2):e20 (18 pages).
Bernier et al., Analysis of human skin emanations by gas chromatography/mass spectrometry. 1. Thermal desorption of attractants for the yellow fever mosquito (Aedes aegypti) from handled glass beads. Anal Chem. 1999; 71:1-7.
Boekhoff, I. et al., Pheromone-induced stimulation of inositoltrisphosphate formation in insect antennae is mediated by G-proteins. J Comp Physiol B. 1990; 160:99-103.
Bohbot et al., Molecular characterization of the Aedes aegypti odorant receptor gene family, Insect. Mol Biol. 2007; 16:525-37.
Bohbot et al: "Insect Repellents: Modulators of Mosquito Odorant Receptor Activity", Plos One, vol. 5, No. 8,(2010), p. e12138.

Bohlen et al., A bivalent tarantula toxin activates the capsaicin receptor, TRPV1, by targeting the outer pore domain. Cel. 2010; 141: 834-45.
Brady et al., The role of body odours in the relative attractiveness of different men to malarial vectors in Burkina Faso. Ann Trap Med Parasitol. 1997; 91:S121-2.
Breer, H. et al., Rapid kinetics of second messenger formation in olfactory transduction. Nature. 1990;345:65-8.
CAS Registry No. 1290271-73-6; May 5, 2011.
CAS Registry No. 1287847-77-1; May 1, 2011.
CAS Registry No. 1278492-10-6; Apr. 11, 2011.
CAS Registry No. 1182613-44-0; Sep. 11, 2009.
CAS Registry No. 1181196-30-4; Sep. 8, 2009.
CAS Registry No. 1290415-35-8; May 5, 2011.
CAS Registry No. 1289977-38-3; May 4, 2011.
CAS Registry No. 1289450-47-0; May 3, 2011.
CAS Registry No. 1289917-54-9; May 4, 2011.
CAS Registry No. 848989-24-2; Apr. 22, 2005.
CAS Registry No. 440638-11-9; Jul. 29, 2002.
CAS Registry No. 381682-23-1; Jan. 10, 2002.
CAS Registry No. 442631-22-3; Aug. 6, 2002.
CAS Registry No. 423130-78-3; May 30, 2002.
CAS Registry No. 412921-00-7; May 9, 2002.
CAS Registry No. 332385-30-5; Apr. 25, 2001.
CAS Registry No. 423130-74-9; May 30, 2002.
CAS Registry No. 333786-87-1; May 1, 2001.
CAS Registry No. 1286975-43-6; STN Entry Date Apr. 28, 2011.
CAS Registry No. 1286430-12-3; STN Entry Date Apr. 27, 2011.
CAS Registry No. 1209715-08-1; STN Entry Date Mar. 14, 2010.
CAS Registry No. 1180894-98-7; STN Entry Date Sep. 6, 2009.
CAS Registry No. 1091498-95-1; STN Entry Date Dec. 29, 2008.
CAS Registry No. 952921-55-0; STN Entry Date Nov. 11, 2007.
CAS Registry No. 948289-46-1; STN Entry Date Sep. 27, 2007.
CAS Registry No. 948210-77-3; STN Entry Date Sep. 27, 2007.
CAS Registry No. 880800-32-8; STN Entry Date Apr. 18, 2006.
CAS Registry No. 585550-72-7; STN Entry Date Sep. 15, 2003.
Carnevale et al., The aggressiveness of Anopheles gambiae A in relation to the age and sex of the human subjects. Bull World Health Org. 1978; 56:147-54 (Abstract included).
Caterina et al., The capsaicin receptor: a heat-activated ion channel in the pain pathway. Nature. 1997; 389:816-24.
Clyne et al., The odor specificities of a subset of olfactory receptor neurons are governed by Acj6, a POU-domain transcription factor. Neuron. 1999; 22:327-38.
Clyne et al., Candidate taste receptors in Drosophila. Science. 2000; 287:1830-4.
Cork, A. and Park, K.C., Identification of electrophysiologically-active compounds for the malaria mosquito, Anopheles gambiae, in human sweat extracts. Med Vet Entomol. 1996; 10:269-76.
Curtis, C.F., Fact and fiction in mosquito attraction and repulsion. Parasitol Today. 1986; 11:316-8.
Database Registry [online] Chemical Abstracts Service, Columbus, Ohio, US; Jun. 5, 2003 (Jun. 5, 2003) Database accession No. 525582-84-7/RN (1 page).
Database Registry[online] Chemical Abstracts Service, Columbus, Ohio, US; Feb. 21, 2014 (Feb. 21, 2014) Database accession No. 0089984228.
Database CA [online], Chemical Abstracts Service, Columbus, OH, US; Database Accession No. 117:111530 CA.
De Jong, R. and Knols, B.G.J., Olfactory responses of host-seeking Anopheles gambiae s.s. Giles (Diptera: Culicidae). Acta Trap. 1995; 59:333-5.
De Jong, R. and Knols, B.G.J., Selection of biting sites on man by two malaria mosquito species. Experientia. 1995; 51:80-4.
Dekker, T. et al., Innate preference for host-odour blends modulates degree of anthropophagy of; Anopheles gambiae sensu lato (Diptera: Culicidae). J Med Entomol. 2001a; 38:868-71.
Dekker, T. et al., Structure of host-odour plumes influences catch of Anopheles gambiae s.s. and Aedes aegypti in a dual-choice olfactometer. Physiol Entomol. 2001b; 26:124-34.
Dobritsa et al., Integrating the molecular and cellular basis of odor coding in the Drosophila antenna. Neuron. 2003; 37:827-41.

(56) References Cited

OTHER PUBLICATIONS

Eiras, A.E. and Jepson, P.C., Host location by *Aedes aegypti* (Diptera: Culicidae): a wind tunnel study of chemical cues. Bull Entomol Res. 1991; 81:151-60.
Elmore, T. and Smith, D.P., Putative *Drosophila* odor receptor OR43b localizes to dendrites of olfactory neurons. Insect Biochem Mol Biol. 2001; 31:791-8.
Engsontia et al., The red flour beetle's large nose: an expanded odorant receptor gene family in *Tribolium castaneum*. Insect Biochem Mol Biol. 2008; 38:387-97.
Fox et al., Candidate odorant receptors from the malaria vector mosquito *Anopheles gambiae* and evidence of down-regulation in response to blood feeding. Proc Natl Acad Sci USA. 2001; 98:14693-7.
Gao, Q. and Chess, A., Identification of candidate *Drosophila* olfactory receptors from genomic DNA sequence. Genomics. 1999; 60:31-9.
Gilles, The role of carbon dioxide in host-finding by mosquitoes (Diptera: Culicidae): a review. Bull Entomol Res. 1980; 70:525-32.
Goldman et al., Coexpression of two functional odor receptors in one neuron. Neuron. 2005; 45:661-6.
Hallem, E.A. and Carlson, J.R., Coding of Odors by a Receptor Repertoire. Cell. 2006; 125:143-60.
Hallem, E.A. et al., The Molecular Basis of Odor Coding in the *Drosophila* Antenna. Cell. 2004a; 117:965-79.
Hallem, E.A. et al., Olfaction: mosquito receptor for human-sweat odorant. Nature. 2004b; 427:212-3.
Hildebrand, J.G. and Shepherd, G.M., Mechanisms of olfactory discrimination: converging evidence for common principles across phyla. Annu Rev Neurosci. 1997; 20:595-631.
Hill, C.A. et al., G protein-coupled receptors in *Anopheles gambiae*. Science. 2002; 298:176-8.
Holt, R.A. et al., The genome sequence of the malaria mosquito *Anopheles gambiae*. Science. 2002; 298: 129-49.
Jones et al., Functional conservation of an insect odorant receptor gene across 250 million years of evolution. Curr Biol. 2005; 15:R119-21.
Jones, W.D. et al., Two chemosensory receptors together mediate carbon dioxide detection in *Drosophila*. Nature. 2007; 445:86-90.
Jones et al: "Functional agonism of insect odorant receptor ion channels", Proc Natl Acad Sci, vol. 108, No. 21, (2011) pp. 8821-8825.
Jones, P.L. et al., Allosteric Antagonism of Insect Odorant Receptor Ion Channels. PLoS One. 2012;7(1):e30304 (7 pages).
Kellogg, Water vapour and carbon dioxide receptors in *Aedes aegypti*. J Insect Physiol. 1970; 16:99-108.
Kim et al., Identification of novel multi-transmembrane proteins from genomic databases using quasi-periodic structural properties. Bioinformatics. 2000; 16:767-75.
Krieger, J. and Breer, H., Olfactory reception in invertebrates. Science. 1999; 286:720-3.
Krieger, J. et al., A divergent gene family encoding candidate olfactory receptors of the moth *Heliothis virescens*. Eur J Neurosci. 2002; 16:619-28.
Krieger, J. et al., Identification of a cyclic nucleotide- and voltage-activated ion channel from insect antennae. Insect Biochem Mol Biol. 1999; 29:255-67.
Krieger, J. et al., A candidate olfactory receptor subtype highly conserved across different insect orders. J Comp Physiol A. 2003; 189:519-26.
Krotoszynski, B. et al., Characterization of human expired air: a promising investigative and diagnostic technique. J Chromatographic Sci. 1977; 15:239-44.
Kwon, J.Y. et al., The molecular basis of $CO_2$ reception in *Drosophila*. Proc Natl Acad Sci USA. 2007; 104:3574-8.
Labows, J.N. Jr., Human odors—what can they tell us? Perfumer & Flavorist. 1979; 4:12-7.
Larsson et al., Or83b Encodes a Broadly Expressed Odorant Receptor Expressed Odorant Receptor Essential for *Drosophila* Olfaction. Neuron. 2004; 43:703-14.
Laue, M. et al., G-protein activation, identification and immunolocalization in pheromone-sensitive sensilla trichodea of moths. Cell Tissue Res. 1997; 288:149-58.
Lee, S. H. et al., Preparation of triazole derivatives as T-type calcium channel blockers. CAS accession No. 150: 77688.
Lindsay, S.W. et al., Variation in attractiveness of human subjects to malaria mosquitoes (Diptera: Culicidae) in The Gambia. J Med Entomol. 1993; 30:368-73.
Lu et al., Odor Coding in the Maxillary Palp of the Malaria Vector Mosquito *Anopheles gambiae*. Curr Biol. 2007; 17:1533-44.
Liu et al., Distinct Olfactory Signaling Mechanisms in the Malaria Vector Mosquito *Anopheles gambiae*. PLoS Biol. 2010; 8(8): e1000467 (17 pages).
Lundin et al., Membrane topology of the *Drosophila* OR83b odorant receptor. FEBS Lett. 2007; 581(29):5601-4.
Mboera, L.E.G. and Takken, W., Carbon dioxide chemotropism in mosquitoes (Diptera: Culicidae) and its potential in vector surveillance and management programmes. Rev Med Vet Entomol. 1997;85:355-68.
Meijerink, J. and van Loon, J.J.A., Sensitivities of antennal olfactory neurons of the malaria mosquito, *Anopheles gambiae*, to carboxylic acids. J Insect Physiol. 1999; 45:365-73.
Meijerink, J. et al., Olfactory receptors on the antennae of the malaria mosquito *Anopheles gambiae* are sensitive to ammonia and other sweat-borne components. J Insect Physiol. 2001; 47:455-64.
Merrill et al., Molecular characterization of arrestin family members in the malaria vector mosquito, *Anopheles gambiae*. Insect Mol Biol. 2003; 12:641-50.
Merrill et al., Odorant-specific requirements for arrestin function in *Drosophila* olfaction. J Neurobiol. 2005; 63:15-28.
Merrill et al., Visual arrestins in olfactory pathways of *Drosophila* and the malaria vector mosquito *Anopheles gambiae*. Proc Natl Acad Sci USA. 2002; 99:1633-8.
Micheli, F. et al., 2-Methyl-3-furanyl-4/H-1,2,4-triazol-3-ylthioamides: A New class of Selective Orexin 2 Antagonists. Bioorg Med Chem Lett. 2010; 20(22):6405-7.
Milczarska, B. et al., Synthesis and Tuberculostatic Activity of 2-(4,5-Disubstituted-[1,2,4]-triazol-3-ylsulphanyl)-N-phenylacetamides. Phosphorus, Sulfur and Silicon and the Related Elements. 2007; 182(6):1253-74.
Mombaerts, P., Molecular biology of odorant receptors in vertebrates. Annu Rev Neurosci. 1999; 22:487-509.
Muirhead-Thomson, Low Gametocyte Thresholds of Infection of Anopheles with Plasmodium Falciparum. Brit Med J. 1951; I: 1114-7.
Pelosi and Maida, Odorant-binding proteins in insects. Comp Biochem Physiol. 1995; 111B:503-14.
Pitts et al., A highly conserved candidate chemoreceptor expressed in both olfactory and gustatory tissues in the malaria vector *Anopheles gambiae*. Proc Natl Acad Sci USA. 2004; 101:5058-63.
Qiu, Y.T. et al., Olfactory Coding in Antennal Neurons of the Malaria Mosquito, *Anopheles gambia*. Chem Senses. 2006b; 31:845-63.
Qiu, Y.T. et al., Attractiveness of MM-X Traps Baited with Human or Synthetic Odor to Mosquitoes (Diptera: Culicidae) in The Gambia. J Med Entomol. 2007; 44(6):970-83.
Qui, Y.T. et al., Interindividual Variation in the Attractiveness of Human Odours to the Malaria Mosquito *Anopheles gambiae* s. s. Med Vet Entomol. 2006; 20(3):280-7.
Robertson and Wanner, The chemoreceptor superfamily in the honey bee, *Apis mellifera*: Expansion of the odorant, but not gustatory, receptor family. Genome Res. 2006; 16:1395-403.
Robertson, H. et al., Molecular evolution of the insect chemoreceptor gene superfamily in *Drosophila melanogaster*. Proc Natl Acad Sci USA. 2003; 100(2):14537-42.
Romaine,et al: "Narrow SAR in odorant sensing Orco receptor agonists", Bioorganic & Medicinal Chemistry Letters,vol. 24, No. 12,(2014), pp. 2613-2616.
Rützler, M. et al., $G_\alpha$Encoding Gene Family of the Malaria Vector Mosquito *Anopheles gambiae*: Expression Analysis and Immunolocalization of $AG_{\alpha q}$ and $AG_{\alpha o}$ in Female Antennae. J Comp Neurol. 2006; 499(4):533-45.

(56) References Cited

OTHER PUBLICATIONS

Sato, K. et al., Insect olfactory receptors are heteromeric ligand-gated ion channels. Nature. 2008; 452(7190): 1002-6.
Schreck, C.E. et al., Mosquito attraction to substances from the skin of different humans. J Am Mosq Control Assoc. 1990; 6(3):406-10.
Scott, K. et al., A chemosensory gene family encoding candidate gustatory and olfactory receptors in *Drosophila*. Cell. 2001; 104:661-73.
Smith, D.P., *Drosophila* odor receptors revealed. Neuron. 1999; 22:203-4.
Soliman, L. N. et al., Synthesis of some substituted mercaptotriazoles with possible anticonvulsant and monoamine oxidase inhibiting activities. Bulletin of the Faculty of Pharmacy (Cairo University). 1990;28(2):53-8.
Stengl, M., Inositol-trisphosphate-dependent calcium currents precede cation currents in insect olfactory receptor neurons in vitro. J Comp Physiol A. 1994; 174:187-94.
Storkuhl and Kettler, Functional analysis of an olfactory receptor in *Drosophila melanogaster*. Proc Natl Acad Sci USA. 2001; 98:9381-5.
Suh et al., Light Activation of an Innate Olfactory Avoidance Response in *Drosophila*. Curr Biol. 2007; 17:905-8.
Takken and Knols, Odor-mediated behavior of Afrotropical malaria mosquitoes. Annu Rev Entomol. 1999;44:131-57.
Takken, W. et al., Odor-mediated flight behavior of *Anopheles gambiae* giles Sensu Stricto and *An. stephensi* Liston in response to $CO_2$, acetone, and 1-octen-3-ol (Diptera: Culicidae). J Insect Behavior. 1997; 10:395-407.
Takken, W., The role of olfaction in host-seeking of mosquitoes: a review. Insect Sci Applns. 1991; 12:287-95.
Taylor, et al: "Structure-Activity Relationship of a Broad-Spectrum Insect Odorant Receptor Agonist", ACS Chemical Biology, vol. 7, No. 10,(2012), pp. 1647-1652.
Thomas, TCE: Biting activity of *Anopheles gambiae*. Brit Med J. 1951; 2:1402.
Vosshall, L.B. et al., An olfactory sensory map in the fly brain. Cell. 2000; 102:147-59.
Vosshall, L.B. et al., A spatial map of the olfactory receptor expression in the *Drosophila* antenna. Cell. 1999;96:725-36.
Vosshall, L.B., The molecular logic of olfaction in *Drosophila*. Chem Senses. 2001; 26:207-13.
Vosshall, L.B. and Hansson, B.S., A unified nomenclature system for the insectolfactory coreceptor. Chem Senses. 2011; 36(6):497-8.
Wetzel et al., Functional expression and characterization of a *Drosophila* odorant receptor in a heterologous cell system. Proc Natl Acad Sci USA. 2001; 98:9377-80.
Wicher et al., *Drosophila* odorant receptors are both ligand-gated and cyclicnucleotide-activated cation channels. Nature. 2008; 452(7190):1007-11.
Wistrand et al., A general model of G protein-coupled receptor sequences and its application to detect remote homologs. Protein Sci. 2006; 15:509-21.
Xia et al., The molecular and cellular basis of olfactory-driven behavior in *Anopheles gambiae* larvae. Proc Natl Acad Sci USA. 2008; 105:6433-8.
Zwiebel and Takken, Olfactory regulation of mosquito-host interactions. Insect Biochem Mol Biol. 2004; 34:645-52.
First Office Action was dated Jun. 26, 2014 by the State Intellectual Property office of the People's Republic of China for CN Application No. 201180062303.0, which was filed on Oct. 21, 2011 and granted as CN103402988A on Nov. 20, 2013 (Inventor—Zwiebel, et al.; Applicant—Vanderbilt University; (Original—9 pages//Translated—11 pages).
Second Office Action was dated Apr. 16, 2015 by the State Intellectual Property office of the People's Republic of China for CN Application No. 201180062303.0, which was filed on Oct. 21, 2011 and granted as CN103402988A on Nov. 20, 2013 (Inventor—Zwiebel, et al.; Applicant—Vanderbilt University; (Original—6 pages//Translated—8 pages).

Notification of Grant was dated Aug. 5, 2015 by the State Intellectual Property Office of China for Chinese Application No. 201180062303.0 which was filed on Oct. 21, 2011 and published as CN103402988A on Nov. 20, 13 (Inventor—Laurence Zwiebel et al.; Applicant—Vanderbilt University) (Original—1 page).
First Office Action was dated Mar. 1, 2017 by the State Intellectual Property office of the People's Republic of China for CN Application No. 201510683406.9, which was filed on Oct. 20, 2015 and granted as CN105394046 on Mar. 16, 2016 (Inventor—Zwiebel, et al.; Applicant—Vanderbilt University; (Original—6 pages//Translated—7 pages).
Second Office Action was dated Aug. 31, 2017 by the SIPO for CN Application No. 2015106834069, which was filed on Oct. 20, 2015 and published as CN 105394046 on Mar. 16, 2016 (Applicant—Vanderbilt University) (Original—4 pages//Translated—7 pages).
Supplemental European Search Report dated May 28, 2014 for European Patent Application No. 11838461.9, which was filed Oct. 21, 2011 and published as EP 2632257 on Sep. 4, 2013 (Inventor—Zwiebel, et al.; Applicant—Vanderbilt University) (pp. 1-9).
Communication pursuant to Article 94(3) issued by the European Patent Office on Apr. 6, 2017 for Application No. 11838461.9 filed Oct. 21, 2011 and published as EP 2632257 on Sep. 4, 2013 (Applicant—Vanderbilt University; Inventors—Zwiebel et al.) (5 pages).
Communication Pursuant to Article 94(3) EPC dated Jun. 22, 2018 by the European Patent Office for Patent Application No. 11838461.9, which was filed on Oct. 21, 2011 and published as EP 2632257 on Sep. 4, 2013 (Inventor—Zwiebel et al.; Applicant—Vanderbilt University) (5 pages).
International Search Report mailed by the International Bureau dated Jun. 21, 2012 for PCT/US2011/057246 filed Oct. 21, 2011 and published as WO 2012/061039 on May 10, 2012 (Applicant—Vanderbilt University; Inventors—Zwiebel, et al.) (5 pages).
Written Opinion mailed by the International Bureau dated Jun. 21, 2012 for PCT/US2011/057246 filed Oct. 21, 2011 and published as WO 2012/061039 on May 10, 2012 (Applicant—Vanderbilt University; Inventors—Zwiebel, et al.) (6 pages).
International Preliminary Report on Patentability issued by the International Bureau dated Apr. 30, 2013 for PCT/US2011/057246 filed Oct. 21, 2011 and published as WO 2012/061039 on May 10, 2012 (Applicant—Vanderbilt University; Inventors—Zwiebel, et al.) (7 pages).
Preliminary Amendment filed Apr. 25, 2013 for U.S. Appl. No. 13/881,638, filed Oct. 16, 2013 and published as U.S. 2014/0039013 on Feb. 6, 2014 (Inventor—Zwiebel, et al.; Applicant—Vanderbilt University) (pp. 1-5).
Restriction Requirement dated Jun. 9, 2014 for U.S. Appl. No. 13/881,638, filed Oct. 16, 2013 and published as U.S. 2014/0039013 on Feb. 6, 2014 (Inventor—Zwiebel, et al.; Applicant—Vanderbilt University) (pp. 1-12).
Response to Restriction Requirement filed Aug. 8, 2014 for U.S. Appl. No. 13/881,638, filed Oct. 16, 2013 and published as U.S. 2014/0039013 on Feb. 6, 2014 (Inventor—Zwiebel, et al.; Applicant—Vanderbilt University) (pp. 1-7).
Non Final Rejection was dated Dec. 15, 2014 for U.S. Appl. No. 13/881,638, filed Oct. 16, 2013 and granted as U.S. Pat. No. 9,332,757 on May 10, 2016 (Inventor—Zwiebel, et al.; Applicant—Vanderbilt University) (21 Pages).
Response to Non Final Rejection was dated Mar. 16, 2015 for U.S. Appl. No. 13/881,638, filed Oct. 16, 2013 and granted as U.S. Pat. No. 9,332,757 on May 10, 2016 (Inventor—Zwiebel, et al.; Applicant—Vanderbilt University) (13 Pages).
Ex Parte Quayle Action dated Jul. 29, 2015 for U.S. Appl. No. 13/881,638, filed Oct. 16, 2013 and published as U.S. 2014/0039013 on Feb. 6, 2014 (Inventor—Zwiebel, et al.; Applicant—Vanderbilt University) (6 pages).
Response to Ex Parte Quayle Action filed on Sep. 25, 2015 for U.S. Appl. No. 13/881,638, filed Oct. 16, 2013 and published as U.S. 2014/0039013 on Feb. 6, 2014 (Inventor—Zwiebel, et al.; Applicant—Vanderbilt University) (5 pages).

(56) References Cited

OTHER PUBLICATIONS

Notice of Allowance was dated Jan. 12, 2016 for U.S. Appl. No. 13/881,638, filed Oct. 16, 2013 and granted as U.S. Pat. No. 9,332,757 on May 10, 2016 (Inventor—Zwiebel, et al.; Applicant—Vanderbilt University) (7 Pages).
Issue Notification was dated Apr. 20, 2016 for U.S. Appl. No. 13/881,638, filed Oct. 16, 2013 and granted as U.S. Pat. No. 9,332,757 on May 10, 2016 (Inventor—Zwiebel, et al.; Applicant—Vanderbilt University) (1 Page).
Preliminary Amendment filed on Apr. 7, 2016 with the U.S. Patent and Trademark Office for U.S. Appl. No. 15/093,593, filed Apr. 7, 2016 and published as US 2016/0286807 on Oct. 6, 2016 (Inventor—Zwiebel et al.; Applicant—Vanderbilt University) (3 pages).
Restriction Requirement was dated May 2, 2017 by the USPTO for U.S. Appl. No. 15/093,593, filed Apr. 7, 2016 and published as US 2016-0286807 A1 on Oct. 6, 2016 (Applicant—Vanderbilt University; Inventor- Laurence Zwiebel) (11 pages).
Non Final Office Action was dated Jul. 14, 2017 by the USPTO for U.S. Appl. No. 15/093,593, filed Apr. 7, 2016 and published as US 2016-0286807 A1 on Oct. 6, 2016 (Inventor—Laurence Zwiebel, et al.) (8 pages).
Response to Non-Final Office Action and Terminal Disclaimer filed on Oct. 16, 2017 with the U.S. Patent and Trademark Office for U.S. Appl. No. 15/093,593, filed Apr. 7, 2016 and published as US 2016/0286807 on Oct. 6, 2016 (Inventor—Zwiebel et al.; Applicant—Vanderbilt University) (7 pages).
Terminal Disclaimer Review Decision issued on Oct. 24, 2017 by the U.S. Patent and Trademark Office for U.S. Appl. No. 15/093,593, which was filed on Apr. 7, 2016 and published as US 2016/0286807 on Oct. 6, 2016 (Inventor- Zwiebel et al.; Applicant- Vanderbilt University; Attorney Docket No. 22000.0254U8-) (1 page).
Terminal Disclaimer filed on Jan. 31, 2018 with the U.S. Patent and Trademark Office for U.S. Appl. No. 15/093,593, filed Apr. 7, 2016 and published as US 2016/0286807 on Oct. 6, 2016 (Inventor—Zwiebel et al.; Applicant—Vanderbilt University) (2 pages).
Approval of Terminal Disclaimer issued on Jan. 31, 2018 by the U.S. Patent and Trademark Office for U.S. Appl. No. 15/093,593, filed Apr. 7, 2016 and published as US 2016/0286807 on Oct. 6, 2016 (Inventor—Zwiebel et al.; Applicant—Vanderbilt University) (1 page).
Final Office Action issued on Feb. 1, 2018 by the U.S. Patent and Trademark Office for U.S. Appl. No. 15/093,593, filed Apr. 7, 2016 and published as US 2016/0286807 on Oct. 6, 2016 (Inventor—Zwiebel et al.; Applicant—Vanderbilt University) (8 pages).
Notice of Allowance issued on Jun. 5, 2018 by the U.S. Patent and Trademark Office for U.S. Appl. No. 15/093,593, filed Apr. 7, 2016 and published as US 2016/0286807 on Oct. 6, 2016 (Inventor—Zwiebel et al.; Applicant—Vanderbilt University) (7 pages).
Notice of Allowance dated Jul. 9, 2018 by the U.S. Patent and Trademark Office for U.S. Appl. No. 15/093,593, filed Apr. 7, 2016 and published as US 2016/0286807 on Oct. 6, 2016 (Inventor—Zwiebel et al.; Applicant—Vanderbilt University) (3 pages).
Non Final Rejection was dated Mar. 22, 2019 by the USPTO for U.S. Appl. No. 16/145,996, filed Sep. 28, 2018 and published as US-2019-0029256-A1 on Jan. 31, 2019 (Inventor—Lawrence Zwiebel (8 Pages).
Response to Non Final Rejection was dated Jun. 14, 2019 with the USPTO for U.S. Appl. No. 16/145,996, filed Sep. 28, 2018 and published as US-2019-0029256-A1 on Jan. 31, 2019 (Inventor—Lawrence Zwiebel) (5 Pages).
Non Final Rejection was dated Sep. 23, 2019 by the USPTO for U.S. Appl. No. 16/145,996, filed Sep. 28, 2018 and published as US-2019-0029256-A1 on Jan. 31, 2019 (Inventor—Lawrence Zwiebel) (7 Pages).
Response to Non Final Rejection was dated Nov. 25, 2019 with the USPTO for U.S. Appl. No. 16/145,996, filed Sep. 28, 2018 and published as US-2019-0029256-A1 on Jan. 31, 2019 (Inventor—Lawrence Zwiebel) (5 Pages).

Notice of Allowance was dated Mar. 4, 2020 by the USPTO for U.S. Appl. No. 16/145,996, filed Sep. 28, 2018 and published as US-2019-0029256-A1 on Jan. 31, 2019 (Inventor—Lawrence Zwiebel) (8 Pages).
Notice of Allowance was dated Apr. 15, 2020 by the USPTO for U.S. Appl. No. 16/145,996, filed Sep. 28, 2018 and published as US-2019-0029256-A1 on Jan. 31, 2019 (Inventor—Lawrence Zwiebel) (2 Pages).
Notice of Allowance was dated May 20, 2020 by the USPTO for U.S. Appl. No. 16/145,996, filed Sep. 28, 2018 and published as US-2019-0029256-A1 on Jan. 31, 2019 (Inventor—Lawrence Zwiebel) (3 Pages).
Issue Notification was dated Jun. 17, 2020 by the USPTO for U.S. Appl. No. 16/145,996, filed Sep. 28, 2018 and published as US-2019-0029256-A1 on Jan. 31, 2019 (Inventor—Lawrence Zwiebel) (1 Pages).
First Examination Report was dated Jan. 27, 2016 by the Australian Patent Office for AU Application No. 2012254032, which was filed on Apr. 25, 2012 (Applicant-Vanderbilt University) (6 pages).
Second Examination Report was dated Jan. 20, 2017 by the Australian Patent Office for AU Application No. 2012254032, which was filed on Apr. 25, 2012 (Applicant—Vanderbilt University) (14 pages).
Notice of Acceptance was dated Feb. 10, 17 by the Australian Patent Office for Australian Application No. 2012254032 filed Apr. 25, 2012 and granted as AU 2012254032 on Jun. 8, 2017 (Applicant—Vanderbilt University; Inventors—Zwiewel et al.) (4 pages).
Certificate of Grant was dated Jun. 8, 17 by the Australian Patent Office for Australian Application No. 2012254032 filed Apr. 25, 2012 and granted as AU 2012254032 on Jun. 8, 2017 (Applicant—Vanderbilt University; Inventors—Zwiewel et al.) (1 page).
Examination Report No. 1 dated May 21, 2018 by the Intellectual Property Office of Australia for Patent Application No. 2017202652, which was filed on Apr. 21, 2017 (Inventor—Zwiewbel et al.; Applicant—Vanderbilt University) (12 pages).
Examination Report No. 1 dated Dec. 3, 2019 by the Intellectual Property Office of Australia for Patent Application No. 2019203549 (Inventor—Zwiewbel et al.; Applicant—Vanderbilt University) (2 pages).
Office Action dated Dec. 13, 2018 by the Canadian Intellectual Property Office for Patent Application No. 2,835,328, which was filed on Nov. 9, 2013 (Inventor—Zwiebel et al.; Applicant—Vanderbilt University) (3 pages).
Supplementary European Search Report issued by the European Patent Office dated May 13, 2015 for European Application No. 1278194.6 filed Apr. 25, 2012 and published as EP 2704575 on Mar. 12, 2014 (Applicant—Vanderbilt University; Inventors—Zwiebel et al.) (8 Pages).
Communication Pursuant to Article 94(3) EPC dated Jan. 26, 2018 by the European Patent Office for Patent Application No. 12781894.6, which was filed on Apr. 25, 2012 and published as EP 2704575 on Mar. 12, 2014 (Inventor—Zwiebel et al.; Applicant—Vanderbilt University) (8 pages).
European Search Report and Written Opinion were dated Mar. 12, 2020 by the European Patent Office for EP Application No. 19203416.3, filed on Apr. 25, 2012 and published as EP 3653054 on May 20, 2020 (Applicant—Vanderbilt University) (13 Pages).
International Search Report and Written Opinion dated Sep. 17, 2012 for International Patent Application No. PCT/US2012/034847, which was filed on Apr. 25, 2012 and published as WO 2012/154403 on Nov. 15, 2012 (Inventor—Zwiebel, et al.; Applicant—Vanderbilt University) (11 pages).
International Preliminary Report on Patentability dated Mar. 25, 2014 for International Patent Application No. PCT/US2012/034847, which was filed on Apr. 25, 2012 and published as WO 2012/154403 on Nov. 15, 2012 (Inventor—Zwiebel, et al.; Applicant—Vanderbilt University) (8 pages).
Preliminary Amendment was dated Nov. 4, 2013 to the U.S. Patent and Trademark Office for US Application No. PCT/US2012/034847, which was filed on Apr. 25, 12 and published as WO 2012/154403 on Nov. 15, 2012 (Inventor—Laurence Zwiebel et al.; Applicant—Vanderbilt University) (17 Pages).

(56) References Cited

OTHER PUBLICATIONS

Requirement for Restriction/Election was dated Jul. 6, 2015 by the U.S. Patent and Trademark Office for U.S. Appl. No. 14/115,553, filed May 2, 2014 and published as US 2014-0242135 A1 on Feb. 6, 2014 (Inventor—Laurence Zwiebel et al.; Applicant—Vanderbilt University) (10 Pages).
Response to Restriction Requirement was dated Sep. 8, 2015 to the U.S. Patent and Trademark Office for U.S. Appl. No. 14/115,553, filed May 2, 2014 and published as US 2014-0242135 A1 on Feb. 6, 2014 (Inventor—Laurence Zwiebel et al.; Applicant—Vanderbilt University) (15 Pages).
Non Final Rejection was dated Dec. 17, 2015 by the U.S. Patent and Trademark Office for U.S. Appl. No. 14/115,553, filed May 2, 14 and published as US 2014-0242135 A1 on Feb. 6, 14 (Inventor—Laurence Zwiebel et al.; Applicant—Vanderbilt University) (10 Pages).
Response to Non Final Rejection was dated Apr. 18, 2016 to the U.S. Patent and Trademark Office for U.S. Appl. No. 14/115,553, filed May 2, 2014 and published as US 2014-0242135 A1 on Feb. 6, 2014 (Inventor—Laurence Zwiebel et al.; Applicant—Vanderbilt University) (12 Pages).
Final Rejection was dated Jun. 16, 2016 by the U.S. Patent and Trademark Office for U.S. Appl. No. 14/115,553, filed May 2, 2014 and published as US 2014-0242135 A1 on Feb. 6, 2014 (Inventor—Laurence Zwiebel et al.; Applicant—Vanderbilt University) (16 Pages).
Response to Final Rejection was dated Sep. 16, 2016 to the U.S. Patent and Trademark Office for U.S. Appl. No. 14/115,553, filed May 2, 2014 and granted as U.S. Pat. No. 9,578,881 on Feb. 28, 2017 (Inventor—Laurence Zwiebel et al.; Applicant—Vanderbilt University) (17 Pages).
Notice of Allowance was dated Oct. 7, 2016 by the U.S. Patent and Trademark Office for U.S. Appl. No. 14/115,553, filed May 2, 2014 and granted as U.S. Pat. No. 9,578,881 on Feb. 28, 2017 (Inventor—Laurence Zwiebel et al.; Applicant—Vanderbilt University) (7 Pages).
Amendment after Notice of Allowance(Rule 312) was dated Jan. 3, 2017 by the U.S. Patent and Trademark Office for U.S. Appl. No. 14/115,553, filed May 2, 2014 and granted as U.S. Pat. No. 9,578,881 on Feb. 28, 2017 (Inventor—Laurence Zwiebel et al.; Applicant—Vanderbilt University) (119 Pages).
Response to Amendment Under Rule 312 was dated Jan. 9, 2017 by the U.S. Patent and Trademark Office for U.S. Appl. No. 14/115,553, filed May 2, 2014 and granted as U.S. Pat. No. 9,578,881 on Feb. 28, 2017 (Inventor—Laurence Zwiebel et al.; Applicant—Vanderbilt University) (2 Pages).
Issue Notification was dated Feb. 8, 2017 by the U.S. Patent and Trademark Office for U.S. Appl. No. 14/115,553, filed May 2, 2014 and granted as U.S. Pat. No. 9,578,881 on Feb. 28, 2017 (Inventor—Laurence Zwiebel et al.; Applicant—Vanderbilt University) (1 Page).
Non-Final Office Action dated Feb. 7, 2018 by the U.S. Patent and Trademark Office for U.S. Appl. No. 15/443,340, filed Feb. 27, 2017 and published as US 2017/0208809 on Jul. 27, 2017 (Inventor—Zwiebel et al.; Applicant—Vanderbilt University) (10 pages).
Notice of Allowance dated Jul. 13, 2018 by the U.S. Patent and Trademark Office for U.S. Appl. No. 15/443,340, filed Feb. 27, 2017 and published as US 2017/0208809 on Jul. 27, 2017 (Inventor—Zwiebel et al.; Applicant—Vanderbilt University) (7 pages).
Amendment after Notice of Allowance(Rule 312) was dated Oct. 12, 2018 with the U.S. Patent and Trademark Office for U.S. Appl. No. 15/443,340, filed Feb. 27, 2017 and published as US 2017/0208809 on Jul. 27, 2017 (Inventor—Zwiebel et al.; Applicant—Vanderbilt University) (111 Pages).
Response to Amendment Under Rule 312 was dated Oct. 22, 2018 by the U.S. Patent and Trademark Office for U.S. Appl. No. 15/443,340, filed Feb. 27, 2017 and published as US 2017/0208809 on Jul. 27, 2017 (Inventor—Zwiebel et al.; Applicant—Vanderbilt University) (2 Pages).
Amendment after Notice of Allowance(Rule 312) was dated Oct. 12, 2018 with the U.S. Patent and Trademark Office for U.S. Appl. No. 15/443,340, filed Feb. 27, 2017 and published as US 2017/0208809 on Jul. 27, 2017 (Inventor—Zwiebel et al.; Applicant—Vanderbilt University) (4 Pages).
Issue Notification was dated Jan. 9, 2019 by the U.S. Patent and Trademark Office for U.S. Appl. No. 15/443,340, filed Feb. 27, 2017 and published as US 2017/0208809 on Jul. 27, 2017 (Inventor—Zwiebel et al.; Applicant—Vanderbilt University) (1 Page).
Requirement for Restriction was dated Aug. 21, 2019 by the U.S. Patent and Trademark Office for U.S. Appl. No. 16/186,106, filed Nov. 9, 2018 and issued as U.S. Pat. No. 10,813,355 on Oct. 27, 2020 (Inventor—Zwiebel et al.; Applicant—Vanderbilt University) (11 Pages).
Response to Requirement for Restriction was dated Nov. 20, 2019 with the U.S. Patent and Trademark Office for U.S. Appl. No. 16/186,106, filed Nov. 9, 2018 and issued as U.S. Pat. No. 10,813,355 on Oct. 27, 2020 (Inventor—Zwiebel et al.; Applicant—Vanderbilt University) (17 Pages).
Non-Final Office Action was dated Feb. 6, 2020 by the U.S. Patent and Trademark Office for U.S. Appl. No. 16/186,106, filed Nov. 9, 2018 and issued as U.S. Pat. No. 10,813,355 on Oct. 27, 2020 (Inventor—Zwiebel et al.; Applicant—Vanderbilt University) (11 Pages).
Response to Non-Final Office Action was dated Apr. 16, 2020 with the U.S. Patent and Trademark Office for U.S. Appl. No. 16/186,106, filed Nov. 9, 2018 and issued as U.S. Pat. No. 10,813,355 on Oct. 27, 2020 (Inventor—Zwiebel et al.; Applicant—Vanderbilt University) (14 Pages).
Notice of Allowance was dated May 6, 2020 by the U.S. Patent and Trademark Office for U.S. Appl. No. 16/186,106, filed Nov. 9, 2018 and issued as U.S. Pat. No. 10,813,355 on Oct. 27, 2020 (Inventor—Zwiebel et al.; Applicant—Vanderbilt University) (9 Pages).
Amendment after Notice of Allowance(Rule 312) was dated May 21, 2020 by the U.S. Patent and Trademark Office for U.S. Appl. No. 16/186,106, filed Nov. 9, 2018 and issued as U.S. Pat. No. 10,813,355 on Oct. 27, 2020 (Inventor—Zwiebel et al.; Applicant—Vanderbilt University) (12 Pages).
Response to Amendment Under Rule 312 was dated May 29, 2020 by the U.S. Patent and Trademark Office for U.S. Appl. No. 16/186,106, filed Nov. 9, 2018 and issued as U.S. Pat. No. 10,813,355 on Oct. 27, 2020 (Inventor—Zwiebel et al.; Applicant—Vanderbilt University) (3 Pages).
Issue Notification was dated Oct. 8, 2020 by the U.S. Patent and Trademark Office for U.S. Appl. No. 16/186,106, filed Nov. 9, 2018 and issued as U.S. Pat. No. 10,813,355 on Oct. 27, 2020 (Inventor—Zwiebel et al.; Applicant—Vanderbilt University) (1 Page).
Office Action was dated Nov. 1, 2019 by the CN Patent Office for CN Application No. 201680050664, filed on Jul. 12, 2016 and published as CN 107920523 A on Apr. 17, 2018 (Applicant—Vanderbilt University) (Original—4 Pages) (Translation—6 Pages).
International Search Report and Written Opinion dated Sep. 27, 2016 by the International Bureau for PCT/US16/41918, filed on Jul. 12, 2016 and published as WO 2017/011466 on Jan. 19, 2017 (Inventors—Zwiebel et al.; Applicant—Vanderbilt University) (6 pages).
International Preliminary Report on Patentability dated Jan. 16, 2018 by the International Searching Authority for Patent Application No. PCT/US2016/041918, filed Jul. 12, 2016 and published as WO 2017/011466 on Jan. 19, 2017 (Inventor—Zwiebel et al.; Applicant—Vanderbilt University) (5 pages).
Non-Final Office Action dated Nov. 2, 2018 by the U.S. Patent and Trademark Office for U.S. Appl. No. 15/741,999, filed Jan. 4, 2018 and published as US 2018/0192651 on Jul. 12, 2018 (Inventor—Zwiebel et al.; Applicant—Vanderbilt University) (12 pages).
Response to Non-Final Office Action dated Feb. 28, 2019 with the U.S. Patent and Trademark Office for U.S. Appl. No. 15/741,999, filed Jan. 4, 2018 and published as US 2018/0192651 on Jul. 12, 2018 (Inventor—Zwiebel et al.; Applicant—Vanderbilt University) (13 pages).

(56) References Cited

OTHER PUBLICATIONS

Final Rejection was dated Jun. 14, 2019 by the USPTO for U.S. Appl. No. 15/741,999, filed Jan. 4, 2018 and published as US 2018/0192651 A1 on Jul. 12, 2018 (Inventor—Laurence J. Zwiebel) (15 Pages).
Response to Final Office Action dated Sep. 16, 2019 with the U.S. Patent and Trademark Office for U.S. Appl. No. 15/741,999, filed Jan. 4, 2018 and published as US 2018/0192651 on Jul. 12, 2018 (Inventor—Zwiebel et al.; Applicant—Vanderbilt University) (11 pages).
Advisory Action was dated Oct. 3, 2019 by the USPTO for U.S. Appl. No. 15/741,999, filed Jan. 4, 2018 and published as US 2018/0192651 A1 on Jul. 12, 2018 (Inventor—Laurence J. Zwiebel) (4 Pages).
Response to Advisory Action dated Oct. 8, 2019 with the U.S. Patent and Trademark Office for U.S. Appl. No. 15/741,999, filed Jan. 4, 2018 and published as US 2018/0192651 on Jul. 12, 2018 (Inventor—Zwiebel et al.; Applicant—Vanderbilt University) (11 pages).
Non-Final Office Action dated May 15, 2020 by the USPTO for U.S. Appl. No. 15/741,999, filed Jan. 4, 2018 and published as US 2018/0192651 A1 on Jul. 12, 2018 (Applicant—Vanderbilt University) (29 Pages).
Abandonment issued on Jul. 17, 2020 by the USPTO for U.S. Appl. No. 15/741,999, filed Jan. 4, 2018 and published as US 2018/0192651 A1 on Jul. 12, 2018 (Applicant—Vanderbilt University) (3 Pages).
Petition for Review mailed on Jul. 22, 2020 with the U.S. Patent and Trademark Office for U.S. Appl. No. 15/741,999, filed Jan. 4, 2018 and published as US 2018/0192651 on Jul. 12, 2018 (Inventor—Zwiebel et al.; Applicant—Vanderbilt University) (2 pages).
Petition Decision issued on Sep. 3, 2020 by the USPTO for U.S. Appl. No. 15/741,999, filed Jan. 4, 2018 and published as US 2018/0192651 A1 on Jul. 12, 2018 (Applicant—Vanderbilt University) (3 Pages).
Office Action was dated Oct. 17, 2019 by the Australian Patent Office for AU Application No. 2016238305, filed on Mar. 24, 2016 (Applicant—Vanderbilt University) (5 Pages).
Office Action was dated Oct. 20, 2019 by the Brazilian Patent Office for BR Application No. BR1120170204401, filed on Mar. 24, 2016 (Applicant—Vanderbilt University) (2 Pages).
Office Action was dated Nov. 8, 2019 by the CN Patent Office for CN Application No. 2016800234726, filed on Mar. 24, 2016 and published as 107529746 on Jan. 2, 2018 (Applicant—Vanderbilt University) (Original—4 Pages) (Translation—6 Pages).
Extended European Search Report dated Aug. 2, 2018 by the European Patent Office for Patent Application No. 16769719.2, which was filed on Mar. 24, 2016 and published as EP 3273779 on Jan. 31, 2018 (Inventor—Zwiebel et al.; Applicant—Vanderbilt University) (6 pages).
EP Communication pursuant to Article 94(3) EPC was dated Aug. 6, 2019 by the European Patent Office for EP Application No. 16769719.2, filed on Mar. 24, 2016 and published as 3273779 on Jan. 31, 2018 (Applicant—Vanderbuilt University) (5 Pages).
International Search Report and Written Opinion dated Jun. 20, 2016 by the International Bureau for PCT/US2016/24076, filed on Mar. 24, 2016 and published as WO 2016/154471 on Sep. 29, 2016 (Inventors—Zwiebel et al.; Applicant—Vanderbilt University) (10 pages).
International Preliminary Report on Patentability dated Sep. 26, 2017 by the International Bureau for PCT/US2016/24076, filed on Mar. 24, 2016 and published as WO 2016/154471 on Sep. 29, 2016 (Inventors—Zwiebel et al.; Applicant—Vanderbilt University) (8 pages).
Restriction Requirement dated Jan. 8, 2019 by the U.S. Patent and Trademark Office for U.S. Appl. No. 15/561,427, filed Sep. 25, 2017 and published as US 2018/0092359 on Apr. 5, 2018 (Inventor—Zwiebel et al.; Applicant—Vanderbilt University) (9 pages).
Response to Restriction Requirement dated Mar. 8, 2019 with the U.S. Patent and Trademark Office for U.S. Appl. No. 15/561,427, filed Sep. 25, 2017 and published as US 2018/0092359 on Apr. 5, 2018 (Inventor—Zwiebel et al.; Applicant-—Vanderbilt University) (11 pages).
Non Final Rejection was dated Jun. 14, 2019 by the USPTO for U.S. Appl. No. 15/561,427, filed Sep. 25, 2017 and published as US 2018/0092359 A1 on Apr. 5, 2018 (Inventor—Laurence J. Zwiebel) (10 Pages).
Response to Non-Final Office Action dated Sep. 16, 2019 with the U.S. Patent and Trademark Office for U.S. Appl. No. 15/561,427, filed Sep. 25, 2017 and published as US 2018/0092359 on Apr. 5, 2018 (Inventor—Zwiebel et al.; Applicant—Vanderbilt University) (12 pages).
Final Rejection was dated Dec. 31, 2019 by the USPTO for U.S. Appl. No. 15/561,427, filed Sep. 25, 2017 and published as US 2018/0092359 A1 on Apr. 5, 2018 (InventorLaurence J. Zwiebel) (9 Pages).
Response to Final Office Action dated Mar. 24, 2020 with the U.S. Patent and Trademark Office for U.S. Appl. No. 15/561,427, filed Sep. 25, 2017 and published as US 2018/0092359 on Apr. 5, 2018 (Inventor—Zwiebel et al.; Applicant—Vanderbilt University) (9 pages).
Advisory Action was dated Apr. 22, 2020 by the USPTO for U.S. Appl. No. 15/561,427, filed Sep. 25, 2017 and published as US 2018/0092359 A1 on Apr. 5, 2018 (Inventor—Laurence J. Zwiebel) (3 Pages).
Response to Advisory Action dated Apr. 29, 2020 with the U.S. Patent and Trademark Office for U.S. Appl. No. 15/561,427, filed Sep. 25, 2017 and published as US 2018/0092359 on Apr. 5, 2018 (Inventor—Zwiebel et al.; Applicant—Vanderbilt University) (10 pages).
Notice of Allowance was dated Jun. 1, 2020 by the USPTO for U.S. Appl. No. 15/561,427, filed Sep. 25, 2017 and published as US 2018/0092359 A1 on Apr. 5, 2018 (Inventor—Laurence J. Zwiebel) (10 Pages).
Notice of Allowance was dated Jul. 7, 2020 by the USPTO for U.S. Appl. No. 15/561,427, filed Sep. 25, 2017 and published as US 2018/0092359 A1 on Apr. 5, 2018 (Inventor—Laurence J. Zwiebel) (7 Pages).
Issue Notification was dated Sep. 16, 2020 by the USPTO for U.S. Appl. No. 15/561,427, filed Sep. 25, 2017 and published as US 2018/0092359 A1 on Apr. 5, 2018 (Inventor—Laurence J. Zwiebel) (1 Pages).
Examination Report No. 2 dated Nov. 5, 2020, by the Intellectual Property Office of Australia for Patent Application No. 2019203549 (Inventor—Zwiewbel et al.; Applicant—Vanderbilt University (4 pages).
Response to Examination Report No. 1 Filed Oct. 29, 2020, by the Intellectual Property Office of Australia for Patent Application No. 2019203549 (Inventor—Zwiewbel et al. Applicant-Vanderbilt University) (38Ref pages).
EP Communication pursuant to Article 94(3) EPC was dated Aug. 27, 2020 by the European Patent Office for EP Application No. 16769719.2, filed on Mar. 24, 2016 and published as 3273779 on Jan. 31, 2018 (Applicant—Vanderbuilt University) (5 Pages).

\* cited by examiner

VUAA1

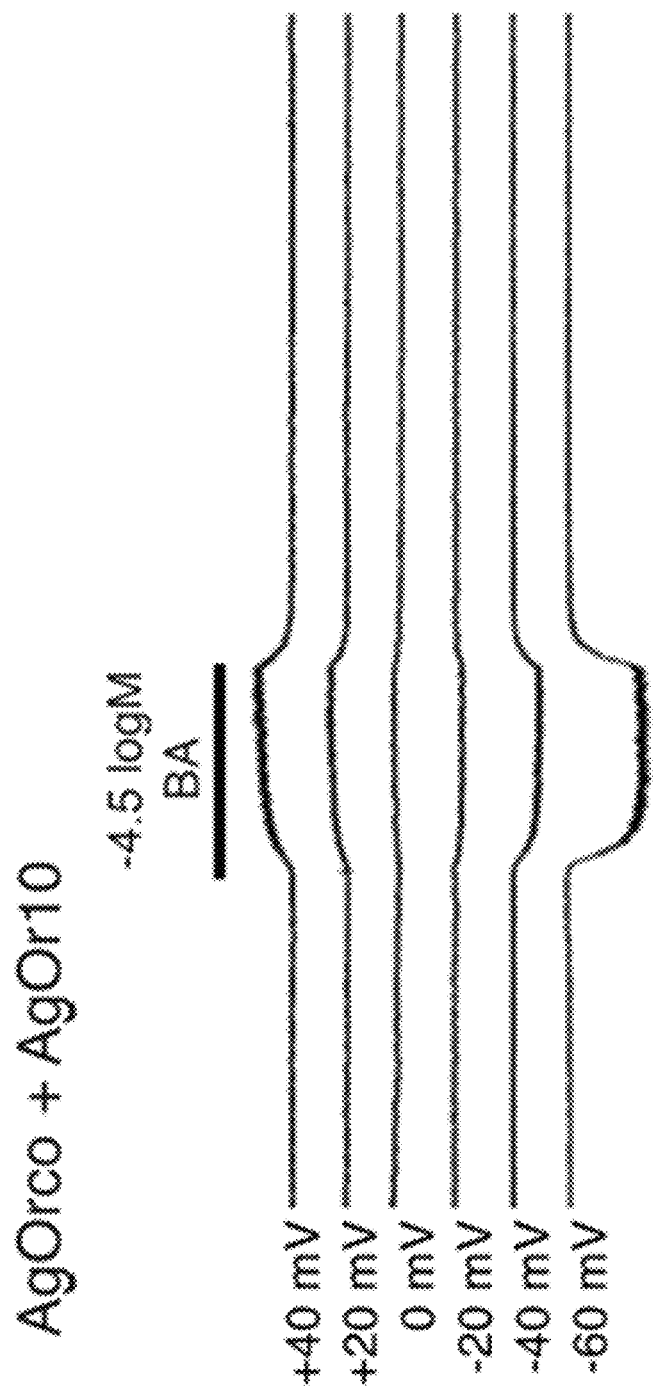

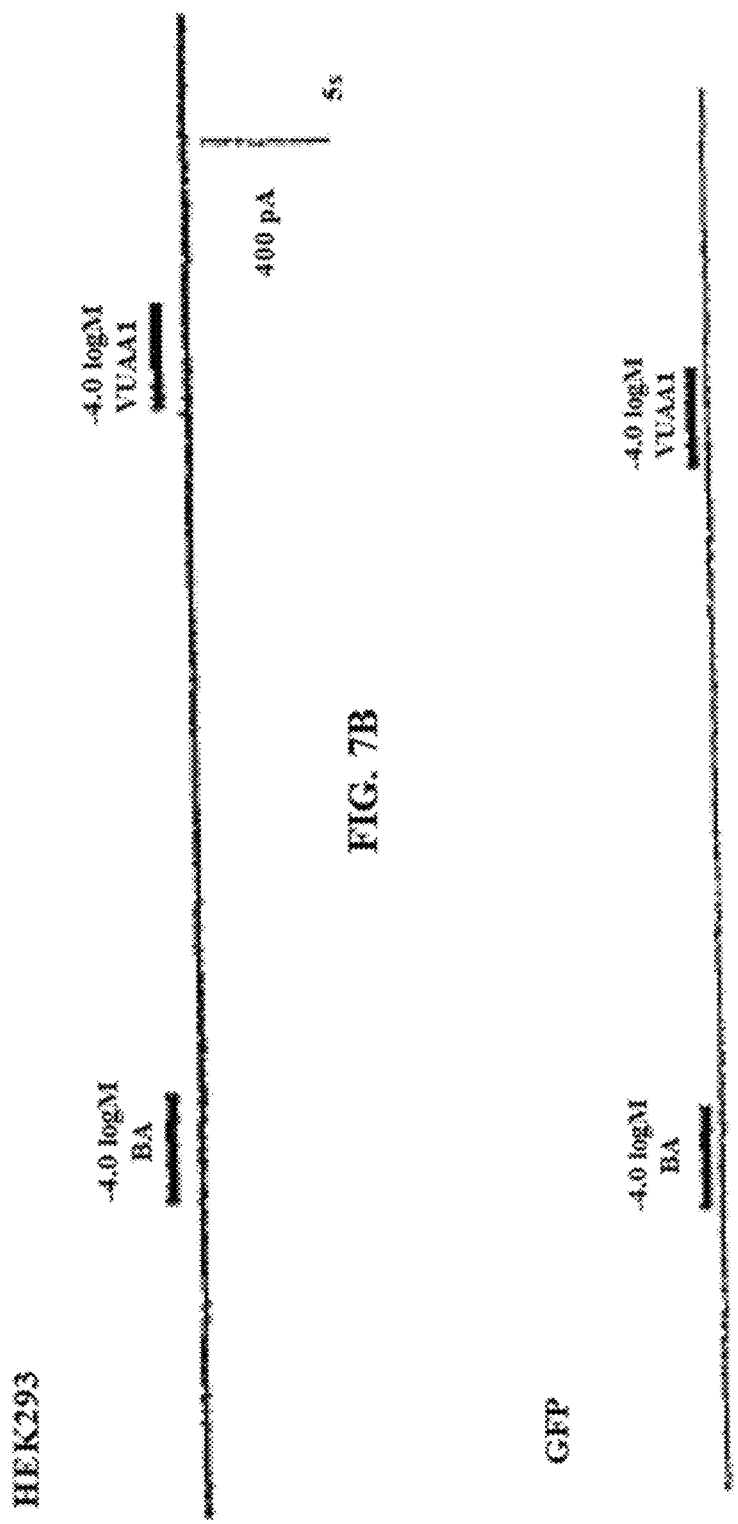

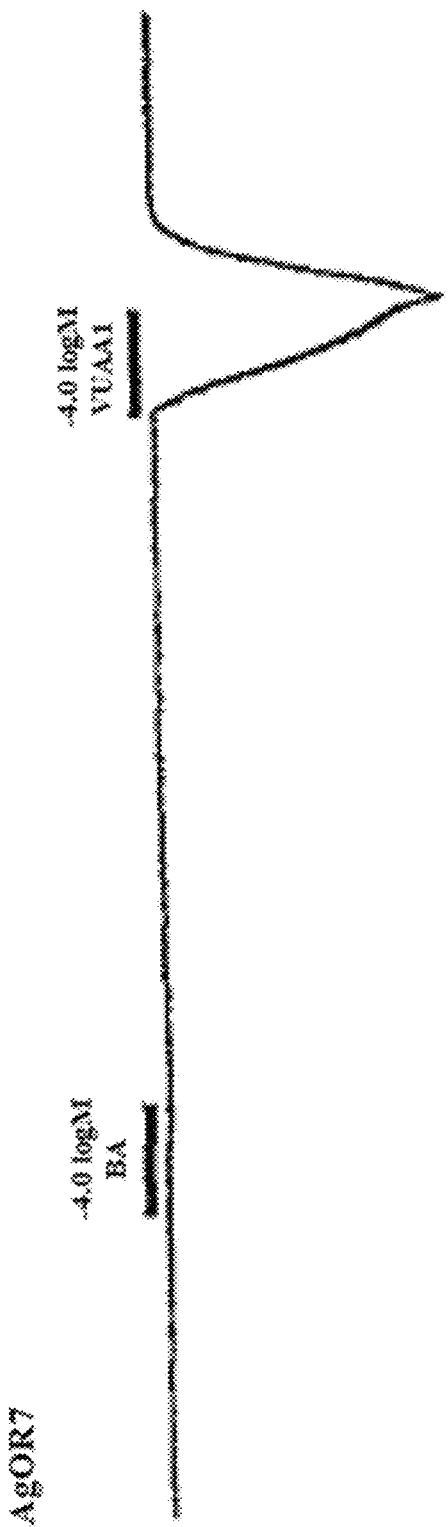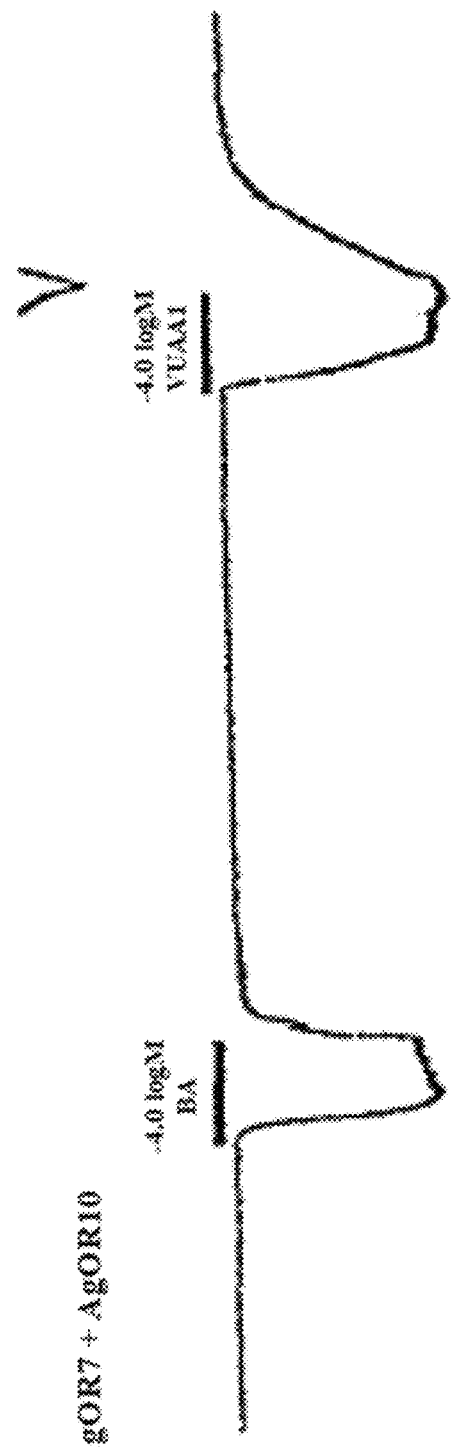

EC$_{50}$ 12.9 μM
102% of VUAA1

EC$_{50}$ 10 μM
136% of VUAA1

$EC_{50}$  AgORco  12.9 µM
AgOr48  9.9 µM
AgOr65  9.6 µM

COMPOSITIONS FOR INHIBITION OF INSECT SENSING

CROSS-REFERENCE TO RELATED APPLICATIONS

This Application is a continuation of U.S. application Ser. No. 16/186,106, filed on Nov. 9, 2018, which is a continuation of U.S. application Ser. No. 15/443,340, filed on Feb. 27, 2017, which is a continuation of U.S. application Ser. No. 14/115,553, filed on May 2, 2014 (now U.S. Pat. No. 9,578,881), which is a U.S. National Phase of International Application No. PCT/US2012/034847, filed on Apr. 25, 2012, which claims the benefit of U.S. Provisional Application No. 61/483,440, filed on May 6, 2011, U.S. Provisional Application No. 61/483,857, filed on May 9, 2011, U.S. Provisional Application No. 61/540,929, filed on Sep. 29, 2011, U.S. Provisional Application No. 61/586,492, filed on Jan. 13, 2012, and U.S. Provisional Application No. 61/625,602, filed on Apr. 17, 2012, the contents of which are incorporated herein by reference in their entireties.

BACKGROUND

Olfaction plays a critical role in insect behaviors among agricultural pests and disease vectors. Hildebrand, et al., 1997, Annu. Rev. Neurosci, 20:595-631. Insect behavior is largely directed by the sensation of environmental olfactory cues (Gilliot C (2005) Entomology. 3rd Edition). The ability of an insect to respond to chemical stimuli is necessary for the insect to reproduce, mate, and feed. For example, insects respond to certain chemical stimuli by moving up a chemical gradient to identify and target a host.

This behavior contributes to the spread of diseases in humans, such as malaria, encephalitis, and dengue fever; as well as, animal and livestock diseases and can result in severe crop damage. More important to human health, the destructive behaviors of disease vector mosquitoes and related dipterans are driven by the sensory modality of olfaction, making it an important area of study (Carey A F, Carlson J R (2011) Proc Natl Acad Sci USA 108: 12987-12995). Mosquitoes, in particular, are believed to use olfaction to identify and target sources of bloodmeal for reproductive purposes.

The primary tool against insect borne diseases and crop damage due to insects is the use of insecticides that kill or repel the insect. However, each of the various forms of insecticide treatment—residual house spraying, crop dusting, insecticide treated clothes, bedding and netting, and chemical larviciding—have drawbacks, including environmental and host toxicity, limited duration and need for insect contact. Biological larviciding can avoid toxicity issues, but takes time and is quite expensive. Chemoprophylaxis is also expensive and may have unacceptable side effects. Finally, segregating populations is expensive and in many cases (third world countries) impractical.

Thus, while there are many different ways to attack insect pests, and each have contributed substantially to limiting the spread of disease and/or crop damage, they also each have limitations that leave room for substantial improvement. Despite advances in the field, there is still a scarcity of compounds that inhibit insect sensing. This need and other needs are satisfied by the present invention.

SUMMARY

In accordance with the purpose(s) of the invention, as embodied and broadly described herein, the invention, in one aspect, relates to entomology and infectious disease. More particular, the invention relates to methods and compositions for disrupting olfactory processes that underly many critical behaviors (e.g., host-targeting) in insects (e.g., mosquitoes).

Disclosed are methods for disrupting insect odorant sensing, the method comprising providing to an insect environment a compound that binds to and/or modulates insect Orco ion channels.

Also disclosed are methods for mediating Orco response, the method comprising providing an effective amount of a disclosed compound, or salt or tautomer thereof, to a Orco receptor, an Orco/ORX complex, or an Orco/Orco complex, wherein the compound binds and/or modulates the receptor or complex.

Also disclosed are compositions comprising a compound that binds to and/or modulates insect Orco ion channels, combined with a suitable carrier.

Also disclosed are articles comprising a compound that binds to and/or modulates insect Orco ion channels.

Also disclosed are compounds having a structure represented by a formula:

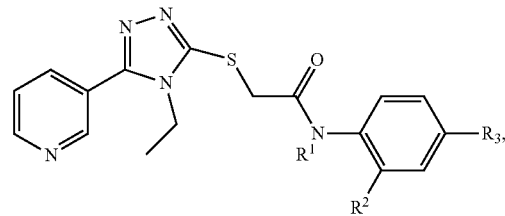

wherein: $R^1$ is hydrogen or is taken together with $R^2$ to be alkanediyl$_{(C1-4)}$, alkenediyl$_{(C1-4)}$, or a substituted version of either of these groups; $R^2$ is hydrogen or is taken together with $R^1$ as defined above; and $R^3$ is hydrogen, hydroxy, nitro, halo, alkyl$_{(C\leq 8)}$, substituted alkyl$_{(C\leq 8)}$, alkenyl$_{(C\leq 8)}$, or substituted alkenyl$_{(C\leq 8)}$; or a salt or tautomer of the formula.

Also disclosed are compounds of the formula:

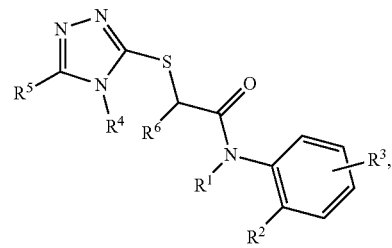

wherein: $R_1$ is hydrogen or is taken together with $R_2$ to be alkanediyl$_{(C1-4)}$, alkenediyl$_{(C1-4)}$, or a substituted version of either of these groups; $R_2$ is hydrogen, alkyl$_{(C\leq 5)}$, substituted alkyl$_{(C\leq 5)}$, or is taken together with $R_1$ as defined above; $R_3$ is hydrogen, hydroxy, nitro, halo, alkyl$_{(C\leq 5)}$, substituted alkyl$_{(C\leq 5)}$, alkenyl$_{(C\leq 5)}$, or substituted alkenyl$_{(C\leq 5)}$; $R_4$ is alkyl$_{(C\leq 5)}$, alkenyl$_{(C\leq 5)}$, aryl$_{(C\leq 10)}$, aralkyl$_{(C\leq 10)}$, heteroaryl$_{(C\leq 8)}$, heteroaralkyl$_{(C\leq 8)}$, or substituted versions of any of these groups; $R_5$ is heteroaryl$_{(C\leq 6)}$ or substituted heteroaryl$_{(C\leq 6)}$; and $R_6$ is hydrogen, alkyl$_{(C\leq 5)}$, substituted alkyl$_{(C\leq 5)}$, alkenyl$_{(C\leq 5)}$, or substituted alkenyl$_{(C\leq 5)}$, or a salt or tautomer of the formula; provided that if $R_1$ and $R_2$ are H and $R_5$ is 3-pyridinyl, then $R_3$ cannot be ethyl.

Also disclosed are compounds of the formula:

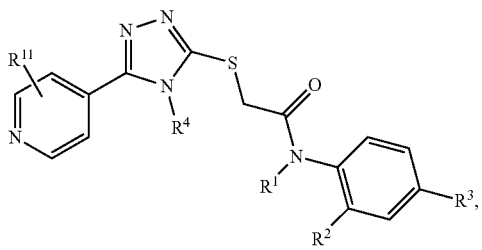

wherein: $R_1$ is hydrogen or is taken together with $R_2$ to be alkanediyl$_{(C1-4)}$, alkenediyl$_{(C1-4)}$, or a substituted version of either of these groups; $R_2$ is hydrogen, alkyl$_{(C\leq 5)}$, substituted alkyl$_{(C\leq 5)}$, or is taken together with $R_1$ as defined above; $R_3$ is hydrogen, hydroxy, nitro, halo, alkyl$_{(C\leq 5)}$, substituted alkyl$_{(C\leq 5)}$, alkenyl$_{(C\leq 5)}$, or substituted alkenyl$_{(C\leq 5)}$; $R_4$ is alkyl$_{(C\leq 5)}$, alkenyl$_{(C\leq 5)}$, aryl$_{(C\leq 10)}$, aralkyl$_{(C\leq 10)}$, heteroaryl$_{(C\leq 8)}$, heteroaralkyl$_{(C\leq 8)}$, or substituted versions of any of these groups; and $R^{11}$ is —H, —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$, or a salt or tautomer of the formula, wherein the compound is not:

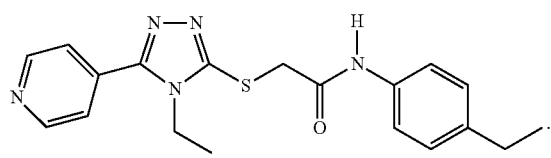 [SMILES: CCc1ccc(NC(=O)CSc2nnc(-c3ccncc3)n2CC)cc1]

Also disclosed are compounds having a structure represented by a formula:

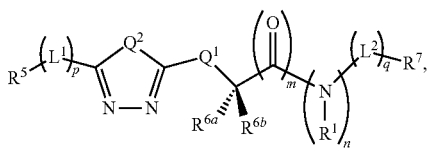

wherein m, n, p, and q are independently 0 or 1; wherein L and L$^2$ are independently divalent organic groups having from 1 to 8 non-hydrogen members; wherein Q$^1$ is —O—, —S—, —S(O)—, or —S(O)$_2$—; wherein Q$^2$ is —O—, —S—, or —NR$^4$; wherein R$^7$ is optionally substituted and selected from monocyclic aryl, bicyclic aryl, monocyclic heteroaryl, bicyclic heteroaryl, and tricyclic heteroaryl; wherein R$^1$ is hydrogen, optionally substituted C1-C4 alkyl, optionally substituted phenyl, optionally substituted benzyl, or a structure represented by a formula selected from:

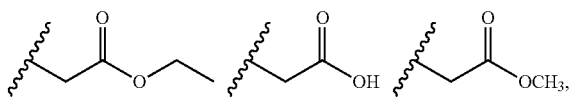

or R$^1$ is taken together with a substituent of R$^7$ to form a five-, six-, or seven-membered heterocylcoalkyl ring; wherein R$^4$ is optionally substituted and selected from (C1-C5) alkyl, (C1-C5) alkenyl, (C6-C10) aryl, (≤C10) aralkyl, (≤C8) heteroaryl, and (≤C8) heteroaralkyl; wherein R$^5$ is optionally substituted aryl or optionally substituted (≤C6) heteroaryl; and wherein R$^{6a}$ and R$^{6b}$ are independently selected from hydrogen, optionally substituted (C1-C5) alkyl, or optionally substituted (C1-C5) alkenyl, or R$^{6a}$ and R$^{6b}$, along with the intermediate carbon, together comprise a C3-C6 cycloalkyl ring or a C2-C5 heterocylcoalkyl ring; or a salt or tautomer thereof, wherein the compound is not:

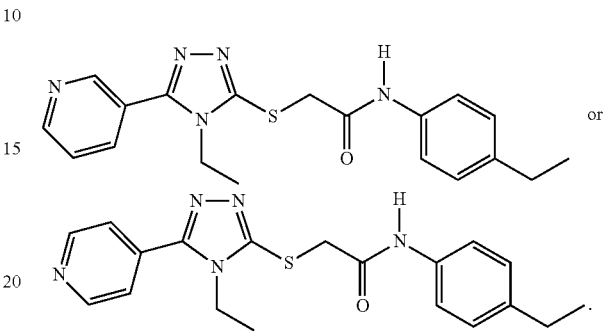

Also disclosed are methods for preparing a compound, the method comprising the steps of: providing a compound having a structure represented by a formula:

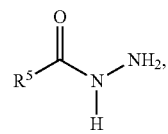

wherein R$_5$ is optionally substituted aryl or optionally substituted (≤C6) heteroaryl; and reacting with R$^4$—N=C=S or R$^4$—N=C=O, thereby yielding a product having the formula:

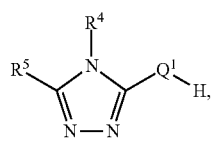

wherein Q$^1$ is —O— or —S—; wherein R$^4$ is optionally substituted and selected from (C1-C5) alkyl, (C1-C5) alkenyl, (C6-C10) aryl, (≤C10) aralkyl, (≤C8) heteroaryl, and (≤C8) heteroaralkyl.

Also disclosed are methods for preparing a compound, the method comprising the steps of: providing a compound having a structure represented by a formula:

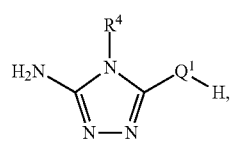

wherein Q$^1$ is —O— or —S—, and wherein R$^4$ is optionally substituted and selected from (C1-C5) alkyl, (C1-C5) alkenyl, (C6-C10) aryl, (≤C10) aralkyl, (≤C8) heteroaryl, and (≤C8) heteroaralkyl; reacting with a compound having a structure represented by a formula:

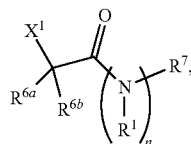

wherein $X^1$ is a leaving group; wherein n is 0 or 1; wherein $R^7$ is optionally substituted (C6-C10) aryl or optionally substituted (≤C6) heteroaryl; wherein $R^1$ is hydrogen or is taken together with a substituent of $R^7$ to be optionally substituted (C1-C4) alkanediyl or optionally substituted (C1-C4) alkenediyl; and wherein $R^{6a}$ and $R^{6b}$ are independently selected from hydrogen, optionally substituted (C1-C5) alkyl, or optionally substituted (C1-C5) alkenyl, or $R^{6a}$ and $R^{6b}$, together with the intermediate carbon, together comprise a C3-C6 cycloalkyl ring or a C2-C5 heterocylcoalkyl ring, thereby yielding a product having the formula:

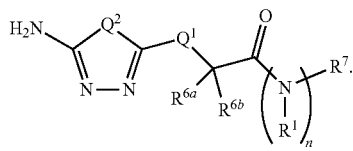

Also disclosed are methods for preparing a compound, the method comprising the steps of: providing a compound having a structure represented by a formula:

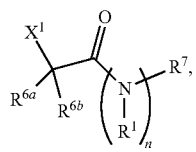

wherein $X^1$ is a leaving group; wherein n is 0 or 1; wherein $R^7$ is optionally substituted (C6-C10) aryl or optionally substituted (≤C6) heteroaryl; wherein $R^1$ is hydrogen or is taken together with a substituent of $R^7$ to be optionally substituted (C1-C4) alkanediyl or optionally substituted (C1-C4) alkenediyl; and wherein $R^{6a}$ and $R^{6b}$ are independently selected from hydrogen, optionally substituted (C1-C5) alkyl, or optionally substituted (C1-C5) alkenyl, or $R^{6a}$ and $R^{6b}$, together with the intermediate carbon, together comprise a C3-C6 cycloalkyl ring or a C2-C5 heterocylcoalkyl ring, reacting with a compound having a structure represented by a formula:

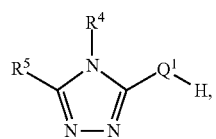

wherein $Q^1$ is —O— or —S—; wherein $R^4$ is optionally substituted and selected from (C1-C5) alkyl, (C1-C5) alkenyl, (C6-C10) aryl, (≤C10) aralkyl, (≤C8) heteroaryl, and (≤C8) heteroaralkyl; and wherein $R^5$ is optionally substituted aryl or optionally substituted (≤C6) heteroaryl; thereby yielding a product having the formula:

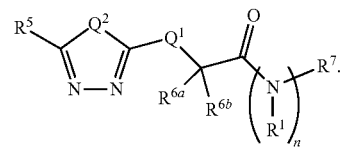

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

(FIG. 3A) Structure of VUAA1. (FIG. 3B) Concentration-response curves (CRCs) generated from Fluro-4 acetoxymethyl ester-based Ca2+ imaging with Orco and Orco+AgOR10 cell lines in response to VUAA1. (FIGS. 3C-D), Whole-cell patch clamp recordings of concentration dependent responses to VUAA1 in cells stably expressing Orco alone (FIG. 3C) and Orco+AgOR10 (FIG. 3D). (FIG. 3E) Benzaldehyde (BA), an AgOR10 agonist, elicits concentration-dependent responses in Orco+AgOR10 cells. (FIG. 3F) Whole-cell current responses to VUAA1 in HEK293 cells expressing DmOrco, HvOrco, and HsOrco. Holding potentials of −60 mV were used in (FIGS. 3C-F).

FIGS. 4A-H. Channel-like currents result from application of VUAA1 to cells expressing Orco alone or in complex. (FIGS. 4A-C), Representative traces of voltage-dependent currents in Orco (FIG. 4A) and Orco+AgOR10 (FIGS. 4B-C) cells. Holding potentials ranged from −60 mV to +40 mV in 20 mV increments. (FIG. 4D), Current-voltage relationships of (FIG. 4A) n=3, (FIG. 4B) n=7, and (FIG. 4C) n=4 from normalized peak currents. Representative traces of Ruthenium Red-blocked inward currents in (FIGS. 4E-F) Orco+AgOR10 and (FIG. 4G) Orco cells. Holding potential was −60 mV for FIGS. 4E, 4F, 4G and 4H. (FIG. 4H) Analysis of Ruthenium Red blockage of VUAA1 and BA-induced currents.

(FIG. 5A) Single-channel recording from an outside-out excised patch pulled from an HEK293 cell-expressing Orco. (FIGS. 5B-D) Expansions of trace (FIG. 5A) before (FIG. 5B) during (FIG. 5C), and after (FIG. 5D) a 5 s application of −4.0 log M VUAA1. All-point current histograms of trace expansions are inset in FIGS. 5B-D. Excised membrane patch was held at −60 mV.

(FIG. 6A) Representative traces of SSR recordings from capitate peg sensilla upon electrode puncture. VUAA1 or vehicle alone (DMSO) was delivered through the glass recording electrode. CpA is discernible from the smaller CpB/C action potentials. Preparations were kept under a steady stream of humidified, synthetic air (21% O2/79% N2) to limit the basal activity of CpA. (FIG. 6B) Expansions of traces as in FIG. 3A. (FIG. 6C) Activity of CpA neuron in response to VUAA1. Spike frequency was calculated every second for the first 10 s after sensillum puncture and every 10 s thereafter. After 60 s, the preparation was pulsed for 2 s with atmospheric air to confirm a functional CpA neuron. Sensilla that did not respond to CO2 or 1-octen-3-ol were excluded from analysis. (FIG. 6D) Activity of CpB/CpC neurons in response to VUAA1 as in FIG. 6C.

FIGS. 7A-F. VUAA1 and BA responses are OR specific. (FIG. 7A), Histogram of normalized currents from concentration-dependent responses in FIGS. 3C-E (n=5). (FIG. 7B) Un-transfected HEK293 cells did not respond to either VUAA1 or BA (n=5). (FIG. 7C) GFP was co-transfected with DmORco or HvOR2 to identify cells expressing the OR. GFP alone cells had no currents from VUAA1 or BA (n=4). (FIGS. 7D-E) For comparison, Orco and Orco+AgOR10 cells both depolarized during VUAA1 application, while only Orco+AgOR10 cells responded to BA. Holding potentials for all recordings were −60 mV. (FIG. 7F) VUAA1 did not elicit currents in cells stably expressing another cation channel, rat transient receptor potential vanilloid 1 (rTRPV1), but did respond to the agonist capsaicin.

(FIG. 8A) Representative trace of whole-cell recordings from cells expressing Orco+AgOR10 with application of 8-Br-cAMP, 8-Br-cGMP, and BA (n=4). (FIG. 8B) Representative trace from Orco cells with application of 8-Br-cAMP, 8-Br-cGMP, and VUAA1 (n=4). Holding potentials for all recordings were −60 mV. (FIG. 8C) Histogram of normalized currents from cyclic nucleotide and control responses (n=5).

(FIG. 45A) EC50 values (expressed as the absolute value of Log molarity) of each effective VUAA compound tested against Orco proteins derived from the Dipteran mosquito *Anopheles gambiae* (Orco), the Lepidopteran moth *Heliothis virescens* (HvOrco), and the Hymenonpteran ant Harpegnathos saltator (HsOrco) are stable across evolutionary time. (FIG. 45B) VUAA compounds are effective regardless of the tuning ORX involved in the complex.

Figure 1:
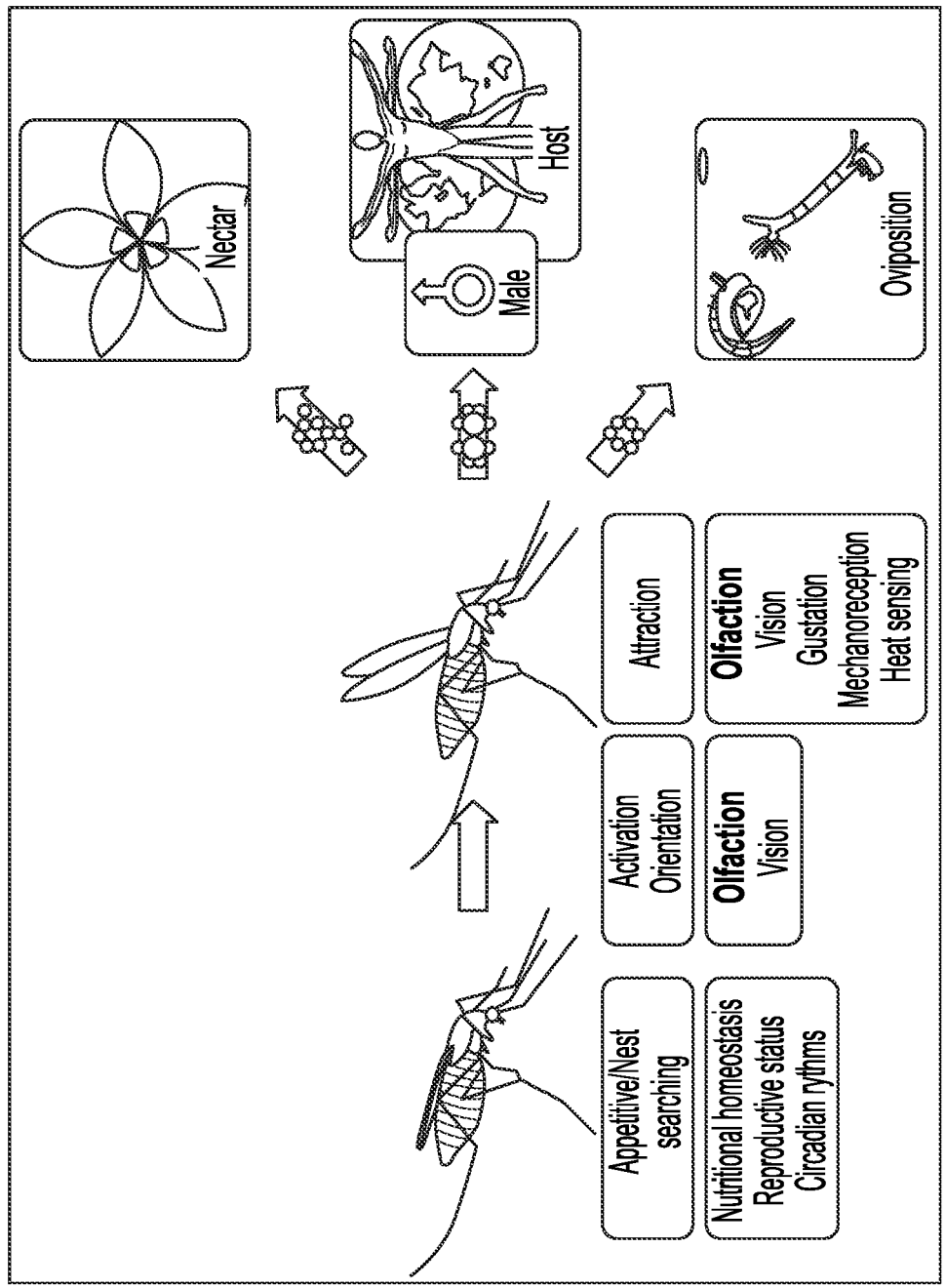
FIG. 1. Olfactory cues make up the principal sensory modalities in mediating several key behaviors in adult mosquitoes. These include nectar feeding, selection of oviposition sites, mate selection and especially host (blood-meal) preference where chemical and temperature inputs synergize most.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. DEFINITIONS

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which a part by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or can not occur, and that the description includes instances where said event or circumstance occurs and instances where it does not.

As used herein, the term "allosteric site" refers to a ligand binding site that is topographically distinct from the orthosteric binding site.

As used herein, the term "modulator" refers to a molecular entity (e.g., but not limited to, a ligand and a disclosed compound) that modulates the activity of the target receptor protein.

As used herein, the term "ligand" refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous ligand" are used interchangeably, and refer to a naturally occurring ligand, found in nature, which binds to a receptor.

As used herein, the term "orthosteric site" refers to the primary binding site on a receptor that is recognized by the endogenous ligand or agonist for that receptor.

The term "contacting" as used herein refers to bringing a disclosed compound and a cell, a target receptor, or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, "$EC_{50}$," is intended to refer to the concentration of a substance (e.g., a compound or a drug) that is required for 50% activation or enhancement of a biological process, or component of a process. For example, $EC_{50}$ can refer to the concentration of agonist that provokes a response halfway between the baseline and maximum response in an appropriate assay of the target activity.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay.

In the context of chemical formulas, the symbol "—" means a single bond, "=" means a double bond, and "≡" means triple bond. The symbol "----" represents an optional bond, which if present is either single or double. The symbol "$\overline{\phantom{----}}$" represents a single bond or a double bond. Thus, for example, the structure

includes the structures

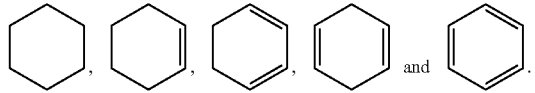

As will be understood by a person of skill in the art, no one such ring atom forms part of more than one double bond. The symbol "∼∼∼" when drawn perpendicularly across a bond, indicates a point of attachment of the group. It is noted that the point of attachment is typically only identified in this manner for larger groups in order to assist the reader in rapidly and unambiguously identifying a point of attachment. The symbol "◀" means a single bond where the group attached to the thick end of the wedge is "out of the page." The symbol "⦀⦀⦀" means a single bond where the group attached to the thick end of the wedge is "into the page". The symbol "∼∼∼" means a single bond where the conformation (e.g., either R or S) or the geometry is undefined (e.g., either E or Z).

For the groups and classes below, the following parenthetical subscripts further define the group/class as follows: "(Cn)" defines the exact number (n) of carbon atoms in the group/class. "(C≤n)" defines the maximum number (n) of carbon atoms that can be in the group/class, with the minimum number as small as possible for the group in question, e.g., it is understood that the minimum number of carbon atoms in the group "alkenyl$_{(C≤8)}$" or the class "alkene$_{(C≤8)}$" is two. For example, "alkoxy$_{(C≤10)}$" designates those alkoxy groups having from 1 to 10 carbon atoms (e.g., 1, 2, 3, 4, 5, 6, 7, 8, 9, or 10), or any range derivable therein (e.g., 3 to 10 carbon atoms). (Cn-n') defines both the minimum (n) and maximum number (n') of carbon atoms in the group. Similarly, "alkyl$_{(C2-10)}$" designates those alkyl groups having from 2 to 10 carbon atoms (e.g., 2, 3, 4, 5, 6, 7, 8, 9, or 10, or any range derivable therein (e.g., 3 to 10 carbon atoms)).

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —OCH$_2$CH$_2$O— units in the polyester, regardless of whether ethylene glycol was used to prepare the polyester. Similarly, a sebacic acid residue in a polyester refers to one or more —CO(CH$_2$)$_8$CO— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "A$^1$," "A$^2$," "A$^3$," and "A$^4$" are used herein as generic symbols to represent various specific substituents. These symbols can be any substituent, not limited to those disclosed herein, and when they are defined to be certain substituents in one instance, they can, in another instance, be defined as some other substituents.

The term "saturated" as used herein means the compound or group so modified has no carbon-carbon double and no carbon-carbon triple bonds, except as noted below. The term does not preclude carbon-heteroatom multiple bonds, for example a carbon oxygen double bond or a carbon nitrogen double bond. Moreover, it does not preclude a carbon-carbon double bond that may occur as part of keto-enol tautomerism or imine/enamine tautomerism.

When used in the context of a chemical group, "hydrogen" means —H; "hydroxy" and "hydroxyl" can be used interchangeably and mean —OH; "oxo" means =O; "halo," "halogen" and "halide", as used herein can be used interchangeably, mean independently —F, —Cl, —Br or —I; "amino" means —NH$_2$; "hydroxyamino" means —NHOH; "nitro" means —NO$_2$; imino means =NH; "cyano" and "nitrile" can be used interchangeably and mean —CN; "isocyanate" means —N=C=O; "azido" means —N$_3$; in a monovalent context "phosphate" means —OP(O)(OH)$_2$ or a deprotonated form thereof, in a divalent context "phosphate" means —OP(O)(OH)O— or a deprotonated form thereof, "mercapto" and "thiol" can be used interchangeably and mean —SH; and "thio" means =S; "sulfonyl" means —S(O)$_2$—; and "sulfinyl" means —S(O)—.

The term "acyl" when used without the "substituted" modifier refers to the group —C(O)R, in which R is a hydrogen, alkyl, aryl, aralkyl or heteroaryl, as those terms are defined above. The groups, —CHO, —C(O)CH$_3$ (acetyl, Ac), —C(O)CH$_2$CH$_3$, —C(O)CH$_2$CH$_2$CH$_3$, —C(O)CH(CH$_3$)$_2$, —C(O)CH(CH$_2$)$_2$, —C(O)C$_6$H$_5$, —C(O)C$_6$H$_4$CH$_3$, —C(O)CH$_2$C6H$_5$, —C(O)(imidazolyl) are non-limiting examples of acyl groups. A "thioacyl" is defined in an analogous manner, except that the oxygen atom of the group —C(O)R has been replaced with a sulfur atom, —C(S)R. When either of these terms are used with the "substituted" modifier one or more hydrogen atom (including the hydrogen atom directly attached the carbonyl or thiocarbonyl group) has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups, —C(O)CH$_2$CF$_3$, —CO$_2$H (carboxyl), —CO$_2$CH$_3$ (methylcarboxyl), —CO$_2$CH$_2$CH$_3$, —C(O)NH$_2$ (carbamoyl), and —CON(CH$_3$)$_2$, are non-limiting examples of substituted acyl groups.

The term "aliphatic" when used without the "substituted" modifier signifies that the compound/group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single bonds (alkanes/alkyl), or unsaturated, with one or more double bonds (alkenes/alkenyl) or with one or more triple bonds (alkynes/alkynyl). When the term "aliphatic" is used without the "substituted" modifier only carbon and hydrogen atoms are present. When the term is used with the "substituted" modifier one or more hydrogen atoms has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "alkyl" when used without the "substituted" modifier refers to a monovalent saturated aliphatic group with a carbon atom as the point of attachment, a linear or branched, cyclo, cyclic or acyclic structure, and no atoms other than carbon and hydrogen. Thus, as used herein cycloalkyl is a subset of alkyl. The groups —CH$_3$ (Me), —CH$_2$CH$_3$ (Et), —CH$_2$CH$_2$CH$_3$ (n-Pr), —CH(CH$_3$)$_2$ (iso-Pr), —CH(CH$_2$)$_2$ (cyclopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (iso-butyl), —C(CH$_3$)$_3$ (tert-butyl), —CH$_2$C(CH$_3$)$_3$ (neo-pentyl), cyclobutyl, cyclopentyl, cyclohexyl, and cyclohexylmethyl are non-limiting examples of alkyl groups. The term "alkanediyl" when used without the "substituted" modifier refers to a divalent saturated aliphatic group, with one or two saturated carbon atom(s) as the point(s) of attachment, a linear or branched, cyclo, cyclic or acyclic structure, no carbon-carbon double or triple bonds, and no atoms other than carbon and hydrogen. The groups, —$CH_2$— (methylene), —$CH_2CH_2$—, —$CH_2C(CH_3)_2$ $CH_2$—, —$CH_2CH_2CH_2$—, and

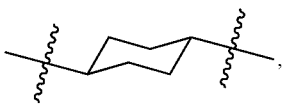 [SMILES: *C1CCC(*)CC1]

are non-limiting examples of alkanediyl groups. The term "alkylidene" when used without the "substituted" modifier refers to the divalent group =CRR' in which R and R' are independently hydrogen, alkyl, or R and R' are taken together to represent an alkanediyl having at least two carbon atoms. Non-limiting examples of alkylidene groups include: =$CH_2$, =$CH(CH_2CH_3)$, and =$C(CH_3)_2$. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$N(CH_3)_2$, —$C(O)NH_2$, —$OC(O)CH_3$, or —$S(O)_2$ $NH_2$. The following groups are non-limiting examples of substituted alkyl groups: —$CH_2OH$, —$CH_2Cl$, —$CF_3$, —$CH_2CN$, —$CH_2C(O)OH$, —$CH_2C(O)OCH_3$, —$CH_2C(O)$ $NH_2$, —$CH_2C(O)CH_3$, —$CH_2OCH_3$, —$CH_2OC(O)CH_3$, —$CH_2NH_2$, —$CH_2N(CH_3)_2$, and —$CH_2CH_2Cl$. An "alkane" refers to the compound H—R, wherein R is alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. The term "halogenated alkyl" or "haloalkyl" is a subset of substituted alkyl, in which one or more hydrogens has been substituted with a halo group (i.e., fluorine, chlorine, bromine, or iodine) and no other atoms aside from carbon, hydrogen and halogen are present. The group, —$CH_2Cl$ is a non-limiting example of a haloalkyl. The term "fluoroalkyl" is a subset of substituted alkyl, in which one or more hydrogens has been substituted with a fluoro group and no other atoms aside from carbon, hydrogen and fluorine are present. The groups, —$CH_2F$, —$CF_3$, and —$CH_2CF_3$ are non-limiting examples of fluoroalkyl groups. An "alkane" refers to the compound H—R, wherein R is alkyl. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is anon-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "alkoxy" when used without the "substituted" modifier refers to the group —OR, in which R is an alkyl, as that term is defined above. Non-limiting examples of alkoxy groups include: —$OCH_3$, —$OCH_2CH_3$, —$OCH_2CH_2CH_3$, —$OCH(CH_3)_2$, —$OCH(CH_2)_2$, —O—cyclopentyl, and —O-cyclohexyl. The terms "alkenyloxy", "alkynyloxy", "aryloxy", "aralkoxy", "heteroaryloxy", and "acyloxy", when used without the "substituted" modifier, refers to groups, defined as —OR, in which R is alkenyl, alkynyl, aryl, aralkyl, heteroaryl, and acyl, respectively. The term "alkoxydiyl" refers to the divalent group —O-alkanediyl-, —O— alkanediyl-O—, or -alkanediyl-O-alkanediyl-. The term "alkylthio" when used without the "substituted" modifier refers to the group —SR, in which R is an alkyl, as that term is defined above. When any of these terms is used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —$C(O)CH_3$, —$N(CH_3)_2$, —$C(O)NH_2$, —$OC(O)CH_3$, or —$S(O)_2NH_2$. The term "alcohol" corresponds to an alkane, as defined above, wherein at least one of the hydrogen atoms has been replaced with a hydroxy group.

The term "alkenyl" when used without the "substituted" modifier refers to an monovalent unsaturated aliphatic group with a carbon atom as the point of attachment, a linear or branched, cyclo, cyclic or acyclic structure, at least one nonaromatic carbon-carbon double bond, no carbon-carbon triple bonds, and no atoms other than carbon and hydrogen. Non-limiting examples of alkenyl groups include: —CH=$CH_2$ (vinyl), —CH=$CHCH_3$, —CH=$CHCH_2CH_3$, —$CH_2CH$=$CH_2$ (allyl), —$CH_2CH$=$CHCH_3$, and —CH=CH—$C_6H_5$. The term "alkenediyl" when used without the "substituted" modifier refers to a divalent unsaturated aliphatic group, with two carbon atoms as points of attachment, a linear or branched, cyclo, cyclic or acyclic structure, at least one nonaromatic carbon-carbon double bond, no carbon-carbon triple bonds, and no atoms other than carbon and hydrogen. The groups, —CH=CH—, —CH=C(CH₃)CH₂—, —CH=CHCH₂—, and

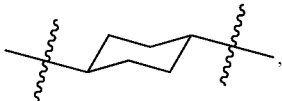

are non-limiting examples of alkenediyl groups. When these terms are used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. The groups, —CH=CHF, —CH=CHCl and —CH=CHBr, are non-limiting examples of substituted alkenyl groups. An "alkene" refers to the compound H—R, wherein R is alkenyl.

The term "cycloalkenyl" as used herein is a non-aromatic carbon-based ring composed of at least three carbon atoms and containing at least one carbon-carbon double bound, i.e., C=C. Cycloalkenyl is a subset of alkenyl. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "alkynyl" when used without the "substituted" modifier refers to a monovalent unsaturated aliphatic group with a carbon atom as the point of attachment, a linear or branched, cyclo, cyclic or acyclic structure, at least one carbon-carbon triple bond, and no atoms other than carbon and hydrogen. As used herein, the term alkynyl does not preclude the presence of one or more non-aromatic carbon-carbon double bonds. The groups, —C≡CH, —C≡CCH₃, and —CH₂C≡CCH₃, are non-limiting examples of alkynyl groups. When alkynyl is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂. An "alkyne" refers to the compound H—R, wherein R is alkynyl.

The term "cycloalkynyl" as used herein is a non-aromatic carbon-based ring composed of at least seven carbon atoms and containing at least one carbon-carbon triple bound, and is a subset of those groups specified by the term "alkynyl." Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl group (carbon number limitation permitting) attached to the first aromatic ring or any additional aromatic ring present. Non-limiting examples of aryl groups include phenyl (Ph), methylphenyl, (dimethyl)phenyl, —C₆H₄CH₂CH₃ (ethylphenyl), naphthyl, and the monovalent group derived from biphenyl. The term "arenediyl" when used without the "substituted" modifier refers to a divalent aromatic group, with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl group (carbon number limitation permitting) attached to the first aromatic ring or any additional aromatic ring present. If more than one ring is present, the rings may be fused or unfused. Non-limiting examples of arenediyl groups include:

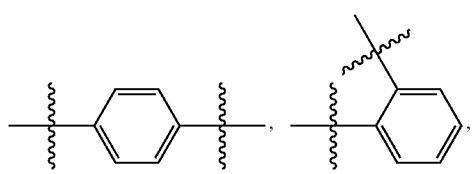

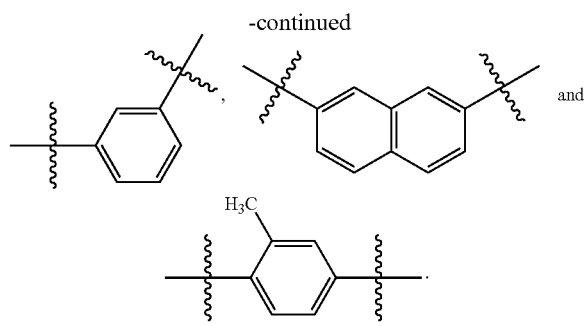

When the term "aryl" is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. An "arene" refers to the compound H—R, wherein R is aryl.

The term "aldehyde" as used herein is represented by the formula —C(O)H. Throughout this specification "C(O)" is a short hand notation for a carbonyl group, i.e., C=O.

The term "alkylamino" when used without the "substituted" modifier refers to the group —NHR, in which R is an alkyl, as that term is defined above. Non-limiting examples of alkylamino groups include: —NHCH$_3$ and —NHCH$_2$CH$_3$. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH$_3$)$_2$, —N(CH$_3$)(CH$_2$CH$_3$), and N-pyrrolidinyl. The terms "alkoxyamino", "alkenylamino", "alkynylamino", "arylamino", "aralkylamino", "heteroarylamino", and "alkylsulfonylamino" when used without the "substituted" modifier, refers to groups, defined as —NHR, in which R is alkoxy, alkenyl, alkynyl, aryl, aralkyl, heteroaryl, and alkylsulfonyl, respectively. A non-limiting example of an arylamino group is —NHC$_6$H$_5$. The term "amido" (acylamino), when used without the "substituted" modifier, refers to the group —NHR, in which R is acyl, as that term is defined above. A non-limiting example of an amido group is —NHC(O)CH$_3$. The term "alkylimino" when used without the "substituted" modifier refers to the divalent group =NR, in which R is an alkyl, as that term is defined above. The term "alkylaminodiyl" refers to the divalent group —NH-alkanediyl-, —NH-alkanediyl-NH—, or -alkanediyl-NH-alkanediyl-. When any of these terms is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. The groups —NHC(O)OCH$_3$ and —NHC(O)NHCH$_3$ are non-limiting examples of substituted amido groups.

The term "aralkyl" when used without the "substituted" modifier refers to the monovalent group -alkanediyl-aryl, in which the terms alkanediyl and aryl are each used in a manner consistent with the definitions provided above. Non-limiting examples of aralkyls are: phenylmethyl (benzyl, Bn) and 2-phenyl-ethyl. When the term is used with the "substituted" modifier one or more hydrogen atom from the alkanediyl and/or the aryl has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. Non-limiting examples of substituted aralkyls are: (3-chlorophenyl)-methyl, and 2-chloro-2-phenyl-eth-1-yl.

The term "carboxylic acid" as used herein is represented by the formula —C(O)OH.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula -(A$^1$O(O)C-A$^2$-C(O)O)$_a$— or -(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula -(A$^1$O-A$^2$O)$_a$—, where A and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyether groups include polyethylene oxide, polypropylene oxide, and polybutylene oxide.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroaryl groups include furanyl, imidazolyl, indolyl, indazolyl (Im), isoxazolyl, methylpyridinyl, oxazolyl, phenylpyridinyl, pyridinyl, pyrrolyl, pyrimidinyl, pyrazinyl, quinolyl, quinazolyl, quinoxalinyl, triazinyl, tetrazolyl, thiazolyl, thienyl, and triazolyl. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. As used herein, the term does not preclude the presence of one or more alkyl, aryl, and/or aralkyl groups (carbon number limitation permitting) attached to the aromatic ring or aromatic ring system. If more than one ring is present, the rings may be fused or unfused. Non-limiting examples of heteroarenediyl groups include:

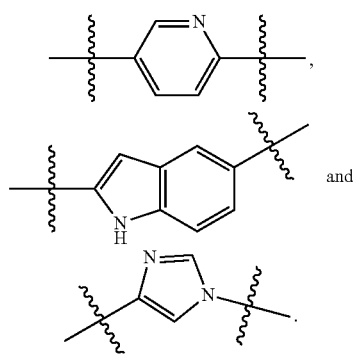

and

When the term "heteroaryl" is used with the "substituted" modifier one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocyclyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxiranyl, thiiranyl, and the like. Alternatively, for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" when used without the "substituted" modifier refers to a monovalent non-aromatic group with a carbon atom or nitrogen atom as the point of attachment, said carbon atom or nitrogen atom forming part of one or more non-aromatic ring structures wherein at least one of the ring atoms is nitrogen, oxygen or sulfur, and wherein the heterocycloalkyl group consists of no atoms other than carbon, hydrogen, nitrogen, oxygen and sulfur. As used herein, the term does not preclude the presence of one or more alkyl groups (carbon number limitation permitting) attached to the ring or ring system. If more than one ring is present, the rings may be fused or unfused. Non-limiting examples of heterocycloalkyl groups include aziridinyl, pyrrolidinyl, piperidinyl, piperazinyl, morpholinyl, thiomorpholinyl, tetrahydrofuranyl, tetrahydrothiofuranyl, tetrahydropyranyl, and pyranyl. When the term "heterocycloalkyl" is used with the "substituted" modifier, one or more hydrogen atom has been independently replaced by —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

The term "ketone" as used herein is represented by the formula A$^1$C(O)A$^2$, where A and A$^2$ can be, independently, an alkyl, cycloalkyl, alkenyl, cycloalkenyl, alkynyl, cycloalkynyl, aryl, or heteroaryl group as described herein.

The term "polyalkylene group" as used herein is a group having two or more CH$_2$ groups linked to one another. The polyalkylene group can be represented by the formula —(CH$_2$)$_a$—, where "a" is an integer of from 2 to 500.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoroalkoxy groups.

The term "silyl" as used herein is represented by the formula -SiA$^1$A$^2$A$^3$, where A$^1$, A$^2$, and A$^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas —S(O)A$^1$, —S(O)$_2$A$^1$, —OS(O)$_2$A$^1$, or —OS(O)$_2$OA$^1$, where A$^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfone" as used herein is represented by the formula A'S(O)$_2$A$^2$, where A$^1$ and A$^2$ can be, independently, an alkyl, cycloalkyl, alkenyl, cycloalkenyl, alkynyl, cycloalkynyl, aryl, or heteroaryl group as described herein. The term "sulfoxide" as used herein is represented by the formula A'S(O)A², where A and A² can be, independently, an alkyl, cycloalkyl, alkenyl, cycloalkenyl, alkynyl, cycloalkynyl, aryl, or heteroaryl group as described herein.

"$R^1$," "$R^2$," "$R^3$," "$R^n$," where n is an integer, as used herein can, independently, possess one or more of the groups listed above. For example, if R is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. It is also contemplated that, in certain aspects, unless expressly indicated to the contrary, individual substituents can be further optionally substituted (i.e., further substituted or unsubstituted).

Suitable monovalent substituents on a substitutable carbon atom of an "optionally substituted" group are independently halogen; $-(CH_2)_{0-4}R^\circ$; $-(CH_2)_{0-4}R^\circ$; $-O(CH_2)_{0-4}R^\circ$, $-O-(CH_2)_{0-4}C(O)OR^\circ$; $-(CH_2)_{0-4}CH(OR^\circ)_2$; $-(CH_2)_{0-4}SR^\circ$; $-(CH_2)_{0-4}Ph$, which may be substituted with $R^\circ$; $-(CH_2)_{0-4}O(CH_2)^\circ$-iPh which may be substituted with $R^\circ$; $-CH=CHPh$, which may be substituted with $R^\circ$; $-(CH_2)_{0-4}(CH_2)_{0-1}$-pyridyl which may be substituted with $R^\circ$; $-NO_2$; $-CN$; $-N_3$; $-(CH_2)_{0-4}N(R^\circ)_2$; $-(CH_2)_{0-4}N(R^\circ)C(O)R^\circ$; $-N(R^\circ)C(S)R^\circ$; $-(CH_2)_{0-4}N(R^\circ)C(O)NR^\circ_2$; $-N(R^\circ)C(S)NR^\circ_2$; $-(CH_2)_{0-4}N(R^\circ)C(O)OR^\circ$; $-N(R^\circ)N(R^\circ)C(O)R^\circ$; $-N(R^\circ)N(R^\circ)C(O)NR^\circ_2$; $-N(R^\circ)N(R^\circ)C(O)OR^\circ$; $-(CH_2)_{0-4}C(O)R^\circ$; $-C(S)R^\circ$; $-(CH_2)_{0-4}C(O)OR^\circ$; $-(CH_2)_{0-4}C(O)SR^\circ$; $-(CH_2)_{0-4}C(O)OSiR^\circ_3$; $-(CH_2)_{0-4}C(O)R^\circ$; $-OC(O)(CH_2)_{0-4}SR-$, $SC(S)SR^\circ$; $-(CH_2)_{0-4}SC(O)R^\circ$; $-(CH_2)_{0-4}C(O)NR^\circ_2$; $-C(S)NR^\circ_2$; $-C(S)SR^\circ$; $-(CH_2)_{0-4}OC(O)NR^\circ_2$; $-C(O)N(OR^\circ)R^\circ$; $-C(O)C(O)R^\circ$; $-C(O)CH_2C(O)R^\circ$; $-C(NOR^\circ)R^\circ$; $-(CH_2)_{0-4}SSR^\circ$; $-(CH_2)_{0-4}S(O)_2R^\circ$; $-(CH_2)_{0-4}S(O)_2OR^\circ$; $-(CH_2)_{0-4}OS(O)_2R^\circ$; $-S(O)_2NR^\circ_2$; $-(CH_2)_{0-4}S(O)R^\circ$; $-N(R^\circ)S(O)_2NR^\circ_2$; $-N(R^\circ)S(O)_2R^\circ$; $-N(OR^\circ)R^\circ$; $-C(NH)NR^\circ_2$; $-P(O)_2R^\circ$; $-P(O)R^\circ_2$; $-OP(O)R^\circ_2$; $-OP(O)(OR^\circ)_2$; $SiR^\circ_3$; $-(C_{1-4}$ straight or branched alkylene)O$-N(R^\circ)_2$; or $-(C_{1-4}$ straight or branched alkylene)C(O)O$-N(R^\circ)_2$, wherein each $R^\circ$ may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of $R^\circ$, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on $R^\circ$ (or the ring formed by taking two independent occurrences of $R^\circ$ together with their intervening atoms), are independently halogen, $-(CH_2)_{0-2}R^\bullet$, -(haloR$^\bullet$), $-(CH_2)_{0-2}OH$, $-(CH_2)_{0-2}OR^\bullet$, $-(CH_2)_{0-2}CH(OR^\bullet)_2$; $-O(haloR^\bullet)$, $-CN$, $-N_3$, $-(CH_2)_{0-2}C(O)R^\bullet$, $-(CH_2)_2C(O)OH$, $-(CH_2)_{0-2}C(O)OR^\bullet$, $-(CH_2)_{0-2}SR^\bullet$, $-(CH_2)_{0-2}SH$, $-(CH_2)_{0-2}NH_2$, $-(CH_2)_{0-2}NHR^\bullet$, $-(CH_2)_{0-2}NR^\bullet_2$, $-NO_2$, $-SiR^\bullet_3$, $-OSiR^\bullet_3$, $-C(O)SR^\bullet$, $-(C1-4$ straight or branched alkylene)C(O)OR$^\bullet$, or $-SSR^\bullet$ wherein each $R^\bullet$ is unsubstituted or where preceded by "halo" is substituted only with one or more halogens, and is independently selected from $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of $R^\circ$ include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, $-O(C(R^*_2))_{2-3}O-$, or $-S(C(R^*_2))_{2-3}S-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: $-O(CR^*_2)_{2-3}O-$, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, $-R^\bullet$, -(haloR$^\bullet$), $-OH$, $-OR^\bullet$, $-O(haloR^\bullet)$, $-CN$, $-C(O)OH$, $-C(O)OR^\bullet$, $-NH_2$, $-NHR^\bullet$, $-NR^\bullet_2$, or $-NO_2$, wherein each $R^\bullet$ is unsubstituted or where preceded by "halo" is substituted only with one or more halogens, and is independently $C_{1-4}$ aliphatic, $-CH_2Ph$, $-O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include $-R^\dagger$, $-NR^\dagger_2$, $-C(O)R^\dagger$, $-C(O)OR^\dagger$, $-C(O)C(O)R^\dagger$, $-C(O)CH_2C(O)R^\dagger$, $-S(O)_2R^\dagger$, $-S(O)_2NR^\dagger_2$, $-C(S)NR^\dagger_2$, $-C(NH)NR^\dagger_2$, or $-N(R^\dagger)S(O)_2R^\dagger$; wherein each $R^\dagger$ is independently hydrogen, $C_{1-6}$ aliphatic which may be substituted as defined below, unsubstituted $-OPh$, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of $R^\dagger$ are independently halogen, $-R^\bullet$, -(haloR$^\bullet$), $-OH$, $-OR^\bullet$, —O(haloR*), —CN, —C(O)OH, —C(O)OR*, —NH₂, —NHR*, —NR*₂, or —NO₂, wherein each R* is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "stable," as used herein, refers to compounds that are not substantially altered when subjected to conditions to allow for their production, detection, and, in certain aspects, their recovery, purification, and use for one or more of the purposes disclosed herein.

The term "leaving group" refers to an atom (or a group of atoms) with electron withdrawing ability that can be displaced as a stable species, taking with it the bonding electrons. Examples of suitable leaving groups include halides and sulfonate esters, including, but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (see, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15 carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15 carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

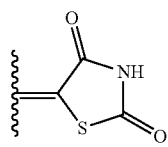 [SMILES: *=C1SC(=O)NC1=O]

regardless of whether thiazolidinedione is used to prepare the compound. In some embodiments the radical (for example an alkyl) can be further modified (i.e., substituted alkyl) by having bonded thereto one or more "substituent radicals." The number of atoms in a given radical is not critical to the present invention unless it is indicated to the contrary elsewhere herein.

"Organic radicals," as the term is defined and used herein, contain one or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5, 6, 7, 8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfate, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as a sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans (E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomers as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines is (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as 3H and $^{14}C$ are incorporated, are useful in drug and/or substrate tissue distribution assays. Tritiated, i.e., 3H, and carbon-14, i.e., $^{14}C$, isotopes are particularly preferred for their ease of preparation and detectability. Further, substitution with heavier isotopes such as deuterium, i.e., 2H, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almarasson, O., et. al., The Royal Society of Chemistry, 1889-1896, 2004. Examples of co-crystals include p-toluenesulfonic acid and benzenesulfonic acid.

It is also appreciated that certain compounds described herein can be present as an equilibrium of tautomers. For example, ketones with an α-hydrogen can exist in an equilibrium of the keto form and the enol form.

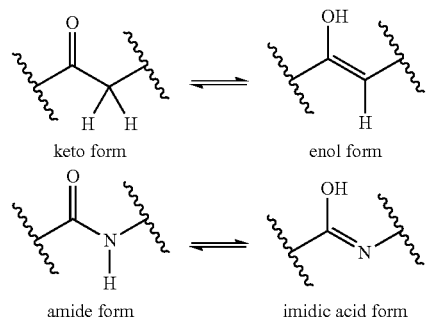

Unless stated to the contrary, the invention includes all such possible tautomers.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

Any undefined valency on an atom of a structure shown in this application implicitly represents a hydrogen atom bonded to the atom. When a group "R" is depicted as a "floating group" on a ring system, for example, in the formula:

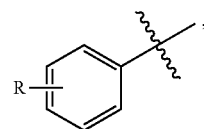

then R may replace any hydrogen atom attached to any of the ring atoms, including a depicted, implied, or expressly defined hydrogen, so long as a stable structure is formed.

When a group "R" is depicted as a "floating group" on a fused ring system, as for example in the formula:

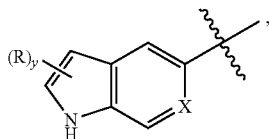

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutations of these compounds can not be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. INSECT ODORANT SENSING

Insects interpret their chemical environment through the use of a family of cell-surface odorant receptors (ORs) to sense volatile chemicals known as odorants. The ability of an insect to respond to this chemical stimuli is necessary for the insect to find plant nectar, mate, feed, and for oviposition.

Most odors are detected via a family of odorant receptors ("ORs"), which form heteromeric complexes consisting of a well-conserved OR co-receptor ("ORco") ion channel and a non-conserved tuning OR that provides coding specificity to each complex. ORco functions as a non-selective cation channel and is expressed in the majority of olfactory receptor neurons (ORNs). As the destructive behaviors of many insects are principally driven by olfaction, ORco represents a novel target for behavior-based control strategies. For odorant reception to take place, a member of the ORco family of ORs must be present to couple to another highly diverse OR (ORX) that is responsible for sensing different odors. Each insect species has many ORs, but only one OR83b family member now renamed ORco. There have been no reported ORco ligands to date.

The OR co-receptor (Orco) is required for all OR-based chemoreception in insects, which is the only lineage to possess this unique and highly conserved ion channel that is present in most ORNs. In fact, it is understood that ORco is so highly conserved between insects that an ORCo of one insect can be used in combination with a tuning OR from another insect and maintain activity. For example, ORco from *Drosophila* can be utilized in combination with AgOR10 or AgOR65 without affecting odorant sensing. Insect ORs are distinct from their mammalian counterparts in that they are not related to any known GPCRs and possess an inverse 7-TM topology. Recently it was shown that Orco is a non-selective cation channel, but it is unclear what roles, if any, second messengers may play. In heterologous expression, Orco is capable of forming functional channels independent of any tuning OR, although the in vivo consequence of this capacity is unknown. Tuning ORs expressed in the absence of Orco have no demonstrable functional capacity in heterologous systems or in vivo, as Orco is required not only for proper signal transduction, but also for trafficking of the OR complex to the ORN membrane.

As part of a High-Throughput Screen to identify compounds that modulate OR activity, the present inventors have discovered the first ORco family activator. This ORco family activator, termed VUAA-1, has theoretical ability to activate all ORX/ORco complexes across all insect taxa. The host-seeking behavior of blood-feeding insects and the plant-feeding behavior of agricultural pests is principally driven through their sense of smell. In the former case, this blood-feeding behavior serves as the foundation for their ability to transit disease and in the latter case, the plant-feeding behavior forms the basis for their ability to act as an agricultural pest. The capacity to disrupt olfactory-mediated behavior through direct chemical interference, as by VUAA1 or its analogs, would be a major advance in the fight against vector-borne diseases and agricultural pests, and modulation of the ORco complex would render the insect incapable of performing its usual behaviors, such as host-seeking and nectar feeding.

1. Insects a. Mosquitoes

Mosquito, from the Spanish or Portuguese meaning "little fly," is a common insect in the family Culicidae. Mosquitoes resemble crane flies (family Tipulidae) and chironomid flies (family Chironomidae), with which they are sometimes confused by the casual observer.

Mosquitoes go through four stages in their life-cycle: egg, larva, pupa, and adult or imago. Adult females lay their eggs in water, which can be a salt-marsh, a lake, a puddle, a natural reservoir on a plant, or an artificial water container such as a plastic bucket. The first three stages are aquatic and last 5-14 days, depending on the species and the ambient temperature; eggs hatch to become larvae, then pupae. The adult mosquito emerges from the pupa as it floats at the water surface. Adults live for 4-8 weeks.

Female mosquitoes have mouthparts that are adapted for piercing the skin of plants and animals. While males typically feed on nectar and plant juices, the female needs to obtain nutrients from a "blood meal" before she can produce eggs.

Mosquito larvae have a well-developed head with mouth brushes used for feeding, a large thorax with no legs and a segmented abdomen. Larvae breathe through spiracles located on the eighth abdominal segment, or through a siphon, and therefore must come to the surface frequently. The larvae spend most of their time feeding on algae, bacteria, and other micro-organisms in the surface microlayer. They dive below the surface only when disturbed. Larvae swim either through propulsion with the mouth brushes, or by jerky movements of the entire body. Larvae develop through four stages, or instars, after which they metamorphose into pupae. At the end of each instar, the larvae molt, shedding their exoskeleton, or skin, to allow for further growth. Length of the adult varies but is rarely greater than 16 mm (0.6 in), and weight up to 2.5 mg (0.04 grain). All mosquitoes have slender bodies with three sections: head, thorax and abdomen.

The pupa is comma-shaped, as in *Anopheles* when viewed from the side. The head and thorax are merged into a cephalothorax with the abdomen circling around underneath. As with the larvae, pupae must come to the surface frequently to breathe, which they do through a pair of respiratory trumpets on the cephalothorax. However, pupae do not feed during this stage. After a few days, the dorsal surface of the cephalothorax splits and the adult mosquito emerges. The pupa is less active than larva.

The duration from egg to adult varies among species and is strongly influenced by ambient temperature. Mosquitoes can develop from egg to adult in as little as five days but usually take 10-14 days in tropical conditions. The variation of the body size in adult mosquitoes depends on the density of the larval population and food supply within the breeding water. Adult flying mosquitoes frequently rest in a tunnel that they build right below the roots of the grass.

Adult mosquitoes usually mate within a few days after emerging from the pupal stage. In most species, the males form large swarms, usually around dusk, and the females fly into the swarms to mate. Males live for about a week, feeding on nectar and other sources of sugar. Females will also feed on sugar sources for energy but usually require a blood meal for the development of eggs. After obtaining a full blood meal, the female will rest for a few days while the blood is digested and eggs are developed. This process depends on the temperature but usually takes 2-3 days in tropical conditions. Once the eggs are fully developed, the female lays them and resumes host seeking. The cycle repeats itself until the female dies. Their lifespan depends on temperature, humidity, and also their ability to successfully obtain a blood meal while avoiding host defenses.

The head is specialized for acquiring sensory information and for feeding. The head contains the eyes and a pair of long, many-segmented antennae. The antennae are important for detecting host odors as well as odors of breeding sites where females lay eggs. In all mosquito species, the antennae of the males in comparison to the females are noticeably bushier and contain auditory receptors to detect the characteristic whine of the female. The compound eyes are distinctly separated from one another. Their larvae only possess a pit-eye ocellus. The compound eyes of adults develop in a separate region of the head. New ommatidia are added in semicircular rows at the rear of the eye; during the first phase of growth, this leads to individual ommatidia being square, but later in development they become hexagonal. The hexagonal pattern will only become visible when the carapace of the stage with square eyes is molted. The head also has an elongated, forward-projecting "stinger-like" proboscis used for feeding, and two sensory palps. The maxillary palps of the males are longer than their proboscis whereas the females' maxillary palps are much shorter. As with many members of the mosquito family, the female is equipped with an elongated proboscis that she uses to collect blood to feed her eggs.

The thorax is specialized for locomotion. Three pairs of legs and a pair of wings are attached to the thorax. The insect wing is an outgrowth of the exoskeleton. The *Anopheles* mosquito can fly for up to four hours continuously at 1 to 2 kilometres per hour (0.62 to 1.2 mph) travelling up to 12 km (7.5 mi) in a night.

The abdomen is specialized for food digestion and egg development. This segmented body part expands considerably when a female takes a blood meal. The blood is digested over time serving as a source of protein for the production of eggs, which gradually fill the abdomen.

In order for the mosquito to obtain a blood meal it must circumvent the vertebrate physiological responses. The mosquito, as with all blood-feeding arthropods, has mechanisms to effectively block the hemostasis system with their saliva, which contains a mixture of secreted proteins. Mosquito saliva negatively affects vascular constriction, blood clotting, platelet aggregation, angiogenesis and immunity and creates inflammation. Universally, hematophagous arthropod saliva contains at least one anticlotting, one antiplatelet, and one vasodilatory substance. Mosquito saliva also contains enzymes that aid in sugar feeding and antimicrobial agents to control bacterial growth in the sugar meal. The composition of mosquito saliva is relatively simple as it usually contains fewer than 20 dominant proteins. Despite the great strides in knowledge of these molecules and their role in bloodfeeding achieved recently, scientists still cannot ascribe functions to more than half of the molecules found in arthropod saliva. One promising application is the development of anti-clotting drugs based on saliva molecules, which might be useful for approaching heart-related disease, because they are more user-friendly blood clotting inhibitors and capillary dilators.

Two important events in the life of female mosquitoes are egg development and blood digestion. After taking a blood meal the midgut of the female synthesizes proteolytic enzymes that hydrolyze the blood proteins into free amino acids. These are used as building blocks for the synthesis of egg yolk proteins.

b. Other Insect Disease Vectors

In addition to mosquitoes, the inventors contemplate application of the compounds and methods of the present invention against other insect disease vectors, including those that promote non-human disease. For example, aphids are the vectors of many viral diseases in plants. Fleas (such as the human flea, *Pulex irritans*, and the oriental rat flea, *Xenopsylla cheopis*) transmit bubonic plague, murine typhus and tapeworms. The glassy-winged sharpshooter transmits the *Xylella fastidiosa* bacterium among plants, resulting in diseases of grapes, almonds, and many other cultivated plants. Phlebotomine sand flies transmit leishmaniasis, bartonellosis, sandfly fever and pappataci fever. Ticks of the genus *Ixodes* are vectors of Lyme disease and babesiosis, and along with lice, transmit various members of the bacterial genus *Rickettsia*. Triatomine bugs such as *Rhodnius prolixus* are vectors of Chagas disease. Several genera of Tsetse flies are vectors of human African trypanosomiasis (also known as "African sleeping sickness").

c. Agricultural Pests

The following is a list of agricultural pests for crops such as wheat, barley, oats, jowar, nuts, maize, soybean, sorghum, pea, potato, cucumber, tomato, grams, rabi, rice fruits, ornamental plants, including flowers, and trees which may be targeted using the methods and compositions of the present invention.

Termites. *Odontotermes obesus* Rambur and *Microtermes obesi* Holmgren. Social insects that live underground in colonies; attack young seedlings as well as grownup plants; the attacked plants rather wither and ultimately die.

Stem-borer. *Sesamia inferens* Walker. Moths are straw-coloured, lay eggs in clusters inside the leaf-sheaths; pinkish-brown caterpillars bore into stems and kill central shoots; causing dead-hearts Gujhia weevil. *Tanymecus indius* Faust. Adults are earthern-grey weevils; grubs feed on roots, whereas the adults cut growing-points or nibble at margins of leaves; severer at the seeding stage.

Cutworms. *Agrotis ipsilon* Hufner and *A. flammantra* Schiffer-Mueller. Caterpillars are general feeders.

Thrip. *Anaphothrips flavinctus* Karny. Nymphs and adults lacerate tender leaves, causing characteristics whitish streaks; low temprature favourable to rapid multiplication.

Wheat aphids. *Schizaphis* (*Toxoptera*) *graminum* Rondani, *Rhopalosiphum maidis* Fitch and *Sitobion avenae* Fabricius. Nymphs and adults suck sap from leaves, tender shoots and immature grain; multiply extremely fast, forming large colonies.

Surface grasshopper. *Chrotogonus trachypterus* Blanchard. Adults stout, mud-like in colour; polyphagous, feeding on foilage and tender shoots.

Shoot fly. *Atherigona naqvii* Steyskal. The fly has assumed the status of a pest recently; maggots attack seedlings and kill the central shoots, causing dead-hearts.

Galerucid beetle. *Madurasia obscurella* Jacoby. Adult beetles feed on foilage and make small circular holes in the leaves; active during July-October.

Jassid. *Empoasca herri* Pruthi. Nymphs and adults remain on the underside of the leaves and suck the sap; leaves turn brown and crumple.

Plume moth borer. *Exelastis atomosa* Walsingham. A specific pest of red-gram; slender buff-colored moths, having plumose wings; greenish-brown hairy caterpillars feed on flowers and later on bore into pods to feed on the developing seeds inside.

Gram pod fly. *Agromyza obtusa* Mallas. A serious pest of red-grain; the small metallic-black fly lays eggs on pods; maggots bore into the pods and feed on the seeds; occasionally early in the season, grubs mine leaves.

Hairy caterpillars. *Amsacta moorei* Butlei, Albistriga Walker, *Diacrisia obliqua* Walker, *Euproctis fraterna* Moore, *E. scintillans* Walker Polyphagous. Caterpillars feed gregariously and voraciously on foliage.

Cowpea stem fly. *Melangromyza phaseoli* Coquillett. A small blue-black fly, thrusts eggs into the epidermis of soft stems; pale-yellow maggots after mining leaves travel towards stem through the petiole and kill the young plants; the vigour of old plants is adversely affected.

Aphids. *Aphis craccivora* Kochi and *A. cardui* L. Colonies of nymphs and adults infest the tender growing shoots, flowers and young pods and suck the sap; infested parts dry and no pod or seed formation takes place.

Whitefly. *Bemisia tabaci* Gennadius. The flies suck the sap from leaves and tender growing parts, which dry and wither. They act as the vector of yellow mosaic of legumes.

Sphinx moth. *Agrius convolvuli* Linnaeus. Stout dark-brown moth; homed caterpillars defoliate plants by feeding voraciously.

Leaf caterpillars. *Azazia rubicans* Biosduval. Sporadic; the adult moth resembles a dry leaf; green caterpillars feed on leaves and tender plant parts.

Gram pod borer. *Helicoverpa* (*Heliothis*) *obsoleta fabricius* Polyphagous. Moth yellowish brown; caterpillar green, with dark broken grey lines, feed on foilage, later on bore into pods and feed on the seeds within.

Gram caterpillars. *Helicoverpa* (*Heliothis*) *armigera* Hubner and *H. zea*, Boddie (*obsoleta fabricius*). Polyphagous; moths stout, light brown; caterpillars yellowish, make holes in pods and feed on the seeds within.

Other pod borers. *Etiella zinckenella* Treitdche. Adult, greyish brown, with a distinct pale white band along the front margin of the forewings; tiny greenish caterpillars, with 5 black spots on the prothoracic shield, enter the pods and eat the seeds; more serious on green pea, specially in northern India. *Adisura athinsoni* Moore. A serious pest in Karnataka; moths pale-yellowish brown; the brownish-green caterpillars feed on the seeds by boring into the ripening pods. *Maruca testutalis* Geyer. A minor pest; adults with fuscous forewings, having transverse white markings; pale-brownish caterpillars bore into the pods of various pulses (kharif pulses as well) to eat seeds inside Cut worms. *Agrotis psilon* Hubner, *A. flammatra* Schiffer-Mueller, *A. segetum* Schiffer-Mueiler, *A. spinifere* Hubner.

Aphids. *Aphis crassivora* Koch, *A. medicagenis* Koch and *Macrosiphum pisi* Hubner Polyphagous. Nocturnal, stout larvae, feed on leaves of young plants and cut the older ones at the ground level. Colonies of nymphs and adults attack tender shoots, flowers and young pods and suck the sap; infested parts dry up. *A. medicagenis* is black, whereas *M. pisi* is green, and *A. crassivora* is brownish.

Pea leaf-miner. *Phytomza atzicornis* Meigen. A major pest of pea; polyphagous; maggots make zigzag mines in the leaves; eat green matter and pupate inside; infected leaves become whitish and dry up.

Pea stem fly. *Melanagromyza phaseoli* Coquillett. A major pest of pea, it also attacks kharif pulses; maggots attack young seeds inside the pods. The same as for the gram podd borer.

Pea semi-loopers. *Plasia orichalcea* Fabricius and *P. nigrisigna* Walker. Polyphagous; moths with a golden patch on the forewings (*P. orichalces*); green caterpillars feed on leaves during December to March.

Blue butterfly. *Cosmolyee baeticus*. Short pale-green caterpillars feed on the leaves, flowers and pods of pea.

Lucerne caterpillar. *Laphygma exigua* Hubner. Occasionally a serious pest of pea; dark-brown moths lay eggs on the lower portion of the young plants; caterpillars feed on the leaves.

Stem-borer beetles. *Oberea brevis* Gahan Nupserha bicolor Thomson. Pale brown longicom beetles; grubs bore into the stems of growing plants.

Gray weevils. *Myllocerus* spp. Adults feed on leaves, nibbling the leaf margins in the initial stage.

Shoot fly. *Atherigona soccata* Rodani. Damage caused during the early seeding stage, larvae cut the growing points, causing dead-hearts; tillers do develop after the central shoot is killed, but the yield from these tillers is rather poor; commoner is early-sown rabi or late-sown kharif crops.

Stem borers. *Chilo zonellus* (*partellus*) Swinhoe Ragi and *Sesamia inferens* Walker. Moth, dirty brownish, nocturnal, caterpillars feed on foilage and bore into the stems, causing dead-hearts; also tunnel the stem and bore into earheads.

Sorghum midge. *Contarinia sorghicola* Coquillett. The insect has assumed the status of a serious pest recently; cosmopolitan; the tiny pinkish fly lay eggs inside the glumes and the larvae feed on the ovaries, thus preventing seed formation.

Aphids. *Phopalosiphum maidis* Fitch and *Aphis sacchari* Zehntner. Nymphs and adults suck the sap from the leaves and shoots, exclude honeydew, on which a sooty mould grows, giving the leaves a black appearance and interfering with photosynthesis.

Deccan wingless grasshopper/Boliver Phadka grasshopper. *Colemania sphenaroides/Hieroglyphus bolivar*. Eggs are laid in the soil 75-200 mm deep; hoppers and adults feed on foilage, at times causing severe defoliation of the crops; adults of *C. sphenaroides* are wingless, whereas those of *H. nigrorepletus* are short winged and can fly short distances only.

Earhead bug. *Calocoris angustatus* Lethierry. Nymphs and adult bugs suck the sap from tender grains at the milky stage, making them chaffy.

Sorghum shoot bug. *Peregrinus maidis* Ashmead. Nymphs and adult bugs suck the sap from the leaves and whorls, which turn pale green.

Hairy caterpillars. *Amsacta moorei* Butler, *Estigmene lactinae* Cramer. General feeders, frequently causing severe defoliation; caterpillars of *A. moorei* are red whereas those of *E. lactinae* are black.

Earhead caterpillars. *Eublemma (Heliothis) armigera* Hubner and other species. Occur throughout the country; caterpillars feed on maturing grains.

Mites. *Oligonychus indicus* Hirst and *Schizotetranychus andropogoni* Hirst. Colonies of nymphs and adults suck the sap from the undersurface of the leaves, causing reddish-brown spots and patches.

Blister beetles. *Lytta tenuicollis* Pallasi and *Zonabris pustulata* Thunberg. Adult beetles feed on pollen and flowers.

Leaf roller. *Marasmia trapezalis* Guenee. Slender, yellowish-green caterpillars fold and roll the leaves near the tips and feed inside on the chlorophyll.

Shoot fly. *Atherigone approximata* Malloch. The flies cut the growing-points, causing dead-hearts during the seedling stage, whereas in the advanced stage; they feed on earheads and cut down peduncles.

Bajra midge. *Geromyia pennisetti* Harris. The larvae destroy the ovaries seriously, affecting the development of seeds.

Ragi white borer. *Saluria inficita* Walker. A specific pest of ragi; creamy white caterpillars bore into the stems close to the soil surface; adults are dark brown, with a pale-white band along the margin of each forewing.

Black hairy caterpillar. *Estigmene exigua* Hubner. Also known as woolly bear caterpillar; feed on leaves and earheads; the adults are creamy white moths with characteristic crimson marks on the head and the body.

Lucerne caterpillar. *Spcdoptera exigua* Hubner. Smooth, brownish-green caterpillars feed on foilage, moving in large numbers from field to field; common in nurseries.

Ragi-root aphid. *Tetraneura hirsuta* Baker. Minute, pale-white insect, found damaging roots, resulting in a gradual drying up of plants; infestation by the presence of black ants.

Ragi jassid. *Cicadulina bipunctella bipunctella*. Nymphs and adults suck the sap from the leaves and stems; an important vector of ragi mosaic virus.

Almond weevil. *Myllocerus laetivirens* Marshall; *Mylocerus undecimpustulatus* Faust and *M. discolor* Boheman *Amblyrrhinus poricollis* Boheman. Polyphagous pest; young weevils feed on roots, whereas the adult weevils feed on the foilage; initially they cut irregular holes and gradually eat up entire leaves leaving only the midribs.

Almond beetle. *Mimastra cyanura* Hope. Adult beetles appear in swarms during May, defoliate the trees, causing huge losses; peak activity is reached during July-August.

San Jose Scale. *Quadraspidiotus perniciosus* Comstock. Ash-coloured insects infest leaves, twigs and fruits and suck the sap; nursery plants may die if the attack is severe; active from March to December (3-4 generations).

Woolly aphid. *Eriosoma lanigerum* Hausmann. A cosmopolitan sucking insect; colonies look like white cottony patches on branches, twigs and main roots below ground;

multiplication is very rapid; active from March to December, maximum activity during July-August.

Root borer. *Dorysthenes hugelli* Redtenbacher. Shining, chestnut-red beetles lay eggs in soil during July-August; grubs feed exclusively on thick roots and other organic matter, their longevity is 3½ years; sandy soil preferred by the pest.

Tent caterpillar. *Malacosoma indicum* Walker. Caterpillars feed gregariously on leaves at night and hide during the day in small tent-like structures of webs; moths lay eggs in bands (strips) around small twigs in May; caterpillars hatch out in the next spring.

Leopard moth. *Zeuzera* sp. White moths of attractive patterns are seen at dusk during may to July; eggs are laid singly in cracks of barks; pinkish-white young caterpillars bore into branches and stems during July-August and feed within 22 months.

Apple blossom thrip. *Taenniothrips rhopalantennalis* Shunister. Minute insects lay eggs in flower buds and nymphs and adults scrape tissues therefrom so there is no fruit-setting.

Leaf-defoliating and fruit-eating beetles. *Adoretus duvauceli* Blanchard, *A. versutus* Harold *Anomala lineatopennis* Blanchard, *B. rufiventris* Redtenbacher, *Holotrichia longiplennis* Blanchard, *Hilyotrogus holosericus* Redtenbacher, *Lucanus lunifer* Hope, *Lachnosterna coriacea* Hope, *Macronota 4-lineata* Hope, *Melolontha furcicauda* Ancy, *Mimela passerinii* Arrow, *M. pectoralis* Blanchard and *Mylabris mevilenta* Marshall. Beetles lay eggs on soil during rainy season; grubs feed on vegetation under ground till next summer; beetles come out in June and feed on foilage and some species also attack the tender fruits usually during night. The affected fruits lose their market value.

Apple leaf-rollers. *Cacoecia sarcosttega* Meyrick, *C. ecicyota* Meyrick, *C. pomivora* Meyrick, *C. termias* Meyrick, and *C. subsidiaria* Meyrick. Polyphagous; larvae feed on the leaves, buds and flowers; after rolling or webbing them together, caterpillars feed within on soft tissues; fruit-setting is adversely affected.

Apple hawk moth. *Langia zeuzeroides* Moore. Sporadic; caterpillars defoilate trees during April to August; egg (2.5×2.0 mm), full fed larva (125×10 mm), pupa (50×20 mm) and moth (wing expanse 112×132 mm) are conspicuously big.

Apple leaf-miner. *Gracillaria zachrysa* Meyrick. Young caterpillars make several mines on leaf surface; later they leave mines, roll young leaves longitudinally into tubular or cone-shaped pouch and feed within; the maximum damage during summer (April-May) and in autumn (September-October).

Blossom thrip. *Tacniothrips rhopalantennalis* Shunister. Eggs laid in flower-buds before the buds open; nymphs feed on petals and vital flower parts by lacerating tissues and sucking the sap; fruit formation is considerably reduced.

Hairy caterpillars. *Euproctis signata* Blanchard, *E. fraterna* Moore, and *E. flava* Fabricius. Caterpillars feed voraciously and defoliate trees; *E. signata* is commoner on apple trees.

Indian Gypsy moth, *Lymantria obfuscata* Walker. Round, greyish-brown eggs are laid in clusters during June-July under the bark on tree trunks and are covered with yellowish-brown hairs; these hatch after 8-9 months; larvae feed gregariously at night and defoliate the trees completely.

Apricot chalcid. *Eurytoma samsonowi* Vasiljev. Adults emerge from dry fruits in the end of February; lay eggs inside young fruits; grubs feed on the developing seeds, fruit growth is arrested and fruits fall prematurely; pupation takes place inside the seeds; maximum activity in April-May.

Apricot weevil. *Emperorhinus defoliator* Marshall. Adults defoliate the trees during summer.

Apricot chafer beetle. *Anomala polita* Blanchard. Adult feed on shoots and leaves.

Tissue-borers. *Tryporyza incertulas* Walker, *Tryporyza innotata* Snellen, *Sesamia inferens* Walker, *Procerus indius* Kapur, *Chilo infuscatellus* Snellen, *C. simplex* Butler, and *C. zonellus* Swinhoe. Caterpillars bore into stems and pupate within; the central shoot withers and produces a dead-heart; affected plants turn yellow and there is no grain formation; ear-heads appear white and chaffy; active throughout the year, except between April and May and between October and November.

Gundhi bugs. *Leptocorisa varicornis* Fabricius and *L. acuta* Thunberg. Nymphs and adults suck the milky sap of tender grains; affected earheads stand erect like normal ones, but without any grain formation; often the crop is completely destroyed; early varieties, if transplanted late, become more susceptible; active during May to November.

Paddy gall fly. *Pachdiplosis oryzae* Wood Mason. Maggots attack the base of the growing-point and produce long, tubular silvery galls (silver shoots); plant growth is adversely affected; active during May to September-November.

Rice hispa. *Dicladispa armigera* (Olivier). Small blue-black beetles, covered with spines; the grubs make long winding tunnels into leaves, whereas adults scrape the chlorophyl, affected leaves turn whitish and membranous and ultimately dry up.

Blue leaf beetle. *Leptispa pygmaea* Baly. Found in association with hispa, especially in Karnataka.

Paddy caseworm. *Nymphula depunctalis* Guenee. A small white moth, with yellow and dark specks on the wings; greenish caterpillars cut the leaves and form tabular cases around them; several tubes may be seen floating on water or hanging from the plant; the larvae feed on green tissues.

Swarming caterpillar. *Spodoptera mauritia* Boisduval. Sporadic, caterpillars appear in big swarms, causing heavy losses, specially when cold weather is suddenly followed by a spell of warmth or drought (30-40 days) is followed by heavy rains; normally appear in July-August.

Armyworms. *Mythimna unipuncta* Haworth and *M. albistigma*. Caterpillars march from field to field and voraciously feed on foilage; appear after heavy rains or early floods.

Rice grasshoppers. *Hieroglyphus banian* Fabricius, *H. nigrorepletus* Beliver, *H. furcifer* Serv., *H. oryzaevorus* Carl *Acrida exultata* Linnaeus, *A. turrita linnaeus Aelopus famulus* Kirby, *A. Aularaches miliaris Loxya bidentata* Willemse, *O. multidentata* Will, and *O. velox fabricius*. Appear immediately after rains; nymphs and adults devour leaves and tender shoots and also newly-formed ear-heads; active from July to October-November.

Paddy jassids. *Nephotettix apicalis* Motschulsky and *N. impicticeps* Fabricius. Adults small, green, with black spots on forewings; nymphs and adults suck plant sap; affected plants turn yellow and growth is adversely affected.

White leaf hoppers. *Tettigella spectra* Distant. Adults larger than those of *Nephotettix* spp. and white; both nymphs and adults suck sap from young leaves; infested leaves turn yellow.

Fulgorid bug. *Nilaparvartha lugens* Stal. Minor pest; recorded feeding or ripening ear-heads.

Paddy thrip. *Cloethrips oryzae* Williams. Nymphs and adult lacerate tissues; affected leaves present yellowish streaks; tips curl and wither.

Whorl maggot. *Hydrellia* sp. Minor pest; common during kharif, maggots feed in the worlds of developing leaves.

Paddy mealy bug. *Ripersia oryzae* Green. Colonies of reddish-white soft insects infest succulent paddy stems, hidden by outer leaf-sheaths, suck cell sap; growth gets stunted; affects ear-head formation.

Rice root aphid. *Tetraneura hirsuta* Baker. Colonies of nymphs and adults suck sap from roots just below soil surface, affected plants become pale and wither.

Paddy leaf-roller. *Cnaphalocrocis medinalis* Guenee. Sporadic pest; caterpillars roll the leaf tips and feed inside.

Paddy skippers. *Pelopides mathias fabricius*. Adult, a dark-brown butterfly; caterpillar, smooth and green, feeds on leaves.

Paddy root weevil. *Echinocnemus oryzae* Marshal. Small grey weevil, grubs attack paddy roots and affect the growth of plants.

Other pests include the Asiatic Garden Beetle, Asparagus Beetles, Bean Leaf Beetle, Beet Webworm, Bluegrass Billbug, Brown Marmorated Stink Bug, Cabbage and Seedcom Maggot, Cabbage Looper, Cabbage Webworm, Carpenter Ant, Carpenter Bee, Carpet Beetles, Catalpa Sphinx Caterpillar, Celery Leaftier, Cereal Leaf Beetle, European Corn Borer, Click Beetle, Colorado Potato Beetle, Confused Flour Beetle, Corn Earworm, Cucumber Beetle, Cutworms, Diamondback Moth, Eggplant Lace Bug, Flea Beetles, Fungus Gnat, Green Peach Aphid, Hornworms, Hunting Billbug, Imported Cabbageworm, Indian Meal Moth, Japanese Beetle, Lace Bugs, Leaf-Footed Bugs, Mexican Bean Beetle, Onion Thrips, Parsleyworm, Pepper Maggot, Pepper Weevil, Pickleworm, Potato Aphid, Potato Tuberworm, Raspberry Crown Borer, Rednecked Cane Borer, Rhubarb Curculio, Root-knot Nematode, Rose Chafer, Rose Scale, Sap Beetles, Sawtoothed Grain Beetle, Wireworms, Squash Bug, Squash Vine Borer, Tarnished Plant Bug, Twig Girdler/ Twig Pruner, Vegetable Weevil, Virginia Pine, Sawfly, Wheel Bug, White Grubs, Whitefringed Beetles, Winter Grain Mite, and Yellow Ant.

2. Mosquito-Borne Disease

Mosquitoes are a vector agent that carry disease-causing viruses and parasites from person to person without catching the disease themselves. The principal mosquito borne diseases are the viral diseases yellow fever, dengue fever and Chikungunya, transmitted mostly by the *Aedes aegypti*, and malaria carried by the genus *Anopheles*. Though originally a public health concern, HIV is now thought to be almost impossible for mosquitoes to transmit.

Mosquitoes are estimated to transmit disease to more than 700 million people annually in Africa, South America, Central America, Mexico and much of Asia, with millions of resulting deaths. At least 2 million people annually die of these diseases.

Methods used to prevent the spread of disease, or to protect individuals in areas where disease is endemic include vector control aimed at mosquito eradication, disease prevention, using prophylactic drugs and developing vaccines and prevention of mosquito bites, with insecticides, nets and repellents. Since most such diseases are carried by "elderly" females, scientists have suggested focusing on these to avoid the evolution of resistance.

a. Protozoa

The mosquito genus *Anopheles* carries the malaria parasite (see *Plasmodium*). Worldwide, malaria is a leading cause of premature mortality, particularly in children under the age of five. It is widespread in tropical and subtropical regions, including parts of the Americas (22 countries), Asia, and Africa. Each year, there are approximately 350-500 million cases of malaria, killing between one and three million people, the majority of whom are young children in sub-Saharan Africa. Ninety percent of malaria-related deaths occur in sub-Saharan Africa. Malaria is commonly associated with poverty, and can indeed be a cause of poverty and a major hindrance to economic development.

Five species of the *Plasmodium* parasite can infect humans; the most serious forms of the disease are caused by *Plasmodium falciparum*. Malaria caused by *Plasmodium vivax*, *Plasmodium ovale* and *Plasmodium malariae* causes milder disease in humans that is not generally fatal. A fifth species, *Plasmodium knowlesi*, is a zoonosis that causes malaria in macaques but can also infect humans.

Malaria is naturally transmitted by the bite of a female *Anopheles* mosquito. When a mosquito bites an infected person, a small amount of blood is taken, which contains malaria parasites. These develop within the mosquito, and about one week later, when the mosquito takes its next blood meal, the parasites are injected with the mosquito's saliva into the person being bitten. After a period of between two weeks and several months (occasionally years) spent in the liver, the malaria parasites start to multiply within red blood cells, causing symptoms that include fever, and headache. In severe cases the disease worsens, leading to hallucinations, coma, and death.

A wide variety of antimalarial drugs are available to treat malaria. In the last 5 years, treatment of *P. falciparum* infections in endemic countries has been transformed by the use of combinations of drugs containing an artemisinin derivative. Severe malaria is treated with intravenous or intramuscular quinine or, increasingly, the artemisinin derivative artesunate. Several drugs are also available to prevent malaria in travelers to malaria-endemic countries (prophylaxis). Resistance has developed to several antimalarial drugs, most notably chloroquine.

Malaria transmission can be reduced by preventing mosquito bites by distribution of inexpensive mosquito nets and insect repellents, or by mosquito-control measures such as spraying insecticides inside houses and draining standing water where mosquitoes lay their eggs.

Although many are under development, the challenge of producing a widely available vaccine that provides a high level of protection for a sustained period is still to be met.

b. Helminthiasis

Some species of mosquito can carry the filariasis worm, a parasite that causes a disfiguring condition (often referred to as elephantiasis) characterized by a great swelling of several parts of the body; worldwide, around 40 million people are living with a filariasis disability. The thread-like filarial nematodes (roundworms) are members of the superfamily Filarioidea, also known as "filariae." There are 9 known filarial nematodes which use humans as the definitive host. These are divided into 3 groups according to the niche within the body that they occupy: lymphatic filariasis, subcutaneous filariasis, and serous cavity filariasis. Lymphatic filariasis is caused by the worms *Wuchereria bancrofti*, *Brugia malayi*, and *Brugia timori*. These worms occupy the lymphatic system, including the lymph nodes, and in chronic cases these worms lead to the disease elephantiasis. Subcutaneous filariasis is caused by *Loa loa* (the African eye worm), *Mansonella streptocerca*, *Onchocerca volvulus*, and *Dracunculus medinensis* (the guinea worm). These worms occupy the subcutaneous layer of the skin, in the fat layer. Serous cavity filariasis is caused by the worms *Mansonella perstans* and *Mansonella ozzardi*, which occupy the serous cavity of the abdomen. In all cases, the transmitting vectors are either blood sucking insects (flies or mosquitoes), or copepod crustaceans in the case of *Dracunculus medinensis*.

Individuals infected by filarial worms may be described as either "microfilaraemic" or "amicrofilaraemic," depending on whether or not microfilaria can be found in their peripheral blood. Filariasis is diagnosed in microfilaraemic cases primarily through direct observation of microfilaria in the peripheral blood. Occult filariasis is diagnosed in amicrofilaraemic cases based on clinical observations and, in some cases, by finding a circulating antigen in the blood.

C. Viruses

The viral disease yellow fever, an acute hemorrhagic disease, is transmitted mostly by *Aedes aegypti* mosquitoes. The virus is a 40 to 50 nm enveloped RNA virus with positive sense of the Flaviviridae family. The yellow fever virus is transmitted by the bite of female mosquitoes (the yellow fever mosquito, *Aedes aegypti*, and other species) and is found in tropical and subtropical areas in South America and Africa, but not in Asia. The only known hosts of the virus are primates and several species of mosquito. The origin of the disease is most likely to be Africa, from where it was introduced to South America through the slave trade in the 16th century. Since the 17th century, several major epidemics of the disease have been recorded in the Americas, Africa and Europe. In the 19th century, yellow fever was deemed one of the most dangerous infectious diseases.

Clinically, yellow fever presents in most cases with fever, nausea, and pain and it generally subsides after several days. In some patients, a toxic phase follows, in which liver damage with jaundice (giving the name of the disease) can occur and lead to death. Because of the increased bleeding tendency (bleeding diathesis), yellow fever belongs to the group of hemorrhagic fevers. The WHO estimates that yellow fever causes 200,000 illnesses and 30,000 deaths every year in unvaccinated populations; around 90% of the infections occur in Africa.

A safe and effective vaccine against yellow fever has existed since the middle of the 20th century and some countries require vaccinations for travelers. Since no therapy is known, vaccination programs are, along with measures to reduce the population of the transmitting mosquito, of great importance in affected areas. Since the 1980s, the number of cases of yellow fever has been increasing, making it a reemerging disease.

Dengue fever and dengue hemorrhagic fever (DHF) are acute febrile diseases also transmitted by *Aedes aegypti* mosquitoes. These occur in the tropics, can be life-threatening, and are caused by four closely related virus serotypes of the genus Flavivirus, family Flaviviridae. It is also known as breakbone fever, since it can be extremely painful. It occurs widely in the tropics, and increasingly in southern China. Unlike malaria, dengue is just as prevalent in the urban districts of its range as in rural areas. Each serotype is sufficiently different that there is no cross-protection and epidemics caused by multiple serotypes (hyperendemicity) can occur. Dengue is transmitted to humans by the *Aedes* (Stegomyia) *aegypti* or more rarely the *Aedes albopictus* mosquito. The mosquitoes that spread dengue usually bite at dusk and dawn but may bite at any time during the day, especially indoors, in shady areas, or when the weather is cloudy. The WHO says some 2.5 billion people, two fifths of the world's population, are now at risk from dengue and estimates that there may be 50 million cases of dengue infection worldwide every year. The disease is now endemic in more than 100 countries.

Other viral diseases like epidemic polyarthritis, Rift Valley fever, Ross River Fever, St. Louis encephalitis, West Nile virus (WNV), Japanese encephalitis, La Crosse encephalitis and several other encephalitis type diseases are carried by several different mosquitoes. Eastern equine encephalitis (EEE) and Western equine encephalitis (WEE) occurs in the United States where it causes disease in humans, horses, and some bird species. Because of the high mortality rate, EEE and WEE are regarded as two of the most serious mosquito-borne diseases in the United States. Symptoms range from mild flu-like illness to encephalitis, coma and death. *Culex* and *Culiseta* are also involved in the transmission of disease. WNV has recently been a concern in the United States, prompting aggressive mosquito control programs.

d. Transmission

A mosquito's period of feeding is often undetected; the bite only becomes apparent because of the immune reaction it provokes. When a mosquito bites a human, she injects saliva and anti-coagulants. For any given individual, with the initial bite there is no reaction but with subsequent bites the body's immune system develops antibodies and a bite becomes inflamed and itchy within 24 hours. This is the usual reaction in young children. With more bites, the sensitivity of the human immune system increases, and an itchy red hive appears in minutes where the immune response has broken capillary blood vessels and fluid has collected under the skin. This type of reaction is common in older children and adults. Some adults can become desensitized to mosquitoes and have little or no reaction to their bites, while others can become hyper-sensitive with bites causing blistering, bruising, and large inflammatory reactions, a response known as Skeeter Syndrome.

3. Insect Olfactory Receptors

The ability to detect and respond to the chemical environment is a critical sensory input into many essential behaviors of hematophagous (blood-feeding) insects (Zwiebel and Takken, 2004) (FIG. 1). The search for vertebrate blood meals typically involves a flight of some distance to reach the host. This behavior consists of a series of behavioral stages, beginning with the activation of a receptive insect by the host chemical odor (kairomone) and ending when the insect alights on the host (Takken, 1991). At close range, attraction is mediated by several odorants, one of which is $CO_2$. In combination with other host-derived organic chemicals, $CO_2$ acts as a synergist as it greatly enhances the attraction triggered by other volatiles (Gilles, 1980). Moreover, it appears that mosquitoes respond to changes in the concentration of $CO_2$, rather than its presence or absence. In *Ae. aegypti*, changes in the firing rate of $CO_2$ receptors have been observed with increases in concentration of as little as 0.01% (Kellogg, 1970), while alterations in behavior have been observed after increases of 0.03-0.05% (Eiras and Jepson, 1991). Furthermore, a close examination of the role of $CO_2$ revealed that the turbulence of the odor plume in the laboratory greatly affected the responsiveness of *Ae. aegypti* and *An. gambiae* s.s. (Dekker et al., 2001a). *An. gambiae* has also been shown to be attracted to acetone, lactic acid (Acree et al., 1968), carboxylic acids (Meijerink and van Loon, 1999), ammonia, 4-methyl-phenol, -octen-3-ol, and other components of sweat (Cork and Park, 1996; Meijerink et al., 2001), as well as to the odor of human feet, expired air and several unidentified components of Limburger cheese (De Jong and Knols, 1995). Furthermore, the often-cited differences in human attractiveness for mosquitoes (Curtis, 1986) is almost certainly olfactory based (Qiu et al., 2006a; Schreck et al., 1990). This within-host differential behavior is most particularly expressed in anthropophilic culicids such as *Ae. aegypti* and *An. gambiae* s.s. (de Jong and Knols, 1995; Lindsay et al., 1993; Schreck et al., 1990). Host age, but not gender, may affect these inter-individual differences (Carnevale et al., 1978); race also appears to have no effect (Schreck et al., 1990). Young children have been shown to be less attractive to Anophelines than adults (Muirhead-Thomson, 1951; Thomas, 1951). Studies on the chemical composition of human volatiles (Bernier et al., 1999; Krotoszynski et al., 1977; Labows, 1979) revealed the existence of a large number (>350) of chemicals, and work is in progress to study the most important components of these volatiles regulating mosquito behavior. Lastly, it is also clear that responses to $CO_2$ affect inter-individual differences in attractiveness (Brady et al., 1997) and, thus, $CO_2$ serves as a universal attractant to many mosquito species (Gillies, 1980; Takken et al., 1997; Takken and Knols, 1999). It has been reported that $CO_2$ stimulation synergizes with host body odor and has an activating effect on host-seeking anopheline mosquitoes, inducing take-off and sustained flight behaviors (Dekker et al., 2001b; Gillies, 1980; Mboera and Takken, 1997).

Figure 2:
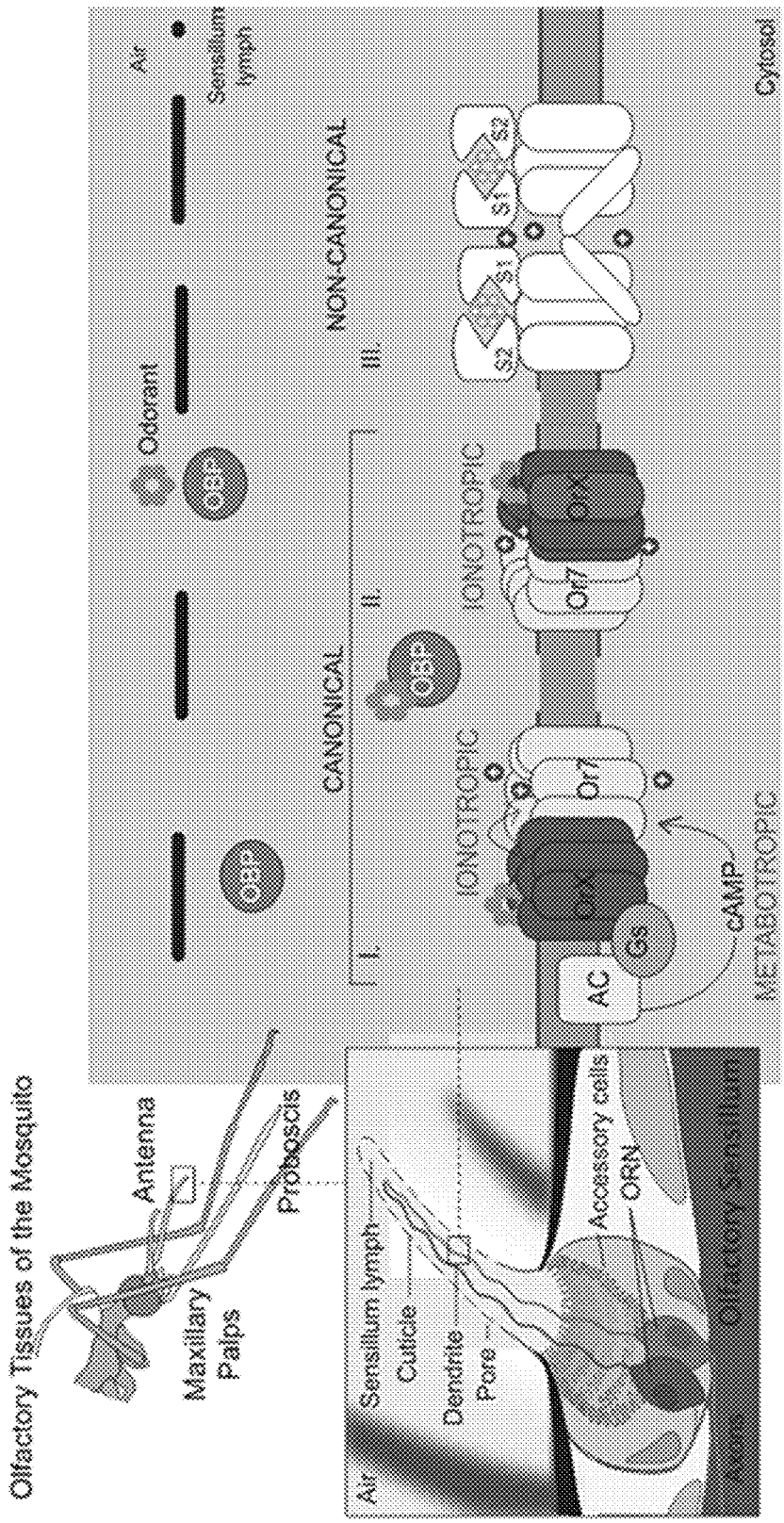
FIG. 2. Canonical and Non-Canonical Models of General Insect Olfactory Signal Transduction. Schematic incorporating recent insights into molecular interactions in the lumen and dendritic membrane of insect ORNs. General odorants entering through cuticular pores are loaded onto OBPs that facilitate transport to conventional ORs (ORx) within the context of canonical OR complexes. Transport of odorants is directed by a specific OBP which may physically interact with the conventional and/or 83b (ORco) family OR. Pheromone-sensitive pathways are likely to involve additional molecular components. In canonical models (I, II), conventional ORs (OrX) bind odorants and physically interact with highly conserved, non-conventional 83b family ORs (Orco in *An. gambiae*) to form functional heteromultimers expressed in a majority of ORNs. In this model, binding of odorants activates ionotropic (Sato et al., 2008) and, possibly, metabotropic (Wicher et al., 2008) signaling pathways. In other ORNs, non-canonical ORs (III), such as members of the IGluR/IR gene family (Benton et al., 2009) respond to atypical odorant that in some cases (e.g., ammonia and lactic acid) are associated with human-derived kairomones.

In a process that is analogous to the sense of smell in humans as well as other insects, mosquito olfaction is initiated by the process of chemosensory signal transduction by which chemical signals (typically environmental cues) are translated into neuronal activity and, ultimately, behavioral outputs. In *An. gambiae*, this takes place within specialized hair-like structures called sensilla that are dispersed throughout the antennae and other head appendages on adult and larval-stage anopheline mosquitoes (Zwiebel and Takken, 2004) (FIG. 2).

Until recently, much of the inventors' view of insect olfactory signal transduction at the molecular level has been strongly influenced by observations made in vertebrates, crustaceans and nematodes (Hildebrand and Shepherd, 1997; Krieger and Breer, 1999). The canonical model involves a family of heptahelical G-protein-coupled receptors (GPCRs) that activate downstream effectors via heterotrimeric GTP-binding (G) proteins and traditional second messengers. It has long been assumed, although not fully accepted (see below), that the canonical model of olfactory signal transduction would also hold true in insects, in which several of the "usual" molecular suspects have been identified and, in part, functionally characterized. These include arrestins (Merrill et al., 2002; 2003; 2005), odorant-binding proteins (OBPs) (Pelosi and Maida, 1995), a heterotrimeric G-protein (Laue et al., 1997) as well as a CNG (Baumann et al., 1994; Krieger et al., 1999) and an IP3-gated ion channel (Stengl, 1994). In one study using the cockroach, it was demonstrated that pheromone exposure of insect antennal preparations caused a rapid increase in IP3 levels (Breer et al., 1990), which in a follow-up study could be inhibited by pertussis toxin (Boekhoff et al., 1990), indicating that the IP3 increase is dependent on either a Goα or a Goto G-protein subunit. More recently, the inventors carried out a molecular survey of G-protein expression in the olfactory appendages of *An. gambiae*, in which Gaq localization consistent with involvement in olfactory signal transduction was observed along the dendrites of most olfactory sensory neurons (Rutzler et al., 2006). Furthermore, pheromone receptor neuron activity of *Bombyx mori* could be stimulated with fluoride ions (Laue et al., 1997), which are known to activate heterotrimeric G proteins via binding to the α subunit in combination with magnesium ions (Antonny et al., 1993). However, despite this growing wealth of information, the precise mode of insect olfactory signal transduction remains largely obscure and is therefore the subject of ongoing investigation that has raised serious issues with regard to the validity of GPCR-based paradigms.

Because olfaction was mediated by GPCRs in both vertebrates and at least one invertebrate, it was assumed that insects would also utilize these proteins in olfactory signal transduction. Indeed, using a variety of approaches, a large family of candidate ORs has been identified in *D. melanogaster* (Clyne et al., 1999) (Gao and Chess, 1999; Vosshall et al., 1999). In the first of these studies, putative *D. melanogaster* ORs (Dors) were identified using a novel computer algorithm that searched for conserved physicochemical features common to known transmembrane proteins (Kim et al., 2000) rather than relying on a sequence homology-based screen (which might miss a divergent member of a particular family). The structures that were ultimately identified using these strategies led to the identification of a highly divergent family of receptors, displaying between 10% and 75% identity and bearing no significant homology to any other GPCR family (Smith, 1999). Another chemosensory receptor family was also described in *D. melanogaster* and *An. gambiae* and is presumed to comprise gustatory (taste) receptors (Clyne et al., 2000; Hill et al., 2002; Scott et al., 2001). The other circumstantial criterion to infer olfactory function has been provided by various in situ expression pattern studies that have demonstrated that the majority of these genes were selectively and stereotypically expressed in the fly olfactory sensory neurons (Clyne et al., 1999) (Elmore and Smith, 2001; Gao and Chess, 1999; Vosshall, 2001; Vosshall et al., 1999). Two-color (double-labeling) in situ hybridization suggests that, with two notable caveats (Goldman et al., 2005), most *D. melanogaster* ORNs are likely to express a single DOR gene (Vosshall et al., 2000), which is analogous to mammalian systems (Mombaerts, 1999), but in stark contrast to the *C. elegans* system. One apparent exception to the one ORN-one receptor principle is the non-conventional DORco. Unlike most other DORs, DORco is expressed throughout the majority of antennal and maxillary palp ORNs of *D. melanogaster*. Putative DORco orthologs have been identified in a wide range of insect species and share many characteristics, including high sequence identity (Pitts et al., 2004), characteristic broad expression pattern (Krieger et al., 2003) and conserved functions (Jones et al., 2005). DORco family members are considered non-conventional ORs as they act as general dimerization partners for other members of the DOR family (Larsson et al., 2004). More recently, Benton, Vosshall and co-workers have identified a novel set of ionotropic glutamate receptors as a new class of insect chemosensory receptors (IRs) that are expressed in DOr83-ORNs associated with coeloconic sensilla where they act in parallel with "classical" insect ORs to respond to ammonia and other environmental cues (Benton et al., 2009; Liu et al., 2010).

Elegant studies by the Vosshall lab have also suggested that insect ORs manifest a novel topology relative to vertebrate ORs (Benton et al., 2006). In the absence of actual structural information insect ORs have been structurally characterized largely based on bioinformatic models derived from vertebrates (Clyne et al., 2000; Vosshall et al., 1999). Indeed, while sequence-based phylogenies recognize that insect ORs in general comprise a distinct family of heptahelical receptors that are an expanded lineage of ancestral chemosensory receptors (Mombaerts, 1999; Robertson et al., 2003) there is a growing awareness that insect ORs are likely to represent a structurally unique set of sensory proteins. These studies provide compelling evidence in support of the view that *Drosophila* ORs are heteromeric complexes between the non-conventional DOR83b and conventional, odorant binding DORs that adopt a novel membrane topology in which the N-terminus is intracellular rather than the extra-cellular localization that is typical of vertebrate ORs and GPCRs (Benton et al., 2006). Independent validation (Lundin et al.) together with recent computational analyses employing hidden Markov modeling that "strongly rejects" classifying arthropod ORs as GPCRs (Wistrand et al., 2006) raise significant concerns regarding the nature of the signaling pathways that are downstream of odorant activation in insects. Indeed, two recent studies provide provocative evidence to suggest that *Drosophila* ORs manifest properties of both ligand-gated (Sato et al.) and cyclic-nucleotide-gated ion channels (Wicher et al., 2008). While these hypotheses still differ in their particulars, there is growing awareness that insect olfactory transduction may diverge from vertebrate paradigms and act as non-GPCR-mediated ion-channels (FIG. 2). In any case, while current hypotheses may differ, the growing possibility that insect olfactory transduction may diverge from vertebrate paradigms and act via non-GPCR-mediated mechanisms such as ion channels (FIG. 2) is compelling.

In the first report of insect ORs outside of the model insect system *D. melanogaster*, members of the inventors' laboratory, as part of a collaborative effort with Drs. John Carlson and Hugh Robertson, were responsible for the identification of a set of candidate Or genes selectively expressed in olfactory tissues of *An. gambiae* (AgORs) (Fox et al., 2001). Moreover, that report also demonstrated that at least one of the initial set of AgORs displays female-specific expression, a feature that may be especially relevant for disease transmission. In a subsequent study, as part of the effort to annotate the recently completed genomic sequence of *An. gambiae* (Holt et al., 2002), the inventors (in collaboration with other groups) utilized bioinformatics and molecular approaches to describe the entire *An. gambiae* GPCR gene family (AgGPCRs); of the 275 putative AgGPCRs, 79 candidate AgORs were described (Hill et al., 2002). Furthermore, a similar bioinformatic approach (using a non-public database) has been used to identify nine candidate Or genes in the heliothine moth *Heliothis virescens* (Krieger et al., 2002), some of which share sequence homology with AgORs. More recently, a large family of candidate Or genes have been identified in the genome sequence of the honey bee, *Apis mellifera* (Robertson and Wanner, 2006), *Ae. aegypti* (Bohbot et al., 2007) and the red flour beetle, *Tribolium* casteneum (Engsontia et al., 2008).

Thus far, insect ORs have been extensively deorphanized in a number of heterologous systems. The first successful functional studies of insect ORs were carried out for DOR43a using a *Xenopus* oocyte expression system (Wetzel et al., 2001), and over-expression in *D. melanogaster* (Storkuhl and Kettler, 2001) showed increased sensitivity to a set of four odorants. The Carlson laboratory has used a novel experimental approach that takes advantage of a genetic strain of *D. melanogaster* in which a chromosomal deletion has resulted in the loss of the endogenous receptors (DOR$_2$2a/b) from the ab3A ORN. The resultant formation of a "empty neuron" system facilitates the specific targeting of exogenous OR genes into the empty neuron, thereby allowing electrophysiological assessment of the ability of the novel receptor to carry out chemosensory signal transduction within the ab3A neuron upon stimulation with a diverse set of odorants (Dobritsa et al., 2003). This system has been used effectively to functionally characterize nearly all the DORs (Hallem et al., 2004a) (Hallem and Carlson, 2006), leading to a highly developed map of the multidimensional "odor space" of the DORs. As part of a long-standing collaboration between the Carlson lab and that of the inventors, multiple AgORs have also been functionally characterized in the *Drosophila* empty neuron (Hallem et al., 2004b; Lu et al., 2007). These studies, along with the success in functionally expressing over 40 AgORs in *Xenopus* and cell culture systems, have lead to significant advances in understanding the molecular basis for olfactory sensitivity in larval (Xia et al., 2008) and adult (Lu et al., 2007) *An. gambiae*. For example, $CO_2$ which acts as universal attractant for many species of mosquitoes (Takken and Knols, 1999), elicits avoidance in *Drosophila* where it has been identified as an active component of the "stress odorant" that targets a discrete population of sensory neurons (Suh et al., 2007) and where a pair of highly conserved putative gustatory receptors {Gr21a and Gr63a} have been shown to both be both necessary and sufficient to mediate olfactory sensitivity to $CO_2$ in *Drosophila* (Jones et al., 2007; Kwon et al., 2007). As part of a comprehensive study of the olfactory processes on the maxillary palp in *An gambiae*, the inventors have identified three Gr21a/63a homologs (AgGrs22-24) as the molecular partners required that together comprise the anopheline $CO_2$ receptor (Lu et al., 2007).

C. COMPOUNDS

In one aspect, the invention relates to a compound having a structure represented by a formula:

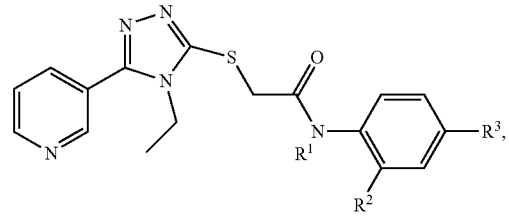

wherein: $R^1$ is hydrogen or is taken together with $R^2$ to be alkanediyl$_{(C1-4)}$, alkenediyl$_{(C1-4)}$, or a substituted version of either of these groups; $R^2$ is hydrogen or is taken together with $R^1$ as defined above; and $R^3$ is hydrogen, hydroxy, nitro, halo, alkyl$_{(C≤8)}$, substituted alkyl$_{(C≤8)}$, alkenyl$_{(C≤8)}$, or substituted alkenyl$_{(C≤8)}$; or a salt or tautomer of the formula.

In various aspects, the invention relates to a compound having a structure represented by a formula:

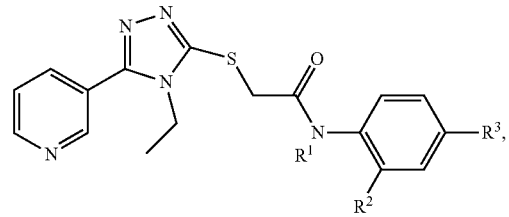

wherein: $R^1$ is hydrogen or is taken together with $R^2$ to be alkanediyl$_{(C1-4)}$, alkenediyl$_{(C1-4)}$, or a substituted version of either of these groups; $R^2$ is hydrogen or is taken together with $R^1$ as defined above; and $R^3$ is hydrogen, hydroxy, nitro, halo, alkyl$_{(C≤8)}$, substituted alkyl$_{(C≤8)}$, alkenyl$_{(C≤8)}$, or substituted alkenyl$_{(C≤8)}$; or a salt or tautomer of the formula, provided that the compound is not:

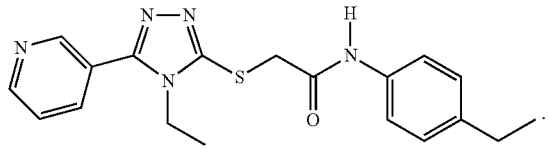 [SMILES: CCc1ccc(NC(=O)CSc2nnc(-c3cccnc3)n2CC)cc1]

In a further aspect, the invention relates to a compound of the formula:

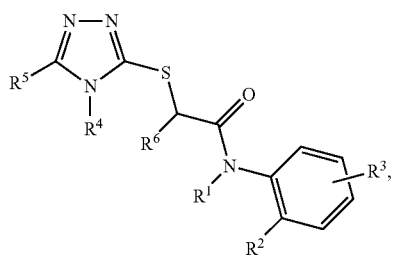

wherein: $R^1$ is hydrogen or is taken together with $R_2$ to be alkanediyl$_{(C1-4)}$, alkenediyl$_{(C1-4)}$, or a substituted version of either of these groups; $R_2$ is hydrogen, alkyl$_{(C≤5)}$, substituted alkyl$_{(C≤5)}$, or is taken together with $R_1$ as defined above; $R_3$ is hydrogen, hydroxy, nitro, halo, alkyl$_{(C≤5)}$, substituted alkyl$_{(C≤5)}$, alkenyl$_{(C≤5)}$, or substituted alkenyl$_{(C≤5)}$; $R_4$ is alkyl$_{(C≤5)}$, alkenyl$_{(C≤5)}$, aryl$_{(C≤10)}$, aralkyl$_{(C≤10)}$, heteroaryl$_{(C≤8)}$, heteroaralkyl$_{(C≤8)}$, or substituted versions of any of these groups; $R_5$ is heteroaryl$_{(C≤6)}$ or substituted heteroaryl$_{(C≤6)}$; and $R_6$ is hydrogen, alkyl$_{(C≤5)}$, substituted alkyl$_{(C≤5)}$, alkenyl$_{(C≤5)}$, or substituted alkenyl$_{(C≤5)}$, or a salt or tautomer of the formula; provided that if $R_1$ and $R_2$ are H and $R_5$ is 3-pyridinyl, then $R_3$ cannot be ethyl.

In a further aspect, the compound is further defined by the formula:

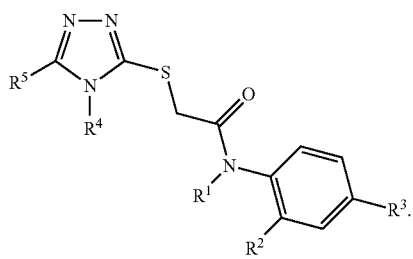

In a further aspect, the compound is further defined by the formula:

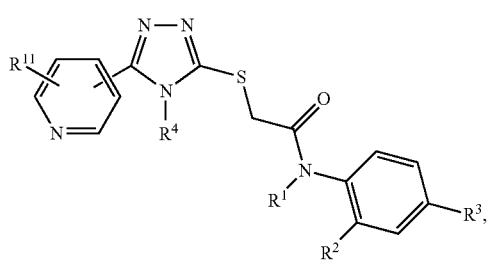

wherein $R^{11}$ is —H, —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$.

In a further aspect, the compound is further defined by the formula:

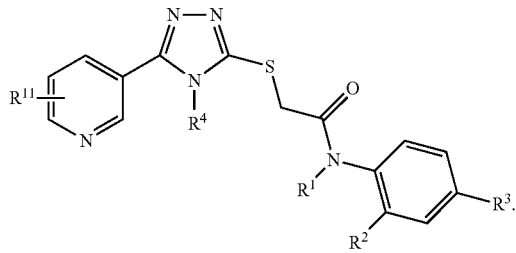

In a further aspect, the compound is further defined by the formula:

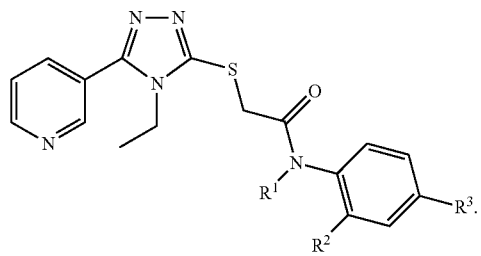

In a further aspect, the compound is further defined by the formula:

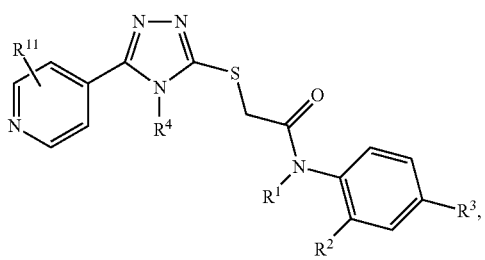

wherein: $R_1$ is hydrogen or is taken together with $R_2$ to be alkanediyl$_{(C1-4)}$, alkenediyl$_{(C1-4)}$, or a substituted version of either of these groups; $R_2$ is hydrogen, alkyl$_{(C≤5)}$, substituted alkyl$_{(C≤5)}$, or is taken together with $R_1$ as defined above; $R_3$ is hydrogen, hydroxy, nitro, halo, alkyl$_{(C≤5)}$, substituted alkyl$_{(C≤5)}$, alkenyl$_{(C≤5)}$, or substituted alkenyl$_{(C≤5)}$; $R_4$ is alkyl$_{(C≤5)}$, alkenyl$_{(C≤5)}$, aryl$_{(C≤10)}$, aralkyl$_{(C≤10)}$, heteroaryl$_{(C≤8)}$, heteroaralkyl$_{(C≤8)}$, or substituted versions of any of these groups; and $R^{11}$ is —H, —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$, or a salt or tautomer of the formula, wherein the compound is not:

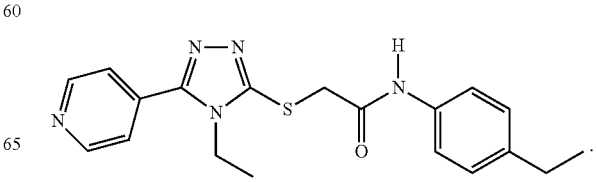

In a further aspect, the compound is further defined by the formula:

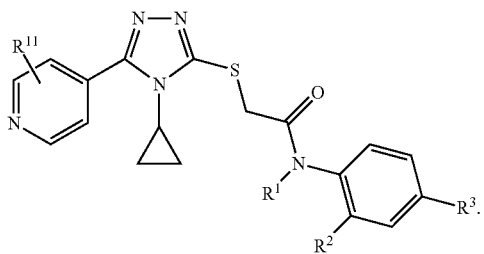

In various aspects, the invention relates to a compound having a structure represented by a formula:

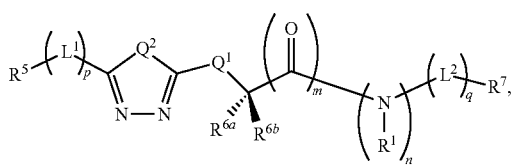

wherein m, n, p, and q are independently 0 or 1; wherein L and $L^2$ are independently divalent organic groups having from 1 to 8 non-hydrogen members; wherein $Q^1$ is —O—, —S—, —S(O)—, or —S(O)$_2$—; wherein $Q^2$ is —O—, —S—, or —NR$^4$; wherein $R^7$ is optionally substituted and selected from monocyclic aryl, bicyclic aryl, monocyclic heteroaryl, bicyclic heteroaryl, and tricyclic heteroaryl; wherein $R^1$ is hydrogen, optionally substituted C1-C4 alkyl, optionally substituted phenyl, optionally substituted benzyl, or a structure represented by a formula selected from:

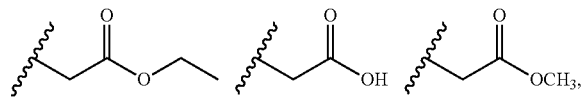

or $R^1$ is taken together with a substituent of $R^7$ to form a five-, six-, or seven-membered heterocylcoalkyl ring; wherein $R^4$ is optionally substituted and selected from (C1-C5) alkyl, (C1-C5) alkenyl, (C6-C10) aryl, (≤C10) aralkyl, (≤C8) heteroaryl, and (≤C8) heteroaralkyl; wherein $R^5$ is optionally substituted aryl or optionally substituted (≤C6) heteroaryl; and wherein $R^{6a}$ and $R^{6b}$ are independently selected from hydrogen, optionally substituted (C1-C5) alkyl, or optionally substituted (C1-C5) alkenyl, or $R^{6a}$ and $R^{6b}$, along with the intermediate carbon, together comprise a C3-C6 cycloalkyl ring or a C2-C5 heterocylcoalkyl ring; or a salt or tautomer thereof, wherein the compound is not:

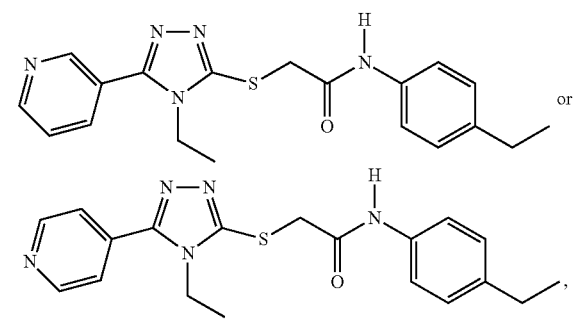

In various aspects, the invention relates to a compound having a structure represented by a formula:

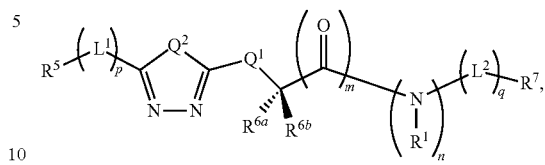

wherein m, n, p, and q are independently 0 or 1; wherein $L^1$ and $L^2$ are independently divalent organic groups having from 1 to 8 non-hydrogen members; wherein $Q^1$ is —O—, —S—, —S(O)—, or —S(O)$_2$—; wherein $Q^2$ is —O—, —S—, or —NR$^4$; wherein $R^7$ is optionally substituted and selected from monocyclic aryl, bicyclic aryl, monocyclic heteroaryl, bicyclic heteroaryl, and tricyclic heteroaryl; wherein $R^1$ is hydrogen, optionally substituted C1-C4 alkyl, optionally substituted phenyl, optionally substituted benzyl, or a structure represented by a formula selected from:

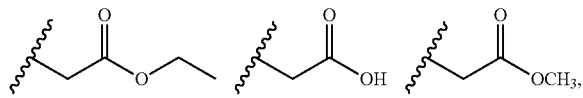

or $R^1$ is taken together with a substituent of $R^7$ to form a five-, six-, or seven-membered heterocylcoalkyl ring; wherein $R^4$ is optionally substituted and selected from (C1-C5) alkyl, (C1-C5) alkenyl, (C6-C10) aryl, (≤C10) aralkyl, (≤C8) heteroaryl, and (≤C8) heteroaralkyl; wherein $R^5$ is optionally substituted aryl or optionally substituted (≤C6) heteroaryl; and wherein $R^{6a}$ and $R^{6b}$ are independently selected from hydrogen, optionally substituted (C1-C5) alkyl, or optionally substituted (C1-C5) alkenyl, or $R^{6a}$ and $R^{6b}$, along with the intermediate carbon, together comprise a C3-C6 cycloalkyl ring or a C2-C5 heterocylcoalkyl ring; or a salt or tautomer thereof, wherein the compound is not:

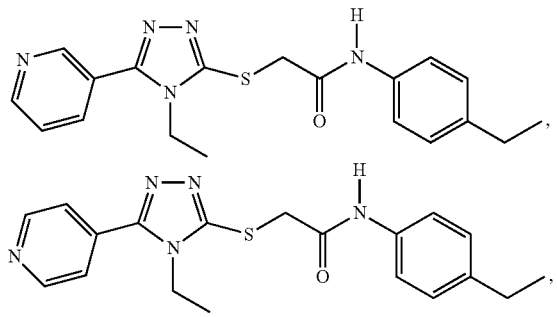

or wherein the compound is not:

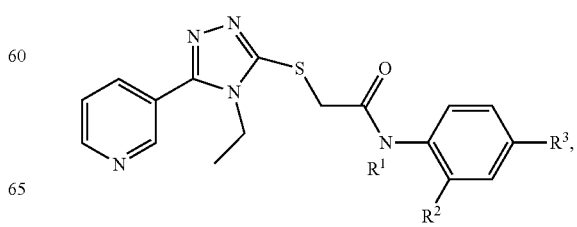

wherein: R¹ is hydrogen or is taken together with R² to be alkanediyl$_{(C1-4)}$, alkenediyl$_{(C1-4)}$, or a substituted version of either of these groups; R² is hydrogen or is taken together with R¹ as defined above; and R³ is hydrogen, hydroxy, nitro, halo, alkyl$_{(C≤8)}$, substituted alkyl$_{(C≤8)}$, alkenyl$_{(C≤8)}$, or substituted alkenyl$_{(C≤8)}$; or a salt or tautomer of the formula.

In a further aspect, the compound comprises:

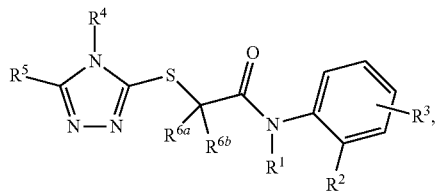

wherein R² is hydrogen, hydroxy, nitro, halo, optionally substituted (C1-C5) alkyl, optionally substituted (C2-C5) alkenyl, or optionally substituted (C2-C5) alkynyl; or R² is taken together with R₁ to be optionally substituted (C1-C4) alkanediyl or optionally substituted (C1-C4) alkenediyl; and wherein R³ is hydrogen, hydroxy, nitro, halo, optionally substituted (C1-C5) alkyl, optionally substituted (C2-C5) alkenyl, or optionally substituted (C2-C5) alkynyl.

In a further aspect, the compound comprises:

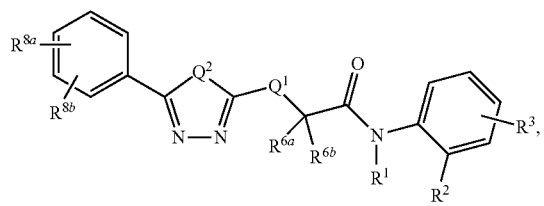

wherein R² is hydrogen, hydroxy, nitro, halo, optionally substituted (C1-C5) alkyl, optionally substituted (C2-C5) alkenyl, or optionally substituted (C2-C5) alkynyl; or R² is taken together with R¹ to be optionally substituted (C1-C4) alkanediyl or optionally substituted (C1-C4) alkenediyl; wherein R³ is hydrogen, hydroxy, nitro, halo, optionally substituted (C1-C5) alkyl, optionally substituted (C2-C5) alkenyl, or optionally substituted (C2-C5) alkynyl; and wherein R$^{8a}$ and R$^{8b}$ are independently selected from hydrogen, hydroxy, nitro, halo, optionally substituted (C1-C5) alkyl, or optionally substituted (C1-C5) alkenyl; or R$^{8a}$ and R$^{8b}$ are positioned on adjacent carbons and are taken together to be optionally substituted (C1-C4) alkanediyl or optionally substituted (C1-C4) alkenediyl.

In a further aspect, the compound comprises:

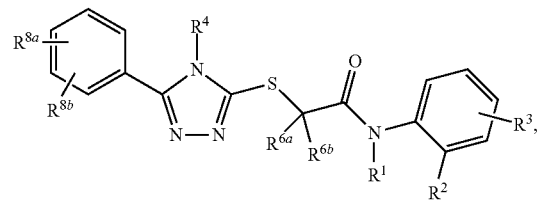

wherein R⁴ is optionally substituted and selected from (C1-C5) alkyl, (C1-C5) alkenyl, (C6-C10) aryl, (≤C10) aralkyl, (≤C8) heteroaryl, and (≤C8) heteroaralkyl.

In a further aspect, wherein the compound is not:

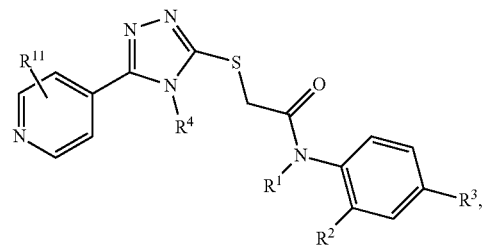

wherein: R₁ is hydrogen or is taken together with R₂ to be alkanediyl$_{(C1-4)}$, alkenediyl$_{(C1-4)}$, or a substituted version of either of these groups; R₂ is hydrogen, alkyl$_{(C≤5)}$, substituted alkyl$_{(C≤5)}$, or is taken together with R₁ as defined above; R₃ is hydrogen, hydroxy, nitro, halo, alkyl$_{(C≤5)}$, substituted alkyl$_{(C≤5)}$, alkenyl$_{(C≤5)}$, or substituted alkenyl$_{(C≤5)}$; R₄ is alkyl$_{(C≤5)}$, alkenyl$_{(C≤5)}$, aryl$_{(C≤10)}$, aralkyl$_{(C≤10)}$, heteroaryl$_{(C≤8)}$, heteroaralkyl$_{(C≤8)}$, or substituted versions of any of these groups; and R¹¹ is —H, —OH, —F, —Cl, —Br, —I, —NH₂, —NO₂, —CO₂H, —CO₂CH₃, —CN, —SH, —OCH₃, —OCH₂CH₃, —C(O)CH₃, —N(CH₃)₂, —C(O)NH₂, —OC(O)CH₃, or —S(O)₂NH₂, or a salt or tautomer of the formula.

In a further aspect, the compound comprises:

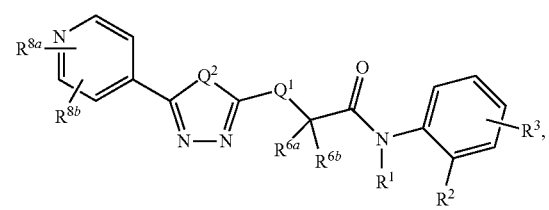

wherein R² is hydrogen, hydroxy, nitro, halo, optionally substituted (C1-C5) alkyl, optionally substituted (C2-C5) alkenyl, or optionally substituted (C2-C5) alkynyl; or R² is taken together with R¹ to be optionally substituted (C1-C4) alkanediyl or optionally substituted (C1-C4) alkenediyl; wherein R³ is hydrogen, hydroxy, nitro, halo, optionally substituted (C1-C5) alkyl, optionally substituted (C2-C5) alkenyl, or optionally substituted (C2-C5) alkynyl; and wherein R$^{8a}$ and R$^{8b}$ are independently selected from hydrogen, hydroxy, nitro, halo, optionally substituted (C1-C5) alkyl, or optionally substituted (C1-C5) alkenyl; or R$^{8a}$ and R$^{8b}$ are positioned on adjacent carbons and are taken together to be optionally substituted (C1-C4) alkanediyl or optionally substituted (C1-C4) alkenediyl.

In a further aspect, the compound comprises:

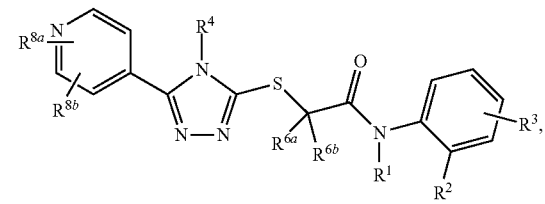

wherein R⁴ is optionally substituted and selected from (C1-C5) alkyl, (C1-C5) alkenyl, (C6-C10) aryl, (≤C10) aralkyl, (≤C8) heteroaryl, and (≤C8) heteroaralkyl.

In a further aspect, the compound comprises:

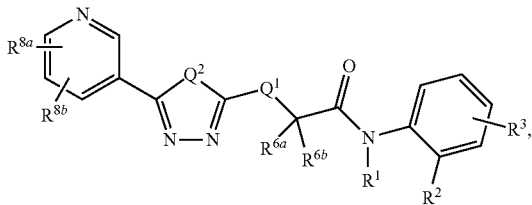

wherein R² is hydrogen, hydroxy, nitro, halo, optionally substituted (C1-C5) alkyl, optionally substituted (C2-C5) alkenyl, or optionally substituted (C2-C5) alkynyl; or R² is taken together with R¹ to be optionally substituted (C1-C4) alkanediyl or optionally substituted (C1-C4) alkenediyl; wherein R³ is hydrogen, hydroxy, nitro, halo, optionally substituted (C1-C5) alkyl, optionally substituted (C2-C5) alkenyl, or optionally substituted (C2-C5) alkynyl; and wherein $R^{8a}$ and $R^{8b}$ are independently selected from hydrogen, hydroxy, nitro, halo, optionally substituted (C1-C5) alkyl, or optionally substituted (C1-C5) alkenyl; or $R^{8a}$ and $R^{8b}$ are positioned on adjacent carbons and are taken together to be optionally substituted (C1-C4) alkanediyl or optionally substituted (C1-C4) alkenediyl.

In a further aspect, the compound comprises:

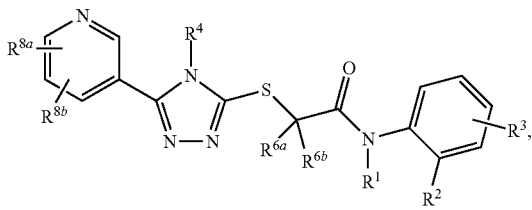

wherein R⁴ is optionally substituted and selected from (C1-C5) alkyl, (C1-C5) alkenyl, (C6-C10) aryl, (≤C10) aralkyl, (≤C8) heteroaryl, and (≤C8) heteroaralkyl.

In a further aspect, the compound comprises:

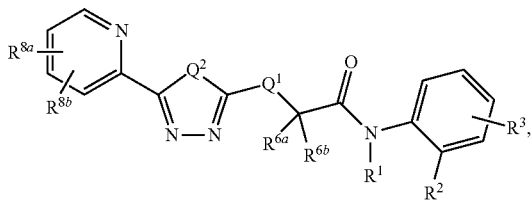

wherein R² is hydrogen, hydroxy, nitro, halo, optionally substituted (C1-C5) alkyl, optionally substituted (C2-C5) alkenyl, or optionally substituted (C2-C5) alkynyl; or R² is taken together with R¹ to be optionally substituted (C1-C4) alkanediyl or optionally substituted (C1-C4) alkenediyl; wherein R³ is hydrogen, hydroxy, nitro, halo, optionally substituted (C1-C5) alkyl, optionally substituted (C2-C5) alkenyl, or optionally substituted (C2-C5) alkynyl; and wherein $R^{8a}$ and $R^{8b}$ are independently selected from hydrogen, hydroxy, nitro, halo, optionally substituted (C1-C5) alkyl, or optionally substituted (C1-C5) alkenyl; or $R^{8a}$ and $R^{8b}$ are positioned on adjacent carbons and are taken together to be optionally substituted (C1-C4) alkanediyl or optionally substituted (C1-C4) alkenediyl.

In a further aspect, the compound comprises:

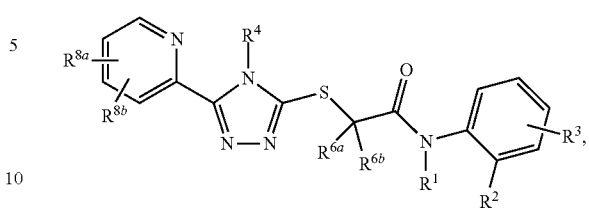

wherein R⁴ is optionally substituted and selected from (C1-C5) alkyl, (C1-C5) alkenyl, (C6-C10) aryl, (≤C10) aralkyl, (≤C8) heteroaryl, and (≤C8) heteroaralkyl.

In a further aspect, the compound comprises:

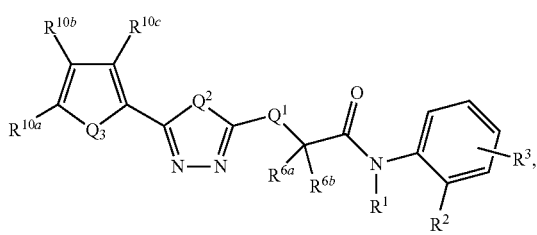

wherein Q³ is —O—, —S—, or —NR⁹; wherein R² is hydrogen, hydroxy, nitro, halo, optionally substituted (C1-C5) alkyl, optionally substituted (C2-C5) alkenyl, or optionally substituted (C2-C5) alkynyl; or R² is taken together with R¹ to be optionally substituted (C1-C4) alkanediyl or optionally substituted (C1-C4) alkenediyl; wherein R³ is hydrogen, hydroxy, nitro, halo, optionally substituted (C1-C5) alkyl, optionally substituted (C2-C5) alkenyl, or optionally substituted (C2-C5) alkynyl; wherein R⁹ is optionally substituted and selected from (C1-C5) alkyl, (C1-C5) alkenyl, (C6-C10) aryl, (≤C10) aralkyl, (≤C8) heteroaryl, and (≤C8) heteroaralkyl; and wherein each of $R^{10a}$, $R^{10b}$, and $R^{10c}$ is independently selected from hydrogen, hydroxy, nitro, halo, optionally substituted (C1-C5) alkyl, or optionally substituted (C1-C5) alkenyl; or any two of $R^{10a}$, $R^{10b}$ and $R^{10c}$ are positioned on adjacent carbons and are taken together to be optionally substituted (C1-C4) alkanediyl or optionally substituted (C1-C4) alkenediyl.

In a further aspect, the compound comprises:

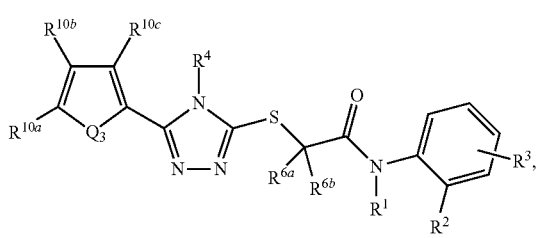

wherein R⁴ is optionally substituted and selected from (C1-C5) alkyl, (C1-C5) alkenyl, (C6-C10) aryl, (≤C10) aralkyl, (≤C8) heteroaryl, and (≤C8) heteroaralkyl.

In a further aspect, the compound comprises:

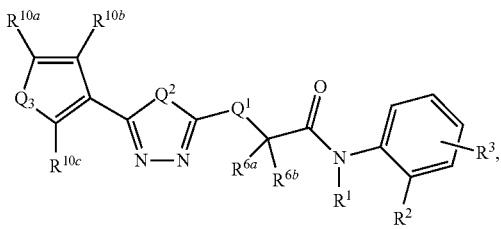

wherein $Q^3$ is —O—, —S—, or —NR$^9$; wherein $R^2$ is hydrogen, hydroxy, nitro, halo, optionally substituted (C1-C5) alkyl, optionally substituted (C2-C5) alkenyl, or optionally substituted (C2-C5) alkynyl; or $R^2$ is taken together with $R^1$ to be optionally substituted (C1-C4) alkanediyl or optionally substituted (C1-C4) alkenediyl; wherein $R^3$ is hydrogen, hydroxy, nitro, halo, optionally substituted (C1-C5) alkyl, optionally substituted (C2-C5) alkenyl, or optionally substituted (C2-C5) alkynyl; wherein $R^9$ is optionally substituted and selected from (C1-C5) alkyl, (C1-C5) alkenyl, (C6-C10) aryl, (≤C10) aralkyl, (≤C8) heteroaryl, and (≤C8) heteroaralkyl; and wherein each of $R^{10a}$, $R^{10b}$, and $R^{10c}$ is independently selected from hydrogen, hydroxy, nitro, halo, optionally substituted (C1-C5) alkyl, or optionally substituted (C1-C5) alkenyl; or any two of $R^{10a}$, $R^{10b}$, and $R^{10c}$ are positioned on adjacent carbons and are taken together to be optionally substituted (C1-C4) alkanediyl or optionally substituted (C1-C4) alkenediyl.

In a further aspect, the compound comprises:

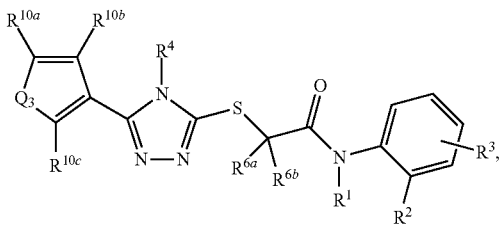

wherein $R^4$ is optionally substituted and selected from (C1-C5) alkyl, (C1-C5) alkenyl, (C6-C10) aryl, (≤C10) aralkyl, (≤C8) heteroaryl, and (≤C8) heteroaralkyl.

In a further aspect, the compound binds to and/or modulates insect Orco ion channels.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Structure

Suitable substituents are described below.

a. L$^1$ Groups

In one aspect, L$^1$ is a divalent organic groups having from 1 to 8 non-hydrogen members. For example, L can have 1, 2, 3, 4, 5, 6, 7, or 8 non-hydrogen members. In a further aspect, L$^1$ is selected from

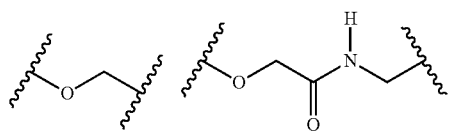

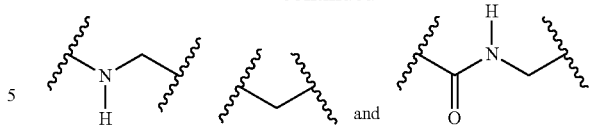

In a further aspect, L$^1$ is present when p is 1. In a further aspect, L is absent when p is 0.

b. L$^2$ Groups

In one aspect, L$^2$ is a divalent organic groups having from 1 to 8 non-hydrogen members. For example, L$^2$ can have 1, 2, 3, 4, 5, 6, 7, or 8 non-hydrogen members. In a further aspect, L$^2$ is selected from

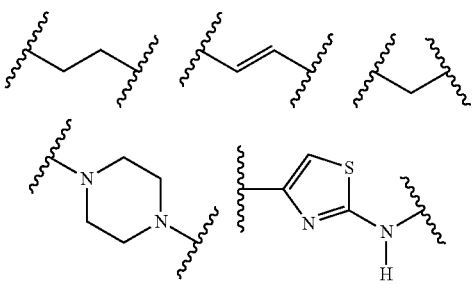

In a further aspect, L$^2$ is present when q is 1. In a further aspect, L$^2$ is absent when q is 0.

c. Q$^1$ Groups

In one aspect, Q$^1$ is —O—, —S—, —S(O)—, or —S(O)$_2$—. In a further aspect, Q$^1$ is —O— or —S—. In a further aspect, Q$^1$ is —O—. In a further aspect, Q$^1$ is —S—. In a further aspect, Q$^1$ is —S(O)—. In a further aspect, Q$^1$ is —S(O)$_2$—.

d. Q$^2$ Groups

In one aspect, Q$^2$ is —O—, —S—, or —NR$^4$. In a further aspect, Q$^2$ is —O—. In a further aspect, Q$^2$ is —S—. In a further aspect, Q$^2$ is —NR$^4$.

e. Q$^3$ Groups

In one aspect, Q$^3$ is —O—, —S—, or —NR$^9$. In a further aspect, Q$^3$ is —O—. In a further aspect, Q$^3$ is —S—. In a further aspect, Q$^3$ is —NR$^9$.

f. R$^1$ Groups

In one aspect, R$^1$ is hydrogen, optionally substituted C1-C4 alkyl, optionally substituted phenyl, optionally substituted benzyl, or a structure represented by a formula selected from:

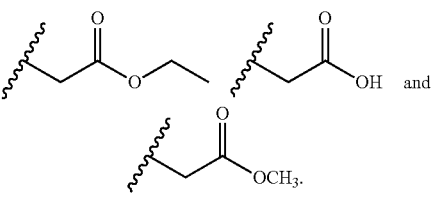

In a further aspect, R is hydrogen.

In a further aspect, R is methyl, ethyl, n-propyl, i-propyl, n-butyl, i-butyl, s-butyl, t-butyl, optionally substituted phenyl, optionally substituted benzyl, or a structure represented by a formula selected from:

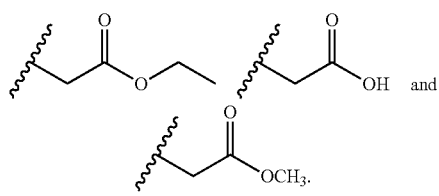

In a further aspect, R is hydrogen, and wherein $R^2$ is hydrogen, hydroxy, nitro, halo, optionally substituted (C1-C5) alkyl, optionally substituted (C2-C5) alkenyl, or optionally substituted (C2-C5) alkynyl.

In a further aspect, $R^1$ is taken together with a substituent of $R^7$ to form a five-, six-, or seven-membered heterocylcoalkyl ring. In a further aspect, $R^1$ is taken together with a substituent of $R^7$ to be optionally substituted (C1-C4) alkanediyl or optionally substituted (C1-C4) alkenediyl. In a further aspect, $R^1$ is hydrogen or is taken together with $R^2$ to be alkanediyl$_{(C1-4)}$, alkenediyl$_{(C1-4)}$, or a substituted version of either of these groups. In a further aspect, $R_1$ and $R_2$ are taken together to be ethanediyl.

g. $R^2$ Groups

In one aspect, $R^2$ is hydrogen, hydroxy, nitro, halo, optionally substituted (C1-C5) alkyl, or optionally substituted (C1-C5) alkenyl. In a further aspect, $R_2$ is hydrogen. In a further aspect, $R^2$ is hydrogen or is taken together with $R^1$ as defined above.

h. $R^3$ Groups

In one aspect, $R^3$ is hydrogen, hydroxy, nitro, halo, optionally substituted (C1-C5) alkyl, or optionally substituted (C1-C5) alkenyl. In a further aspect, $R_3$ is hydrogen. In a further aspect, $R_3$ is halo, for example, fluoro, chloro, or bromo. In a further aspect, $R_3$ is alkyl$_{(C \leq 5)}$. In a further aspect, the $R_3$ alkyl$_{(C \leq 5)}$ has no quaternary carbon atoms. In a further aspect, $R_3$ is methyl, ethyl, n-propyl, or isopropyl. In a further aspect, $R_3$ is alkenyl$_{(C \leq 5)}$. In a further aspect, $R_3$ is vinyl. In a further aspect, $R^3$ is hydrogen, hydroxy, nitro, halo, alkyl$_{(C \leq 5)}$, substituted alkyl$_{(C \leq 8)}$, alkenyl$_{(C \leq 8)}$, or substituted alkenyl$_{(C \leq 8)}$.

i. $R^4$ Groups

In one aspect, $R^4$ is optionally substituted and selected from (C1-C5) alkyl, (C1-C5) alkenyl, (C6-C10) aryl, ($\leq$C10) aralkyl, ($\leq$C8) heteroaryl, and ($\leq$C8) heteroaralkyl. In a further aspect, $R_4$ is alkyl$_{(C \leq 5)}$, alkenyl$_{(C \leq 5)}$, aryl$_{(C \leq 10)}$, aralkyl$_{(C \leq 10)}$, heteroaryl$_{(C \leq 8)}$, heteroaralkyl$_{(C \leq 8)}$, or substituted versions of any of these groups. In a further aspect, $R_4$ is alkyl$_{(C \leq 5)}$, for example, ethyl, propyl, or cyclopropyl. In a further aspect, $R_4$ is alkenyl$_{(C \leq 5)}$, for example, allyl. In a further aspect, $R^4$ comprises a structure represented by a formula selected from.

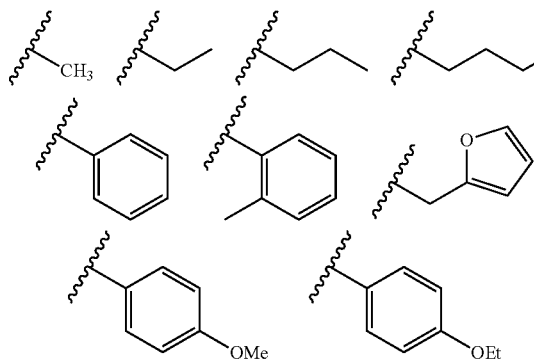

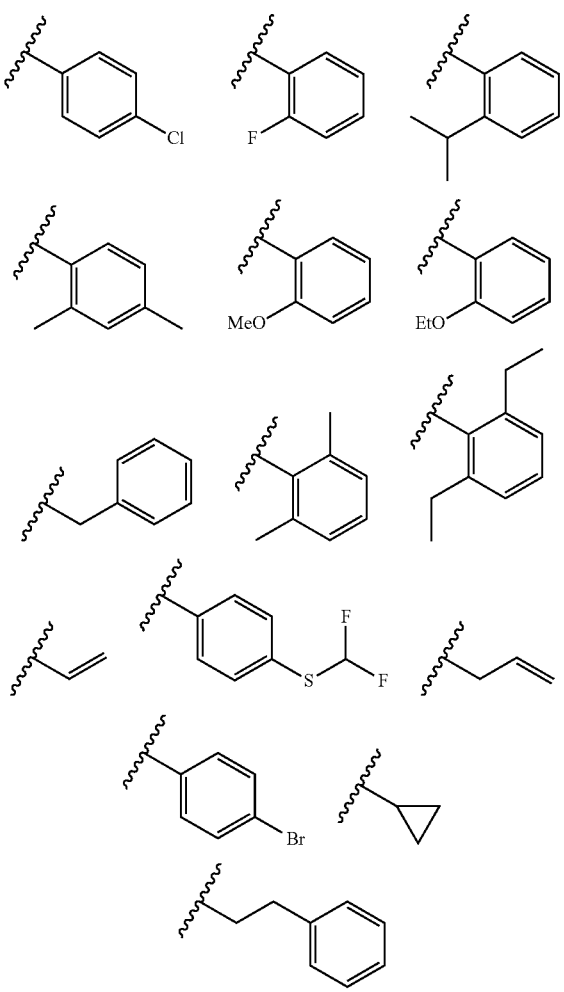

j. $R^5$ Groups

In one aspect, $R^5$ is optionally substituted aryl or optionally substituted ($\leq$C6) heteroaryl. In a further aspect, $R_5$ is pyridinyl, for example, 3-pyridinyl or 4-pyridinyl. In a further aspect, $R_5$ is pyrazolyl or methylpyrazolyl.

In a further aspect, $R^5$ is selected from:

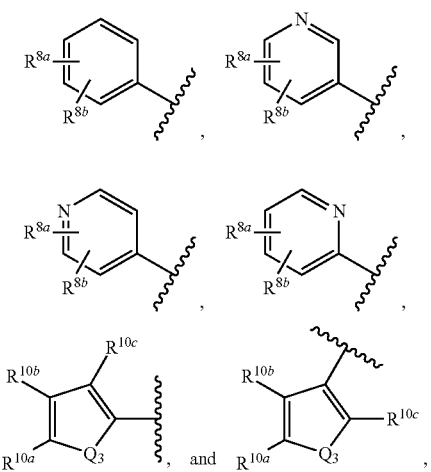

In a further aspect, R⁵ is selected from:

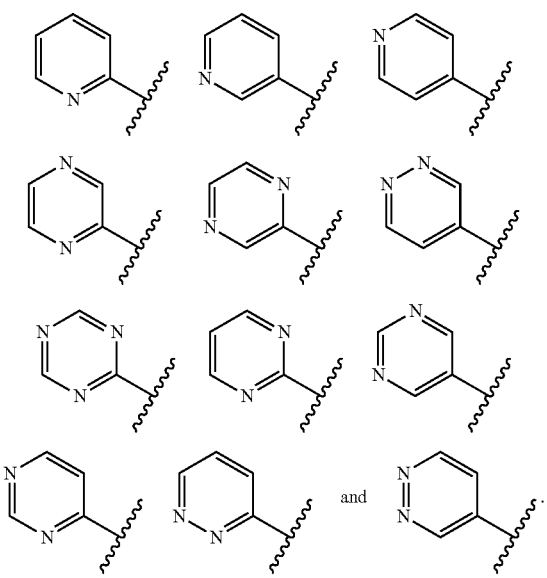

In a further aspect R⁵ is selected from:

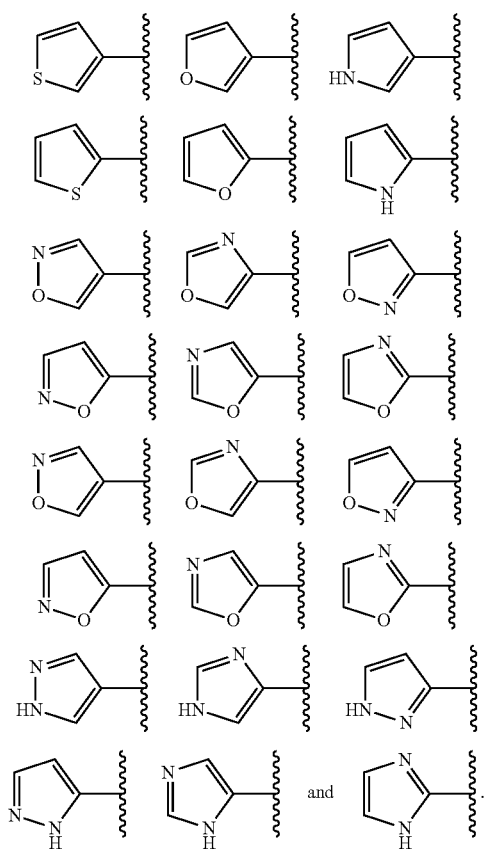

In a further aspect, R⁵ is selected from:

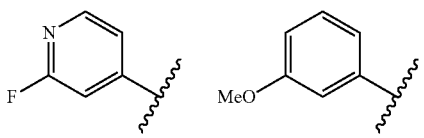

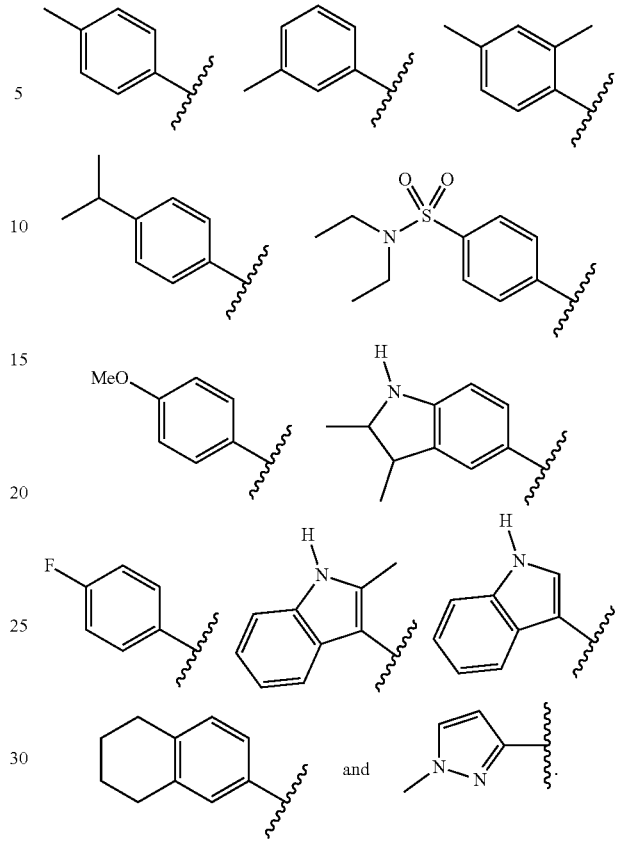

In a further aspect, R⁵ is substituted with 0-3 groups independently selected from hydroxy, nitro, halo, carboxyl, carboxy(C1-C4)alkyl, phenyl, benzyl, benzyloxy, amino, alkyl(C1-C4)amino, dialkyl(C1-C4, C1-C4)amino, C1-C4 alkyoxyl, C1-C5 alkyl, and C1-C5 alkenyl.

k. R⁶ Groups

In one aspect, R⁶ᵃ and R⁶ᵇ are independently selected from hydrogen, optionally substituted (C1-C5) alkyl, or optionally substituted (C1-C5) alkenyl. In a further aspect, R⁶ᵃ is hydrogen. In a further aspect, R⁶ᵇ is hydrogen. In a further aspect, R⁶ᵃ is non-hydrogen. In a further aspect, R⁶ᵇ is non-hydrogen. In a further aspect, R⁶ᵃ is optionally substituted (C1-C5) alkyl or optionally substituted (C1-C5) alkenyl. In a further aspect, R⁶ᵇ is optionally substituted (C1-C5) alkyl or optionally substituted (C1-C5) alkenyl.

In a further aspect, R⁶ᵃ is methyl, ethyl, n-propyl, i-propyl, n-butyl, i-butyl, s-butyl, or t-butyl. In a further aspect, R⁶ᵇ is methyl, ethyl, n-propyl, i-propyl, n-butyl, i-butyl, s-butyl, or t-butyl. In a further aspect, R⁶ᵃ and R⁶ᵇ, along with the intermediate carbon, together comprise a C3-C6 cycloalkyl ring or a C2-C5 heterocylcoalkyl ring.

l. R⁷ Groups

In one aspect, R⁷ is optionally substituted and selected from monocyclic aryl, bicyclic aryl, monocyclic heteroaryl, bicyclic heteroaryl, and tricyclic heteroaryl. In a further aspect, R⁷ is substituted. In a further aspect, R⁷ is unsubstituted. In a further aspect, R⁷ is monocyclic aryl or monocyclic heteroaryl. In a further aspect, R⁷ is bicyclic aryl, bicyclic heteroaryl, or tricyclic heteroaryl. In a further aspect, R⁷ is monocyclic aryl or bicyclic aryl. In a further aspect, R⁷ is monocyclic heteroaryl, bicyclic heteroaryl, or tricyclic heteroaryl.

In a further aspect, R⁷ is substituted with 0-3 groups independently selected from hydroxy, nitro, halo, carboxyl, carboxy(C1-C4)alkyl, phenyl, benzyl, benzyloxy, amino, alkyl(C1-C4)amino, dialkyl(C1-C4, C1-C4)amino, C1-C4 alkyoxyl, C1-C5 alkyl, C1-C5 alkenyl, and C1-C6 sulfonamido.
In a further aspect, $R^7$ comprises a structure represented by a formula selected from:
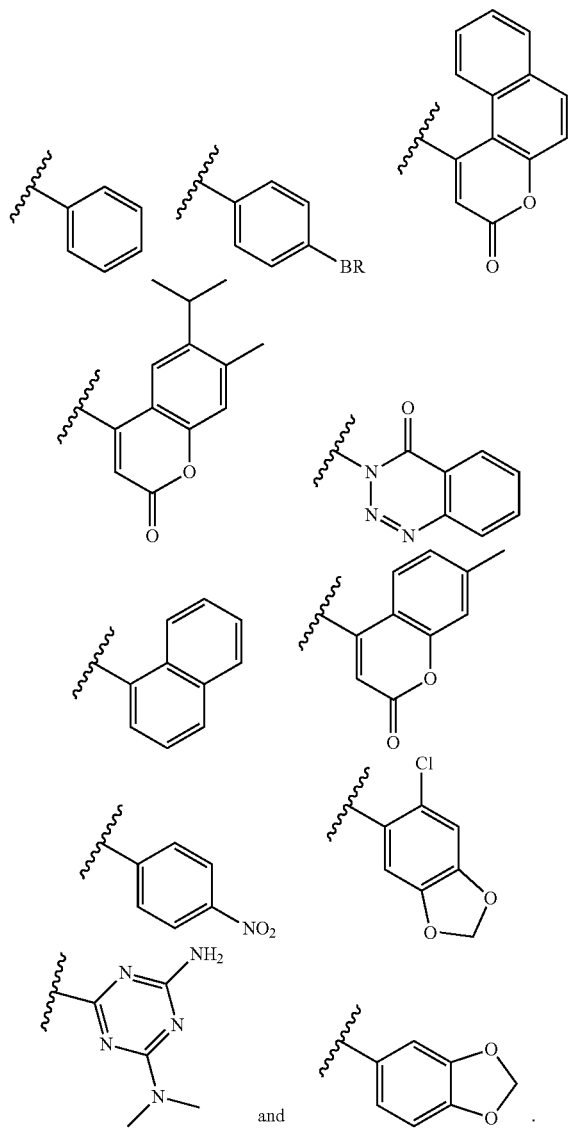
In a further aspect,
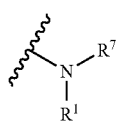
comprises a structure represented by a formula selected from:
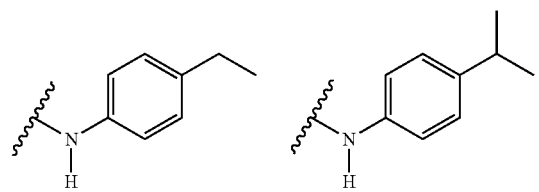
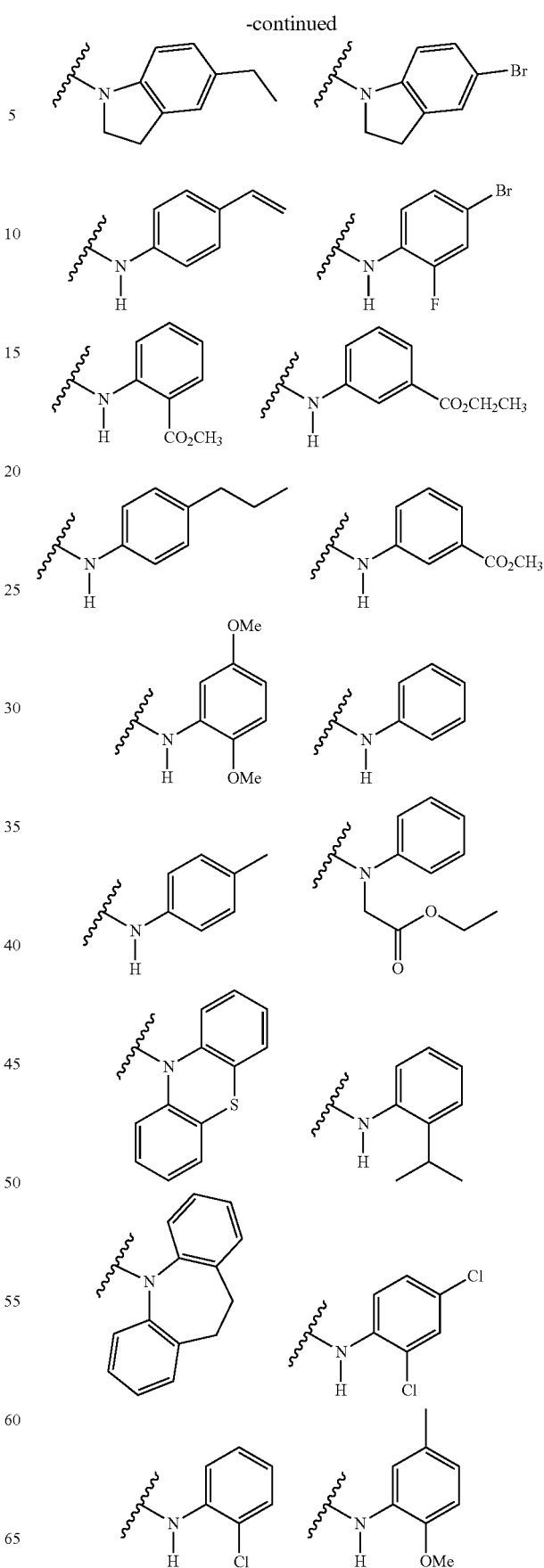

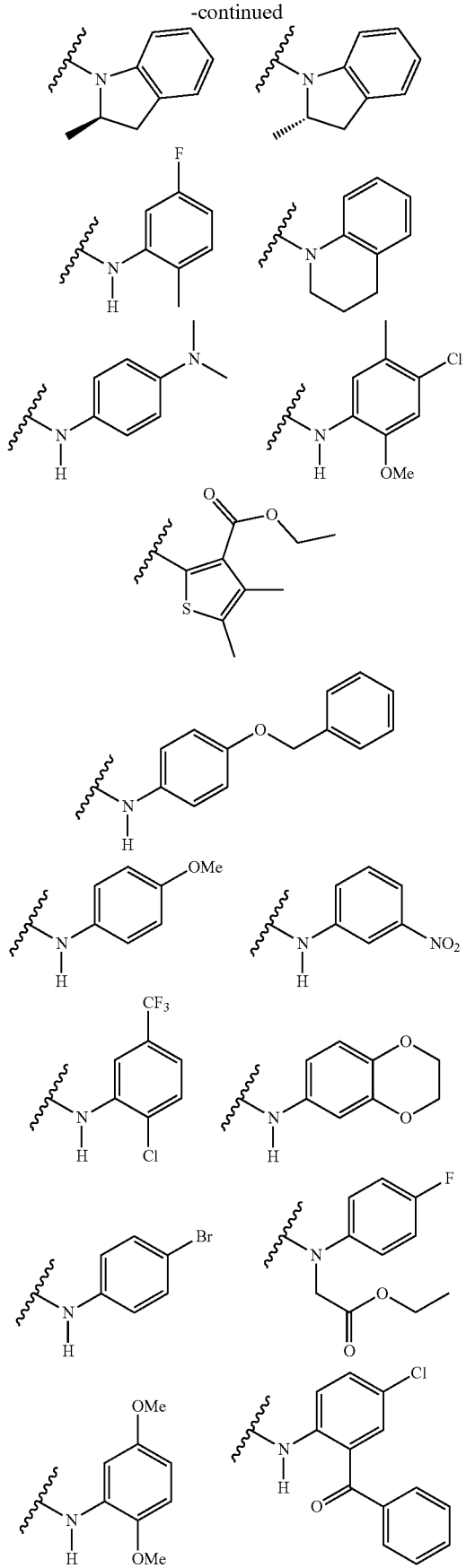
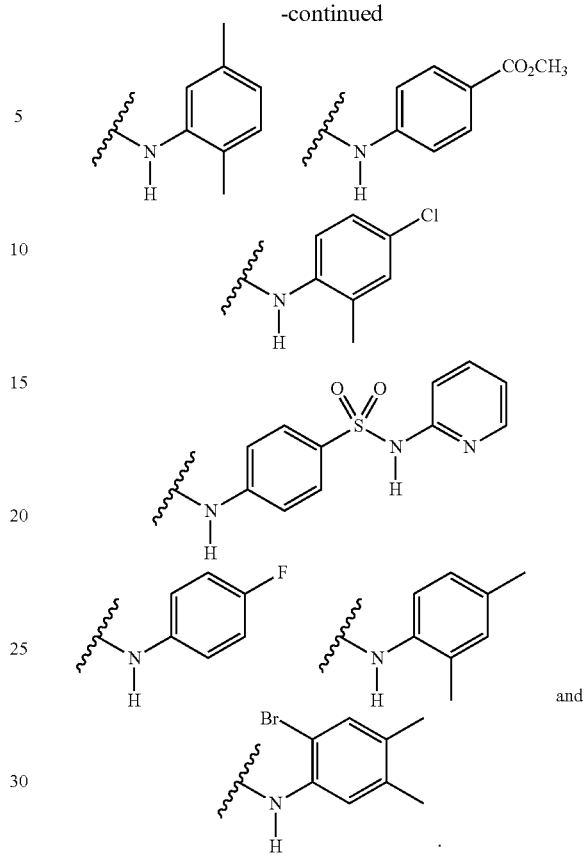

m. $R_5$ Groups

In one aspect, wherein each of $R^{8a}$ and $R^{8b}$ is independently selected from hydrogen, hydroxy, nitro, halo, optionally substituted (C1-C5) alkyl, or optionally substituted (C1-C5) alkenyl. In a further aspect, $R^{8a}$ and $R^{8b}$ are positioned on adjacent carbons and are taken together to be optionally substituted (C1-C4) alkanediyl or optionally substituted (C1-C4) alkenediyl.

n. $R^9$ Groups

In one aspect, $R^9$ is optionally substituted and selected from (C1-C5) alkyl, (C1-C5) alkenyl, (C6-C10) aryl, (≤C10) aralkyl, (≤C8) heteroaryl, and (≤C8) heteroaralkyl.

o. $R^{10}$ Groups

In one aspect, each of $R^{10a}$, $R^{10b}$, and $R^{10c}$ is independently selected from hydrogen, hydroxy, nitro, halo, optionally substituted (C1-C5) alkyl, or optionally substituted (C1-C5) alkenyl. In a further aspect, any two of $R^{10a}$, $R^{10b}$, and $R^{10c}$ are positioned on adjacent carbons and are taken together to be optionally substituted (C1-C4) alkanediyl or optionally substituted (C1-C4) alkenediyl.

p. $R^{11}$ Groups

In one aspect, $R^{11}$ is —H, —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, or —S(O)$_2$NH$_2$. In a further aspect, $R_7$ is hydrogen. In a further aspect, $R_7$ is fluoro.

2. Example Compounds

In various aspects, the disclosed compounds can be present having one or more structures represented by formulae listed below:

In one aspect, a disclosed compound can have the formula (I):
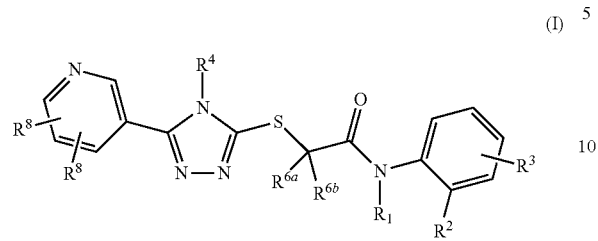
Exemplary compound within Formula (I) include, but are not limited to:
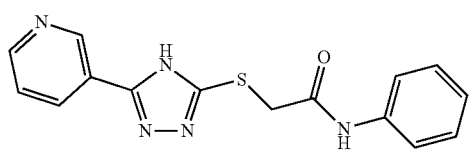
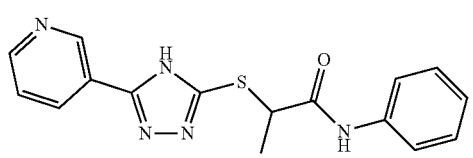
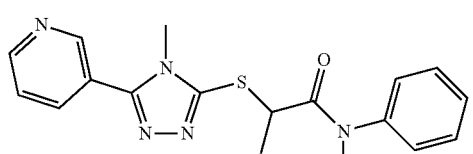
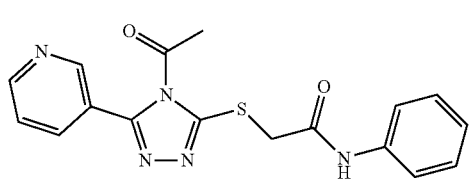
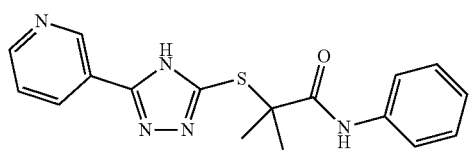
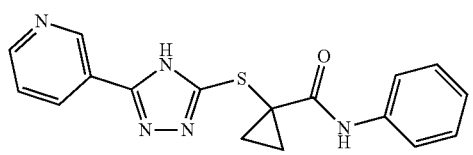
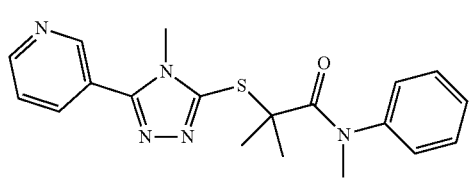
-continued
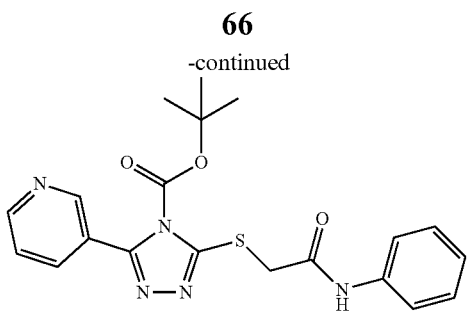
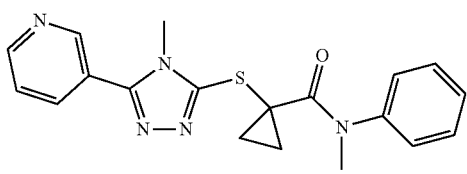
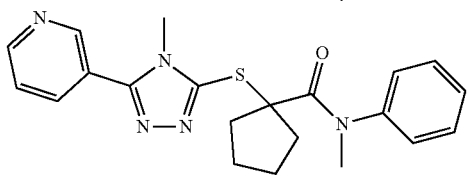
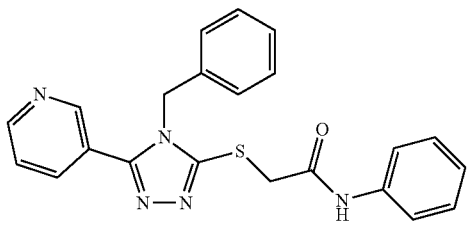
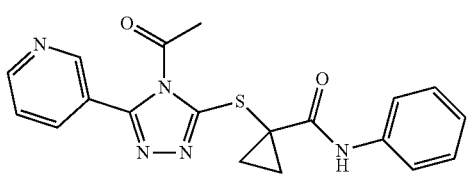
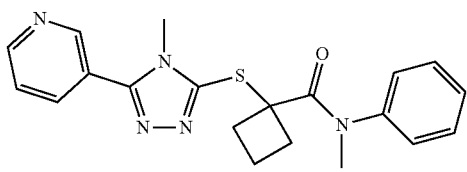
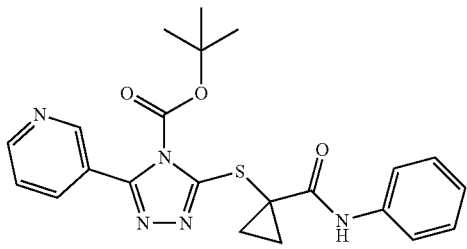
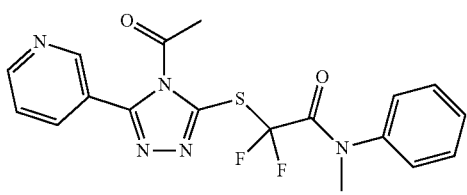

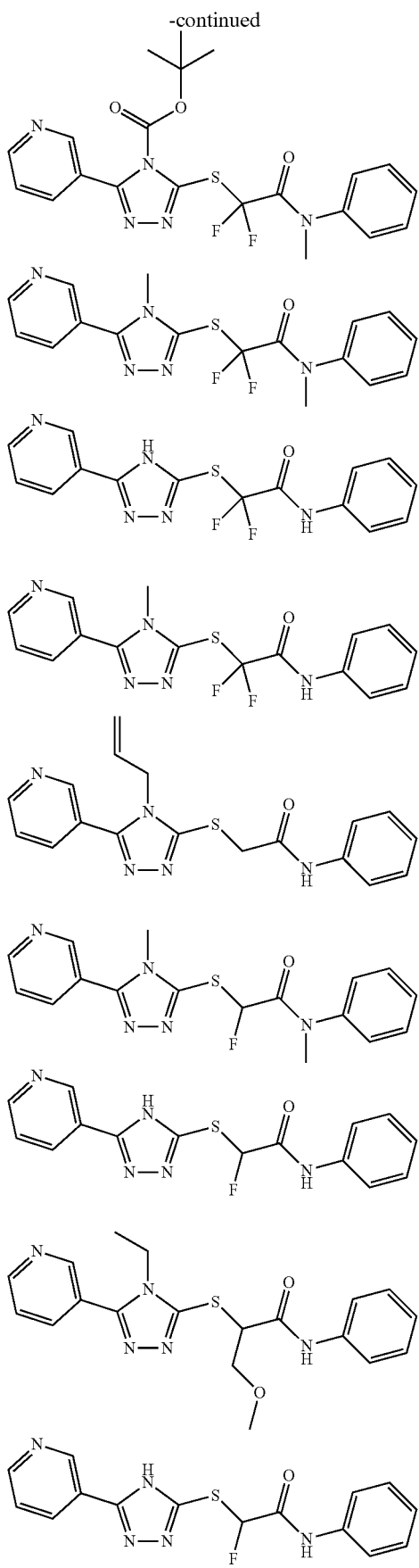
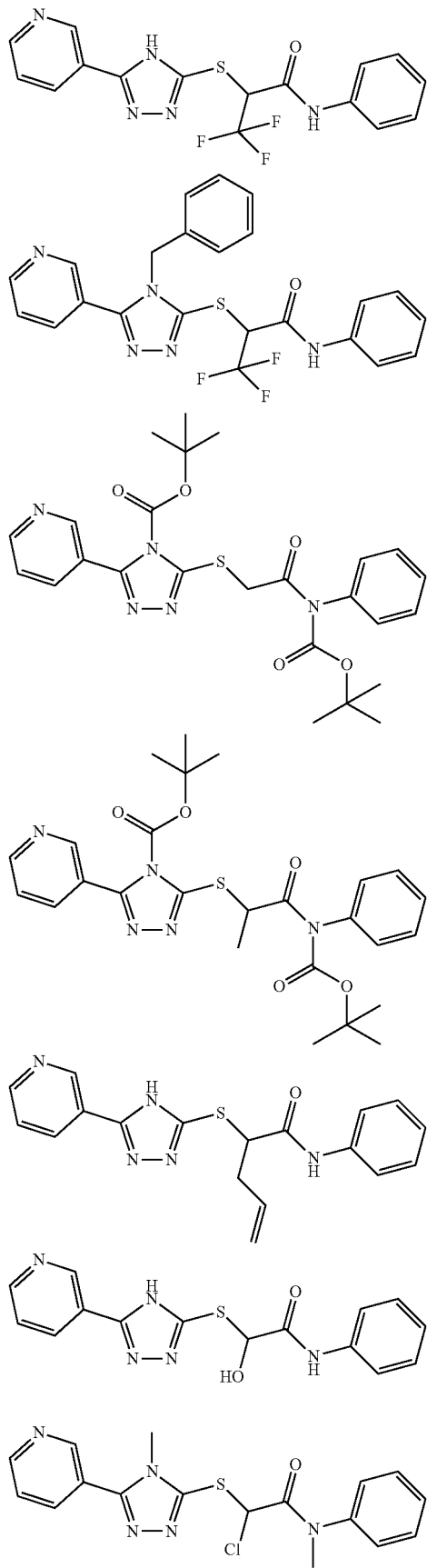

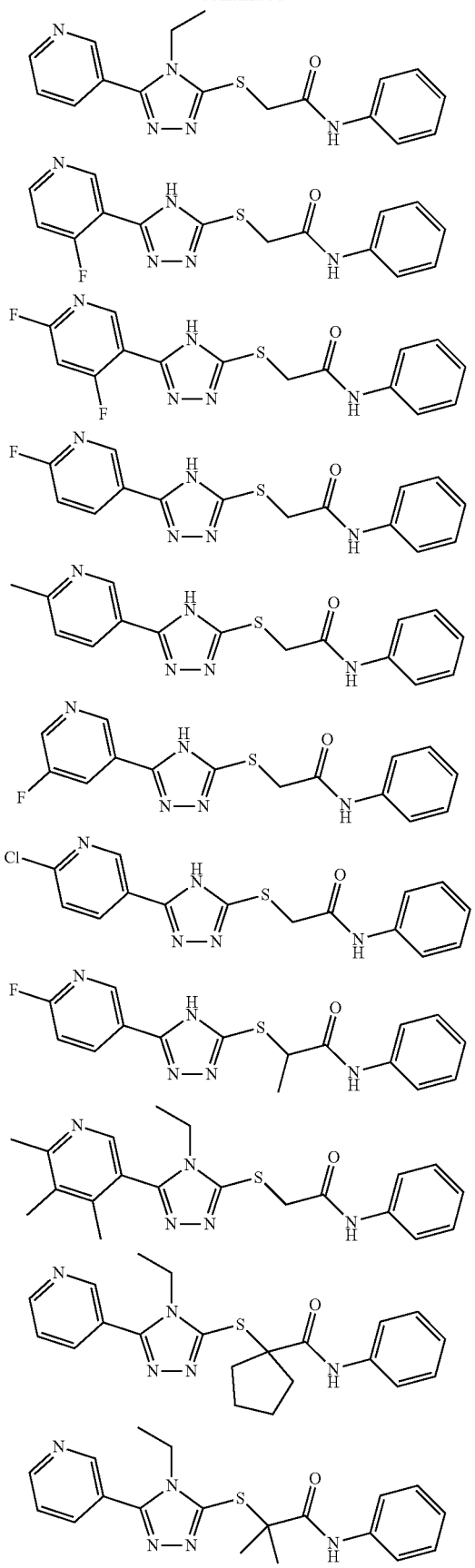
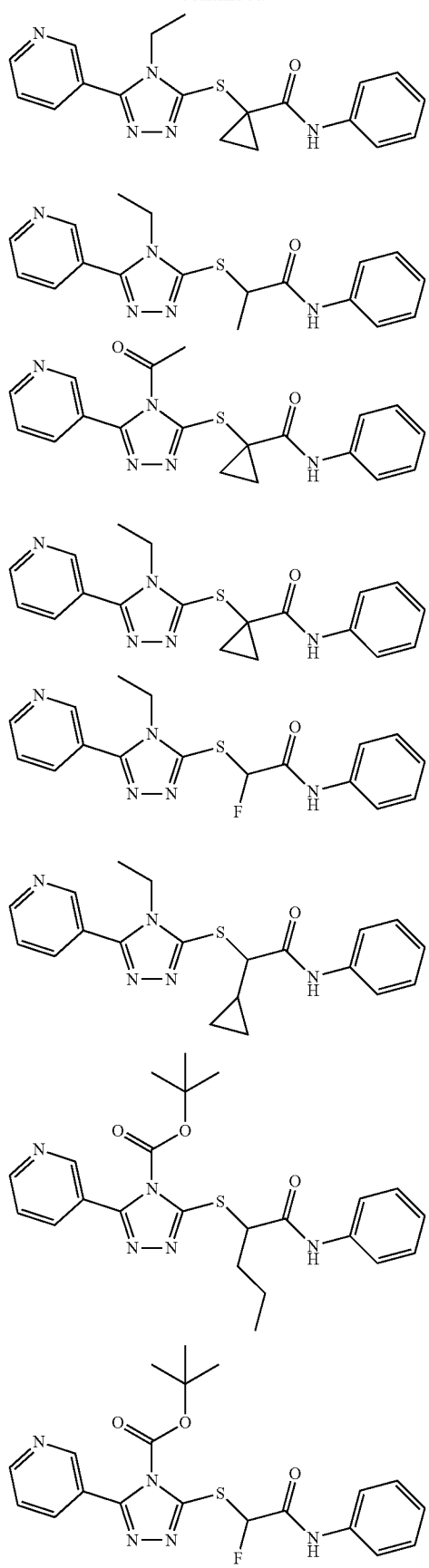

71
-continued
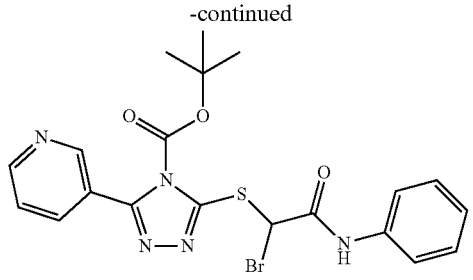
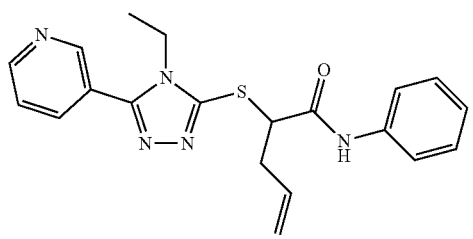
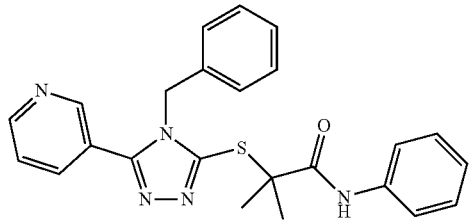
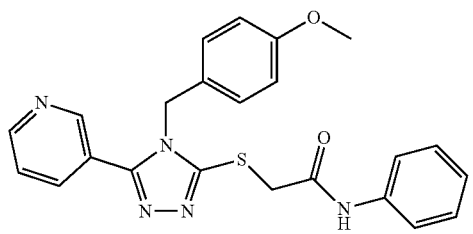
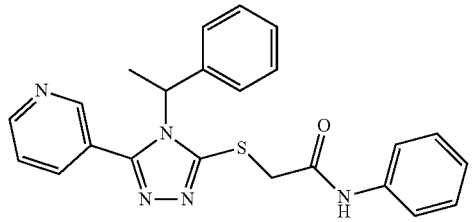
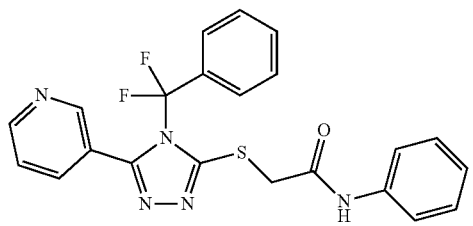
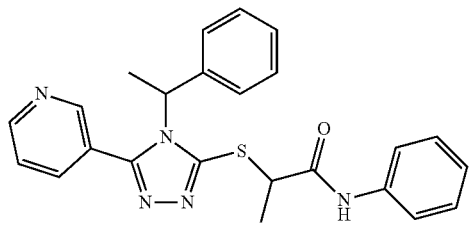
72
-continued
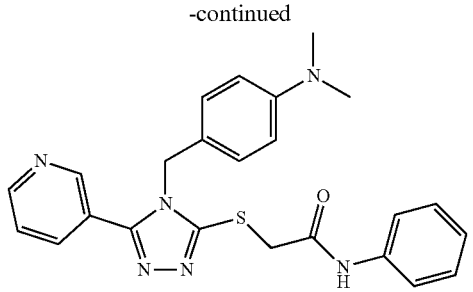
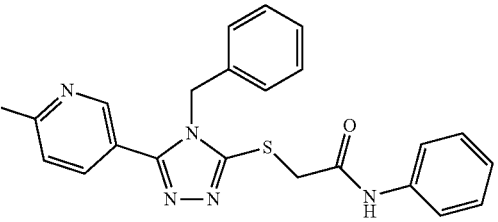
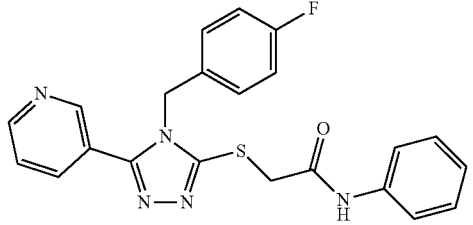
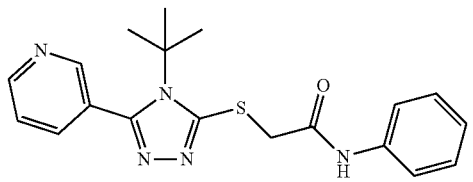
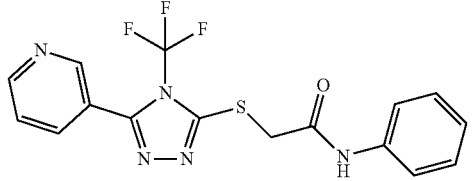
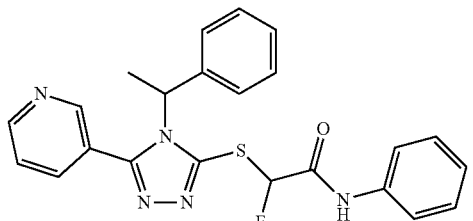
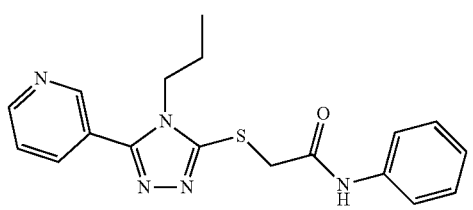
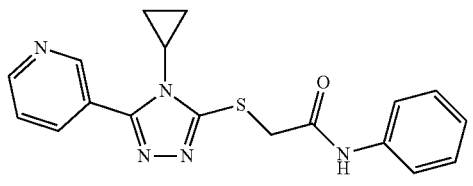

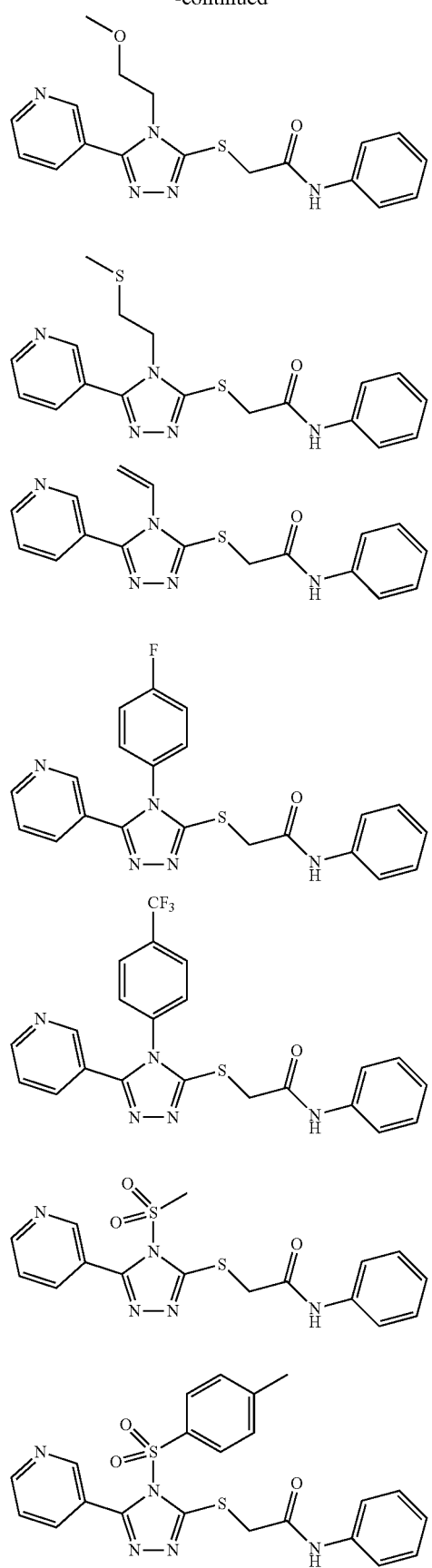
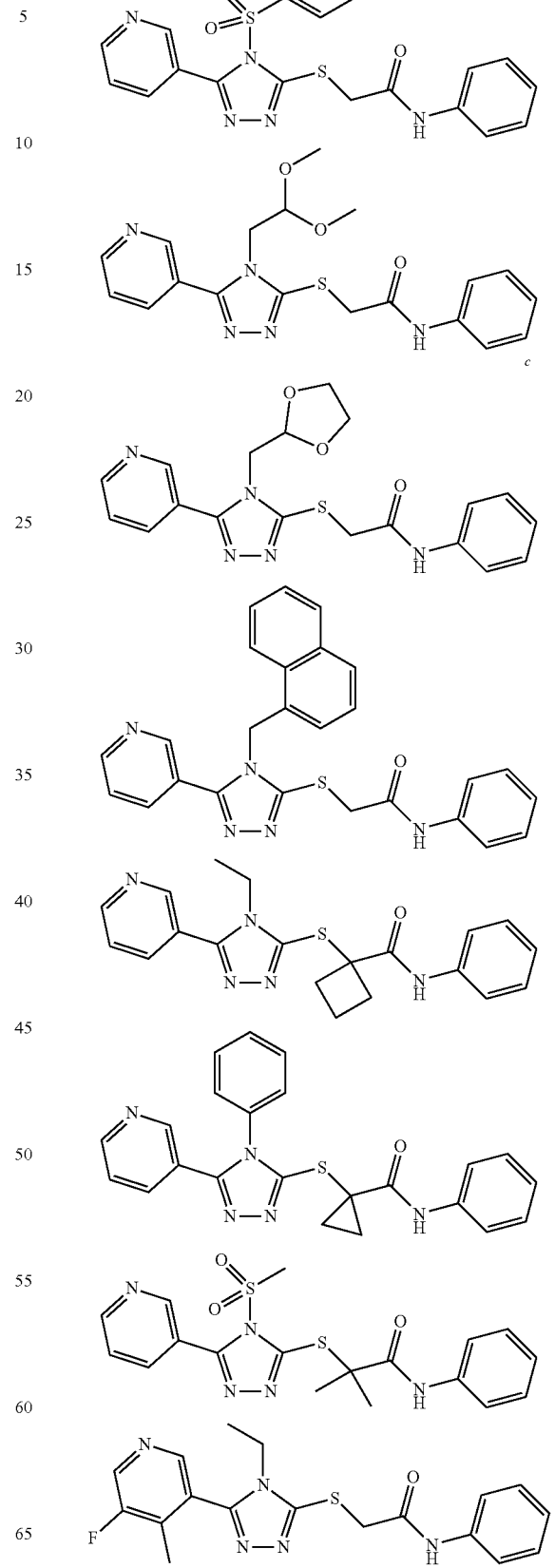

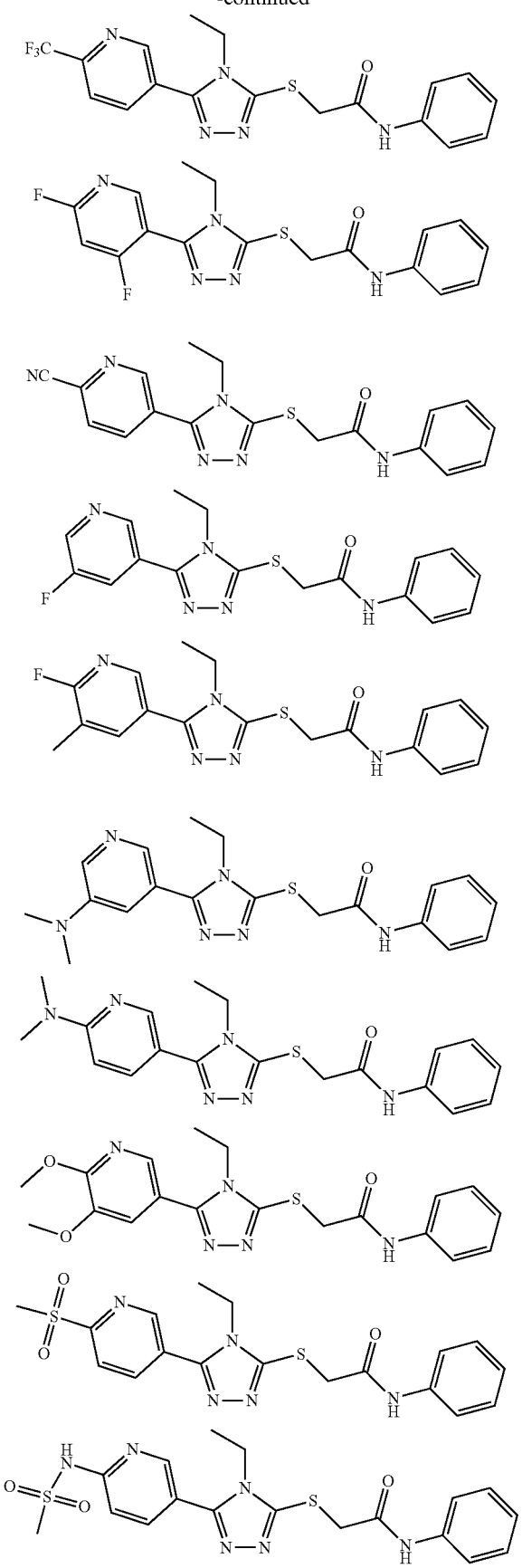
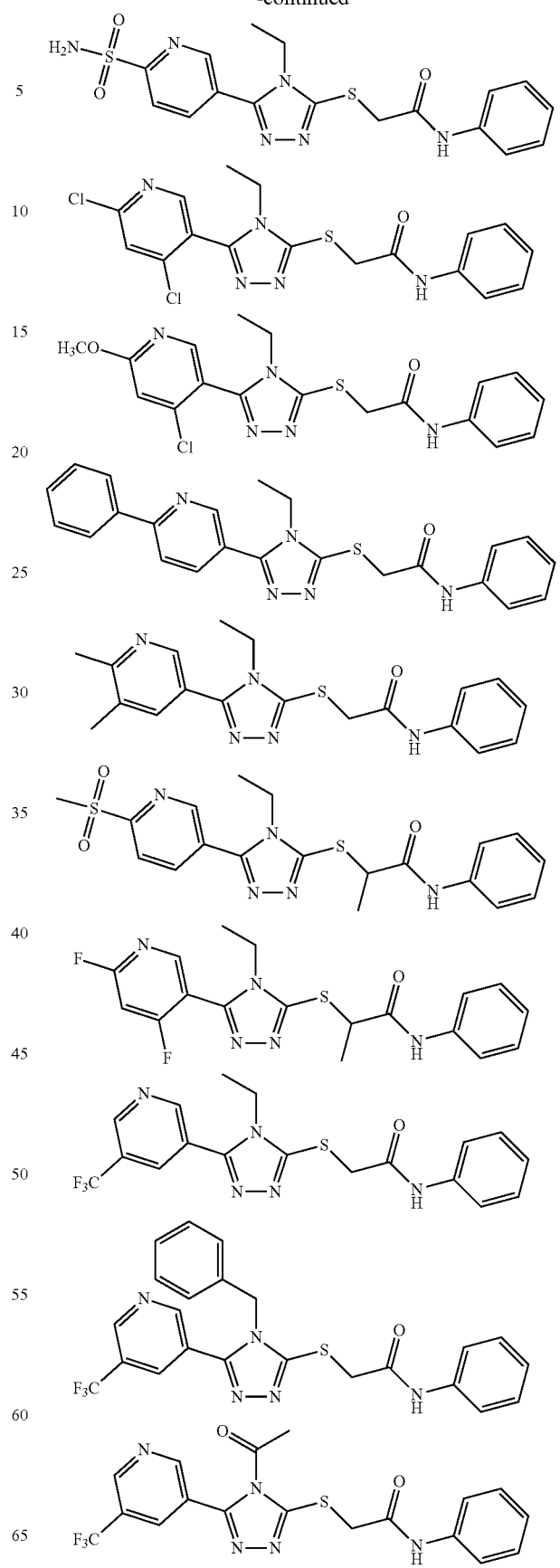

77
-continued
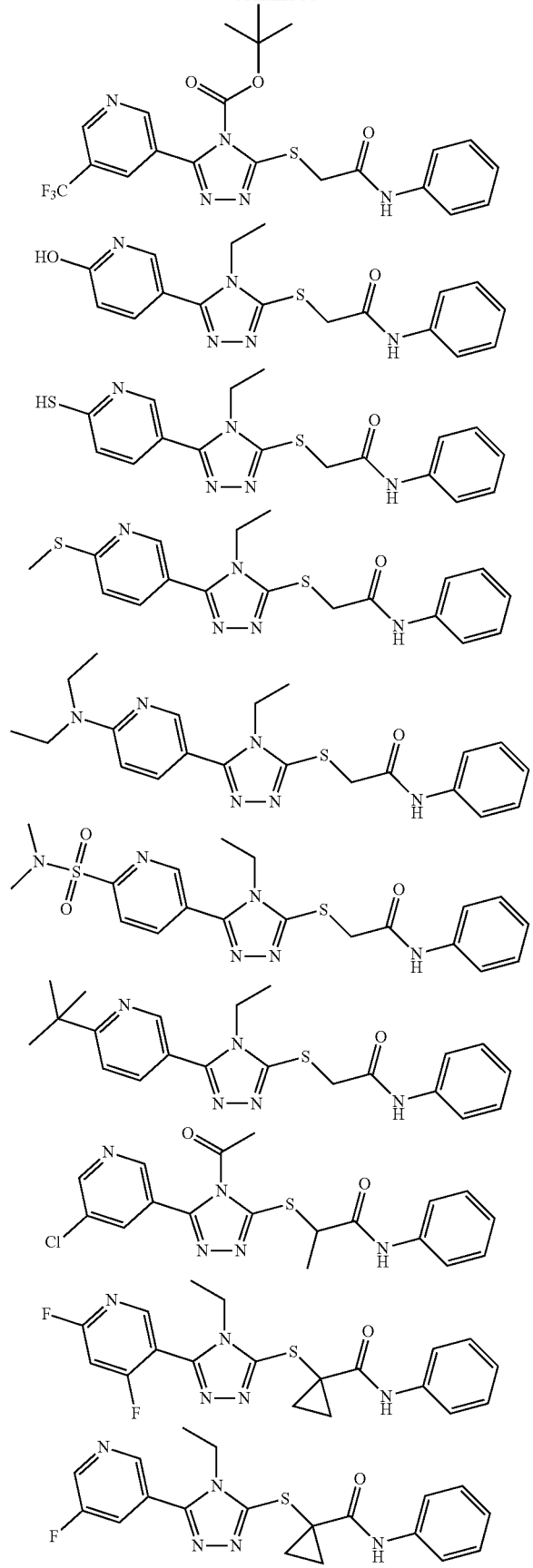
78
-continued
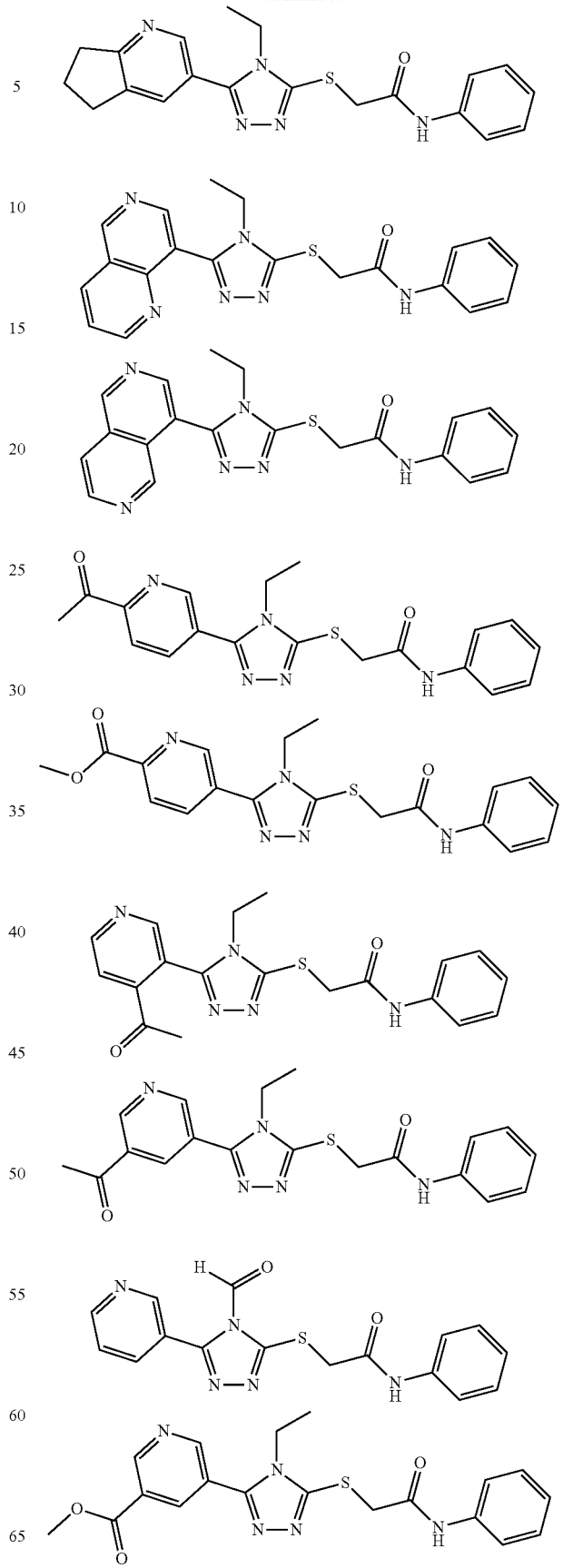

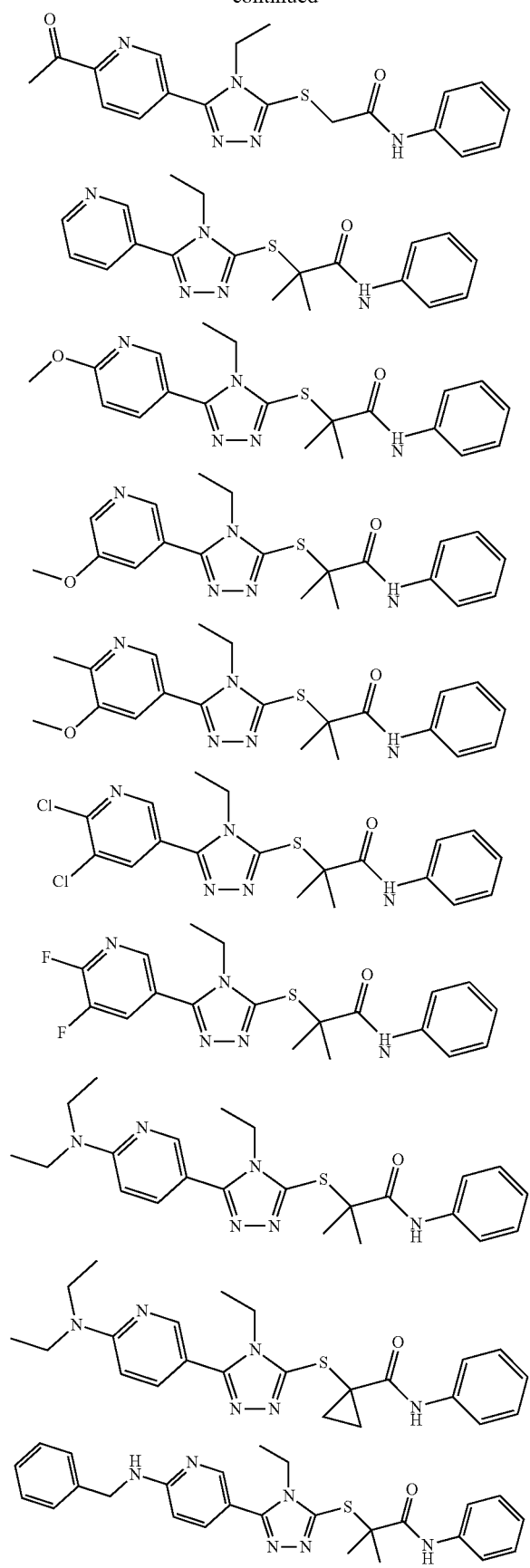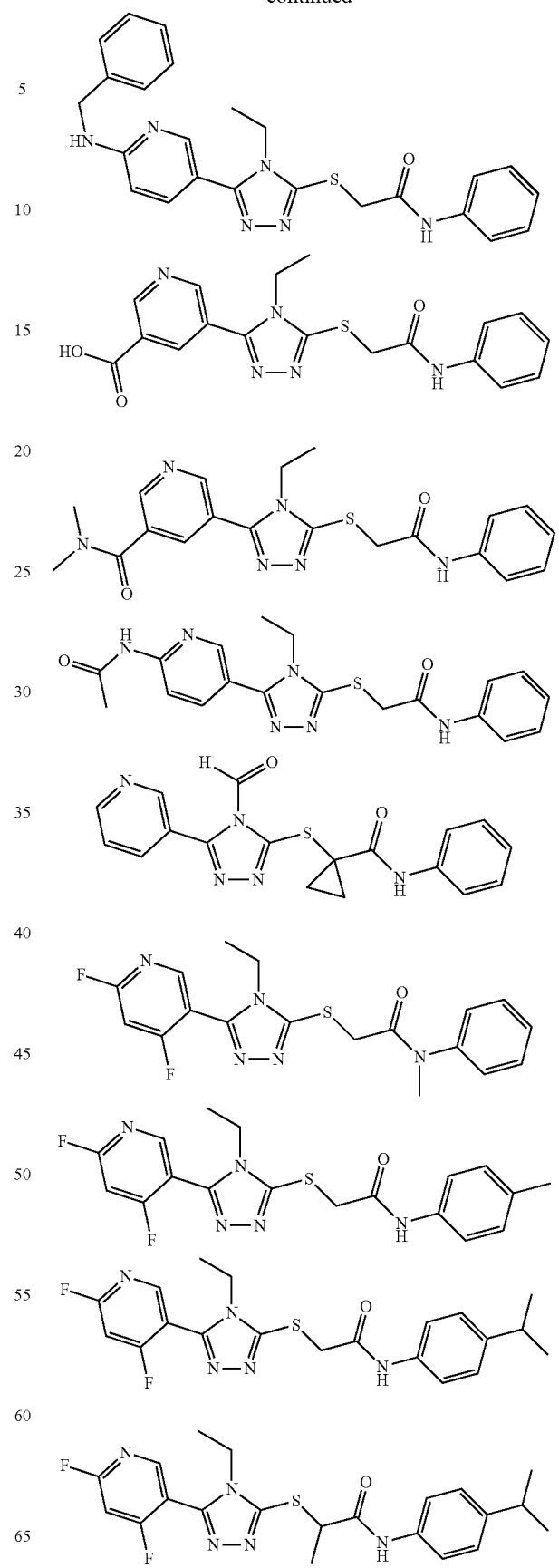

-continued
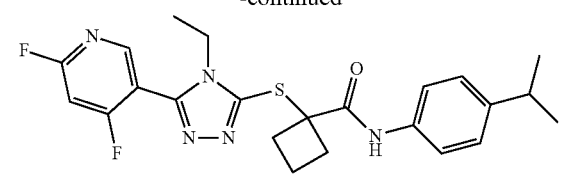
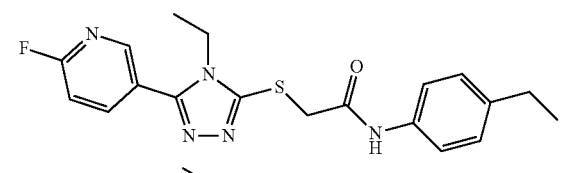
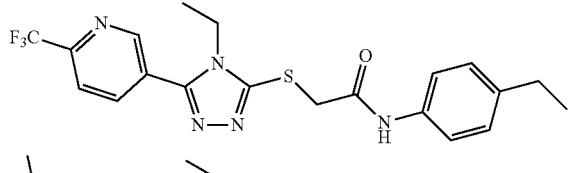
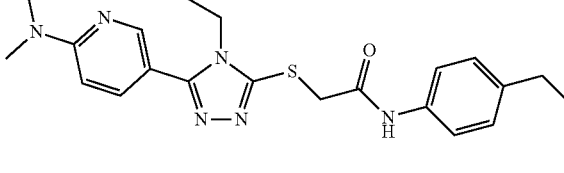
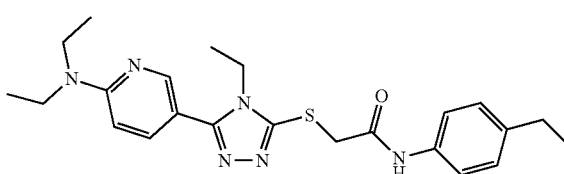
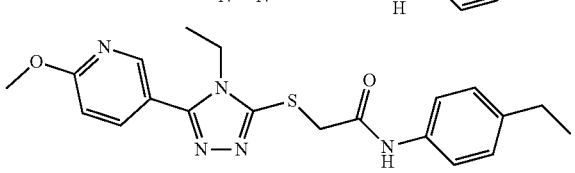
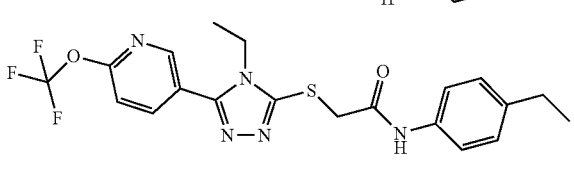
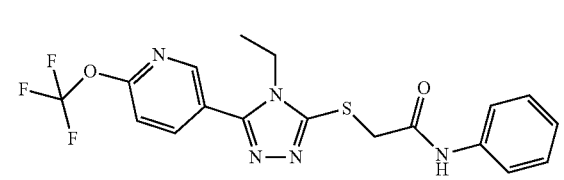
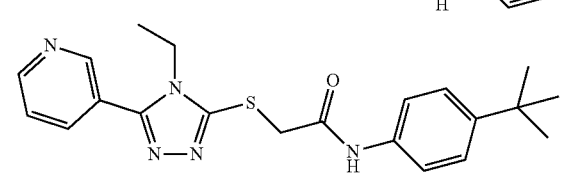
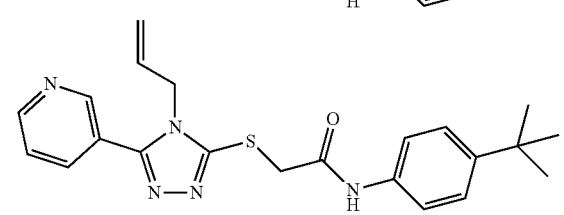
-continued
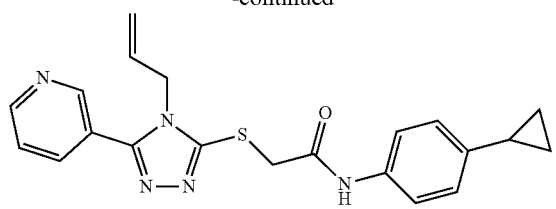
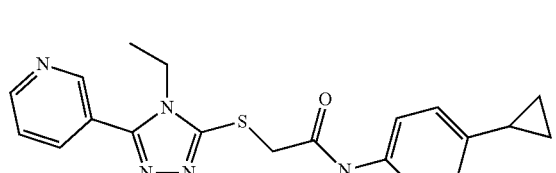
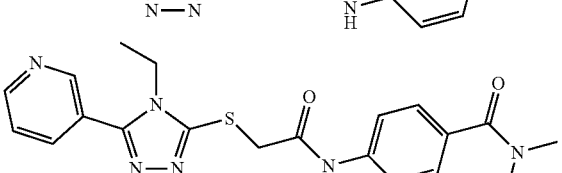
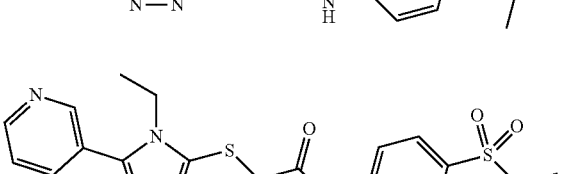
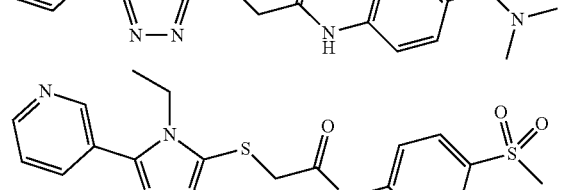
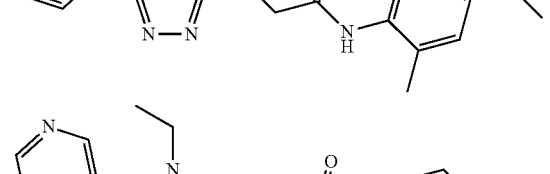
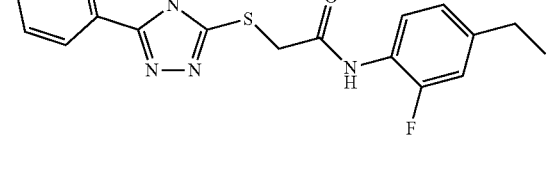
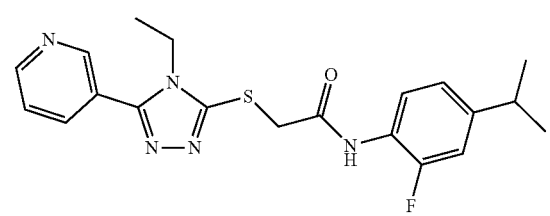

-continued
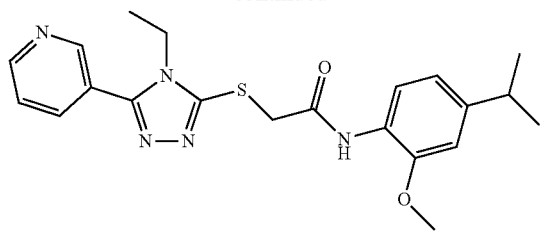
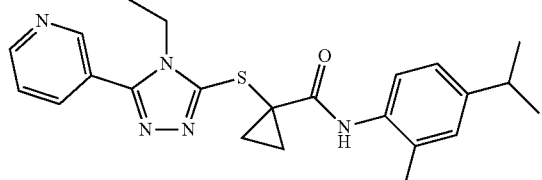
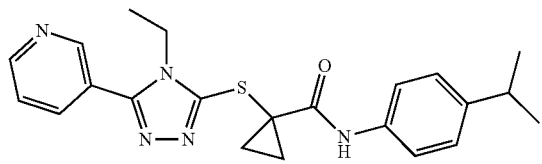
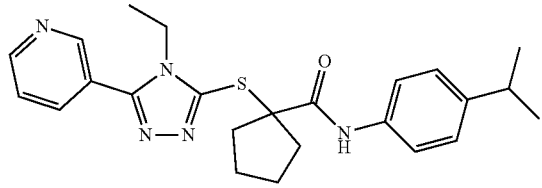
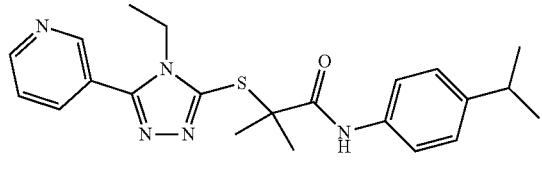
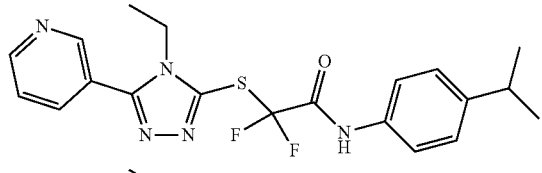
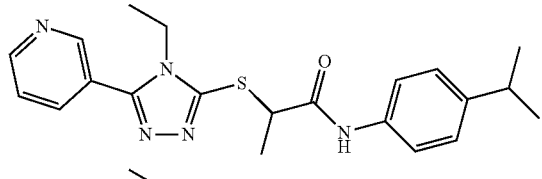
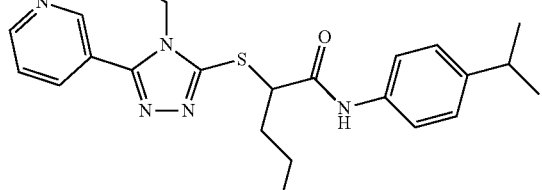
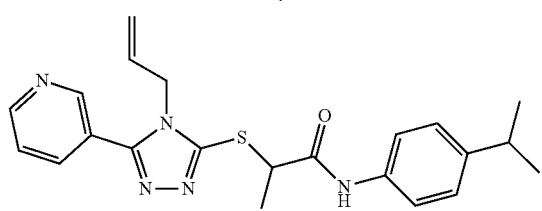
-continued
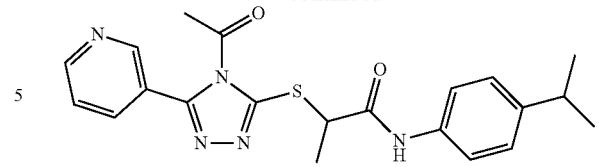
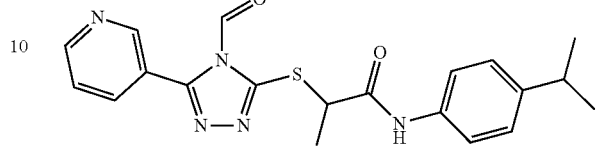
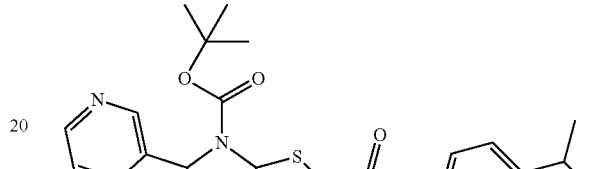
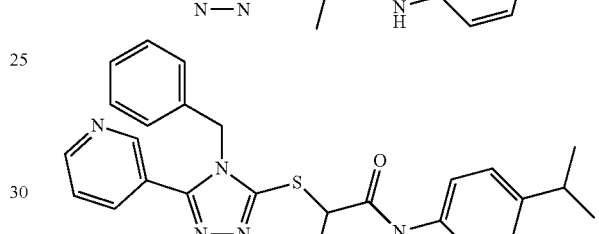
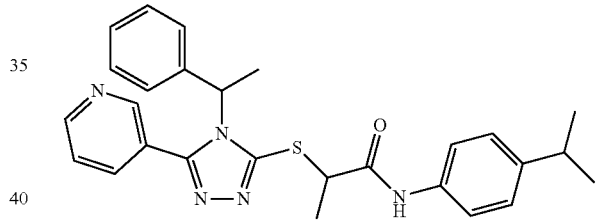
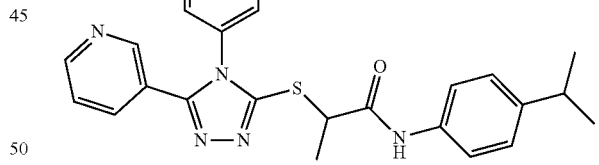
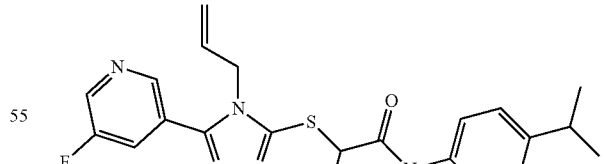
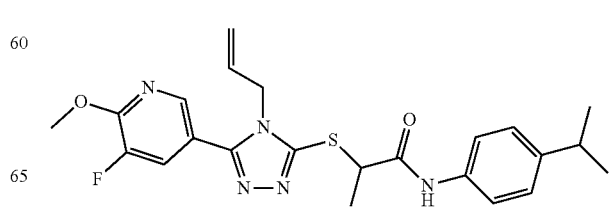

-continued
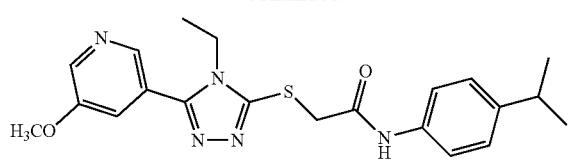
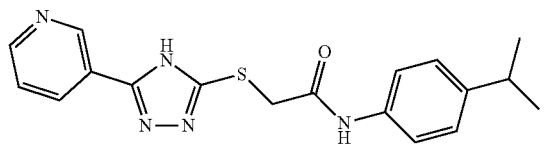
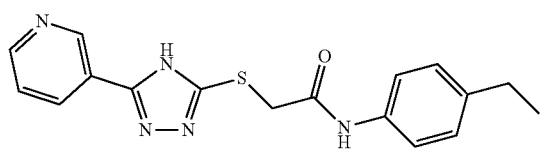

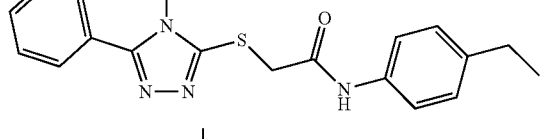
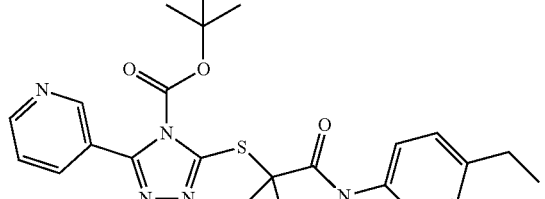
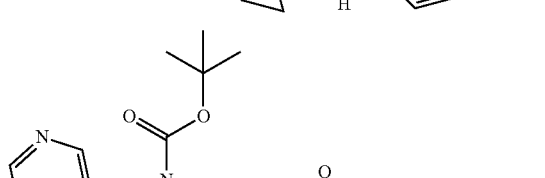
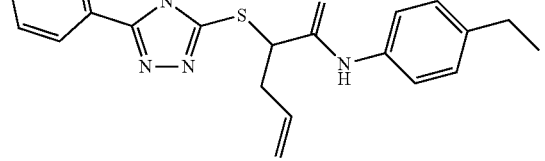
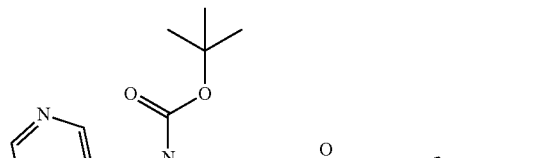
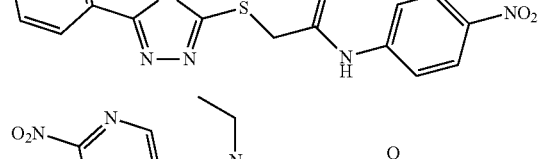
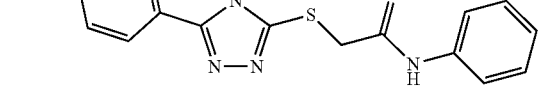
-continued
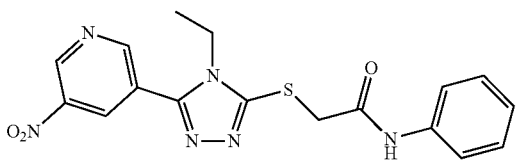
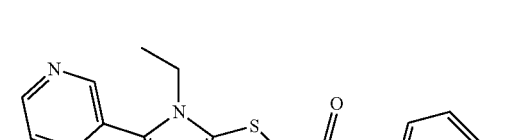
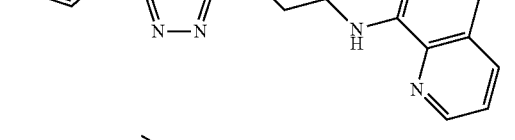
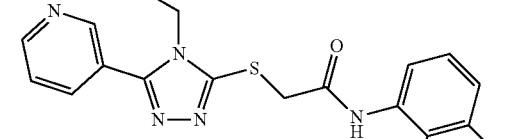
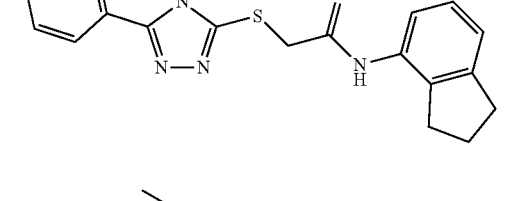
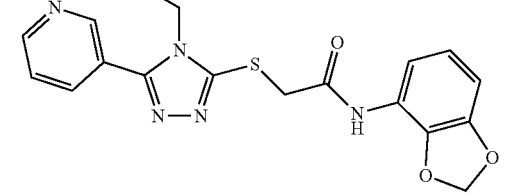
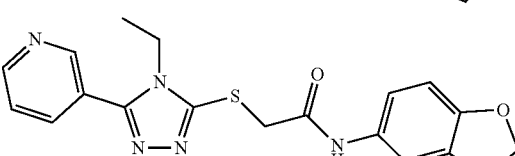
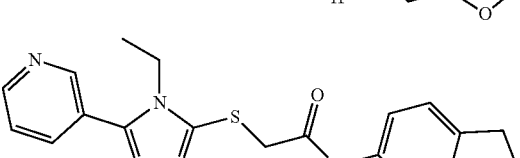
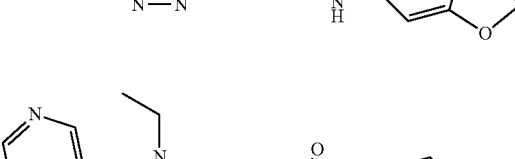
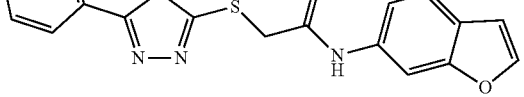

87
-continued
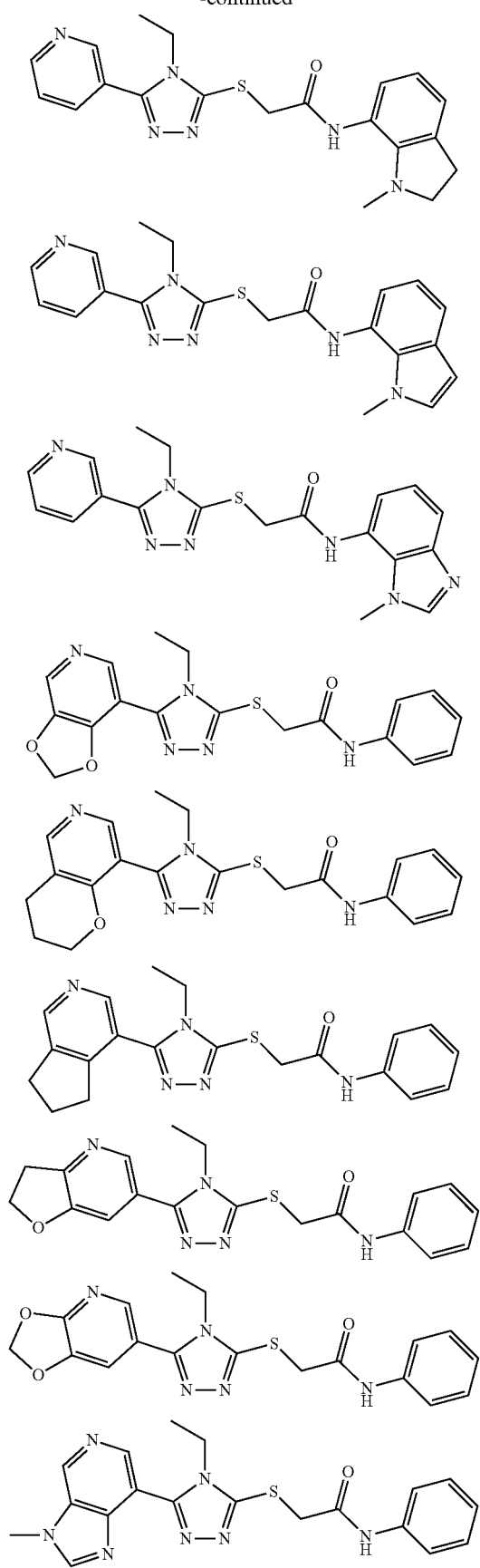
88
-continued
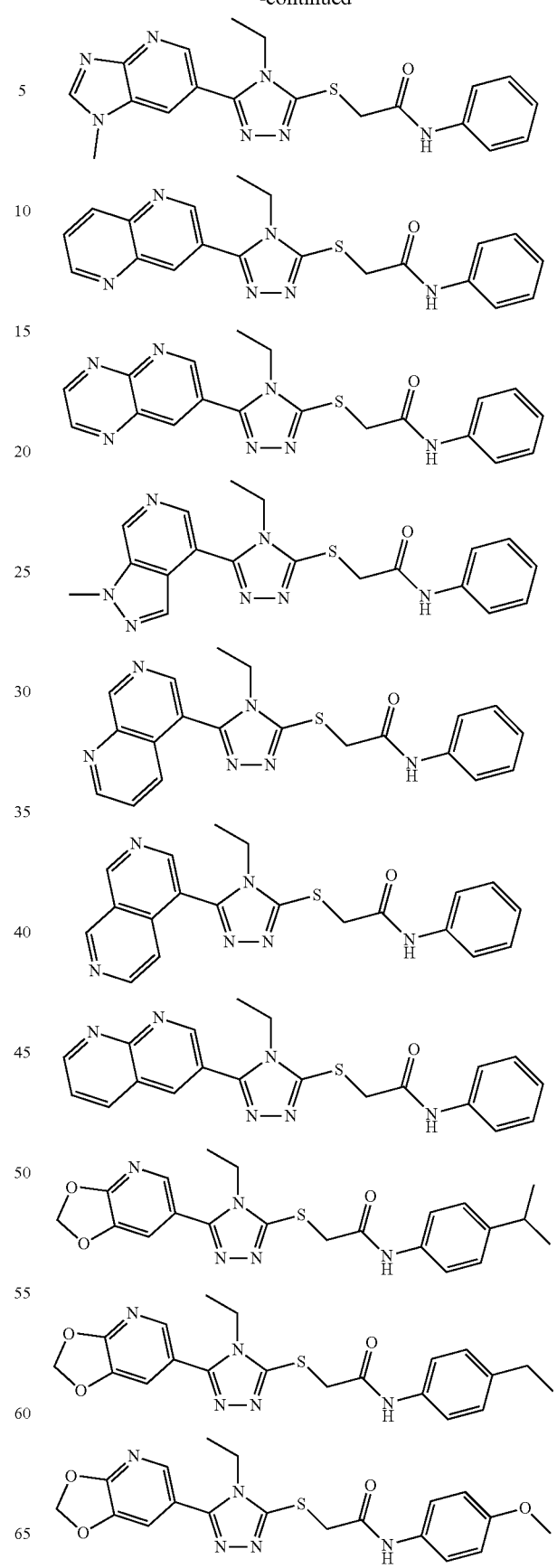

In one aspect a disclosed compound can have the formula (II):
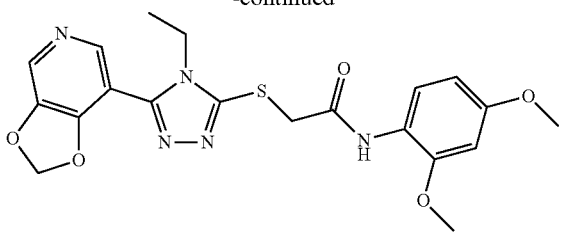
Exemplary compound within Formula (II) include, but are not limited to:
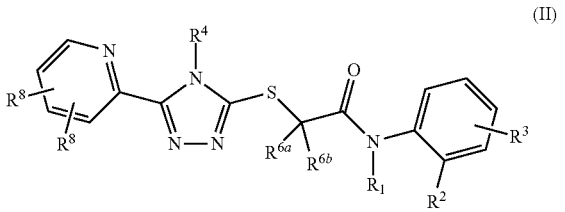

91
-continued
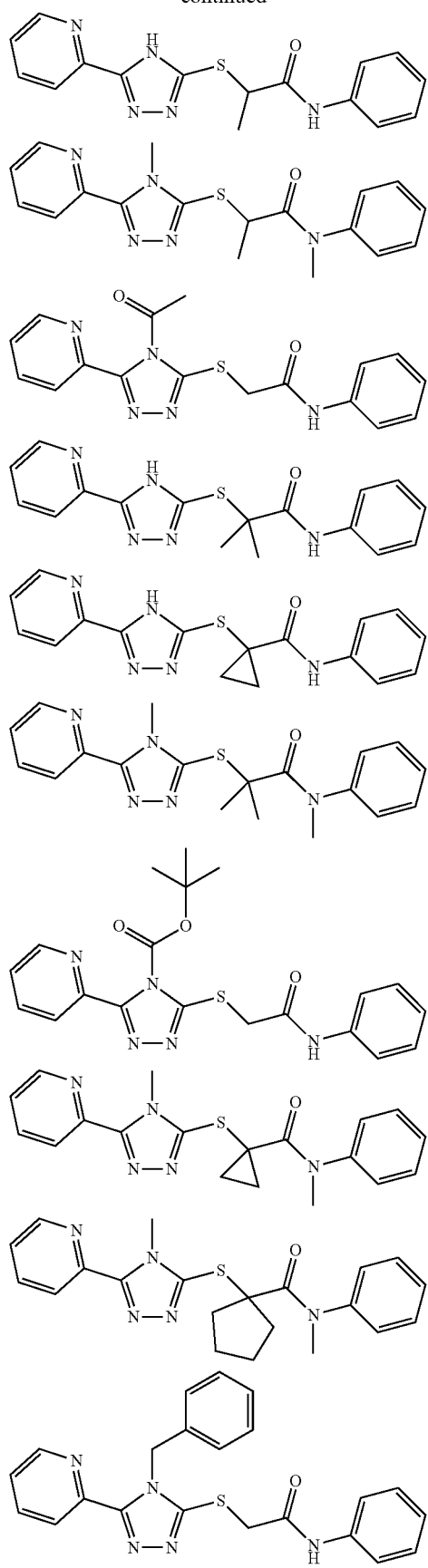
92
-continued
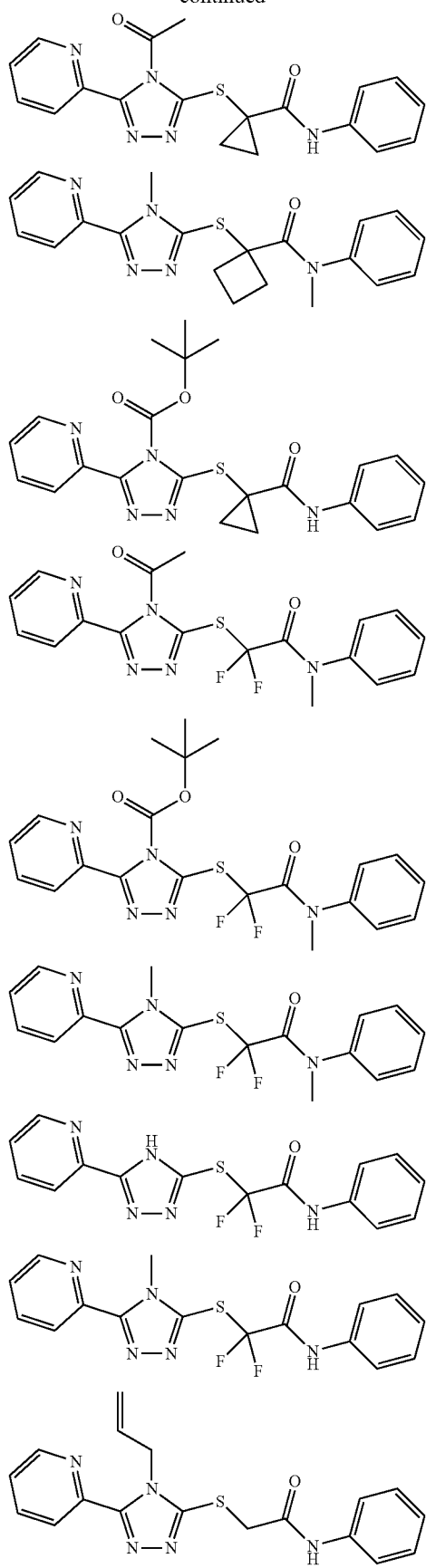

-continued
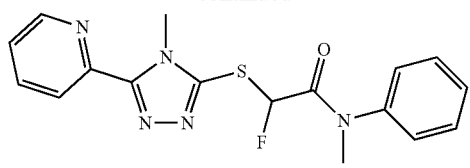
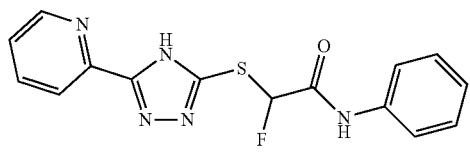
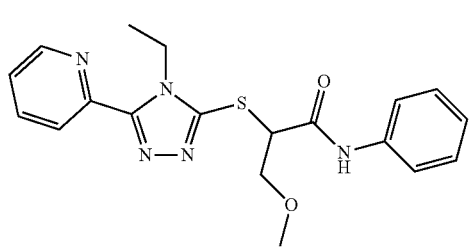
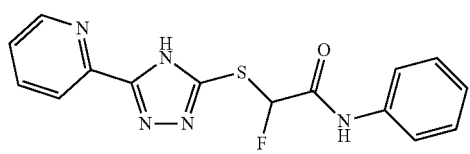
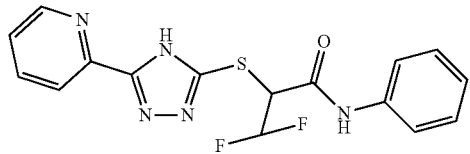
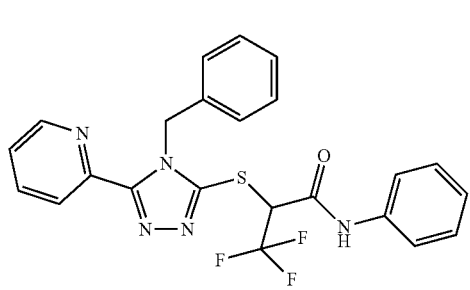
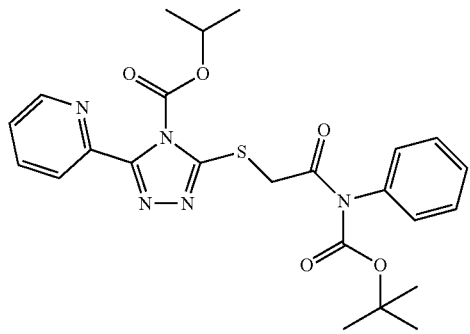
-continued
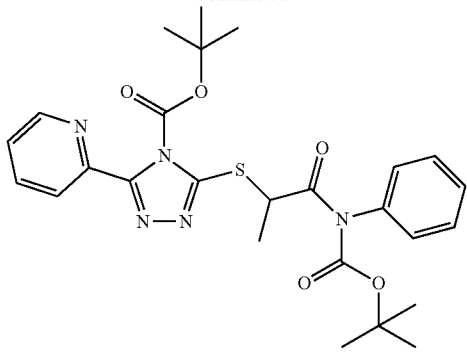
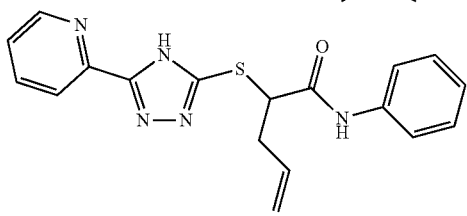
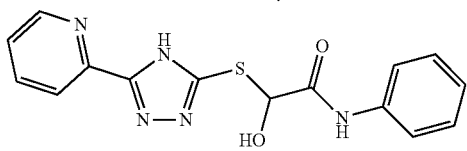
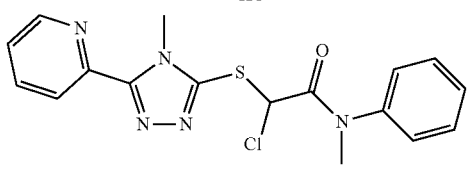
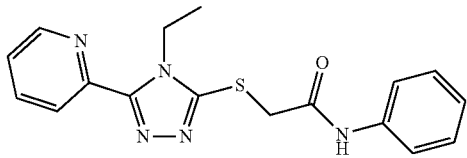
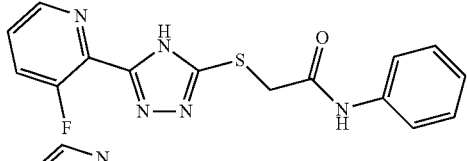
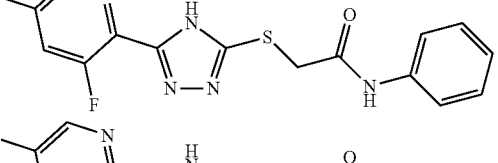
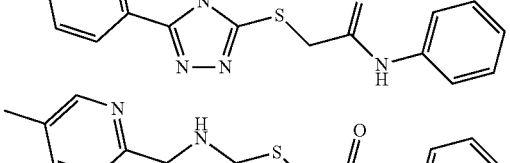
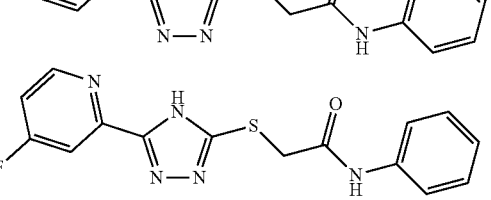

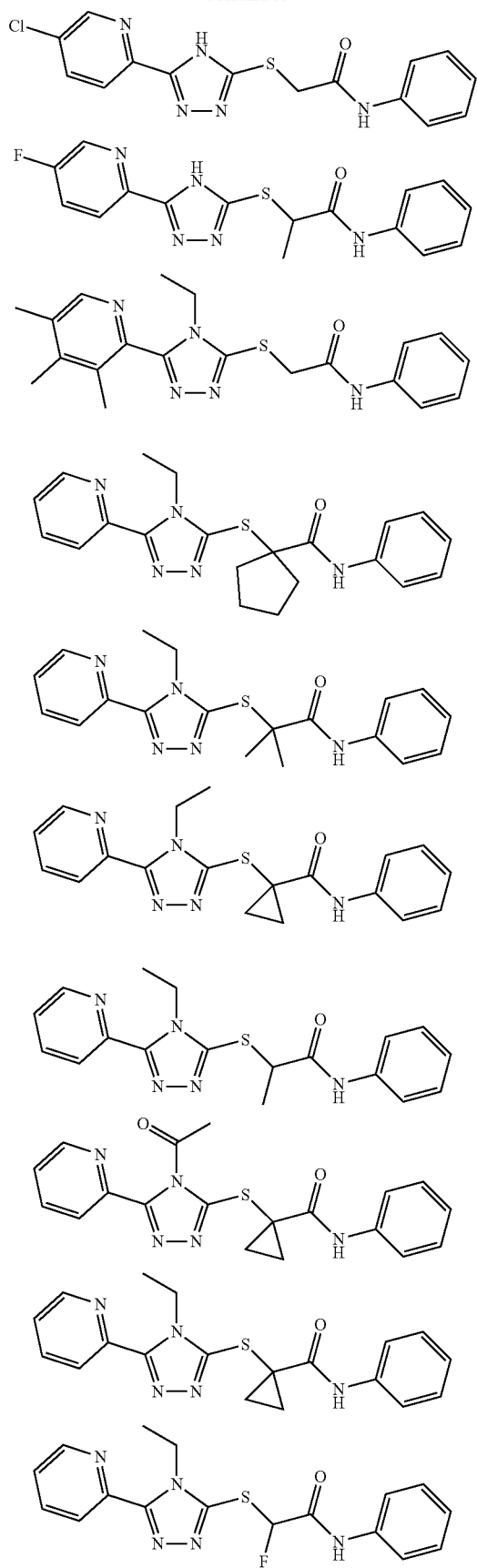
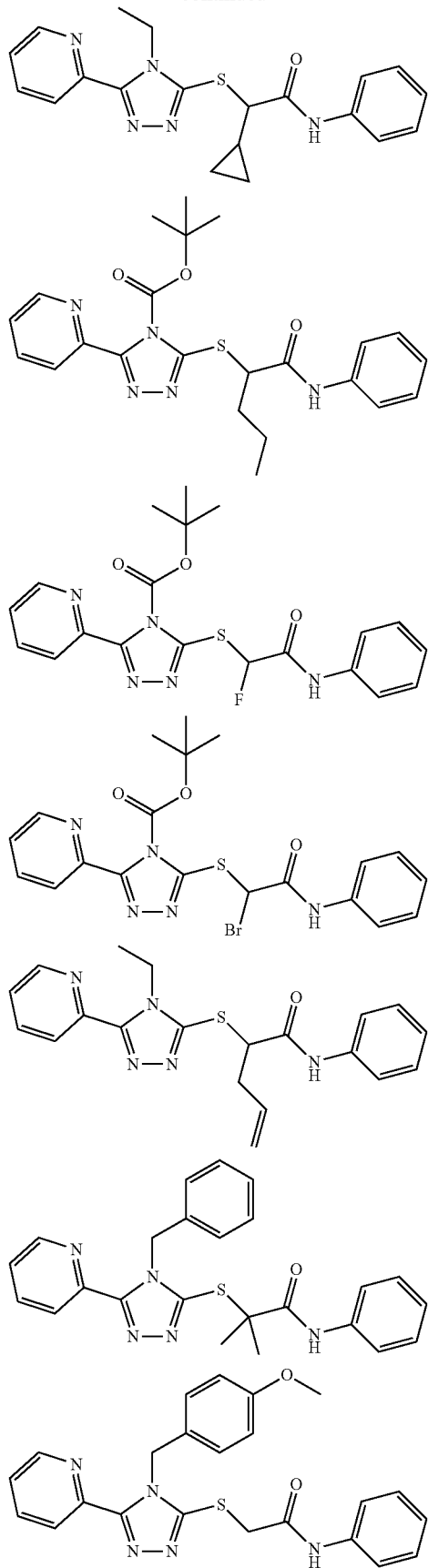

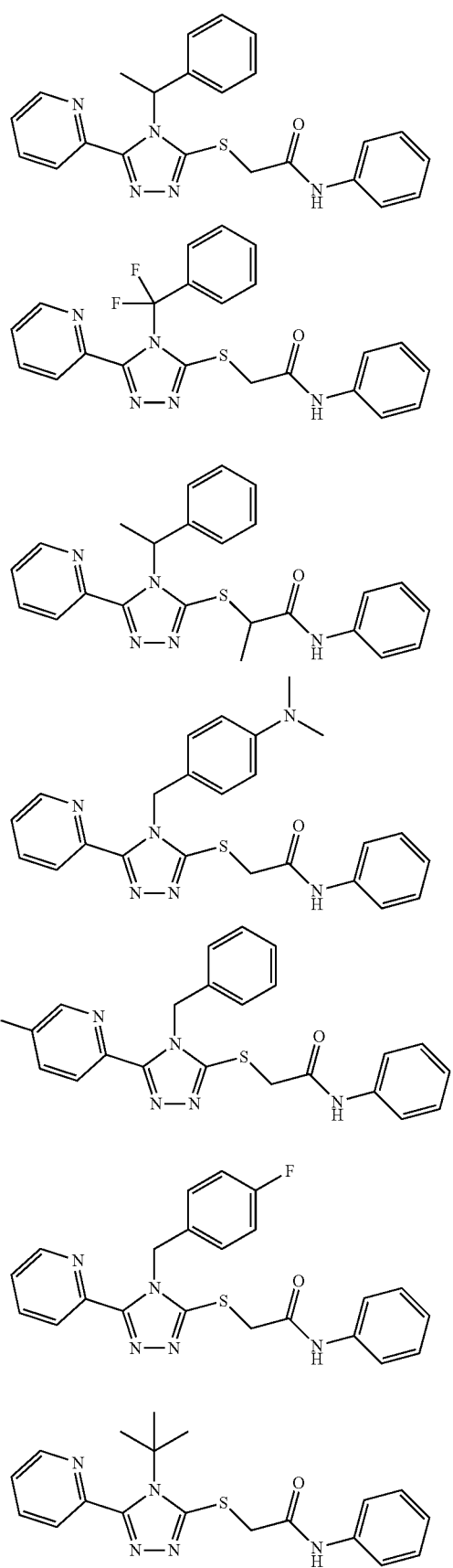
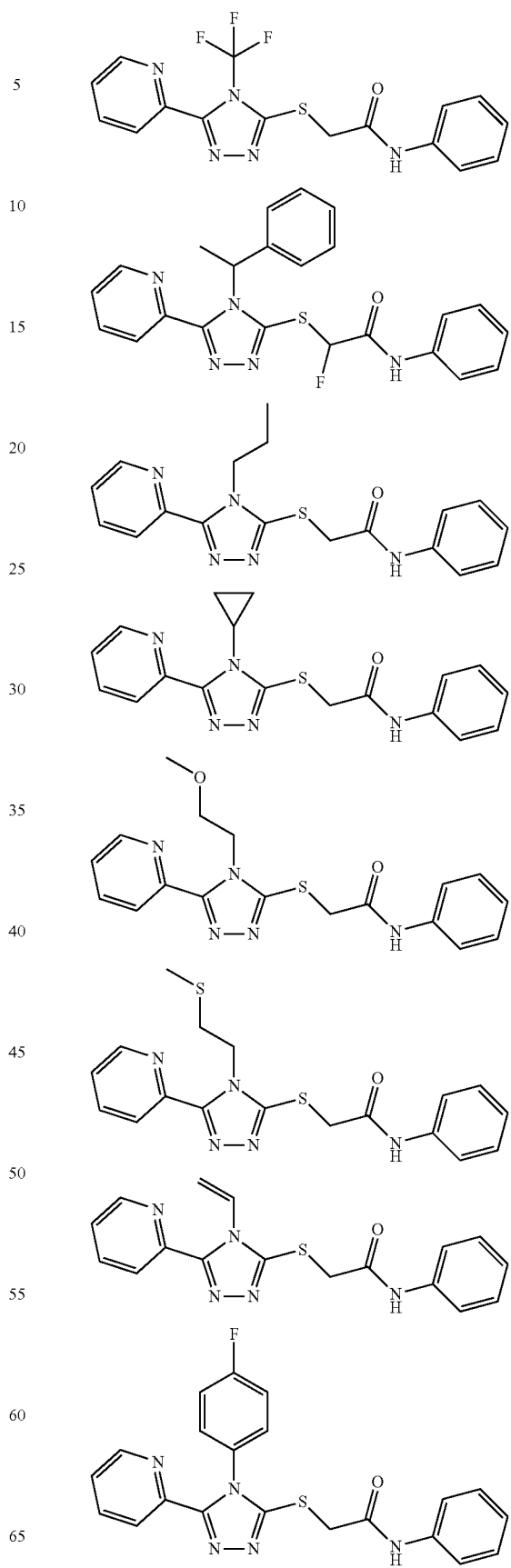

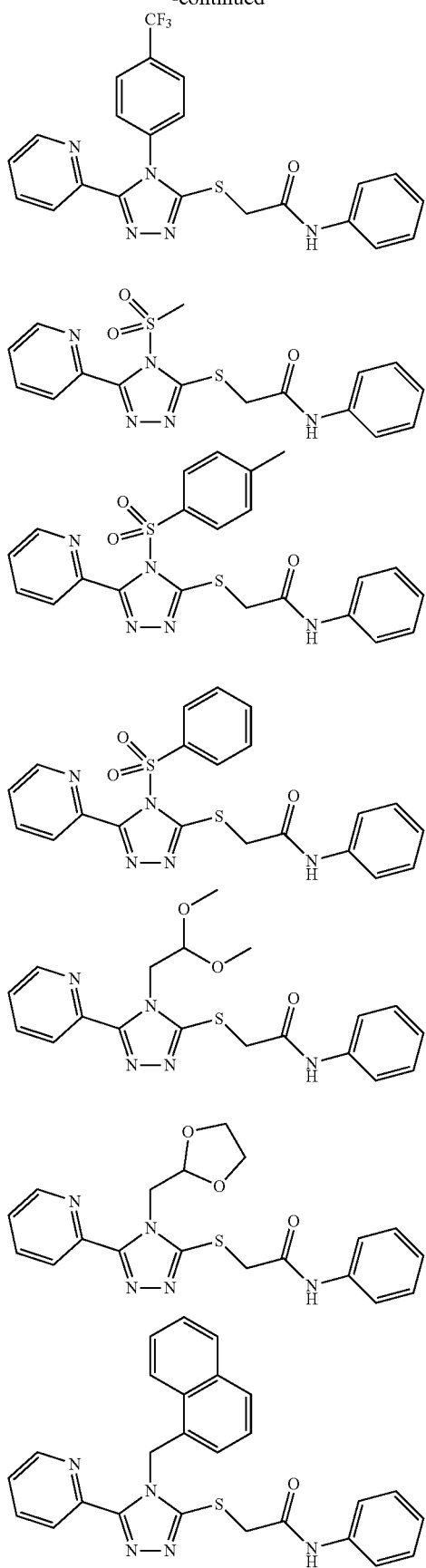
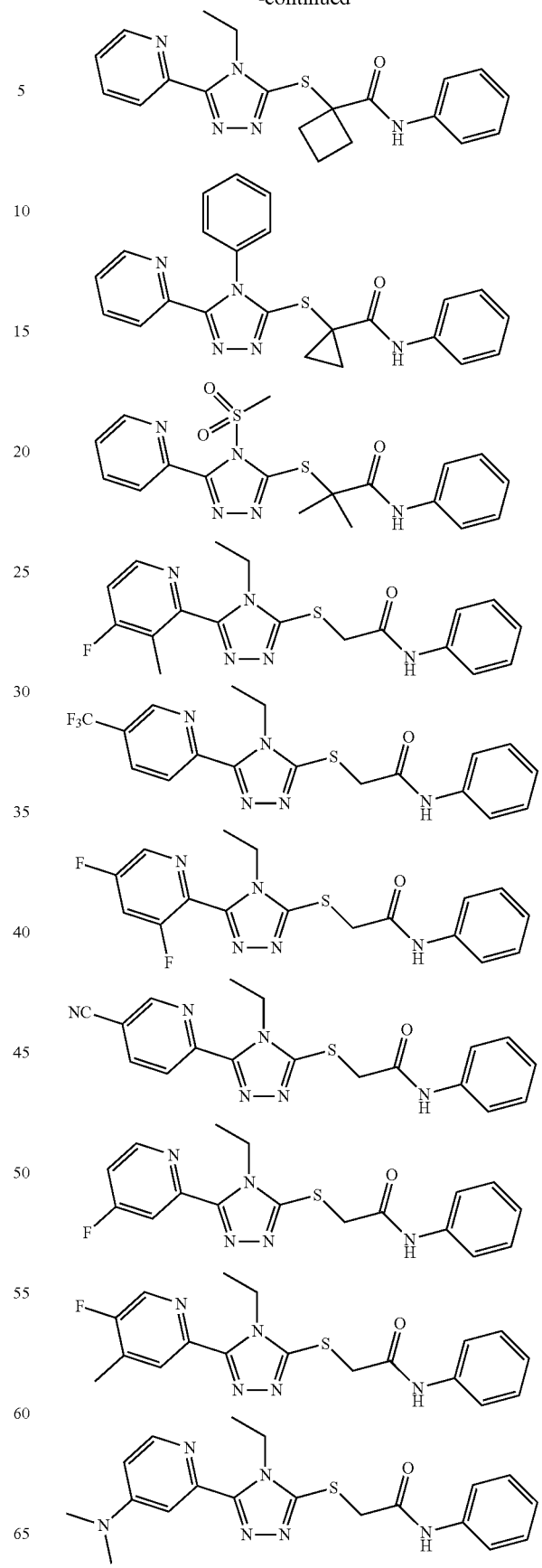

101
-continued
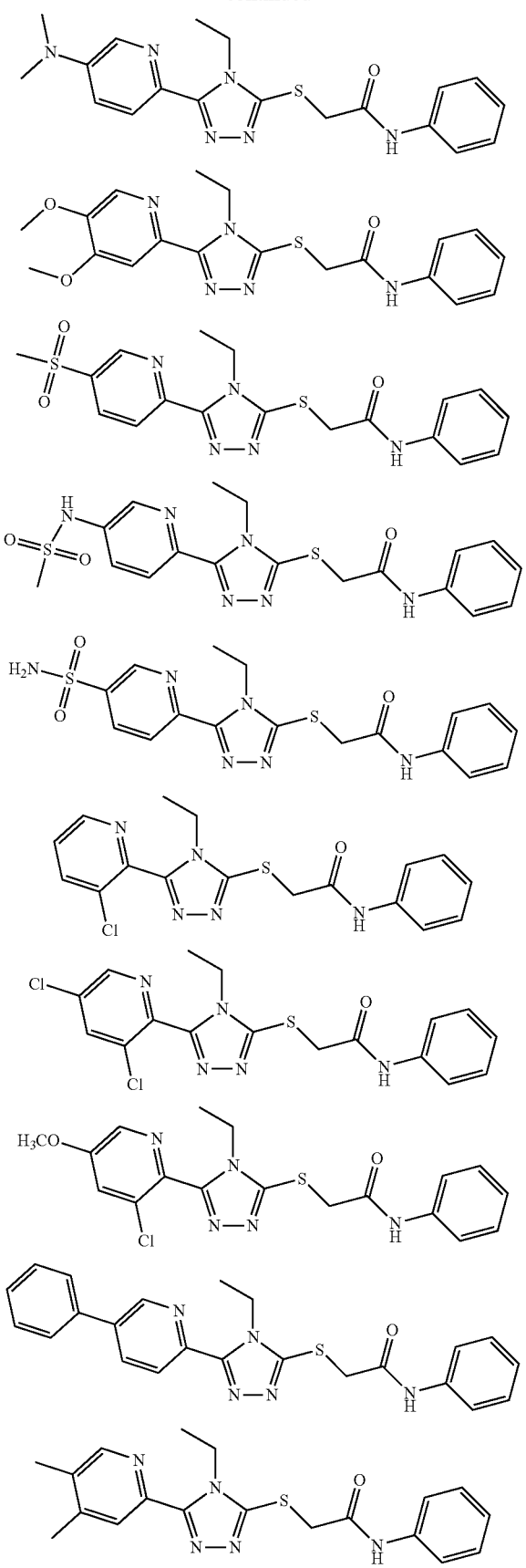
102
-continued
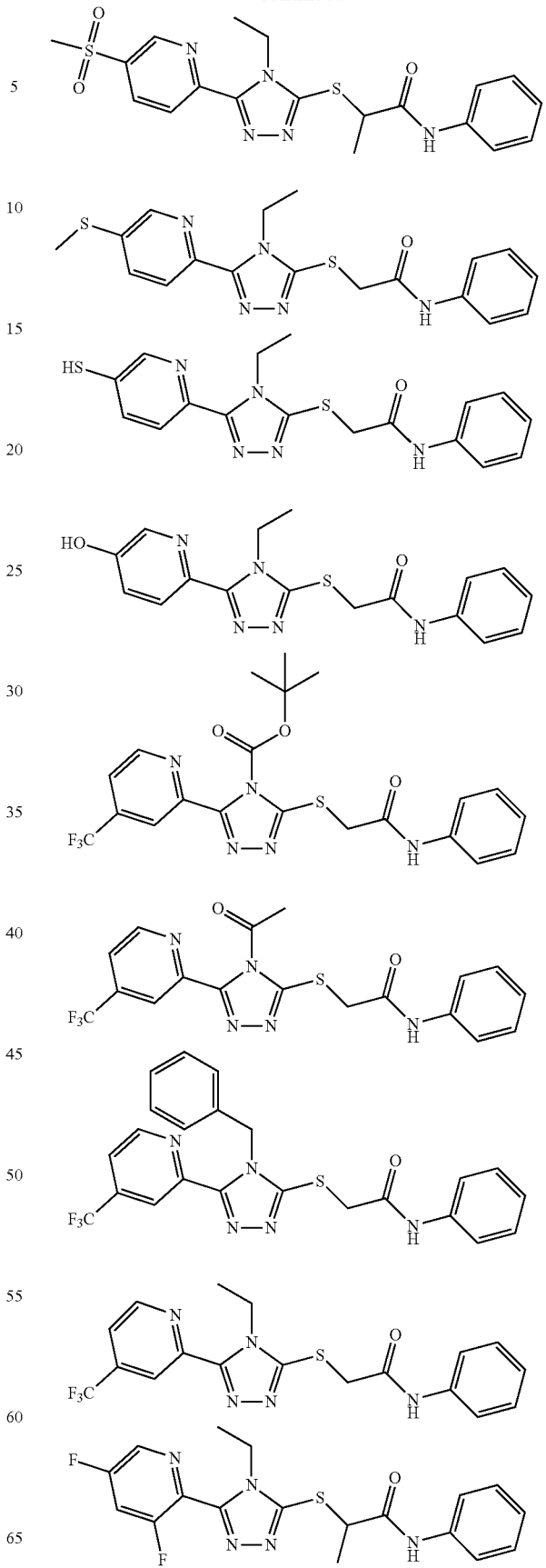

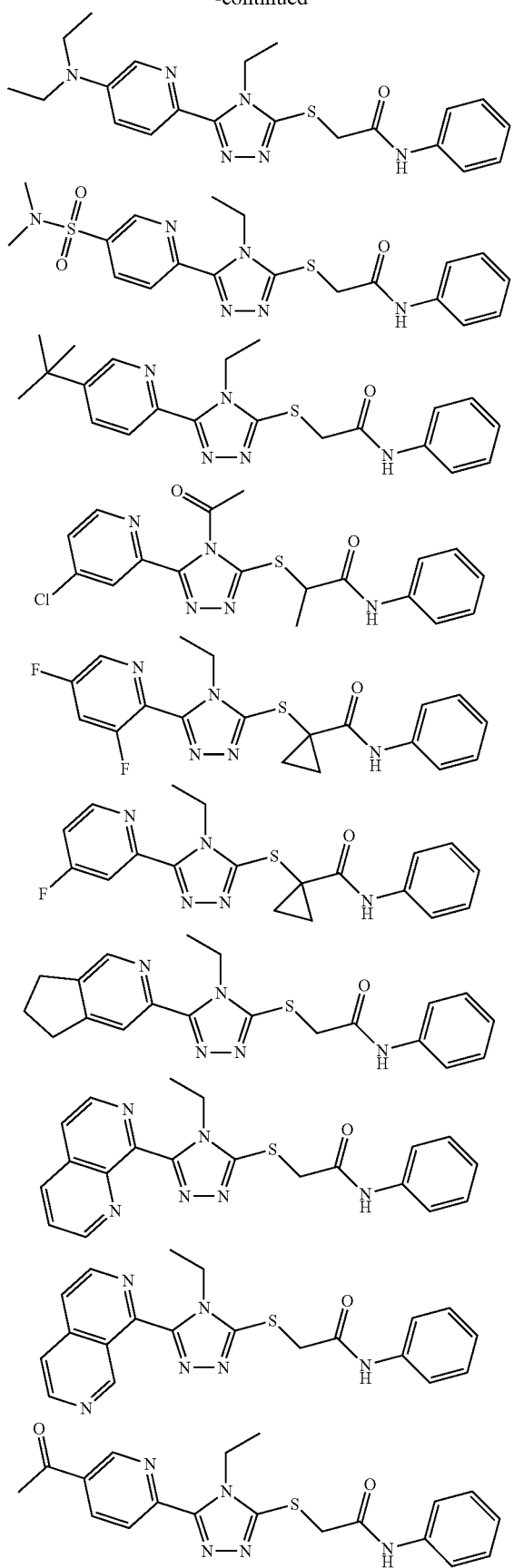
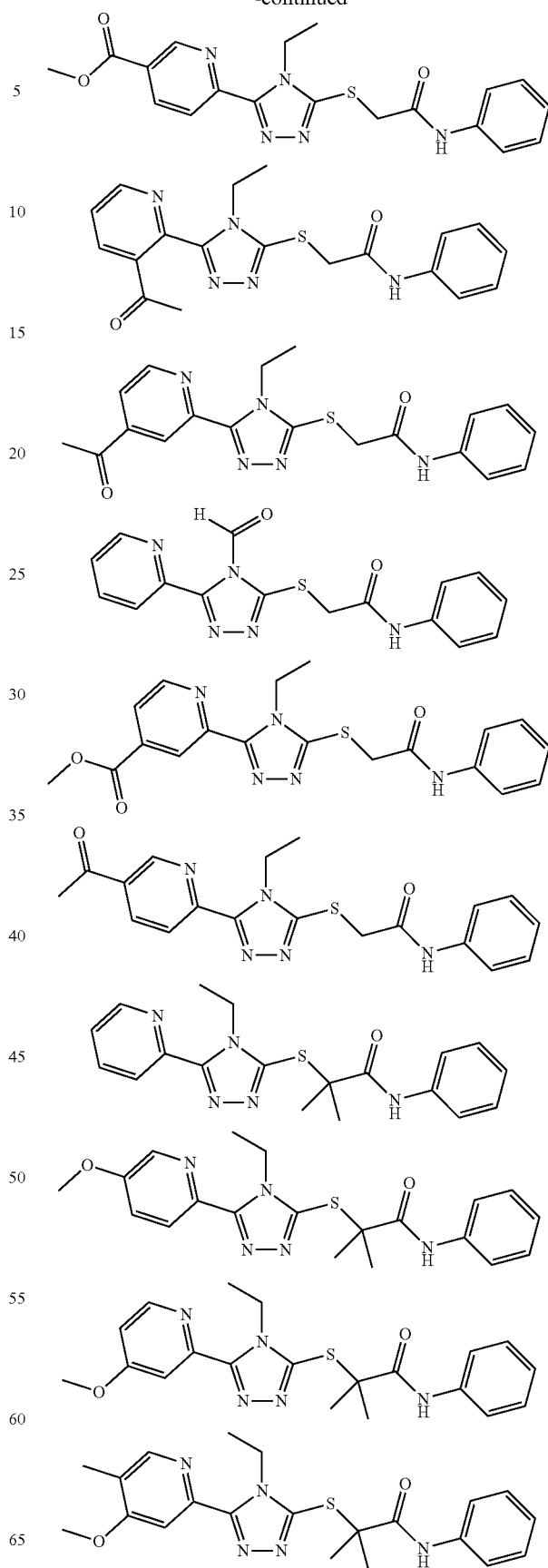

105
-continued
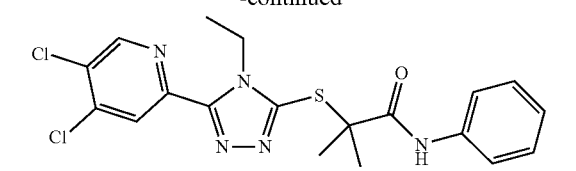
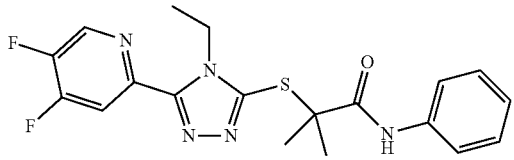
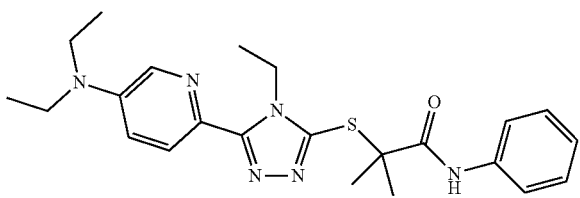
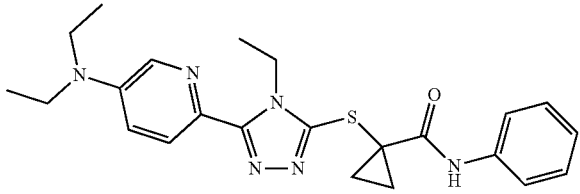
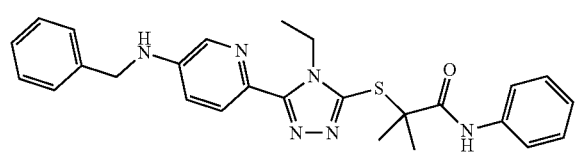
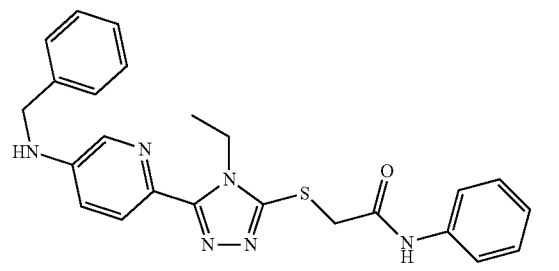
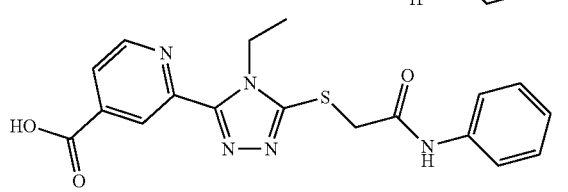
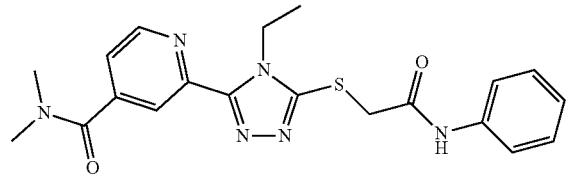
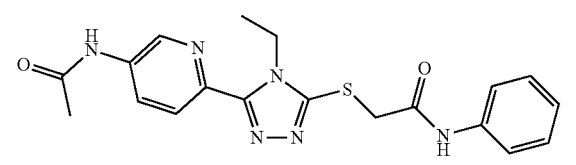
106
-continued
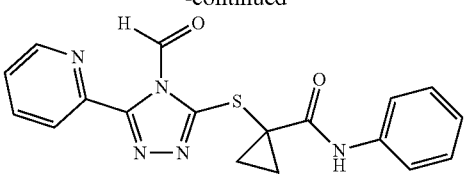
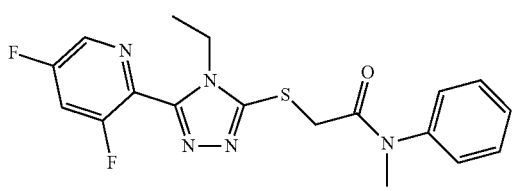
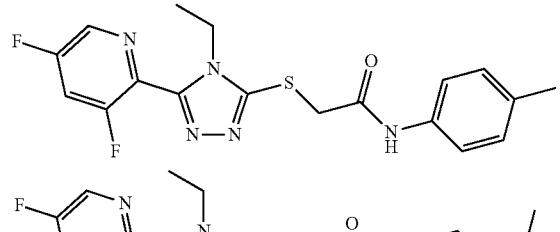

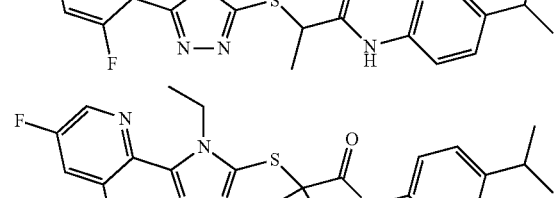
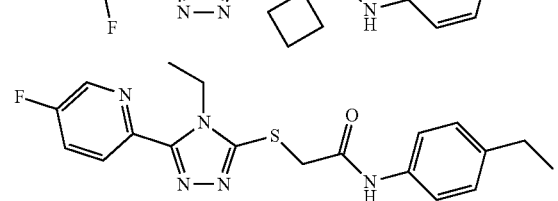
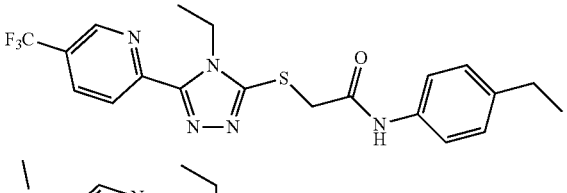
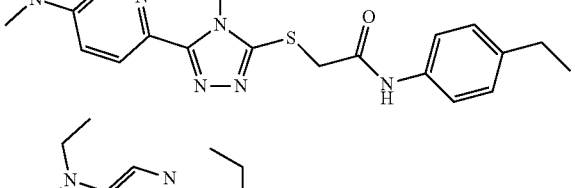
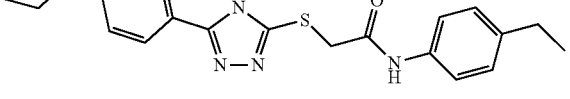

107
-continued

108
-continued

109
-continued
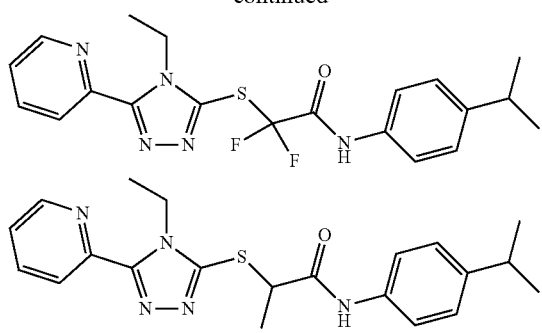
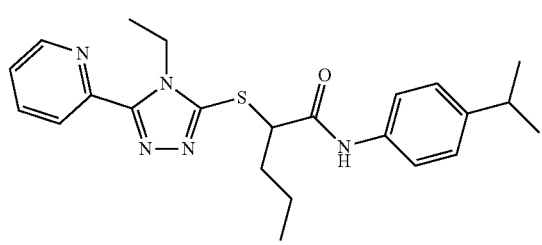
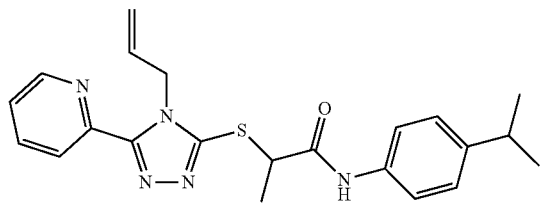
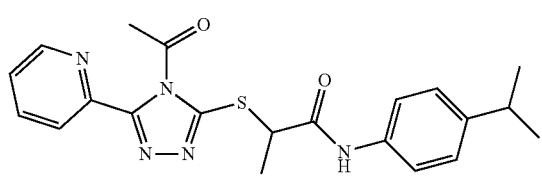
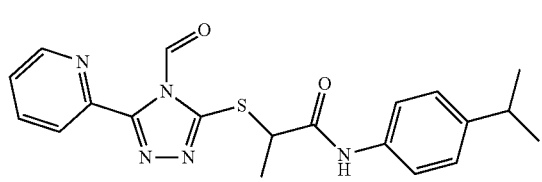
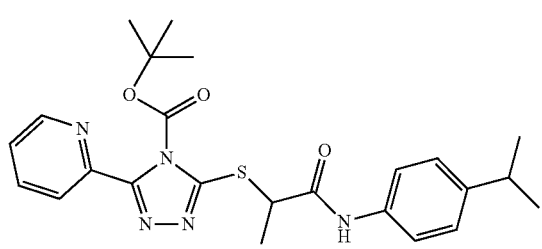
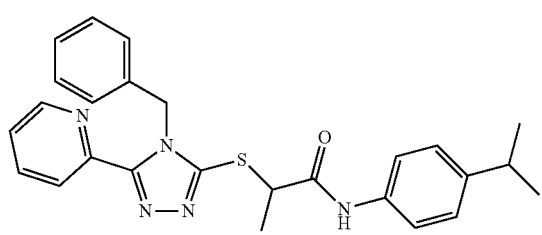
110
-continued
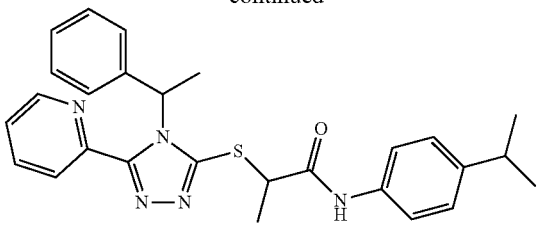
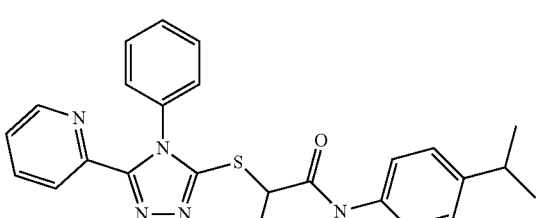
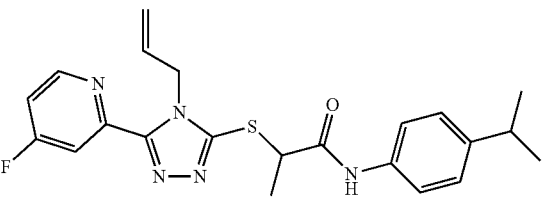
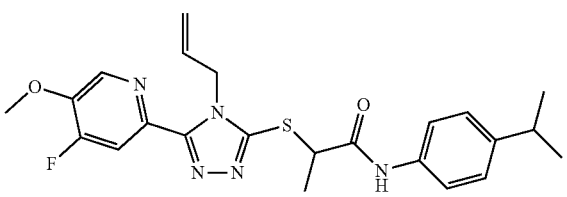
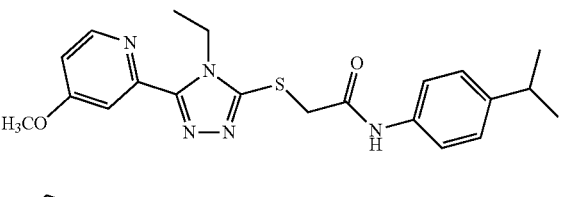
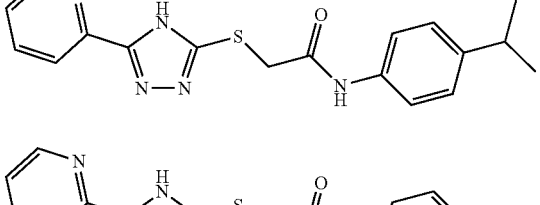

111
-continued
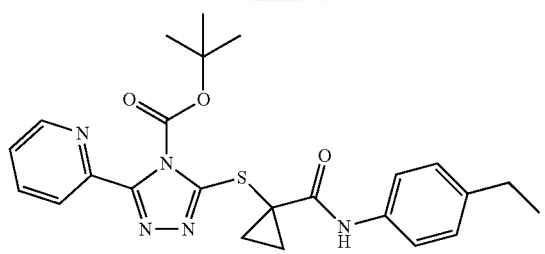
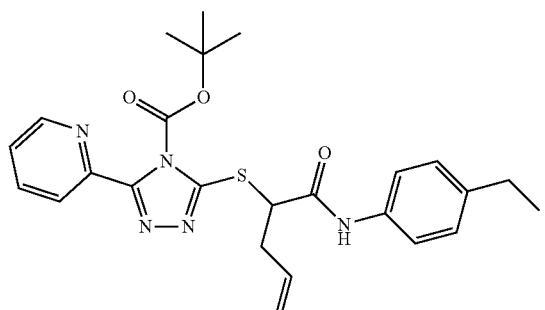
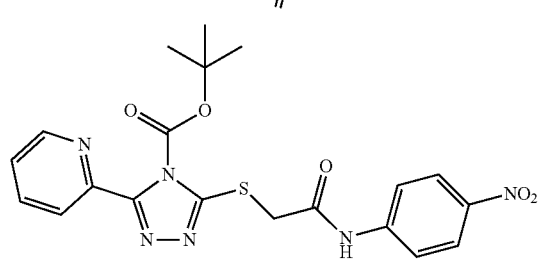
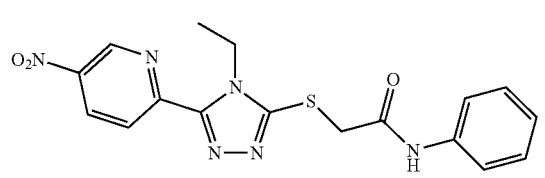
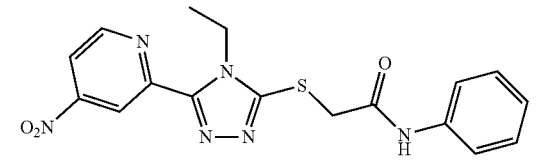
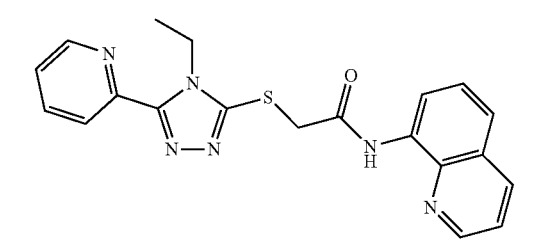
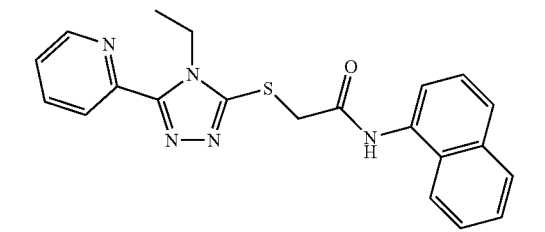
112
-continued
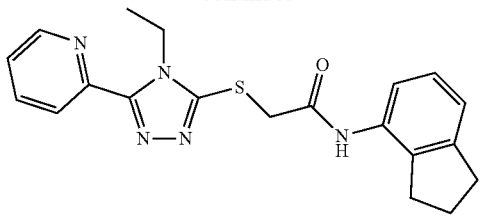
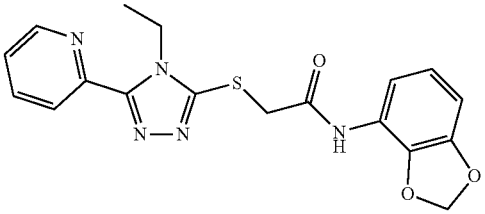
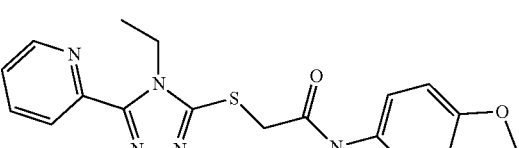
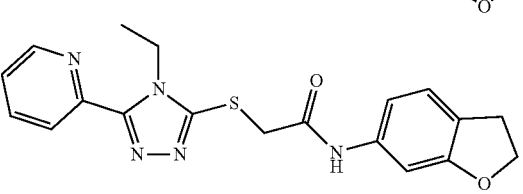
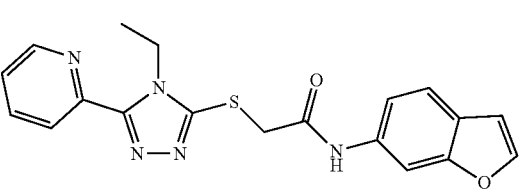
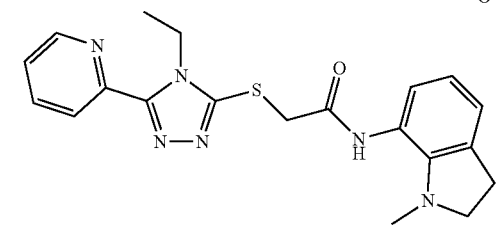
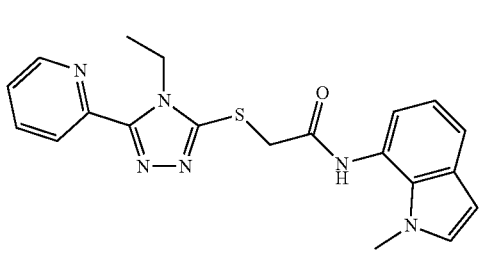
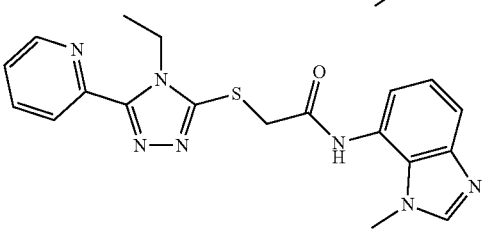

113
-continued
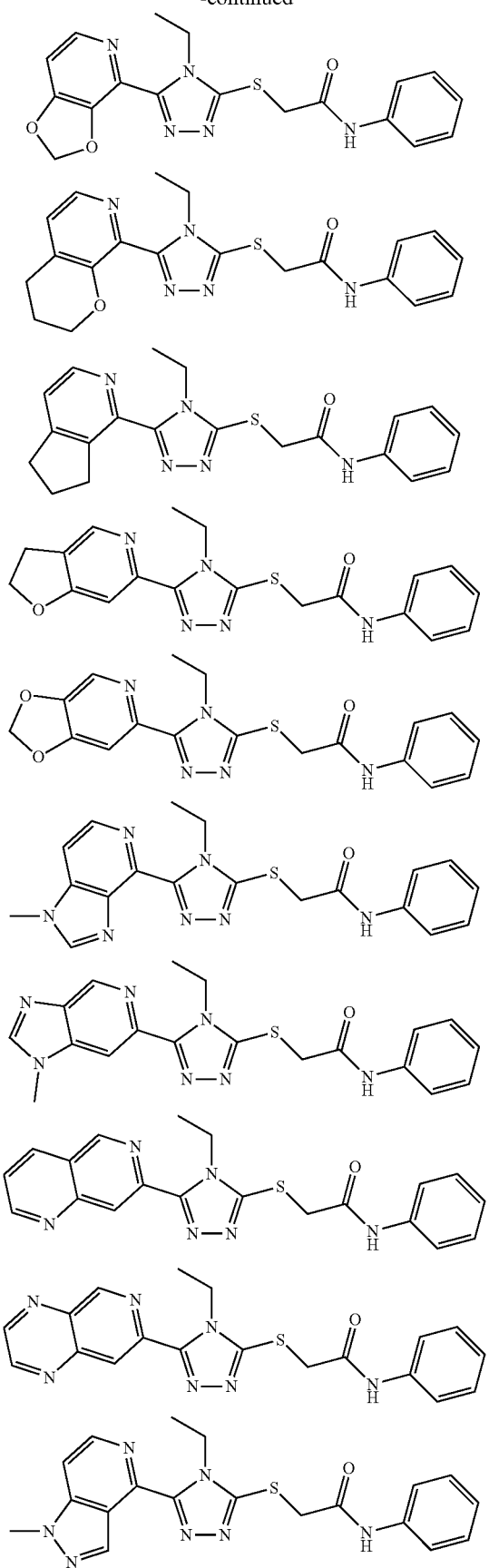
114
-continued
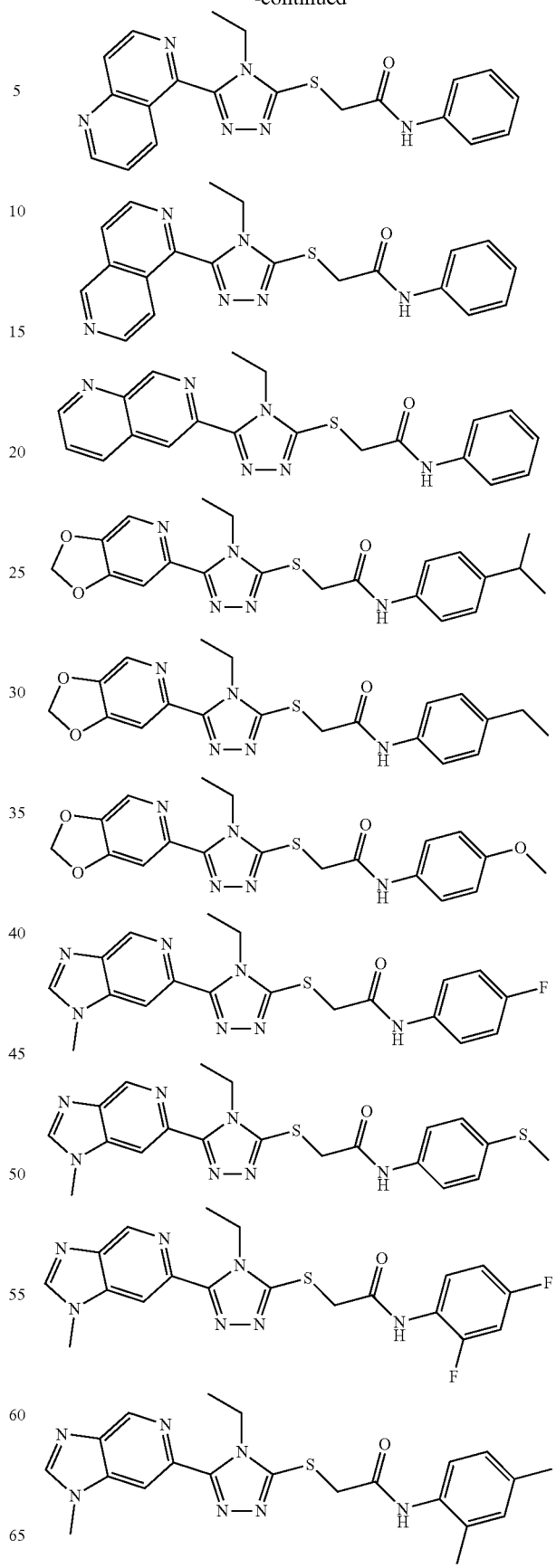

-continued
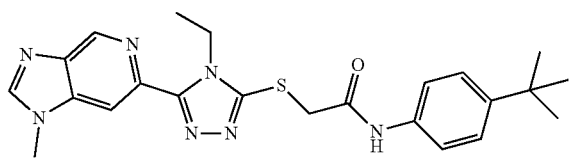
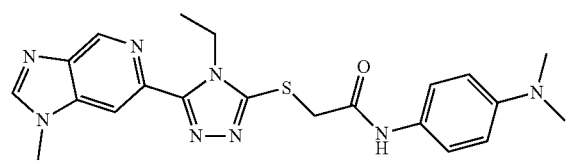
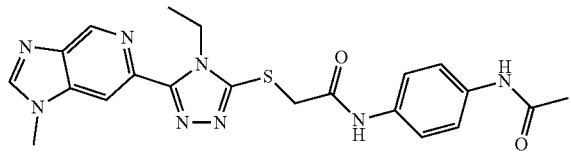
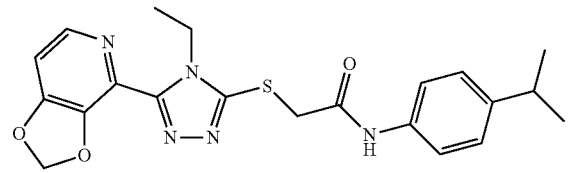
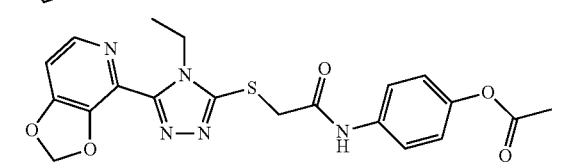
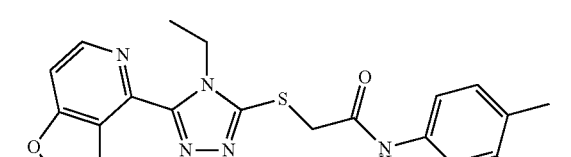
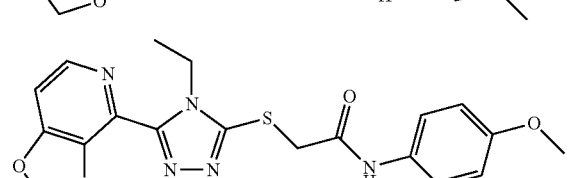
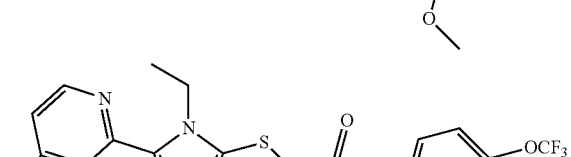
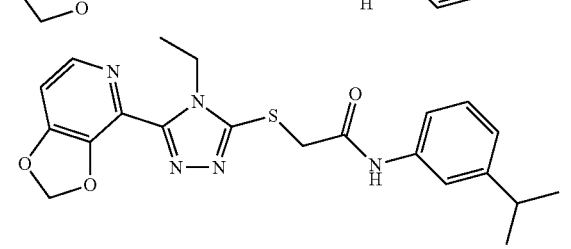
-continued
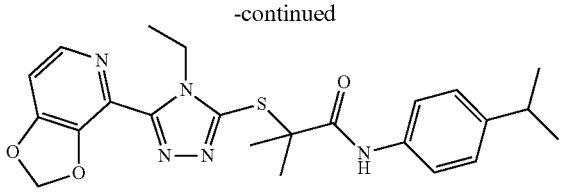
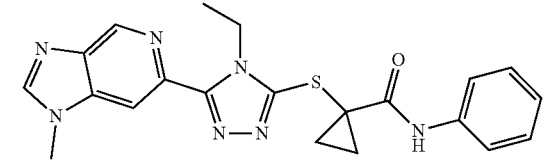
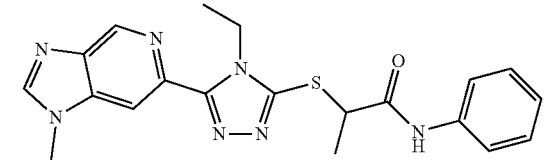
In one aspect, a disclosed compound can have the formula (III):
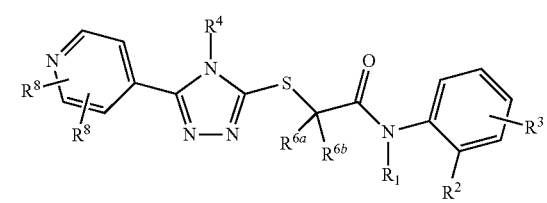
Exemplary compound within Formula (III) include, but are not limited to:
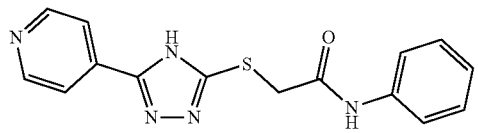
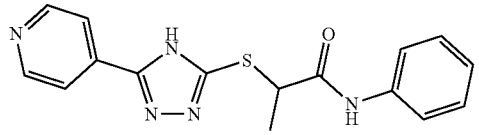
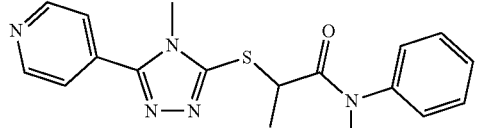
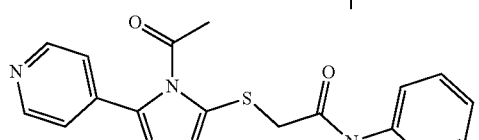
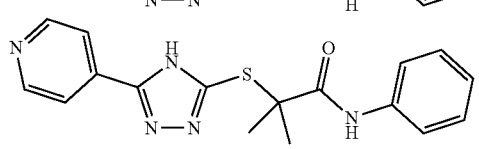

117
-continued
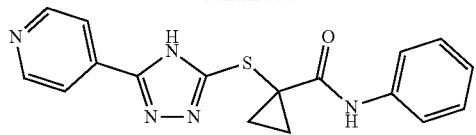
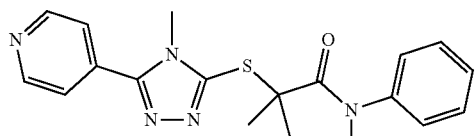
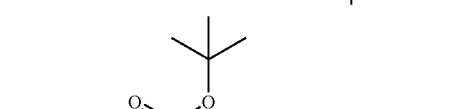
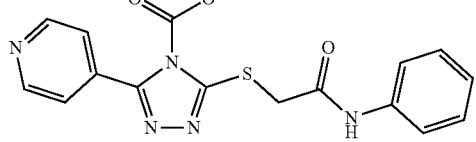
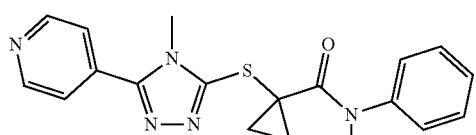
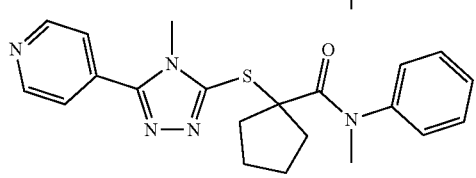
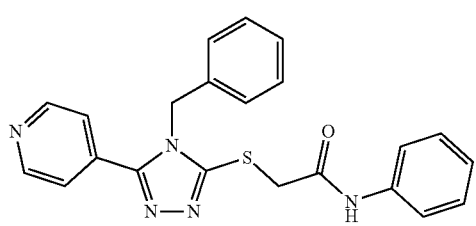
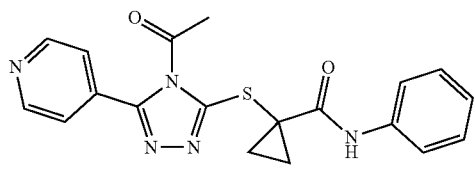
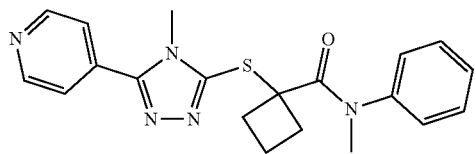
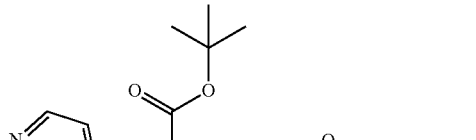
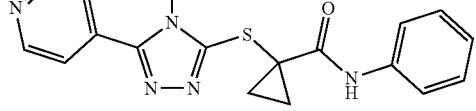
118
-continued
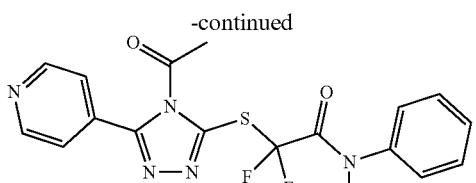
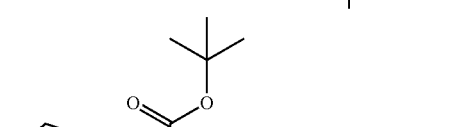
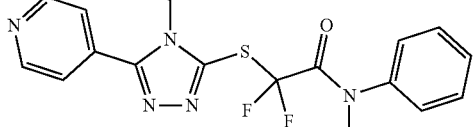
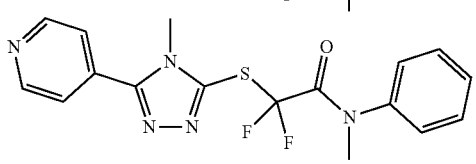
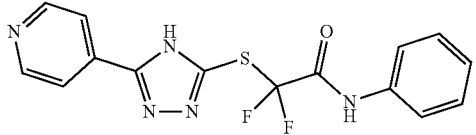
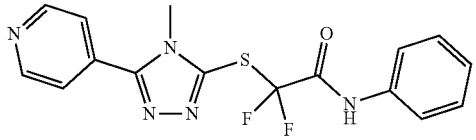
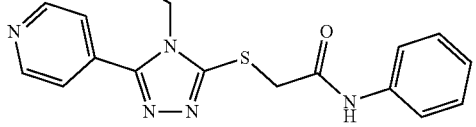
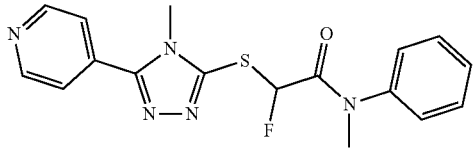
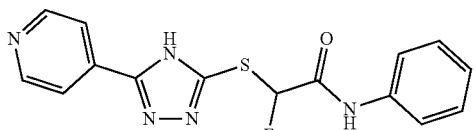
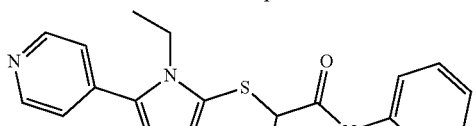
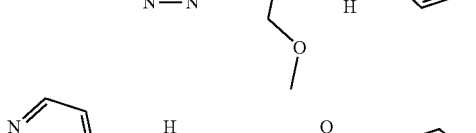

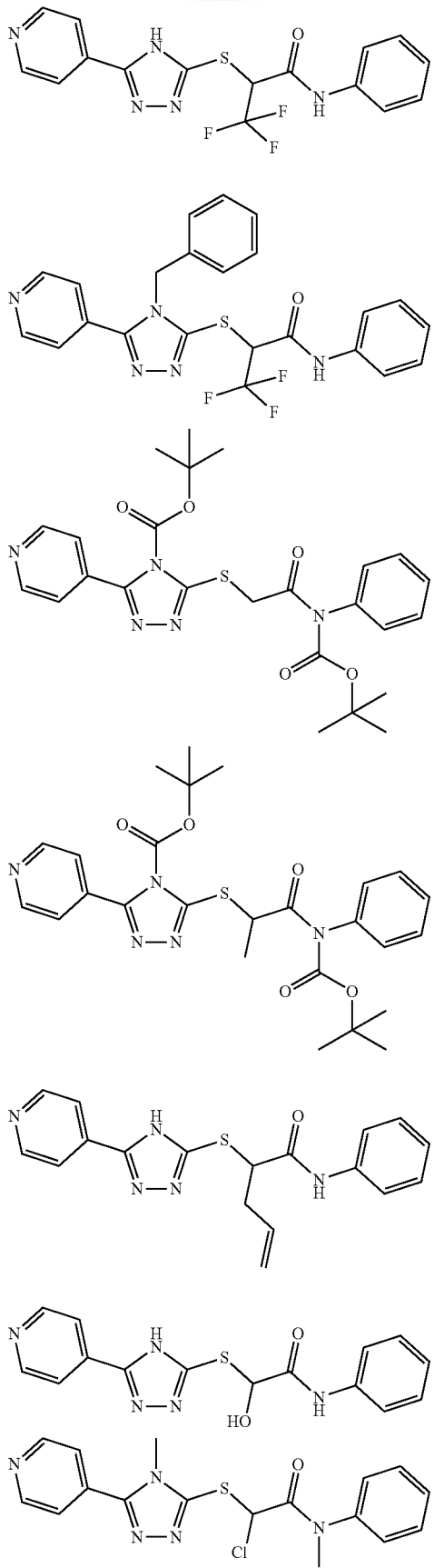
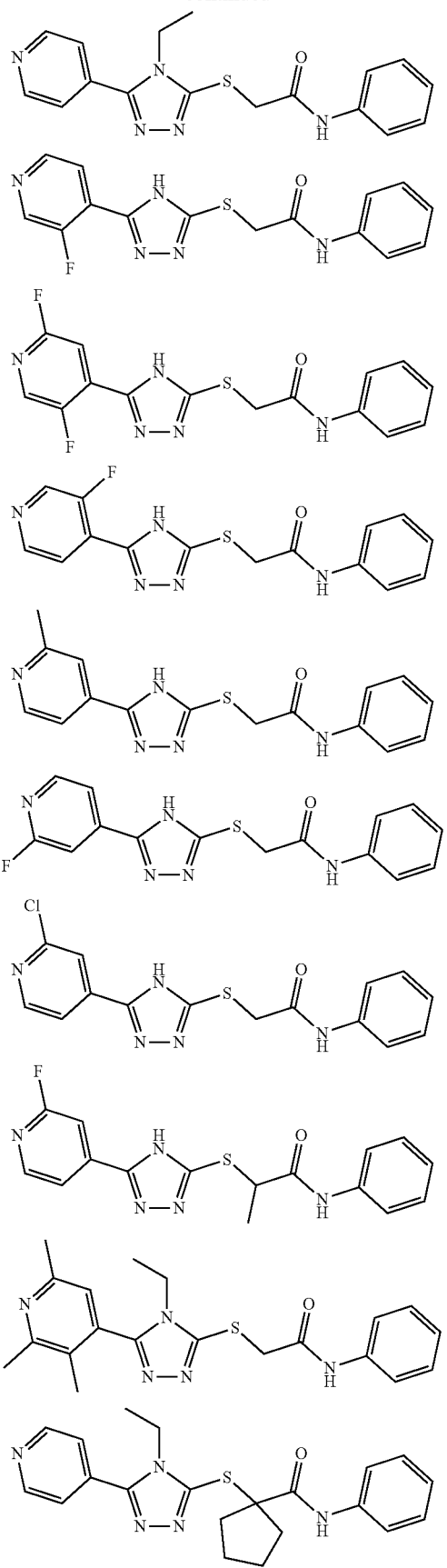

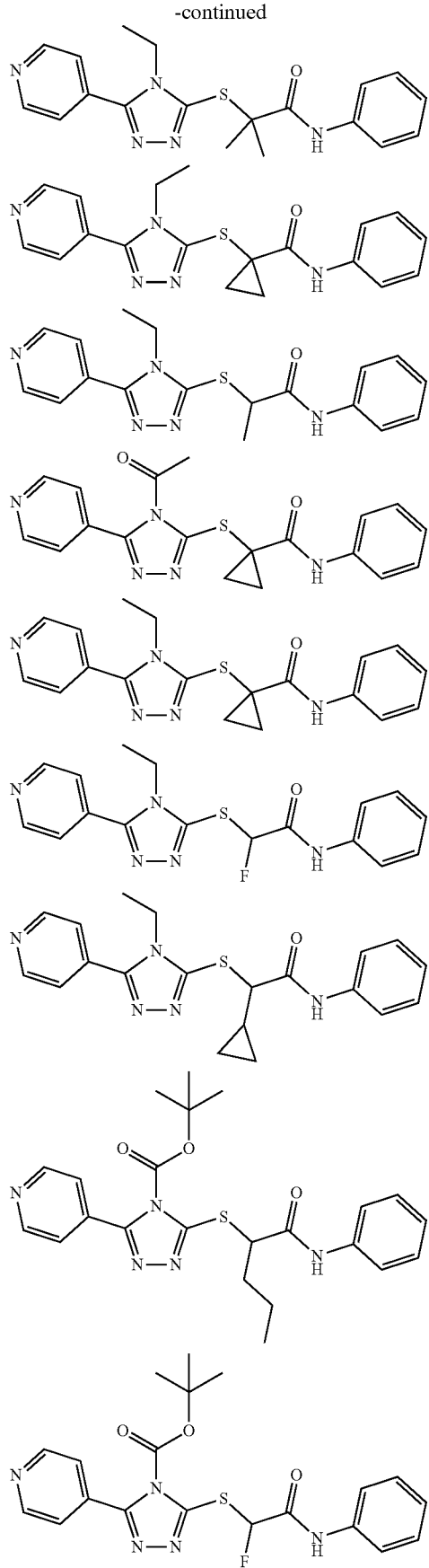
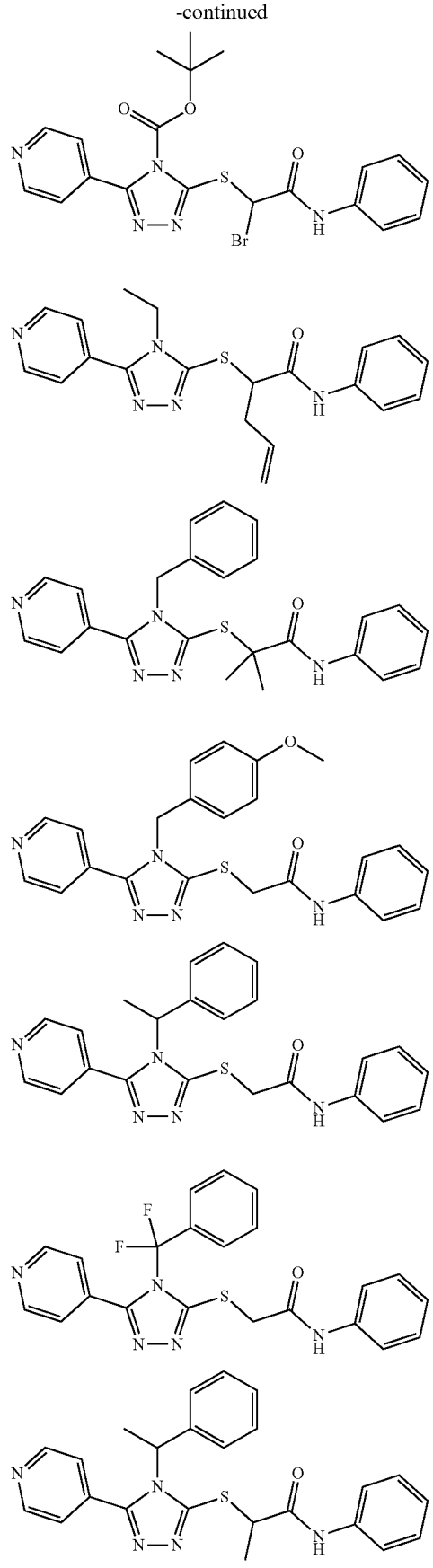

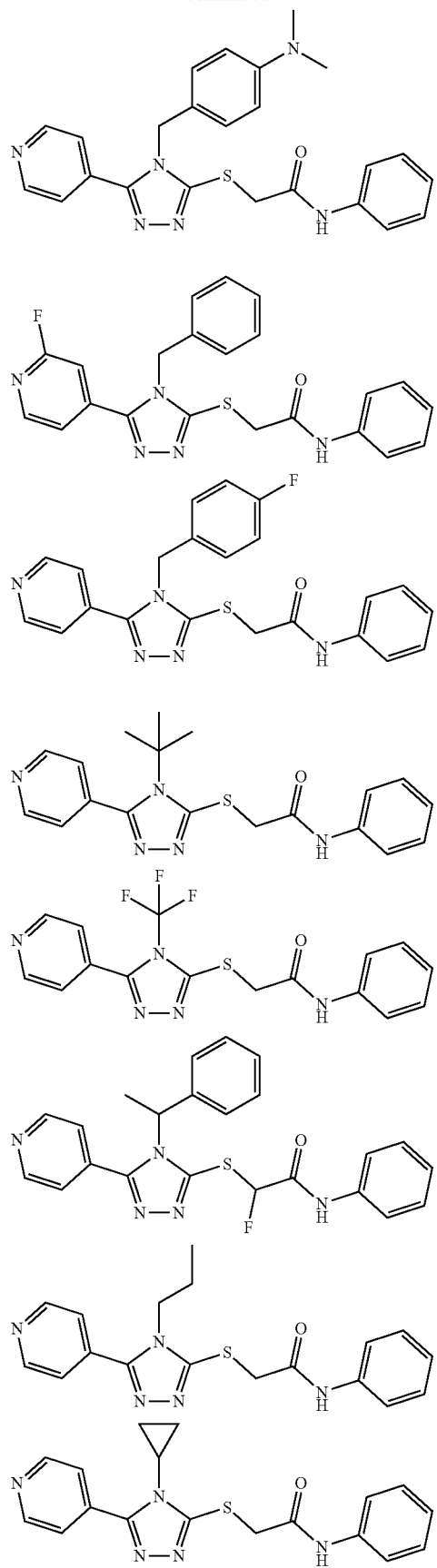
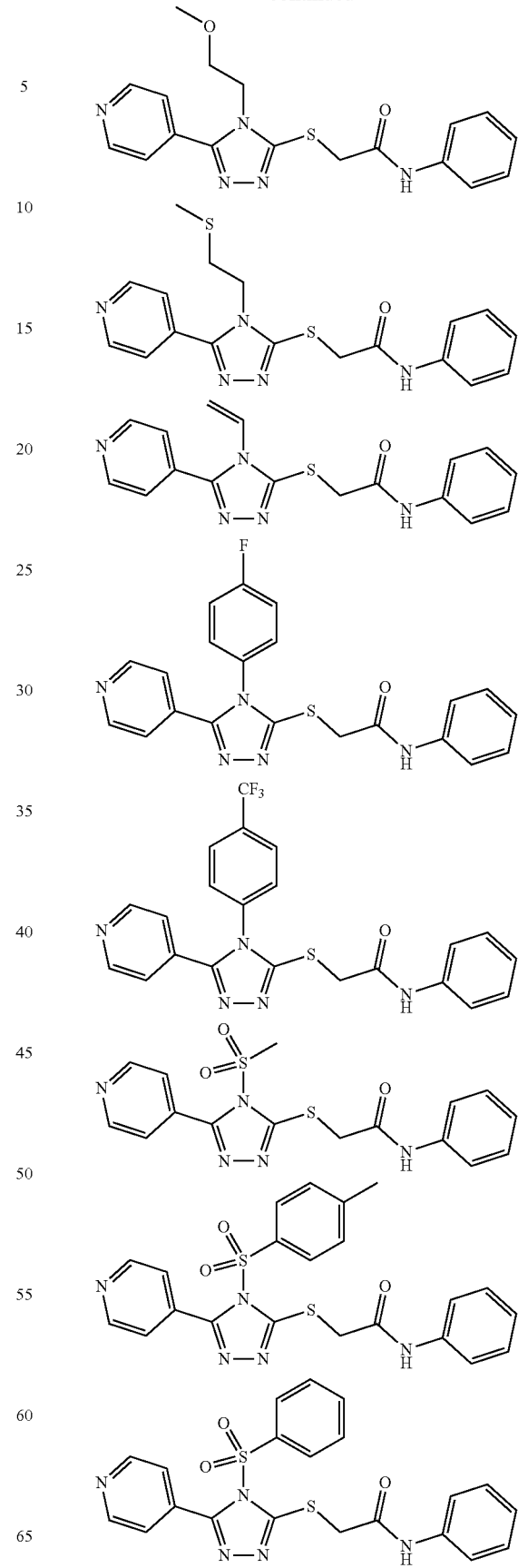

-continued
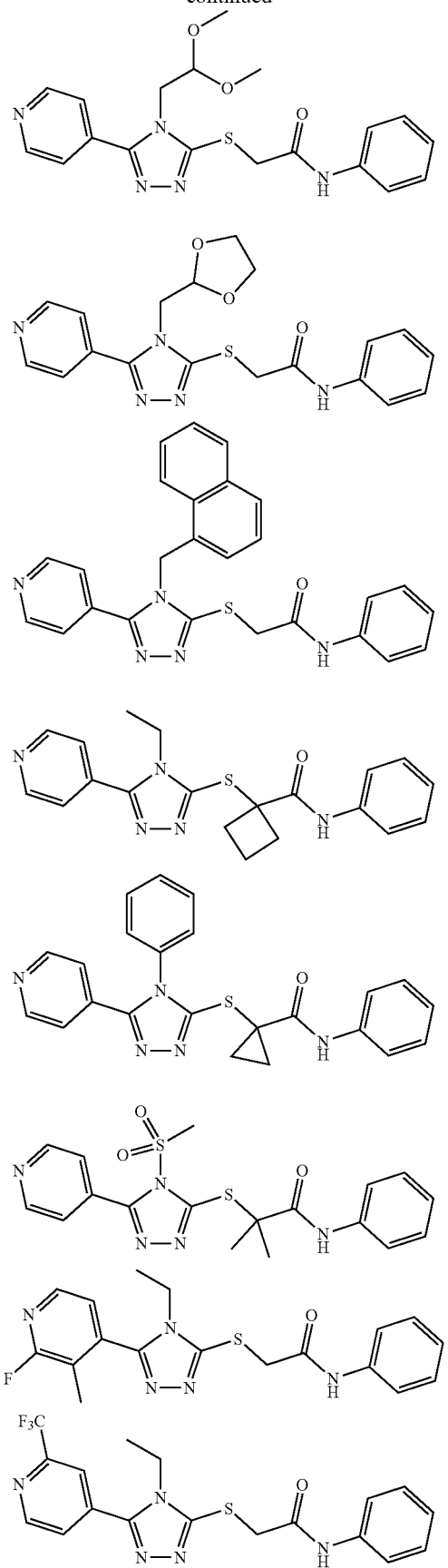
-continued
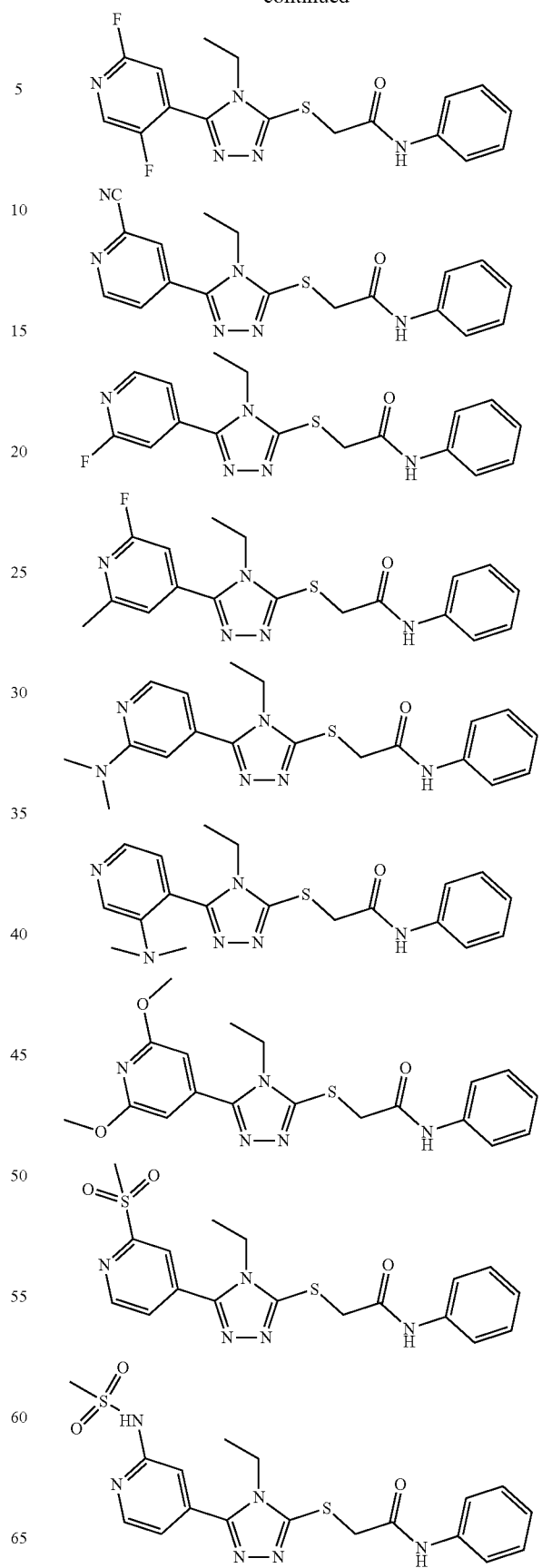

-continued
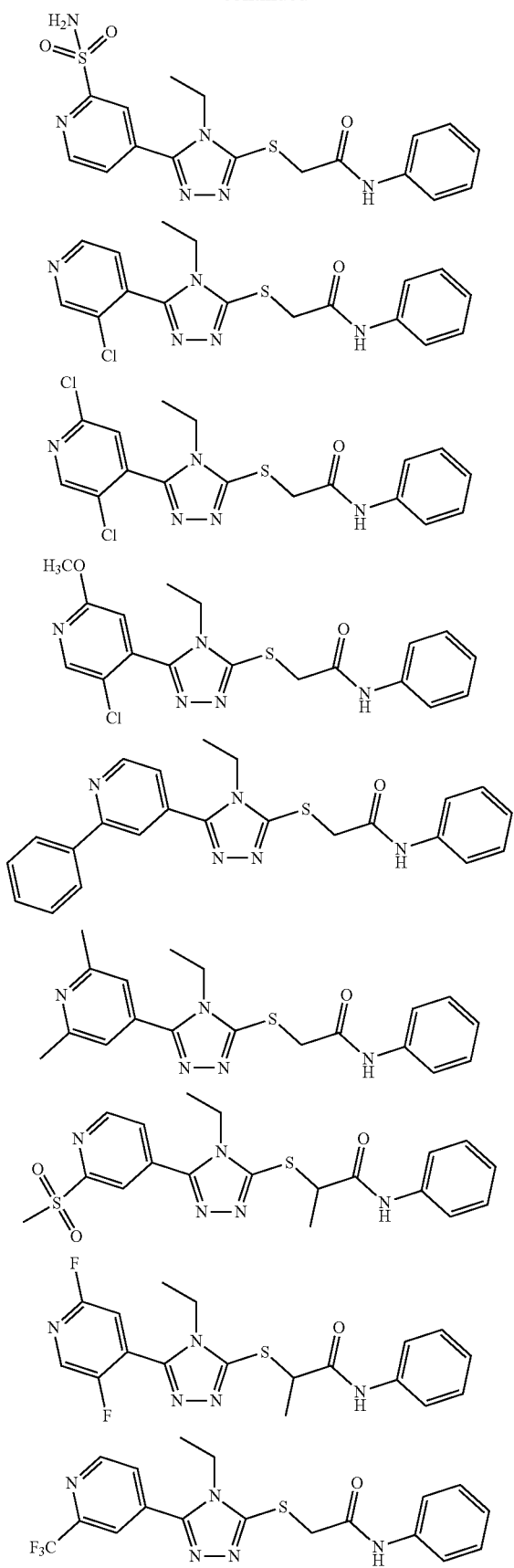
-continued
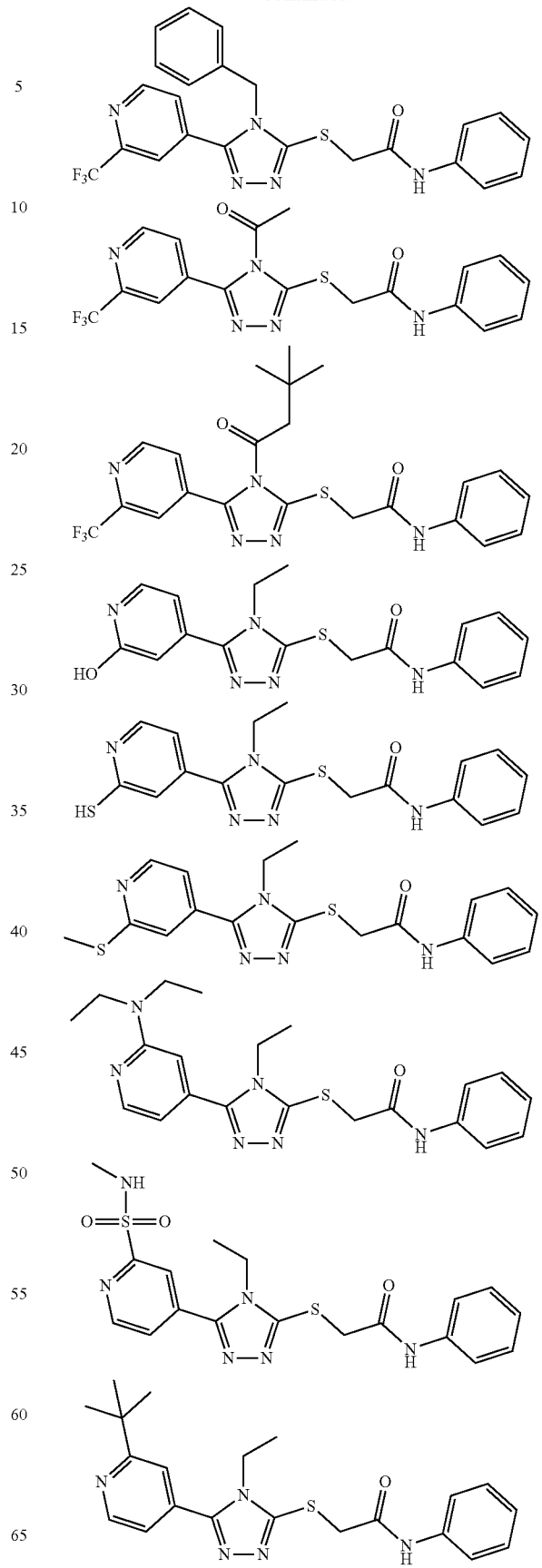

-continued

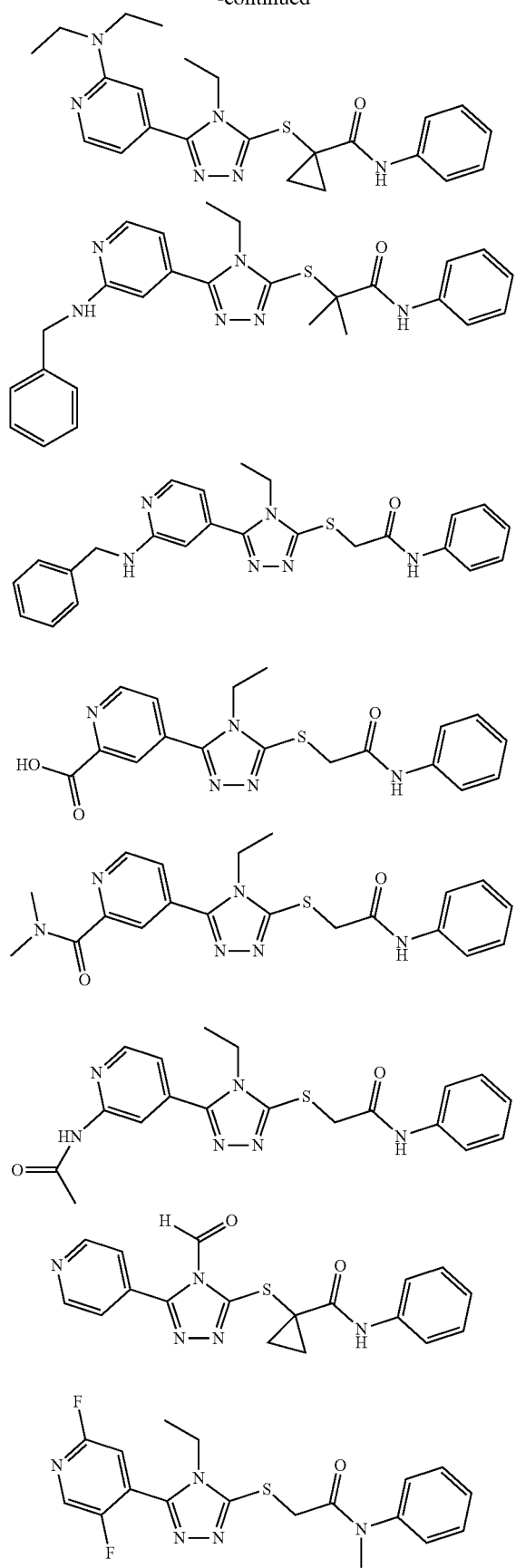
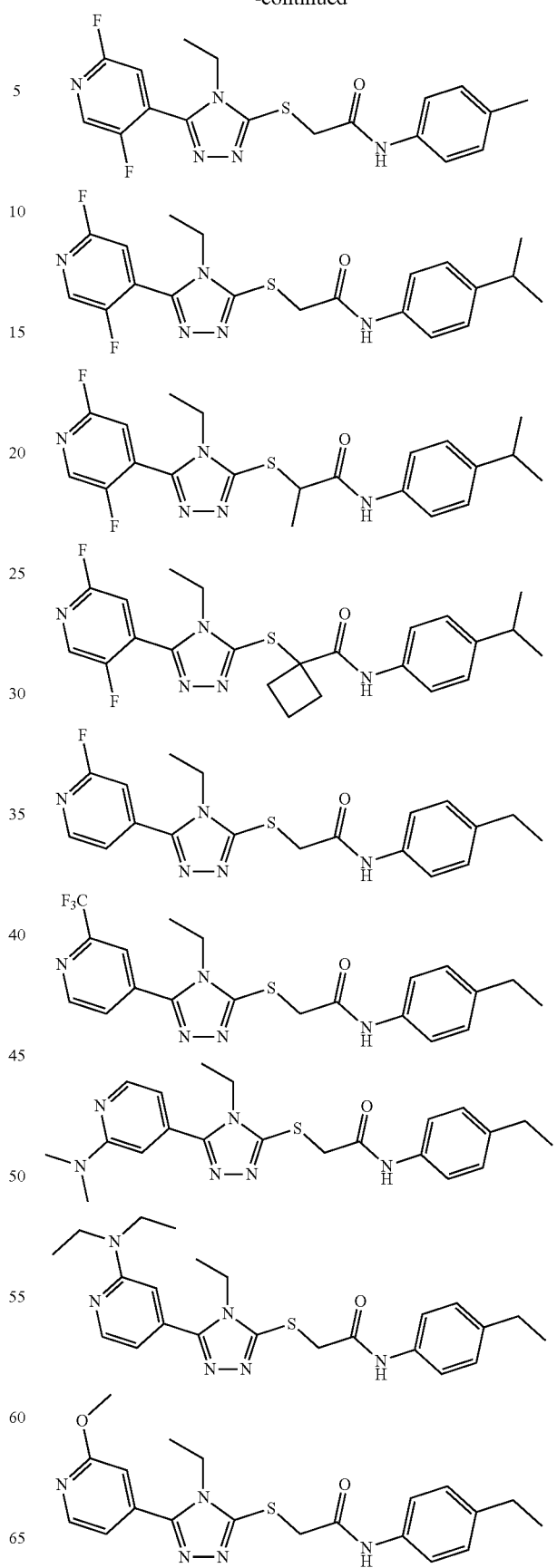

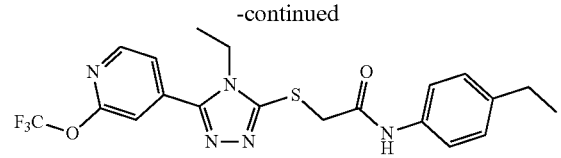
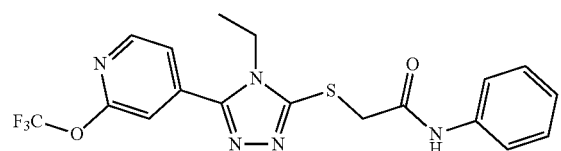
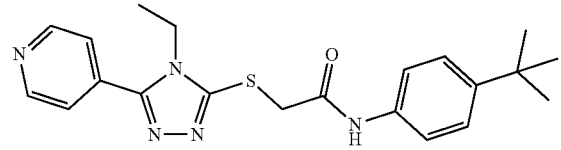
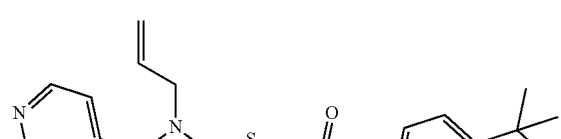
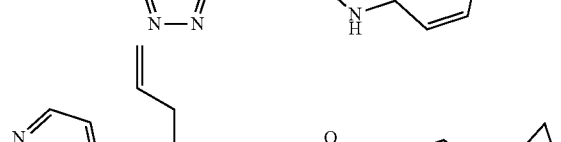
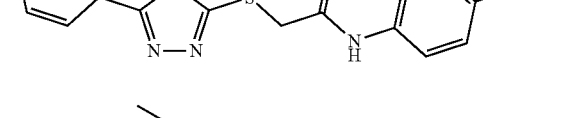
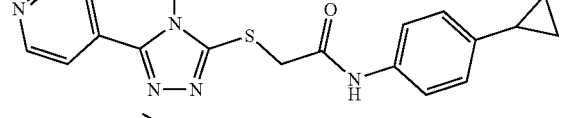
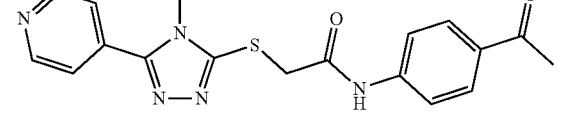
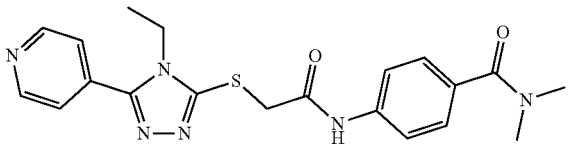
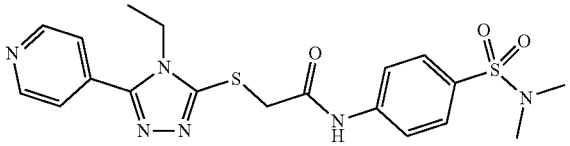
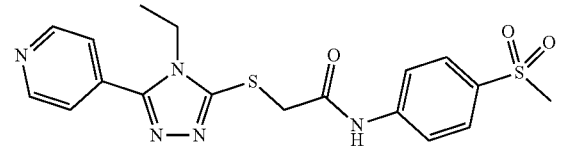
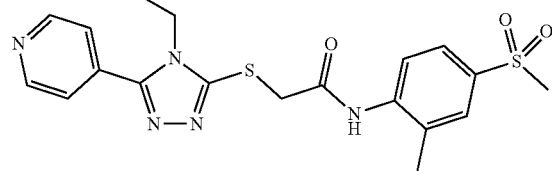
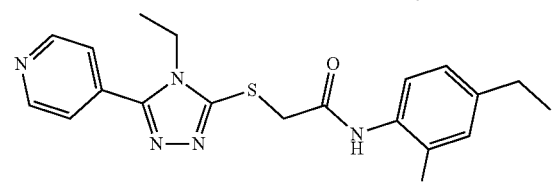
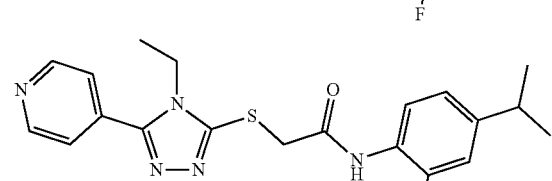
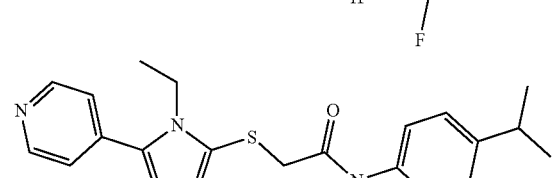
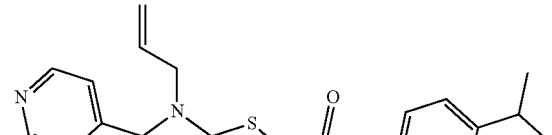
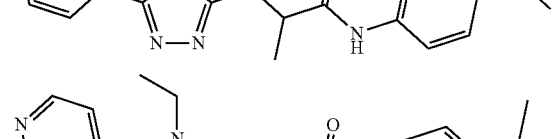
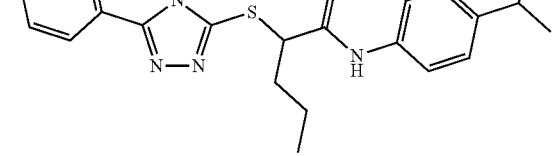
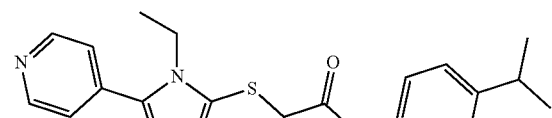
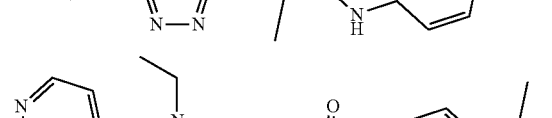
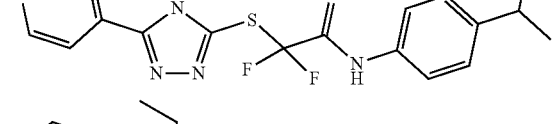
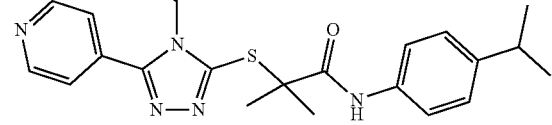

135
-continued
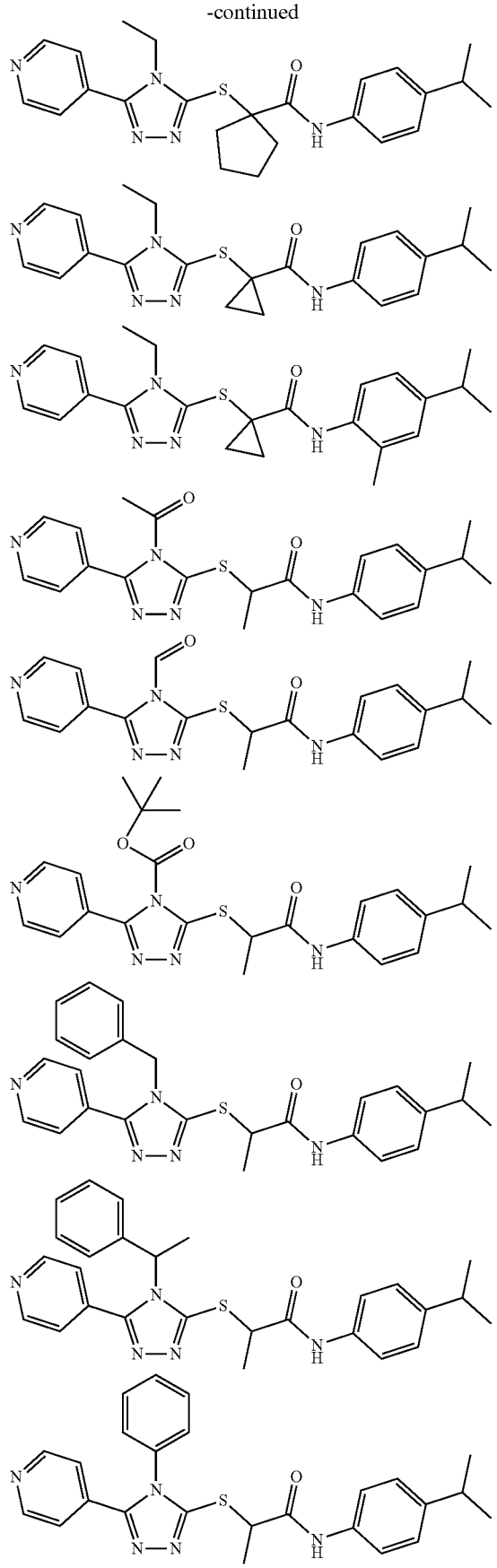
136
-continued
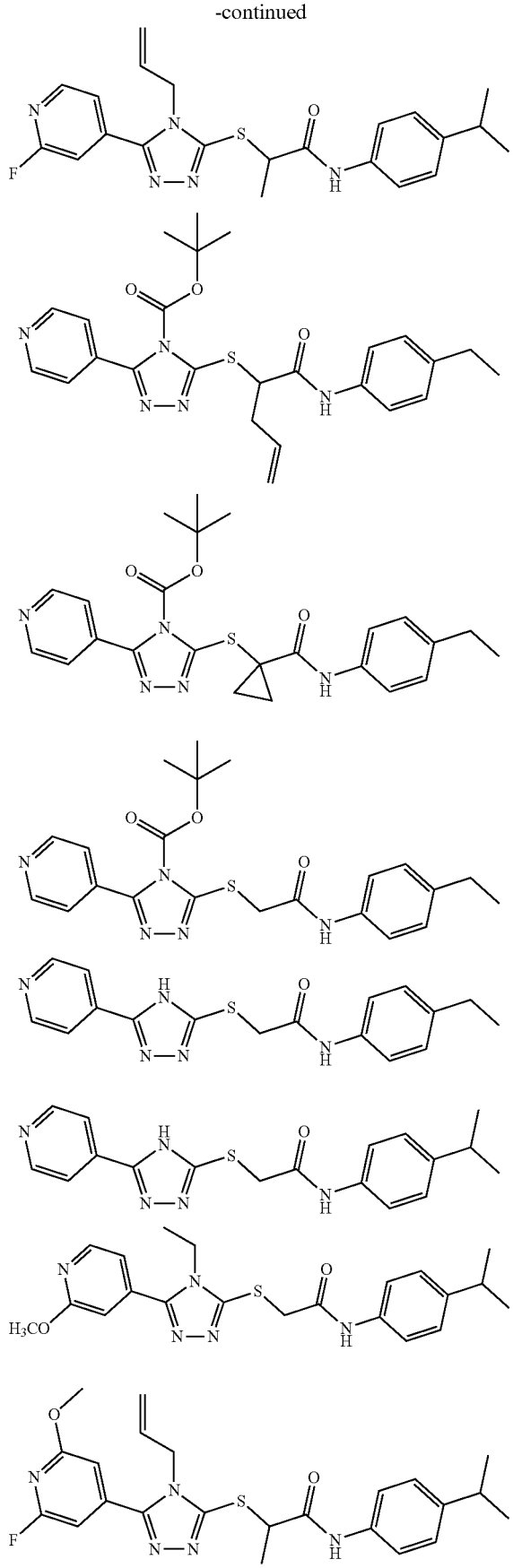

137
-continued
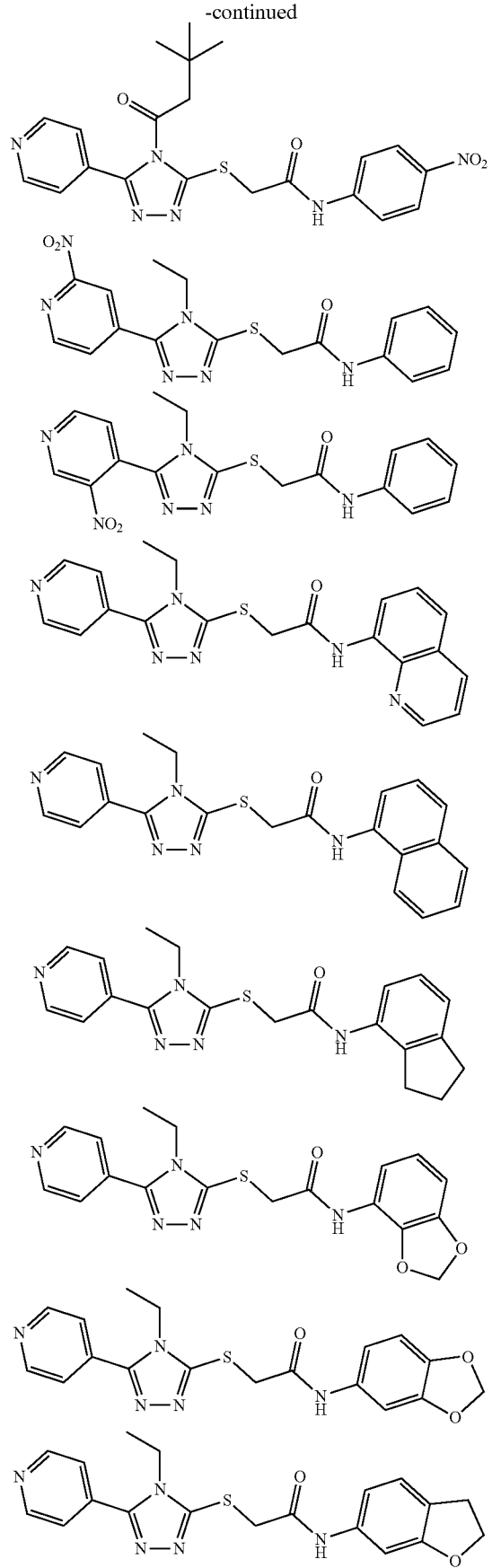
138
-continued
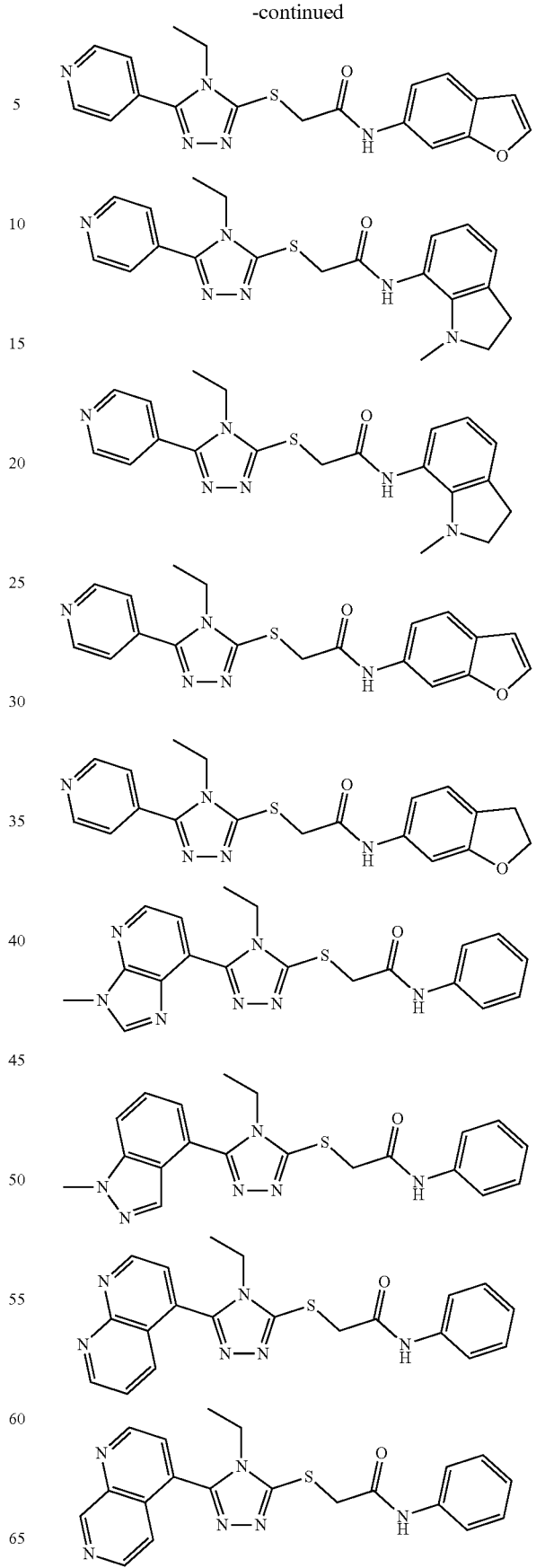

-continued
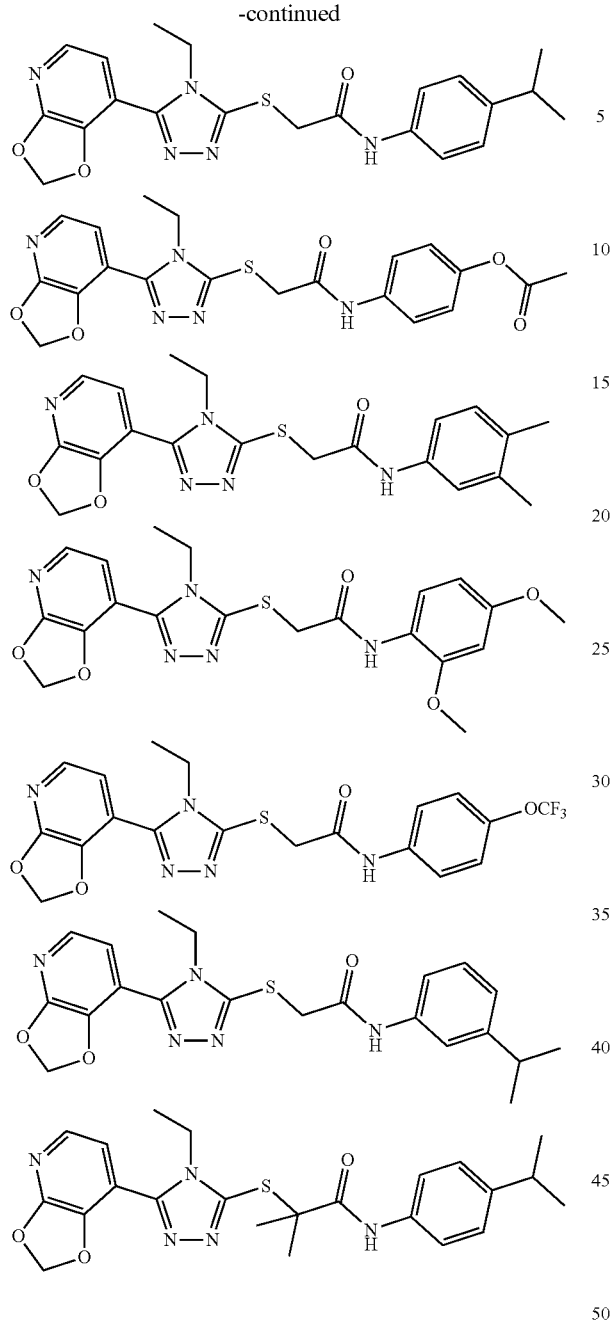
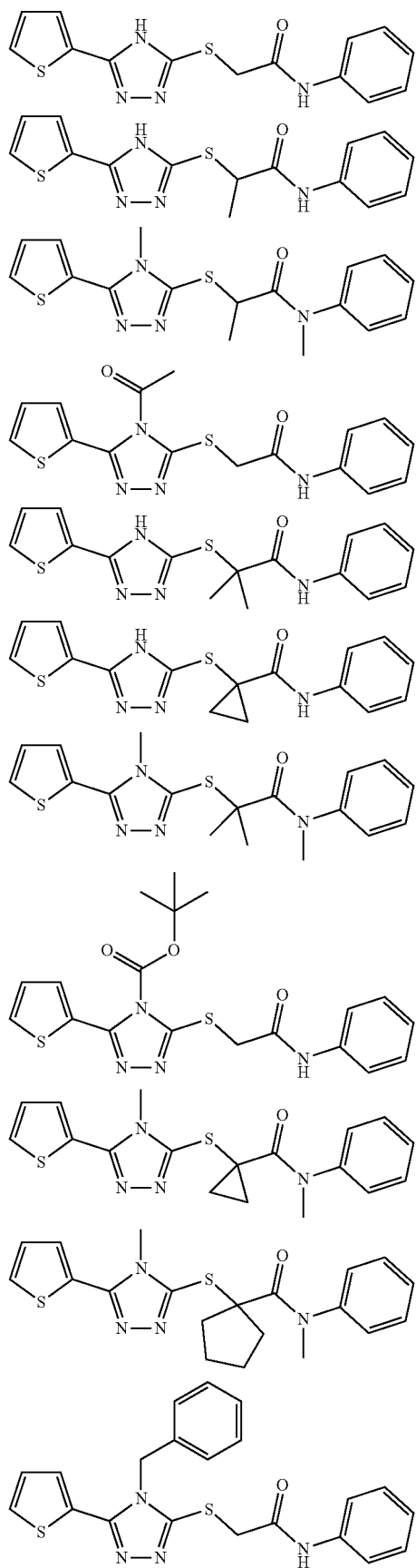
In one aspect, a disclosed compound can have the formula (IV):
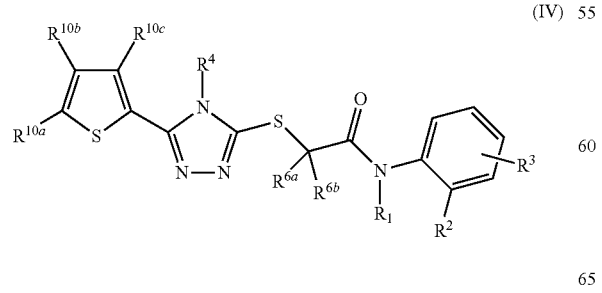
Exemplary compound within Formula (IV) include, but are not limited to:

-continued
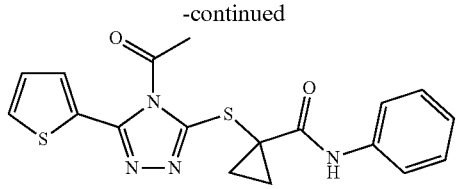
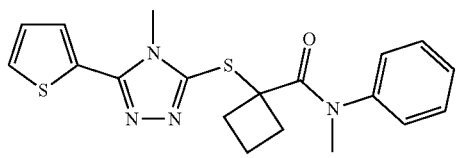
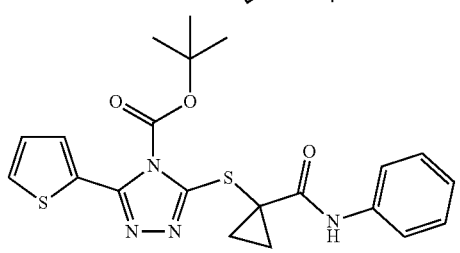
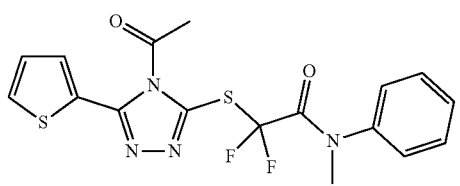
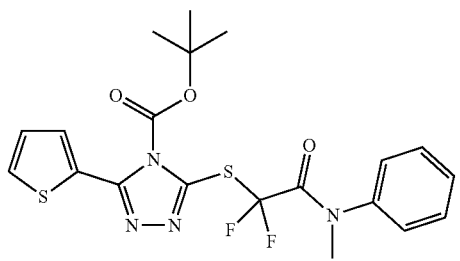
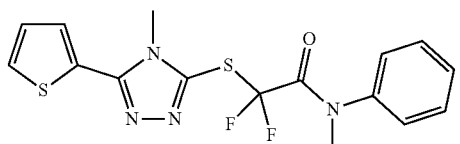
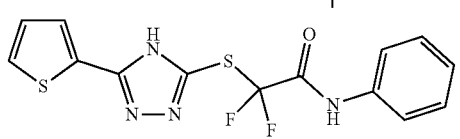
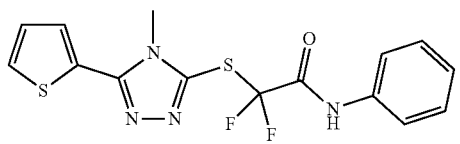
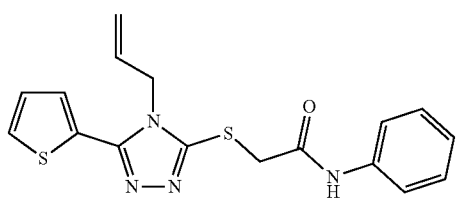
-continued
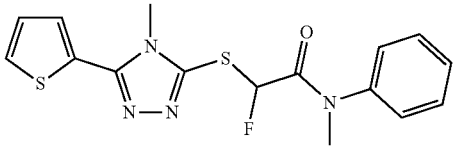
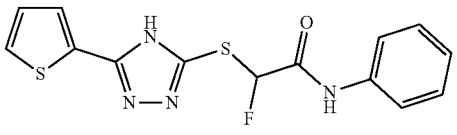
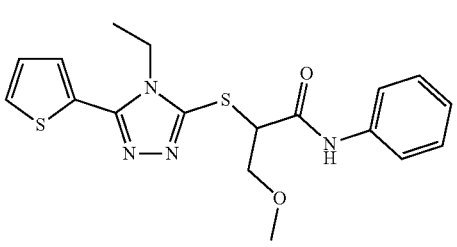
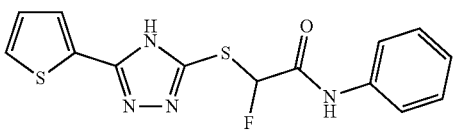
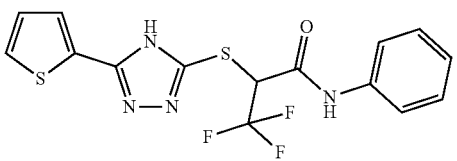
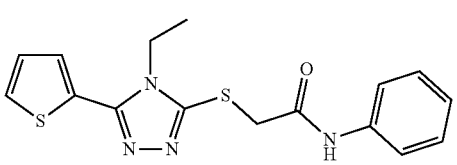
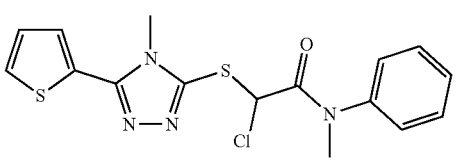
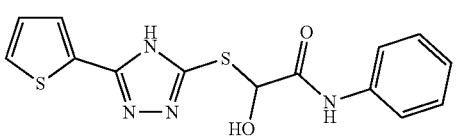
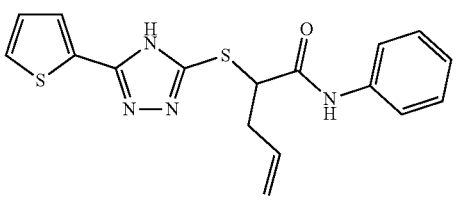

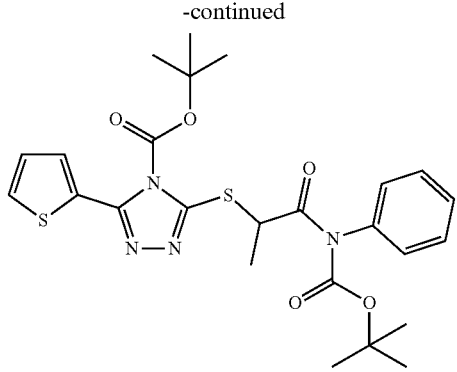
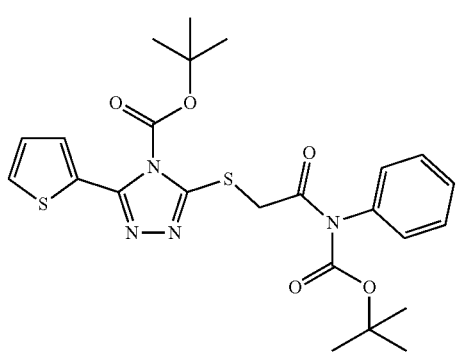
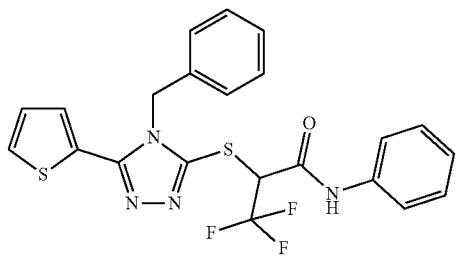
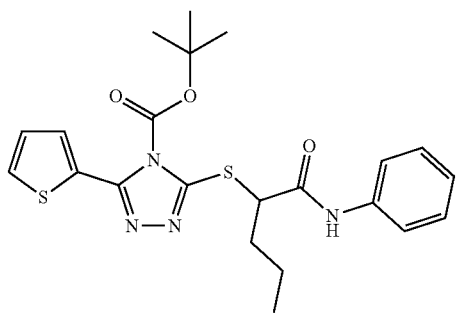
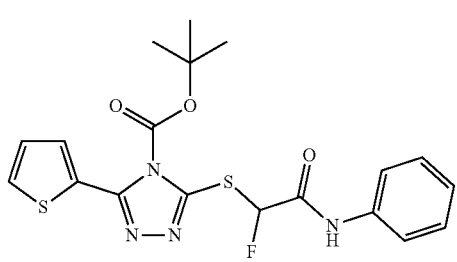
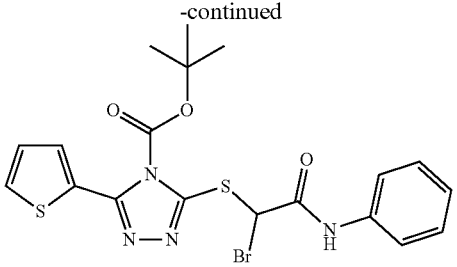
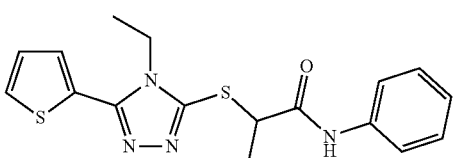
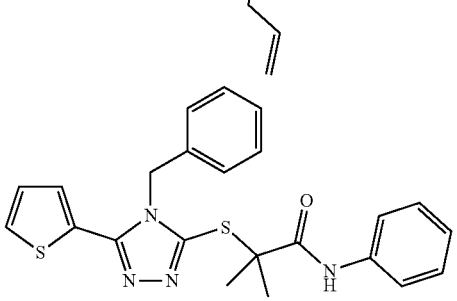
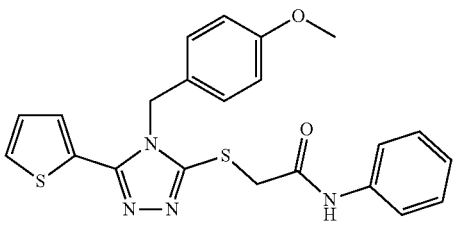
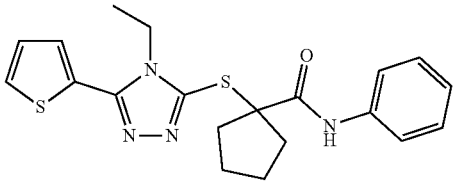
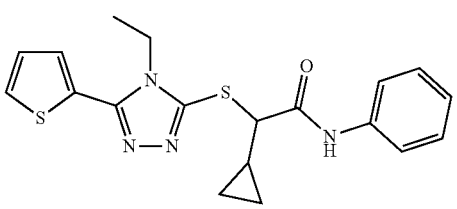
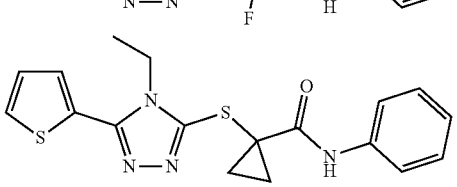

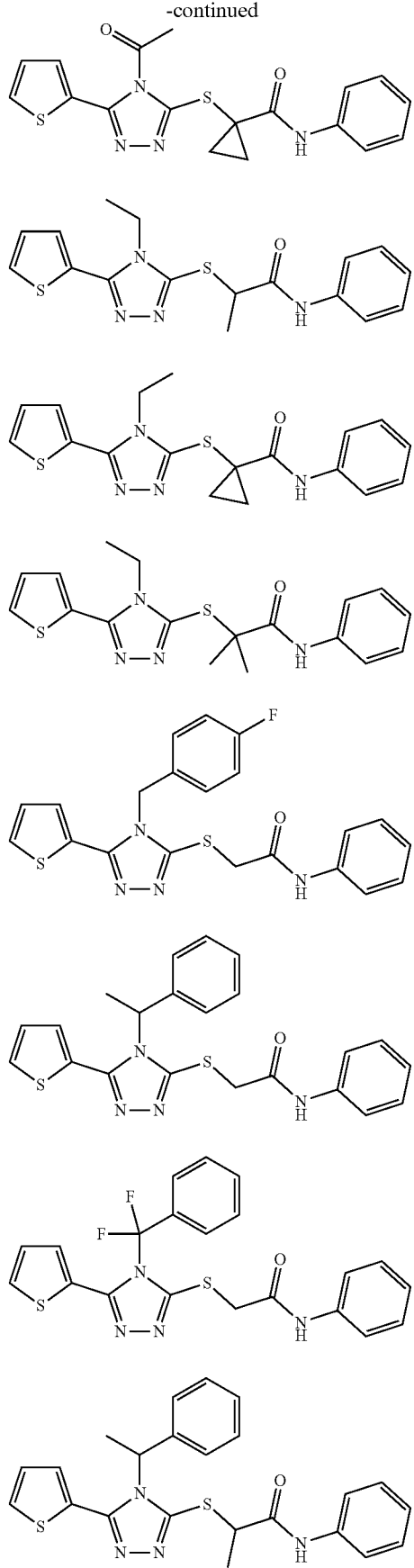
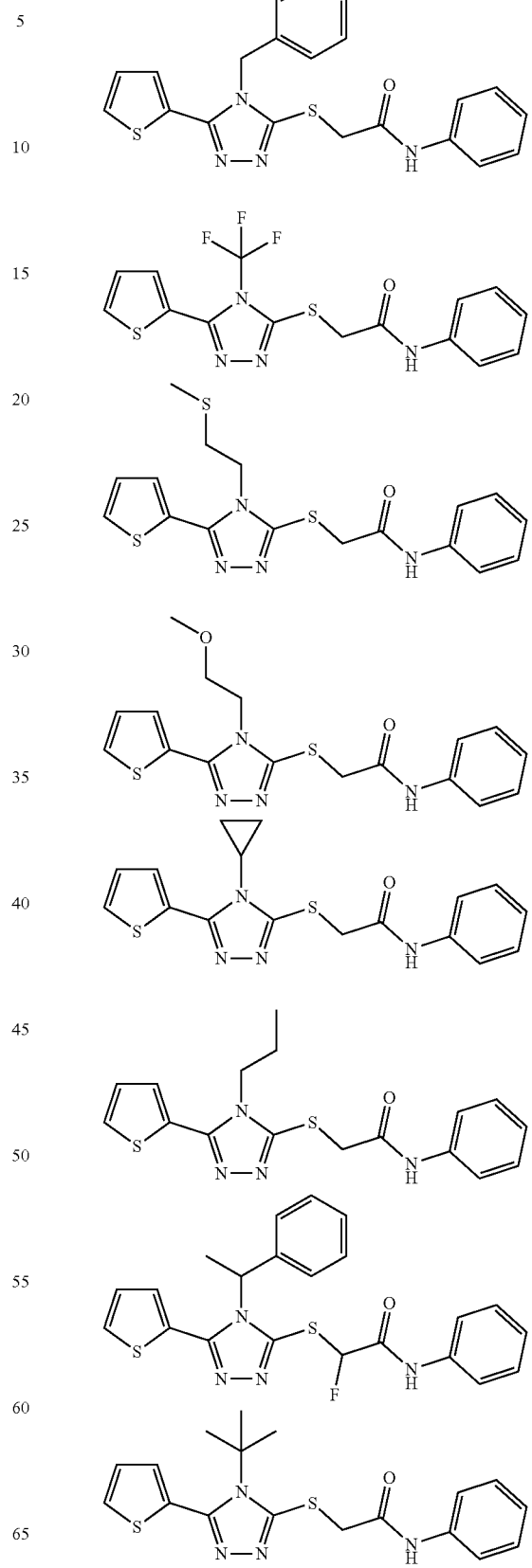

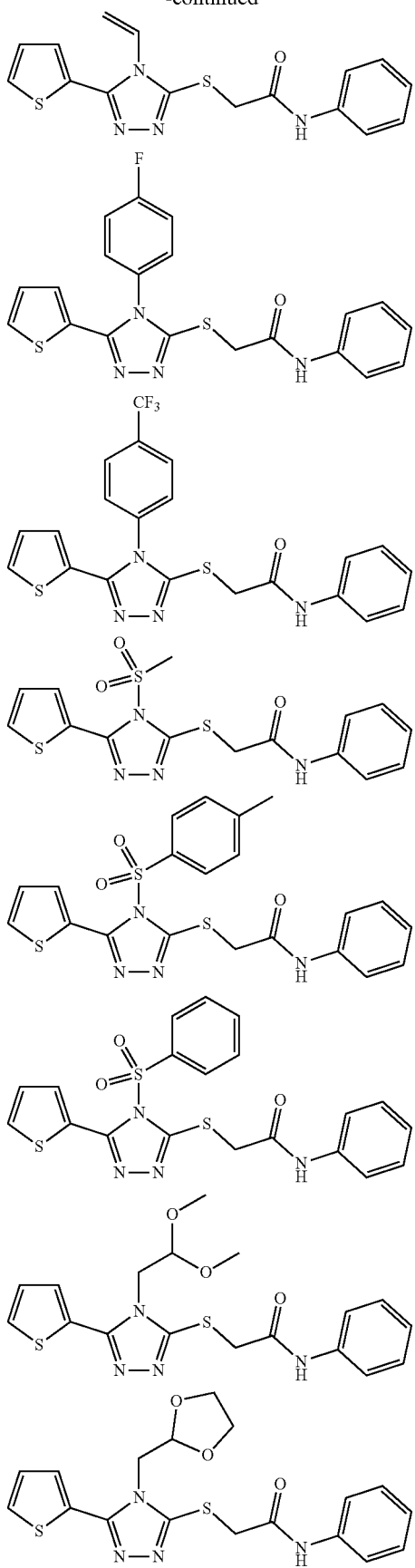
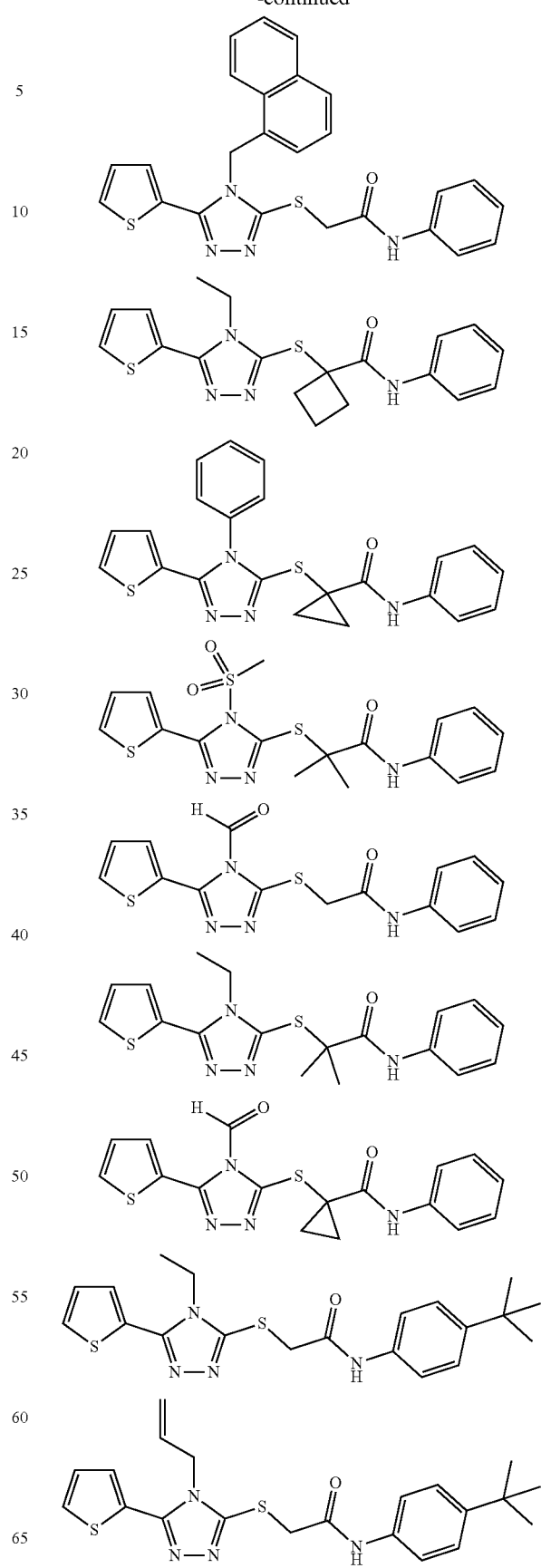

-continued
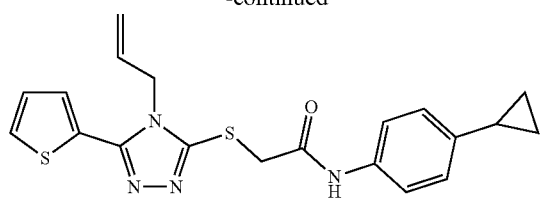
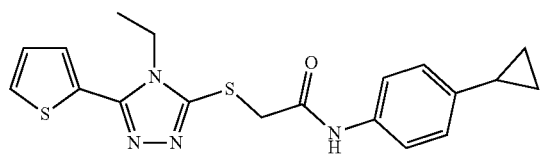
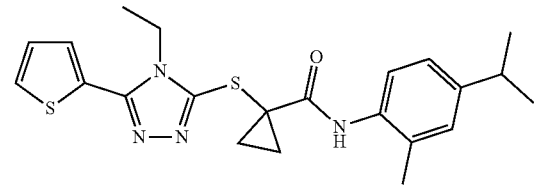
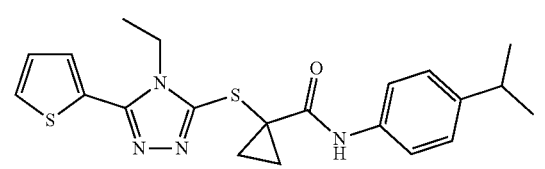
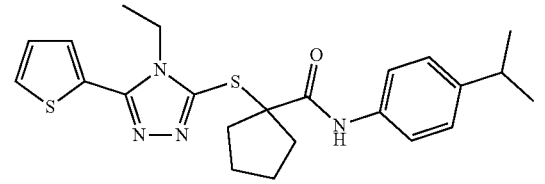
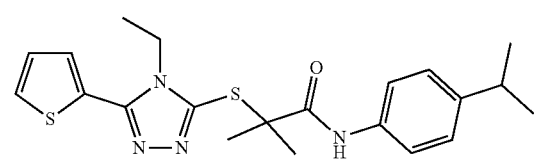
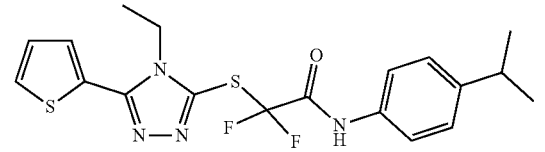
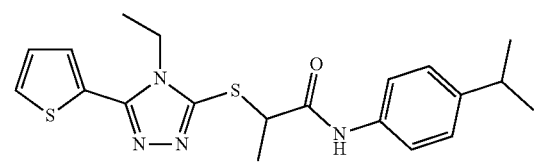
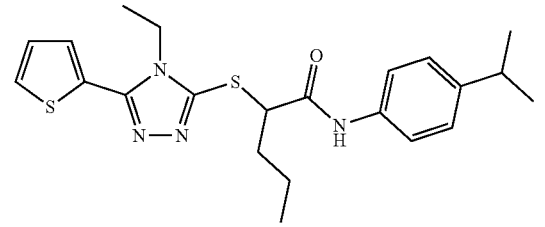
-continued
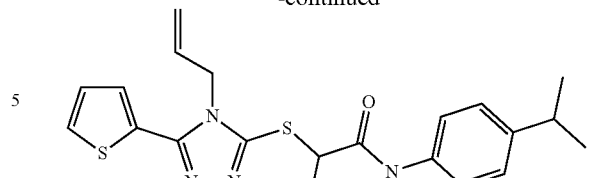
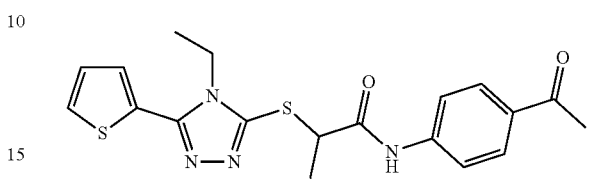
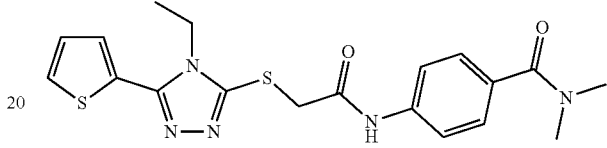
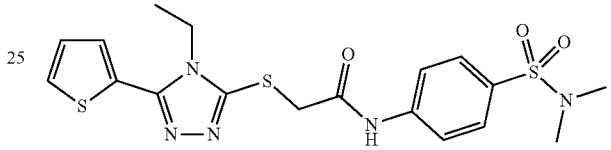
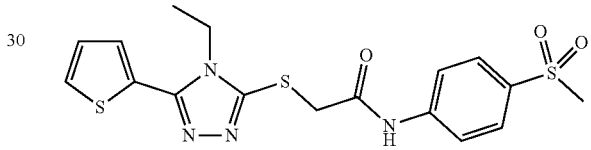
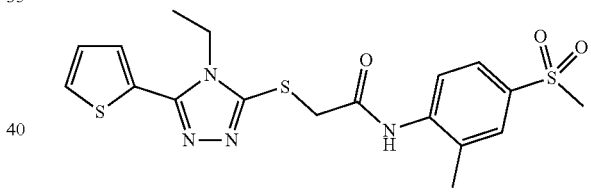
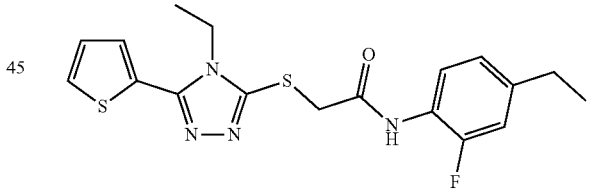
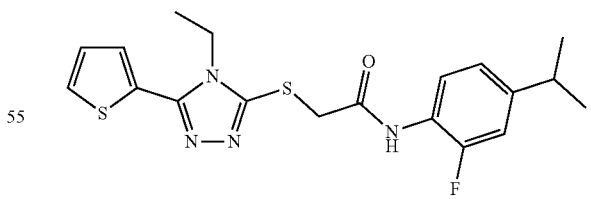
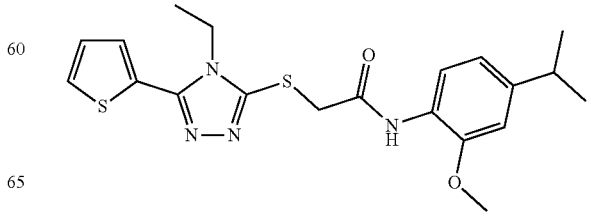

151
-continued
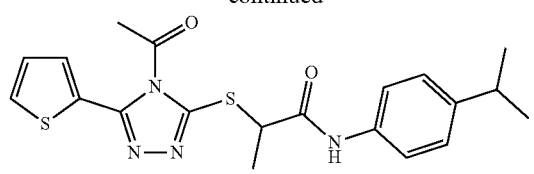
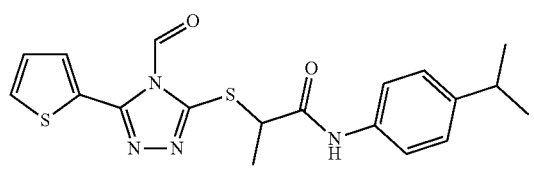
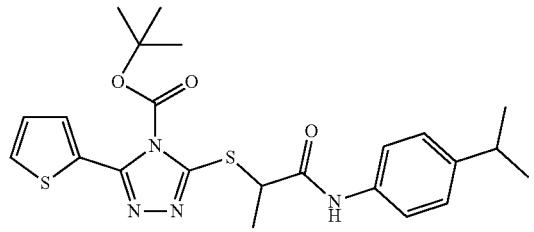
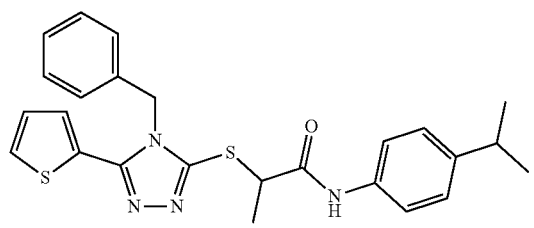
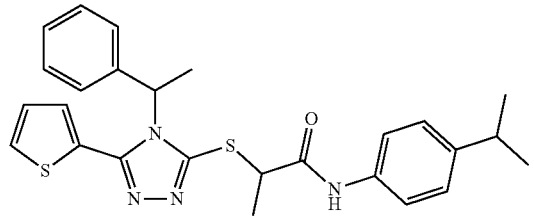
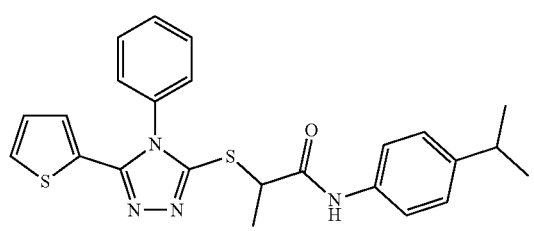
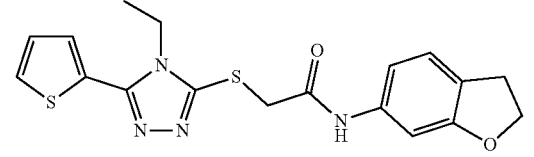
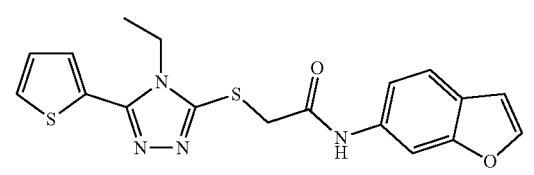
152
-continued
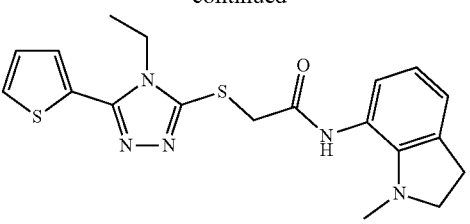
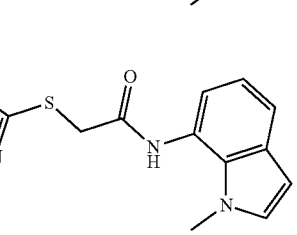
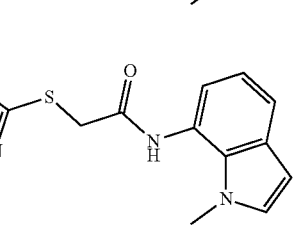
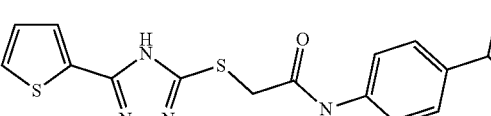
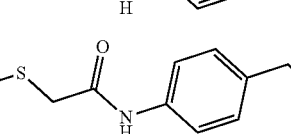
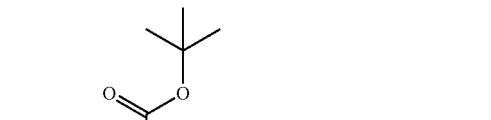
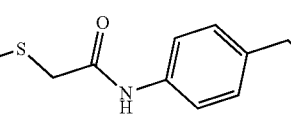
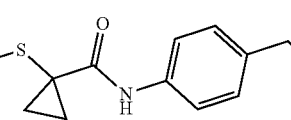
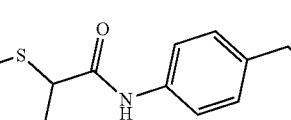

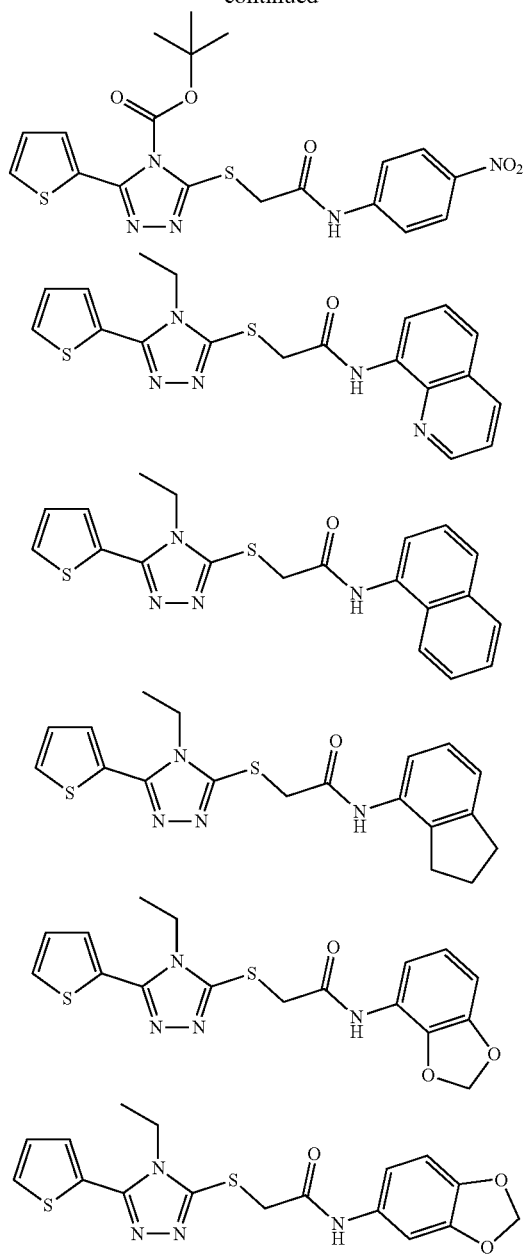
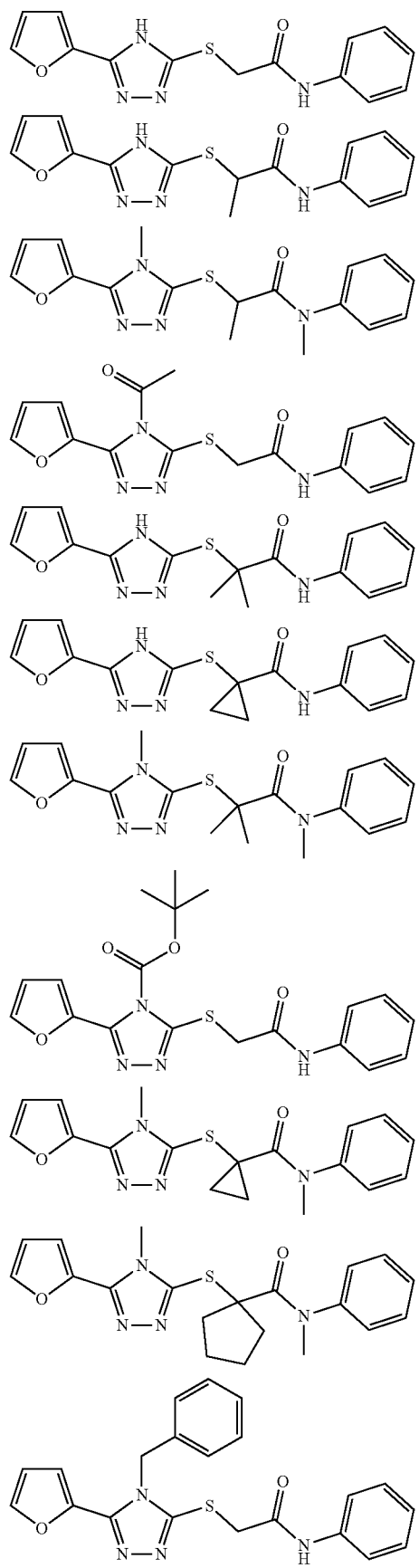
In one aspect, a disclosed compound can have the formula (V):
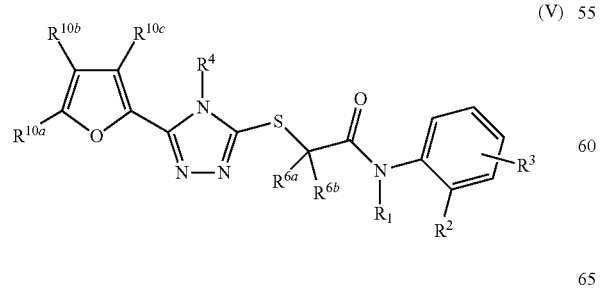
Exemplary compound within Formula (V) include, but are not limited to:

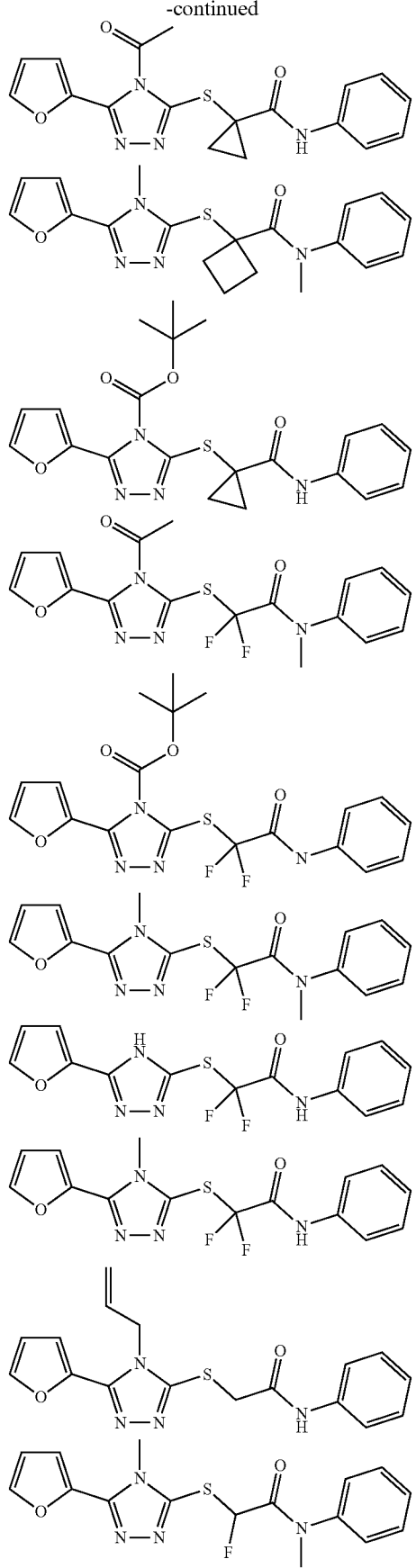
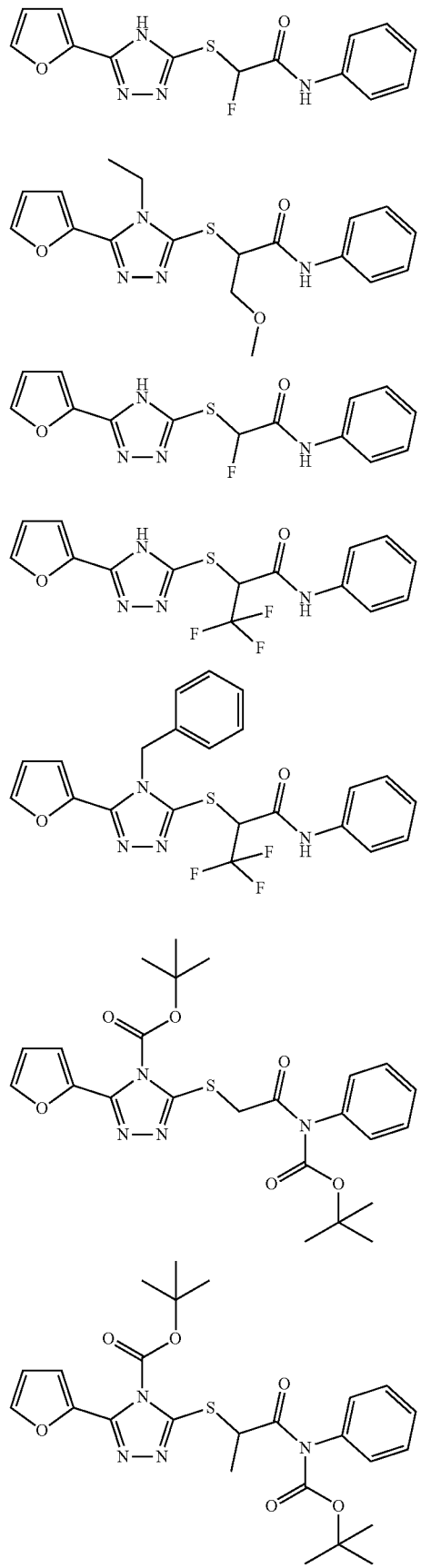

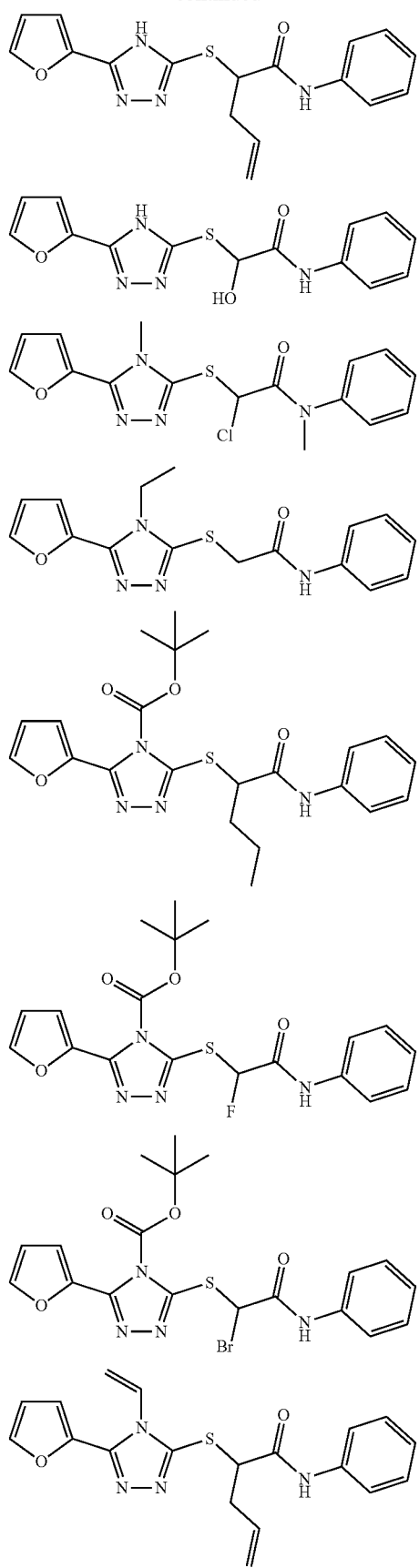
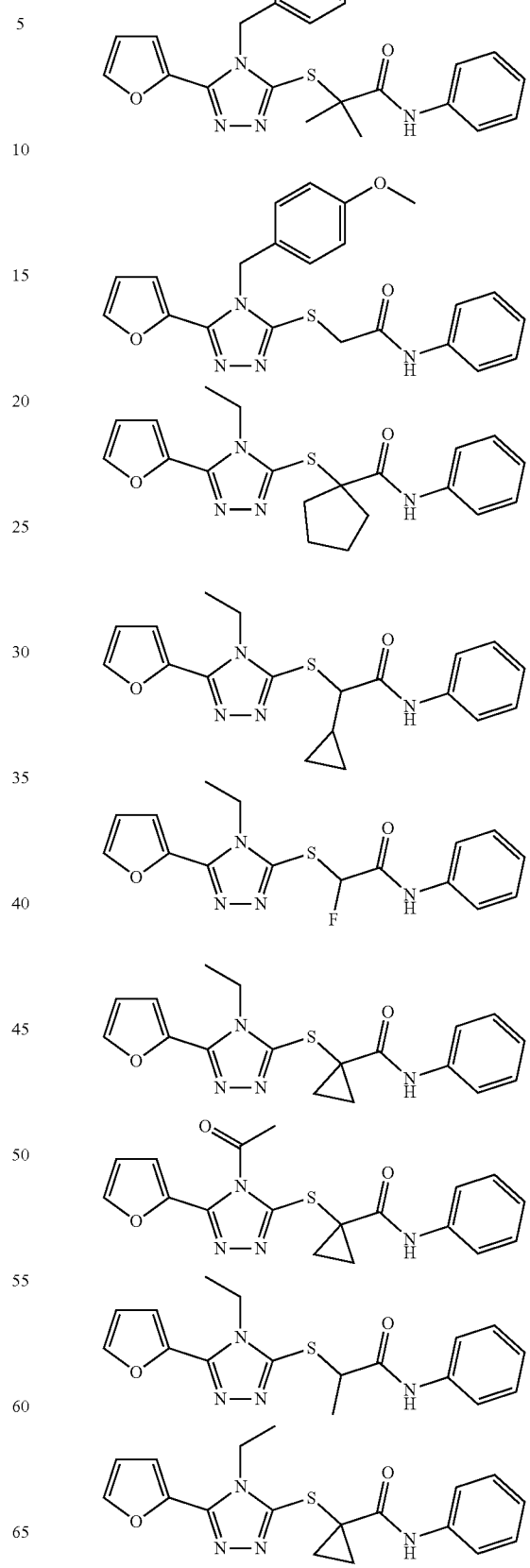

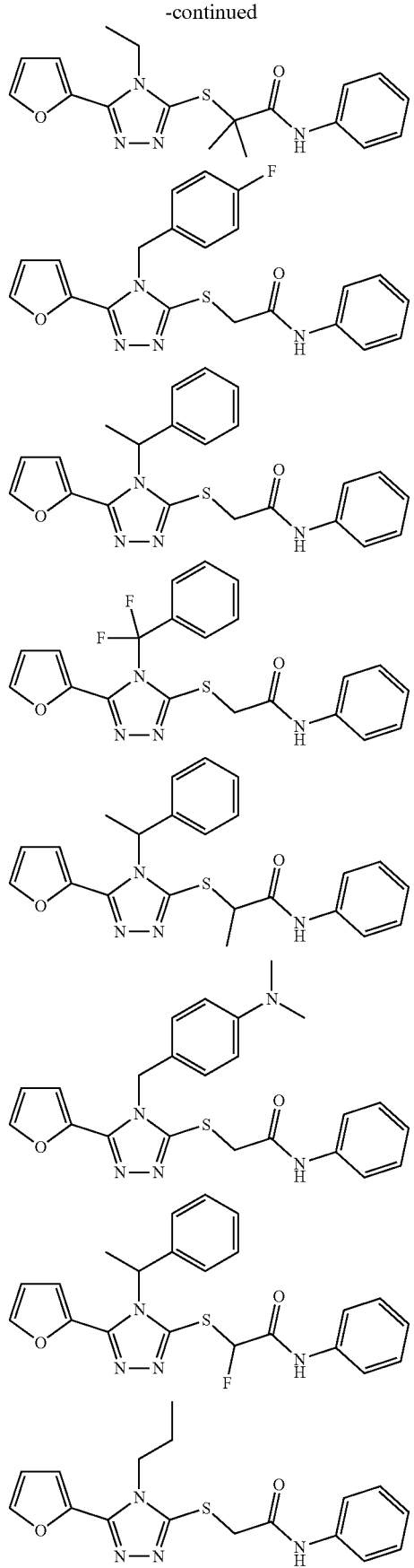
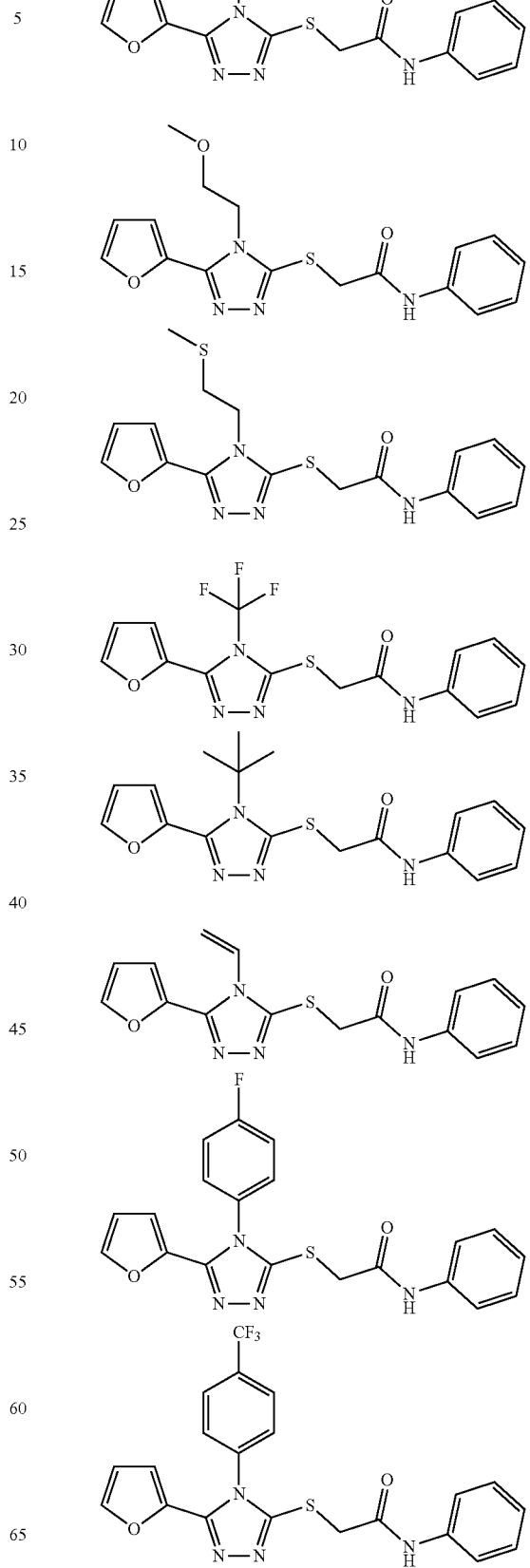

-continued
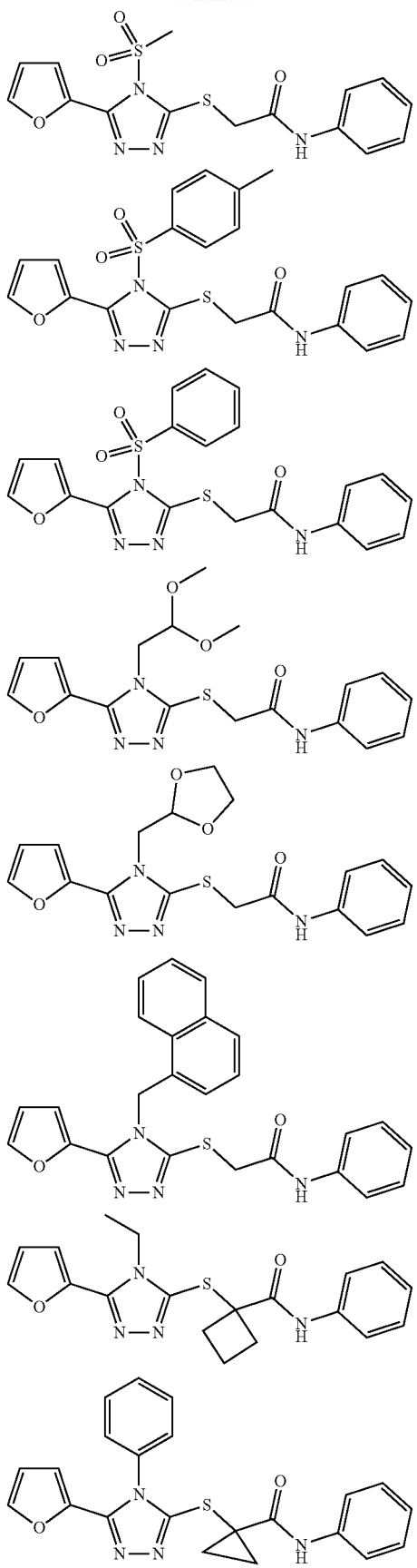
-continued
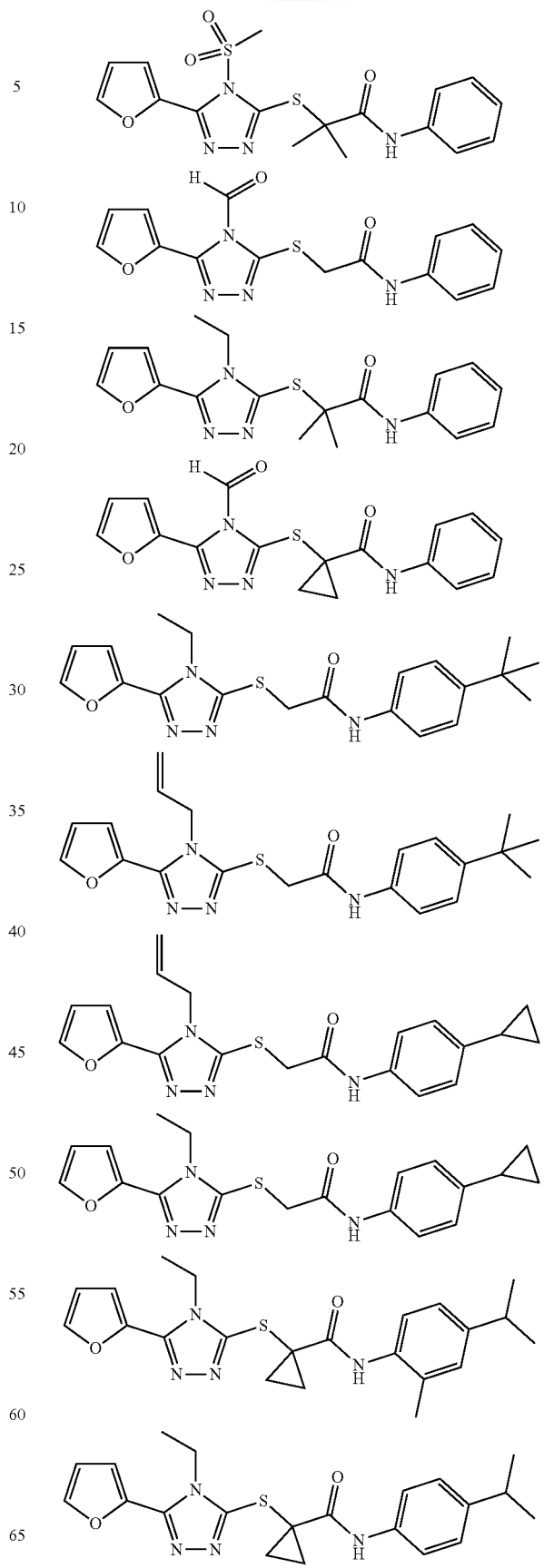

163
-continued
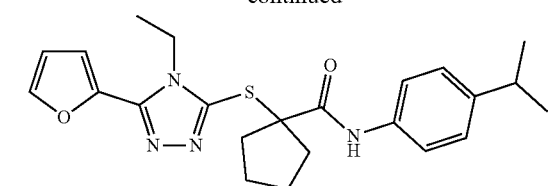
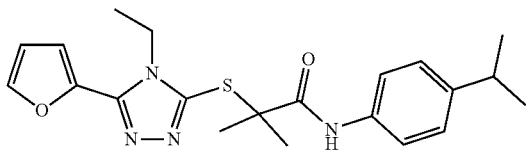
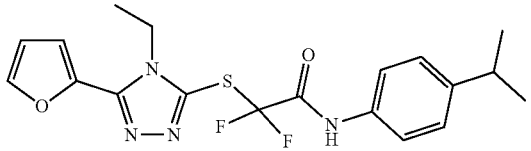
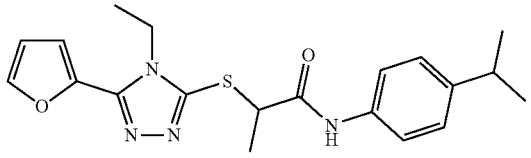
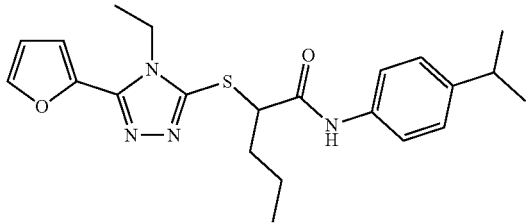
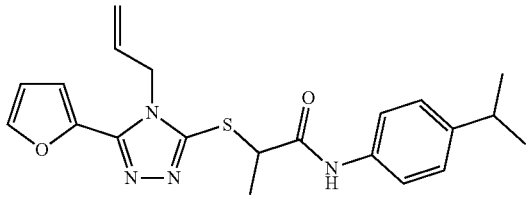
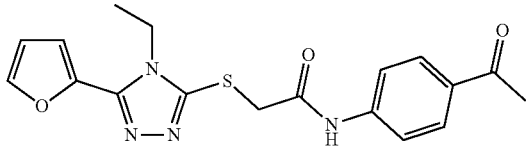
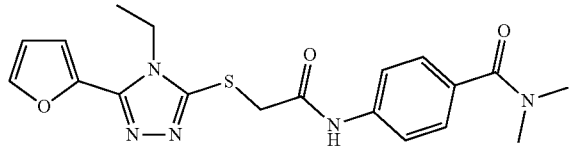
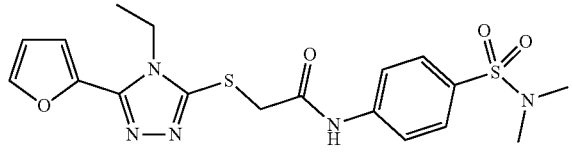
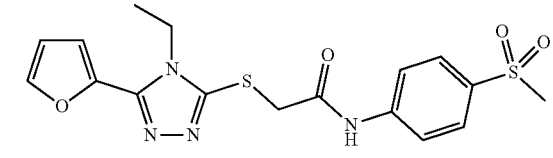
164
-continued
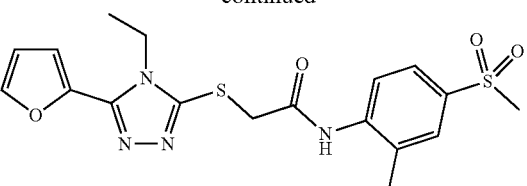
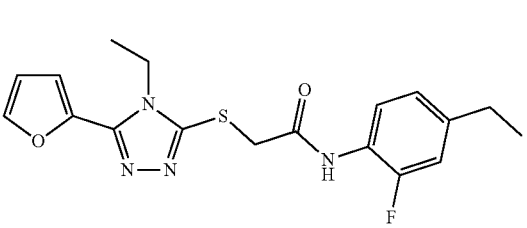
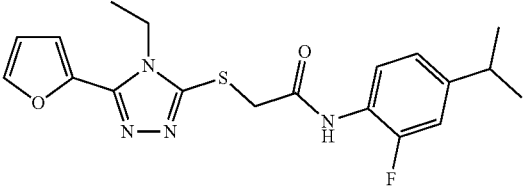
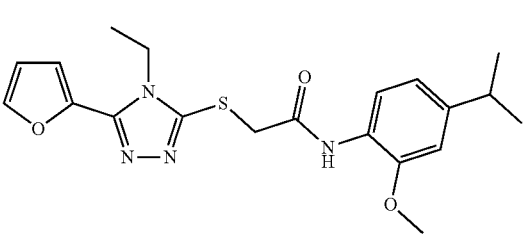
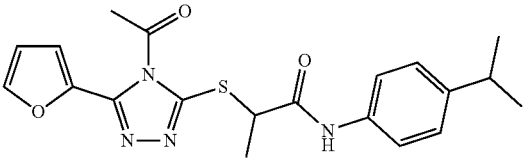
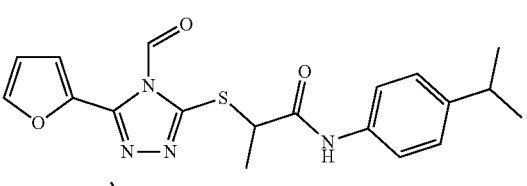
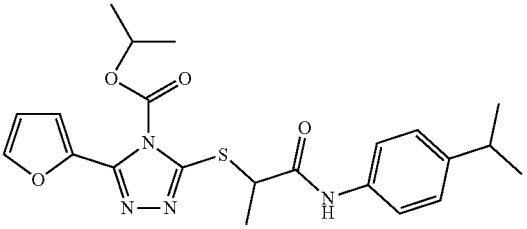
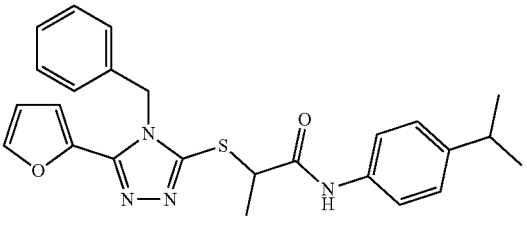

165
-continued
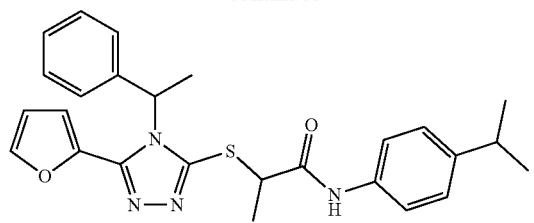
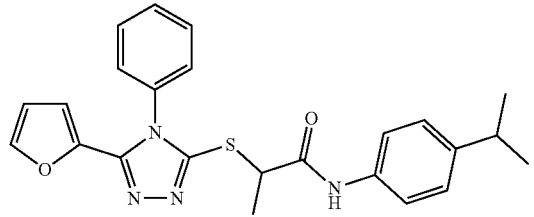
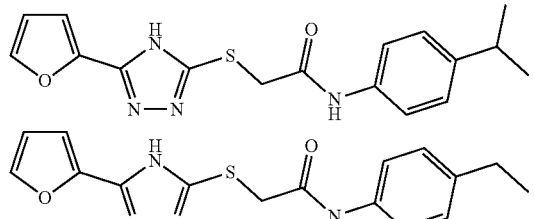
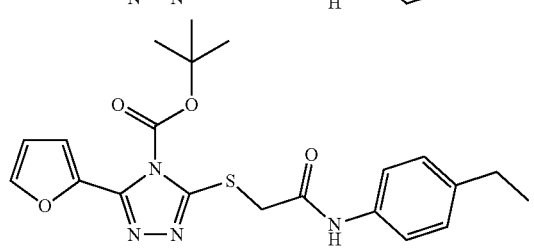
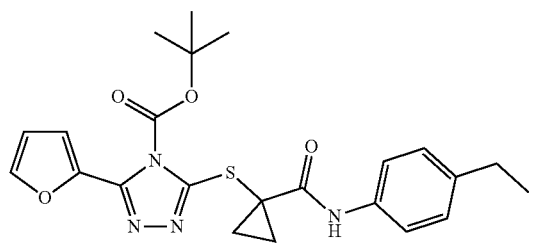
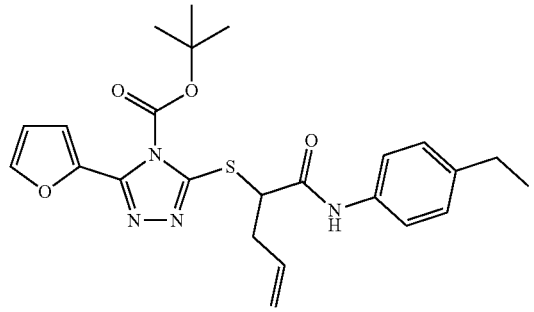
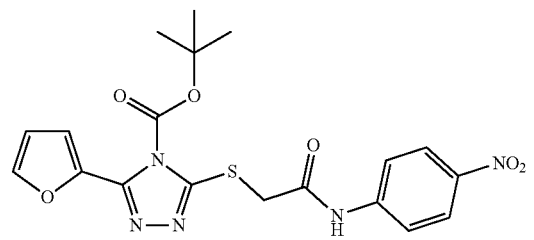
166
-continued
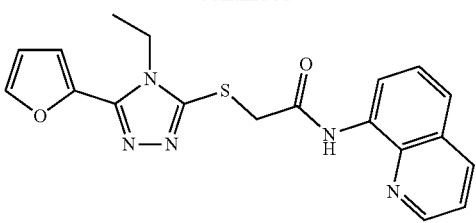
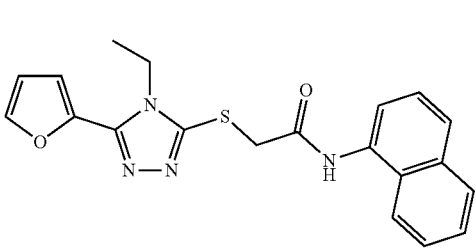
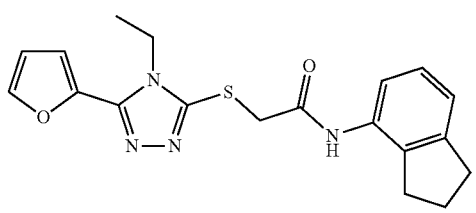
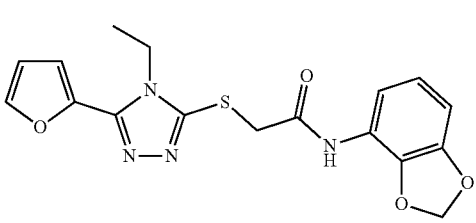
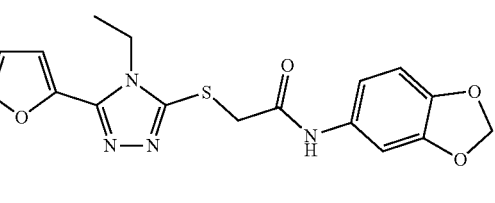
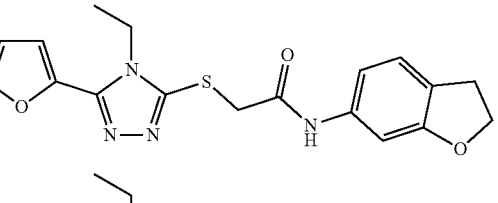
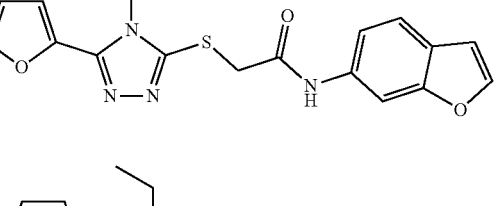
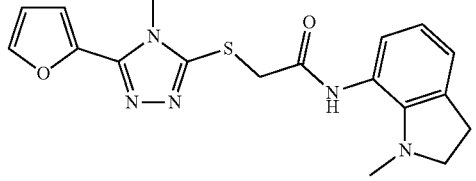

-continued
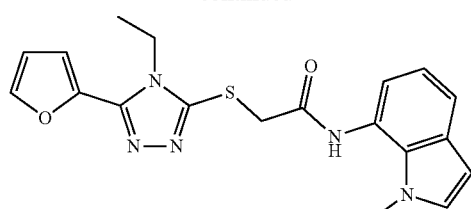
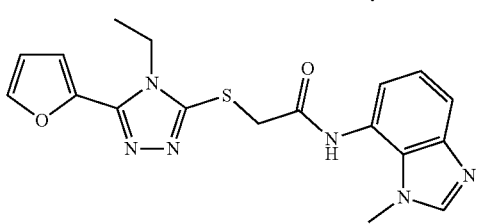
In one aspect, a disclosed compound can have the formula (VI):
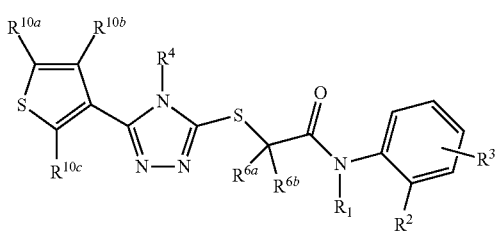
Exemplary compound within Formula (VI) include, but are not limited to:
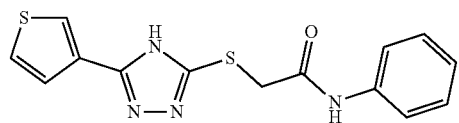
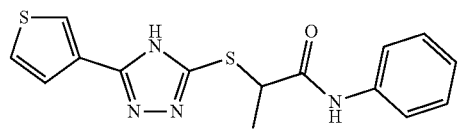
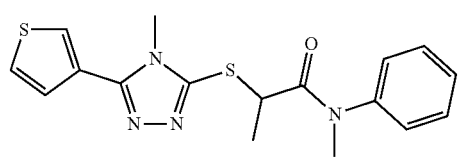
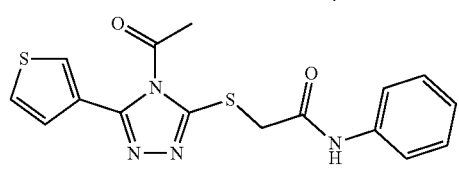
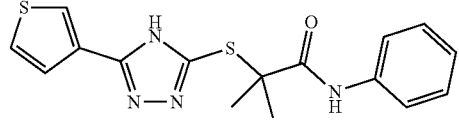
-continued
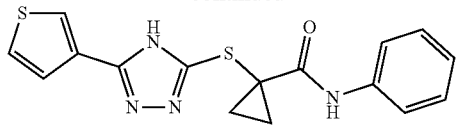
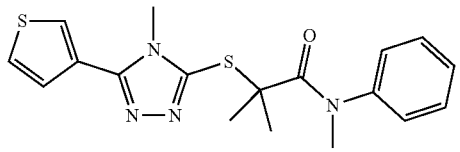
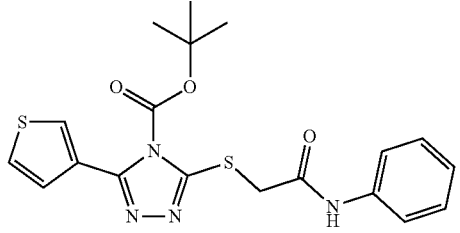
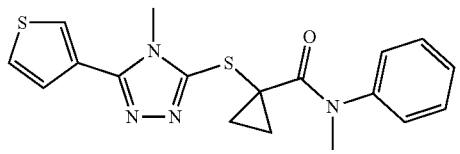
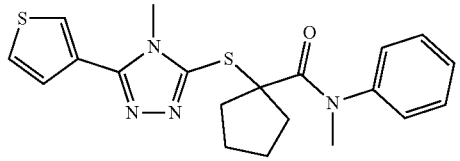
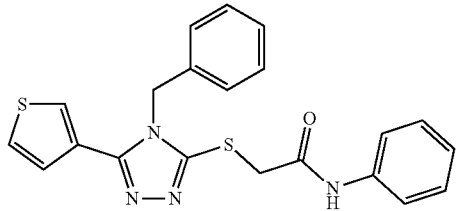
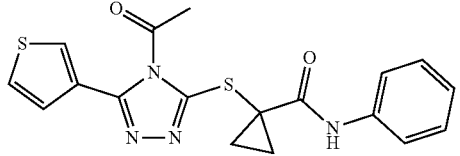
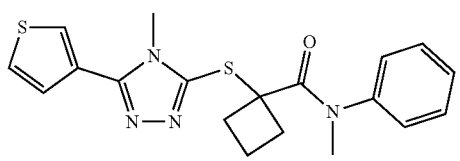
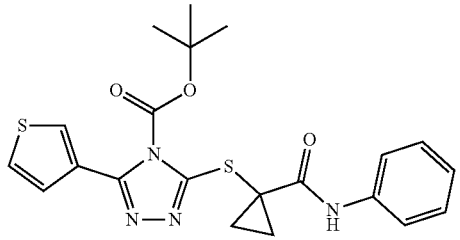

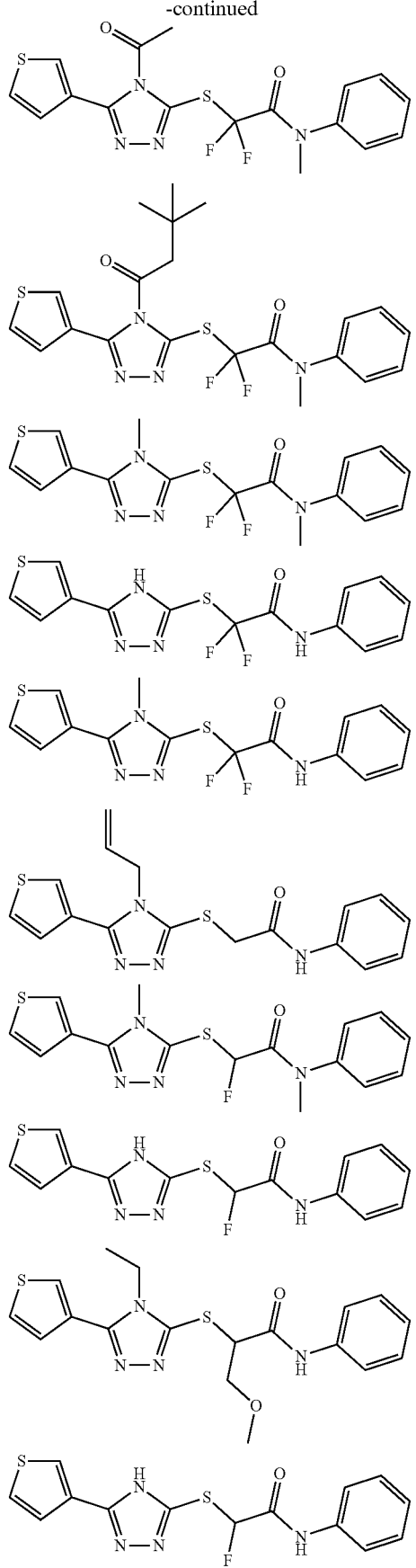

171
-continued
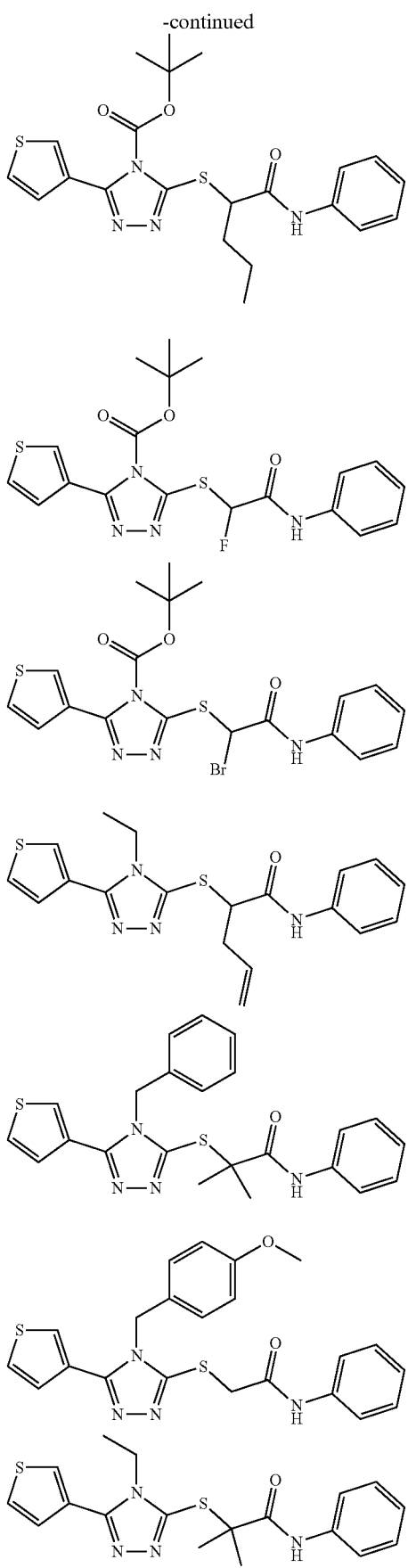
172
-continued
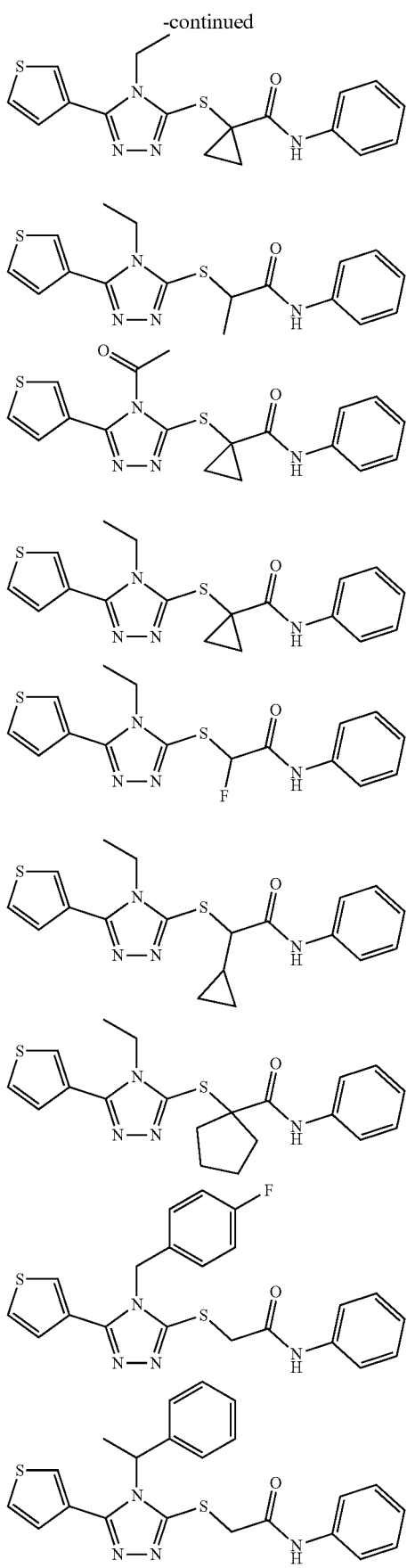

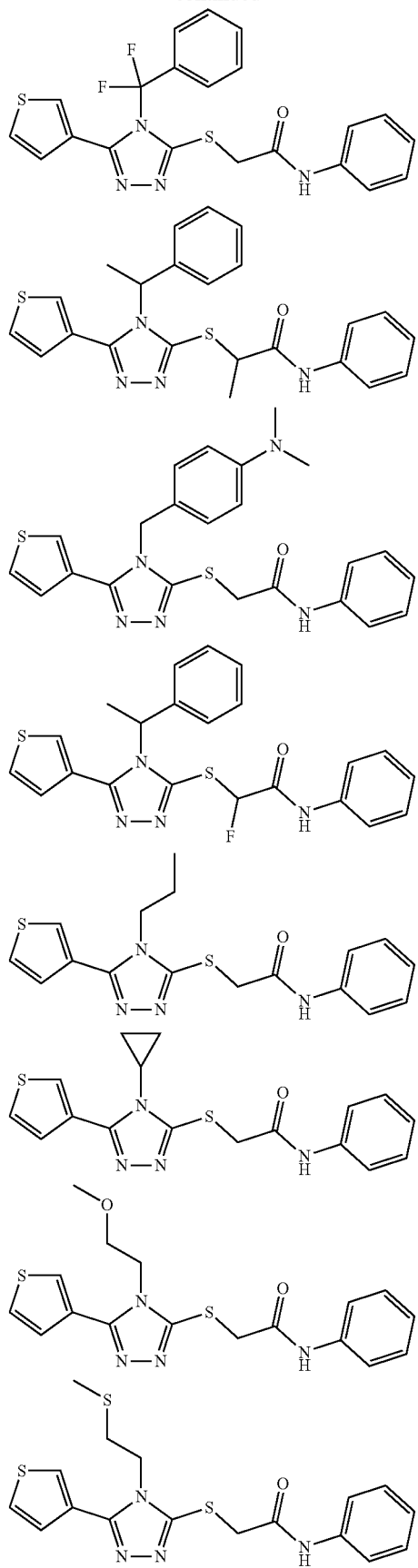
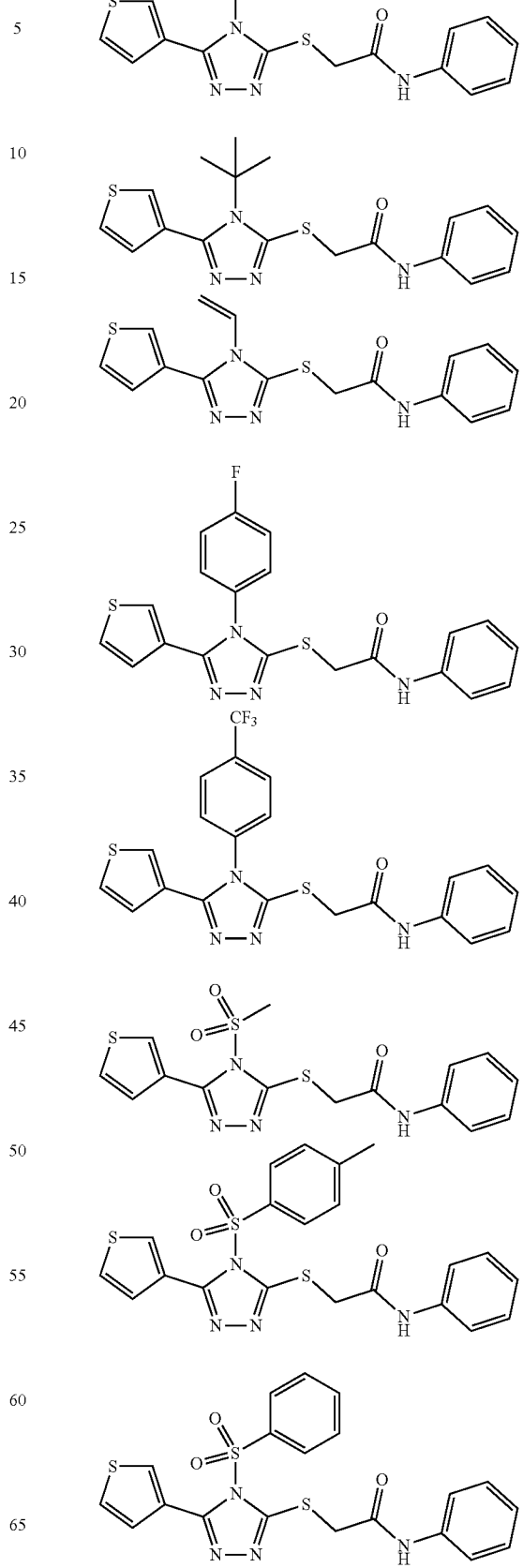

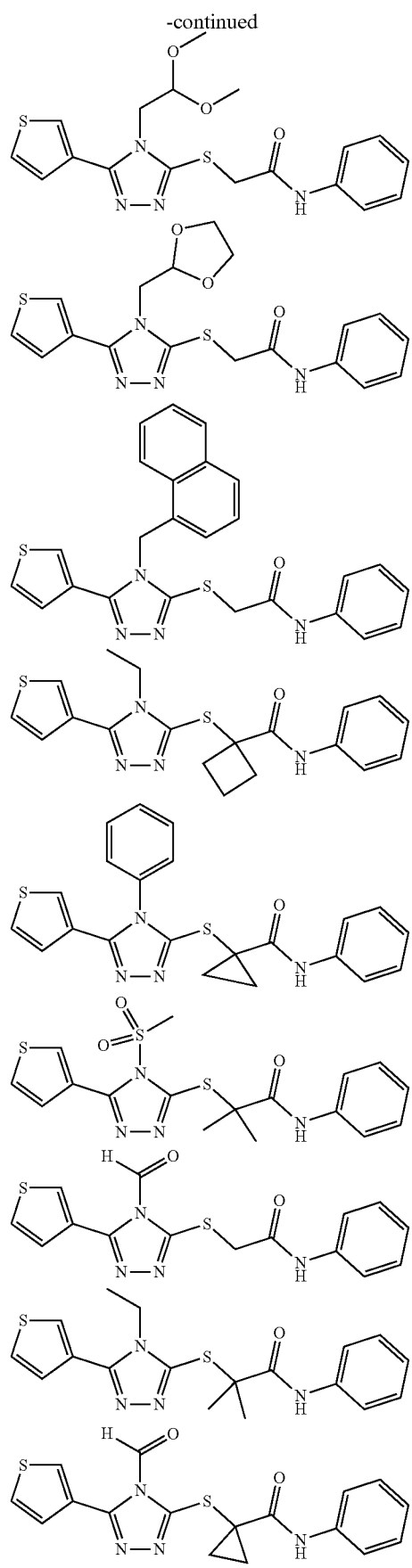
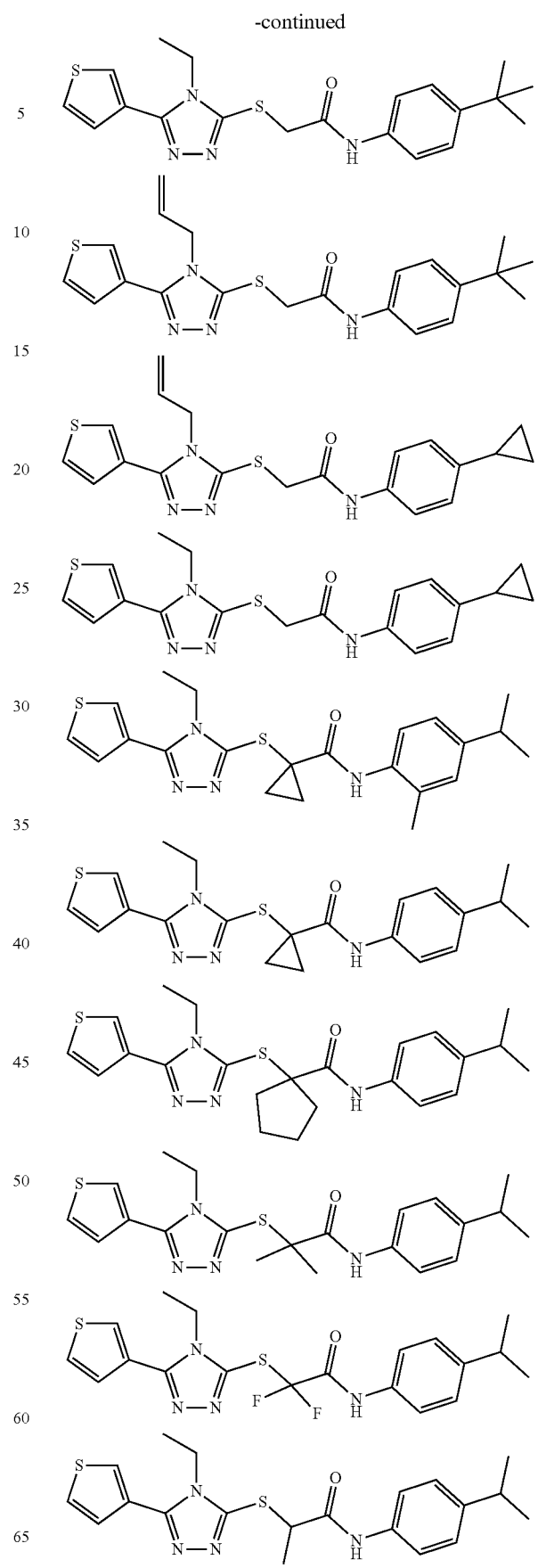

-continued
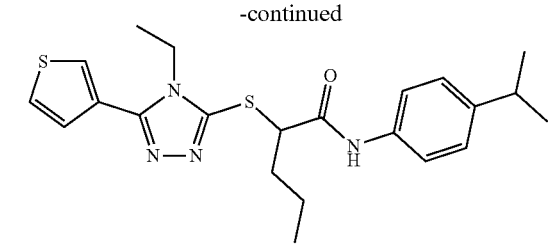
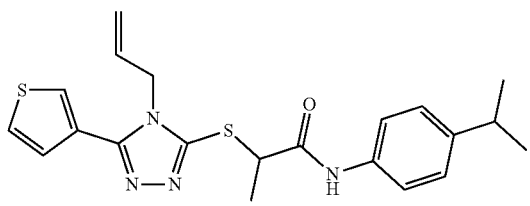
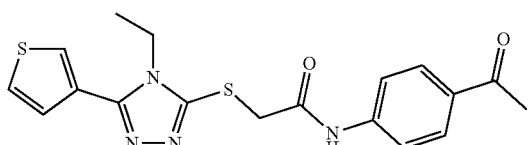
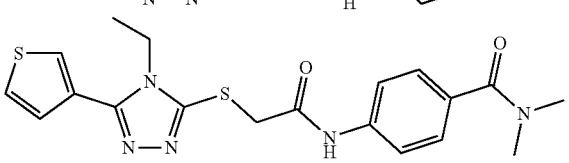
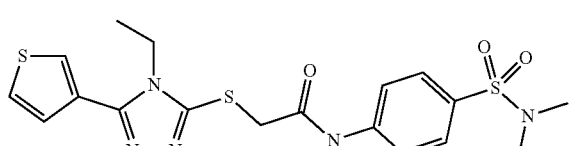
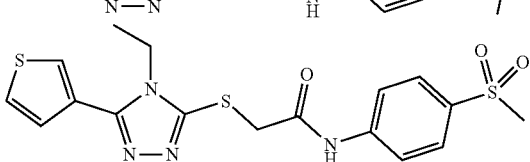
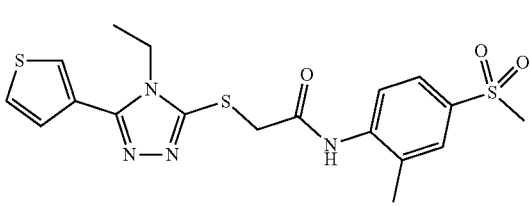
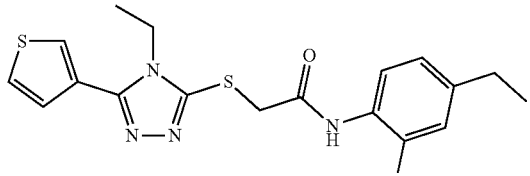
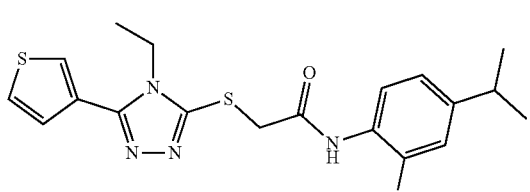
-continued
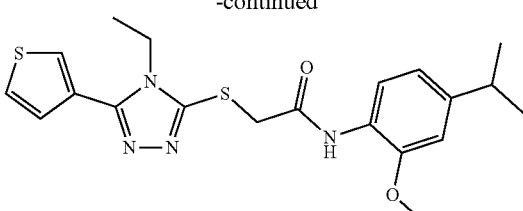
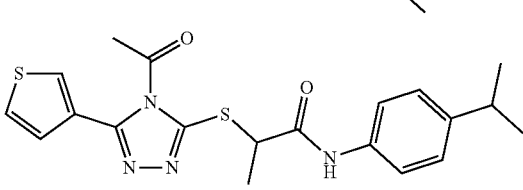
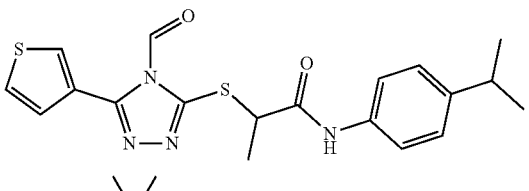
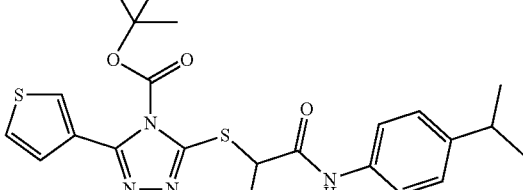
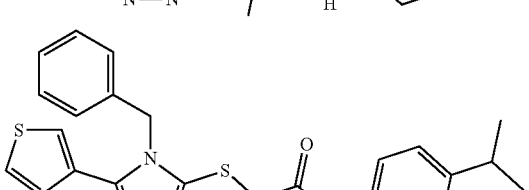
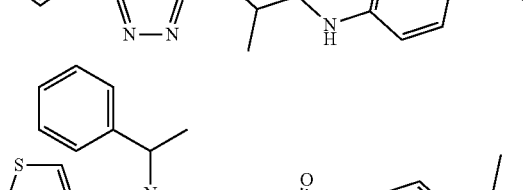
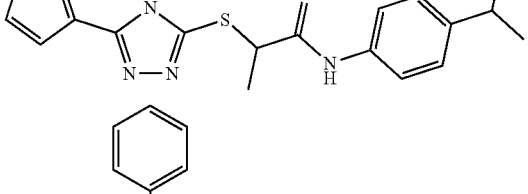
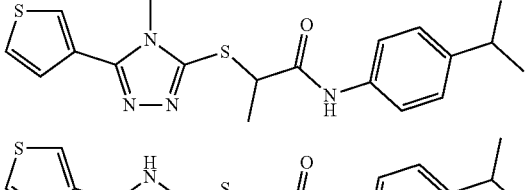
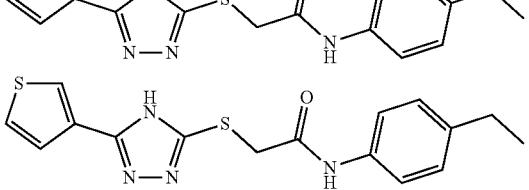

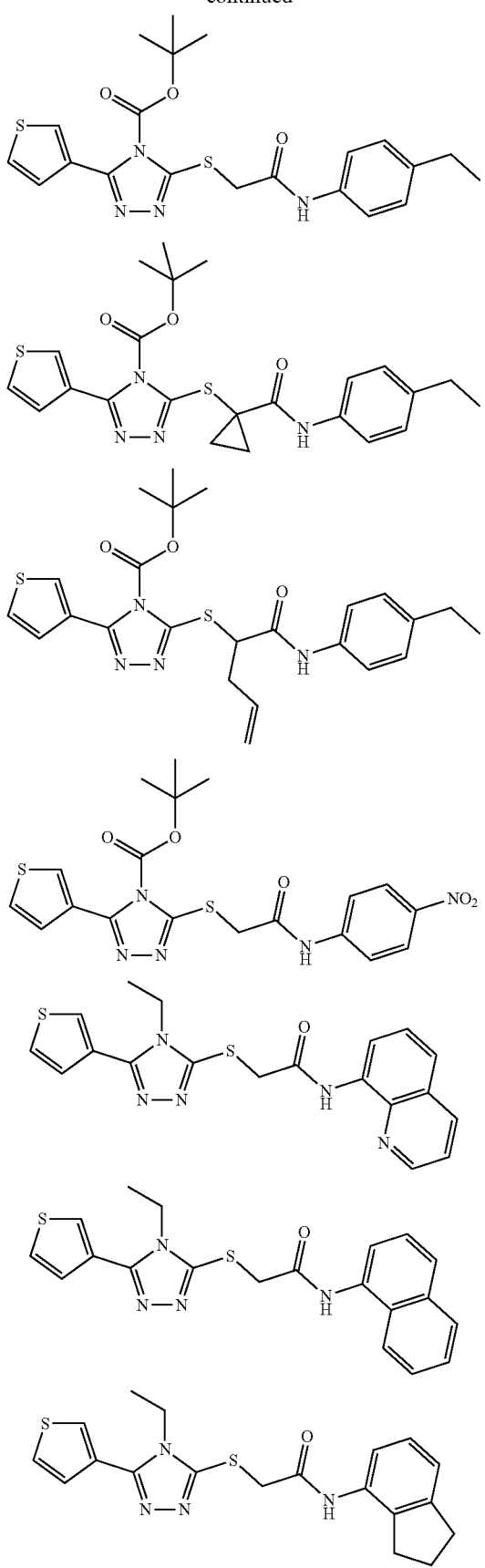
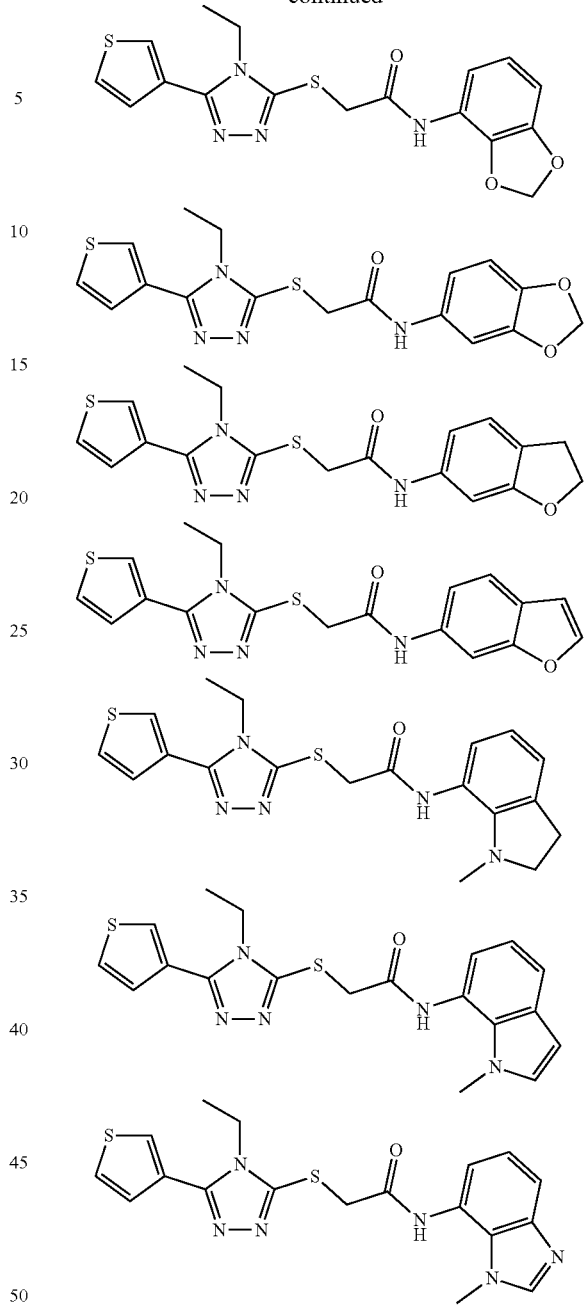
In one aspect, a disclosed compound can have the formula (VII):
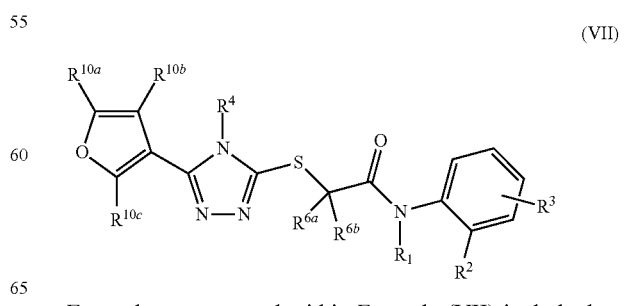
Exemplary compound within Formula (VII) include, but are not limited to:

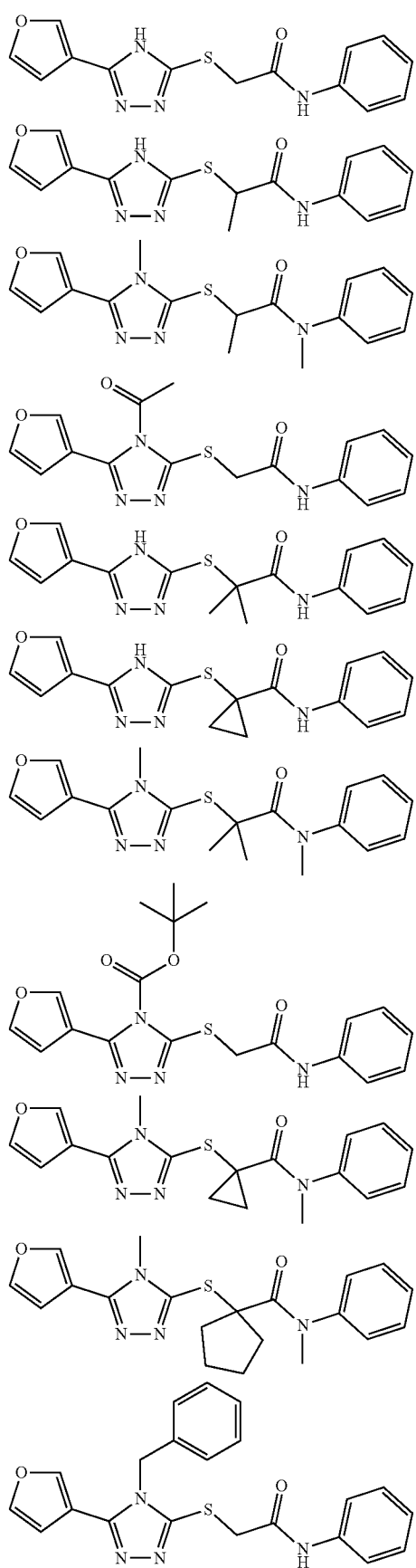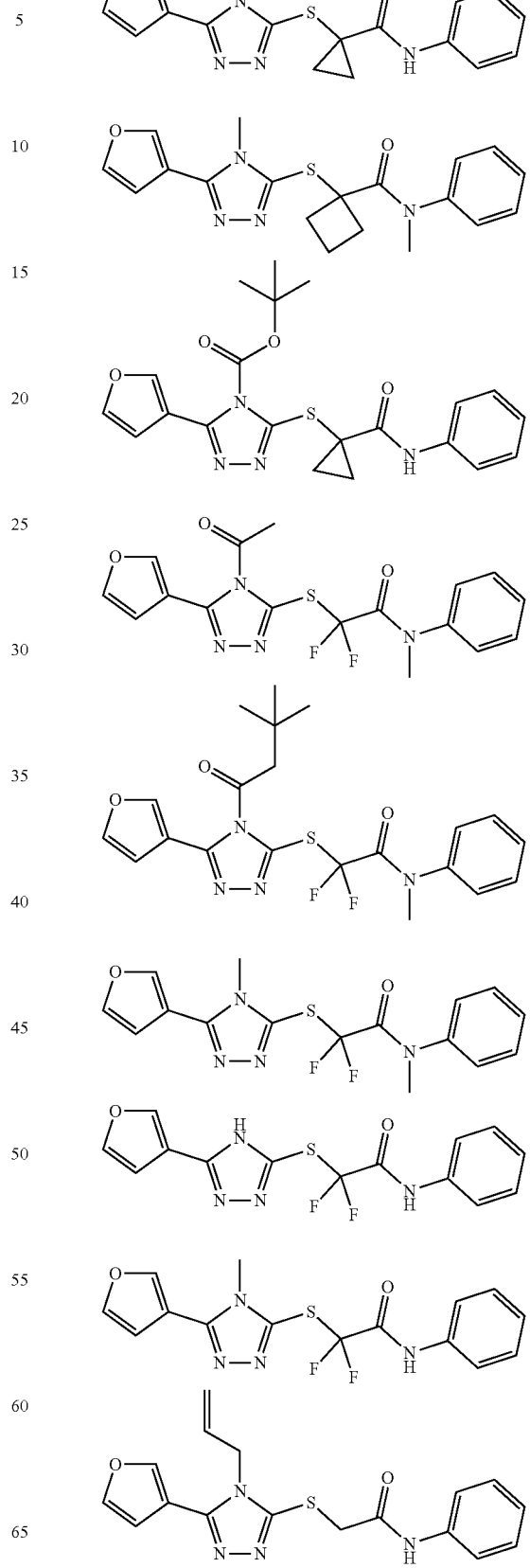

183
-continued
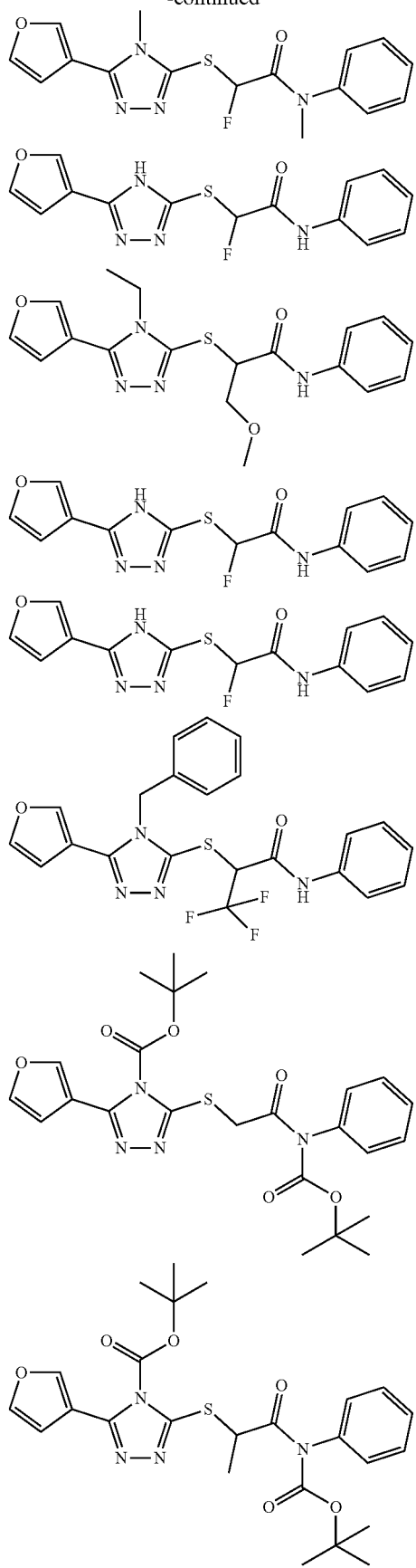
184
-continued
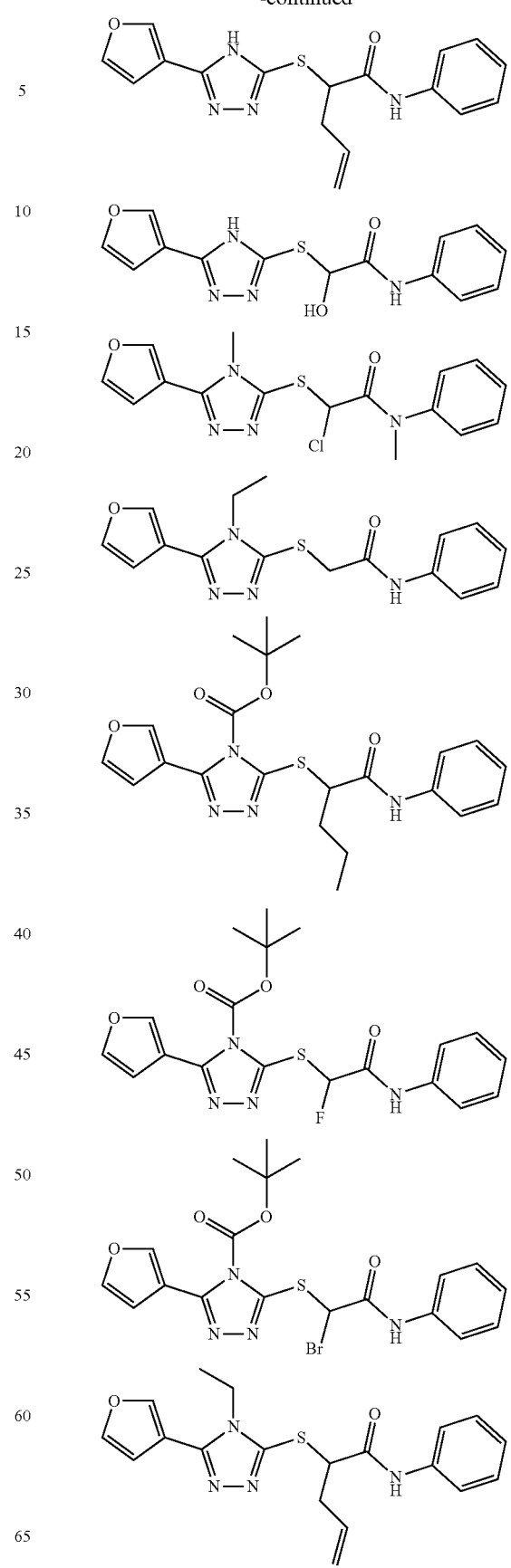

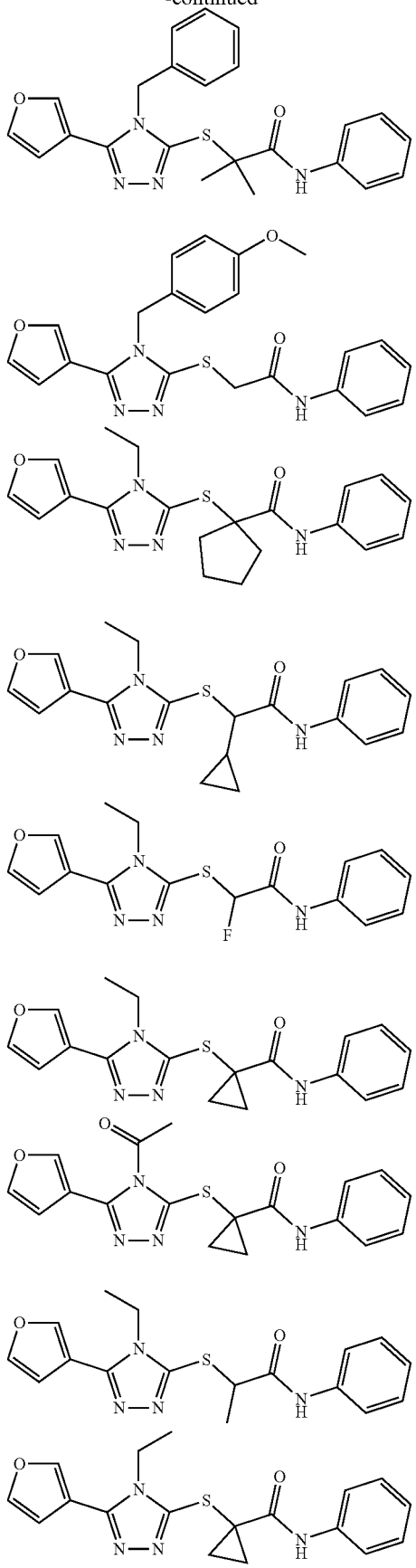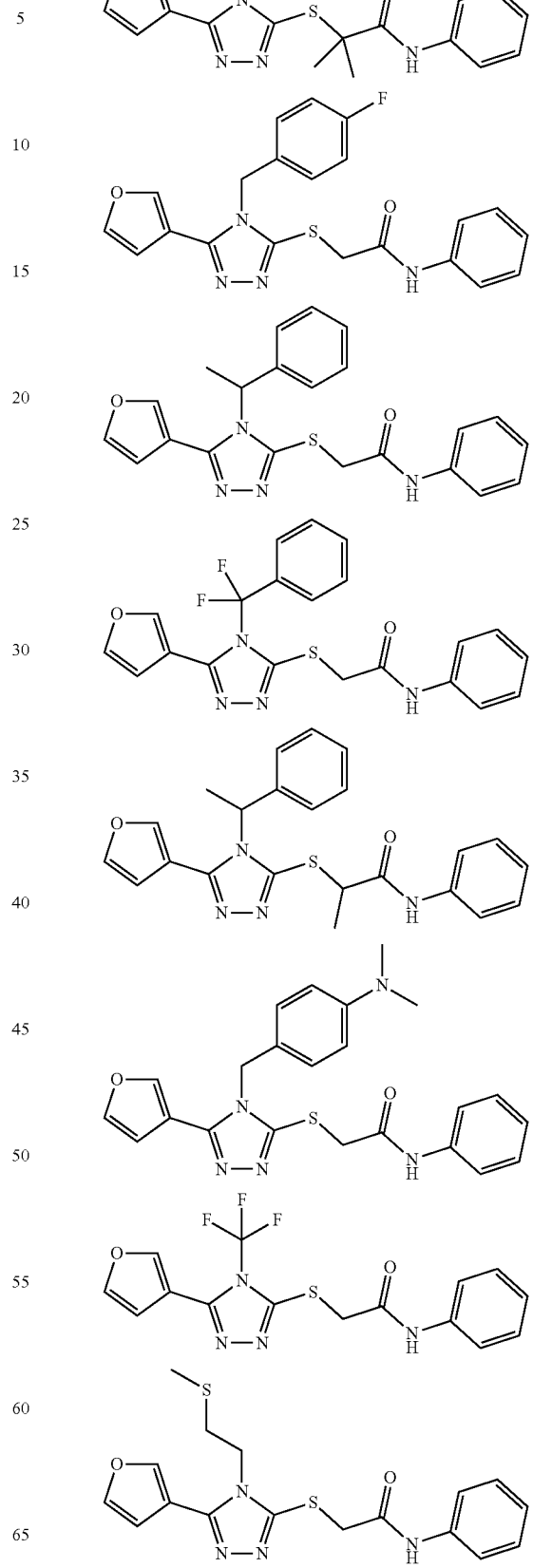

187
-continued
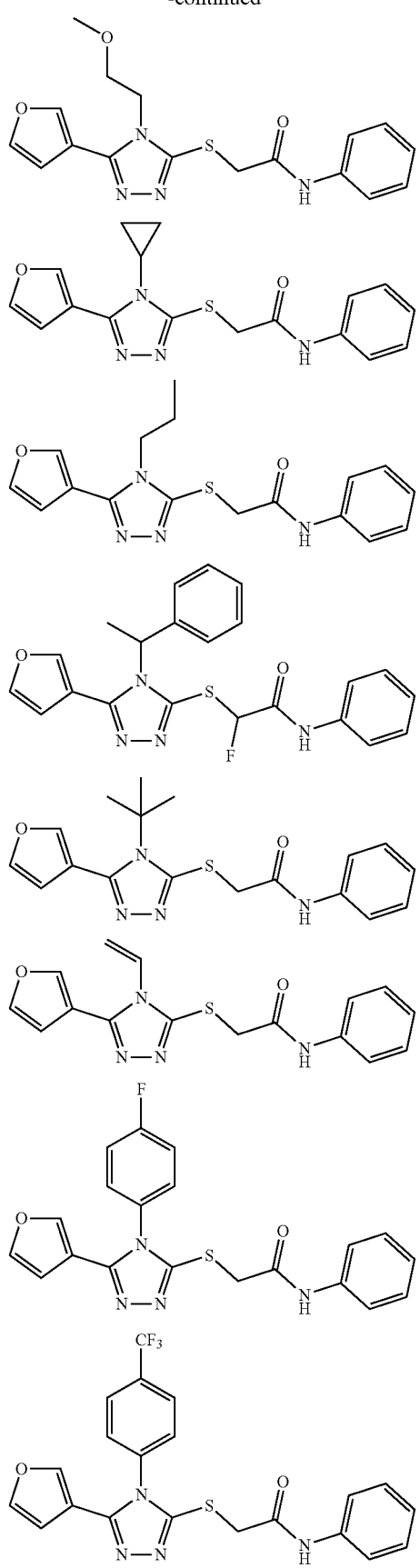
188
-continued
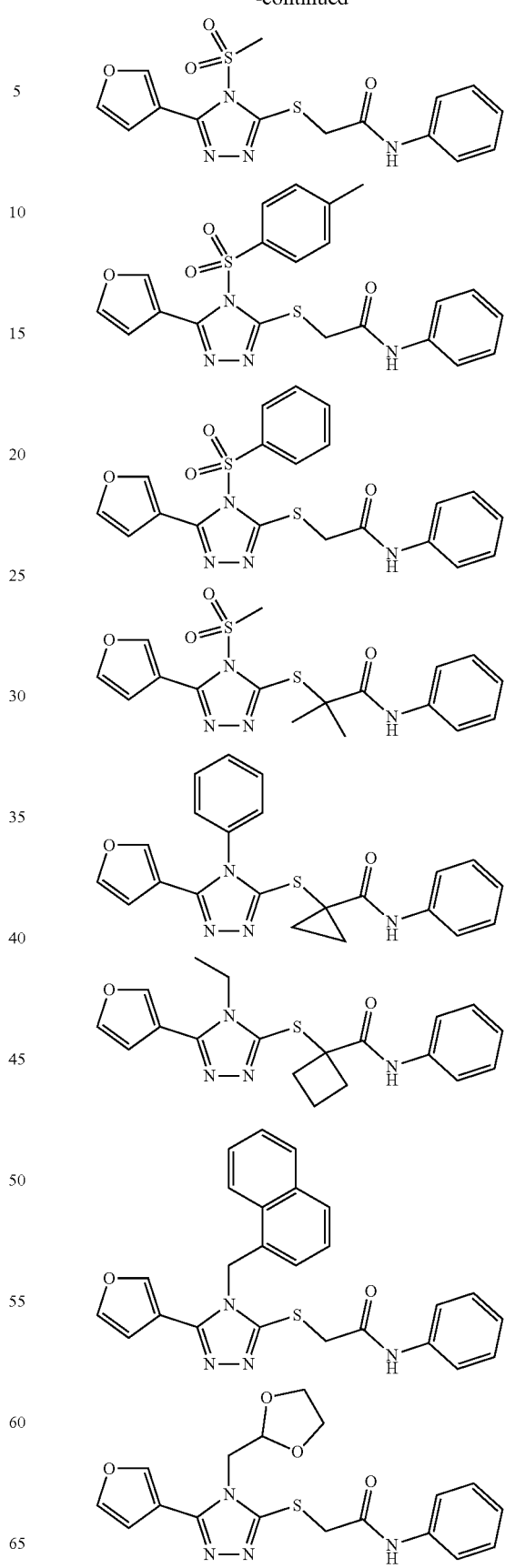

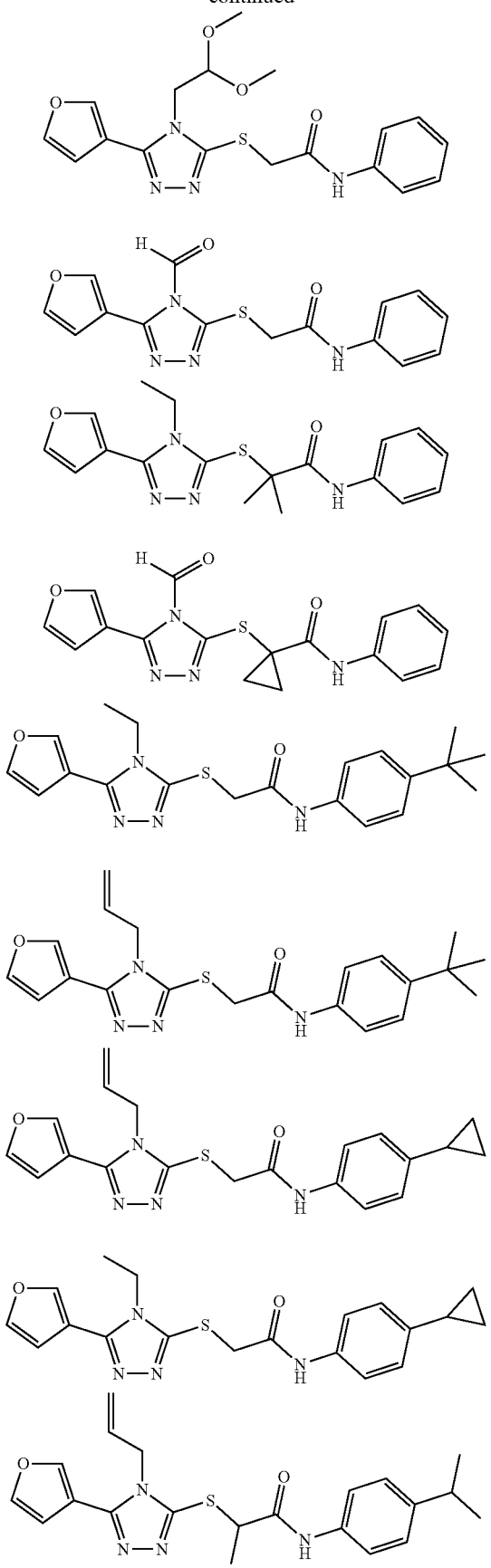
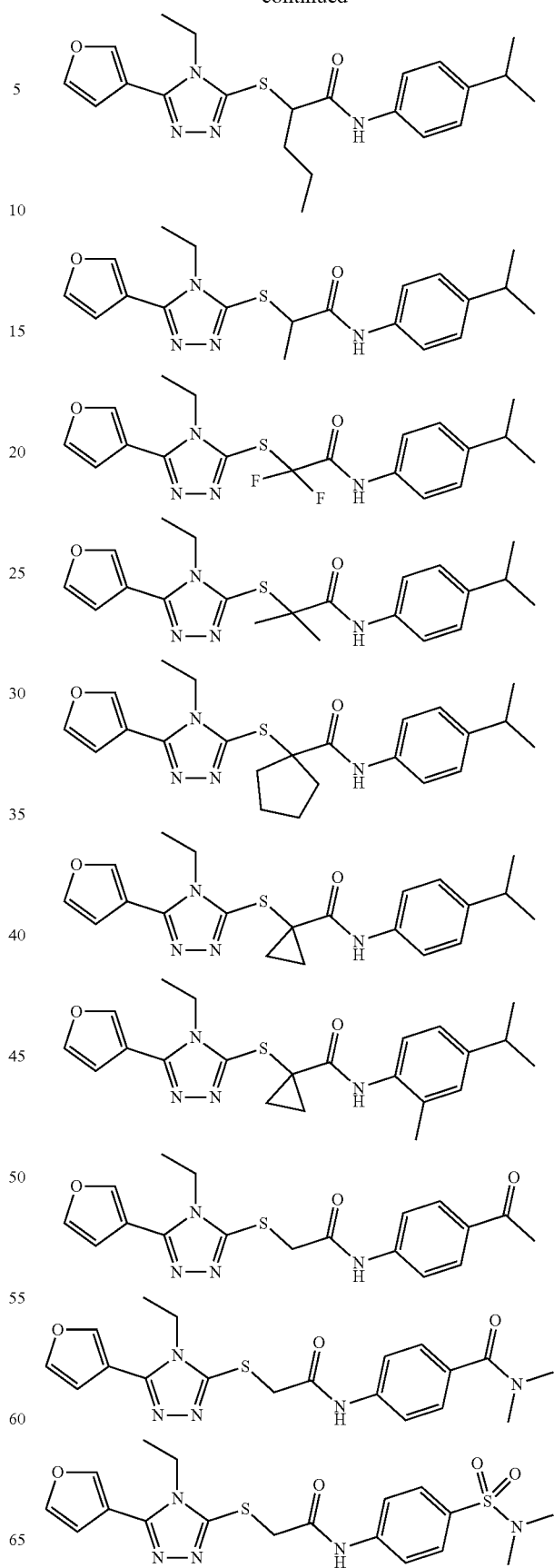

191
-continued
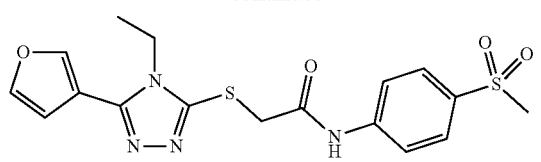
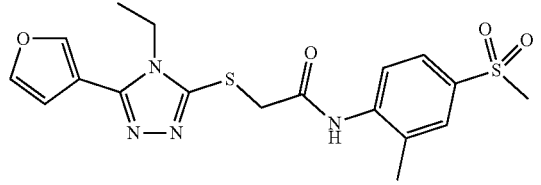
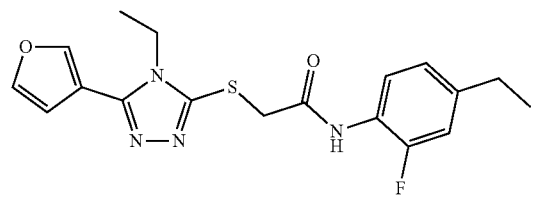
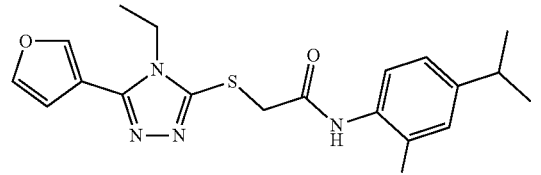
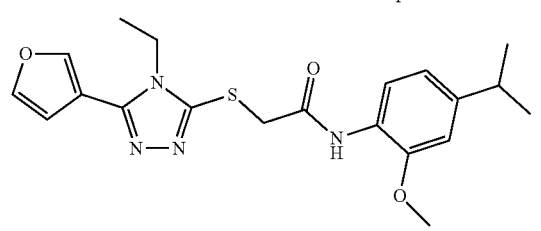
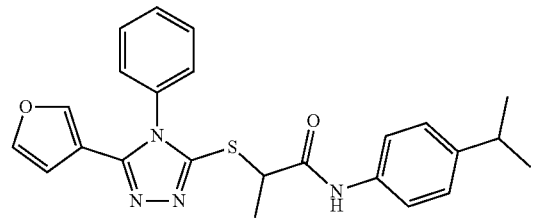
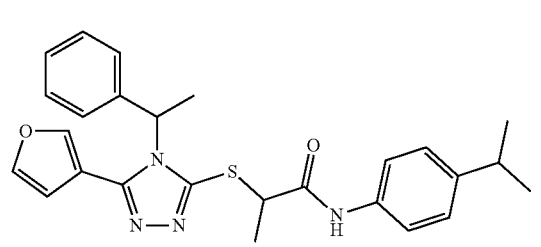
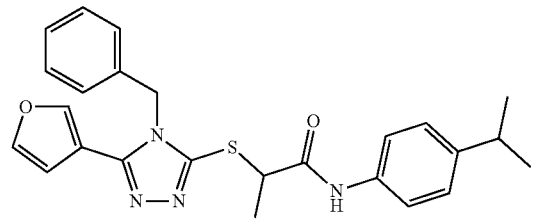
192
-continued
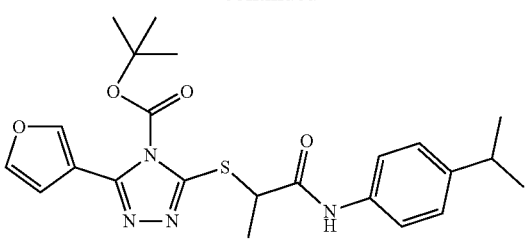
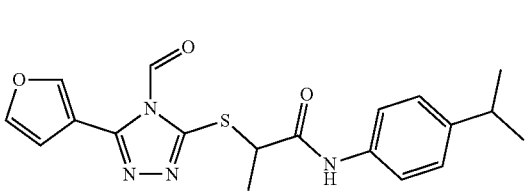
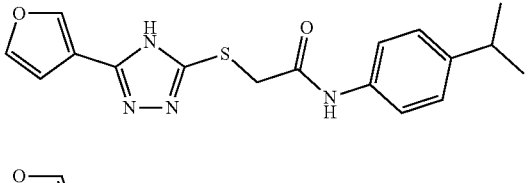
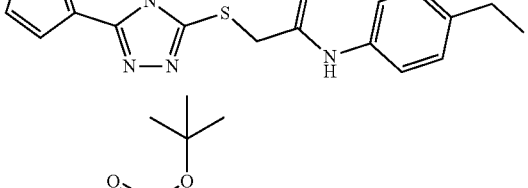
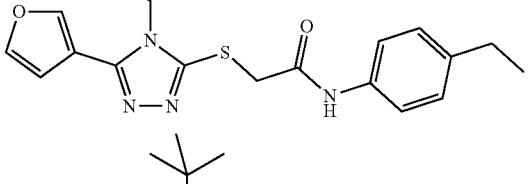
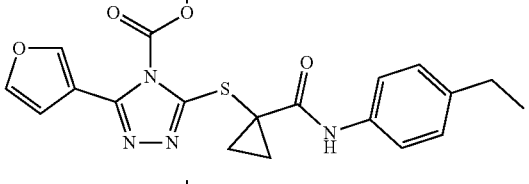
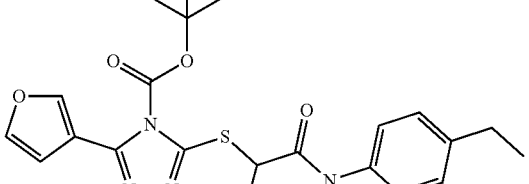
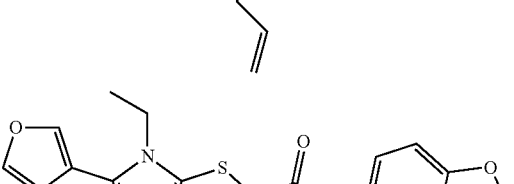

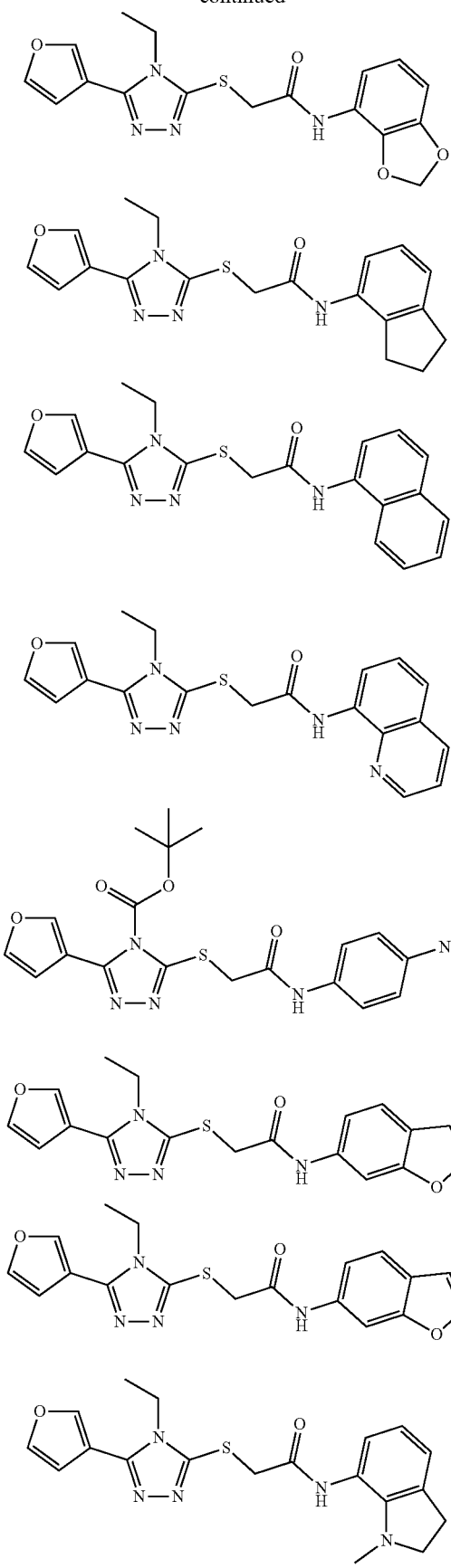
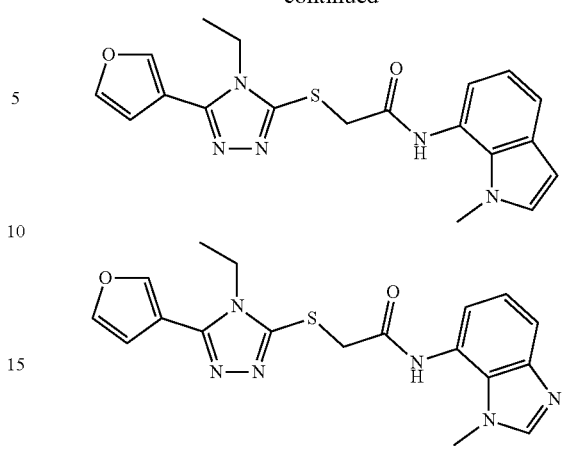
In one aspect, a disclosed compound can have the formula (VIII):
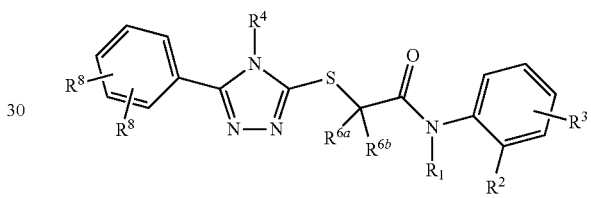
Formula (VIII)
Exemplary compound within Formula (VIII) include, but are not limited to:
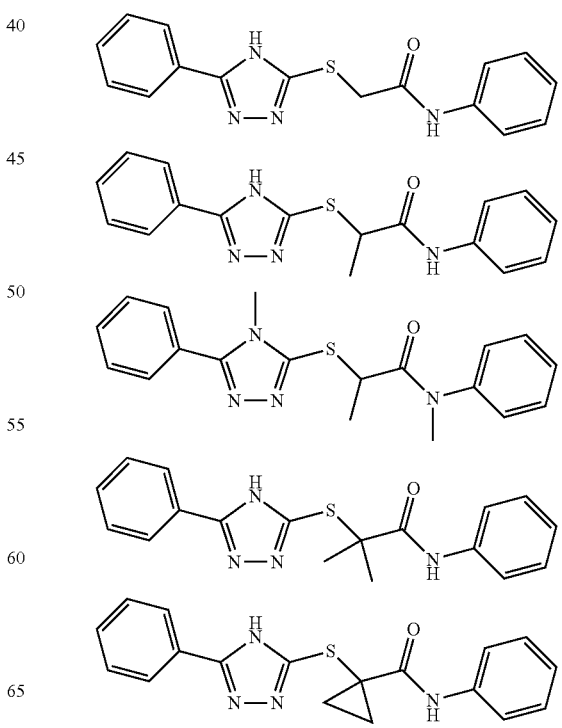

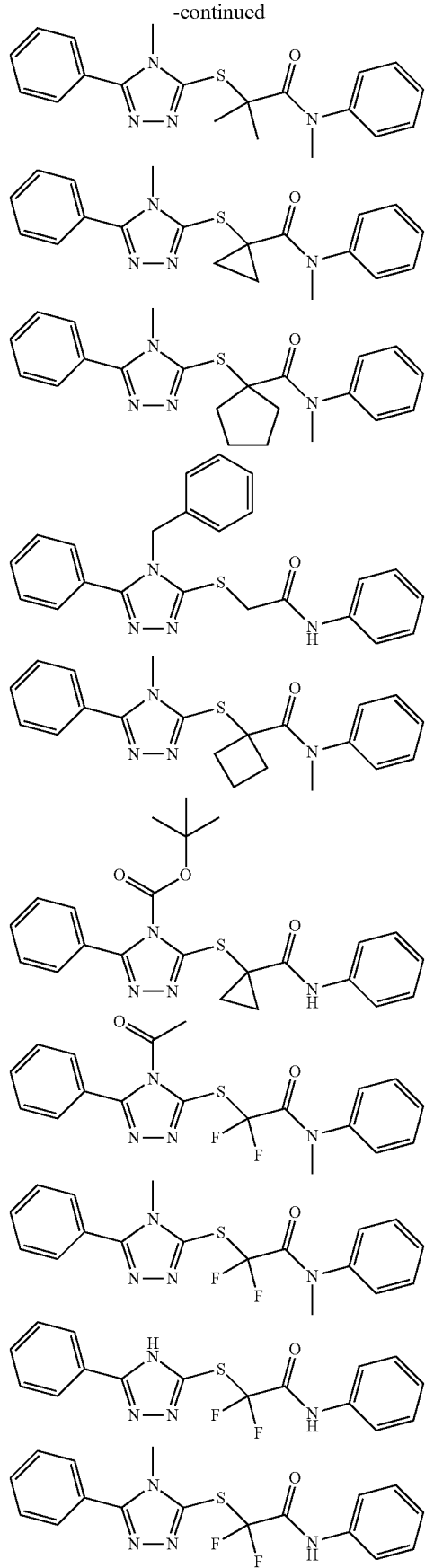
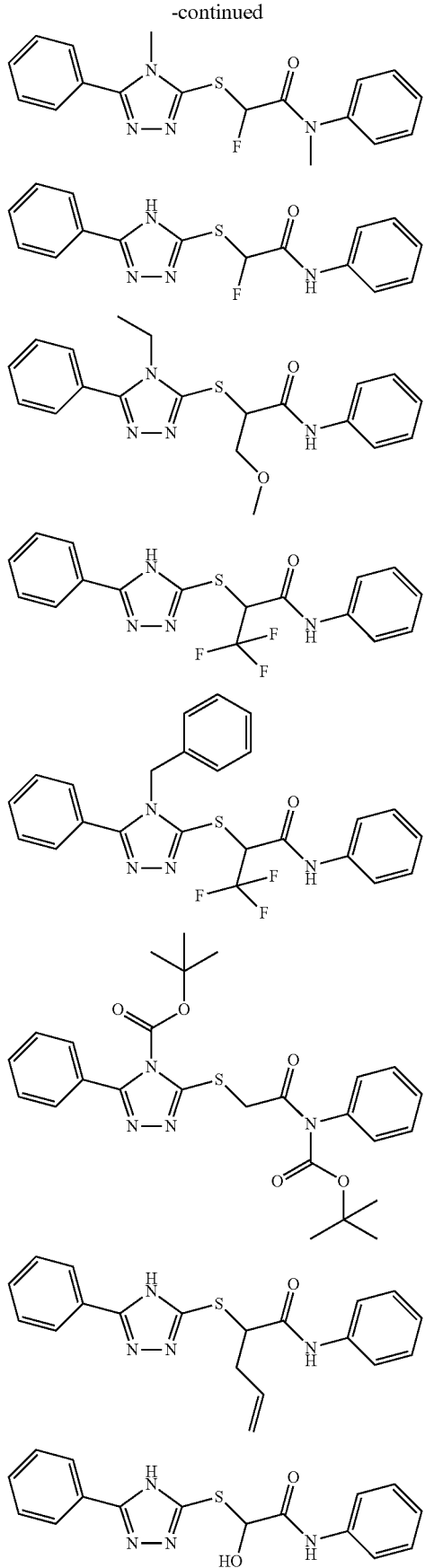

197
-continued
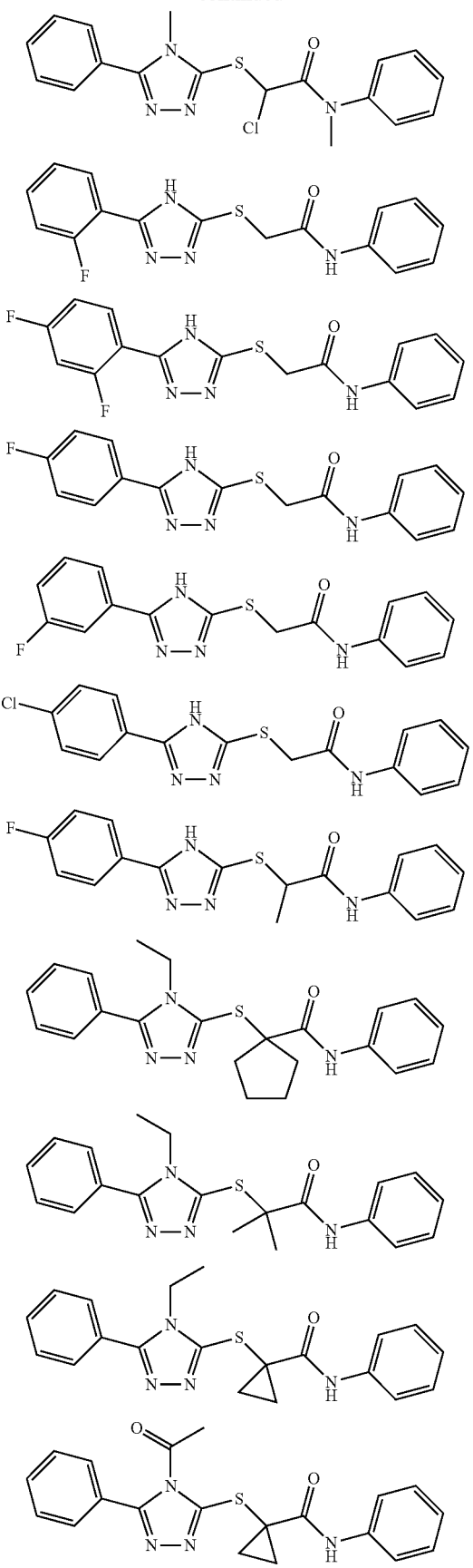
198
-continued
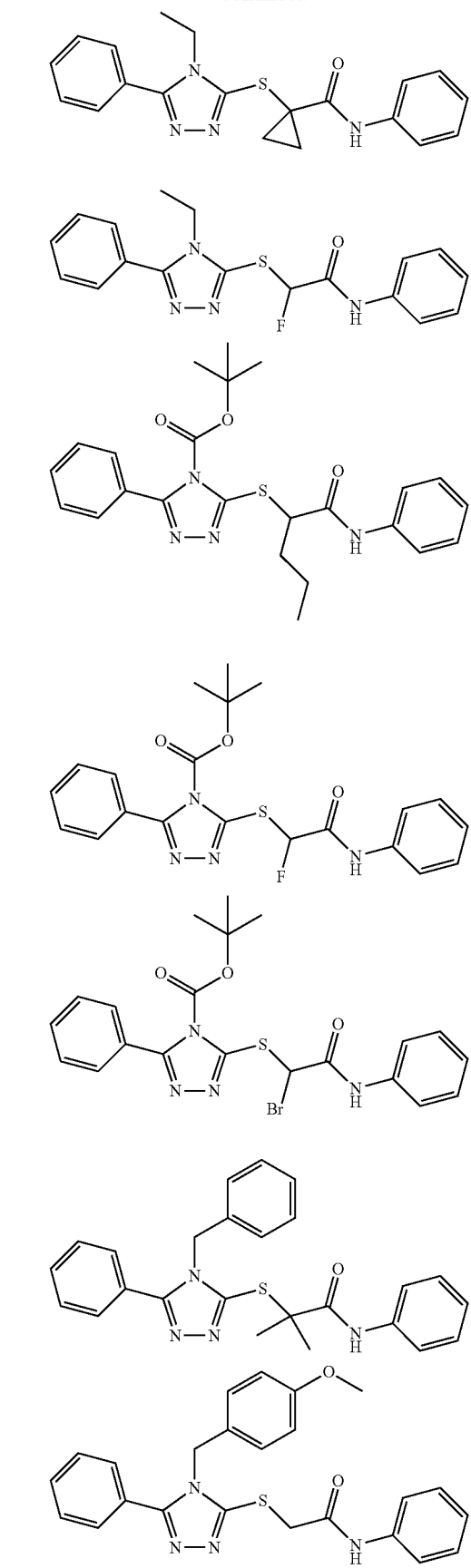

199
-continued
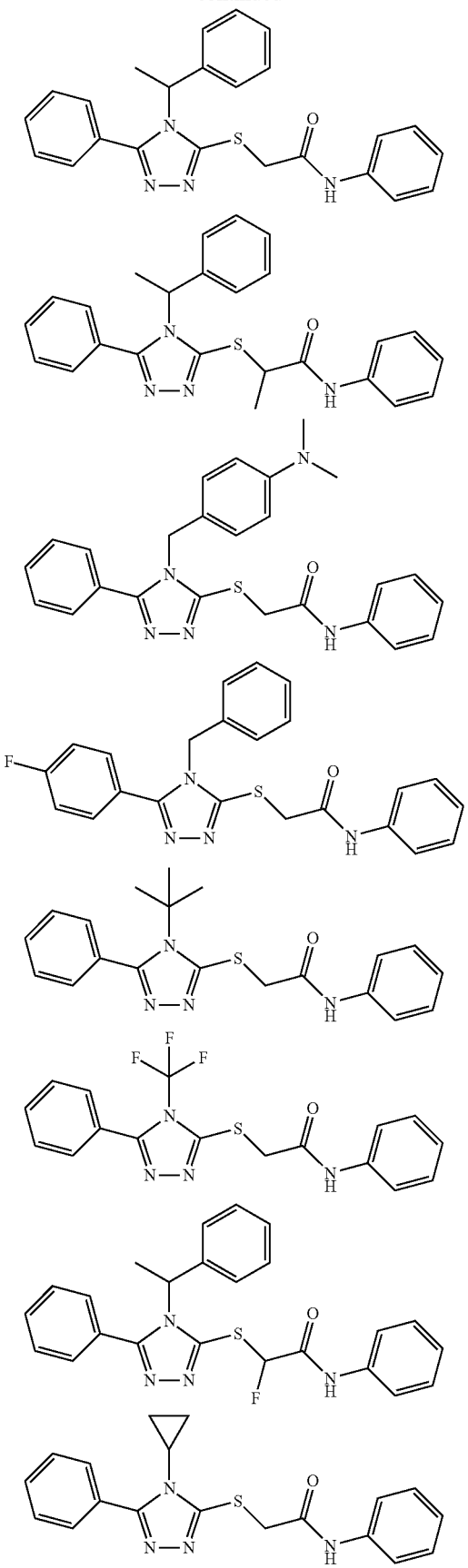
200
-continued
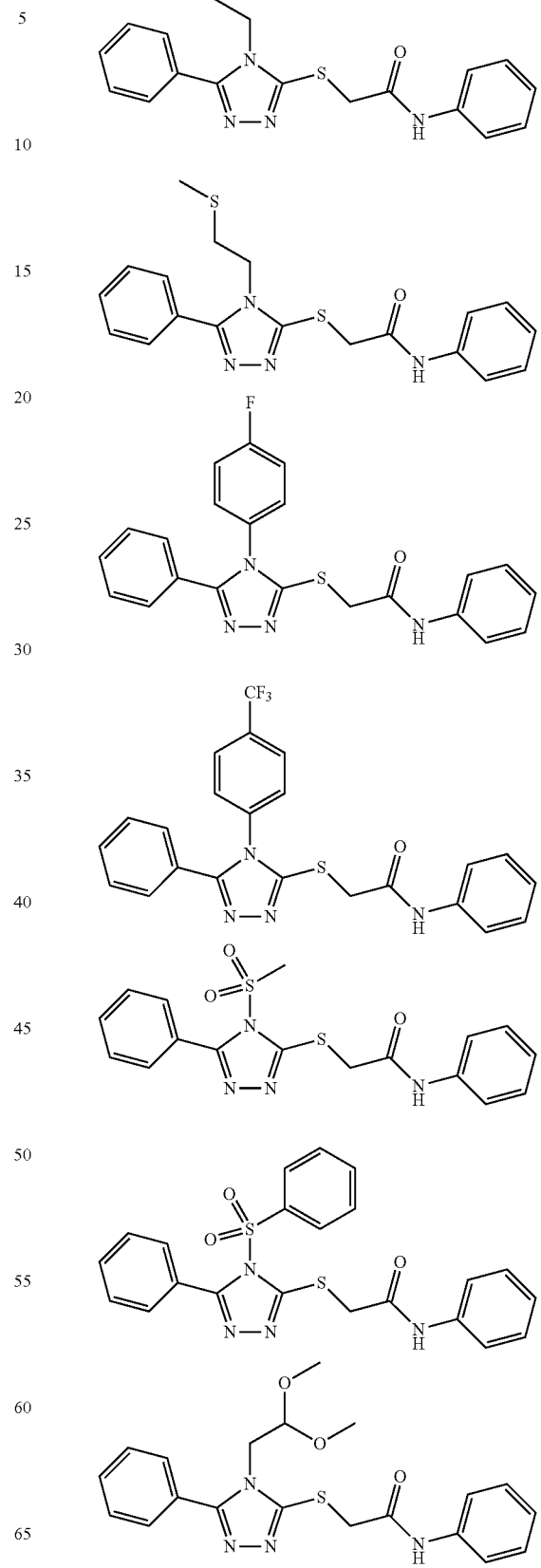

201
-continued
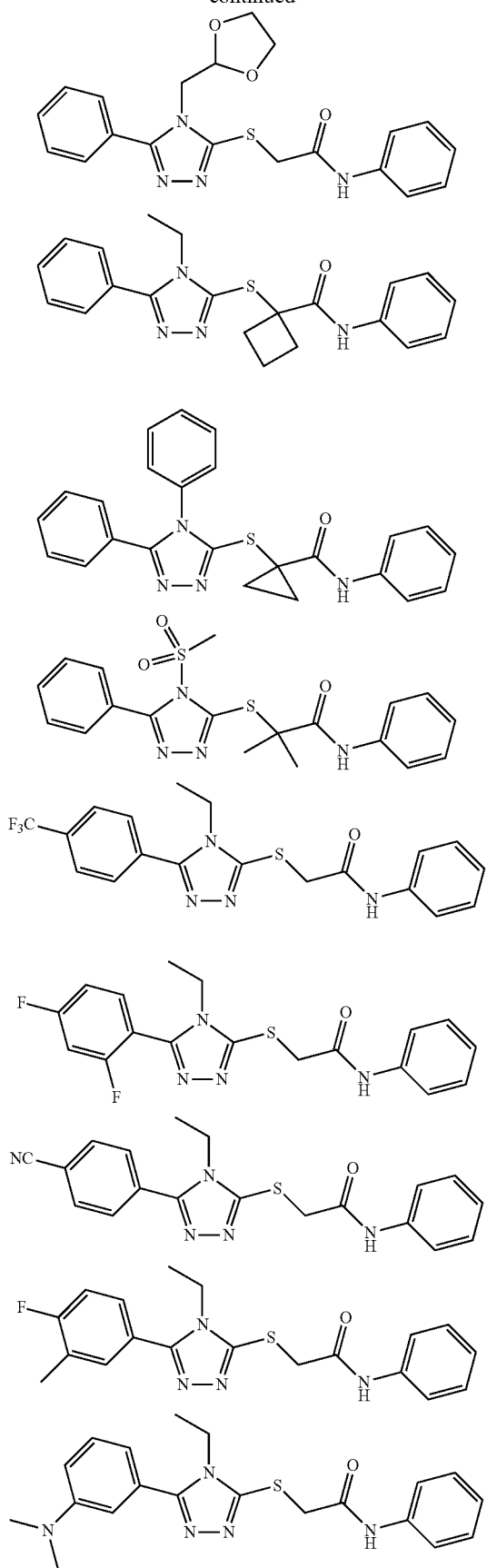
202
-continued
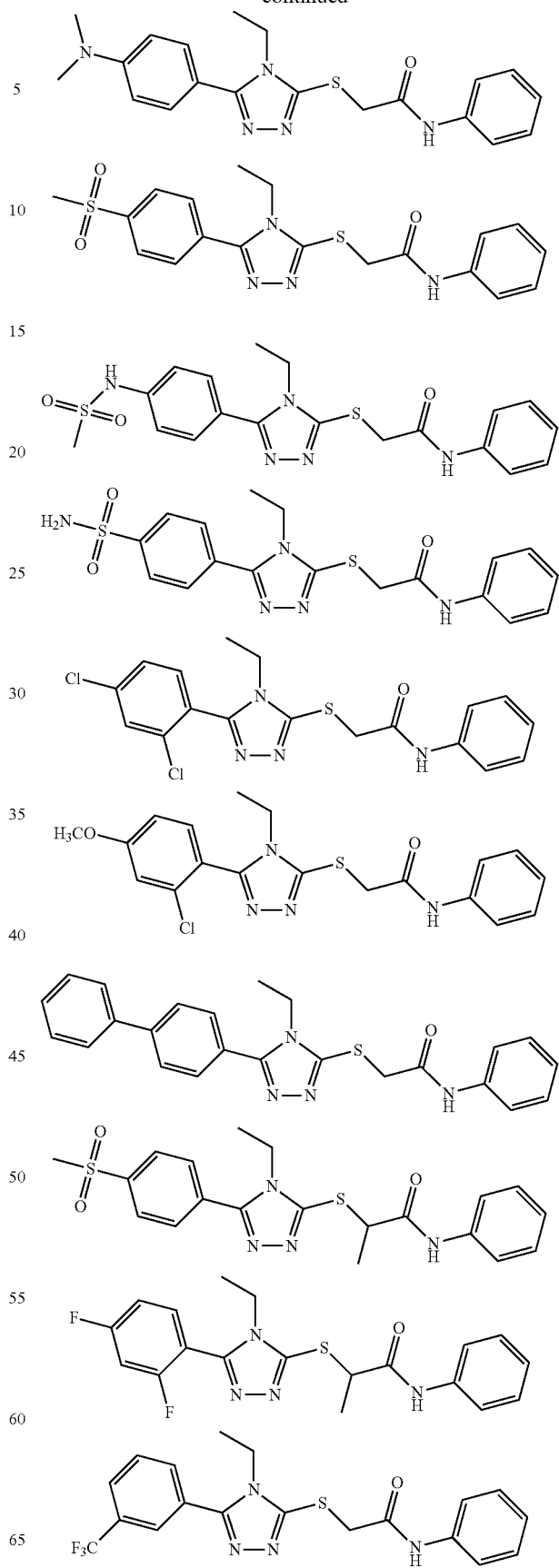

203
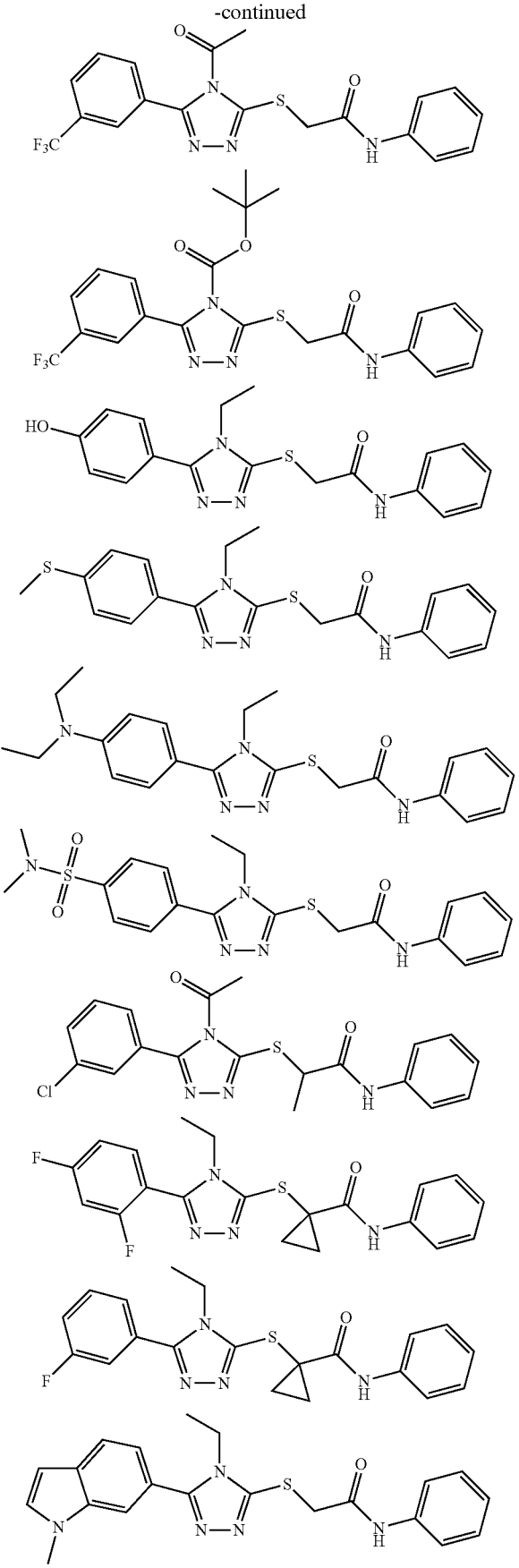
204
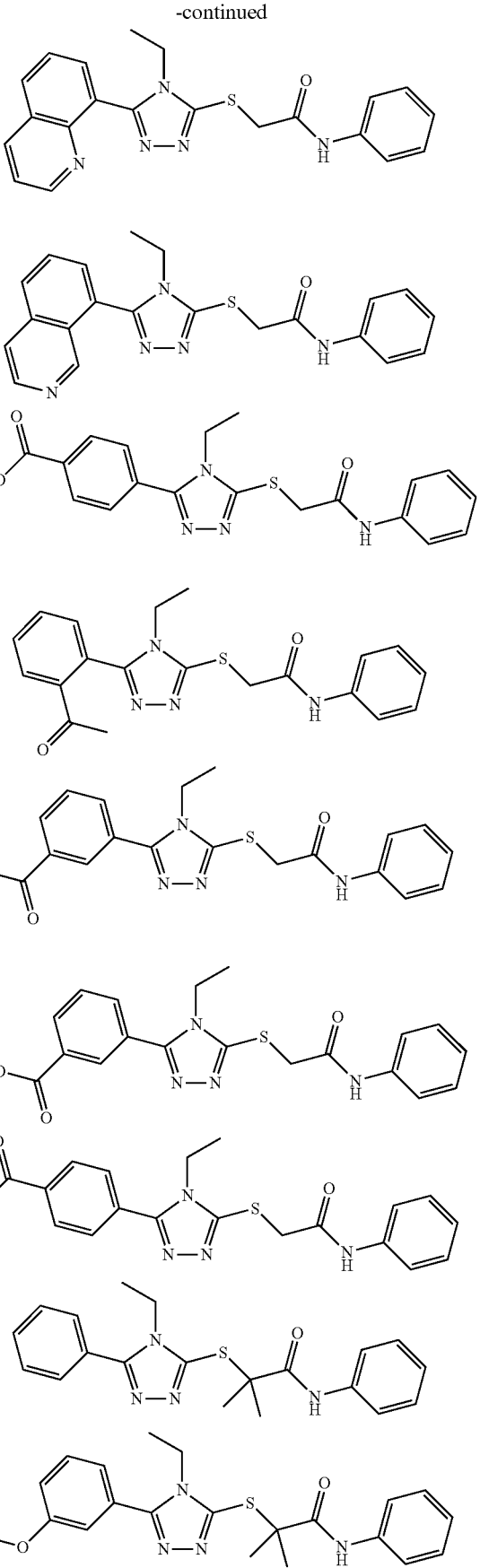

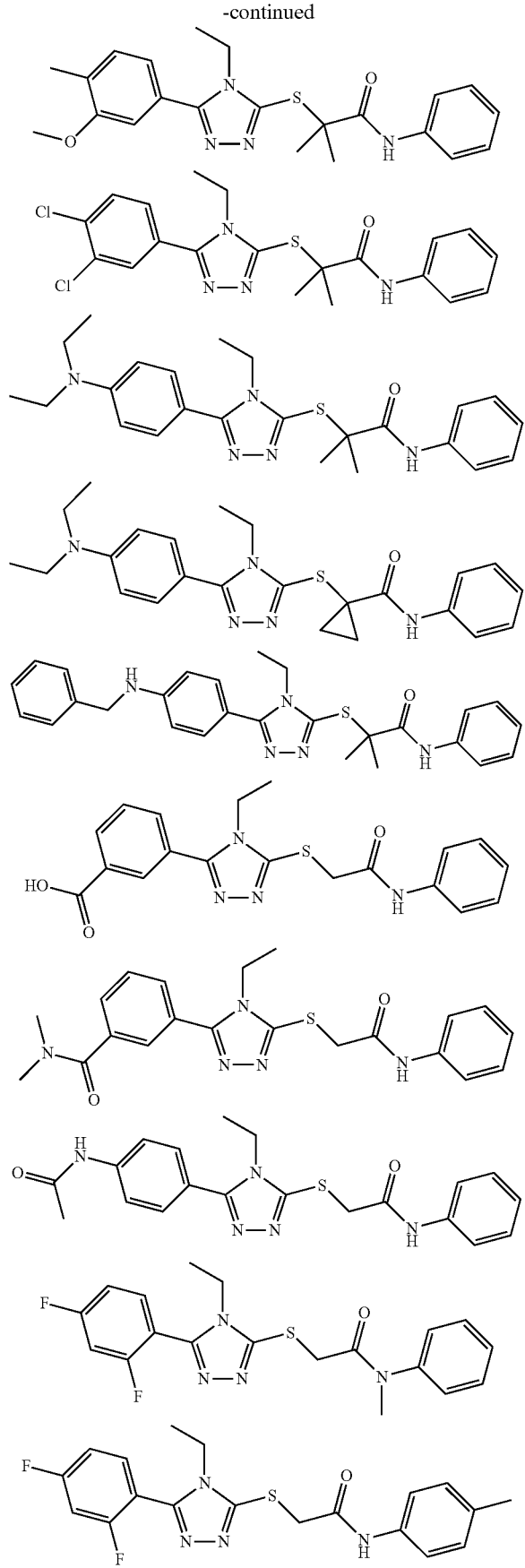
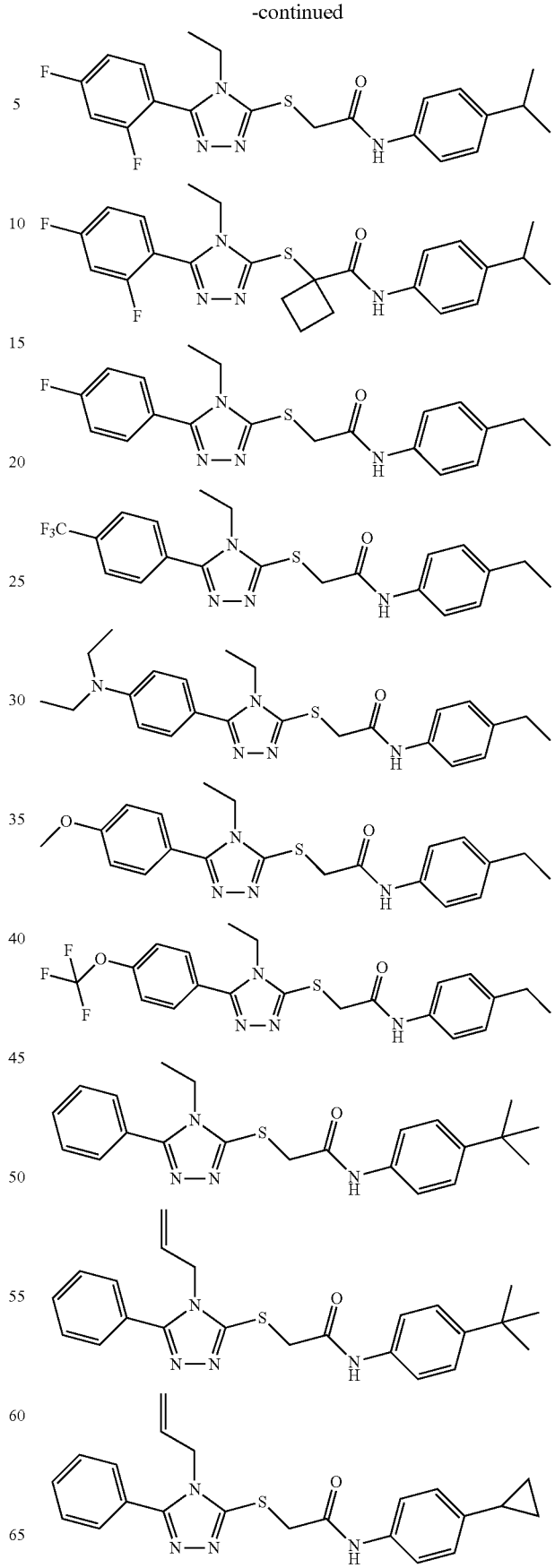

207
-continued
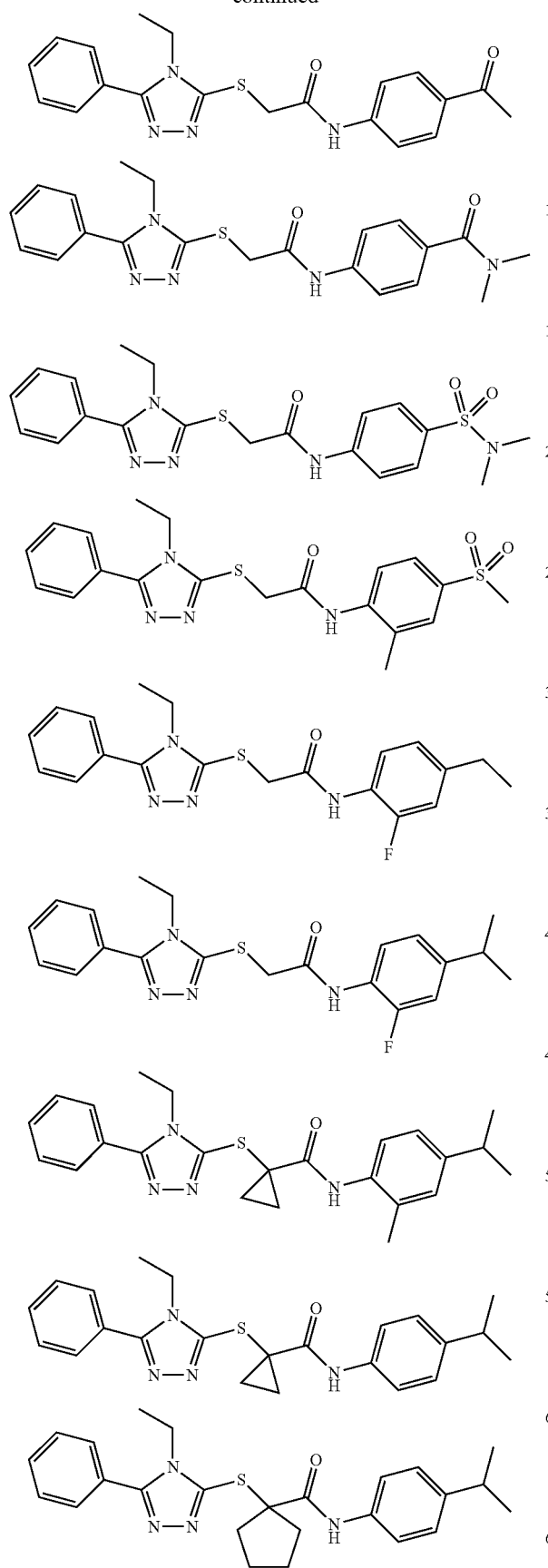
208
-continued
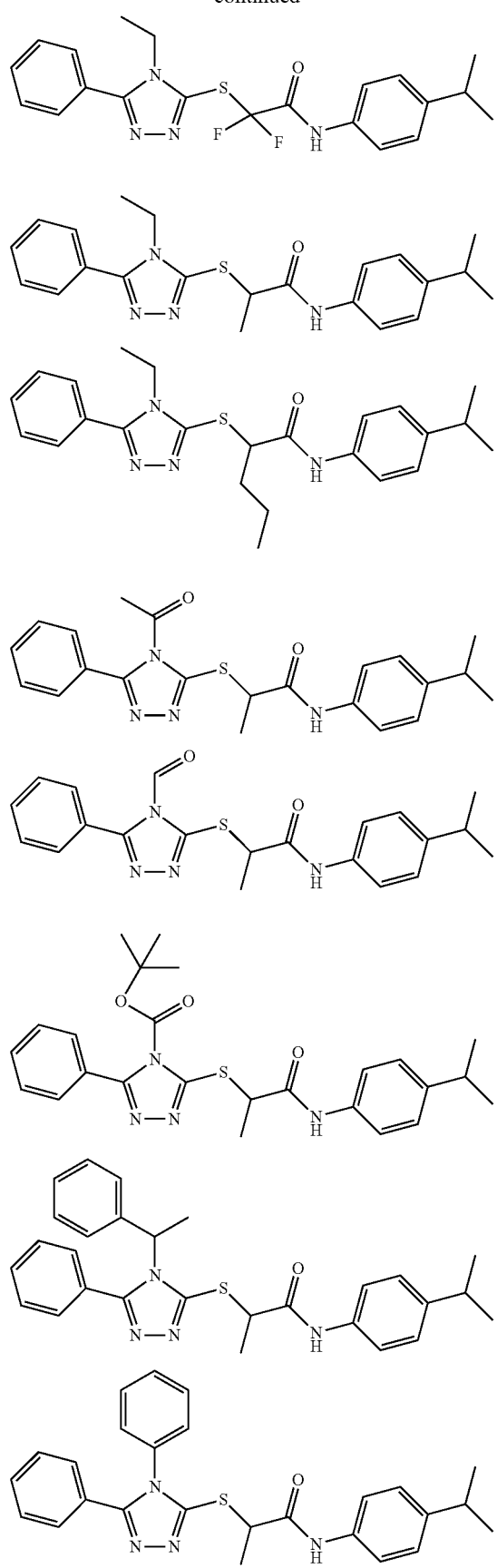

-continued

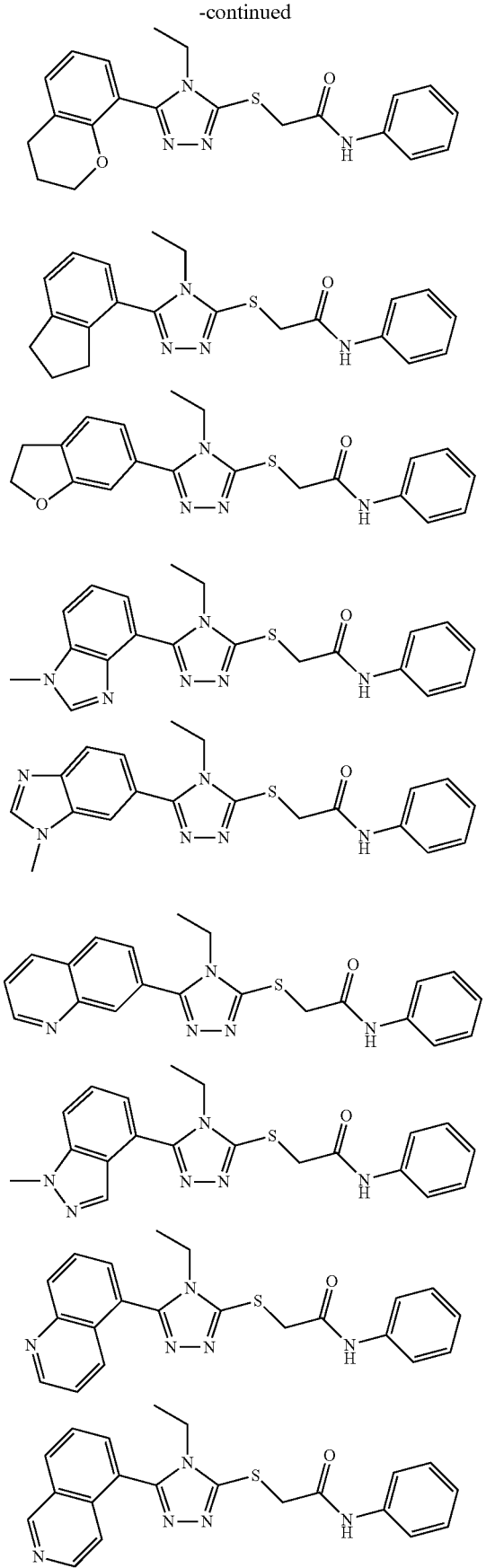
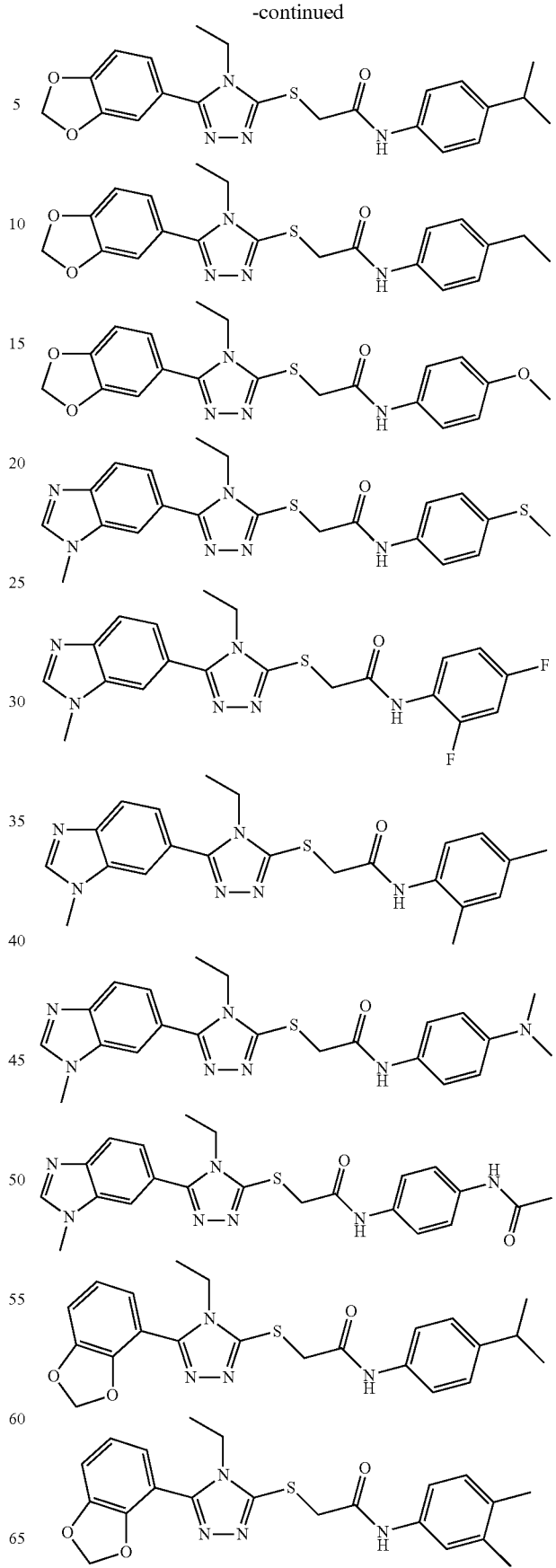

213
-continued
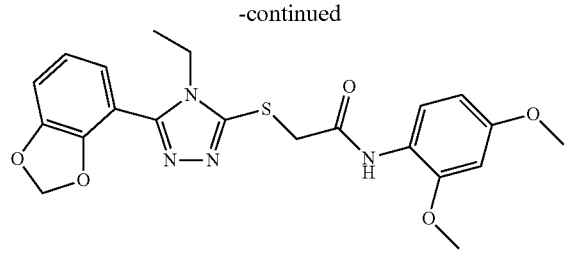
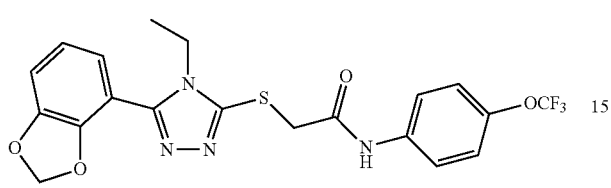
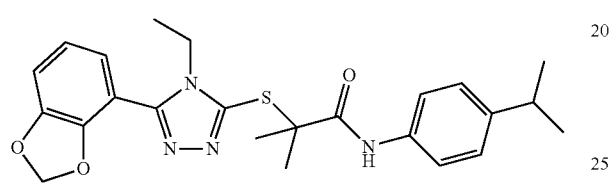
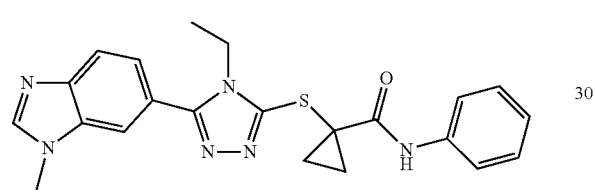
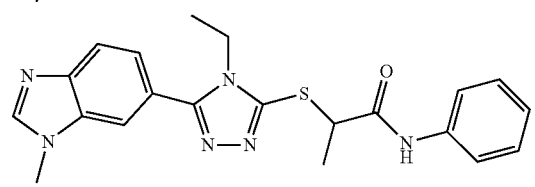
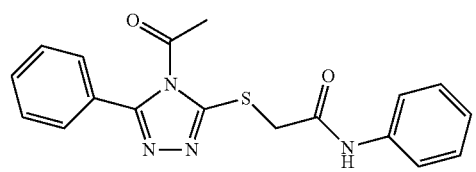
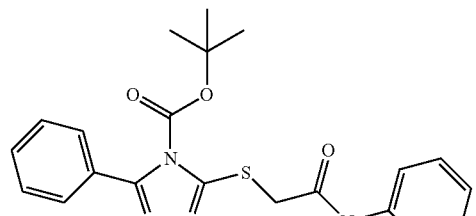
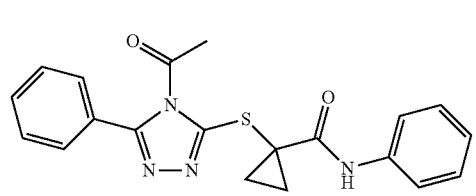
214
-continued
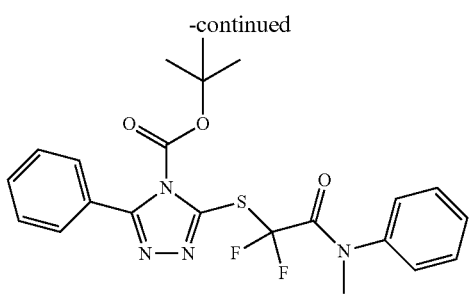
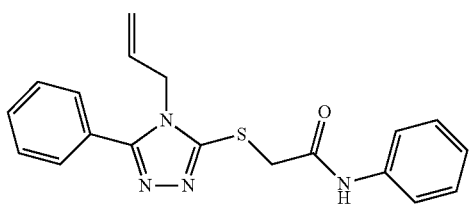
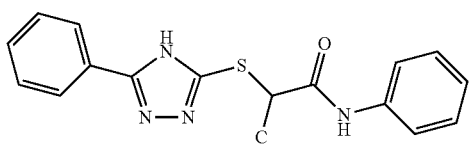
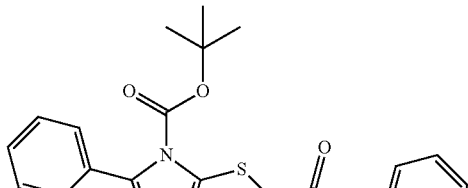
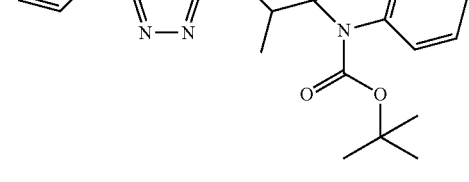
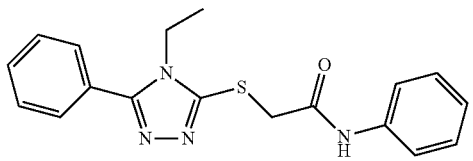
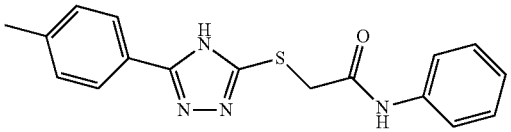
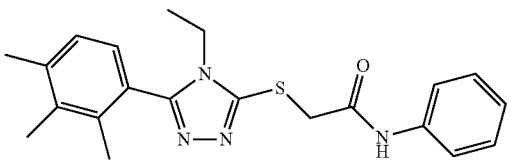
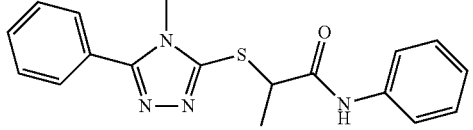

215
-continued
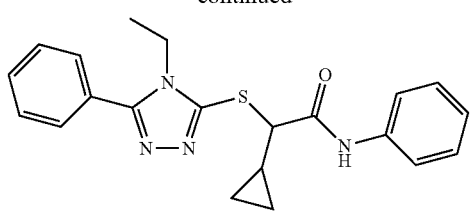
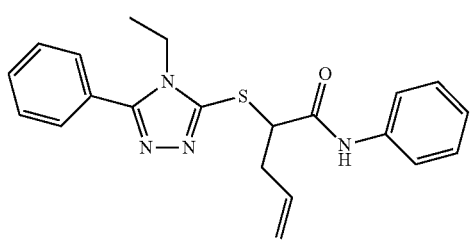
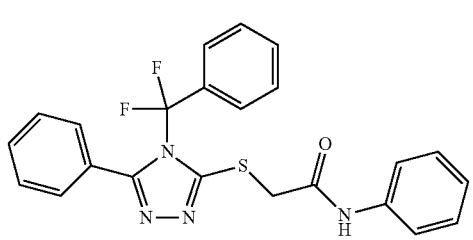
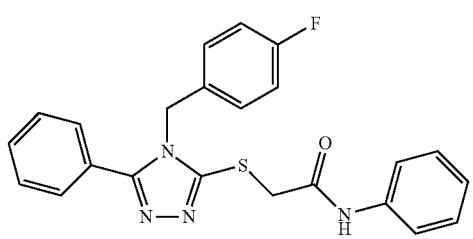
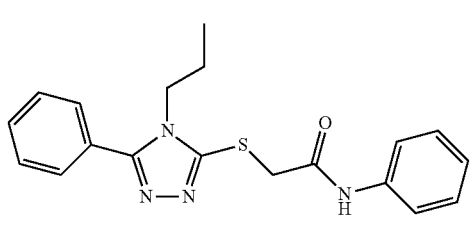
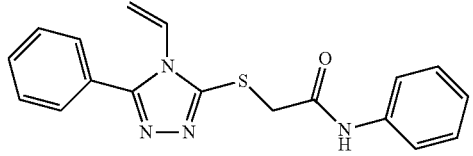
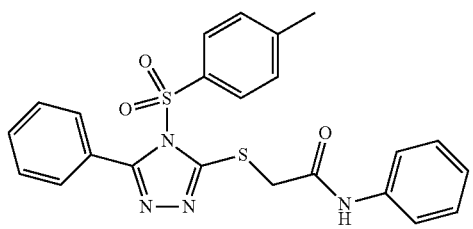
216
-continued
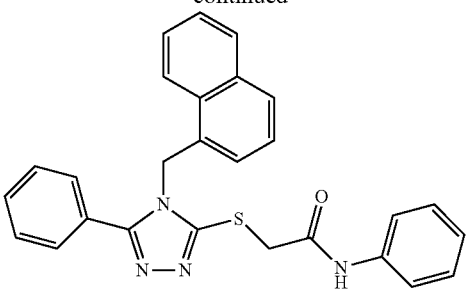
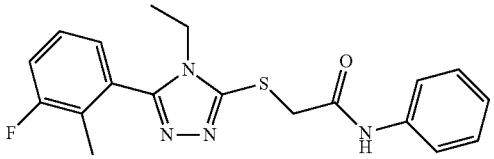
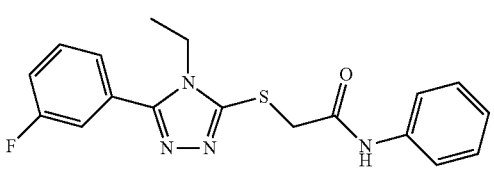
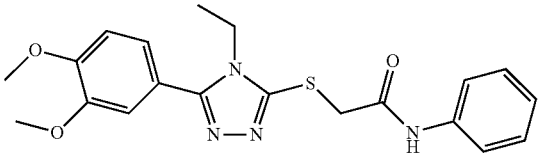
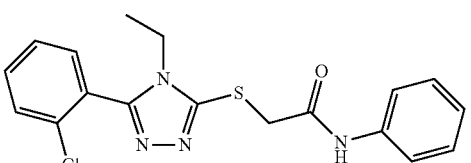
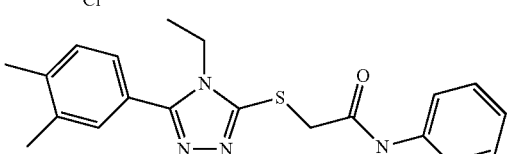
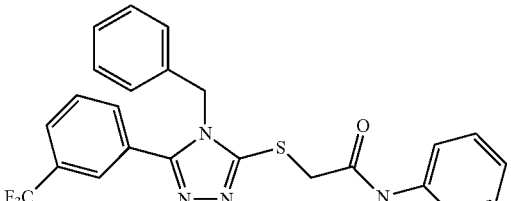
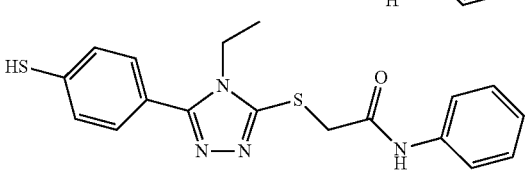
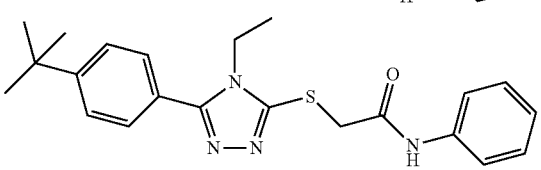

217
-continued
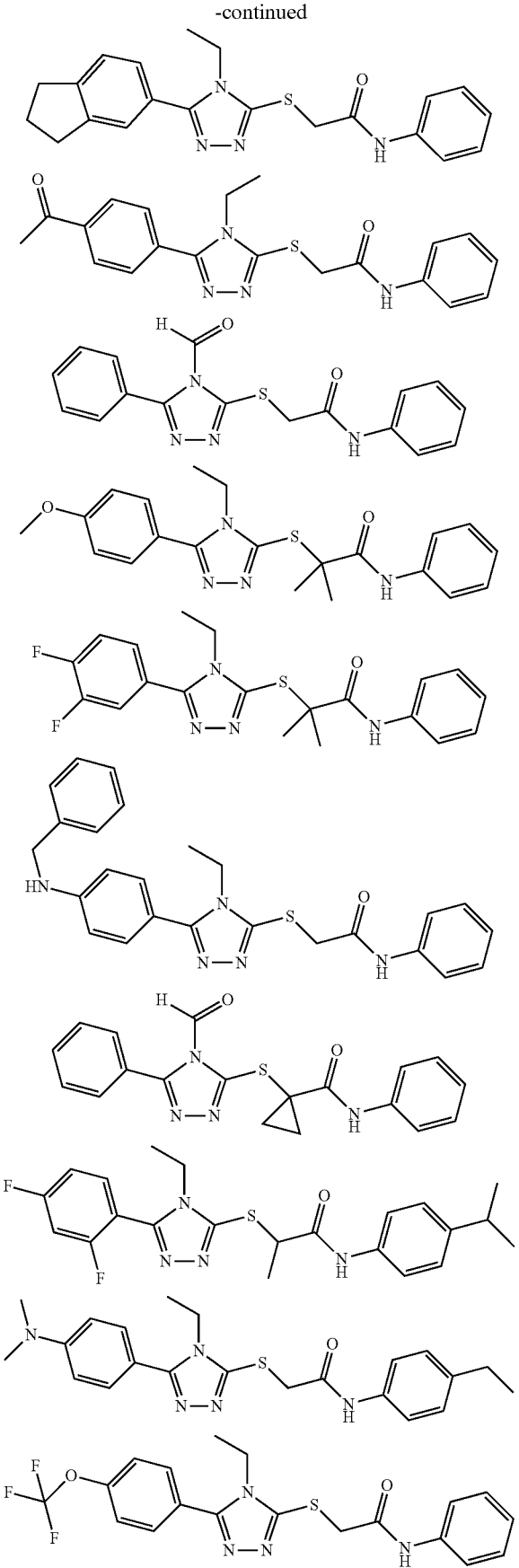
218
-continued
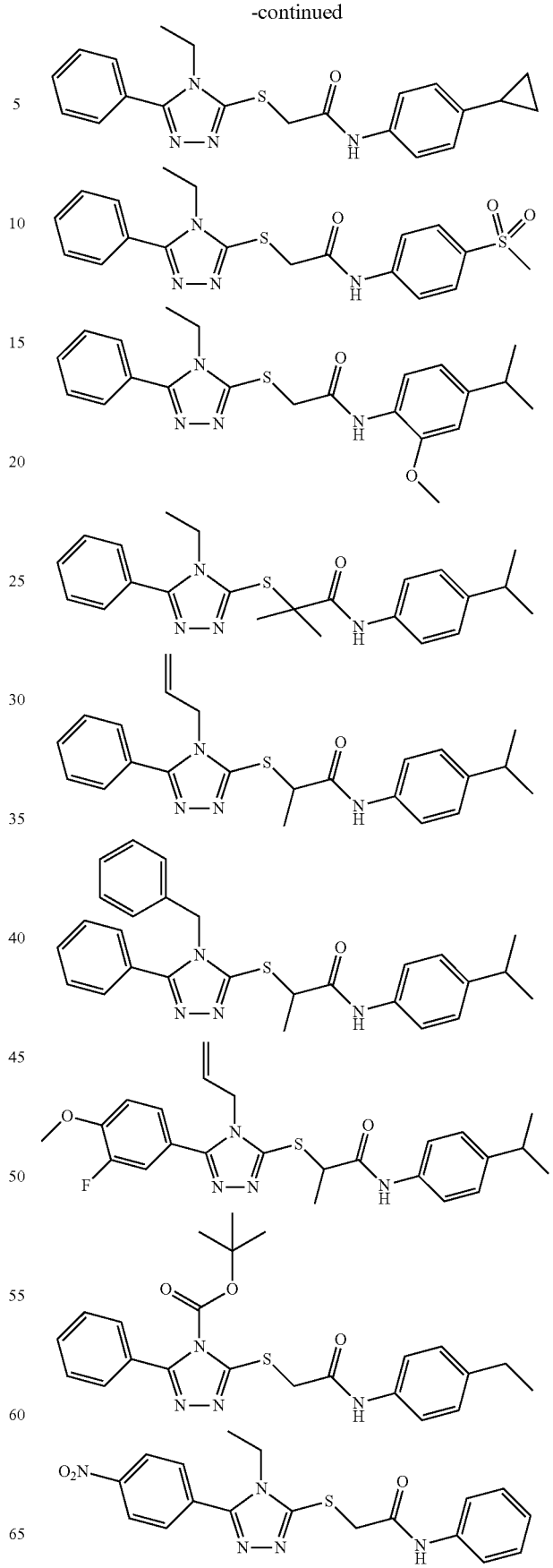

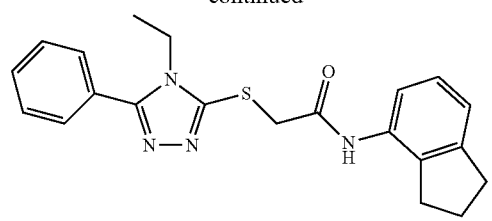
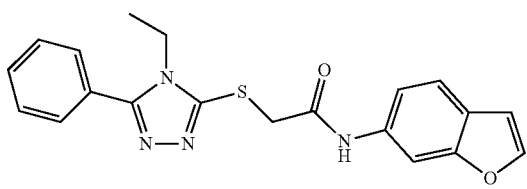
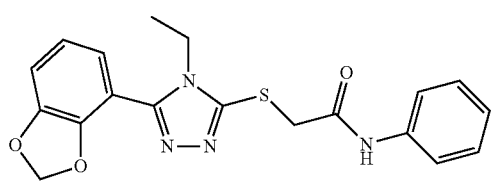
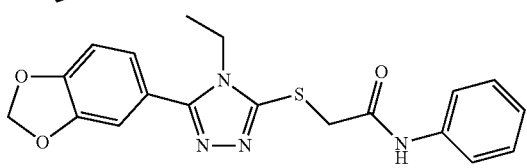
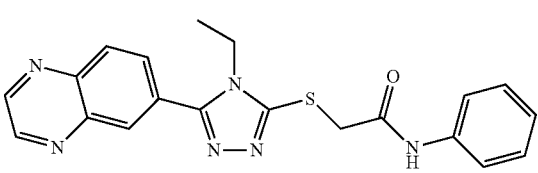
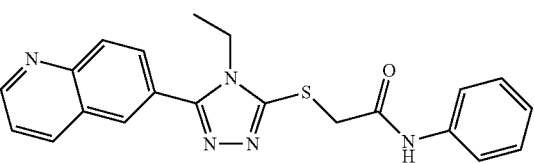
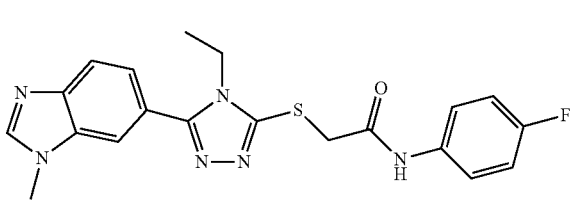
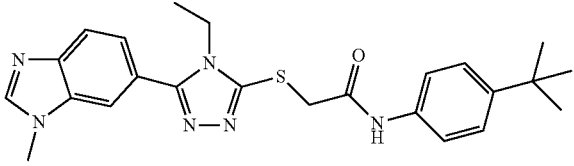
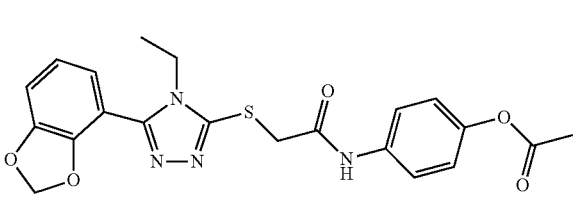
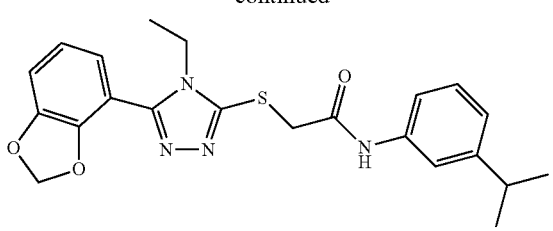
For example, a disclosed compound can have a structure selected from:
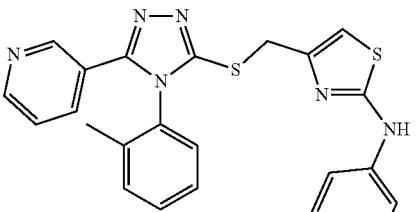
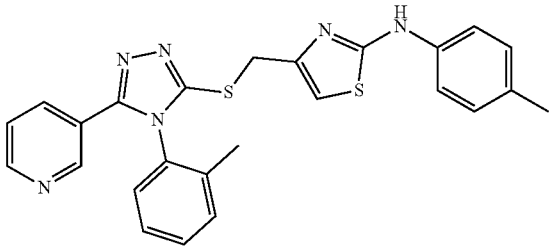
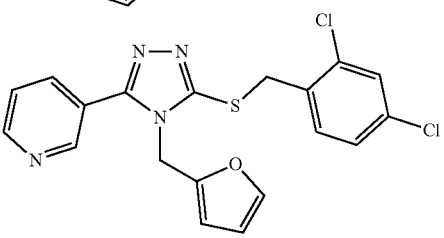
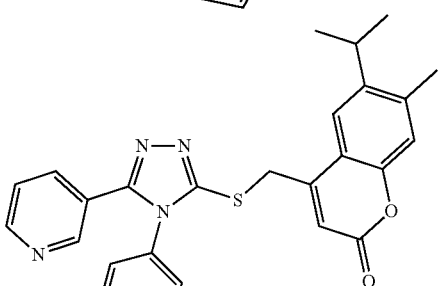
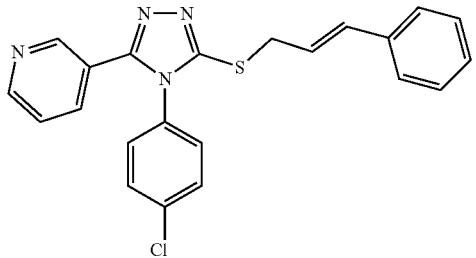

221
-continued
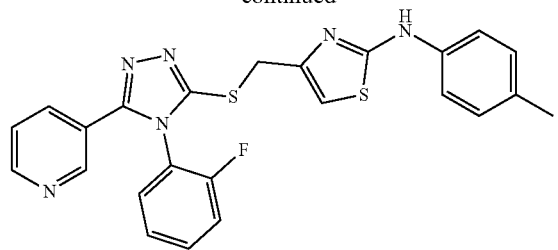
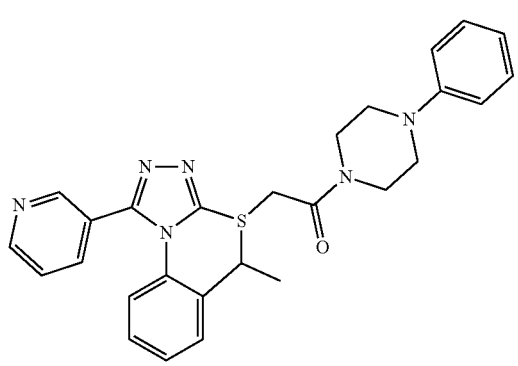 [SMILES: CC(C)c1ccccc1-n1c(SCC(=O)N2CCN(c3ccccc3)CC2)nnc1-c1cccnc1]
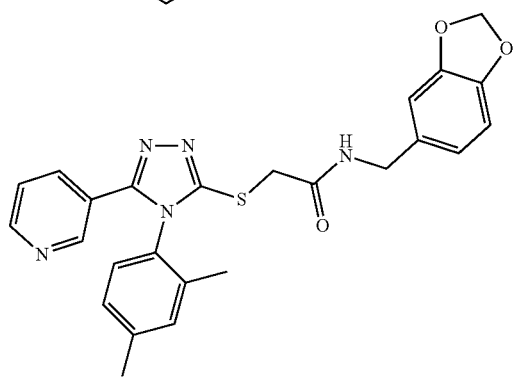
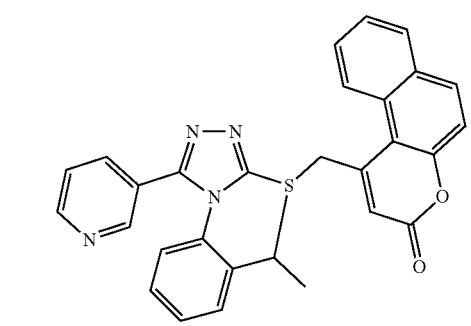
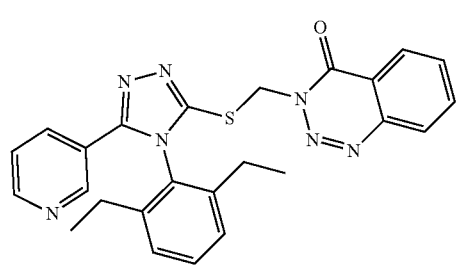
222
-continued
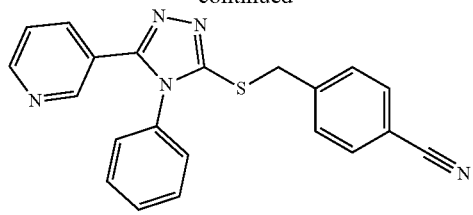
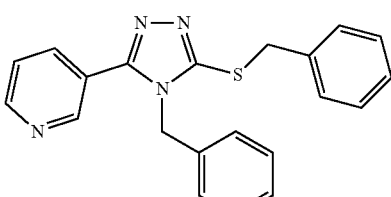
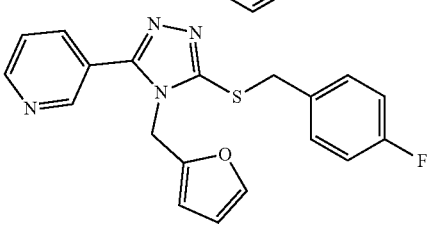
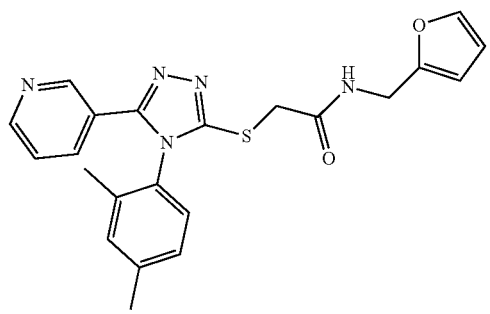
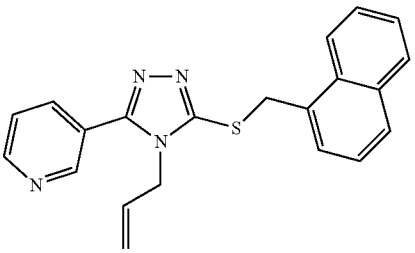
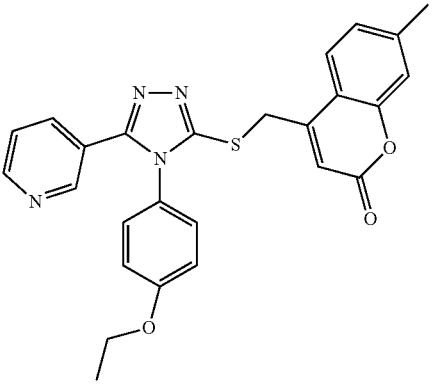

223
-continued
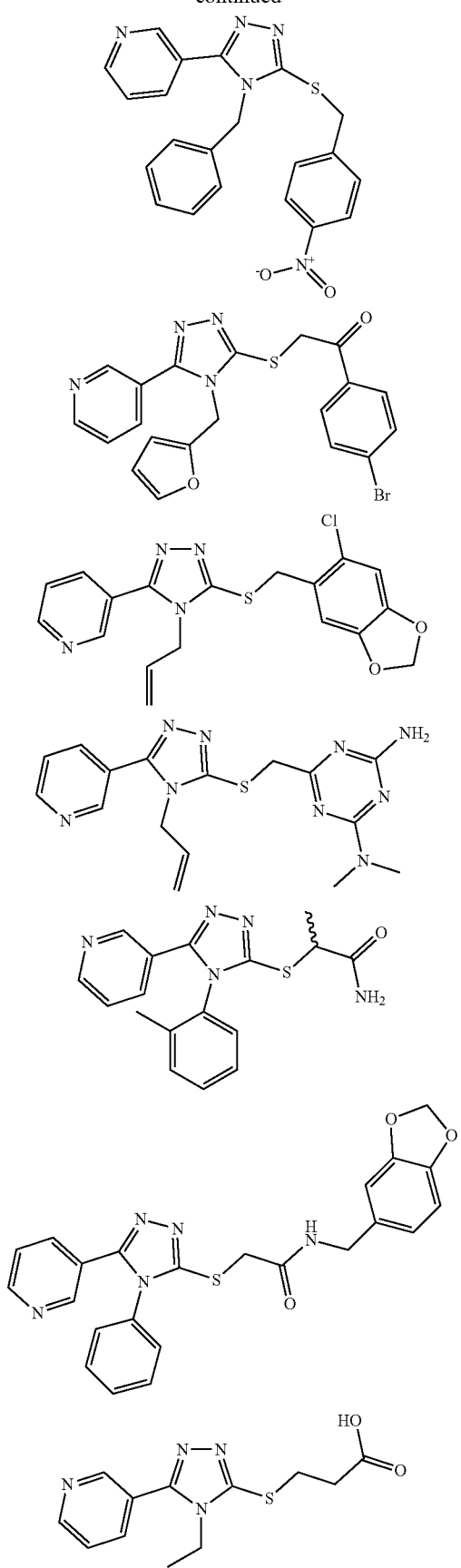
224
-continued
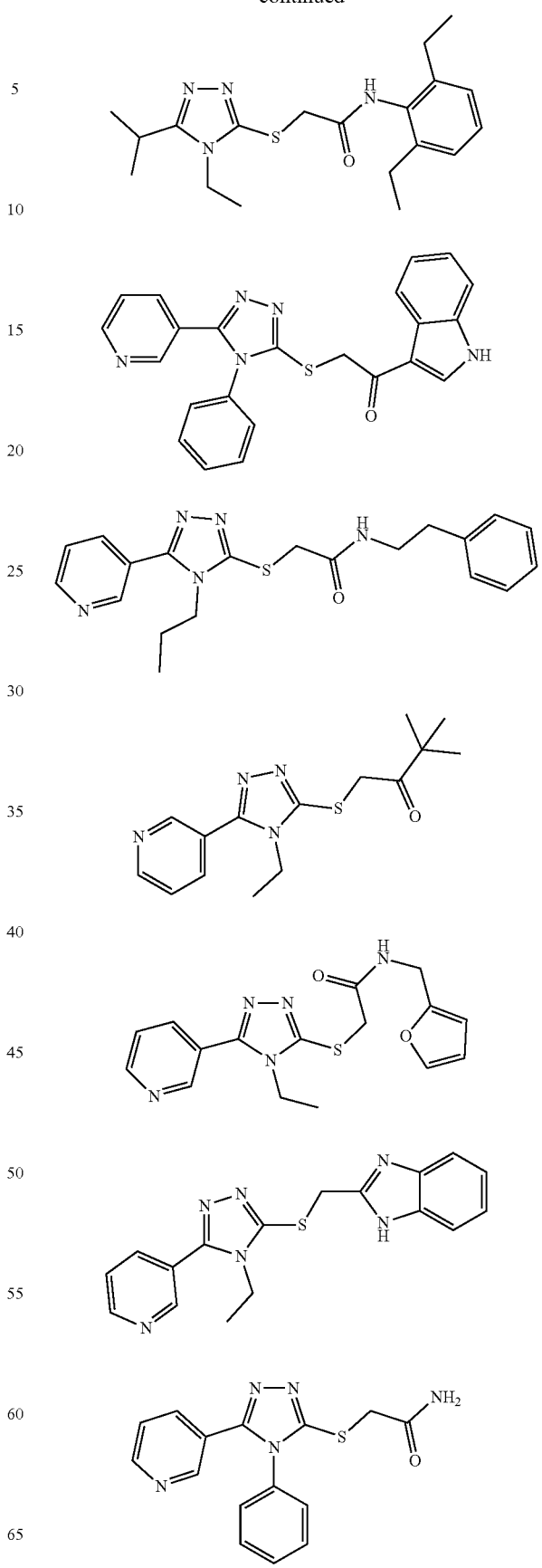

225
-continued
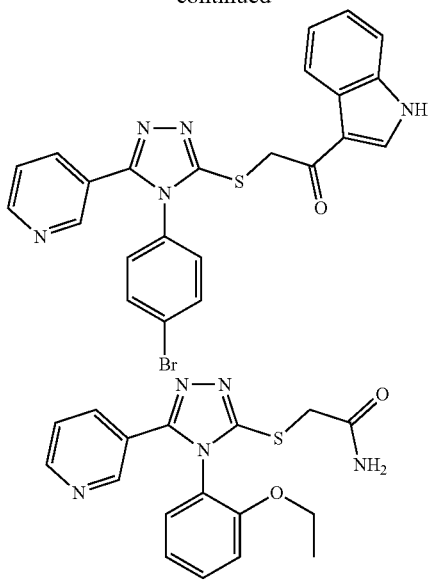
226
-continued
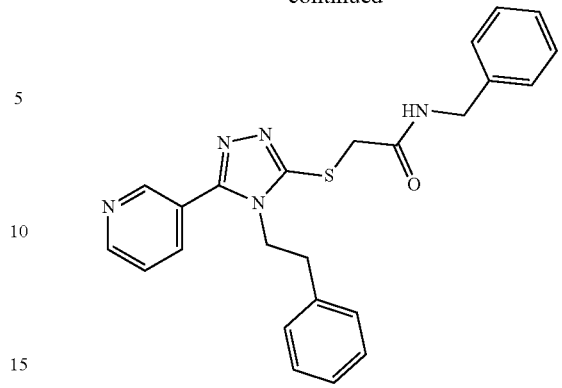
It is understood that the disclosed compounds can be used in connection with the disclosed methods, compositions, kits, and uses.
3. Activity
The activity against insect odorant sensory receptors was evaluated for various disclosed compounds, and the data were collected in Table 1.

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [triazole-S-CH2-C(O)NH-C6H4-iPr, H on triazole] | | | N/A | N/A | N/A | N/A | | N/A | N/A | | N/A | N/A |
| [triazole-S-CH2-C(O)NH-C6H4-iPr, NH2 on triazole] | | N/A | N/A | N/A | N/A | N/A | | | N/A | | N/A | N/A |
| [triazole-S-CH2-C(O)NH-C6H4-iPr, Br on triazole] | | | N/A | N/A | N/A | N/A | | N/A | N/A | | N/A | N/A |
| [triazole-S-CH2-C(O)NH-C6H4-C(O)OEt, iPr on triazole] | N/A | | N/A | N/A | N/A | N/A | | | N/A | | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | | | |
| [structure] | N/A | N/A | N/A | N/A | N/A | N/A | N/A | N/A | N/A | N/A | N/A | N/A |
| [structure] | N/A | N/A | N/A | N/A | N/A | N/A | N/A | N/A | N/A | N/A | N/A | N/A |
| [structure] | N/A | N/A | N/A | N/A | N/A | N/A | N/A | N/A | N/A | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | | | |
| [structure] | N/A | N/A | N/A | N/A | N/A | N/A | | | 13.90 | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | | | |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | | | | | | | | | | |
| [structure] | N/A | N/A | N/A | N/A | N/A | N/A | | | | | | |
| [structure] | N/A | N/A | N/A | N/A | N/A | N/A | N/A | N/A | | N/A | N/A | |
| [structure] | N/A | N/A | N/A | N/A | N/A | N/A | | | | | | |
| [structure] | N/A | N/A | N/A | N/A | N/A | N/A | N/A | N/A | | N/A | N/A | |

-continued

| Structure | Orco Agonist | | Orco + 48 Agonist | | Orco + 65 Agonist | | Orco 10 + Orco | | | | Orco 28 + Orco | | |
|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase |
| [structure: 4-methylphenyl amide-CH2-S-triazole(ethyl)-pyridine] | N/A | N/A | N/A | N/A | N/A | N/A | | | | | N/A | N/A | N/A |
| [structure: 4-isopropylphenyl amide-CH2-S-triazole(ethyl)-pyridine] | N/A | N/A | N/A | N/A | N/A | N/A | | N/A | | | | | |
| [structure: 2-methoxy-5-acetamido-phenyl amide-CH2-S-triazole(ethyl)-pyridine] | N/A | N/A | N/A | N/A | N/A | N/A | | | | | | | |
| [structure: benzodioxine amide-CH2-S-triazole(ethyl)-pyridine] | N/A | N/A | N/A | N/A | N/A | N/A | | | | | | | |
| [structure: phenyl amide-CH2-S-triazole-pyridine] | N/A | N/A | N/A | N/A | N/A | N/A | | | | | N/A | N/A | N/A |

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| (structure) | N/A | N/A | N/A | N/A | N/A | N/A | | | | | | N/A | N/A | |
| (structure) | N/A | N/A | N/A | N/A | N/A | N/A | N/A | | | | N/A | N/A | N/A | |
| (structure) | N/A | N/A | N/A | N/A | N/A | N/A | | | | | | N/A | N/A | |
| (structure) | N/A | N/A | N/A | N/A | N/A | N/A | N/A | | | | N/A | N/A | N/A | |
| (structure) | N/A | N/A | N/A | N/A | N/A | N/A | N/A | | | | N/A | N/A | N/A | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure: 2-F-phenyl amide] | N/A | N/A | N/A | N/A | N/A | N/A | | | | N/A | N/A | N/A |
| [structure: 2-F-phenyl amide] | N/A | N/A | N/A | N/A | N/A | N/A | | | | | | N/A |
| [structure: 2-methylester phenyl amide] | N/A | N/A | N/A | N/A | N/A | N/A | | | | N/A | | N/A |
| [structure: 2-methylester phenyl amide] | N/A | N/A | N/A | N/A | N/A | N/A | | | | | | N/A |
| [structure: 4-F-phenyl amide] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | | Orco 28 + Orco | | |
|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase |
| (4-fluorophenyl amide) | N/A | N/A | N/A | N/A | N/A | N/A | | | | | N/A | N/A | N/A |
| (2,4-difluorophenyl amide) | N/A | N/A | N/A | N/A | N/A | N/A | | | | | N/A | N/A | N/A |
| (2,4-difluorophenyl amide) | N/A | N/A | N/A | N/A | N/A | N/A | | | | | N/A | N/A | N/A |
| (chloro-morpholinosulfonyl phenyl) | N/A | N/A | N/A | N/A | N/A | N/A | | | | | N/A | N/A | N/A |
| (chloro-morpholinosulfonyl phenyl) | N/A | N/A | N/A | N/A | N/A | N/A | | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| | N/A | N/A | N/A | N/A | N/A | N/A | | | | N/A | N/A | N/A |
| | N/A | N/A | N/A | N/A | N/A | N/A | | | | | | |
| | N/A | N/A | N/A | N/A | N/A | N/A | | | | N/A | N/A | N/A |
| | N/A | N/A | N/A | N/A | N/A | N/A | | | | | | |
| | N/A | N/A | N/A | N/A | N/A | N/A | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure: 2-F-phenyl-NH-C(O)-CH2-S-triazole-pyridyl] | N/A | N/A | N/A | N/A | N/A | N/A | | | | N/A | N/A | N/A |
| [structure: 2-methylester-phenyl-NH-C(O)-CH2-S-triazole-pyridyl] | N/A | N/A | N/A | N/A | N/A | N/A | | | | | | N/A |
| [structure: 2-methylester-phenyl-NH-C(O)-CH2-S-triazole-pyridyl] | N/A | N/A | N/A | N/A | N/A | N/A | | | 15.15 | | | 18.02 |
| [structure: 3-F-phenyl-NH-C(O)-CH2-S-triazole-pyridyl] | N/A | N/A | N/A | N/A | N/A | N/A | | | | | | N/A |
| [structure: 3-F-phenyl-NH-C(O)-CH2-S-triazole-pyridyl] | N/A | N/A | N/A | N/A | N/A | N/A | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (ethyl benzoate-triazole-pyridine structure) | N/A | N/A | | | | | | | | N/A | N/A | N/A |
| (ethyl benzoate-S-triazole-pyridine structure) | N/A | N/A | N/A | N/A | | | | | | | | |
| (4-bromophenyl-S-triazole-pyridine structure) | N/A | N/A | N/A | N/A | N/A | N/A | | | | | | |
| (4-fluorophenyl-S-triazole-pyridine structure) | N/A | N/A | N/A | N/A | N/A | N/A | | | | N/A | N/A | N/A |
| (4-bromophenyl-S-triazole-pyridine structure) | N/A | N/A | N/A | N/A | N/A | N/A | | | | N/A | N/A | N/A |
| (4-fluorophenyl-S-triazole-pyridine structure) | N/A | N/A | N/A | N/A | N/A | N/A | | | | | 11.09 | 11.23 |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [4-chlorophenyl amide, methyl-triazole-S-CH2, pyridyl] | N/A | N/A | N/A | N/A | N/A | N/A | | | | N/A | N/A | N/A |
| [4-methoxyphenyl amide, methyl-triazole-S-CH2, pyridyl] | N/A | N/A | N/A | N/A | N/A | N/A | | | | N/A | N/A | N/A |
| [4-methoxyphenyl amide, methyl-triazole-S-CH2, pyridyl] | N/A | N/A | N/A | N/A | N/A | N/A | | | | N/A | N/A | N/A |
| [ethyl benzoate amide, methyl-triazole-S-CH2, pyridyl] | N/A | N/A | N/A | N/A | N/A | N/A | | | | N/A | N/A | N/A |
| [ethyl benzoate amide, methyl-triazole-S-CH2, pyridyl] | N/A | N/A | N/A | N/A | N/A | N/A | | | | | | |
| [2,4-difluorophenyl amide, methyl-triazole-S-CH2, pyridyl] | N/A | N/A | N/A | N/A | N/A | N/A | | | | N/A | N/A | N/A |

-continued

| Structure | Orco Agonist EC50 | Orco Agonist % value Of VUAA1 | Orco + 48 Agonist EC50 | Orco + 48 Agonist % value Of VUAA1 | Orco + 65 Agonist EC50 | Orco + 65 Agonist % value Of VUAA1 | Orco 10 + Orco Agonist % of control | Orco 10 + Orco Antagonist % Reduction | Orco 10 + Orco Potentiator % increase | Orco 28 + Orco Agonist % of control | Orco 28 + Orco Antagonist % Reduction | Orco 28 + Orco Potentiator % increase |
|---|---|---|---|---|---|---|---|---|---|---|---|---|
| [2,4-difluorophenyl amide triazole pyridine] | N/A | N/A | N/A | N/A | N/A | N/A | | | | N/A | N/A | N/A |
| [2,4-dimethylphenyl amide triazole pyridine] | N/A | N/A | N/A | N/A | N/A | N/A | | | | | | |
| [2,4-dimethylphenyl amide triazole pyridine isomer] | N/A | N/A | N/A | N/A | N/A | N/A | | | | N/A | N/A | 12.63 |
| [2,5-dimethoxyphenyl ketone triazole pyridine] | N/A | N/A | N/A | N/A | N/A | N/A | | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| | N/A | N/A | N/A | N/A | N/A | N/A | | | | N/A | N/A | N/A |
| | N/A | N/A | N/A | N/A | N/A | N/A | | | | N/A | N/A | N/A |
| | N/A | N/A | N/A | N/A | N/A | N/A | | | | N/A | N/A | N/A |
| | N/A | N/A | N/A | N/A | N/A | N/A | | | | N/A | N/A | N/A |
| | N/A | N/A | N/A | N/A | N/A | N/A | | | | N/A | N/A | N/A |
| | N/A | N/A | N/A | N/A | N/A | N/A | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | | | | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | | N/A |
| [structure] | N/A | N/A | N/A | N/A | N/A | N/A | | | | | 13.76 | |
| [structure] | N/A | N/A | N/A | N/A | N/A | N/A | | | | | | |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (mesityl ketone methylthiotriazole pyridine) | N/A | N/A | | | | | | | | | 18.21 | |
| (nitrobenzyl thiomethyltriazole pyridine) | N/A | N/A | | | N/A | N/A | | | N/A | | | N/A |
| (cyclohexylamide ethyltriazole pyridine) | | | | | N/A | N/A | N/A | N/A | N/A | N/A | N/A | N/A |
| (isopropylphenyl ketone ethyltriazole pyridine) | N/A | N/A | | | | | | | | N/A | N/A | N/A |

-continued

| Structure | Orco Agonist EC50 | Orco Agonist % value Of VUAA1 | Orco + 48 Agonist EC50 | Orco + 48 Agonist % value Of VUAA1 | Orco + 65 Agonist EC50 | Orco + 65 Agonist % value Of VUAA1 | Orco 10 + Orco Agonist % of control | Orco 10 + Orco Antagonist % Reduction | Orco 10 + Orco Potentiator % increase | Orco 28 + Orco Agonist % of control | Orco 28 + Orco Antagonist % Reduction | Orco 28 + Orco Potentiator % increase |
|---|---|---|---|---|---|---|---|---|---|---|---|---|
| (benzimidazole-CH2-S-triazole-pyridine) | N/A | N/A | N/A | N/A | N/A | N/A | | | 7.5 | | | 15.1 |
| (hydroxyquinoline-CH2-S-triazole-pyridine) | N/A | N/A | N/A | N/A | N/A | N/A | | | | N/A | N/A | N/A |
| (indoline-CO-CH2-S-triazole-pyridine) | N/A | N/A | N/A | N/A | N/A | N/A | | N/A | | N/A | N/A | N/A |
| (ethylphenyl-NH-CO-CH2-S-triazole-pyridine) | N/A | N/A | 18.2 | N/A | N/A | N/A | N/A | | | N/A | N/A | N/A |
| (ethyl benzoate-NH-CO-CH2-S-triazole-pyridine) | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (ethyl benzoate triazole structure) | N/A | N/A | | | N/A | N/A | | | | | | |
| (4-Br phenyl triazole structure) | | N/A | N/A | N/A | N/A | N/A | | N/A | N/A | | N/A | N/A |
| (4-Br phenyl N-methyl triazole structure) | | N/A | N/A | N/A | N/A | N/A | | N/A | N/A | | N/A | N/A |
| (4-methoxy phenyl triazole structure) | N/A | N/A | N/A | N/A | N/A | N/A | | | | N/A | N/A | N/A |
| (4-methoxy phenyl triazole structure) | N/A | N/A | N/A | N/A | N/A | N/A | | | | | | |

| Structure | Orco Agonist | | Orco + 48 Agonist | | | Orco + 65 Agonist | | | Orco 10 + Orco | | | Orco 28 + Orco | | |
|---|---|---|---|---|---|---|---|---|---|---|---|---|---|---|
| | EC50 | % value Of VUAA1 | EC50 | % value Of VUAA1 | Agonist % of control | EC50 | % value Of VUAA1 | Agonist % of control | Antagonist % Reduction | Potentiator % increase | Agonist % of control | Antagonist % Reduction | Potentiator % increase |
| (p-tolyl amide) | 262 μM | 100% | 996 μM | 100% | | 335 μM | 100% | | N/A | N/A | N/A | N/A | N/A |
| (p-ethylphenyl amide) | 69 μM | 57% | 14 μM | 100% | 101.8035043 | 47 μM | 100% | | | N/A | | | |
| (p-acetylphenyl amide) | N/A | | N/A | N/A | | N/A | N/A | | | | | | |
| (p-acetylphenyl amide) | N/A | | N/A | N/A | | N/A | N/A | | | | | | |
| (p-vinylphenyl amide) | 102 μM | 57% | 37.4 μM | 77% | | 105 | <VUAA1 | | N/A | N/A | N/A | N/A | N/A |
| (6-bromopyridyl amide) | | | N/A | | | N/A | | | N/A | N/A | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (alkyne-phenyl amide triazole) | | | N/A | N/A | N/A | N/A | | N/A | N/A | N/A | N/A | N/A |
| (ethyl-pyridyl amide triazole) | | | N/A | N/A | N/A | N/A | | N/A | N/A | N/A | N/A | N/A |
| (N-methyl ethyl-phenyl amide triazole) | | | N/A | N/A | N/A | N/A | | N/A | N/A | N/A | N/A | N/A |
| (isopropyl-phenyl amide triazole) | 12.9 μM | 102% | 9.9 μM | 109% | 9.6 μM | N/A | >VUAA1 | N/A | N/A | N/A | N/A | N/A |
| (propyl-phenyl amide triazole) | 63 μM | 87% | 19.8 μM | N/A | N/A | N/A | <VUAA1 | N/A | N/A | N/A | N/A | N/A |
| (isopropyl-phenyl amide sulfone triazole) | | | N/A | N/A | N/A | N/A | | N/A | N/A | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure) | N/A | | | N/A | N/A | N/A | N/A | N/A | N/A | N/A | N/A | N/A |
| (structure) | | N/A | N/A | N/A | N/A | N/A | | N/A | N/A | N/A | N/A | N/A |
| (structure) | N/A | N/A | N/A | N/A | N/A | N/A | | N/A | N/A | N/A | N/A | N/A |
| (structure) | | N/A | N/A | N/A | N/A | N/A | | N/A | N/A | N/A | N/A | N/A |
| (structure) | N/A | | 2.2 μM | | N/A | N/A | N/A | | | N/A | N/A | N/A |
| (structure) | N/A | | | | N/A | N/A | N/A | N/A | N/A | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 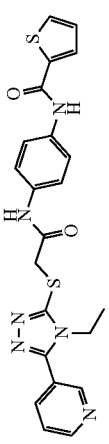 | N/A | N/A | N/A | N/A | N/A | N/A | N/A | N/A | N/A | N/A | N/A | N/A |
| 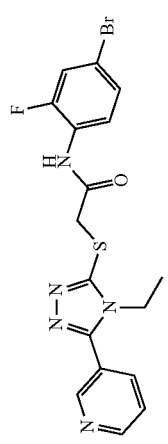 | 192 μM | <VUAA1 | | | | | <VUAA1 | 0.00 | N/A | N/A | N/A | N/A |
| 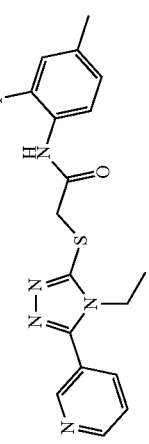 | | | N/A | N/A | N/A | N/A | | N/A | N/A | N/A | N/A | N/A |
| 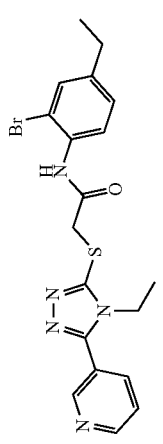 | | | N/A | N/A | N/A | N/A | | N/A | N/A | N/A | N/A | N/A |
| 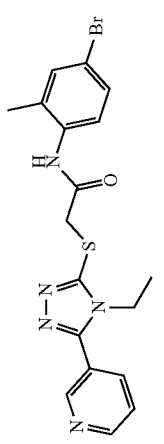 | | | | | N/A | N/A | | N/A | N/A | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value of VUAA1 | EC50 | % value of VUAA1 | EC50 | % value of VUAA1 | Agonist % of control | Antagonist % Reduction | Potentiator % increase | Agonist % of control | Antagonist % Reduction | Potentiator % increase |
| (2-methyl-4-ethylphenyl amide, pyridinyl-ethyl-triazolyl-S-CH2-C(O)-NH) | | | N/A | N/A | N/A | N/A | | N/A | N/A | N/A | N/A | N/A |
| (5-bromo-indoline, pyridinyl-ethyl-triazolyl-S-CH2-C(O)-N) | 55 μM | 59% | | | N/A | N/A | >VUAA1 | 59% | N/A | N/A | N/A | N/A |
| (5-ethyl-indoline, pyridinyl-ethyl-triazolyl-S-CH2-C(O)-N) | 35 μM | 121% | 12.8 μM | | N/A | N/A | >VUAA1 | N/A | N/A | N/A | N/A | N/A |
| (5-fluoro-indoline, pyridinyl-ethyl-triazolyl-S-CH2-C(O)-N) | | | N/A | N/A | N/A | N/A | | N/A | N/A | N/A | N/A | N/A |
| (5-methyl-indoline, pyridinyl-ethyl-triazolyl-S-CH2-C(O)-N) | | | N/A | N/A | | | | N/A | N/A | | | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (5-OMe indoline) | N/A | N/A | N/A | N/A | N/A | N/A | N/A | N/A | N/A | N/A | N/A | N/A |
| (5-NMe2 indoline) | | | N/A | N/A | N/A | N/A | | N/A | N/A | N/A | N/A | N/A |
| (5-iPr indoline) | | | N/A | N/A | N/A | N/A | | N/A | N/A | N/A | N/A | N/A |
| (5-tBu indoline) | | | N/A | N/A | N/A | N/A | | N/A | N/A | N/A | N/A | N/A |
| (5-Cl 2-Me indoline) | | | N/A | N/A | N/A | N/A | | N/A | N/A | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure: tetrahydroquinoline-CF3 with triazole-pyridine] | | | N/A | N/A | N/A | N/A | N/A | N/A | N/A | N/A | N/A | N/A |
| [structure: tetrahydroquinoline-Br with triazole-pyridine] | N/A | N/A | N/A | N/A | N/A | N/A | N/A | N/A | N/A | | | |
| [structure: methoxy-acetamido-phenyl with triazole-pyridine] | | | N/A | N/A | N/A | N/A | N/A | N/A | N/A | | | |
| [structure: methoxy-acetamido-phenyl isomer with triazole-pyridine] | N/A | N/A | N/A | N/A | N/A | N/A | | | | N/A | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | | | | | | | | N/A | N/A | N/A |
| [structure] | N/A | N/A | N/A | N/A | N/A | N/A | | | | | | |
| [structure] | N/A | N/A | N/A | N/A | N/A | N/A | | | | N/A | | N/A |
| [structure] | N/A | N/A | N/A | N/A | N/A | N/A | | | 10.23 | | 10.89 | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | | | |
| [structure] | N/A | N/A | N/A | N/A | N/A | N/A | | | | | | |
| [structure] | N/A | N/A | N/A | N/A | N/A | N/A | | | | | | |
| [structure] | N/A | N/A | N/A | N/A | N/A | N/A | | | 12.1 | | | 17.24 |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | 15.74 | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (benzyl-S-triazole-pyridine, N-ethyl) | N/A | N/A | N/A | N/A | N/A | N/A | | | | N/A | N/A | N/A |
| (4-methoxybenzoyl hydrazide-S-triazole-pyridine, N-ethyl) | N/A | N/A | N/A | N/A | N/A | N/A | | | | | | N/A |
| (3-fluorobenzyl-S-triazole-pyridine, N-ethyl) | N/A | N/A | N/A | N/A | N/A | N/A | | | | N/A | N/A | N/A |
| (4-methylthiazole-NH-CO-CH2-S-triazole-pyridine, N-propyl) | N/A | N/A | N/A | N/A | N/A | N/A | | | | | | |
| (thiazole-NH-CO-CH2-S-triazole-pyridine, N-propyl) | N/A | N/A | N/A | N/A | N/A | N/A | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | 12.58 | | | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure: methyl benzoate-NH-C(O)-CH2-S-triazole(N-propyl)-pyridyl] | N/A | N/A | N/A | N/A | N/A | N/A | | | | | | |
| [structure: indole-C(O)-CH2-S-triazole(N-allyl)-pyridyl] | N/A | N/A | N/A | N/A | N/A | N/A | | | | | | |
| [structure: 3-Cl-4-OMe-phenyl-NH-C(O)-CH2-S-triazole(N-allyl)-pyridyl] | N/A | N/A | N/A | N/A | N/A | N/A | | | | | | |
| [structure: indol-3-yl-C(O)-CH2-S-triazole(N-allyl)-pyridyl] | N/A | N/A | N/A | N/A | N/A | N/A | N/A | N/A | N/A | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| *(4-fluorophenyl amide structure)* | N/A | N/A | N/A | N/A | N/A | N/A | | | | | | |
| *(2-trifluoromethylphenyl amide structure)* | N/A | N/A | N/A | N/A | N/A | N/A | | | | | | |
| *(2,3-dihydrobenzo[1,4]dioxin amide structure)* | N/A | N/A | N/A | N/A | N/A | N/A | | | | | | |
| *(4-bromophenyl amide structure)* | N/A | N/A | N/A | N/A | N/A | N/A | | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (4-methoxyphenyl triazole allyl pyridine) | N/A | N/A | N/A | N/A | N/A | N/A | | | | | | |
| (chloro-benzodioxole triazole allyl pyridine) | N/A | N/A | N/A | N/A | N/A | N/A | | 16.91 | | | | |
| (2-fluorophenyl triazole allyl pyridine) | N/A | N/A | N/A | N/A | N/A | N/A | | | | | | |
| (4-acetylphenyl triazole allyl pyridine) | N/A | N/A | N/A | N/A | N/A | N/A | | | | | | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | | | |
| [structure] | N/A | N/A | N/A | N/A | N/A | N/A | | | | | | |
| [structure] | N/A | N/A | N/A | N/A | N/A | N/A | | | | | | |
| [structure] | N/A | N/A | N/A | N/A | N/A | N/A | | | | | | |

-continued

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| | N/A | N/A | N/A | N/A | N/A | N/A | | | | | N/A | N/A | N/A | |
| | N/A | N/A | N/A | N/A | N/A | N/A | | 13.43 | | | N/A | N/A | N/A | |
| | N/A | N/A | N/A | N/A | N/A | N/A | | | | | N/A | N/A | N/A | |
| | N/A | N/A | N/A | N/A | N/A | N/A | | | | | N/A | N/A | N/A | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | 17.15 | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [sulfonamide-phenyl acetamide-thio-triazole-allyl-pyridine] | N/A | N/A | N/A | N/A | N/A | N/A | | | | N/A | N/A | N/A |
| [benzodioxole acetamide-thio-triazole-allyl-pyridine] | N/A | N/A | N/A | N/A | N/A | N/A | | | | N/A | N/A | N/A |
| [chloro-methoxyphenyl acetamide-thio-triazole-allyl-pyridine] | N/A | N/A | N/A | N/A | N/A | N/A | | | | N/A | N/A | N/A |
| [fluorophenyl acetamide-thio-triazole-allyl-pyridine] | N/A | N/A | N/A | N/A | N/A | N/A | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [2-(trifluoromethyl)phenyl triazole thioacetamide structure] | N/A | N/A | N/A | N/A | N/A | N/A | | | | N/A | N/A | N/A |
| [benzodioxole triazole thioacetamide structure] | N/A | N/A | N/A | N/A | N/A | N/A | | | | N/A | N/A | N/A |
| [4-methoxyphenyl triazole thioacetamide structure] | N/A | N/A | N/A | N/A | N/A | N/A | | | | N/A | N/A | N/A |
| [4-bromophenyl triazole thioacetamide structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (2-fluorophenyl amide) | N/A | N/A | N/A | N/A | N/A | N/A | | | | N/A | N/A | N/A |
| (4-acetylphenyl amide) | N/A | N/A | N/A | N/A | N/A | N/A | | | | N/A | N/A | N/A |
| (3-methoxyphenyl amide) | N/A | N/A | N/A | N/A | N/A | N/A | | | | N/A | N/A | N/A |
| (2,4-dimethylphenyl amide) | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure) | N/A | N/A | N/A | N/A | N/A | N/A | | | | N/A | N/A | N/A |
| (structure) | N/A | N/A | N/A | N/A | N/A | N/A | | | | | | |
| (structure) | N/A | N/A | N/A | N/A | N/A | N/A | | | | N/A | N/A | N/A |
| (structure) | N/A | N/A | N/A | N/A | N/A | N/A | | | | N/A | N/A | N/A |
| (structure) | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | | Orco 28 + Orco | | |
|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase |
| (structure) | N/A | N/A | N/A | N/A | N/A | N/A | | | | | N/A | N/A | N/A |
| (structure) | N/A | N/A | N/A | N/A | N/A | N/A | | 7.93 | | | | | |
| (structure) | N/A | N/A | N/A | N/A | N/A | N/A | | | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure) | N/A | N/A | N/A | N/A | N/A | N/A | | | | | | |
| (structure) | N/A | N/A | N/A | N/A | N/A | N/A | | | | | | |
| (structure) | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (ethyl ester thiophene triazole furan pyridine structure) | N/A | N/A | N/A | N/A | N/A | N/A | | 30.44 | | N/A | N/A | N/A |
| (fluorophenyl thiazole triazole furan pyridine structure) | N/A | N/A | N/A | N/A | N/A | N/A | | | | N/A | N/A | N/A |
| (methoxyphenyl ketone triazole furan pyridine structure) | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| [structure] | N/A | N/A | N/A | N/A | N/A | N/A | | | | | N/A | N/A | N/A | |
| [structure] | N/A | N/A | N/A | N/A | N/A | N/A | | | | | N/A | N/A | N/A | |
| [structure] | N/A | N/A | N/A | N/A | N/A | N/A | | 46.34 | | | N/A | N/A | N/A | |
| [structure] | N/A | N/A | N/A | N/A | N/A | N/A | | 16.64 | | | N/A | N/A | N/A | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure: 2-chlorobenzyl-S-triazole-furan-pyridine] | N/A | N/A | N/A | N/A | N/A | N/A | | 33.76 | | N/A | N/A | N/A |
| [structure: 4-chloro-2-methoxy-5-methylbenzyl-S-triazole-furan-pyridine] | N/A | N/A | N/A | N/A | N/A | N/A | | 28.40 | | N/A | N/A | N/A |
| [structure: 2,4-dichlorobenzyl-S-triazole-furan-pyridine] | N/A | N/A | N/A | N/A | N/A | N/A | | 49.50 | | N/A | N/A | N/A |
| [structure: 2,4-dimethoxybenzyl-S-triazole-furan-pyridine] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure: indoline-triazole-furan] | N/A | N/A | N/A | N/A | N/A | N/A | | | | N/A | N/A | N/A |
| [structure: phenothiazine-triazole-furan] | N/A | N/A | N/A | N/A | N/A | N/A | | 53.70 | | N/A | N/A | N/A |
| [structure: hydroxyquinazoline-triazole-cyclohexyl] | N/A | N/A | N/A | N/A | N/A | N/A | | | | | | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [cyclohexyl-piperidinyl triazole thioether structure] | N/A | N/A | N/A | N/A | N/A | N/A | | | | | | |
| [N-cyclohexyl amide triazole thioether structure] | N/A | N/A | N/A | N/A | N/A | N/A | | | | | | |
| [N-cyclopentyl amide triazole thioether structure] | N/A | N/A | N/A | N/A | N/A | N/A | | | | | | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (4-methylpiperidine-triazole-cyclohexyl-pyridine structure) | N/A | N/A | N/A | N/A | N/A | N/A | | | | N/A | N/A | N/A |
| (piperidine-triazole-cyclohexyl-pyridine structure) | N/A | N/A | N/A | N/A | N/A | N/A | | | | N/A | N/A | N/A |
| (tolyl-amide-triazole-phenyl-pyridine structure) | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
|  | N/A | N/A | N/A | N/A | N/A | N/A | | | | NA | N/A | N/A |
|  | N/A | N/A | N/A | N/A | N/A | N/A | | | | N/A | N/A | N/A |
|  | N/A | N/A | N/A | N/A | N/A | N/A | | | 13.63 | | | |
|  | N/A | N/A | N/A | N/A | N/A | N/A | | | | | | 15.18 |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (ethyl ester triazole-pyridine structure) | N/A | N/A | N/A | N/A | N/A | N/A | | | | | | |
| (carboxylic acid triazole-pyridine structure) | N/A | N/A | N/A | N/A | N/A | N/A | | | | | | |
| (tolyl amide triazole-pyridine structure) | N/A | N/A | N/A | N/A | N/A | N/A | | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | | | |
| [structure] | N/A | N/A | N/A | N/A | N/A | N/A | | | | | | |
| [structure] | N/A | N/A | N/A | N/A | N/A | N/A | | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (triazole-thioacetamide-phenyl) | N/A | N/A | N/A | N/A | N/A | N/A | | | | | | |
| (triazole-thioacetamide-benzodioxole) | N/A | N/A | N/A | N/A | N/A | N/A | | | | | | |
| (triazole-thio-piperazine-methoxyphenyl) | N/A | N/A | N/A | N/A | N/A | N/A | N/A | N/A | N/A | | | |
| (triazole-thio-acetonitrile) | N/A | N/A | N/A | N/A | N/A | N/A | | | | N/A | N/A | N/A |

-continued

| Structure | Orco Agonist EC50 | Orco Agonist % value Of VUAA1 | Orco + 48 Agonist EC50 | Orco + 48 Agonist % value Of VUAA1 | Orco + 65 Agonist EC50 | Orco + 65 Agonist % value Of VUAA1 | Orco 10 + Orco Agonist % of control | Orco 10 + Orco Antagonist % Reduction | Orco 10 + Orco Potentiator % increase | Orco 28 + Orco Agonist % of control | Orco 28 + Orco Antagonist % Reduction | Orco 28 + Orco Potentiator % increase |
|---|---|---|---|---|---|---|---|---|---|---|---|---|
| [structure] | N/A | N/A | N/A | N/A | N/A | N/A | | | 16.29 | N/A | N/A | N/A |
| [structure] | N/A | N/A | N/A | N/A | N/A | N/A | | | | | N/A | N/A |
| [structure] | N/A | N/A | N/A | N/A | N/A | N/A | | | | N/A | N/A | N/A |
| [structure] | N/A | N/A | N/A | N/A | N/A | N/A | | 20.08 | | N/A | N/A | N/A |

-continued
| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 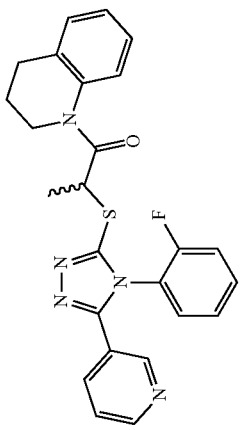 | N/A | N/A | N/A | N/A | N/A | N/A | | | | N/A | N/A | N/A |
| 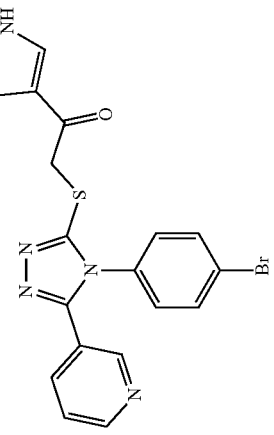 | N/A | N/A | N/A | N/A | N/A | N/A | | | | | | 19.9 |

| Structure | Orco Agonist | | Orco + 48 Agonist | | Orco + 65 Agonist | | Orco 10 + Orco | | | Orco 28 + Orco | |
|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 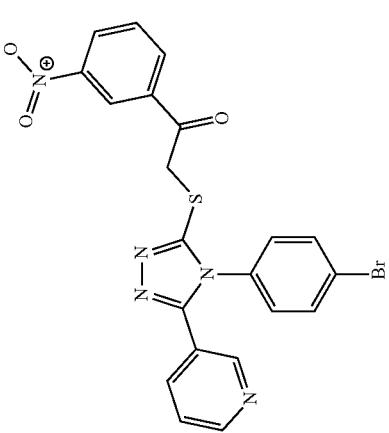 | N/A | N/A | N/A | N/A | N/A | N/A | | | | | |
| 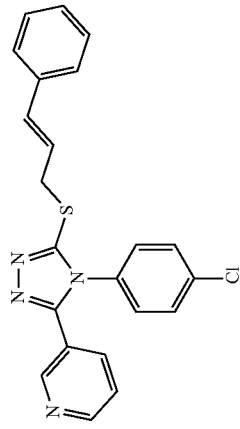 | N/A | N/A | N/A | N/A | N/A | N/A | | | 48.08 | | 20.56 |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | | | | | | | | | | |
| [structure] | N/A | N/A | N/A | N/A | N/A | N/A | | | | | | |
| [structure] | N/A | N/A | N/A | N/A | N/A | N/A | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure) | N/A | N/A | N/A | N/A | N/A | N/A | | | | | | |
| (structure) | N/A | N/A | N/A | N/A | N/A | N/A | N/A | | | N/A | N/A | N/A |
| (structure) | N/A | N/A | N/A | N/A | N/A | N/A | N/A | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | 47.91 | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | | Orco 28 + Orco | | |
|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase |
| [structure] | N/A | N/A | N/A | N/A | N/A | N/A | | | | | | | |
| [structure] | N/A | N/A | N/A | N/A | N/A | N/A | | | | | | | |
| [structure] | N/A | N/A | N/A | N/A | N/A | N/A | | | | | | | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | 16.73 | | | | |
| [structure] | N/A | N/A | N/A | N/A | N/A | N/A | | | | | | |
| [structure] | N/A | N/A | N/A | N/A | N/A | N/A | | | | | | 16.12 |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure) | N/A | N/A | N/A | N/A | N/A | N/A | | | | | | |
| (structure) | N/A | N/A | N/A | N/A | N/A | N/A | | | | | | |
| (structure) | N/A | N/A | N/A | N/A | N/A | N/A | | | | | | |

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| 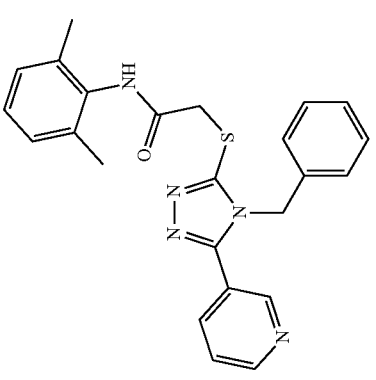 | N/A | N/A | N/A | N/A | N/A | N/A | | | | | | | | |
| 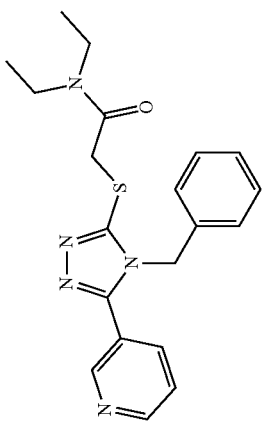 | N/A | N/A | N/A | N/A | N/A | N/A | | | | | | | | |
| 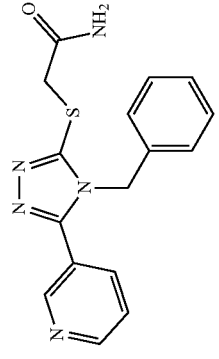 | N/A | N/A | N/A | N/A | N/A | N/A | | | | | | | | |

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| [ethyl ester triazole structure] | N/A | N/A | N/A | N/A | N/A | N/A | | | | | | | | |
| [isopropyl ester triazole structure] | N/A | N/A | N/A | N/A | N/A | N/A | | | | | N/A | N/A | N/A | |
| [morpholinoethyl triazole structure] | N/A | N/A | N/A | N/A | N/A | N/A | | | | | N/A | N/A | N/A | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | | | | |
| [structure] | N/A | N/A | N/A | N/A | N/A | N/A | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | | | |
| [structure] | N/A | N/A | N/A | N/A | N/A | N/A | | | | | | |
| [structure] | N/A | N/A | N/A | N/A | N/A | N/A | | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (dimethylisoxazole-triazole-tolyl-pyridine) | N/A | N/A | N/A | N/A | N/A | N/A | | | | | | N/A |
| (ethyl ester triazole-methoxyphenyl-pyridine) | N/A | N/A | N/A | N/A | N/A | N/A | | | | N/A | | N/A |
| (amide-triazole-tolyl-pyridine) | N/A | N/A | N/A | N/A | N/A | N/A | | 56.98 | 16.98 | N/A | N/A | N/A |
| (thiazole-anilino-triazole-tolyl-pyridine) | N/A | N/A | N/A | N/A | N/A | N/A | | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure) | N/A | N/A | N/A | N/A | N/A | N/A | | | | | | |
| (structure) | N/A | N/A | N/A | N/A | N/A | N/A | | 52.47 | | | | |
| (structure) | N/A | N/A | N/A | N/A | N/A | N/A | | | | | | |
| (structure) | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | 24.77 | | | | |
| [structure] | N/A | N/A | N/A | N/A | N/A | N/A | N/A | | | N/A | N/A | N/A |
| [structure] | N/A | N/A | N/A | N/A | N/A | N/A | N/A | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (2-Cl-phenyl amide structure) | N/A | N/A | N/A | N/A | N/A | N/A | | | | N/A | N/A | N/A |
| (4-F-phenyl amide structure) | N/A | N/A | N/A | N/A | N/A | N/A | | | | N/A | N/A | N/A |
| (2,4-dimethyl-phenyl amide structure) | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure 1] | N/A | N/A | N/A | N/A | N/A | N/A | | | | N/A | N/A | N/A |
| [structure 2] | N/A | N/A | N/A | N/A | N/A | N/A | | | | N/A | N/A | N/A |
| [structure 3] | N/A | N/A | N/A | N/A | N/A | N/A | | | | N/A | N/A | N/A |

-continued
| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 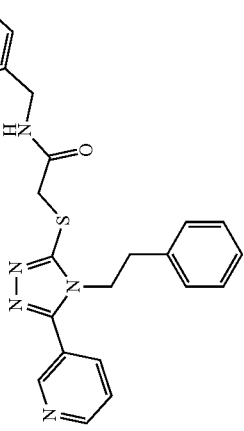 | N/A | N/A | N/A | N/A | N/A | N/A | | | | | | 15.9 |
| 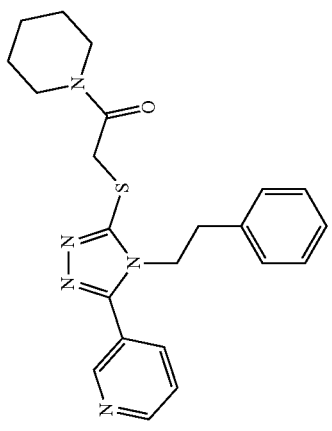 | N/A | N/A | N/A | N/A | N/A | N/A | N/A | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure 1) | N/A | N/A | N/A | N/A | N/A | N/A | | | | N/A | N/A | N/A |
| (structure 2) | N/A | N/A | N/A | N/A | N/A | N/A | | | | N/A | N/A | N/A |
| (structure 3) | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure: triazole with phenethyl, pyridyl, S-CH2-C(O)NH2] | N/A | N/A | N/A | N/A | N/A | N/A | | | | N/A | N/A | N/A |
| [structure: triazole with phenethyl, pyridyl, S-CH2-C(O)NHMe] | N/A | N/A | N/A | N/A | N/A | N/A | | | | N/A | N/A | N/A |
| [structure: triazole with ethoxyphenyl, pyridyl, S-CH2-C(O)-(3-nitrophenyl)] | N/A | N/A | N/A | N/A | N/A | N/A | | 22.28 | | | 25.53 | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | | | | | | | | | | 14.71 |
| [structure] | N/A | N/A | N/A | N/A | N/A | N/A | N/A | | | N/A | N/A | N/A |
| [structure] | N/A | N/A | N/A | N/A | N/A | N/A | N/A | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 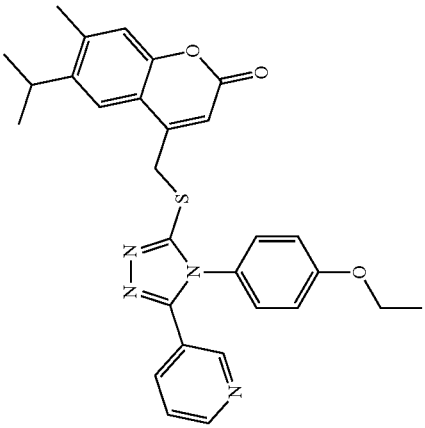 | N/A | N/A | N/A | N/A | N/A | N/A | | 48.28 | | | N/A | N/A |
| 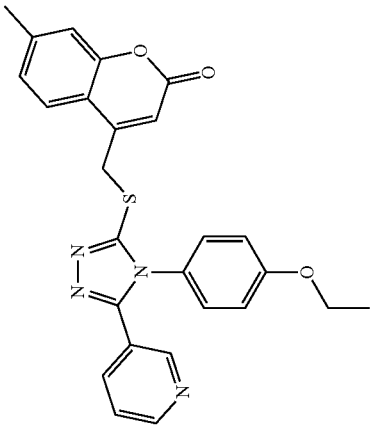 | N/A | N/A | N/A | N/A | N/A | N/A | | 12.48 | | N/A | N/A | N/A |

-continued
| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 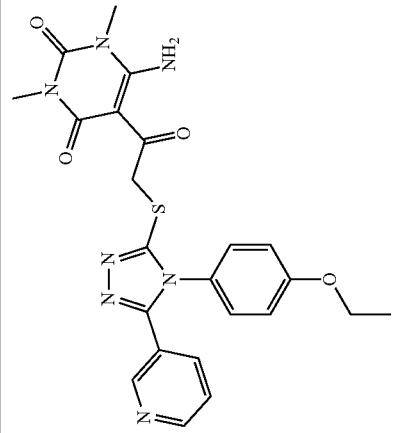 | N/A | N/A | N/A | N/A | N/A | N/A | | | | N/A | N/A | N/A |
| 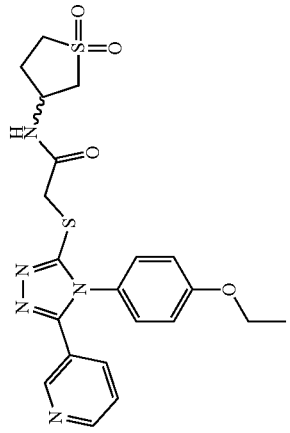 | N/A | N/A | N/A | N/A | N/A | N/A | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure) | N/A | N/A | N/A | N/A | N/A | N/A | | | | N/A | N/A | N/A |
| (structure) | N/A | N/A | N/A | N/A | N/A | N/A | | 29.87 | | | | |
| (structure) | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (tetrahydroquinoline-triazole-pyridine structure) | N/A | N/A | N/A | N/A | N/A | N/A | | | | N/A | N/A | N/A |
| (morpholine-triazole-pyridine structure) | N/A | N/A | N/A | N/A | N/A | N/A | | | | N/A | N/A | N/A |
| (methyl ester-triazole-pyridine structure) | N/A | N/A | N/A | N/A | N/A | N/A | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | 31.14 | N/A | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| [structure] | N/A | N/A | N/A | N/A | N/A | N/A | | | | | N/A | N/A | N/A | |
| [structure] | N/A | N/A | N/A | N/A | N/A | N/A | | | | | | | | |
| [structure] | N/A | N/A | N/A | N/A | N/A | N/A | | | | | N/A | N/A | N/A | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| | N/A | N/A | N/A | N/A | N/A | N/A | | 26.04 | | N/A | N/A | N/A |
| | N/A | N/A | N/A | N/A | N/A | N/A | | 15.51 | | N/A | N/A | N/A |
| | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 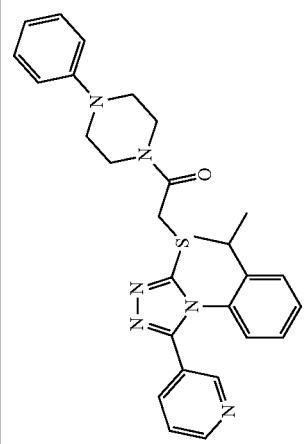 | N/A | N/A | N/A | N/A | N/A | N/A | | 42.29 | | N/A | N/A | N/A |
| 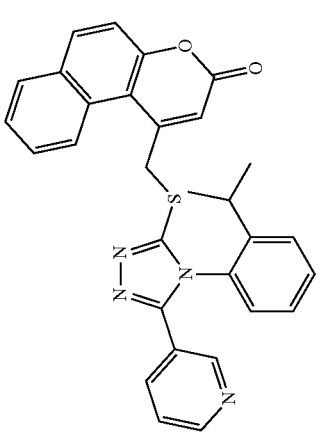 | N/A | N/A | N/A | N/A | N/A | N/A | | 26.15 | | N/A | N/A | N/A |
| 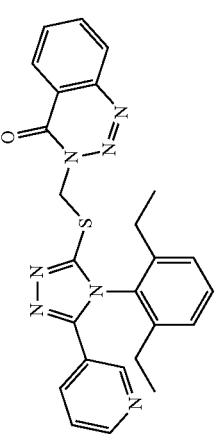 | N/A | N/A | N/A | N/A | N/A | N/A | | 25.00 | | | 22.91 | |

| Structure | Orco Agonist | | Orco + 48 Agonist | | Orco + 65 Agonist | | Orco 10 + Orco | | | | Orco 28 + Orco | | |
|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase |
| (structure) | N/A | N/A | N/A | N/A | N/A | N/A | | | | | N/A | N/A | N/A |
| (structure) | N/A | N/A | N/A | N/A | N/A | N/A | | | | | N/A | N/A | N/A |
| (structure) | N/A | N/A | N/A | N/A | N/A | N/A | | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | | | | | | | | | | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | | | N/A | N/A | | | | N/A | N/A | N/A |
| [structure] | N/A | N/A | <VUAA1 | <VUAA1 | N/A | N/A | N/A | N/A | NA | N/A | N/A | N/A |
| [structure] | N/A | N/A | | | N/A | N/A | N/A | N/A | N/A | N/A | N/A | N/A |
| [structure] | N/A | N/A | | | N/A | N/A | N/A | N/A | N/A | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [4-vinylphenyl amide, 1-ethyl-5-(pyridin-4-yl)-1,2,4-triazol-3-ylthio] | N/A | N/A | <VUAA1 | <VUAA1 | N/A | N/A | N/A | N/A | N/A | N/A | N/A | N/A |
| [4-isopropylphenyl amide, 1-ethyl-5-(pyridin-4-yl)-1,2,4-triazol-3-ylthio] | 7.4 µM | 136% | 3.5 µM | 112% | 8.2 µM | N/A | N/A | N/A | N/A | N/A | N/A | N/A |
| [4-isopropylphenyl amide, 1-ethyl-5-(3-fluoropyridin-4-yl)-1,2,4-triazol-3-ylthio] | 100 µM | 38% | 75.2 µM | 62% | N/A | N/A | N/A | N/A | N/A | N/A | N/A | N/A |
| [4-propylphenyl amide, 1-ethyl-5-(pyridin-4-yl)-1,2,4-triazol-3-ylthio] | N/A | N/A | <VUAA1 | <VUAA1 | N/A | N/A | N/A | N/A | N/A | N/A | N/A | N/A |
| [4-isopropylphenyl amide, 1-ethyl-5-(pyridin-4-yl)-1,2,4-triazol-3-ylthio] | N/A | N/A | | | N/A | N/A | N/A | N/A | N/A | N/A | N/A | N/A |
| [4-bromo-2-fluorophenyl amide, 1-ethyl-5-(pyridin-4-yl)-1,2,4-triazol-3-ylthio] | N/A | N/A | <VUAA1 | <VUAA1 | N/A | N/A | N/A | N/A | N/A | | | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [triazole-S-CH2-C(O)-NH-(4-chloro-2-methylphenyl); triazole N-ethyl, C-pyridyl] | N/A | N/A | N/A | N/A | N/A | N/A | | | | | | 17.69 |
| [triazole-S-CH2-C(O)-NH-(2-benzoyl-4-chlorophenyl); triazole N-ethyl, C-pyridyl] | N/A | N/A | N/A | N/A | N/A | N/A | | | | | | |
| [triazole-S-CH2-C(O)-NH-(4-(N-pyridin-2-yl-sulfamoyl)phenyl); triazole N-ethyl, C-pyridyl] | N/A | N/A | N/A | N/A | N/A | N/A | | | 12.31 | | | 15.45 |
| [triazole-S-CH2-C(O)-NH-(5-acetamido-2-methoxyphenyl); triazole N-ethyl, C-pyridyl] | N/A | N/A | N/A | N/A | N/A | N/A | | | | | | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (indoline-ethyl-pyridyl-triazole-S-acetyl) | N/A | N/A | N/A | N/A | N/A | N/A | | | | | | |
| (phenyl-NH-thiophene carbonyl, ethyl-pyridyl-triazole) | N/A | N/A | N/A | N/A | N/A | N/A | N/A | N/A | N/A | N/A | N/A | N/A |
| (methoxy-morpholinosulfonyl-phenyl, ethyl-pyridyl-triazole) | N/A | N/A | N/A | N/A | N/A | N/A | N/A | N/A | N/A | N/A | N/A | N/A |
| (ethylphenyl-NH, cyclopropyl-pyridyl-triazole) | N/A | N/A | 13 μM | | N/A | N/A | N/A | N/A | N/A | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [triazole-S-CH2-C(O)NH-(4-isopropylphenyl), N-cyclopropyl, pyridyl] | 3.5 µM | N/A | 1.9 µM | 122% | 3.1 µM | N/A | N/A | N/A | N/A | N/A | N/A | N/A |
| [triazole, N-propyl, 4-isopropylphenyl, pyridyl] | N/A | N/A | 19 µM | N/A | N/A | N/A | N/A | N/A | N/A | N/A | N/A | N/A |
| [triazole, N-allyl, 4-isopropylphenyl, pyridyl] | N/A | N/A | <VUAA1 | <VUAA1 | N/A | N/A | N/A | N/A | N/A | N/A | N/A | N/A |
| [triazole, N-isopropyl, 4-isopropylphenyl, pyridyl] | N/A | N/A | | | N/A | N/A | N/A | N/A | N/A | N/A | N/A | N/A |
| [triazole, N-cyclopropyl, 4-propylphenyl, pyridyl] | N/A | N/A | <VUAA1 | <VUAA1 | N/A | N/A | N/A | N/A | N/A | N/A | N/A | N/A |
| [triazole, N-cyclopropyl, 4-vinylphenyl, pyridyl] | N/A | N/A | <VUAA1 | <VUAA1 | N/A | N/A | N/A | N/A | N/A | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure: 4-bromo-2-fluorophenyl amide, thio-triazole, cyclopropyl, pyridyl] | N/A | N/A | <VUAA1 | <VUAA1 | N/A | N/A | N/A | N/A | N/A | N/A | N/A | N/A |
| [structure: 4-isopropylphenyl amide, thio-triazole, sec-butyl, pyridyl] | N/A | N/A | | | N/A | N/A | | | | | | N/A |
| [structure: 4-isopropylphenyl amide, thio-triazole, isobutyl, pyridyl] | N/A | N/A | | | N/A | N/A | N/A | N/A | N/A | N/A | N/A | N/A |
| [structure: 4-isopropylphenyl amide, thio-triazole, n-butyl, pyridyl] | N/A | N/A | | | N/A | N/A | N/A | N/A | N/A | N/A | N/A | N/A |
| [structure: 4-isopropylphenyl amide, thio-triazole, cyclopentyl, pyridyl] | N/A | N/A | | | N/A | N/A | N/A | N/A | N/A | N/A | N/A | N/A |

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| [cyclohexyl-triazole-S-CH2-C(O)NH-(4-isopropylphenyl), pyridyl] | N/A | N/A | N/A | N/A | N/A | N/A | N/A | N/A | N/A | | N/A | N/A | N/A | |
| [phenyl-triazole-S-CH2-C(O)NH-(4-isopropylphenyl), pyridyl] | N/A | N/A | N/A | N/A | N/A | N/A | | | | | | | | |
| [N-ethyl-benzyl-triazole-S-CH2-C(O)NH-(4-aminophenyl)] | N/A | N/A | N/A | N/A | N/A | N/A | | | | | | | | |
| [N-ethyl-benzyl-triazole-S-CH2-C(O)NH-(3-chloro-4-morpholinophenyl)] | N/A | N/A | N/A | N/A | N/A | N/A | | | | | | | | |
| [N-ethyl-benzyl-triazole-S-CH2-C(O)NH-(4-methylphenyl)] | N/A | N/A | N/A | N/A | N/A | N/A | | | | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (sulfonamide-phenyl-NHC(O)CH2S-triazole-ethyl-benzyl) | N/A | N/A | N/A | N/A | N/A | N/A | | | | | | |
| (morpholine-phenyl-NHC(O)CH2S-triazole-ethyl-benzyl) | N/A | N/A | N/A | N/A | N/A | N/A | | | | | | |
| (benzodioxine-NHC(O)CH2S-triazole-ethyl-benzyl) | N/A | N/A | N/A | N/A | N/A | N/A | | | | | | |
| (methoxyphenyl-NHC(O)CH2S-triazole-ethyl-benzyl) | N/A | N/A | N/A | N/A | N/A | N/A | | | | | | 12.7 |
| (phenyl-NHC(O)CH2S-triazole-ethyl-benzyl) | N/A | N/A | N/A | N/A | N/A | N/A | | | | N/A | N/A | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [benzyl-ethyl-triazole-S-CH2-C(O)NH-benzo[1,3]dioxole] | N/A | N/A | N/A | N/A | N/A | N/A | | | | N/A | N/A | N/A |
| [benzyl-ethyl-triazole-S-CH2-C(O)NH-(2-F-phenyl)] | N/A | N/A | N/A | N/A | N/A | N/A | | | | N/A | N/A | N/A |
| [benzyl-ethyl-triazole-S-CH2-C(O)NH-(2-OH-phenyl)] | N/A | N/A | N/A | N/A | N/A | N/A | | | | N/A | N/A | N/A |
| [(4-methoxybenzyl)-ethyl-triazole-S-CH2-C(O)NH-(3-methoxycarbonylphenyl)] | N/A | N/A | N/A | N/A | N/A | N/A | | | | | | |

-continued

| Structure | Orco Agonist EC50 | Orco Agonist % value Of VUAA1 | Orco + 48 Agonist EC50 | Orco + 48 Agonist % value Of VUAA1 | Orco + 65 Agonist EC50 | Orco + 65 Agonist % value Of VUAA1 | Orco 10 + Orco Agonist % of control | Orco 10 + Orco Antagonist % Reduction | Orco 10 + Orco Potentiator % increase | Orco 28 + Orco Agonist % of control | Orco 28 + Orco Antagonist % Reduction | Orco 28 + Orco Potentiator % increase |
|---|---|---|---|---|---|---|---|---|---|---|---|---|
| [structure] | N/A | N/A | N/A | N/A | N/A | N/A | N/A | 57.34 | | N/A | N/A | N/A |
| [structure] | N/A | N/A | N/A | N/A | N/A | N/A | | | | | | |
| [structure] | N/A | N/A | N/A | N/A | N/A | N/A | N/A | | | | | N/A |
| [structure] | N/A | N/A | N/A | N/A | N/A | N/A | | | | | | |
| [structure] | N/A | N/A | N/A | N/A | N/A | N/A | | | | | | |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | | Orco 28 + Orco | | |
|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase |
| [structure] | N/A | N/A | N/A | N/A | N/A | N/A | | 18.47 | | | N/A | N/A | N/A |
| [structure] | N/A | N/A | N/A | N/A | N/A | N/A | | | | | N/A | N/A | N/A |
| [structure] | N/A | N/A | N/A | N/A | N/A | N/A | | 62.21 | | | N/A | N/A | N/A |
| [structure] | N/A | N/A | N/A | N/A | N/A | N/A | | 8.24 | | | | | |
| [structure] | N/A | N/A | N/A | N/A | N/A | N/A | | 31.15 | | | N/A | N/A | N/A |

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| (structure) | N/A | N/A | | | | | | 44.74 | | | N/A | N/A | N/A | |
| (structure) | N/A | N/A | N/A | N/A | N/A | N/A | | | | | | | | |
| (structure) | N/A | N/A | N/A | N/A | N/A | N/A | | | | | N/A | N/A | N/A | |
| (structure) | N/A | N/A | N/A | N/A | N/A | N/A | | | | | N/A | N/A | N/A | |
| (structure) | N/A | N/A | N/A | N/A | N/A | N/A | | | | | N/A | N/A | N/A | |

| Structure | Orco Agonist EC50 | Orco Agonist % value Of VUAA1 | Orco + 48 Agonist EC50 | Orco + 48 Agonist % value Of VUAA1 | Orco + 65 Agonist EC50 | Orco + 65 Agonist % value Of VUAA1 | Orco 10 + Orco Agonist % of control | Orco 10 + Orco Antagonist % Reduction | Orco 10 + Orco Potentiator % increase | Orco 28 + Orco Agonist % of control | Orco 28 + Orco Antagonist % Reduction | Orco 28 + Orco Potentiator % increase |
|---|---|---|---|---|---|---|---|---|---|---|---|---|
| Br-dimethylphenyl / furan | N/A | N/A | N/A | N/A | N/A | N/A | | | | | | 12.28 |
| 4-chlorophenyl / thiophene | N/A | N/A | N/A | N/A | N/A | N/A | | | | N/A | N/A | N/A |
| Cl-CF3-phenyl / furan | N/A | N/A | N/A | N/A | N/A | N/A | | 15.97 | | | | |
| Cl-methylphenyl / thiophene | N/A | N/A | N/A | N/A | N/A | N/A | | | | N/A | N/A | N/A |
| F-phenyl / furan | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value of VUAA1 | EC50 | % value of VUAA1 | EC50 | % value of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | | | N/A |
| [structure] | N/A | N/A | N/A | N/A | N/A | N/A | | | | N/A | | N/A |
| [structure] | N/A | N/A | N/A | N/A | N/A | N/A | | | | N/A | | N/A |
| [structure] | N/A | N/A | N/A | N/A | N/A | N/A | | | | | | |
| [structure] | N/A | N/A | N/A | N/A | N/A | N/A | | | | N/A | | N/A |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure: 2-methoxy-5-methylphenyl amide with triazole-S-CH2, N-ethyl, phenoxymethyl] | N/A | N/A | N/A | N/A | N/A | N/A | | 33.67 | | | 17.21 | N/A |
| [structure: 2,5-dimethoxyphenyl amide with triazole-S-CH2, N-ethyl, phenoxymethyl] | N/A | N/A | N/A | N/A | N/A | N/A | | 38.62 | | N/A | N/A | N/A |
| [structure: benzodioxine amide with triazole-S-CH2, N-ethyl, phenoxymethyl] | N/A | N/A | N/A | N/A | N/A | N/A | | | | N/A | N/A | N/A |
| [structure: 3-(ethoxycarbonyl)phenyl amide with triazole-S-CH2, N-ethyl, phenoxymethyl] | N/A | N/A | N/A | N/A | N/A | N/A | | | | N/A | N/A | N/A |
| [structure: 2-(ethoxycarbonyl)phenyl amide with triazole-S-CH2, N-ethyl, phenoxymethyl] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 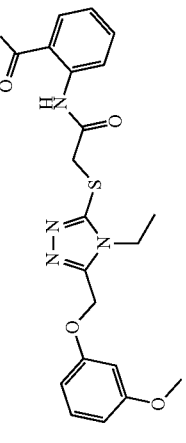 | N/A | N/A | N/A | N/A | N/A | N/A | | 72.23 | | N/A | N/A | N/A |
| 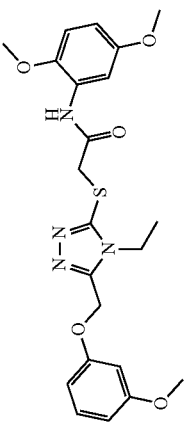 | N/A | N/A | N/A | N/A | N/A | N/A | | 30.79 | | N/A | N/A | N/A |
| 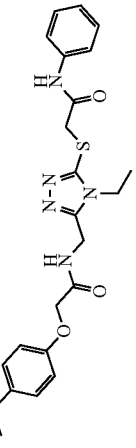 | N/A | N/A | N/A | N/A | N/A | N/A | | 13.06 | | | | |
| 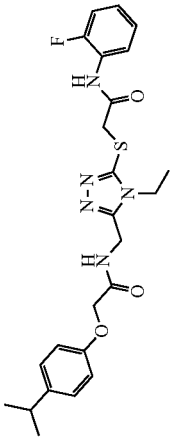 | N/A | N/A | N/A | N/A | N/A | N/A | | 11.35 | | | | |

-continued

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| [structure] | N/A | N/A | N/A | N/A | N/A | N/A | | | | | | | | |
| [structure] | N/A | N/A | N/A | N/A | N/A | N/A | | 7.54 | | | | | | |
| [structure] | N/A | N/A | N/A | N/A | N/A | N/A | | | | | N/A | N/A | N/A | |
| [structure] | N/A | N/A | N/A | N/A | N/A | N/A | | 59.64 | | | N/A | N/A | N/A | |
| [structure] | N/A | N/A | N/A | N/A | N/A | N/A | | | | | N/A | N/A | N/A | |
| [structure] | N/A | N/A | N/A | N/A | N/A | N/A | | | | | N/A | N/A | N/A | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| ![structure] | N/A | N/A | N/A | N/A | N/A | N/A | | | | N/A | N/A | N/A |
| ![structure] | N/A | N/A | N/A | N/A | N/A | N/A | | 49.09 | | N/A | N/A | N/A |
| ![structure] | N/A | N/A | N/A | N/A | N/A | N/A | | | 18.19 | N/A | N/A | N/A |
| ![structure] | N/A | N/A | N/A | N/A | N/A | N/A | | | | N/A | N/A | N/A |
| ![structure] | N/A | N/A | N/A | N/A | N/A | N/A | | | | N/A | N/A | N/A |
| ![structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (dimethylpyrimidine-S-triazole-ethyl-S-acetamide-phenyl) | N/A | N/A | N/A | N/A | N/A | N/A | | | | | | |
| (dimethylpyrimidine-S-triazole-ethyl-S-acetyl-tetrahydroquinoline) | N/A | N/A | N/A | N/A | N/A | N/A | | | | N/A | N/A | N/A |
| (chlorobenzyl-S-triazole-ethyl-S-acetamide-benzoic acid) | N/A | N/A | N/A | N/A | N/A | N/A | | | | N/A | N/A | N/A |
| (furylmethyl-triazole-pyridine-S-acetamide-chloro-methoxy-methylphenyl) | N/A | N/A | N/A | N/A | N/A | N/A | | 25.31 | | N/A | N/A | N/A |
| (phenyl-acetamide-triazole-ethyl-S-acetamide-methyl benzoate) | N/A | N/A | N/A | N/A | N/A | N/A | | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure) | N/A | N/A | N/A | N/A | N/A | N/A | | | | | | N/A |
| (structure) | N/A | N/A | N/A | N/A | N/A | N/A | | | | N/A | | N/A |
| (structure) | N/A | N/A | N/A | N/A | N/A | N/A | | | | | | N/A |
| (structure) | N/A | N/A | N/A | N/A | N/A | N/A | | 13.11 | | N/A | 37.93 | |
| (structure) | N/A | N/A | N/A | N/A | N/A | N/A | | | | | | |
| (structure) | N/A | N/A | N/A | N/A | N/A | N/A | | | | | | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [indole-triazole-S-CH2-C(O)-NH-3,4-dimethoxyphenyl] | N/A | N/A | | | | | | | | N/A | N/A | N/A |
| [indole-triazole-S-CH2-C(O)-tetrahydroquinoline] | N/A | N/A | N/A | N/A | N/A | N/A | | | | | | |
| [indole-triazole-S-CH2-C(O)-indoline] | N/A | N/A | N/A | N/A | N/A | N/A | | | | | | |
| [indole-triazole-S-CH2-C(O)-NH-benzodioxane] | N/A | N/A | N/A | N/A | N/A | N/A | | 17.90 | | N/A | N/A | N/A |
| [methylindole-triazole-CH2-S-CH2-C(O)-NH-4-acetylphenyl] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure 1) | N/A | N/A | | | | | | | | | | |
| (structure 2) | N/A | N/A | | | | | | | | | | |
| (structure 3) | N/A | N/A | N/A | N/A | N/A | N/A | N/A | N/A | N/A | | | |
| (structure 4) | N/A | N/A | N/A | N/A | N/A | N/A | | | | N/A | N/A | N/A |
| (structure 5) | N/A | N/A | N/A | N/A | N/A | N/A | | | | N/A | N/A | N/A |
| (structure 6) | N/A | N/A | N/A | N/A | N/A | N/A | | | | N/A | N/A | N/A |

-continued

| Structure | Orco Agonist EC50 | Orco Agonist % value Of VUAA1 | Orco + 48 Agonist EC50 | Orco + 48 Agonist % value Of VUAA1 | Orco + 65 Agonist EC50 | Orco + 65 Agonist % value Of VUAA1 | Orco 10 + Orco Agonist % of control | Orco 10 + Orco Antagonist % Reduction | Orco 10 + Orco Potentiator % increase | Orco 28 + Orco Agonist % of control | Orco 28 + Orco Antagonist % Reduction | Orco 28 + Orco Potentiator % increase |
|---|---|---|---|---|---|---|---|---|---|---|---|---|
| [structure] | N/A | N/A | N/A | N/A | N/A | N/A | | | | | | N/A |
| [structure] | N/A | N/A | N/A | N/A | N/A | N/A | N/A | | | N/A | N/A | N/A |
| [structure] | N/A | N/A | N/A | N/A | N/A | N/A | | | 21.48 | N/A | N/A | N/A |
| [structure] | N/A | N/A | N/A | N/A | N/A | N/A | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | | | |
| [structure] | N/A | N/A | N/A | N/A | N/A | N/A | N/A | N/A | N/A | | | |
| [structure] | N/A | N/A | N/A | N/A | N/A | N/A | | | | | | |
| [structure] | | | | | | | | | | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| | N/A | N/A | N/A | N/A | N/A | N/A | | | | | | 13.62 |
| | N/A | N/A | N/A | N/A | N/A | N/A | | | | | | |
| | N/A | N/A | N/A | N/A | N/A | N/A | | | | | | |
| | N/A | N/A | N/A | N/A | N/A | N/A | | | | | | |
| | N/A | N/A | N/A | N/A | N/A | N/A | | | | | | |

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| 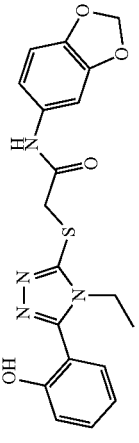 | N/A | N/A | N/A | N/A | N/A | N/A | | | | | | | | |
| 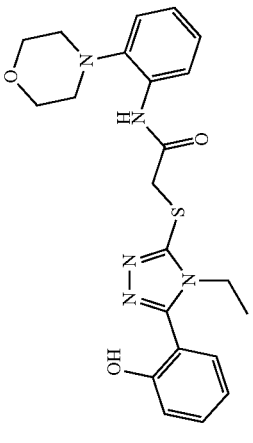 | N/A | N/A | N/A | N/A | N/A | N/A | | | | | | | | |
| 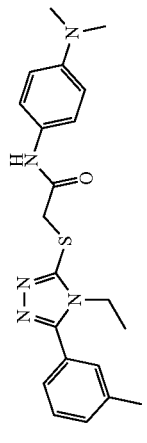 | N/A | N/A | N/A | N/A | N/A | N/A | | 29.54 | | | N/A | N/A | N/A | |
| 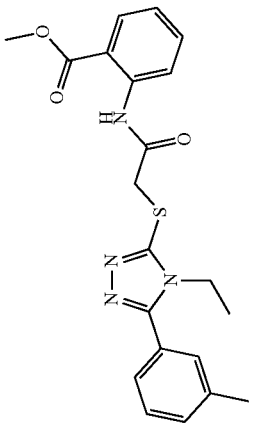 | N/A | N/A | N/A | N/A | N/A | N/A | | 16.03 | | | | | | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| [structure] | N/A | N/A | N/A | N/A | N/A | N/A | | | | N/A | N/A | N/A |
| [structure] | N/A | N/A | N/A | N/A | N/A | N/A | | | | | | |
| [structure] | N/A | N/A | N/A | N/A | N/A | N/A | | | | N/A | N/A | N/A |
| [structure] | N/A | N/A | N/A | N/A | N/A | N/A | | | | | | |
| [structure] | N/A | N/A | N/A | N/A | N/A | N/A | | | | | | |
| [structure] | N/A | N/A | N/A | N/A | N/A | N/A | | | | | | |

-continued

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| 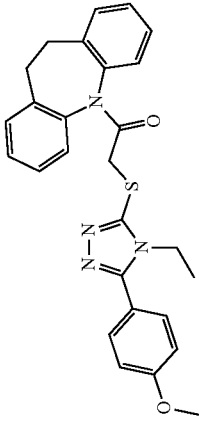 | N/A | N/A | N/A | N/A | N/A | N/A | | 41.48 | | | N/A | N/A | N/A | |
| 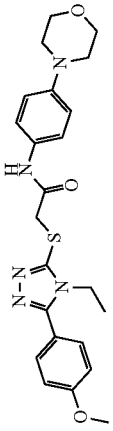 | N/A | N/A | N/A | N/A | N/A | N/A | | | | | | | | |
| 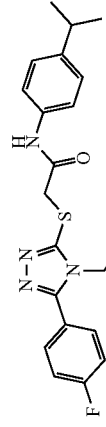 | N/A | N/A | N/A | N/A | N/A | N/A | | | | | | | | |
| 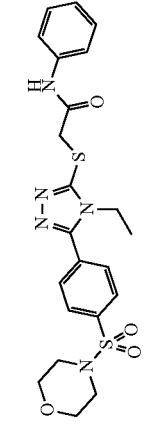 | N/A | N/A | N/A | N/A | N/A | N/A | N/A | N/A | | | N/A | N/A | N/A | |
| 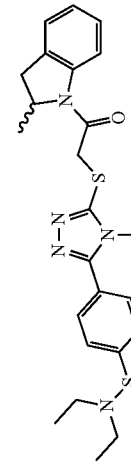 | N/A | N/A | N/A | N/A | N/A | N/A | | | | | N/A | N/A | N/A | |
| | N/A | N/A | N/A | N/A | N/A | N/A | | 31.53 | | | N/A | N/A | N/A | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (2,3-dimethylindole-triazole-S-acetamide-methoxyphenyl) | N/A | N/A | N/A | N/A | N/A | N/A | | 24.94 | | | | |
| (pyrrole-triazole-S-acetamide-isopropylphenyl) | N/A | N/A | N/A | N/A | N/A | N/A | | N/A | N/A | | | |
| (phenothiazine-acetyl-triazole-furan) | N/A | N/A | N/A | N/A | N/A | N/A | | 48.26 | | | | |
| (furan-triazole-S-acetamide-chloromethoxymethylphenyl) | N/A | N/A | N/A | N/A | N/A | N/A | | | | | 28.73 | |
| (furan-triazole-S-acetamide-benzodioxin) | N/A | N/A | N/A | N/A | N/A | N/A | | | | | | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (carbazole-ethyl/triazole-furan amide structure) | N/A | N/A | N/A | N/A | N/A | N/A | | | | N/A | N/A | N/A |
| (isopropylphenyl/triazole-furan amide structure) | N/A | N/A | N/A | N/A | N/A | N/A | N/A | N/A | N/A | | | |
| (methoxyphenyl/triazole-furan amide structure) | N/A | N/A | N/A | N/A | N/A | N/A | | | | | | |
| (dibenzazepine/triazole-furan structure) | | | | | | | | 13.40 | | | | |

-continued

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| [structure] | N/A | N/A | N/A | N/A | N/A | N/A | | | | | | | | |
| [structure] | N/A | N/A | N/A | N/A | N/A | N/A | | | | | N/A | N/A | N/A | |
| [structure] | N/A | N/A | N/A | N/A | N/A | N/A | | 28.44 | | | N/A | N/A | N/A | |
| [structure] | N/A | N/A | N/A | N/A | N/A | N/A | | | | | N/A | N/A | N/A | |
| [structure] | N/A | N/A | N/A | N/A | N/A | N/A | | | | | N/A | N/A | N/A | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (ethyl benzoate triazole-thiophene) | N/A | N/A | N/A | N/A | N/A | N/A | | | | | | |
| (methyl benzoate triazole-thiophene) | N/A | N/A | N/A | N/A | N/A | N/A | | | | | | |
| (isopropyl phenyl triazole-thiophene) | N/A | N/A | N/A | N/A | N/A | N/A | | | | | | |
| (benzodioxine triazole-thiophene) | N/A | N/A | N/A | N/A | N/A | N/A | N/A | N/A | N/A | N/A | N/A | N/A |
| (furan amide phenyl triazole-thiophene) | N/A | N/A | N/A | N/A | N/A | N/A | | | | | | |
| (tetrahydroquinoline triazole-thiophene) | N/A | N/A | N/A | N/A | N/A | N/A | | | | | | |

-continued

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (structure) | N/A | N/A | N/A | N/A | N/A | N/A | | | | | | N/A |
| (structure) | N/A | N/A | N/A | N/A | N/A | N/A | | | | N/A | N/A | N/A |
| (structure) | N/A | N/A | N/A | N/A | N/A | N/A | | | | N/A | N/A | N/A |
| (structure) | N/A | N/A | N/A | N/A | N/A | N/A | | | | N/A | N/A | N/A |
| (structure) | N/A | N/A | N/A | N/A | N/A | N/A | | 32.93 | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| (isopropyl-phenyl pyrrole triazole thioacetamide) | N/A | N/A | 13.7 μM | Poor | N/A | N/A | N/A | N/A | N/A | N/A | N/A | N/A |
| (tetrahydroquinoline methylfuran triazole thioacetyl) | N/A | N/A | N/A | N/A | N/A | N/A | | | | | | |
| (dihydroquinolinone methylfuran triazole thioacetyl) | N/A | N/A | N/A | N/A | N/A | N/A | N/A | | | | | |
| (ethyl benzoate methylfuran triazole thioacetamide) | N/A | N/A | N/A | N/A | N/A | N/A | N/A | | | | | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 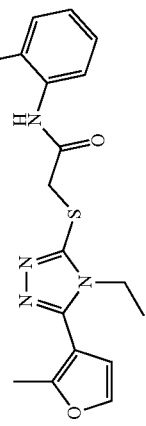 | N/A | N/A | N/A | N/A | N/A | N/A | | | | | N/A | N/A |
| 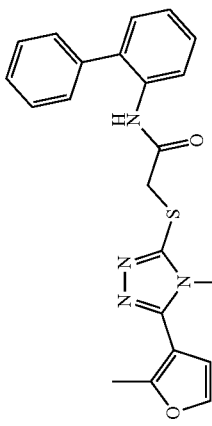 | N/A | N/A | N/A | N/A | N/A | N/A | | | | N/A | N/A | N/A |
| 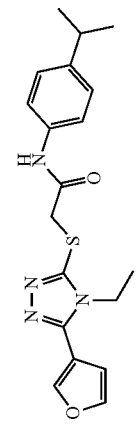 | | | N/A | N/A | N/A | N/A | N/A | N/A | N/A | N/A | N/A | N/A |
| 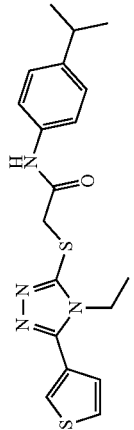 | | | N/A | N/A | N/A | N/A | N/A | N/A | N/A | N/A | N/A | N/A |
| 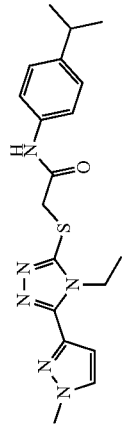 | <VUAA1 | <VUAA1 | | | | | N/A | N/A | N/A | N/A | N/A | N/A |

-continued

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| [structure] | <VUAA1 | <VUAA1 | N/A | N/A | N/A | N/A | N/A | N/A | N/A | | N/A | N/A | N/A | |
| [structure] | N/A | N/A | 16.8 μM | N/A | N/A | N/A | N/A | N/A | N/A | | N/A | N/A | N/A | |
| [structure] | N/A | N/A | N/A | N/A | N/A | N/A | | | | | | | | |
| [structure] | N/A | N/A | N/A | N/A | N/A | N/A | | | | | | | | |
| [structure] | N/A | N/A | N/A | N/A | N/A | N/A | | | | | | | | |

| Structure | Orco Agonist | | Orco + 48 Agonist | | Orco + 65 Agonist | | Orco 10 + Orco | | | | Orco 28 + Orco | | | |
|---|---|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | | Agonist % of control | Antagonist % Reduction | Potentiator % increase | |
| (thiazole-oxadiazole-benzyl amide structure) | N/A | N/A | | | | | | | | | | | | |
| (isopropyl thiazole-oxadiazole-benzyl amide structure) | N/A | N/A | N/A | N/A | N/A | N/A | | | | | N/A | N/A | N/A | |
| (chloro-maleimide-benzyl sulfonamide structure) | N/A | N/A | N/A | N/A | N/A | N/A | | | | | N/A | N/A | N/A | |
| (chloroacetamide ethylphenyl structure) | | | N/A | N/A | N/A | N/A | N/A | N/A | N/A | | N/A | N/A | N/A | |
| (bromo-fluoro-aniline structure) | | | N/A | N/A | N/A | N/A | N/A | N/A | N/A | | N/A | N/A | N/A | |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 2-bromo-5-aminopyridine | | | N/A | N/A | N/A | N/A | | N/A | N/A | N/A | N/A | N/A |
| 4-propylaniline | | | N/A | N/A | N/A | N/A | | N/A | N/A | N/A | N/A | N/A |
| 4-butylaniline | | | N/A | N/A | N/A | N/A | | N/A | N/A | N/A | N/A | N/A |
| 4-isopropylaniline | | | N/A | N/A | N/A | N/A | | N/A | N/A | N/A | N/A | N/A |
| 4-tert-butylaniline | | | N/A | N/A | N/A | N/A | | N/A | N/A | N/A | N/A | N/A |

| Structure | Orco Agonist | | Orco + 48 Agonist | | Orco + 65 Agonist | | Orco 10 + Orco | | | Orco 28 + Orco | | |
|---|---|---|---|---|---|---|---|---|---|---|---|---|
| | EC50 | % value Of VUAA1 | EC50 | % value Of VUAA1 | EC50 | % value Of VUAA1 | Agonist % of control | Antagonist % Reduction | Potentiator % increase | Agonist % of control | Antagonist % Reduction | Potentiator % increase |
| 4-ethyl-2-bromoaniline | | | N/A | N/A | N/A | N/A | | N/A | N/A | N/A | N/A | N/A |
| 5-bromoindoline | | | N/A | N/A | N/A | N/A | | N/A | N/A | N/A | N/A | N/A |
| 5-bromoindole | | | N/A | N/A | N/A | N/A | | N/A | N/A | N/A | N/A | N/A |
| 4-ethynylaniline | | | N/A | N/A | N/A | N/A | | N/A | N/A | N/A | N/A | N/A |
| 2-fluoro-4-methylaniline | | | N/A | N/A | N/A | N/A | | N/A | N/A | N/A | N/A | N/A |

D. METHODS OF MAKING THE COMPOUNDS

In one aspect, the invention relates to methods of making compounds useful as inhibitors of insect odorant sensory receptors. In one aspect, the invention relates to the disclosed synthetic manipulations. In a further aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Route I

In one aspect, intermediates useful for the preparation of compounds of the present invention can be prepared generically by the synthetic scheme as shown below.

SCHEME 1A

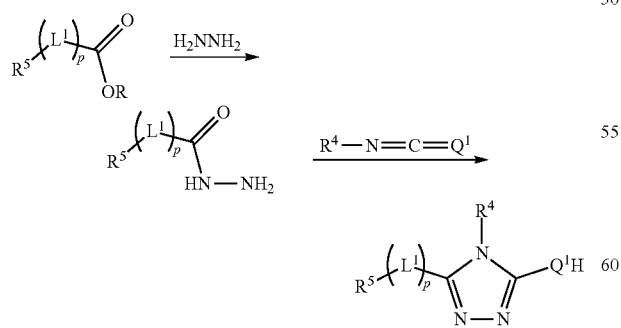

Compounds are represented in generic form, with substituents as noted in compound descriptions elsewhere herein. A more specific example is set forth below.

SCHEME 1B

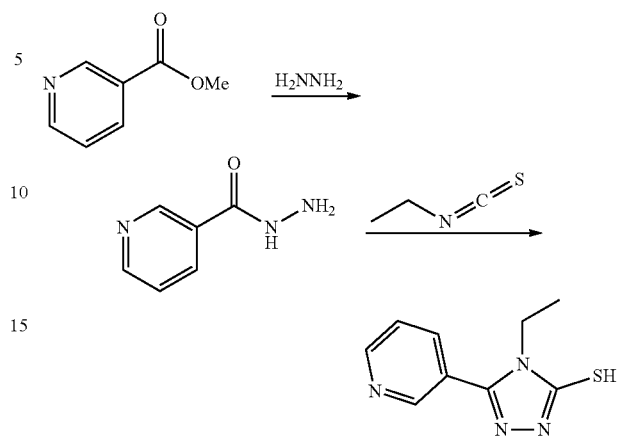

In this example, methyl nicotinate is treated with hydrazine to yield nicotinohydrazide. This product is reacted with isothiocyanatoethane to provide 4-ethyl-5-(pyridin-3-yl)-4H-1,2,4-triazole-3-thiol.

Thus, in one aspect, the invention relates to a method for preparing a compound, the method comprising the steps of: providing a compound having a structure represented by a formula:

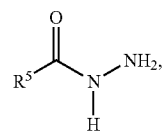

wherein $R^5$ is optionally substituted aryl or optionally substituted ($\leq$C6) heteroaryl; and reacting with $R^4$—N=C=S or $R^4$—N=C=O, thereby yielding a product having the formula:

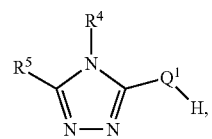

wherein $Q^1$ is —O— or —S—; wherein $R^4$ is optionally substituted and selected from (C1-C5) alkyl, (C1-C5) alkenyl, (C6-C10) aryl, ($\leq$C10) aralkyl, ($\leq$C8) heteroaryl, and ($\leq$C8) heteroaralkyl.

In a further aspect, providing comprises treating a compound having a structure represented by a formula:

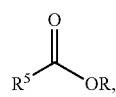

wherein R is optionally substituted and selected from alkyl, heteroalkyl, aryl, and heteroaryl, with hydrazine, thereby yielding a product having the formula:

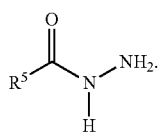

2. Route II

In one aspect, compounds of the present invention can be prepared generically by the synthetic scheme as shown below.

SCHEME 2A

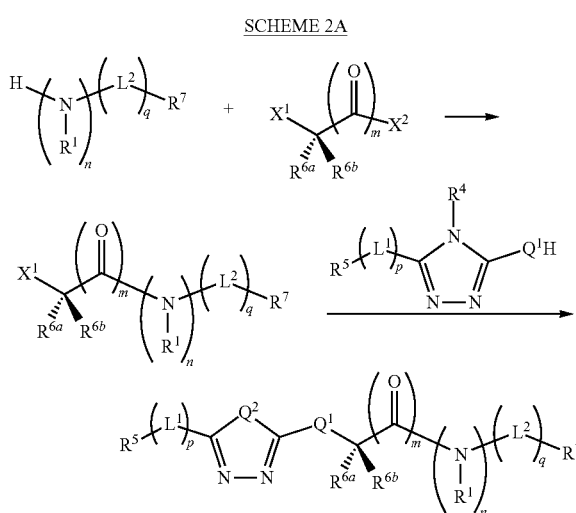

Compounds are represented in generic form, with substituents as noted in compound descriptions elsewhere herein. A more specific example is set forth below.

SCHEME 2B

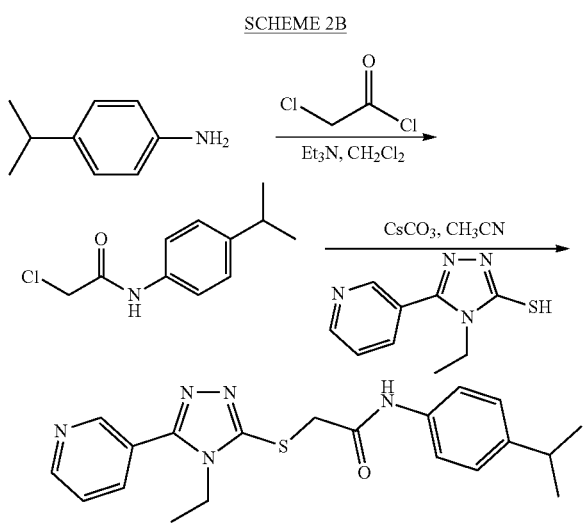

In this example, 4-isopropylaniline is treated with 2-chloroacetyl chloride to form the corresponding amide. This product can then be reacted with, for example, 4-ethyl-5-(pyridin-3-yl)-4H-1,2,4-triazole-3-thiol from Route I, above, to yield 2-((4-ethyl-5-(pyridin-3-yl)-4H-1,2,4-triazol-3-yl)thio)-N-(4-isopropylphenyl)acetamide.

Thus, in one aspect, the invention relates to a method for preparing a compound, the method comprising the steps of: providing a compound having a structure represented by a formula:

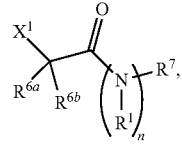

wherein $X^1$ is a leaving group; wherein n is 0 or 1; wherein $R^7$ is optionally substituted (C6-C10) aryl or optionally substituted ($\leq$C6) heteroaryl; wherein $R^1$ is hydrogen or is taken together with a substituent of $R^7$ to be optionally substituted (C1-C4) alkanediyl or optionally substituted (C1-C4) alkenediyl; and wherein $R^{6a}$ and $R^{6b}$ are independently selected from hydrogen, optionally substituted (C1-C5) alkyl, or optionally substituted (C1-C5) alkenyl, or $R^{6a}$ and $R^{6b}$, together with the intermediate carbon, together comprise a C3-C6 cycloalkyl ring or a C2-C5 heterocylcoalkyl ring, reacting with a compound having a structure represented by a formula:

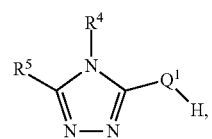

wherein $Q^1$ is —O— or —S—; wherein $R^4$ is optionally substituted and selected from (C1-C5) alkyl, (C1-C5) alkenyl, (C6-C10) aryl, ($\leq$C10) aralkyl, ($\leq$C8) heteroaryl, and ($\leq$C8) heteroaralkyl; and wherein $R^5$ is optionally substituted aryl or optionally substituted ($\leq$C6) heteroaryl; thereby yielding a product having the formula:

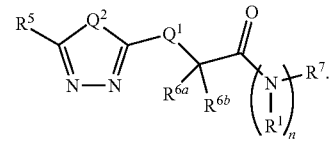

In a further aspect, providing comprises treating a compound having a structure represented by a formula:

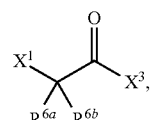

wherein $X^1$ is a leaving group; wherein $X^3$ is chloro or bromo; and wherein $R^{6a}$ and $R^{6b}$ are independently selected from hydrogen, optionally substituted (C1-C5) alkyl, or optionally substituted (C1-C5) alkenyl, or $R^{6a}$ and $R^{6b}$, together with the intermediate carbon, together comprise a C3-C6 cycloalkyl ring or a C2-C5 heterocylcoalkyl ring, with a compound having the formula:

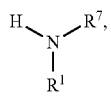

wherein $R^7$ is optionally substituted (C6-C10) aryl or optionally substituted (≤C6) heteroaryl; and wherein $R^1$ is hydrogen or is taken together with a substituent of $R^7$ to be optionally substituted (C1-C4) alkanediyl or optionally substituted (C1-C4) alkenediyl; and thereby yielding a product having the formula:

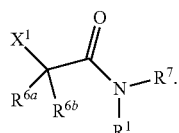

In a further aspect, the method further comprises oxidation to yield a product having the formula:

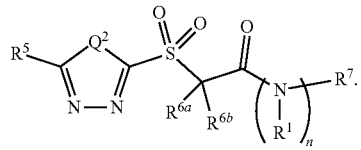

In a further aspect, the method further comprises reduction to yield a product having the formula:

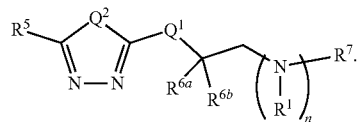

3. Route III

In one aspect, compounds of the present invention can be prepared generically by the synthetic scheme as shown below.

SCHEME 3A

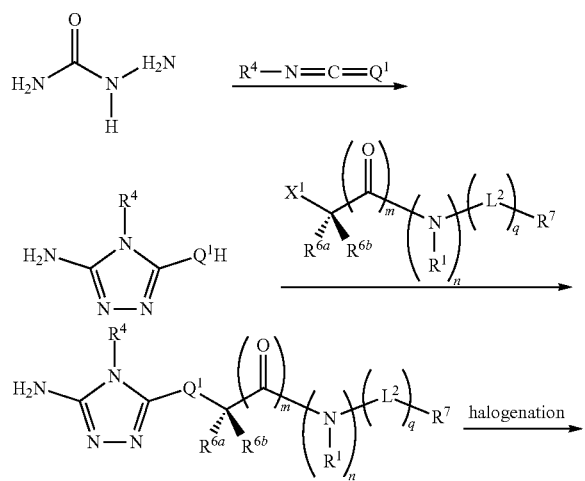

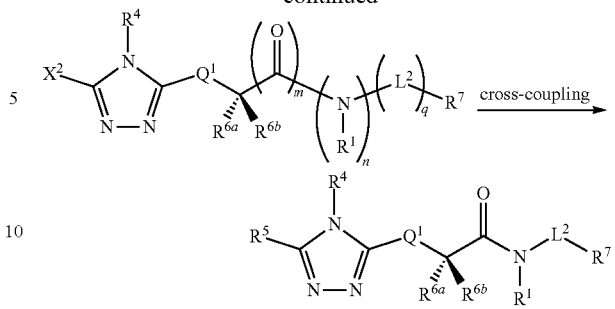

Compounds are represented in generic form, with substituents as noted in compound descriptions elsewhere herein. A more specific example is set forth below.

SCHEME 3B

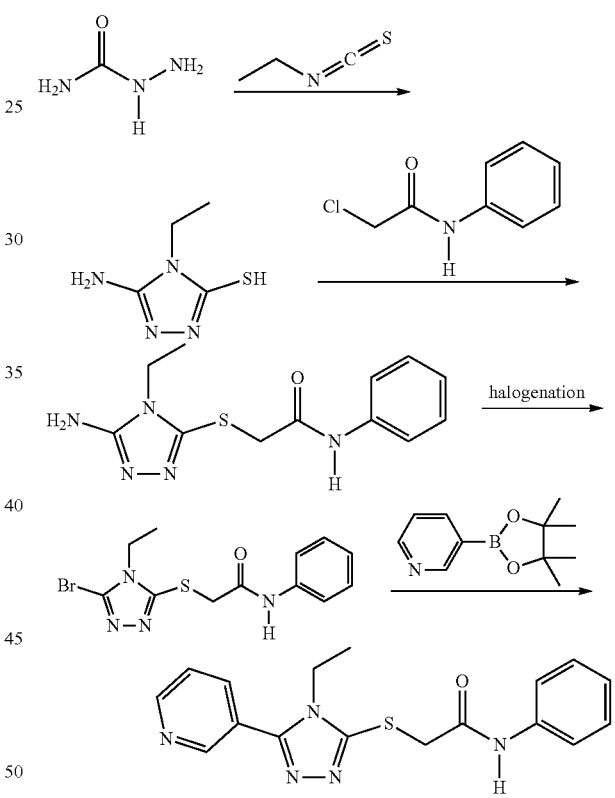

In this example, hydrazinecarboxamide is treated with isothiocyanatoethane to provide 5-amino-4-ethyl-4H-1,2,4-triazole-3-thiol. This product can be reacted with, for example, 2-chloro-N-phenylacetamide to yield 2-((5-amino-4-ethyl-4H-1,2,4-triazol-3-yl)thio)-N-phenylacetamide. Halogenation affords 2-((5-bromo-4-ethyl-4H-1,2,4-triazol-3-yl)thio)-N-phenylacetamide, which can be reacted in a transition metal mediated cross-coupling reaction (e.g., Suzuki coupling) to provide 2-((4-ethyl-5-(pyridin-3-yl)-4H-1,2,4-triazol-3-yl)thio)-N-phenylacetamide. For example, halogenation can be accomplished by reaction with a diazotiation reagent such as isoamylnitrite or sodium nitrite, followed by reaction with an appropriate halogen source such as copper (I) bromide, affords.

Thus, in one aspect, the invention relates to a method for preparing a compound, the method comprising the steps of: providing a compound having a structure represented by a formula:

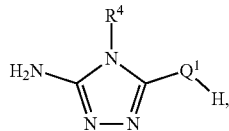

wherein $Q^1$ is —O— or —S—, and wherein $R^4$ is optionally substituted and selected from (C1-C5) alkyl, (C1-C5) alkenyl, (C6-C10) aryl, (≤C10) aralkyl, (≤C8) heteroaryl, and (≤C8) heteroaralkyl; reacting with a compound having a structure represented by a formula:

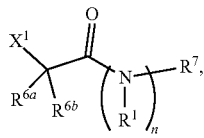

wherein $X^1$ is a leaving group; wherein n is 0 or 1; wherein $R^7$ is optionally substituted (C6-C10) aryl or optionally substituted (≤C6) heteroaryl; wherein $R^1$ is hydrogen or is taken together with a substituent of $R^7$ to be optionally substituted (C1-C4) alkanediyl or optionally substituted (C1-C4) alkenediyl; and wherein $R^{6a}$ and $R^{6b}$ are independently selected from hydrogen, optionally substituted (C1-C5) alkyl, or optionally substituted (C1-C5) alkenyl, or $R^{6a}$ and $R^{6b}$, together with the intermediate carbon, together comprise a C3-C6 cycloalkyl ring or a C2-C5 heterocylcoalkyl ring, thereby yielding a product having the formula:

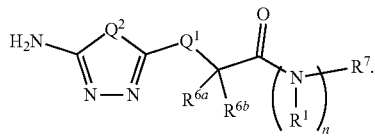

In a further aspect, providing comprises treating a compound having a structure represented by a formula:

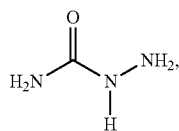

with $R^4$—N=C=S, $R^4$—N=C=O, thereby yielding a product having the formula:

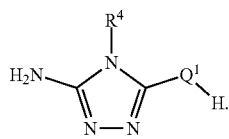

In a further aspect, the method further comprises halogenation to yield a product having the formula:

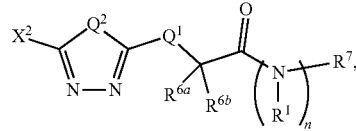

wherein $X^2$ is chloro, bromo, or iodo.

In a further aspect, the method further comprises transition metal-mediated cross-coupling reaction to yield a product having the formula:

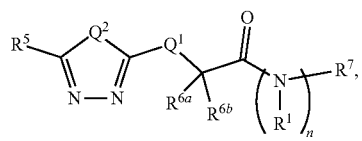

wherein $R_5$ is optionally substituted aryl or optionally substituted (≤C6) heteroaryl.

E. DELIVERY SYSTEMS

In one aspect, the invention relates to delivery systems comprising a disclosed compound or a product of a disclosed method of making.

1. Misting Systems

In one aspect, a disclosed compound of the present invention can be advantageously dispersed into an environment using a misting system. The environment may be a single-family dwelling yard, and street, a neighborhood, a subdivision, a township or a city. Examples of misting systems are shown in U.S. Pat. Nos. 7,306,167 and 7,090,147, and U.S. Patent Publication 2006/0260183, both of which are hereby incorporated by reference.

2. Baits and Pellets

In many cases, it would be desirable to apply a disclosed compound of the present invention in solid form. Solid pest control compositions typically are less prone to volatile dissemination of the active agent, and in some instances may be more readily and conveniently applied; for example, solid pest control compositions may be dropped from a helicopter or airplane or other elevated conveyance onto the surface of a large body of water somewhat more readily than can liquids. In addition, solid control agents are believed to be more able to penetrate a vegetative canopy when disseminated from an elevated conveyance.

When it is desired to form a solid composition for mosquitoes, a number of criteria are desirable. First, the solid pest control composition should be sufficiently durable to allow the control composition to be transported in bulk, such as by rail car or via bagged transport. Second, the solid composition, which generally will include a carrier and an active control agent, must be compatible with the pest target area environment; consequently, the carrier should be readily biodegradable. Third, the solid pest control composition should readily and quickly release the control agent when applied into a water column or when otherwise contacted by water, such as rain.

The prior art has provided numerous pest control compositions. For instance, U.S. Pat. No. 6,391,328 describes a process for treating organisms with a composition that includes a carrier, an active ingredient, and a coating. The carrier material is said to include silica, cellulose, metal oxides, clays, paper, infusorial earth, slag, hydrophobic materials, polymers such as polyvinyl alcohol and the like. Control of the release of rate of the active ingredient is said to be obtained via choice of coating material, which is said to be a fatty acid, alcohol or ester. Similar technology purportedly is disclosed in U.S. Pat. Nos. 6,387,386; 6,350,461; 6,346,262; 6,337,078; 6,335,027; 6,001,382; 5,902,596; 5,885,605; 5,858,386; 5,858,384; 5,846,553 and 5,698,210 (all by Levy to Lee County Mosquito Control District, Fort Meyers, Fla.).

Another pest control composition is disclosed in U.S. Pat. Nos. 5,824,328, 5,567,430, 5,983,390, and 4,418,534. In accordance with the purported teaching of these patents, the activation is provided in the form of a material that includes a super absorbent polymer and inert diluents.

U.S. Patent Publication 2007/0160637 discloses a pest control agent formed by providing a porous starch and an active control agent absorbed within the porous starch, and compressing the porous starch in the presence of heat to form discrete plural particles, including one or more binders, and one or more secondary absorbents/fillers. The particles can be prepared via pelletizing in a commercial pellet mill. The particles are sufficiently durable to withstand bulk transport, such as by rail car or bag shipment, and will release the control agent quickly upon contact with water, such that, for instance, the control agent may be released when the pest control agent is introduced to standing water.

3. Volatile Organic Compounds

In various aspects, it may be helpful to include one or more inactive agents in a pest control formulation that promote the distribution of a disclosed compound into an environment. One particular class of inactive agents is volatile organic compounds, or VOCs. VOCs are defined more generally as organic chemicals that have a high vapor pressure at ordinary, room-temperature conditions. Their high vapor pressure results from a low boiling point, which causes large numbers of molecules to evaporate or sublimate from the liquid or solid form of the compound and enter the surrounding air. The usefulness of such compounds in pest formulations is to promote the evaporation of active compounds that would otherwise be less prone to evaporation. Examples of useful pesticide VOCs include chlorpyrifos, 1,3-dichloropropene, trifuralin, methyl bromide, demthoate, metam-sodium, oxyfluorfen, permethrin, limonene, chloropicrin, bifenthrin, and bensulide. The use of these composition must, however, be balanced against their potential for environmental toxicity.

F. TOPICAL FORMULATIONS

In one aspect, the invention relates topical formulations comprising agents of the present invention. Including the active agent, such formulations will contain a variety of compounds and compositions that are typical for use with topical delivery. The following is a discussion of agents for use in preparation of topical formulations.

1. Film Forming Agents

Film formers are materials or compound, which, upon drying, can produce a continuous film on skin. This can increase the durability of a composition while also resulting in reduced moisture loss from skin. The CTFA Handbook at volume 3, pages 3187-3192, provides a wide range of film formers that can be used in the context of the present invention, all of which are incorporated by reference. Non-limiting examples of such film formers include Polysilicone-6, Polysilicone-8, Polysilicone-11, Polysilicone-14, VP/Dimethiconylacrylate/Polycarbamyl/Polyglycol Ester, VP/Dimethylaminoethylmethacrylate Copolymer, VP/Dimethylaminoethylmethacrylate/Polycarbamyl Polyglycol Ester, VP/Eicosene Copolymer, VP/Hexadecene Copolymer, VP/Methacrylamide/Vinyl Imidazole Copolymer, VP/Polycarbamyl Polyglycol Ester, VP/VA Copolymer, Polyester-1, Polyester-2, Polyester-3, Polyester-4, Polyester-5, Polyester-7, Polyester-8, and Polyester-10.

2. Ester Containing Solvents

Esters are covalent compounds formed between acids and alcohols. They can be used to stabilize and solubilize agents in the context of the present invention. The CTFA Handbook at volume 3, pages 3079-3088, provides a wide range of ester containing solvents that can be used in the context of the present invention, all of which are incorporated by reference. Non-limiting examples of such solvents include C12-15 Alkyl benzoate, neopentyl glycol diheptanoate, dipropylene glycol dibenzoate, and PPG-15 stearyl ether benzoate.

3. Gelling Agents

The compounds of the present invention can be formulated as a transparent gel. Gelling agents such as dimethicone/bis-isobutyl PPG-20 crosspolymer can used to create the gel-based primer. Further, a wide range of gelling agents is commercially available from Dow Corning (Midland, Mich. (USA)). A non-limiting example includes Dow Corning EL-8050 ID, which is a blend of dimethicone/bis-isobutyl PPG-20 crosspolymer and isododecane.

4. Additional Skin Conditioning Agents and Emollients

Non-limiting examples of skin conditioning agents and emollients that can be used with the compositions of the present invention include amino acids, chondroitin sulfate, diglycerin, erythritol, fructose, glucose, glycerol polymers, glycol, 1,2,6-hexanetriol, honey, hyaluronic acid, hydrogenated honey, hydrogenated starch hydrolysate, inositol, lactitol, maltitol, maltose, mannitol, natural moisturizing factor, PEG-15 butanediol, polyglyceryl sorbitol, salts of pyrollidone carboxylic acid, potassium PCA, propylene glycol, sodium glucuronate, sodium PCA, sorbitol, sucrose, trehalose, urea, and xylitol.

Other examples include acetylated lanolin, acetylated lanolin alcohol, acrylates/C 10-30 alkyl acrylate crosspolymer, acrylates copolymer, alanine, algae extract, aloe barbadensis, aloe-barbadensis extract, aloe barbadensis gel, althea *Officinalis* extract, aluminum starch octenylsuccinate, aluminum stearate, apricot (*Prunus armeniaca*) kernel oil, arginine, arginine aspartate, arnica montana extract, ascorbic acid, ascorbyl palmitate, aspartic acid, avocado (*Persea gratissima*) oil, barium sulfate, barrier sphingolipids, butyl alcohol, beeswax, behenyl alcohol, beta-sitosterol, BHT, birch (*Betula alba*) bark extract, borage (*Borago officinalis*) extract, 2-bromo-2-nitropropane-1,3-diol, butcherbroom (*Ruscus aculeatus*) extract, butylene glycol, *Calendula officinalis* extract, *Calendula officinalis* oil, candelilla (*Euphorbia cerifera*) wax, canola oil, caprylic/capric triglyceride, cardamon (*Elettaria cardamomum*) oil, carnauba (*Copernicia cerifera*) wax, carrageenan (*Chondrus crispus*), carrot (*Daucus carota sativa*) oil, castor (*Ricinus communis*) oil, ceramides, ceresin, ceteareth-5, ceteareth-12, ceteareth-20, cetearyl octanoate, ceteth-20, ceteth-24, cetyl acetate, cetyl octanoate, cetyl palmitate, chamomile (*Anthemis nobilis*) oil, cholesterol, cholesterol esters, cholesteryl hydroxystearate, citric acid, clary (*Salvia sclarea*) oil, cocoa (*Theobroma cacao*) butter, coco-caprylate/caprate, coconut (*Cocos nucifera*) oil, collagen, collagen amino acids, corn (*Zea mays*) oil, fatty acids, decyl oleate, dextrin, diazolidinyl urea, dimethicone copolyol, dimethiconol, dioctyl adipate, dioctyl succinate, dipentaerythrityl hexacaprylate/hexacaprate, DMDM hydantoin, DNA, erythritol, ethoxydiglycol, ethyl linoleate, *Eucalyptus globulus* oil, evening primrose (*Oenothera biennis*) oil, fatty acids, tructose, gelatin, geranium maculatum oil, glucosamine, glucose glutamate, glutamic acid, glycereth-26, glycerol, glyceryl distearate, glyceryl hydroxystearate, glyceryl laurate, glyceryl linoleate, glyceryl myristate, glyceryl oleate, glyceryl stearate, glyceryl stearate SE, glycine, glycol stearate, glycol stearate SE, glycosaminoglycans, grape (*Vitis vinifera*) seed oil, hazel (*Corylus americana*) nut oil, hazel (*Corylus avellana*) nut oil, hexylene glycol, honey, hyaluronic acid, hybrid safflower (*Carthamus tinctorius*) oil, hydrogenated castor oil, hydrogenated coco-glycerides, hydrogenated coconut oil, hydrogenated lanolin, hydrogenated lecithin, hydrogenated palm glyceride, hydrogenated palm kernel oil, hydrogenated soybean oil, hydrogenated tallow glyceride, hydrogenated vegetable oil, hydrolyzed collagen, hydrolyzed elastin, hydrolyzed glycosaminoglycans, hydrolyzed keratin, hydrolyzed soy protein, hydroxylated lanolin, hydroxyproline, imidazolidinyl urea, iodopropynyl butylcarbamate, isocetyl stearate, isocetyl stearoyl stearate, isodecyl oleate, isopropyl isostearate, isopropyl lanolate, isopropyl myristate, isopropyl palmitate, isopropyl stearate, isostearamide DEA, isostearic acid, isostearyl lactate, isostearyl neopentanoate, jasmine (*Jasminum officinale*) oil, jojoba (*Buxus chinensis*) oil, kelp, kukui (*Aleurites moluccana*) nut oil, lactamide MEA, laneth-16, laneth-10 acetate, lanolin, lanolin acid, lanolin alcohol, lanolin oil, lanolin wax, lavender (*Lavandula angustifolia*) oil, lecithin, lemon (*Citrus medica limonum*) oil, linoleic acid, linolenic acid, macadamia *ternifolia* nut oil, magnesium stearate, magnesium sulfate, maltitol, *matricaria* (*Chamomilla recutita*) oil, methyl glucose sesquistearate, methylsilanol PCA, microcrystalline wax, mineral oil, mink oil, *Mortierella* oil, myristyl lactate, myristyl myristate, myristyl propionate, neopentyl glycol dicaprylate/dicaprate, octyldodecanol, octyldodecyl myristate, octyldodecyl stearoyl stearate, octyl hydroxystearate, octyl palmitate, octyl salicylate, octyl stearate, oleic acid, olive (*Olea europaea*) oil, orange (citrus aurantium *dulcis*) oil, palm (*Elaeis guineensis*) oil, palmitic acid, pantethine, panthenol, panthenyl ethyl ether, paraffin, PCA, peach (*Prunus persica*) kernel oil, peanut (*Arachis hypogaea*) oil, PEG-8 C12-18 ester, PEG-15 cocamine, PEG-150 distearate, PEG-60 glyceryl isostearate, PEG-5 glyceryl stearate, PEG-30 glyceryl stearate, PEG-7 hydrogenated castor oil, PEG-40 hydrogenated castor oil, PEG-60 hydrogenated castor oil, PEG-20 methyl glucose sesquistearate, PEG40 sorbitan peroleate, PEG-5 soy sterol, PEG-10 soy sterol, PEG-2 stearate, PEG-8 stearate, PEG-20 stearate, PEG-32 stearate, PEG40 stearate, PEG-50 stearate, PEG-100 stearate, PEG-150 stearate, pentadecalactone, peppermint (*Mentha piperita*) oil, petrolatum, phospholipids, polyamino sugar condensate, polyglyceryl-3 diisostearate, polyquaternium-24, polysorbate 20, polysorbate 40, polysorbate 60, polysorbate 80, polysorbate 85, potassium myristate, potassium palmitate, potassium sorbate, potassium stearate, propylene glycol, propylene glycol dicaprylate/dicaprate, propylene glycol dioctanoate, propylene glycol dipelargonate, propylene glycol laurate, propylene glycol stearate, propylene glycol stearate SE, PVP, pyridoxine dipalmitate, quaternium-15, quaternium-18 hectorite, quaternium-22, retinol, retinyl palmitate, rice (*Oryza sativa*) bran oil, RNA, rosemary (*Rosmarinus officinalis*) oil, rose oil, safflower (*Carthamus tinctorius*) oil, sage (*Salvia officinalis*) oil, salicylic acid, sandalwood (*Santalum album*) oil, serine, serum protein, sesame (*Sesamum indicum*) oil, silk powder, sodium chondroitin sulfate, sodium hyaluronate, sodium lactate, sodium palmitate, sodium PCA, sodium polyglutamate, sodium stearate, soluble collagen, sorbic acid, sorbitan laurate, sorbitan oleate, sorbitan palmitate, sorbitan sesquioleate, sorbitan stearate, sorbitol, soybean (*Glycine soja*) oil, sphingolipids, squalane, squalene, stearamide MEA-stearate, stearic acid, stearoxy dimethicone, stearoxytrimethylsilane, stearyl alcohol, stearyl glycyrrhetinate, stearyl heptanoate, stearyl stearate, sunflower (*Helianthus annuus*) seed oil, sweet almond (*Prunus amygdalus dulcis*) oil, synthetic beeswax, tocopheryl linoleate, tridecyl neopentanoate, tridecyl stearate, triethanolamine, tristearin, urea, vegetable oil, water, waxes, wheat (*Triticum vulgare*) germ oil, and ylang ylang (*Cananga odorata*) oil.

5. Antioxidants

Non-limiting examples of antioxidants that can be used with the compositions of the present invention include acetyl cysteine, ascorbic acid polypeptide, ascorbyl dipalmitate, ascorbyl methylsilanol pectinate, ascorbyl palmitate, ascorbyl stearate, BHA, BHT, t-butyl hydroquinone, cysteine, cysteine HCl, diamylhydroquinone, di-t-butylhydroquinone, dicetyl thiodipropionate, dioleyl tocopheryl methylsilanol, disodium ascorbyl sulfate, distearyl thiodipropionate, ditridecyl thiodipropionate, dodecyl gallate, erythorbic acid, esters of ascorbic acid, ethyl ferulate, ferulic acid, gallic acid esters, hydroquinone, isooctyl thioglycolate, kojic acid, magnesium ascorbate, magnesium ascorbyl phosphate, methylsilanol ascorbate, natural botanical anti-oxidants such as green tea or grape seed extracts, nordihydroguaiaretic acid, octyl gallate, phenylthioglycolic acid, potassium ascorbyl tocopheryl phosphate, potassium sulfite, propyl gallate, quinones, rosmarinic acid, sodium ascorbate, sodium bisulfite, sodium erythorbate, sodium metabisulfite, sodium sulfite, superoxide dismutase, sodium thioglycolate, sorbityl furfural, thiodiglycol, thiodiglycolamide, thiodiglycolic acid, thioglycolic acid, thiolactic acid, thiosalicylic acid, tocophereth-5, tocophereth-10, tocophereth-12, tocophereth-18, tocophereth-50, tocophersolan, tocopheryl linoleate, tocopheryl nicotinate, tocopheryl succinate, and tris(nonylphenyl)phosphite.

6. Structuring Agents

In other non-limiting aspects, the compositions of the present invention can include a structuring agent. Structuring agents, in certain aspects, assist in providing rheological characteristics to the composition to contribute to the composition's stability. In other aspects, structuring agents can also function as an emulsifier or surfactant. Non-limiting examples of structuring agents include stearic acid, palmitic acid, stearyl alcohol, cetyl alcohol, behenyl alcohol, stearic acid, palmitic acid, the polyethylene glycol ether of stearyl alcohol having an average of about 1 to about 21 ethylene oxide units, the polyethylene glycol ether of cetyl alcohol having an average of about 1 to about 5 ethylene oxide units, and mixtures thereof.

7. Emulsifiers

In some non-limiting aspects, the compositions can include one or more emulsifiers. Emulsifiers can reduce the interfacial tension between phases and improve the formulation and stability of an emulsion. The emulsifiers can be nonionic, cationic, anionic, and zwitterionic emulsifiers (See McCutcheon's (1986); U.S. Pat. Nos. 5,011,681; 4,421,769; 3,755,560). Non-limiting examples include esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, TEA stearate, DEA oleth-3 phosphate, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-100 stearate, and mixtures thereof.

8. Silicone Containing Compounds

In non-limiting aspects, silicone containing compounds include any member of a family of polymeric products whose molecular backbone is made up of alternating silicon and oxygen atoms with side groups attached to the silicon atoms. By varying the —Si—O-chain lengths, side groups, and crosslinking, silicones can be synthesized into a wide variety of materials. They can vary in consistency from liquid to gel to solids.

The silicone containing compounds that can be used in the context of the present invention include those described in this specification or those known to a person of ordinary skill in the art. Non-limiting examples include silicone oils (e.g., volatile and non-volatile oils), gels, and solids. In particular aspects, the silicon containing compounds includes a silicone oils such as a polyorganosiloxane. Non-limiting examples of polyorganosiloxanes include dimethicone, cyclomethicone, phenyl trimethicone, trimethylsilylamodimethicone, stearoxytrimethylsilane, or mixtures of these and other organosiloxane materials in any given ratio in order to achieve the desired consistency and application characteristics depending upon the intended application (e.g., to a particular area such as the skin, hair, or eyes). A "volatile silicone oil" includes a silicone oil have a low heat of vaporization, i.e. normally less than about 50 cal per gram of silicone oil. Non-limiting examples of volatile silicone oils include: cyclomethicones such as Dow Corning 344 Fluid, Dow Corning 345 Fluid, Dow Corning 244 Fluid, and Dow Corning 245 Fluid, Volatile Silicon 7207 (Union Carbide Corp., Danbury, Conn.); low viscosity dimethicones, i.e. dimethicones having a viscosity of about 50 est or less (e.g., dimethicones such as Dow Corning 200-0.5 est Fluid). The Dow Corning Fluids are available from Dow Corning Corporation, Midland, Mich. Cyclomethicone and dimethicone are described in the Third Edition of the CTFA Cosmetic Ingredient Dictionary (incorporated by reference) as cyclic dimethyl polysiloxane compounds and a mixture of fully methylated linear siloxane polymers end-blocked with trimethylsiloxy units, respectively. Other non-limiting volatile silicone oils that can be used in the context of the present invention include those available from General Electric Co., Silicone Products Div., Waterford, N.Y. and SWS Silicones Div. of Stauffer Chemical Co., Adrian, Michigan.

9. Essential Oils

Essential oils include oils derived from herbs, flowers, trees, and other plants. Such oils are typically present as tiny droplets between the plant's cells, and can be extracted by several methods known to those of skill in the art (e.g., steam distilled, enfleurage (i.e., extraction by using fat), maceration, solvent extraction, or mechanical pressing). When these types of oils are exposed to air they tend to evaporate (i.e., a volatile oil). As a result, many essential oils are colorless, but with age they can oxidize and become darker. Essential oils are insoluble in water and are soluble in alcohol, ether, fixed oils (veget al), and other organic solvents. Typical physical characteristics found in essential oils include boiling points that vary from about 160 to 240° C. and densities ranging from about 0.759 to about 1.096.

Essential oils typically are named by the plant from which the oil is derived. For example, rose oil or peppermint oil is derived from rose or peppermint plants, respectively. Non-limiting examples of essential oils that can be used in the context of the present invention include sesame oil, macadamia nut oil, tea tree oil, evening primrose oil, Spanish sage oil, Spanish rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, Eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, or ylang ylang. Other essential oils known to those of skill in the art are also contemplated as being useful within the context of the present invention.

10. Thickening Agents

Thickening agents include substances that can increase the viscosity of a composition. Thickeners include those that can increase the viscosity of a composition without substantially modifying the efficacy of the active ingredient within the composition. Thickeners can also increase the stability of the compositions of the present invention.

Non-limiting examples of additional thickening agents that can be used in the context of the present invention include carboxylic acid polymers, crosslinked polyacrylate polymers, polyacrylamide polymers, polysaccharides, and gums. Examples of carboxylic acid polymers include crosslinked compounds containing one or more monomers derived from acrylic acid, substituted acrylic acids, and salts and esters of these acrylic acids and the substituted acrylic acids, wherein the crosslinking agent contains two or more carbon-carbon double bonds and is derived from a polyhydric alcohol (see U.S. Pat. Nos. 5,087,445; 4,509,949; 2,798,053). Examples of commercially available carboxylic acid polymers include carbomers, which are homopolymers of acrylic acid crosslinked with allyl ethers of sucrose or pentaerytritol (e.g., Carbopol™ 900 series from B.F. Goodrich).

Non-limiting examples of crosslinked polyacrylate polymers include cationic and nonionic polymers. Examples are described in U.S. Pat. Nos. 5,100,660; 4,849,484; 4,835, 206; 4,628,078; 4,599,379).

Non-limiting examples of polyacrylamide polymers (including nonionic polyacrylamide polymers including substituted branched or unbranched polymers) include polyacrylamide, isoparaffin and laureth-7, multi-block copolymers of acrylamides and substituted acrylamides with acrylic acids and substituted acrylic acids.

Non-limiting examples of polysaccharides include cellulose, carboxymethyl hydroxyethylcellulose, cellulose acetate propionate carboxylate, hydroxyethylcellulose, hydroxyethyl ethylcellulose, hydroxypropylcellulose, hydroxypropyl methylcellulose, methyl hydroxyethylcellulose, microcrystalline cellulose, sodium cellulose sulfate, and mixtures thereof. Another example is an alkyl substituted cellulose where the hydroxy groups of the cellulose polymer is hydroxyalkylated (particularly hydroxy ethylated or hydroxypropylated) to form a hydroxyalkylated cellulose which is then further modified with a C10-C30 straight chain or branched chain alkyl group through an ether linkage. Typically these polymers are ethers of C10-C30 straight or branched chain alcohols with hydroxyalkylcelluloses. Other useful polysaccharides include scleroglucans comprising a linear chain of (1-3) linked glucose units with a (1-6) linked glucose every three unit.

Non-limiting examples of gums that can be used with the present invention include acacia, agar, algin, alginic acid, ammonium alginate, amylopectin, calcium alginate, calcium carrageenan, carnitine, carrageenan, dextrin, gelatin, gellan gum, guar gum, guar hydroxypropyltrimonium chloride, hectorite, hyaluroinic acid, hydrated silica, hydroxypropyl chitosan, hydroxypropyl guar, karaya gum, kelp, locust bean gum, natto gum, potassium alginate, potassium carrageenan, propylene glycol alginate, sclerotium gum, sodium carboyxmethyl dextran, sodium carrageenan, tragacanth gum, xanthan gum, and mixtures thereof.

11. Vehicles

The compositions of the present invention can be incorporated into all types of are effective in all types of vehicles. Non-limiting examples of suitable vehicles include emulsions (e.g., water-in-oil, water-in-oil-in-water, oil-in-water, oil-in-water-in-oil, oil-in-water-in-silicone emulsions), creams, lotions, solutions (both aqueous and hydro-alcoholic), anhydrous bases (such as lipsticks and powders), gels, and ointments or by other method or any combination of the forgoing as would be known to one of ordinary skill in the art (Remington's, 1990). Variations and other appropriate vehicles will be apparent to the skilled artisan and are appropriate for use in the present invention. In certain aspects, it is important that the concentrations and combinations of the compounds, ingredients, and active agents be selected in such a way that the combinations are chemically compatible and do not form complexes which precipitate from the finished product.

G. COMPOSITIONS

In one aspect, the invention relates to compositions comprising the disclosed compounds, or a functionally acceptable salt, hydrate, solvate, or polymorph thereof. In a still further aspect, the composition is formed as a water-soluble tablet. In a yet further aspect, the composition is formulated as an aerosol. In an even further aspect, the composition is formulated as a sprayable liquid.

In a further aspect, the compositions comprise a compound that binds to and/or modulates insect Orco proteins, combined with a suitable carrier. In a still further aspect, the compound inhibits insect host sensing, plant sensing, or other olfactory driven behaviors. In a yet further aspect, the compound agonizes insect Orco ion channels. In an even further aspect, the compound antagonizes insect Orco. In a still further aspect, the compound potentiates insect Orco ion channels.

In a further aspect, a compound that binds to and/or modulates insect ORX is substantially absent from the composition. In a still further aspect, the composition further comprises a compound that binds to and/or modulates insect ORX.

It is understood that the disclosed compositions can be prepared from the disclosed compounds. It is also understood that the disclosed compositions can be employed in the disclosed methods of using.

It is also contemplated that that the concentrations of the compound in the composition can vary. In non-limiting embodiments, for example, the compositions may include in their final form, for example, at least about 0.0001%, 0.0002%, 0.0003%, 0.0004%, 0.0005%, 0.0006%, 0.0007%, 0.0008%, 0.0009%, 0.0010%, 0.0011%, 0.0012%, 0.0013%, 0.0014%, 0.0015%, 0.0016%, 0.0017%, 0.0018%, 0.0019%, 0.0020%, 0.0021%, 0.0022%, 0.0023%, 0.0024%, 0.0025%, 0.0026%, 0.0027%, 0.0028%, 0.0029%, 0.0030%, 0.0031%, 0.0032%, 0.0033%, 0.0034%, 0.0035%, 0.0036%, 0.0037%, 0.0038%, 0.0039%, 0.0040%, 0.0041%, 0.0042%, 0.0043%, 0.0044%, 0.0045%, 0.0046%, 0.0047%, 0.0048%, 0.0049%, 0.0050%, 0.0051%, 0.0052%, 0.0053%, 0.0054%, 0.0055%, 0.0056%, 0.0057%, 0.0058%, 0.0059%, 0.0060%, 0.0061%, 0.0062%, 0.0063%, 0.0064%, 0.0065%, 0.0066%, 0.0067%, 0.0068%, 0.0069%, 0.0070%, 0.0071%, 0.0072%, 0.0073%, 0.0074%, 0.0075%, 0.0076%, 0.0077%, 0.0078%, 0.0079%, 0.0080%, 0.0081%, 0.0082%, 0.0083%, 0.0084%, 0.0085%, 0.0086%, 0.0087%, 0.0088%, 0.0089%, 0.0090%, 0.0091%, 0.0092%, 0.0093%, 0.0094%, 0.0095%, 0.0096%, 0.0097%, 0.0098%, 0.0099%, 0.0100%, 0.0200%, 0.0250%, 0.0275%, 0.0300%, 0.0325%, 0.0350%, 0.0375%, 0.0400%, 0.0425%, 0.0450%, 0.0475%, 0.0500%, 0.0525%, 0.0550%, 0.0575%, 0.0600%, 0.0625%, 0.0650%, 0.0675%, 0.0700%, 0.0725%, 0.0750%, 0.0775%, 0.0800%, 0.0825%, 0.0850%, 0.0875%, 0.0900%, 0.0925%, 0.0950%, 0.0975%, 0.1000%, 0.1250%, 0.1500%, 0.1750%, 0.2000%, 0.2250%, 0.2500%, 0.2750%, 0.3000%, 0.3250%, 0.3500%, 0.3750%, 0.4000%, 0.4250%, 0.4500%, 0.4750%, 0.5000%, 0.5250%, 0.0550%, 0.5750%, 0.6000%, 0.6250%, 0.6500%, 0.6750%, 0.7000%, 0.7250%, 0.7500%, 0.7750%, 0.8000%, 0.8250%, 0.8500%, 0.8750%, 0.9000%, 0.9250%, 0.9500%, 0.9750%, 1.0%, 1.1%, 1.2%, 1.3%, 1.4%, 1.5%, 1.6%, 1.7%, 1.8%, 1.9%, 2.0%, 2.1%, 20.2%, 20.3%, 20.4%, 20.5%, 20.6%, 20.7%, 20.8%, 20.9%, 3.0%, 3.1%, 30.2%, 3.3%, 3.4%, 3.5%, 3.6%, 30.7%, 30.8%, 3.9%, 40.0%, 40.1%, 40.2%, 40.3%, 40.4%, 40.5%, 40.6%, 40.7%, 40.8%, 4.9%, 5.0%, 5.1%, 5.2%, 5.3%, 5.4%, 5.5%, 5.6%, 5.7%, 5.8%, 5.9%, 60.0%, 6.1%, 6.2%, 6.3%, 6.4%, 60.5%, 60.6%, 6.7%, 60.8%, 6.9%, 7.0%, 70.1%, 7.2%, 7.3%, 70.4%, 7.5%, 7.6%, 7.7%, 7.8%, 7.9%, 8.0%, 8.1%, 8.2%, 8.3%, 8.4%, 8.5%, 8.6%, 8.7%, 8.8%, 8.9%, 9.0%, 9.1%, 9.2%, 9.3%, 9.4%, 9.5%, 9.6%, 9.7%, 9.8%, 9.9%, 10%, 11%, 12%, 13%, 14%, 15%, 16%, 17%, 18%, 19%, 20%, 21%, 22%, 23%, 24%, 25%, 26%, 27%, 28%, 29%, 30%, 35%, 40%, 45%, 50%, 60%, 65%, 70%, 75%, 80%, 85%, 90%, 95%, or 99% or any range derivable therein. In non-limiting aspects, the percentage can be calculated by weight or volume of the total composition. A person of ordinary skill in the art would understand that the concentrations can vary depending on the addition, substitution, and/or subtraction of the compounds, agents, or active ingredients, to the disclosed methods and compositions.

H. ARTICLES

In one aspect, the invention relates to articles comprising the disclosed compounds. In a further aspect, the present invention contemplates the use of VUAA1 or other disclosed compound in the manufacture of certain items such as articles. For example, an article may comprise a material that may be pre-made and then dipped, painted or sprayed with the agent. Alternatively, the materials may be formed in the presence of the agent so as to incorporate the agent integrally thereinto.

In a further aspect, a disclosed compound may be used to coat or impregnate various articles of manufacture, the use of which can help deliver VUAA1 or an analog thereof to a mosquito environment and/or protect a user of the article from mosquito contact. Such articles include netting, such as the type use to exclude insects from dwelling (i.e., in windows and door ways) or to exclude insects from a particular location, such as a bed or room.

In a further aspect, other articles of manufacture include clothing or fabric from which clothing can be produced. Clothing includes hats, veils, masks, shoes and gloves, as well as shirts, pants and underwear. Other articles include bedding, such as sheets, nets, blankets, pillow cases, and mattresses. Still additional articles include tarps, tents, awnings, door flaps, screens, or drapes.

In various aspects, the invention relates to an article comprising a compound that binds to and/or modulates insect Orco ion channels. In a further aspect, the article is formed as clothing or netting. In a still further aspect, the compound inhibits insect host sensing and other olfactory driven behaviors. Ina yet further aspect, the compound agonizes insect Orco ion channels. In an even further aspect, the compound antagonizes insect Orco ion channels. In a still further aspect, the compound potentiates insect Orco ion channels.

In a further aspect, the invention relates to an article comprising a compound that binds to and/or modulates insect Orco ion channels, wherein a compound that binds to and/or modulates insect ORX is substantially absent from the composition. In a still further aspect, the article further comprises a compound that binds to and/or modulates insect ORX.

I. METHODS OF USING THE COMPOUNDS AND COMPOSITIONS

Also provided are various methods of using the disclosed compounds.

1. Disrupting Insect Odorant Sensing

The OR disrupting compounds disclosed herein can affect odorant sensing by acting as an agonist, antagonist, or as a potentiator in combination with another agonist or antagonist. It is understood that an agonist will accentuate and amplify odor reception whereas an antagonist will turn off or reduce odor reception.

In one aspect, the invention relates to a method for disrupting insect odorant sensing, the method comprising providing to an insect environment a compound that binds to and/or modulates insect Orco ion channels.

In a further aspect, the compound inhibits insect host sensing. In a still further aspect, the insect is a mosquito.

In a further aspect, the compound agonizes insect Orco ion channels. In a still further aspect, the compound antagonizes insect Orco ion channels. In a yet further aspect, the compound potentiates insect Orco ion channels.

In a further aspect, providing is performed in the absence of a compound that binds to and/or modulates insect ORX. In a still further aspect, the method further comprises providing to an insect environment a compound that binds to and/or modulates insect ORX.

In a further aspect, the insect environment comprises an agricultural environment. In a still further aspect, the insect environment comprises a potential host. In a yet further aspect, the insect environment comprises an insect nest.

In a further aspect, the compound comprises VUAA2, VUAA3, or VUAA4.

In another aspect, disclosed herein are methods of repelling insects comprising administering any of the compounds disclosed herein to an area, subject, or insect environment. In one aspect, the disclosed compounds can be administered individually or as an active ingredient in a larger composition or article. In one aspect, the disclosed compositions, article, or compounds can be administered as an emulsion, suspension, liquid, or gel. In another aspect the disclosed compositions or compounds can be administered through liquid or gaseous dispersion methods such as through an aerosol. It is understood and herein contemplated that the subject, area, or insect environment can include domestic animals, such as companion animals (e.g., dogs, cats, rabbits), livestock, humans, and plants.

In one aspect, the invention relates to a method for disrupting insect odorant sensing, the method comprising providing to an insect environment a compound that binds to and/or modulates insect Orco ion channels.

In a further aspect, the compound inhibits insect host sensing. In a still further aspect, the insect is a mosquito.

In a further aspect, the compound agonizes insect Orco ion channels. In a still further aspect, the compound antagonizes insect Orco ion channels. In a yet further aspect, the compound potentiates insect Orco ion channels.

In a further aspect, disclosed the compound, composition, or article comprises VUAA2, VUAA3, or VUAA4.

In one aspect the disclosed compounds, articles, and compositions can be used to disrupt transmission of insect-borne disease or crop destruction due to insect pests. Thus, in one aspect disclosed herein are methods of disrupting transmission of insect-borne disease or crop destruction due to insect pests comprising providing to an insect environment a compound that binds to and/or agonizes, antagonizes, or potentiates ORco.

In one aspect, the invention relates to a method for disrupting insect odorant sensing, the method comprising providing to an insect environment a compound that binds to and/or modulates insect Orco ion channels.

In a further aspect, the compound inhibits insect host sensing. In a still further aspect, the insect is a mosquito.

In a further aspect, the compound agonizes insect Orco ion channels. In a still further aspect, the compound antagonizes insect Orco ion channels. In a yet further aspect, the compound potentiates insect Orco ion channels.

In a further aspect, disclosed the compound, composition, or article comprises VUAA2, VUAA3, or VUAA4.

2. Mediating Orco Response

In one aspect, the invention relates to a method for mediating Orco response, the method comprising providing an effective amount of a disclosed compound, or a salt or tautomer thereof, to a Orco receptor, an Orco/ORX complex, or an Orco/Orco complex, wherein the compound binds and/or modulates the receptor or complex. In a further aspect, the compound agonizes insect Orco ion channels. In a further aspect, the compound antagonizes insect Orco ion channels. In a further aspect, the compound potentiates insect Orco ion channels. In a further aspect, providing is performed in the absence of a compound that binds to and/or modulates insect ORX. In a further aspect, the method further comprising providing to an insect environment a compound that binds to and/or modulates insect ORX.

J. REFERENCES

The following references, to the extent that they provide exemplary procedural or other details supplementary to those set forth herein, are specifically incorporated herein by reference.

Acree et al., *Science,* 161:1346-1347, 1968.
Antonny et al., *J. Biol Chem.,* 268:2393-2402, 1993.
Baumann et al., *Embo. J.,* 13:5040-5050, 1994.
Benton et al., *Cell,* 136:149-162, 2009.
Benton et al., *PLoS Biol.,* 4:e20, 2006.
Bernier et al., *Anal. Chem.,* 71:1-7, 1999.
Boekhoff et al., *J Comparative Physiol. B,* 160:99-103, 1990.

Bohbot et al., *Insect. Mol. Biol*, 16:525-537, 2007.
Brady et al., *Ann. Trop. Med. Parasitol.*, 91:5121-122, 1997.
Breer et al., *Nature*, 345:65-68, 1990.
Carnevale et al., *Bull. World Health Organ.*, 56:147-154, 1978.
Clyne et al., *Neuron.*, 22:327-338, 1999.
Clyne et al., *Science*, 287:1830-1834, 2000.
Cork and Park, *Med. Vet. Entomol*, 10:269-276, 1996.
CTFA Cosmetic Ingredient Handbook, Vol. 3, p. 3187-3192.
Curtis, *Parasitology Today*, 11:316-318, 1986.
De Jong and Knols, *Acta Trop.*, 59:333-335, 1995.
De Jong and Knols, *Experientia*, 51:80-84, 1995.
Dekker et al., *J. Med. Entomol*, 38:868-871, 2001a.
Dekker et al., *Physiol. Entomol*, 26:124-134, 2001b.
Dobritsa et al., *Neuron.*, 37:827-841, 2003.
Eiras and Jepson, *Bull. Entomol. Res.*, 81:151-160, 1991.
Elmore and Smith, *Insect Biochem. Mol. Biol*, 31:791-798, 2001.
Engsontia et al., *Insect Biochem. Mol. Biol*, 38:387-397, 2008.
Fox et al., *Proc. Natl. Acad. Sci. USA*, 98:14693-14697, 2001.
Gao and Chess, *Genomics*, 60:31-39, 1999.
Gilles, *Bull. Entomol. Res.*, 70:525-532, 1980.
Goldman et al., *Neuron.*, 45:661-666, 2005.
Hallem and Carlson, *Cell*, 125:143-160, 2006.
Hallem et al., *Cell*, 117:965-979, 2004a.
Hallem et al., *Nature*, 427:212-213, 2004b.
Hildebrand and Shepherd, *Annu. Rev. Neurosci.*, 20:595-631, 1997.
Hill et al., *Science*, 298:176-178, 2002.
Holt et al., *Science*, 298:129-149, 2002.
Jones et al., *Curr. Biol.*, 15:$R_1$19-$R_1$21, 2005.
Jones et al., *Nature*, 445:86-90, 2007.
Kellogg, *J Insect. Physiol*, 16:99-108, 1970.
Kim et al., *Bioinformatics*, 16:767-775, 2000.
Krieger and Breer, *Science*, 286:720-723, 1999.
Krieger et al., *Eur. J. Neurosci.*, 16:619-628, 2002.
Krieger et al., *Insect. Biochem. Mol. Biol*, 29:255-267, 1999.
Krieger et al., *J Comp. Physiol. A Neuroethol. Sens. Neural Behav. Physiol.*, 189:519-526, 2003.
Krotoszynski et al., *J. Chromatographic Sci.*, 15:239-244, 1977.
Kwone et al., *Proc. Natl. Acad. Set USA*, 104:3574-3578, 2007.
Labows Jr., *Perfumer & Flavorist*, 4:12-17, 1979.
Larsson et al., *Neuron.*, 43:703-714, 2004.
Laue et al., *Cell Tissue Res.*, 288:149-158, 1997.
Lindsay et al., *J Med. Entomol.*, 30:308-373, 1993.
Lu et al., *Curr. Biol*, 17:1533-1544, 2007.
Lundin et al., *FEBS Lett.*, 581(29):5601-5604, 2007.
Mboera and Takken, *Rev. Med. Vet. Entomol*, 85:355-368, 1997.
McCutcheon's, Detergents and Emulsifiers, North American Edition, 1986.
Meijerink and van Loon, *J. Insect Physiol*, 45:365-373, 1999.
Meijerink et al., *J. Insect Physiol*, 47:455-464, 2001.
Merrill et al., *Insect Molecul Biol*, 12:641-650, 2003.
Merrill et al., *J. Neurobiol.*, 63:15-28, 2005.
Merrill et al., *Proc. Natl Acad. Sci. USA*, 99:1633-1638, 2002.
Mombaerts, *Annu. Rev. Neurosci.*, 22:487-509, 1999.
Muirhead-Thomson, *Brit. Med. J.*, 1:1114-1117, 1951.
Pelosi and Maida, *Comp. Biochem. Physiol. B Biochem. Mol. Biol*, 111:503-514, 1995.
Pitts et al., *Proc. Natl. Acad. Sci. USA*, 101:5058-5063, 2004.
Qiu et al., *Chem. Senses*, 31:845-863, 2006b.
Qiu et al., *Med. Vet. Entomol*, 20:280-287, 2006a.
Remington's Pharmaceutical Sciences, 18th Ed. Mack Printing Company, 1289-1329, 1990.
Robertson and Wanner, *Genome Res.*, 16:1395-1403, 2006.
Robertson et al., *Proc. Natl. Acad. Sci. USA*, 100(2): 14537-14542, 2003.
Rutzler et al., *J Comp. Neurol*, 499:533-545, 2006.
Sato et al., *Nature*, 452(7190): 1002-1006, 2008.
Schreck et al., *J. Am. Mosq. Control Assoc.*, 6:406-410, 1990.
Scott et al., *Cell*, 104:661-673, 2001.
Smith, *Neuron.*, 22:203-204, 1999.
Stengl, *J. Comp. Physiol. [A]*, 174:187-194, 1994.
Storkuhl and Kettler, *Proc. Natl. Acad. Sci. USA*, 98:9381-9385, 2001.
Suh et al., *Curr. Biol*, 17:905-908, 2007.
Takken and Knols, *Annu. Rev. Entomol*, 44:131-157, 1999.
Takken et al., *J Insect Behavior*, 10:395-407, 1997.
Takken, *Insect Sci. Applns.*, 12:287-295, 1991.
Thomas, *Brit. Med. J*, 2:1402, 1951.
Vosshall et al., *Cell*, 102:147-159, 2000.
Vosshall et al., *Cell*, 96:725-736, 1999.
Vosshall, *Chem. Senses*, 26:207-213, 2001.
Vosshall and Hansson, *Chem. Senses*, advanced access, pub. 3/25/11.
Wetzel et al., *Proc. Natl Acad. Sci. USA*, 98:9377-9380, 2001.
Wicher et al., *Nature*, 452(7190): 1007-1011, 2008.
Wistrand et al., *Protein Sci.*, 15:509-521, 2006.
Xia et al., *Proc. Natl. Acad. Sci. USA*, 105:6433-6438, 2008.
Zwiebel and Takken, *Insect Biochem. Molec. Biol*, 34:645-652, 2004.

The following patent references are specifically incorporated herein by reference: U.S. Pat. Nos. 2,798,053; 3,755,560; 4,418,534; 4,421,769; 4,509,949; 4,599,379; 4,628,078; 4,835,206; 4,849,484; 5,011,681; 5,087,445; 5,100,660; 5,567,430; 5,698,210; 5,824,328; 5,846,553; 5,858,384; 5,858,386; 5,885,605; 5,902,596; 5,983,390; 6,001,382; 6,335,027; 6,337,078; 6,346,262; 6,350,461; 6,387,386; 6,391,328; 7,090,147; 7,306,167; U.S. Patent Pubn. 2006/0260183; and U.S. Patent Publn. 2007/0160637.

K. EXPERIMENTAL

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures or as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

As indicated, some of the Examples were obtained as racemic mixtures of one or more enantiomers or diastereomers. The compounds may be separated by one skilled in the art to isolate individual enantiomers. Separation can be carried out by the coupling of a racemic mixture of compounds to an enantiomerically pure compound to form a diastereomeric mixture, followed by separation of the individual diastereomers by standard methods, such as fractional crystallization or chromatography. A racemic or diastereomeric mixture of the compounds can also be separated directly by chromatographic methods using chiral stationary phases.

1. General

All non-aqueous reactions were performed in flame-dried or oven dried round-bottomed flasks under an atmosphere of argon. Stainless steel syringes or cannulae were used to transfer air- and moisture-sensitive liquids. Reaction temperatures were controlled using a thermocouple thermometer and analog hotplate stirrer. Reactions were conducted at room temperature (rt, approximately 23° C.) unless otherwise noted. Analytical thin-layer chromatography (TLC) was performed on E. Merck silica gel 60 F254 plates and visualized using UV, ceric ammonium molybdate, potassium permanganate, and anisaldehyde stains. Yields were reported as isolated, spectroscopically pure compounds.

2. Materials

Solvents were obtained from either an MBraun MB-SPS solvent system or freshly distilled (tetrahydrofuran was distilled from sodium-benzophenone; diethyl ether was distilled from sodium-benzophenone and used immediately). Commercial reagents were used as received.

3. Instrumentation

HPLC was conducted on a Gilson HPLC system using a Gemini-NX 5u C18 110A 50×21.20 mm column. $^1$H NMR spectra were recorded on Bruker 400 MHz spectrometers and are reported relative to deuterated solvent signals. Data for $^1$H NMR spectra are reported as follows: chemical shift (δ ppm), multiplicity (s=singlet, d=doublet, t=triplet, dd=double of doublets, dt=doublet of triplets, q=quartet, m=multiplet, br=broad, app=apparent), coupling constants (Hz), and integration. LC/MS was conducted and recorded on an Agilent Technologies 6130 Quadrupole instrument. Microwave reactions were conducted on a Biotage Initiator 2.0 microwave reactor.

4. VUAA1

VUAA1 was purchased from Sigma-Aldrich's Rare Chemical Library (CAS #525582-84-7), however it is no longer available from Sigma-Aldrich. To ensure that observed activity was elicited from VUAA1, and not from a contaminant present in the mixture, the purchased compound was subjected to preparative High Performance Liquid Chromatography (HPLC). Briefly, 20 mg of VUAA1 was dissolved in a 50/50 mixture of methanol and DMSO and HPLC was performed on a Phenomenex Luna 30×50 mm C18 prep column with 0.1% Trifluoracetic acid (TFA) in $H_2O$ coupled to an acetonitrile gradient. Appropriate fractions were pooled and passed over a TFA scavenger column (Polymer labs, StratoSpheres SPE PL-HCO3 MP-resin). The solvent was removed by rotary evaporation with a Biotage V10 Roto-vap, yielding white powder. VUAA1 was subsequently re-dissolved in DMSO and assayed as described. The purified VUAA1 was characterized by $^1$H NMR and HRMS (m/z). $^1$H-NMR (400 MHz, DMSO-$d_6$) δ 8.73 (d, J 1.8 Hz, 1H), 8.65 (dd, J 1.5, 4.8 Hz, 1H), 7.97 (dt, J 1.9, 8.0 Hz, 1H), 7.49 (dd, J 2.5, 8.3 Hz, 1H), 7.37 (d, J 8.4 Hz, 2H), 7.04 (d, J 8.4 HZ, 2H), 4.10 (s, 1H), 3.95 (q, J 7.2 Hz, 2H), 2.43 (q, J 7.6 Hz, 2H), 1.13 (t, J 8.0 Hz, 3H), 1.04 (t, J=8.0 Hz, 3H). $^{13}$C-NMR (400 MHz, DMSO-$H_2O$) δ 165.71, 152.92, 151.32, 150.95, 149.07, 139.35, 136.87, 136.33, 128.38, 124.34, 123.90, 119.58, 37.91, 27.97, 16.05, 15.42. HRMS (m/z) [M]$^+$ calculated for $C_{19}H_{22}N_5OS$, 368.1544; found 368.1545.

5. Representative Procedure 1

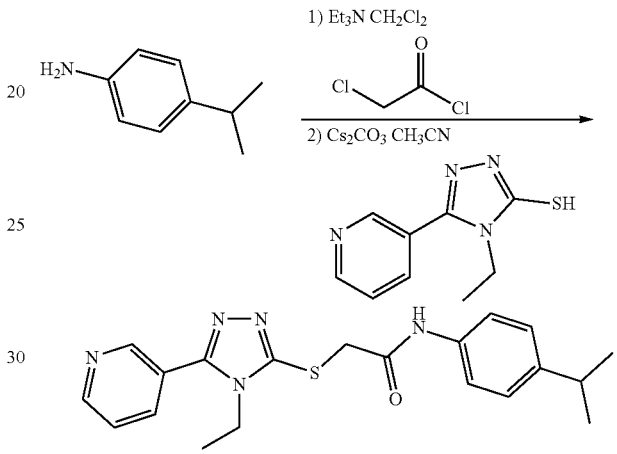

a. Preparation of 2-((4-ethyl-5-(pyridin-3-yl)-4H-1, 2,4-triazol-3-yl)thio)-N-(4-isopropylphenyl)acetamide (VUAA3, VU0455682)

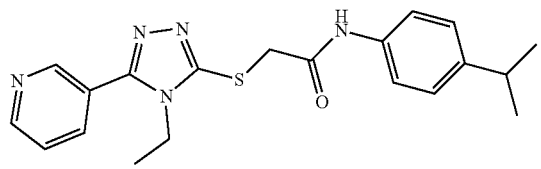 [SMILES: CCn1c(SCC(=O)Nc2ccc(C(C)C)cc2)nnc1-c1cccnc1]

To a solution of 4-isopropylaniline (500 μL, 3.64 mmol) in 24.0 mL of $CH_2Cl_2$ was added triethylamine (500 μL, 3.64 mmol) and chloroacetyl chloride (300 μL, 3.64 mmol). After 2 h, the solution was concentrated and residue redissolved in in 24.0 mL of acetonitrile. To this solution was added 4-ethyl-5-(pyridin-3-yl)-4H-1,2,4-triazole-3-thiol (500 mg, 2.42 mmol) and cesium carbonate (1.58 g, 4.85 mmol). After 16 h, reaction was concentrated and the residue was purified by column chromatography with MeOH/$CH_2Cl_2$ (1:4) to afford 724 mg (77%) of the desired product. $^1$H NMR (CDCl$_3$) δ 10.11 (s, 1H), 8.81 (dd, J=1.5, 4.5 Hz, 2H), 7.55 (dd, J=1.5, 4.5 Hz, 2H), 7.51 (d, J=8.5 Hz, 2H), 7.15 (d, J=8.5 Hz, 2H), 4.05 (q, J=7.3 Hz, 2H), 4.03 (s, 2H), 2.85 (m, 1H), 1.40 (t, J=7.3 Hz, 3H), 1.20 (d, J=7.0 Hz, 3H); $^{13}$C NMR (CDCl$_3$) δ166.1, 153.6, 153.4, 150.8, 145.0, 135.8, 134.3, 126.8, 122.3, 119.8, 40.35, 36.3, 33.6, 24.0, 15.3; LRMS calculated for $C_{20}H_{23}N_5OS$ (M+H)$^+$ m/z: 382.16 Measured 382.3 m/z.

b. Preparation of 2-((4-ethyl-5-(pyridin-3-yl)-4H-1,2,4-triazol-3-yl)thio)-N-(p-tolyl)acetamide (VUAA0, VU0449343)

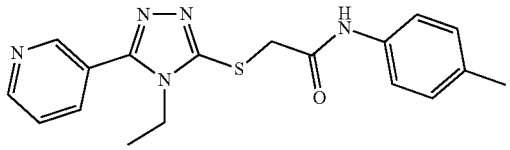 [SMILES: CCn1c(SCC(=O)Nc2ccc(C)cc2)nnc1-c1cccnc1]

The title compound was prepared in a fashion analogous to that used to prepare VUAA3, as described above, using p-toluidine and 4-ethyl-5-(pyridin-3-yl)-4H-1,2,4-triazole-3-thiol: $^1$H NMR (CDCl$_3$) δ 10.25 (s, 1H), 8.80 (d, J=1.77 Hz, 1H), 8.70 (dd, J=1.4. 4.9 Hz, 1H), 7.88 (dt, J=1.8, 8.0 Hz, 1H), 7.40 (m, 3H), 6.98 (d, J=8.3 Hz, 2H), 4.08 (s, 2H), 3.96 (dd, J=7.3, 14.6 Hz, 2H), 2.20 (s, 3H), 1.30 (t, J=7.2 Hz, 3H); $^{13}$C NMR (CDCl$_3$) δ 165.9, 153.0, 152.3, 151.1, 148.6, 135.9, 135.4, 133.5, 129.0, 123.6, 123.0, 119.5, 40.0, 36.8, 20.6, 15.1; LRMS calculated for C$_{18}$H$_{19}$N$_5$OS (M+H)$^+$ m/z: 354.1 Measured 354.2 m/z.

c. Preparation of 2-((4-ethyl-5-(pyridin-3-yl)-4H-1,2,4-triazol-3-yl)thio)-N-(4-vinylphenyl)acetamide (VUAA0.5, VU0431284)

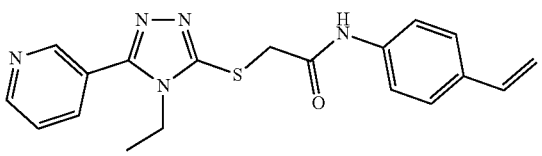 [SMILES: C=Cc1ccc(NC(=O)CSc2nnc(-c3cccnc3)n2CC)cc1]

The title compound was prepared in a fashion analogous to that used to prepare VUAA3, as described above, using 4-vinylaniline and 4-ethyl-5-(pyridin-3-yl)-4H-1,2,4-triazole-3-thiol: $^1$H NMR (CDCl$_3$) δ 10.44 (s, 1H), 8.87 (d, J=1.7 Hz, 1H), 8.79 (dd, J=1.4. 4.9 Hz, 1H), 7.97 (dt, J=1.8, 8.0 Hz, 1H), 7.57 (d, J=8.5 Hz, 2H), 7.49 (dd, J=4.8. 7.8 Hz, 1H), 7.33 (d, J=8.5 Hz, 2H), 6.65 (dd, J=11.0. 17.6 Hz, 1H), 5.65 (d, J=17.5 Hz, 1H), 5.17 (d, J=11.0 Hz, 1H), 4.04 (s, 2H), 4.02 (dd, J=7.2, 14.5 Hz, 2H), 1.40 (t, 7.3 Hz, 3H); $^{13}$C NMR (CDCl$_3$) δ 166.3, 153.4, 152.9, 151.5, 148.8, 137.8, 136.1, 133.6, 126.7, 123.9, 123.1, 119.6, 112.8, 40.3, 36.5, 15.3; LRMS calculated for C$_{19}$H$_{19}$N$_5$OS (M+H)$^+$ m/z: 366.13 Measured 366.2 m/z.

d. Preparation of 2-((4-ethyl-5-(pyridin-3-yl)-4H-1,2,4-triazol-3-yl)thio)-N-(4-isopropylphenyl)acetamide (VUAA2, VU0448520)

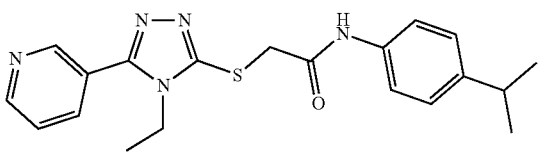 [SMILES: CCn1c(SCC(=O)Nc2ccc(C(C)C)cc2)nnc1-c1cccnc1]

The title compound was prepared in a fashion analogous to that used to prepare VUAA3, as described above, using 4-isopropylaniline and 4-ethyl-5-(pyridin-3-yl)-4H-1,2,4-triazole-3-thiol: $^1$H NMR (CDCl$_3$) δ 10.23 (s, 1H), 8.85 (d, J=2.2 Hz, 1H), 8.75 (dd, J=1.6, 4.9 Hz, 1H), 7.93 (dt, J=1.9, 7.9 Hz, 1H), 7.48 (d, J=8.1 Hz, 2H), 7.45 (dd, J=4.8, 8.1 Hz, 1H), 7.10 (d, J=8.1 Hz, 2H), 4.09 (s, 2H), 4.00 (q, 7.3 Hz, 2H), 2.82 (m, 1H), 1.35 (t, J=7.3 Hz, 3H), 1.17 (d, J=6.9 Hz, 3H); $^{13}$C NMR (CDCl$_3$) δ 166.1, 153.2, 152.6, 151.4, 148.8, 144.8, 136.1, 135.8, 126.7, 123.8, 123.1, 119.78, 40.2, 36.7, 33.5, 23.9, 15.3 LRMS calculated for C$_{20}$H$_{23}$N$_5$OS (M+H)$^+$ m/z: 382.16 Measured 382.0 m/z.

e. Preparation of 2-((4-cyclopropyl-5-(pyridin-4-yl)-4H-1,2,4-triazol-3-yl)thio)-N-(4-isopropylphenyl)acetamide (VUAA4, VU0464190)

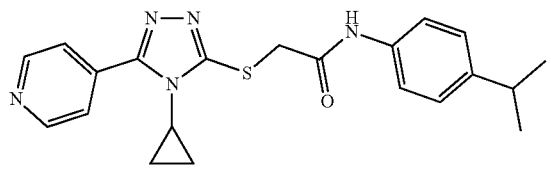 [SMILES: CC(C)c1ccc(NC(=O)CSc2nnc(-c3ccncc3)n2C2CC2)cc1]

The title compound was prepared in a fashion analogous to the general procedure described for VUAA3, using 4-isopropylaniline and 4-cyclopropyl-5-(pyridin-3-yl)-4H-1,2,4-triazole-3-thiol (prepared according to general procedure 3 using isonicotinohydrazide and isothiocyanatocyclopropane). $^1$H NMR (CDCl$_3$) δ 9.98 (s, 2H), 8.79 (d, J=5.6 Hz, 2H), 7.72 (d, J=5.6 Hz, 2H), 7.50 (d, J=8.4 Hz, 2H), 7.15 (d, J=8.4 Hz, 2H), 4.04 (s, 1H), 3.26 (m, 1H), 2.85 (m, 1H), 1.24 (m, 2H), 1.18 (d, J=6.8 Hz, 6H), 0.82 (m, 2H); $^{13}$C NMR (CDCl$_3$) δ 166.2, 156.0, 154.3, 150.2, 144.9, 135.8, 134.1, 126.7, 122.2, 119.7, 35.8, 33.5, 25.8, 23.9, 9.3; LRMS calculated for C$_{20}$H$_{23}$N$_5$OS (M+H)$^+$ m/z: 382.16 Measured 382.3 m/z.

6. Representative Procedure 2

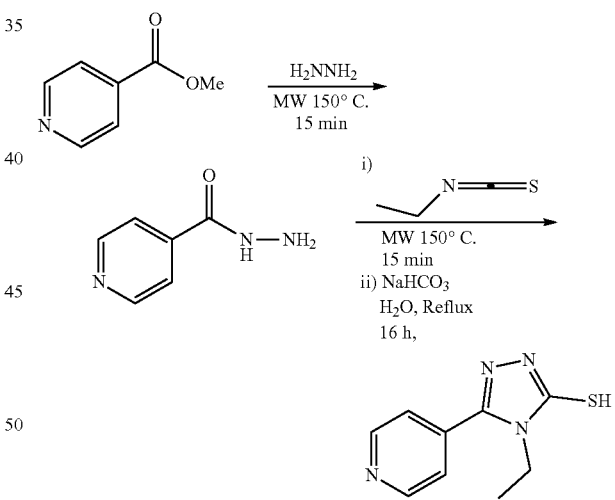

a. Preparation of Isonicotinohydrazide

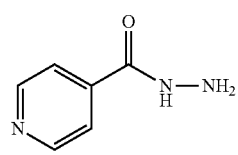

To a solution of methyl isonicotinate (100 mg, 0.73 mmol) in 0.3 mL of ethanol was added hydrazine hydrate (0.35 mL, 7.29 mmol). This reaction mixture was heated in a microwave reactor for 5 min at 150° C. The reaction was allowed to cool to room temperature and diluted with 10 mL of MeOH, then concentrated. The residue was purified by column chromatography with MeOH/CH$_2$Cl$_2$ (1:4) to afford 84 mg (75%) of the desired product. $^1$H NMR (MeOD) δ 8.70 (dd, J=4.8, 1.6 Hz, 2H), 7.77 (dd, J=4.4, 1.6 Hz, 2H). LRMS calculated for C$_6$H$_7$N$_3$O (M+H)$^+$ m/z: 137.05 Measured 137.1 m/z.

b. Preparation of 4-ethyl-5-(pyridin-4-yl)-4H-1,2,4-triazole-3-thiol

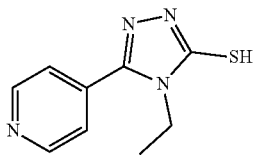

To a solution of isonicotinohydrazide (84 mg, 0.61 mmol) in 1.0 mL of ethanol was added ethyl isothiocyanate (64 μL, 0.74 mmol). This reaction mixture was heated in a microwave reactor for 15 min at 150° C., cooled to room temperature and concentrated. The residue was then re-dissolved 10 ml of H$_2$O and K$_2$CO$_3$ (101.5 mg, 0.74 mmol) was added, then the solution was brought to reflux. After 16 h, the reaction was allowed to cool to room temperature, diluted with methanol and concentrated. The residue was purified by column chromatography with methanol/CH$_2$Cl$_2$ (1:6) to afford 67 mg (53%) of the desired product. $^1$H NMR (MeOD) δ 8.78 (d, J=5.5 Hz, 2H), 7.78 (d, J=6.2 Hz, 2H), 4.26 (q, J=7.2, 2H), 1.33 (t, J=7.3 Hz, 3H) LRMS calculated for C$_9$H$_{10}$N$_4$S (M+H)$^+$ m/z: 207.06. Measured 207.1 m/z.

7. Representative Procedure 3

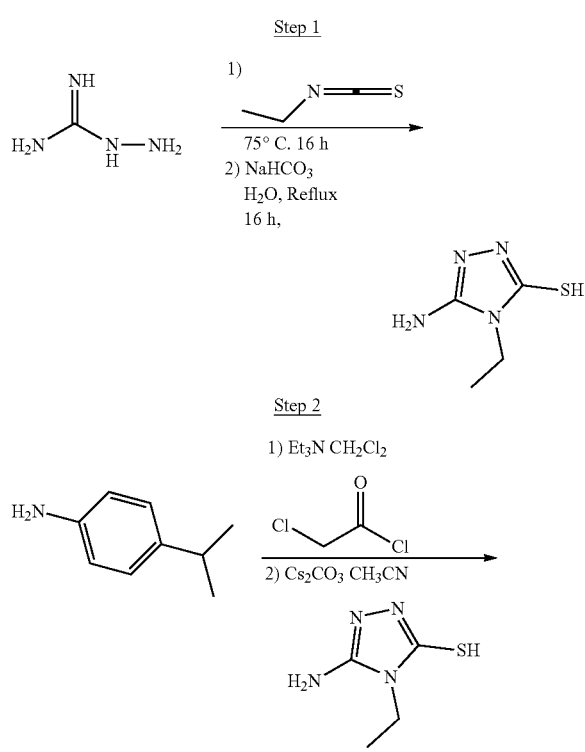

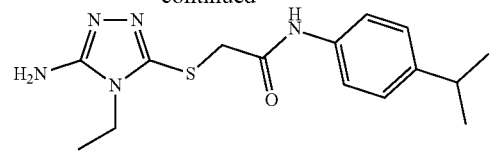

a. Preparation of 5-amino-4-ethyl-4H-1,2,4-triazole-3-thiol

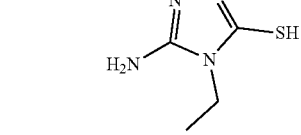

To a solution of aminoguanidine hydrochloride (3.0 g, 27.3 mmol) in 20.0 mL of ethanol was added ethyl isothiocyanate (2.9 mL, 32.7 mmol). This solution was heated in a microwave reactor for 20 min at 150° C., cooled to room temperature and concentrated. The crude reaction mixture was re-dissolved 30 ml of water and K$_2$CO$_3$ (4.5 g, 32.7 mmol) was added. The reaction was allowed to reflux for 16 h. The reaction was allowed to cool to room temperature, diluted with methanol and concentrated. The residue was purified by column chromatography with methanol/CH$_2$Cl$_2$ (1:6) to afford 3.03 g (77%) of the desired product.

b. Preparation of 2-((5-amino-4-ethyl-4H-1,2,4-triazol-3-yl)thio)-N-(4-isopropylphenyl)acetamide (VU0456801)

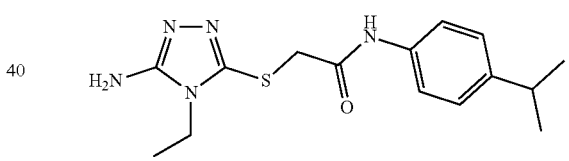

To a solution of 4-isopropylaniline (4.2 mL, 31.5 mmol) in 70.0 mL of CH$_2$Cl$_2$ was added triethyl amine (4.5 mL, 31.5 mmol) and chloroacetyl chloride (2.5 mL, 31.5 mmol). After 2 h, the solution was concentrated, re-dissolved in in 70.0 mL of acetonitrile. To this solution was added 5-amino-4-ethyl-4H-1,2,4-triazole-3-thiol (3.0 g, 21.0 mmol) and cesium carbonate (13.7 g, 42.0 mmol) After 16 h, the reaction was concentrated and the residue was purified by column chromatography with MeOH/CH$_2$Cl$_2$ (1:4) to afford 4.6 g (69%) of the desired product. $^1$H NMR (CDCl$_3$) δ 7.41 (d, J=8.4 Hz, 2H), 7.17 (d, J=8.4 Hz, 2H), 3.94 (q, J=7.4 Hz, 2H), 3.79 (s, 2H), 2.86 (m, 1H), 1.25 (t, J=7.3 Hz, 3H), 1.22 (d, J=7.0 Hz, 6H). LRMS calculated for C$_{15}$H$_{21}$N$_5$OS (M+H)$^+$ m/z: 320.15 Measured 320.2 m/z.

8. Representative Procedure 4

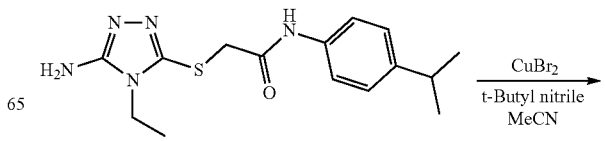

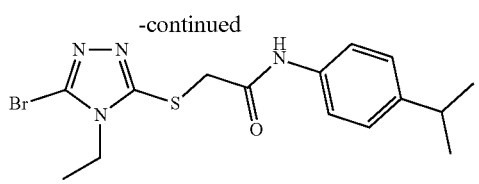

a. Preparation of 2-((5-bromo-4-ethyl-4H-1,2,4-triazol-3-yl)thio)-N-(4-isopropylphenyl)acetamide

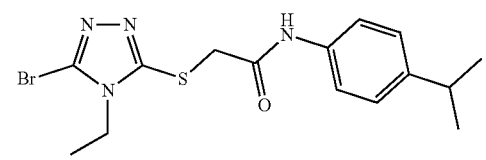 [SMILES: CCn1c(Br)nnc1SCC(=O)Nc1ccc(C(C)C)cc1]

To a solution of t-Butyl Nitrite (0.3 mL, 2.49 mmol) in 2.5 mL of MeCN was added CuBr$_2$ (200 mg, 1.72 mmol). After 15 min, a solution of 2-((5-amino-4-ethyl-4H-1,2,4-triazol-3-yl)thio)-N-(4-isopropylphenyl)acetamide (500 mg, 1.56 mmol) in 2.5 mL of acetonitrile was added dropwise. After 2 h at room temperature, the reaction was concentrated and the residue was purified by column chromatography with MeOH/CH$_2$Cl$_2$ (1:4) to afford 207 mg (34%) of the desired product. $^1$H NMR (CDCl$_3$) δ 9.86 (s, 1H), 7.50 (d, J=8.5 Hz, 2H), 7.17 (d, J=8.5 Hz, 2H), 3.99 (m, 4H), 2.88 (m, 1H), 1.39 (t, 7.3, 3H), 1.23 (d, J=6.9 Hz). LRMS calculated for C$_{15}$H$_{19}$BrN$_4$OS (M+H)$^+$ m/z: 383.05 Measured 383.1 m/z.

9. General Procedure 5

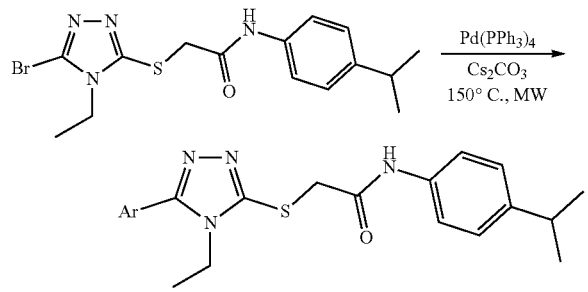

a. Preparation of 2-((4-ethyl-5-(2-fluoropyridin-4-yl)-4H-1,2,4-triazol-3-yl)thio)-N-(4-isopropylphenyl)acetamide (VU0458428)

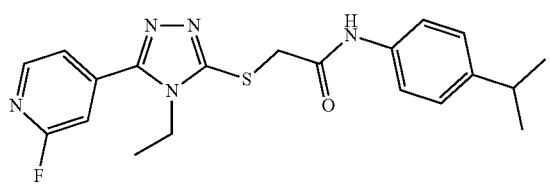 [SMILES: CCn1c(SCC(=O)Nc2ccc(C(C)C)cc2)nnc1-c1ccnc(F)c1]

To a solution of 2-((5-bromo-4-ethyl-4H-1,2,4-triazol-3-yl)thio)-N-(4-isopropylphenyl)acetamide (30 mg, 0.078 mmol) in 7.8 mL of (4:1) THF:H$_2$O was added cesium carbonate (31.0 mg, 0.094 mmol), Pd(PPh$_3$)$_4$ (9.0 mg, 0.008 mmol) and (2-fluoropyridin-4-yl)boronic acid (13.2 mg, 0.094 mmol). The resulting slurry was heated in a microwave reactor at 150° C. for 45 min. After cooling to room temperature, the reaction mixture was filtered over a celite plug and concentrated. The resulting residue was purified by HPLC with H$_2$O/MeCN to afford 16 mg (51%) of the desired product. $^1$H NMR (CDCl$_3$) δ 9.98 (s, 1H), 8.43 (d, J=5.0 Hz, 1H), 7.49 (m, 3H), 7.16 (d, J=8.4 Hz, 2H), 4.08 (q, J=7.2 Hz, 2H), 4.02 (s, 2H), 2.86 (m, 1H), 1.43 (t, 7.2, 3H), 1.21 (d, J=6.9 Hz). LRMS calculated for C$_{20}$H$_{22}$FN$_5$OS (M+H)$^+$ m/z: 400.15 Measured 400.2 m/z.

10. General Procedure 5

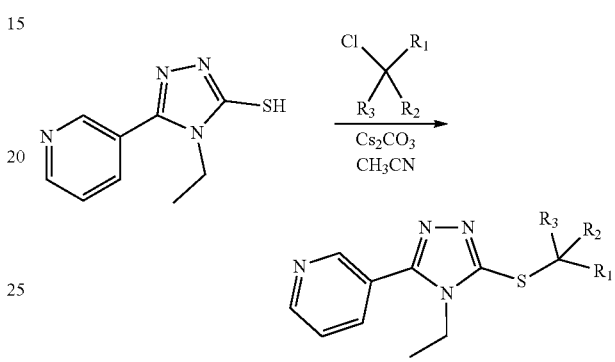

a. Preparation of 2-((4-ethyl-5-(pyridin-3-yl)-4H-1,2,4-triazol-3-yl)thio)-N-(4-ethylphenyl)acetamide (VUAA1, VU0099414)

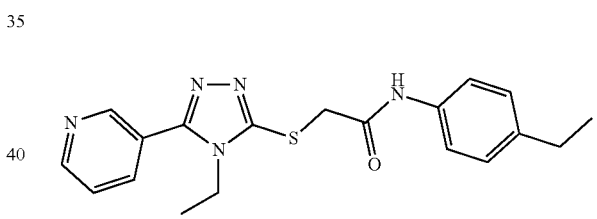

To a solution of 4-ethyl-5-(pyridin-3-yl)-4H-1,2,4-triazole-3-thiol (550 mg, 2.67 mmol) in 25 mL of MeCN was added cesium carbonate (1.8 g, 5.53 mmol) and 2-chloro-N-(4-ethylphenyl)acetamide (802 mg, 4.08 mmol). After 16 h, the reaction was concentrated and the residue was purified by column chromatography with MeOH/CH$_2$Cl$_2$ (1:4) to afford 827 mg (84%) of the desired product. $^1$H NMR (CDCl$_3$) δ 10.20 (s, 1H), 8.87 (d, J=1.7 Hz, 1H), 8.79 (q, J=1.6, 4.9 Hz, 1H), 7.98 (dt, J=2.1, 7.9 Hz, 1H), 7.52 (d, J=8.3 Hz, 2H), 7.49 (dd, J=4.8, 7.9 Hz, 1H), 7.13 (d, J=8.3, 2H), 4.02 (s, 2H), 4.01 (dd, J=7.2, 14.7 Hz, 2H), 2.59 (dd, J=7.6, 15.2 Hz, 2H), 1.40 (t, 7.3 Hz, 3H), 1.19 (t, 7.6 Hz, 3H). HRMS calculated for C$_{19}$H$_{21}$N$_5$OS (M+H)$^+$ m/z: 368.1467 Measured 368.1545 m/z.

11. General Procedure 6

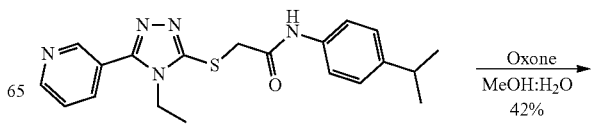

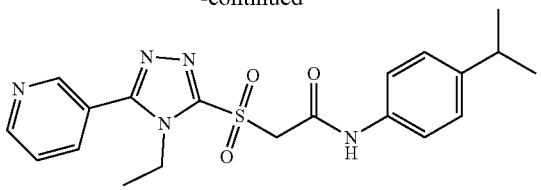

a. Preparation of 2-((4-ethyl-5-(pyridin-3-yl)-4H-1,2,4-triazol-3-yl)sulfonyl)-N-(4-isopropylphenyl)acetamide

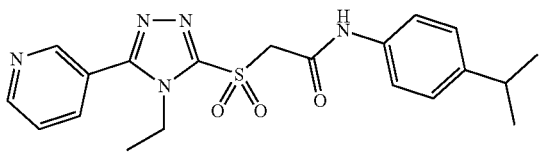 [SMILES: CCn1c(-c2cccnc2)nnc1S(=O)(=O)CC(=O)Nc1ccc(C(C)C)cc1]

To a solution of 2-((4-ethyl-5-(pyridin-3-yl)-4H-1,2,4-triazol-3-yl)thio)-N-(4-isopropylphenyl)acetamide (15 mg, 0.04 mmol) in 1.0 mL of (9:1) MeOH:H$_2$O was added Oxone (500 mg, 0.80 mmol). After 48 h, the reaction was concentrated and the residue was purified by column chromatography with MeOH/CH$_2$Cl$_2$ (1:4) to afford 6.8 mg (42%) of the desired product. $^1$H NMR (CDCl$_3$) δ 9.420 (s, 1H), 8.60 (s, 1H), 8.39 (d, J=5.8, 1H), 7.50 (m, 2H), 7.45 (d, 8.5 Hz, 2H), 7.15 (d, J=8.5 Hz, 2H), 4.81 (s, 2H), 4.38 (q, 7.2 Hz, 2H), 2.83 (m, 1H), 1.42 (t, J=7.3 Hz, 3H), 1.20 (d, J=6.9 Hz, 3H); LRMS calculated for C$_{20}$H$_{23}$N$_5$O$_3$S (M+H)$^+$ m/z: 414.15 Measured 414.2 m/z.

12. General Procedure 7

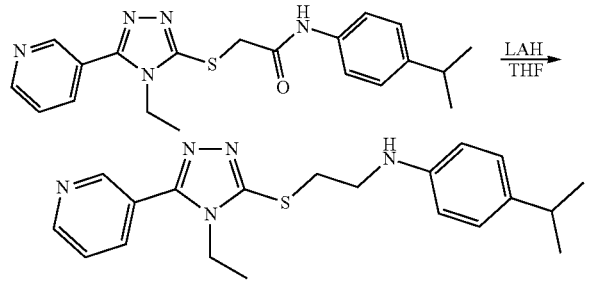

a. Preparation of N-(2-((4-ethyl-5-(pyridin-3-yl)-4H-1,2,4-triazol-3-yl)thio)ethyl)-4-isopropylaniline

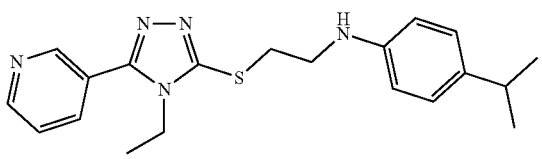 [SMILES: CCn1c(SCCNc2ccc(C(C)C)cc2)nnc1-c1cccnc1]

To a solution of 2-((4-ethyl-5-(pyridin-3-yl)-4H-1,2,4-triazol-3-yl)thio)-N-(4-isopropylphenyl)acetamide (50 ng, 0.13 mmol) in 3.5 mL of THF was added Lithium Aluminum Hydride (26.7 mg, 0.65 mmol). After 16 h, the reaction was diluted with H$_2$O (10 mL) and extracted 3× with CH$_2$Cl$_2$. The combined organics were dried with over MgSO$_4$ and concentrated. The residue was purified by column chromatography with MeOH/CH$_2$Cl$_2$ (1:4) to afford 27.4 mg (56%) of the desired product. $^1$H NMR (CDCl$_3$) δ 8.88 (d, J=2.0 Hz, 1H), 8.78 (d, J=5.1, 1H), 8.01 (d, J=7.1 Hz, 1H), 7.49 (dd, 4.5, 8.0 Hz, 1H), 7.07 (d, J=8.5 Hz, 2H), 6.63 (d, J=8.5 Hz, 2H), 4.01 (q, J=7.3 Hz, 2H), 3.67 (m, 2H), 3.58 (m, 2H), 2.82 (m, 1H), 1.37 (t, J=7.2 Hz, 3H), 1.22 (d, J=7.1 Hz, 6H). LRMS calculated for C$_{20}$H$_{25}$N$_5$S (M+H)$^+$ m/z: 368.18 Measured 368.1 m/z.

13. Cell Culture and Ca2+ Imaging

For transient transfections, ORs were cloned into pCI (Promega) and transfected into Flp-In™ T-REx™293 cell lines (Invitrogen) with Fu GENE6 (Roche). For the creation of stable cell lines, a cell culture expression vector capable of expressing Orco in conjunction with a conventional OR, pcDNA5/FRT/TO (Invitrogen) was modified to create two individual expression cassettes each under the control of a separate CMV/Tet02 promoter and a BGH poly-adenylation signal. Cells (as above) were transfected with the modified pcDNA5 plasmid along with POG44 (a Flp recombinase expression plasmid) to facilitate site-specific recombination. Stable cell lines were selected using Hygromycin B (Invitrogen). Cells were maintained in DMEM (Invitrogen) supplemented with 10% Tetracycline-free FBS (HyClone) and 15 ng/ml Blasticidin. For fluorometric Ca2+ measurements, stable lines expressing ORs of interest were seeded at 20,000 cells/well in black wall, poly-lysine coated 384-well cell culture plates (Greiner) and treated with 0.3 u-g/ul tetracycline (Sigma) overnight to induce OR expression. Cells were dye-loaded with 1.8 uM Fluo-4 AM (Molecular Probes), 2.5 mM Probenecid (Molecular Probes) in assay buffer (20 mM HEPES, IX HBSS) for 45 minutes at 37° C. in 5% CO$_2$ prior to each assay. Ca$^{2+}$ mobilization was assayed in an FDSS6000 (Hamamatsu). Baseline readings were taken for 20 s before automated addition of compound previously diluted in DMSO and assay buffer. Ratios were described as Maximum/Minimum response and each response was normalized to the maximum responder.

14. Patch-Clamp Recording in HEK Cells

Currents from OR-expressing HEK293 cells were amplified with an Axopatch 200b Amplifier (Axon Instruments) and digitized through a Digidata 1322A (Axon Instruments). Electrophysiological data was recorded and analyzed using pCLAMP 10 (Axon Instruments). Electrodes were fabricated from quartz tubing (Sutter Instruments) and pulled to 4-6 MiΩ for whole cell recording. Electrodes were filled with internal solution (120 mM KCl, 30 mM D-glucose, 10 mM HEPES, 2 mM MgCl$_2$, 1.1 mM EGTA, and 0.1 CaCl$_2$) (pH 7.35, 280 mOsm). External (bath) solution contained 130 mM NaCl, 34 mM D-glucose, 10 mM HEPES, 1.5 mM CaCl$_2$, 1.3 mM KH$_2$PO$_4$, and 0.5 MgSO$_4$ (pH 7.35, 300 mOsm). Compounds were diluted in external solution and locally perfused to the recording cell using Perfusion Pencil (Automate Scientific) and controlled by a ValveLink 8.2 controller (Automate Scientific). Whole cell recordings were sampled at 10 kHz and filtered at 5 kHz. Outside-out patches were obtained using 10-15MΩ electrodes pulled from standard glass capillaries (World Precision Instruments) and fire-polished with an MF-830 micro forge (Narishige). Single channel recordings were sampled at 20 kHz. Recordings were reduced to 1 kHz and low-pass filtered at 500 Hz for display and analysis using QuB (SUNY at Buffalo).

15. Single Sensillum Recordings

Single sensillum recordings were performed on 4-7 day old, non-bloodfed *Anopheles gambiae* females maintained on 10% sucrose and a 12/12 light dark cycle. Legs, wings and antennae were removed from cold-anesthetized females that were then restrained on double-stick tape with thread. A glass reference electrode filled with Sensillar lymph ringers (SLR)(Xu, 2005) was placed in the eye and the recording electrode filled with DMSO or VUAA1 diluted in SLR was used to puncture sensilla at their base. Responses were recorded and digitized using a Syntech IDAC-4 and analyzed with AutoSpike software (Syntech). New glass recording pipettes were used for every recording. Data was sampled at 12 kHz.

16. Biological Activity of VUAA1

Figure 3A:
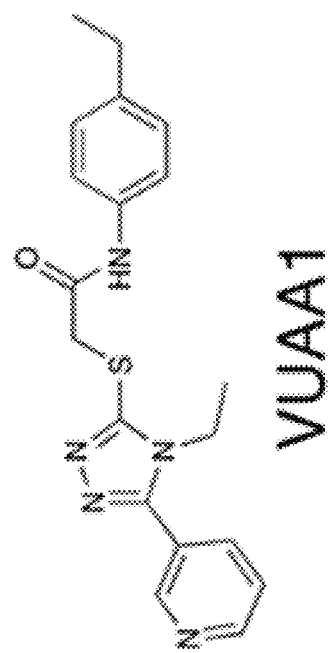
FIGS. 3A-F. VUAA1 evokes macroscopic currents in HEK293 cells expressing Orco and its orthologs.
Figure 3B:
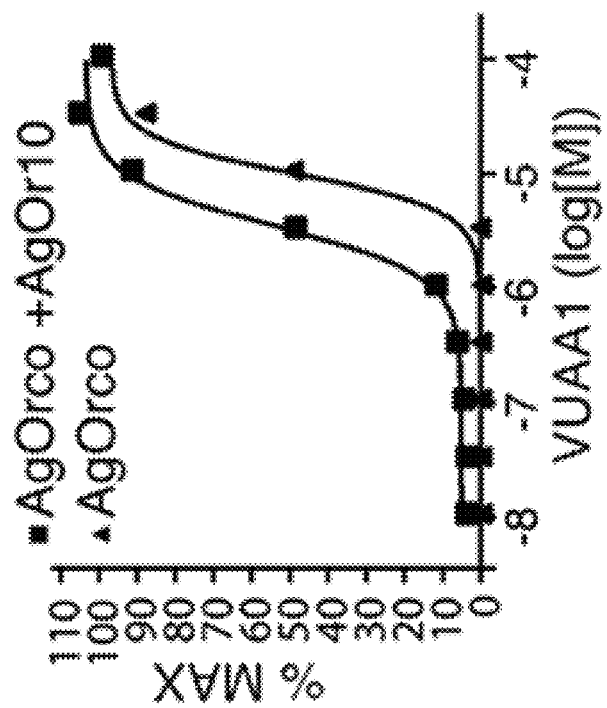
Figure 3C:
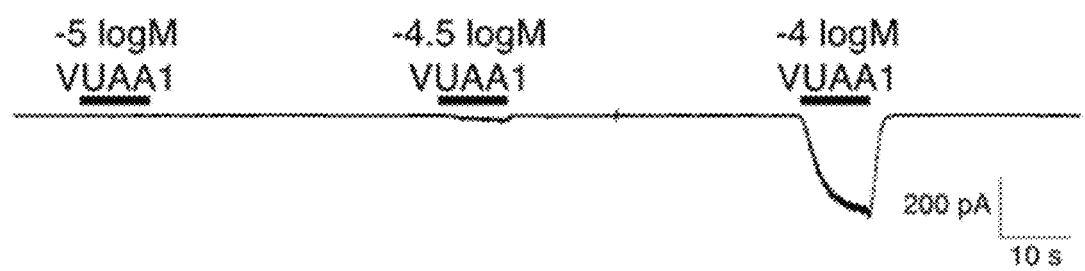

As part of an ongoing, cell based calcium imaging screen for novel small-molecule modulators of AgORs that might disrupt olfactory-driven mosquito behaviors (Rinker et al manuscript in preparation), the inventors identified a number of compounds that activated AgOR10+AgORco-expressing human embryonic kidney (HEK293) cells. One of these compounds, (FIG. 3 A) denoted here as VUAA1, elicited activity consistent with allosteric agonism and was pursued for its novel properties. The identity of VUAA1 was verified using high-resolution mass spectrometry (HRMS) as well as $^1$H and $^{13}$C NMR. When AgORco+AgOR10 cells were tested in a plate-based calcium imaging system, VUAA1 elicited concentration-dependent responses that were not seen in control cells (FIG. 3B). Upon further investigation, VUAA1 proved capable of activating other AgORco+AgOR cell lines as well (unpublished data). As AgORco was the common element among these functional responses, the inventors postulated that VUAA1 was a potential AgORco agonist.

Figure 3D:
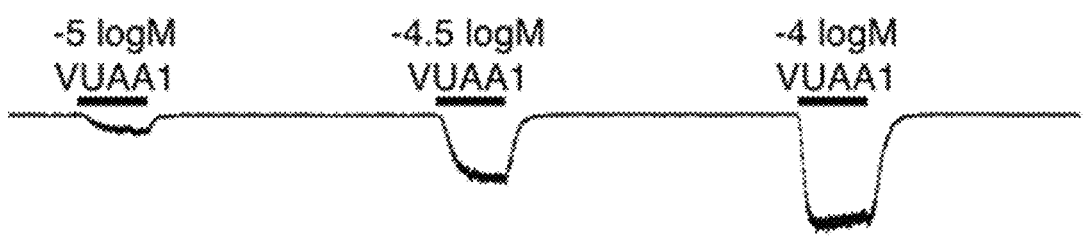
Figure 3E:
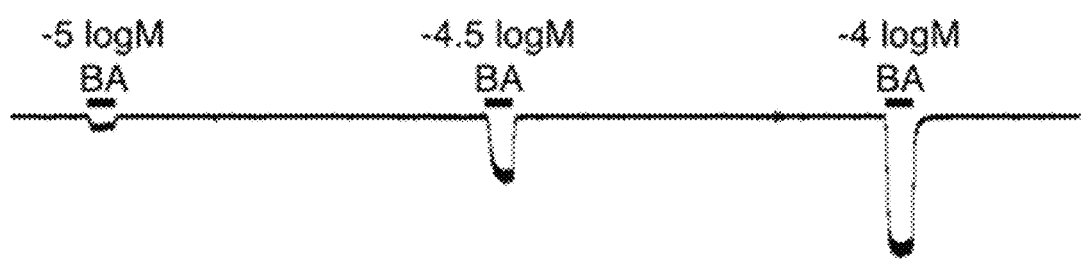
Figure 3F:
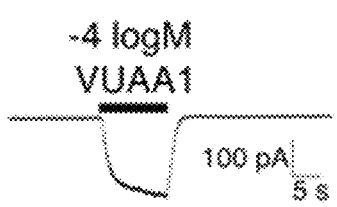
Figure 3F:
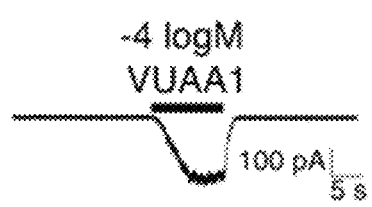
Figure 3F:
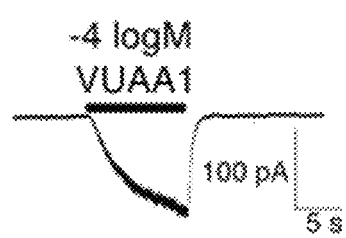

To test the hypothesis that VUAA1 directly agonized AgORco, whole-cell patch clamp responses were examined in AgORco+AgOR10 expressing cells as well as HEK293 cells stably expressing AgORco alone. In these experiments, VUAA1 elicited concentration-dependent inward currents in both AgORo+AgOR10 and AgORco expressing cells (FIGS. 3D-E). The VUAA1-dependent currents in AgORco+AgOR10 cells resembled those resulting from application of benzaldehyde, an orthosteric agonist of AgOR10 (FIG. 3C) (Wang, 2010; Carey, 2010). AgORco+AgOR10 cells were more sensitive to VUAA1 than AgORco cells, producing inward currents at −5.0 log M, a concentration at which AgORco had no response. All currents induced by VUAA1 were AgORco-dependent; no responses were observed in control cells. To investigate the specificity of VUAA1 agonism, the inventors transiently transfected HEK cells with the AgORco orthologs of *Drosophila melanogaster* and *Heliothis virescens*, DmORco and HvOR2 respectively. In cells expressing either ortholog, VUAA1 elicited robust inward currents similar to AgORco-expressing cells (FIG. 3F). These results demonstrate that VUAA1 is a broad-spectrum 83b family agonist, capable of activating non-conventional ORs within and across multiple insect orders. This activity is consistent with their high sequence identities (76% to DmORco and 67% to HvOR2) and demonstrated functional overlap (Jones, 2005).

Figure 4A:
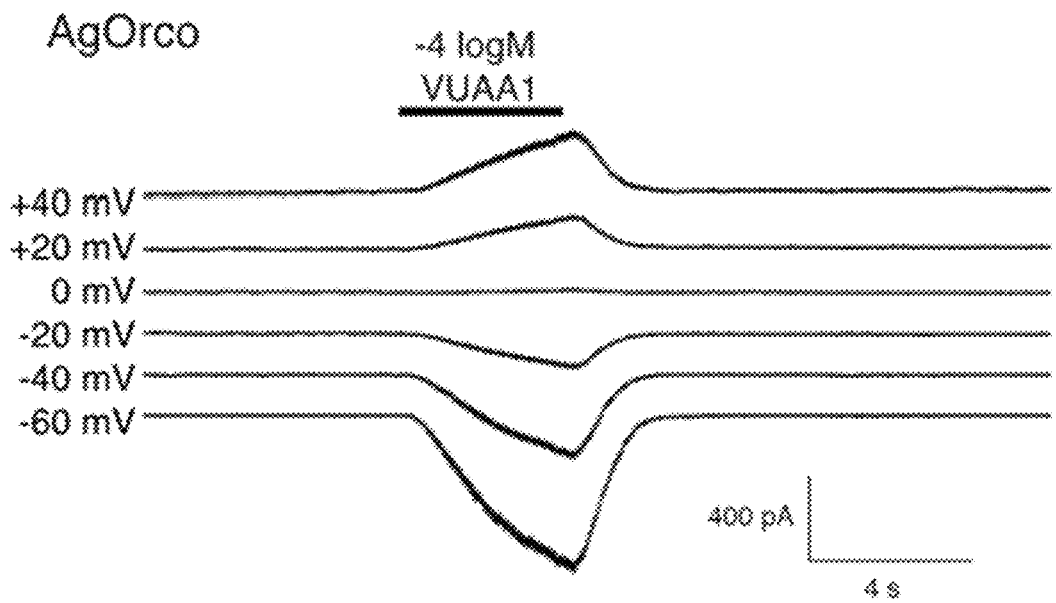
Figure 4B:
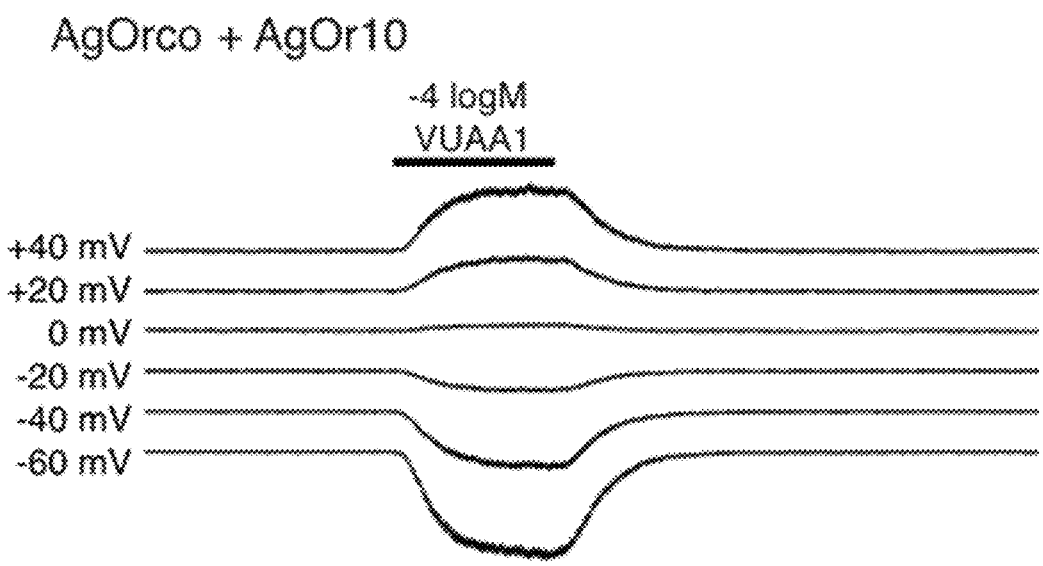
Figure 4D:
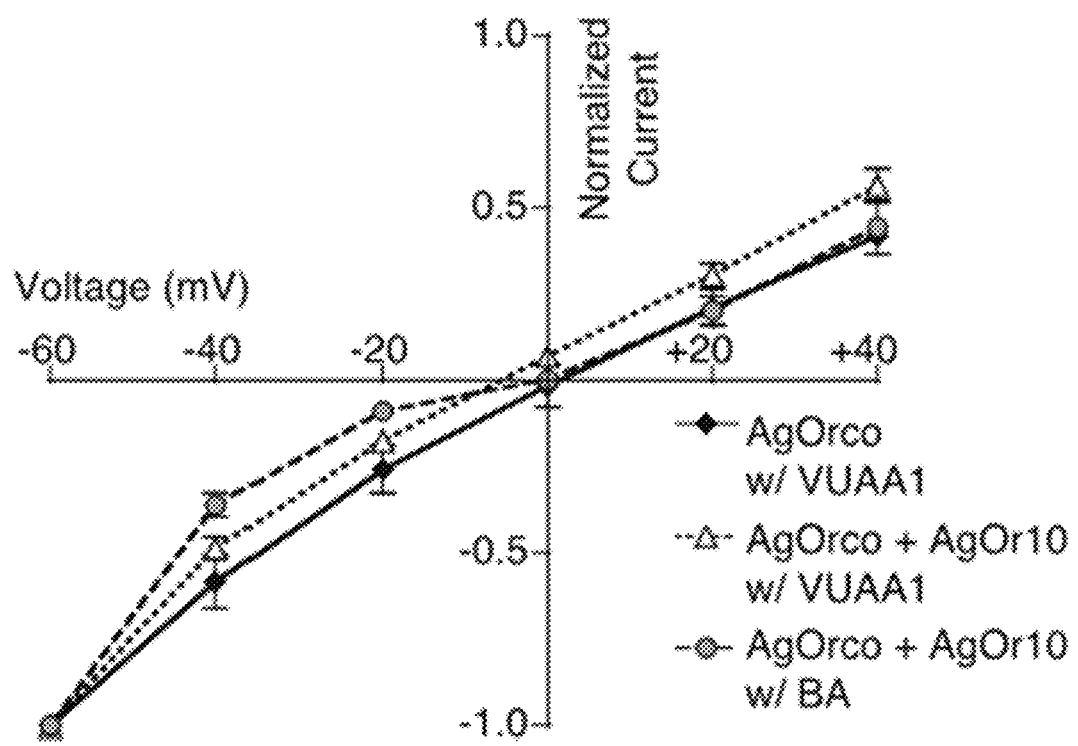
Figure 4E:
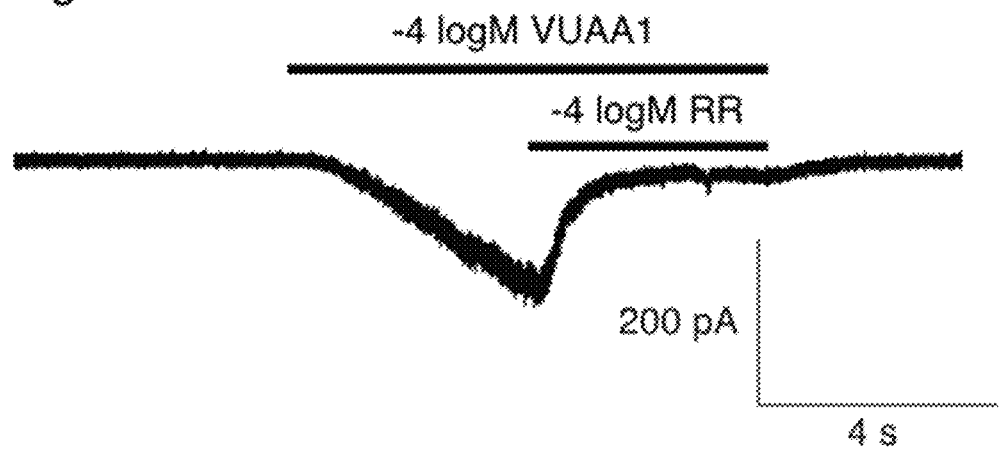
Figure 4F:
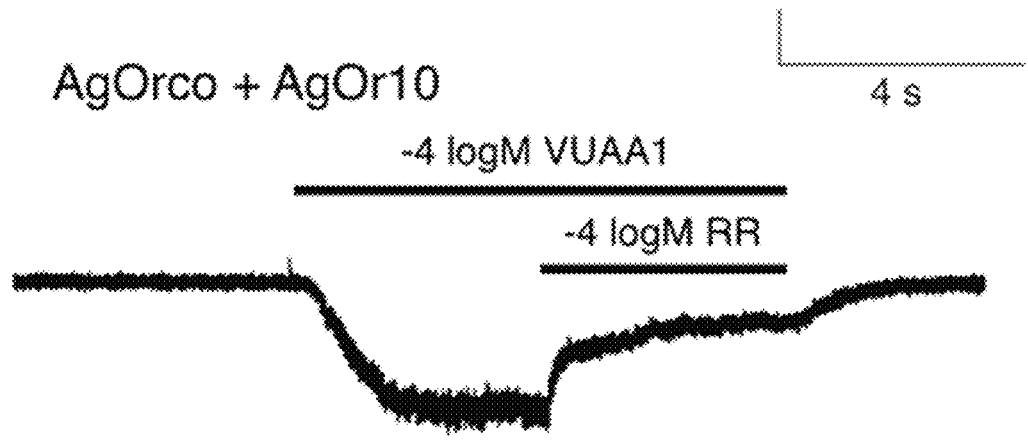
Figure 4G:
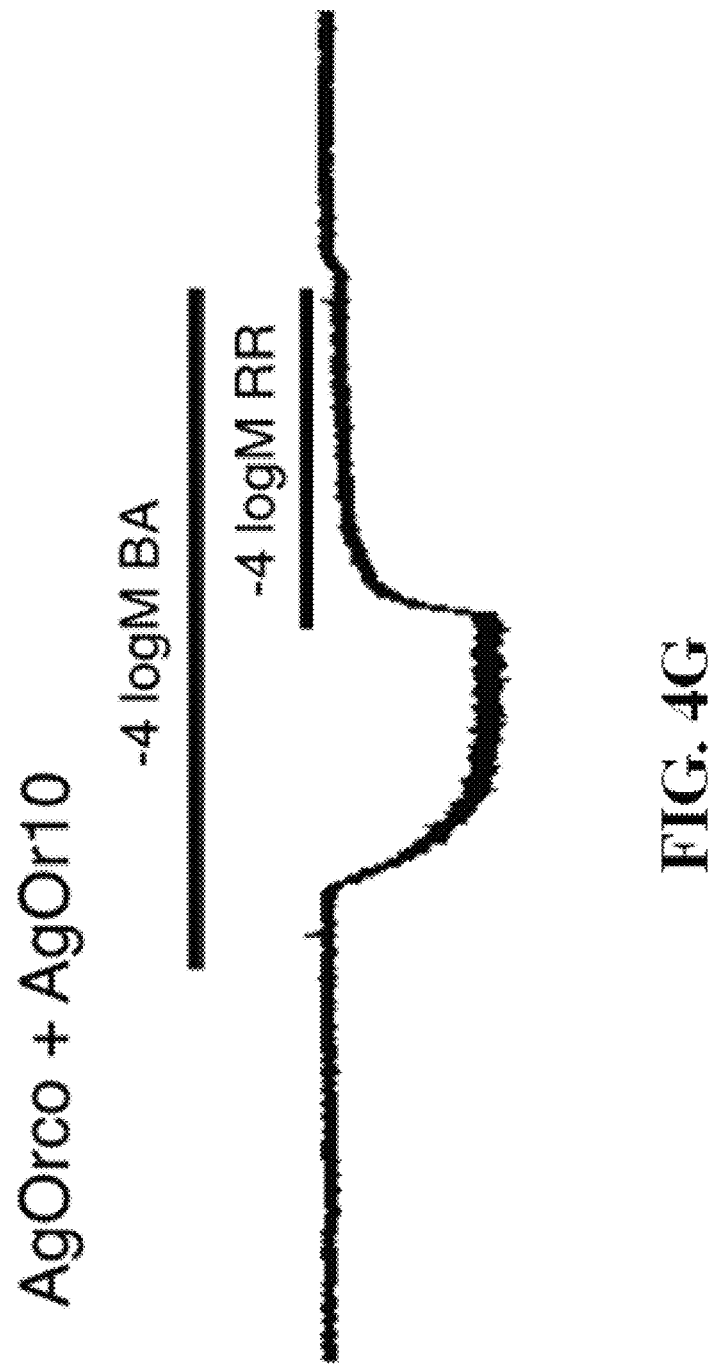
Figure 4H:
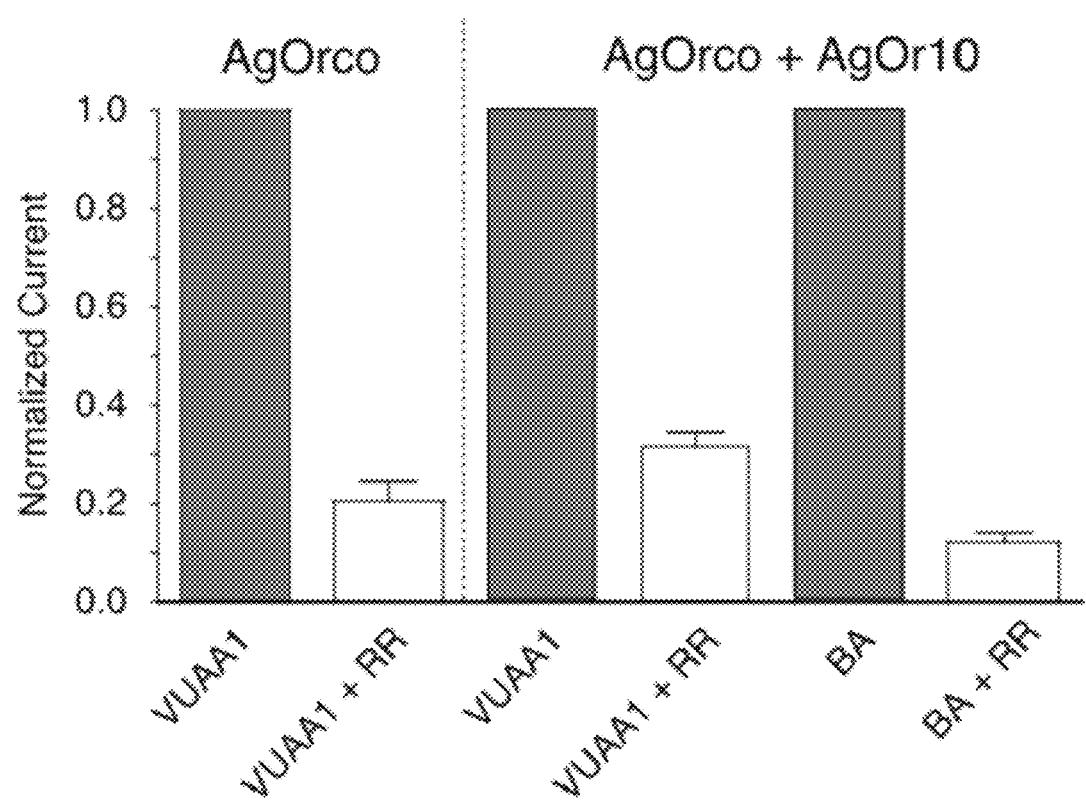

To further investigate the conductive properties of AgORco, the inventors determined the current-voltage relationships of AgORco+AgOR10 complexes as well as AgORco on its own. Currents induced by VUAA-1 or benzaldehyde in AgORco+AgOR10-expressing cells, and those induced by VUAA-1 in AgORco cells, were all nearly symmetrical (FIGS. 4A-H). The reversal potentials of AgORco+AgOR10 complexes were −2.9±1.4 mV (benzaldehyde) and −4.8±3.0 mV (VUAA1) while AgORco alone, in the presence of VUAA1 was +0.4±1.1 mV (mean s.e.m. FIGS. 4A-C). These current-voltage relationships do not indicate any voltage-dependent gating, and the near-zero reversal potentials are consistent with previous reports of insect or complexes that suggested non-selective cation conductance (Sato, 2008; Wicher, 2008). The inventors next examined whether VUAA1 responses could be attenuated by ruthenium red (RR), a promiscuous cation channel blocker previously found to block insect OR currents. Application of RR reduced the benzaldehyde and VUAA1-elicited currents of AgORco+AgOR10 cells by 87.8±1.8% and 68.3±2.8%, respectively (FIGS. 4E-H) while RR reduced VUAA1 responses of AgORco cells by 79.4±4.0% (FIGS. 4G-H). In addition to demonstrating that AgORco+AgOR10 complexes, and AgORco alone act as functional, ligand-gated ion channels, these studies also show that VUAA1 elicits AgOR currents similar to those in response to odorants. To determine the broad-spectrum specificity of VUAA1, the inventors tested VUAA1 on another non-selective cation channel, transient receptor potential vanilloid receptor 1 (TRPV1) (Caterina, 1997; Bohlen, 2010). Capsaicin, but not VUAA1 elicited a robust response in these HEK cells. These results demonstrate that VUAA1 is specific to 83b orthologs, and that VUAA1 is not a broad-spectrum activator of all cation channels.

The inventors next examined whether activation of AgORco involves second messenger-based signaling, which has been reported to contribute to insect olfactory signaling (Wicher, 2008). In these studies, which are consistent with a previously published report (Sato, 2008), two cyclic nucleotide analogs (8-Br cAMP and 8-Br cGMP) were unable to evoke whole-cell currents in AgORco or AgORco+AgOR10 cells, while in both instances OR function was validated by subsequent application of VUAA and benzaldehyde, respectively. While the precise mechanism of signal transfer between a conventional OR and AgORco remains unknown, it is important to note that all channel properties are consistent between and within AgORco and AgORco+AgOR10 complexes. Taken together, the data indicate that the channel properties of AgORco are not significantly altered when complexed with other AgORs and that the ionotropic conductance of AgORco is the principal signaling component of functional AgOR complexes.

Figure 5A:
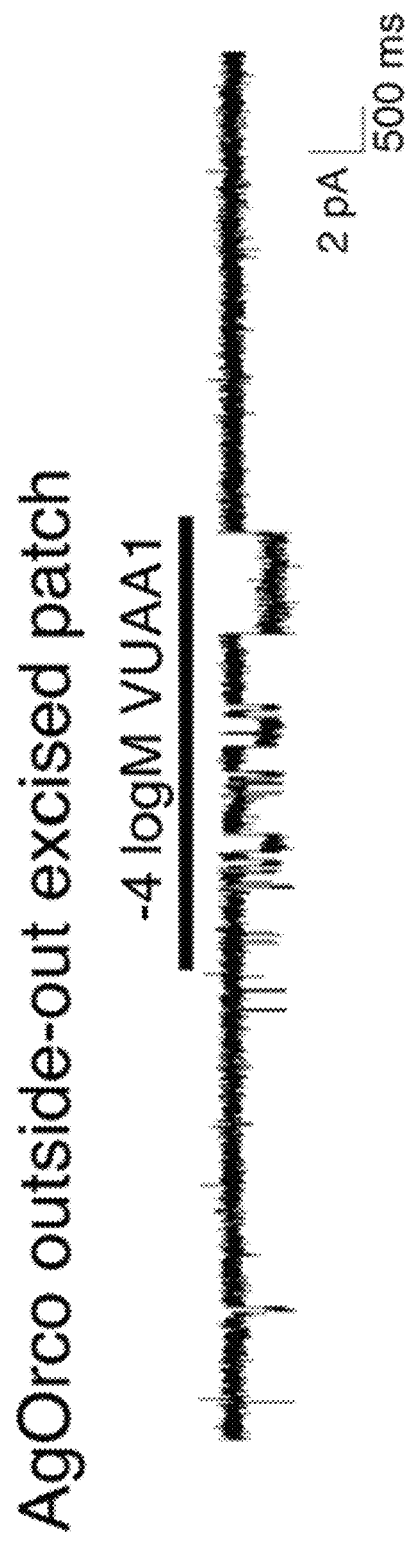
FIGS. 5A-D. Orco is a functional channel and responds to VUAA1 in outside-out membrane patches.
Figure 5B:
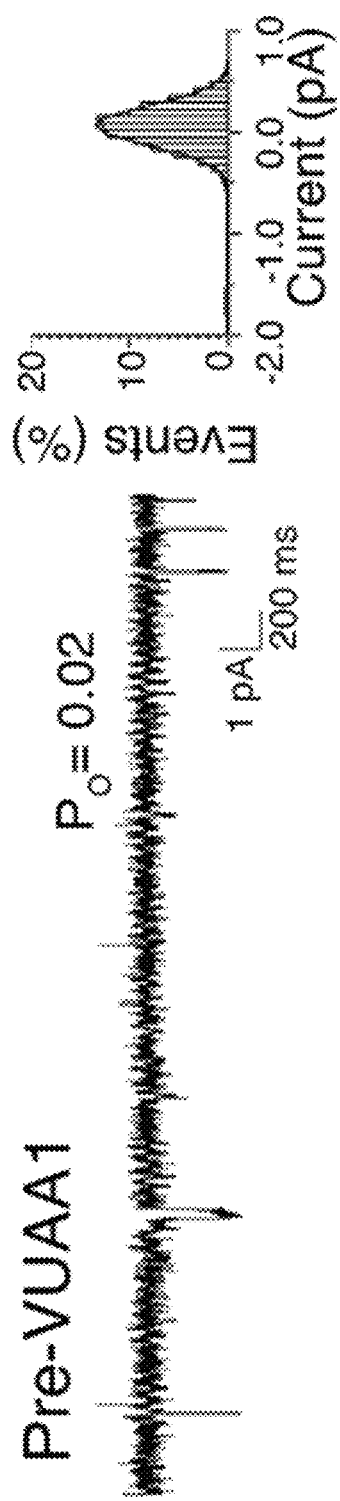
Figure 5C:
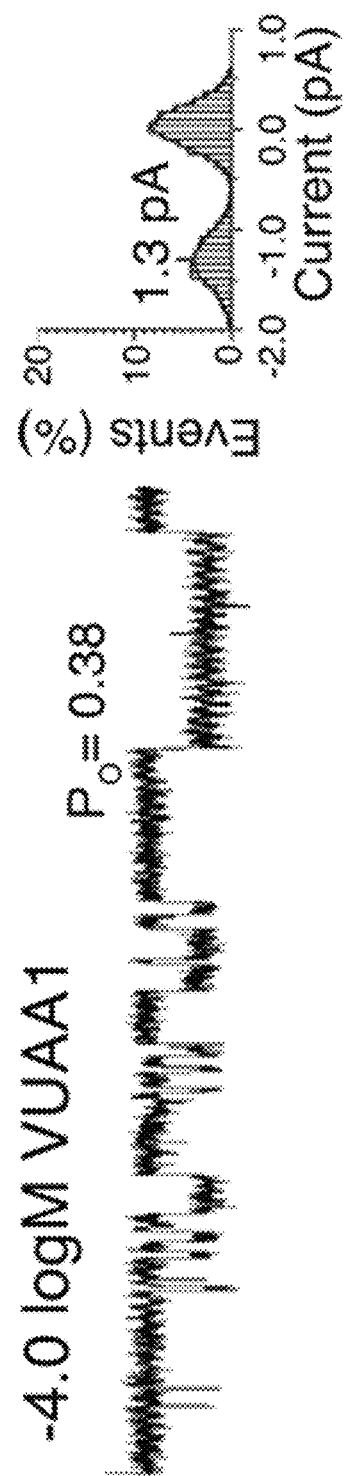
Figure 5D:
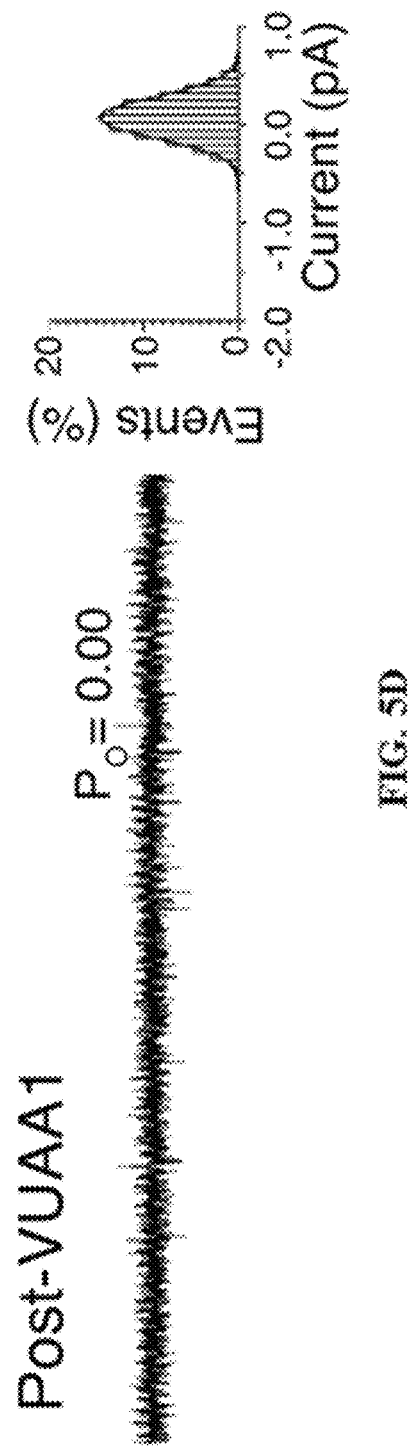

In the next set of studies, outside-out membrane patches were excised from AgORco-expressing cells to examine single-channel currents evoked by VUAA1 (FIG. 5A). Here, spontaneous channel opening was observed before VUAA1 stimulation, but with very low probability ($P_o$=0.02) (FIG. 5B). During a 5 s application of VUAA1 channel opening probability increased to $P_o$=0.38 (FIG. 5C). Subsequent to agonist washout, channel opening probability decreased to 0.00 (FIG. 5D). The average unitary current of AgORco was 1.3±0.3 pA (mean±st. dev.) (FIG. 5C inset) which is consistent with earlier single-channel studies of insect ORs (Sato, 2008). Taken together, these data support our hypothesis that VUAA1 can agonize AgORco in the absence of other intracellular components and provide additional support for the role of VUAA1 as a direct agonist of AgORco and other ORco family members.

The inventors next performed single unit, extracellular electrophysiological recordings on adult female *An. gambiae* to determine whether VUAA1 could activate AgORco-expressing odorant receptor neurons (ORNs) in vivo. ORNs, which express AgORco and a conventional OR are enclosed within the hair-like sensilla present on olfactory tissues. The highly stereotypic capitate peg (Cp) sensilla, which are found on the maxillary palp, contain two OR7 expressing neurons (CpB and CpC) as well as a $CO_2$ sensitive neuron (CpA), which does not express AgORco (Lu, 2007). CpA is clearly distinguished from CpB/C by its large action potential amplitude. The action potential amplitudes of CpB and CpC are much smaller and in some preparations indistinguishable from each other; as a result, the spike activity of CpB and CpC neurons were binned for data analysis. Accordingly, the inventors would expect that if VUAA1 is a specific AgORco agonist, it should selectively increase the spike frequency of the CpB and CpC neurons but have no effect on CpA responses.

Figure 6A:
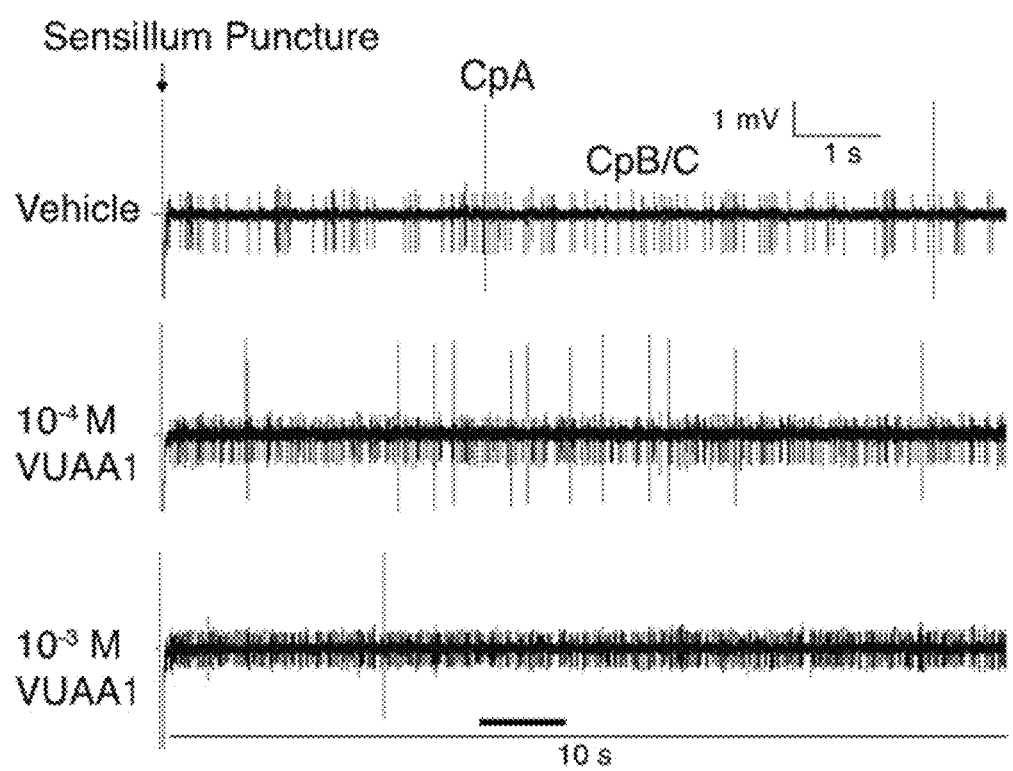
FIGS. 6A-D. VUAA1 activates Orco-expressing neurons in *Anopheles gambiae* females.
Figure 6B:
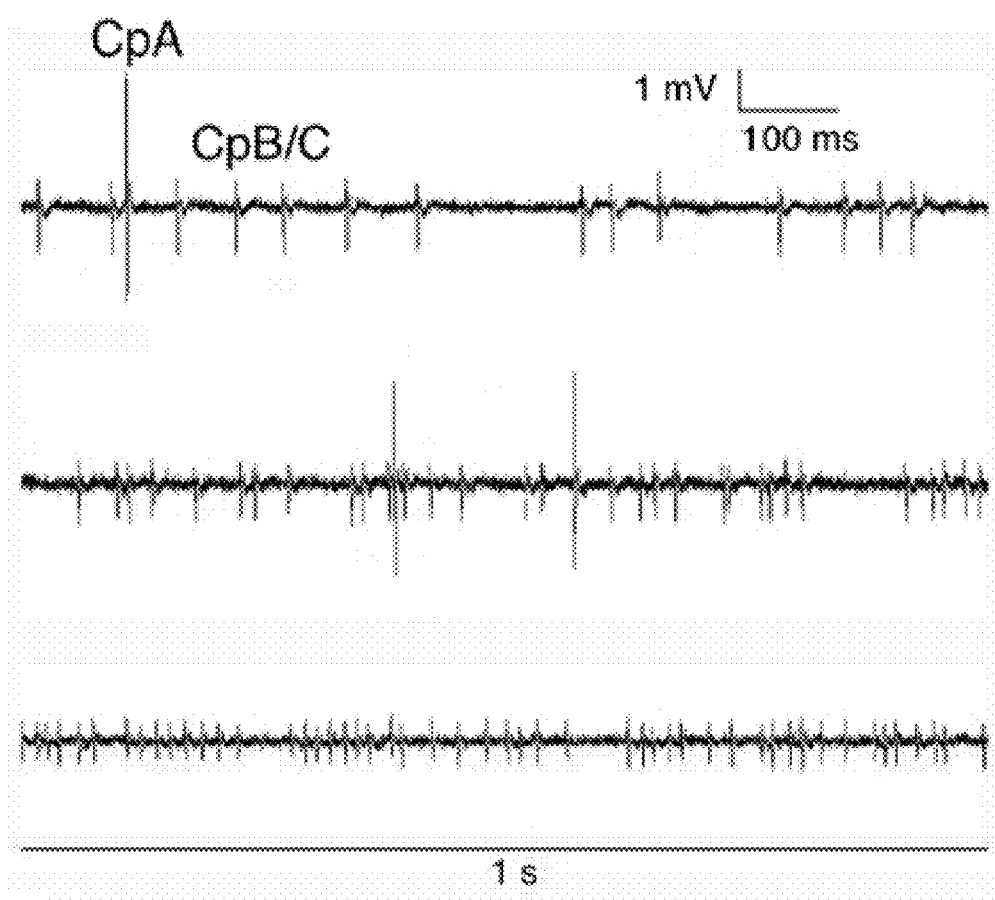
Figure 6C:
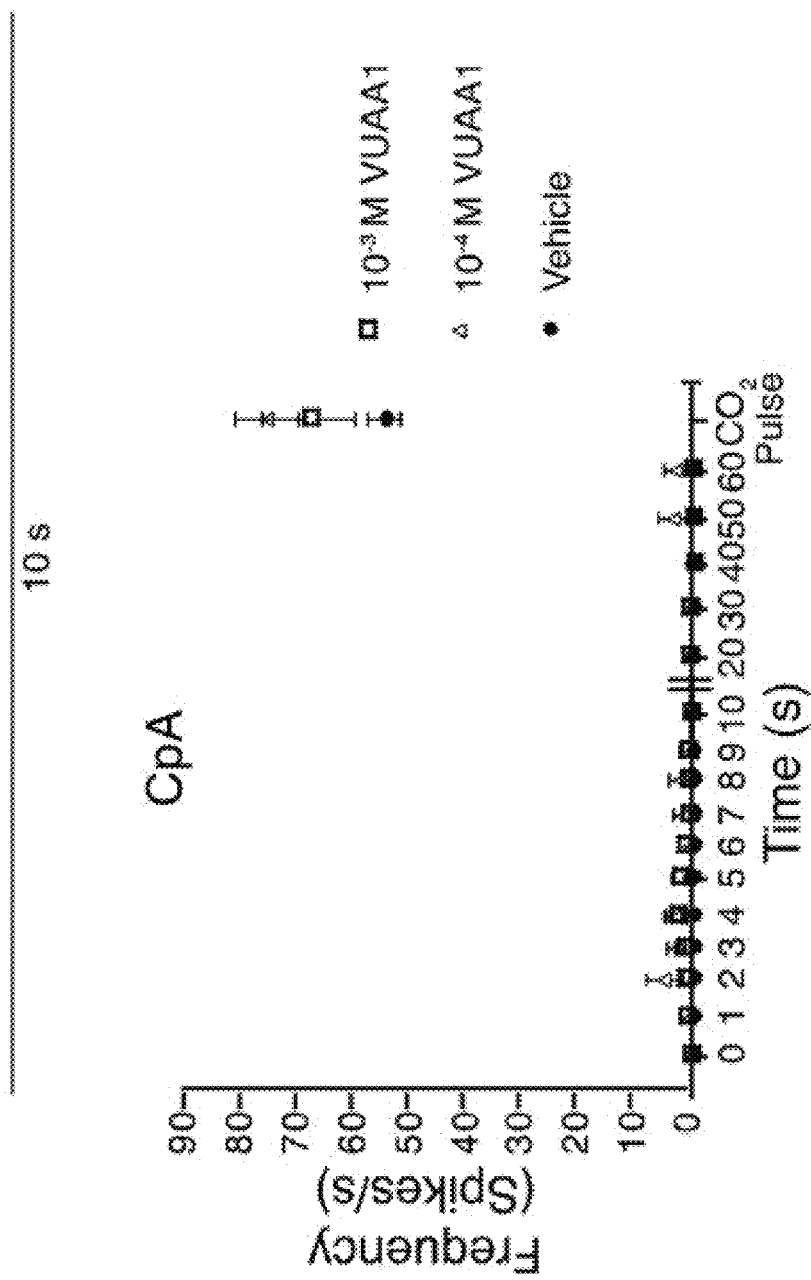
Figure 6D:
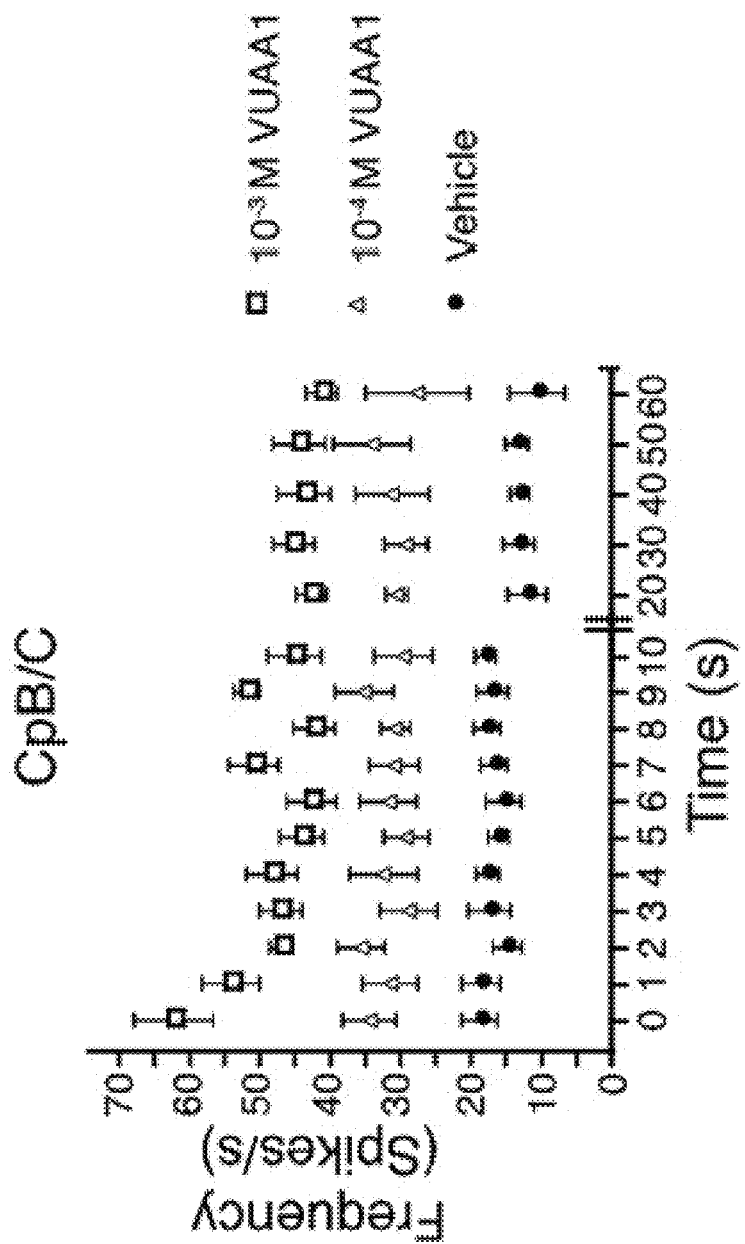
Figure 7A:
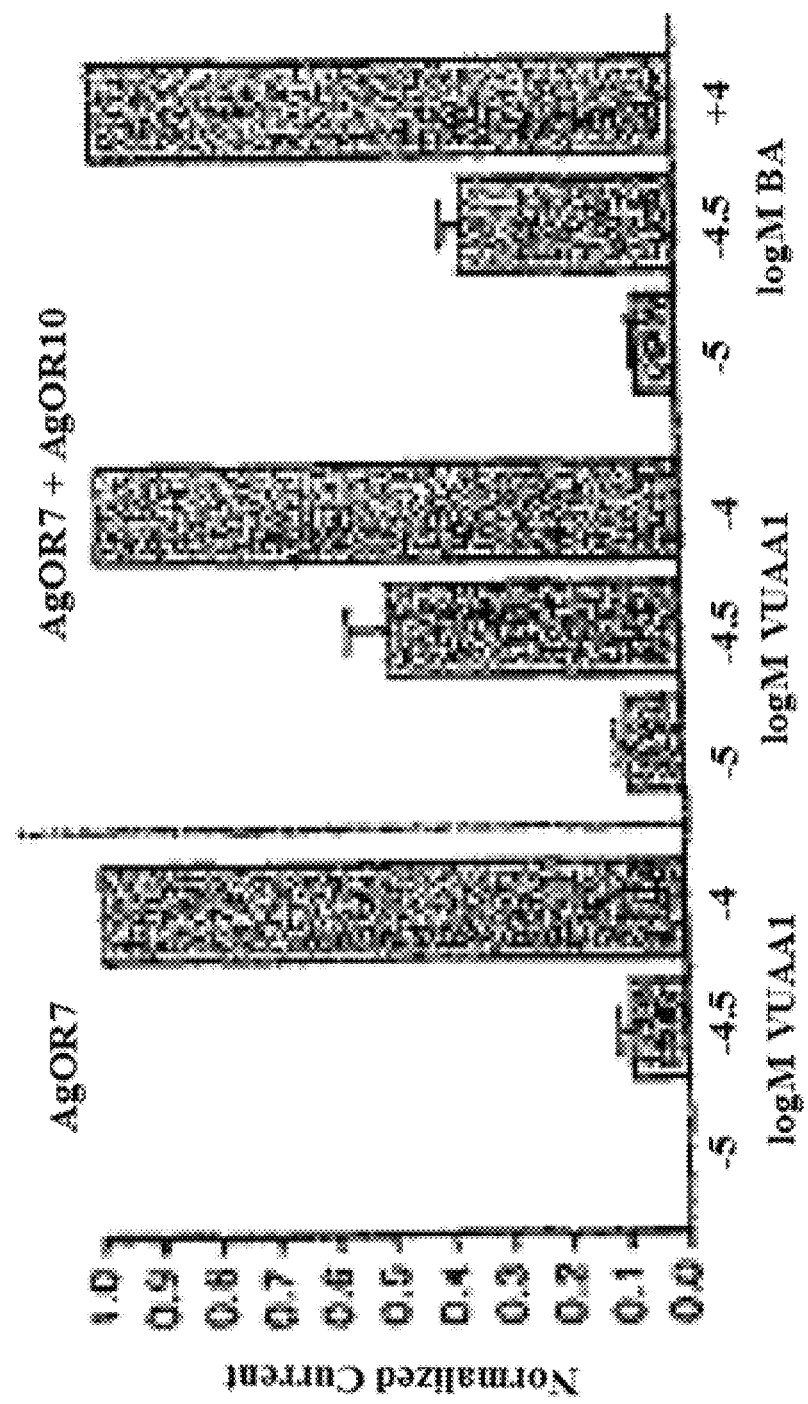
Figure 7F:
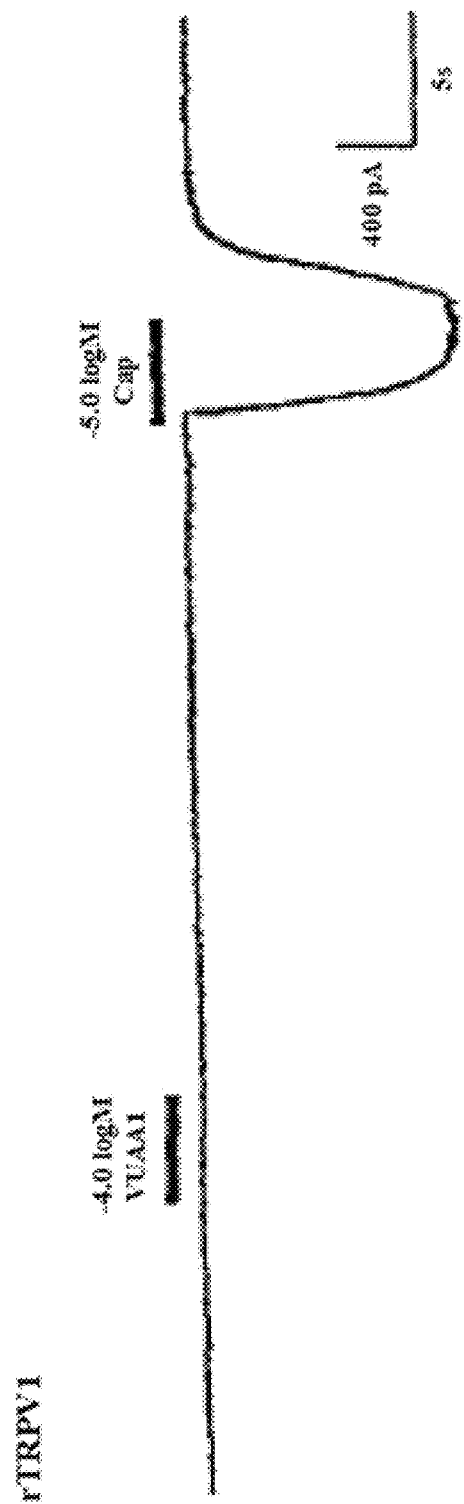
Figure 8A:
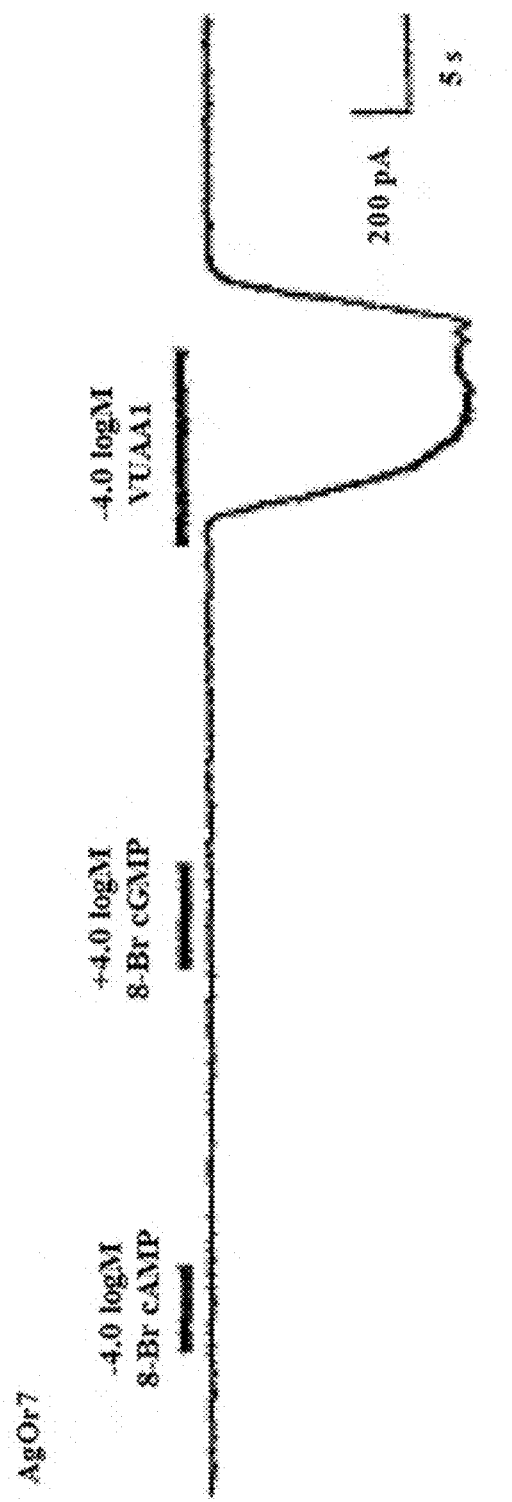
FIGS. 8A-C. 8-Br-cAMP and 8-Br-cGMP did not elicit currents in Orco or Orco+AgOR10 cells.
Figure 8B:
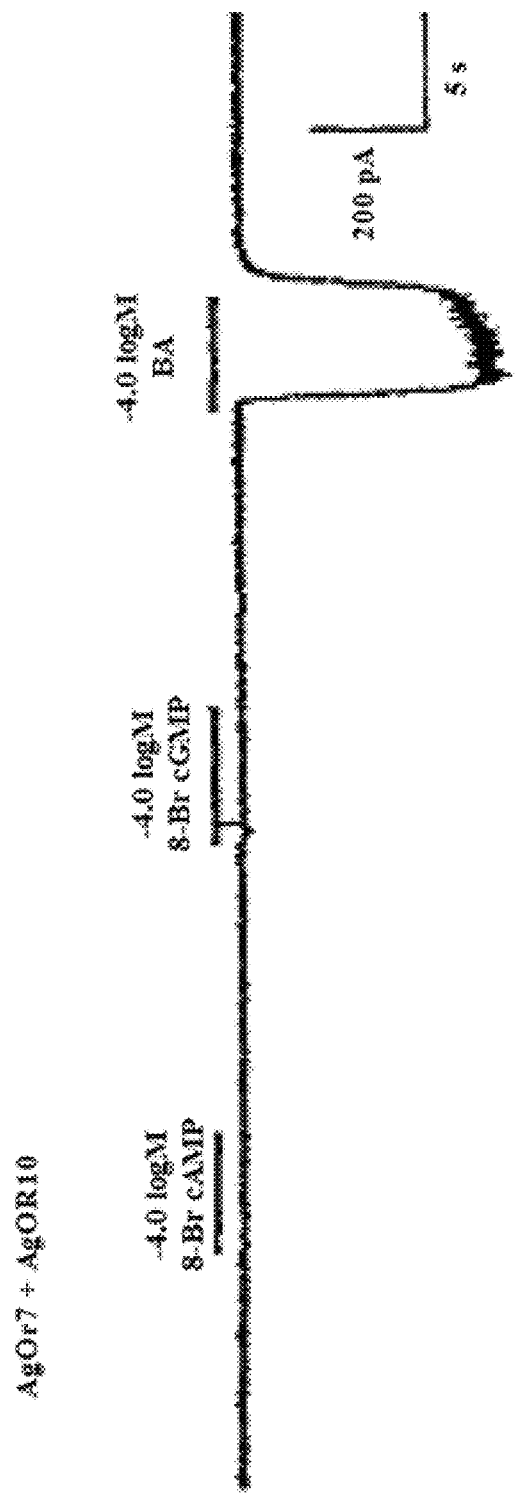
Figure 8C:
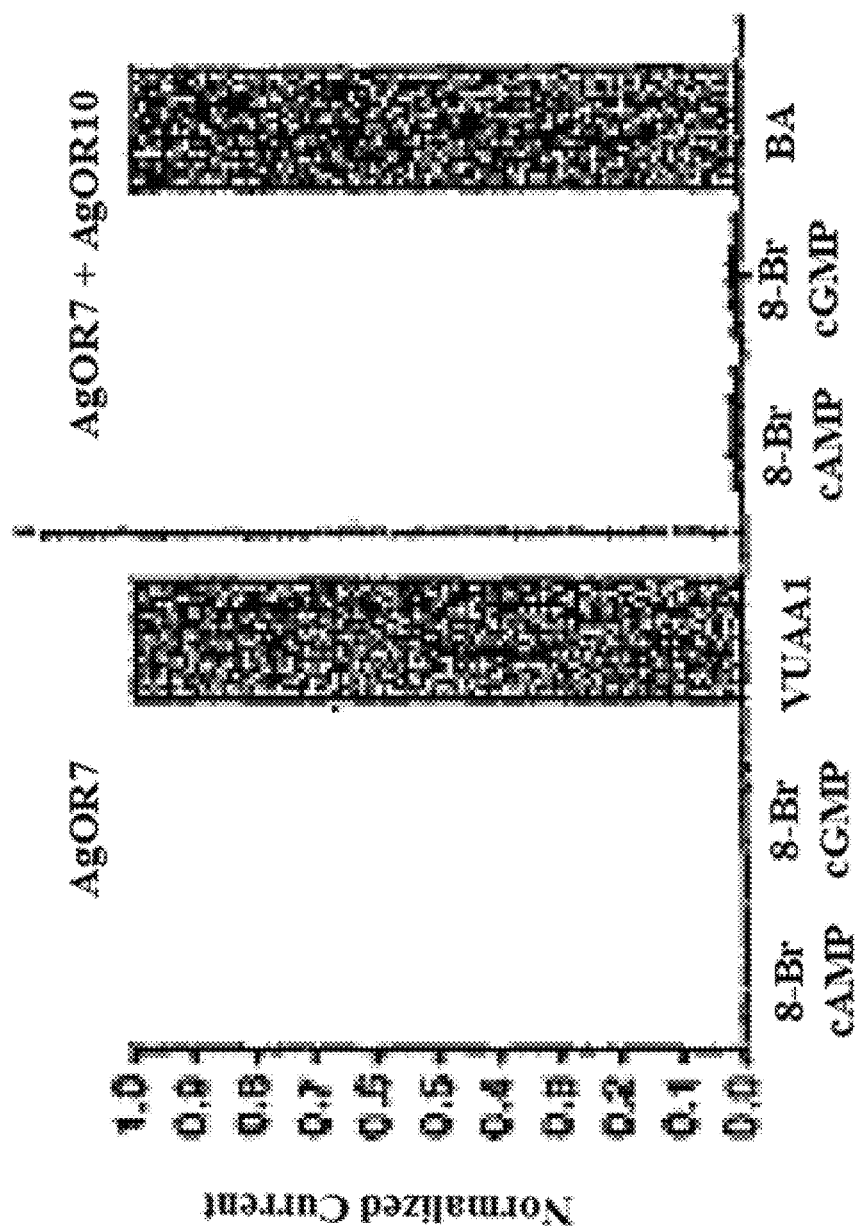
Figure 9:
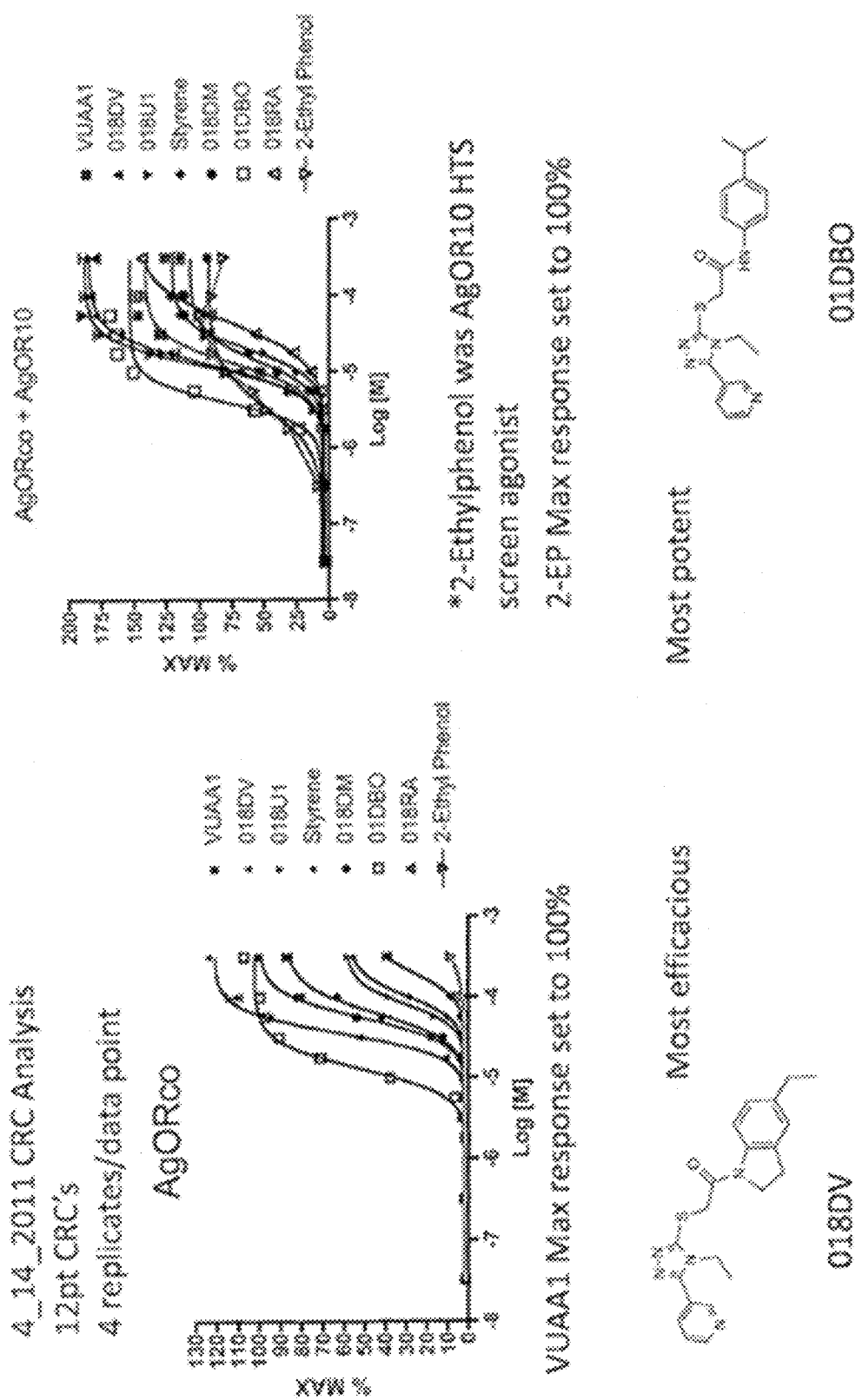
FIG. 9. VUAA1 Analog Agonists. Concentration response curves (CRCs) generated from Fluro-4 acetoxymethyl ester-based Ca imaging with Orco (left) and Orco+AgOR10 (right) cell lines in response to VUAA1 or associated analogs (see "Example 1: Materials and Methods." for detailed descriptions of methods). Orco responses were normalized to VUAA1 while Orco+AgOR10 responses were normalized to 2-ethylphenol (2-EP). Curves were generated using GraphPad Prism.
Figure 10:
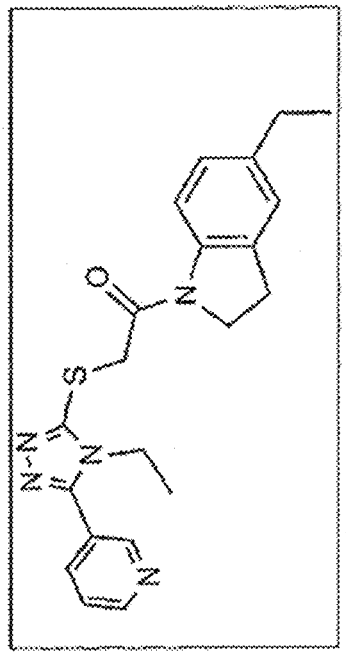
FIG. 10. Activity for Analog VU0449346. (Sub-figure at left titled Orco) Concentration response curve of HEK-293 cells expressing Orco only in response to compound VU0449346 or VUAA1. (Sub-figure at left titled Orco+AgOR10) Concentration response curve of HEK-293 cells expressing Orco+AgOR10 in response to compound VU0449346 or VUAA1. (Inset table, top left) The concentration required to elicit 50% of the maximal response (EC50) for Orco only cells is listed as Orco EC50. Orco MAX is listed as the maximal response elicited from Orco expressing cells in response to VU0449346 (as a percentage of the peak activity of VUAA1, after normalization to 100% of VUAA1 as in FIG. 9). MW—Molecular weight of VU0449346. (Sub-figure at right) Structure of VU0449346.
Figure 10:
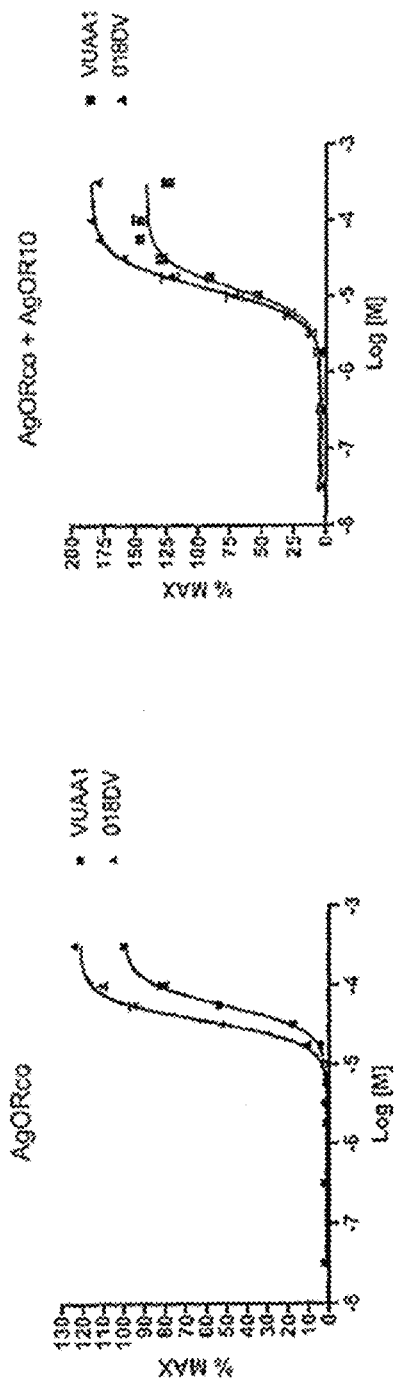
Figure 11:
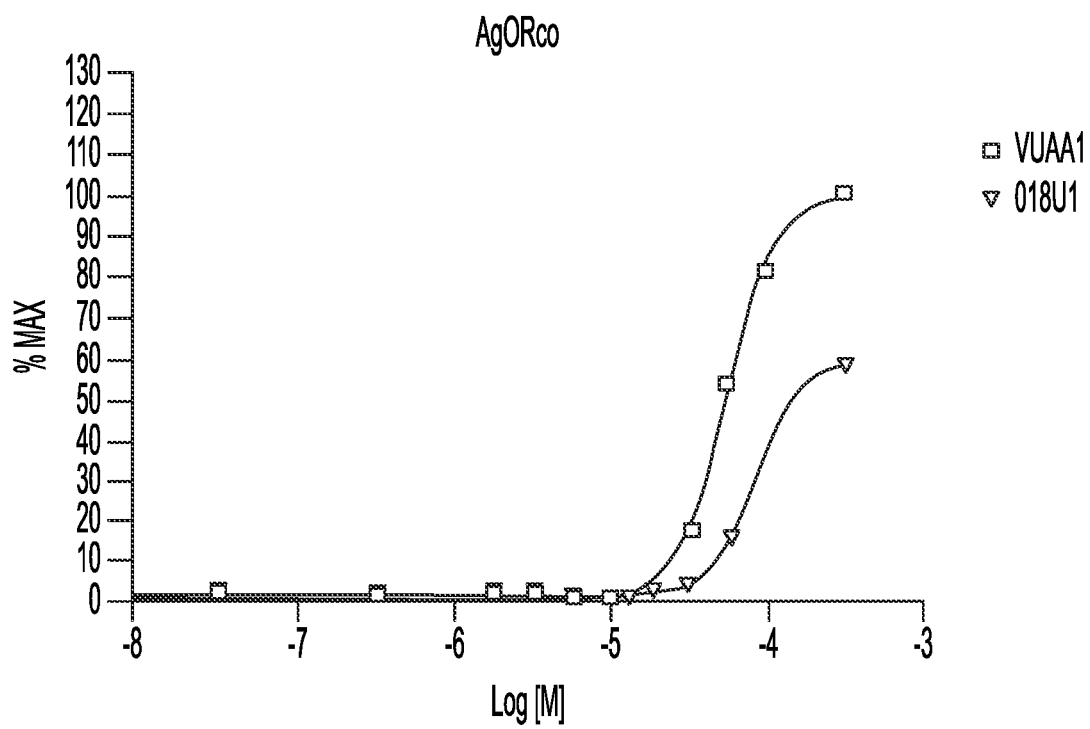
FIG. 11. Activity for Analog VU0448094. As in FIG. 10, but structure activities correspond to compound VU0448094.
Figure 11:
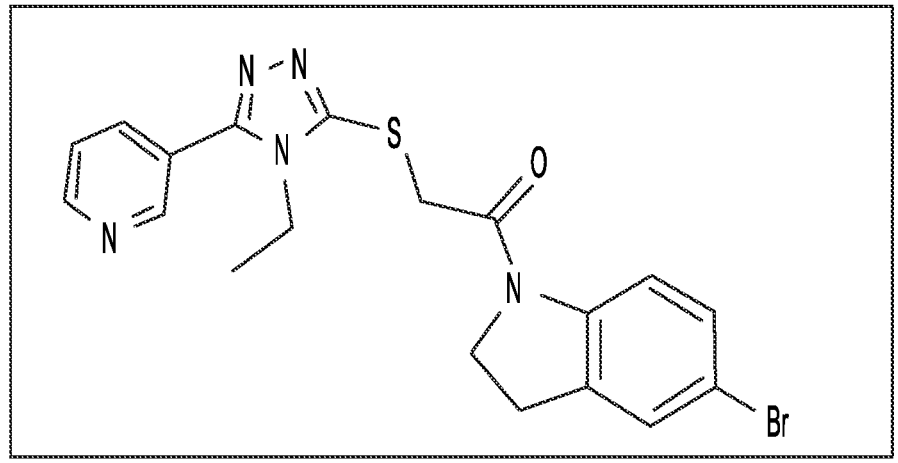
Figure 11:
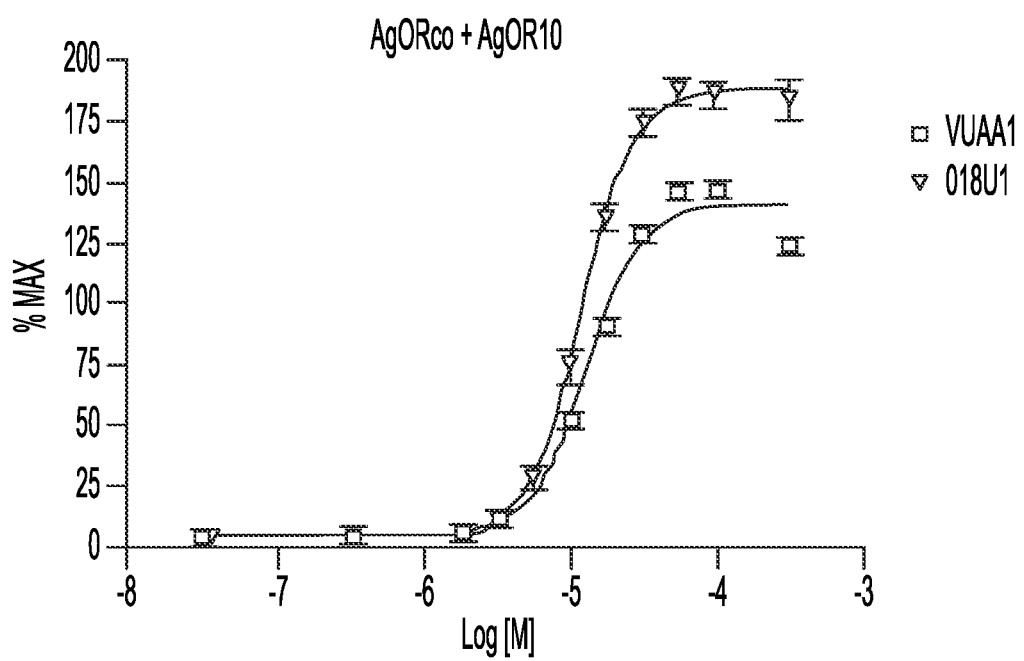
Figure 12:
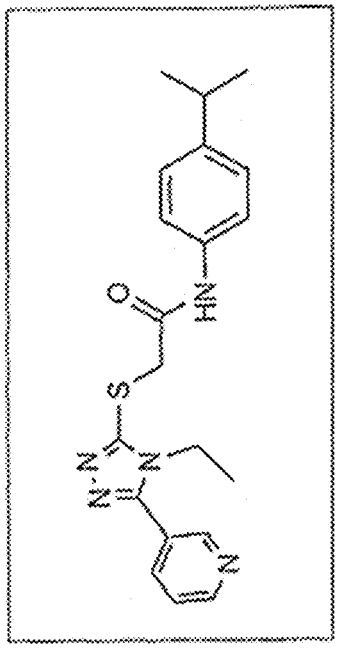
FIG. 12. Activity for Analog VU0448520. As in FIG. 10, but structure and activities correspond to compound VU0448520.
Figure 12:
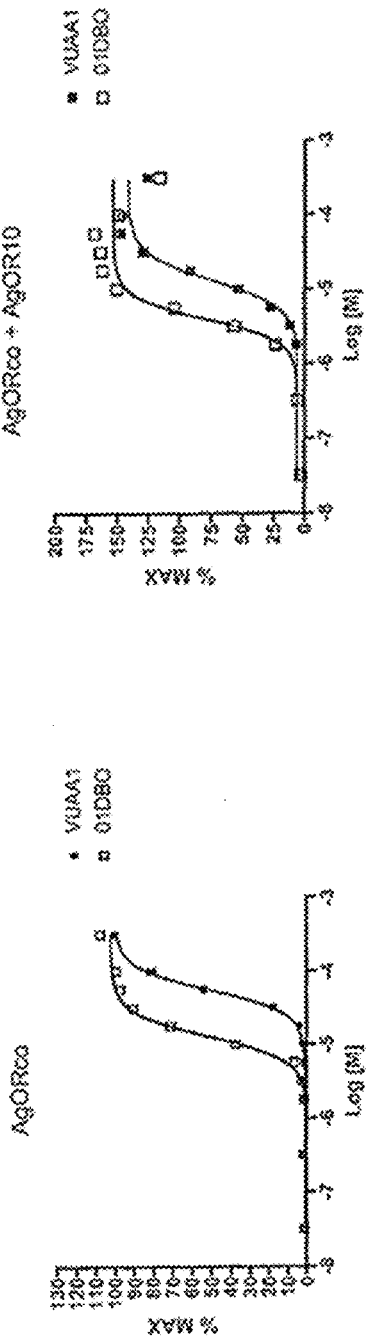
Figure 13:
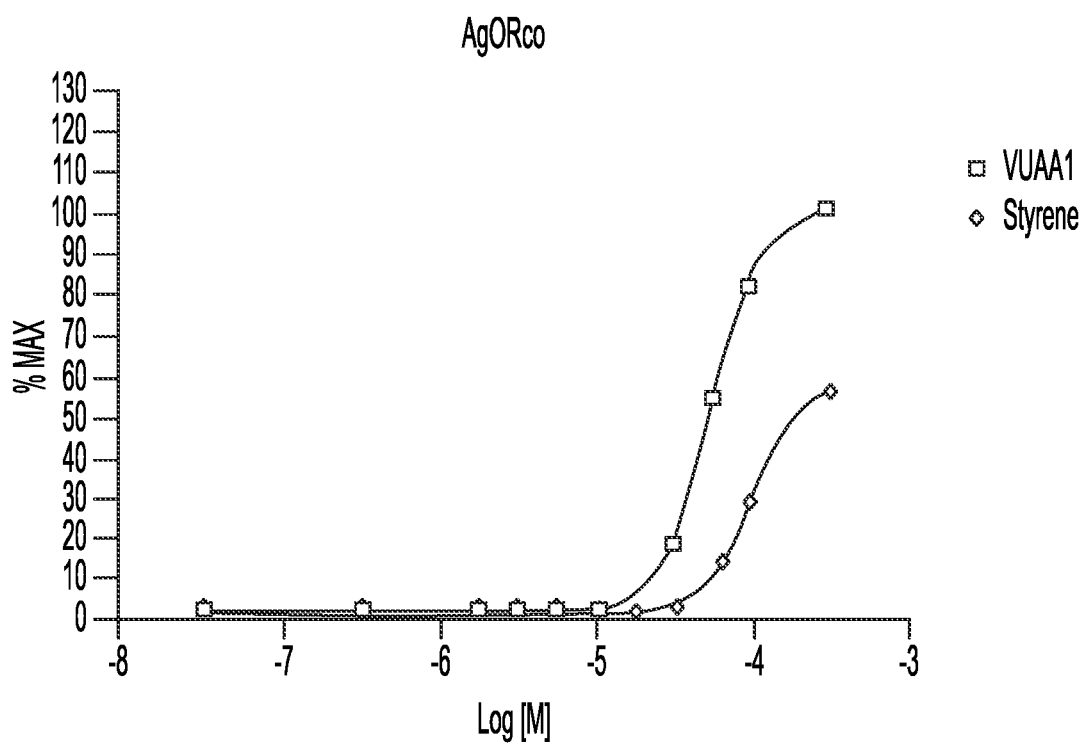
FIG. 13. Activity for Analog VU0431284. As in FIG. 10, but structure and activities correspond to compound VU0431284.
Figure 13:
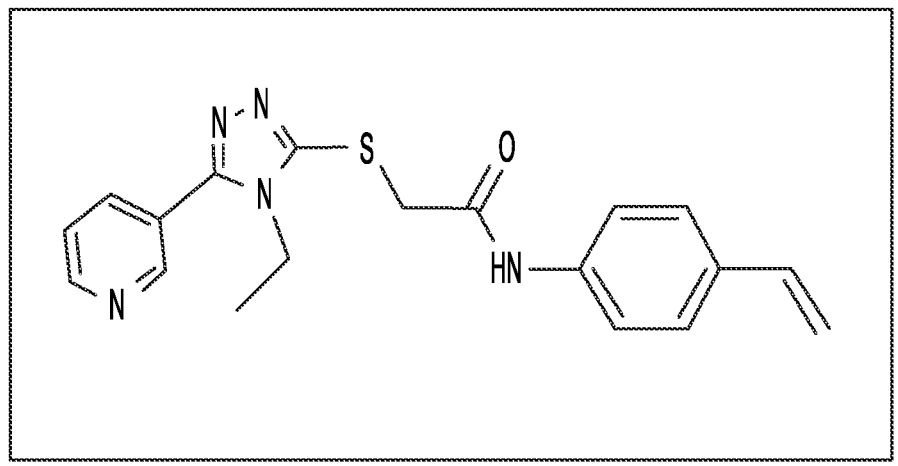
Figure 13:
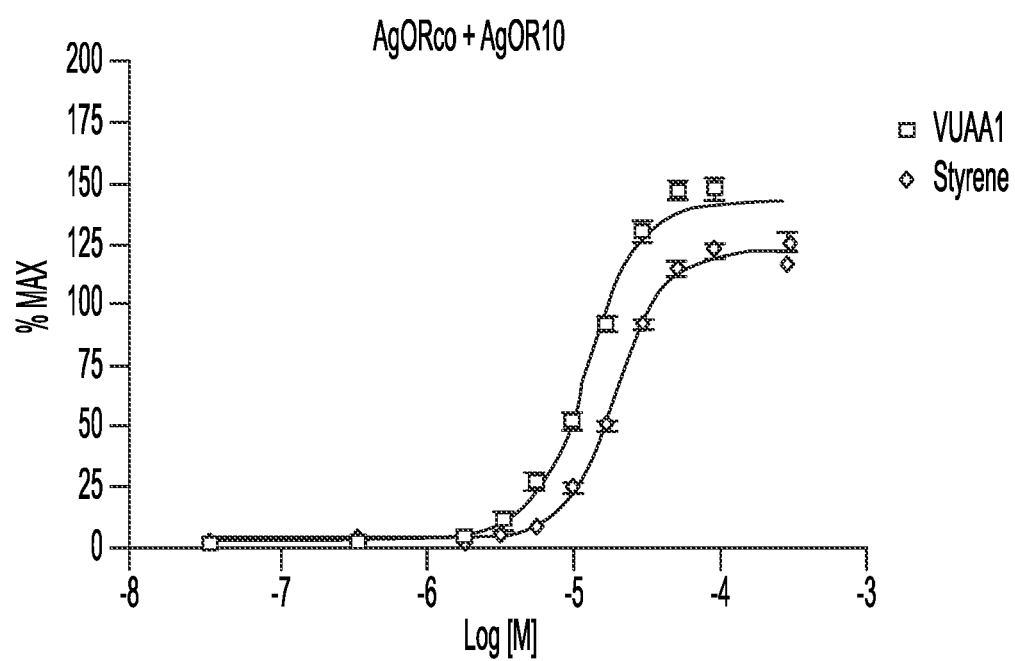
Figure 14:
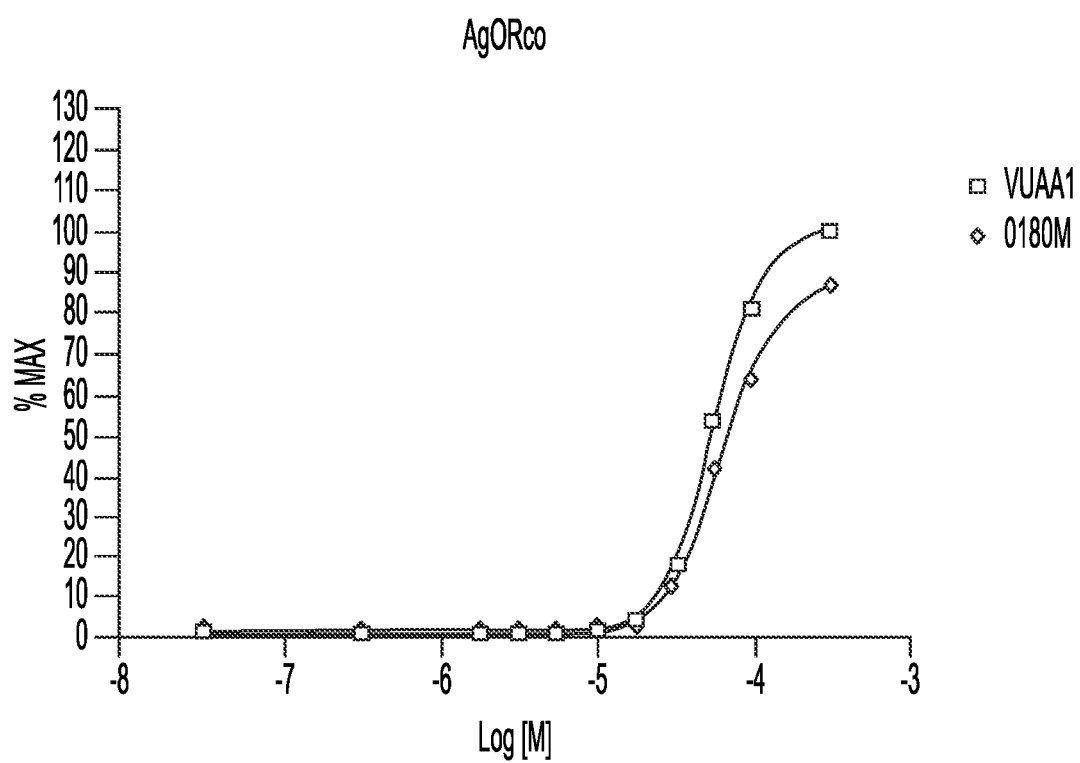
FIG. 14. Activity for Analog VU0449342. As in FIG. 10, but structure and activities correspond to compound VU0449342.
Figure 14:
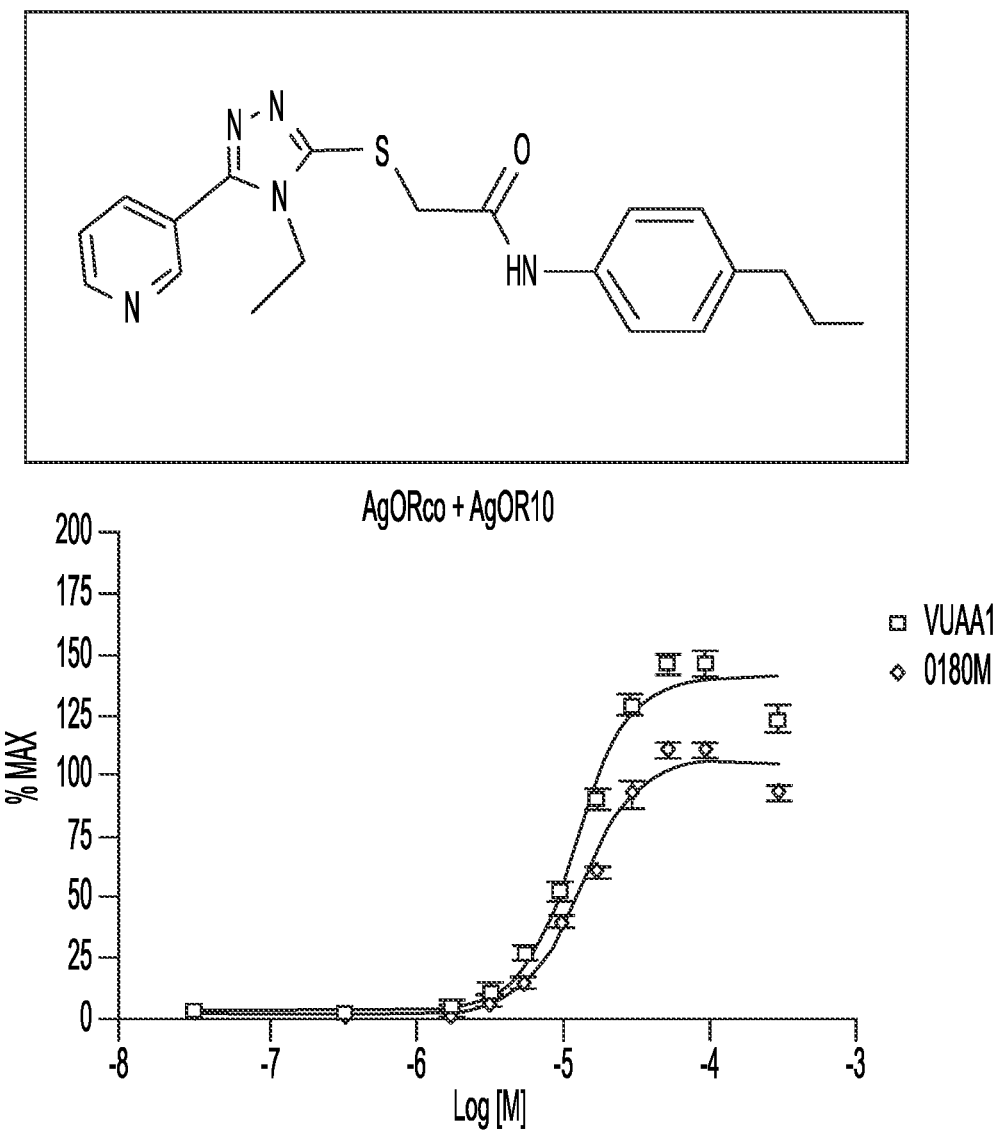
Figure 15:
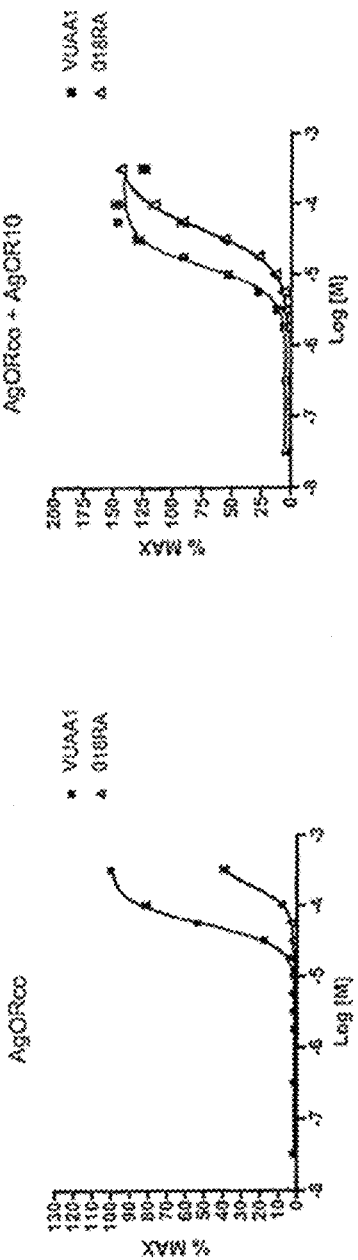
FIG. 15. Activity for Analog VU0448095. As in FIG. 10, but structure and activities correspond to compound VU0448095.
Figure 16:
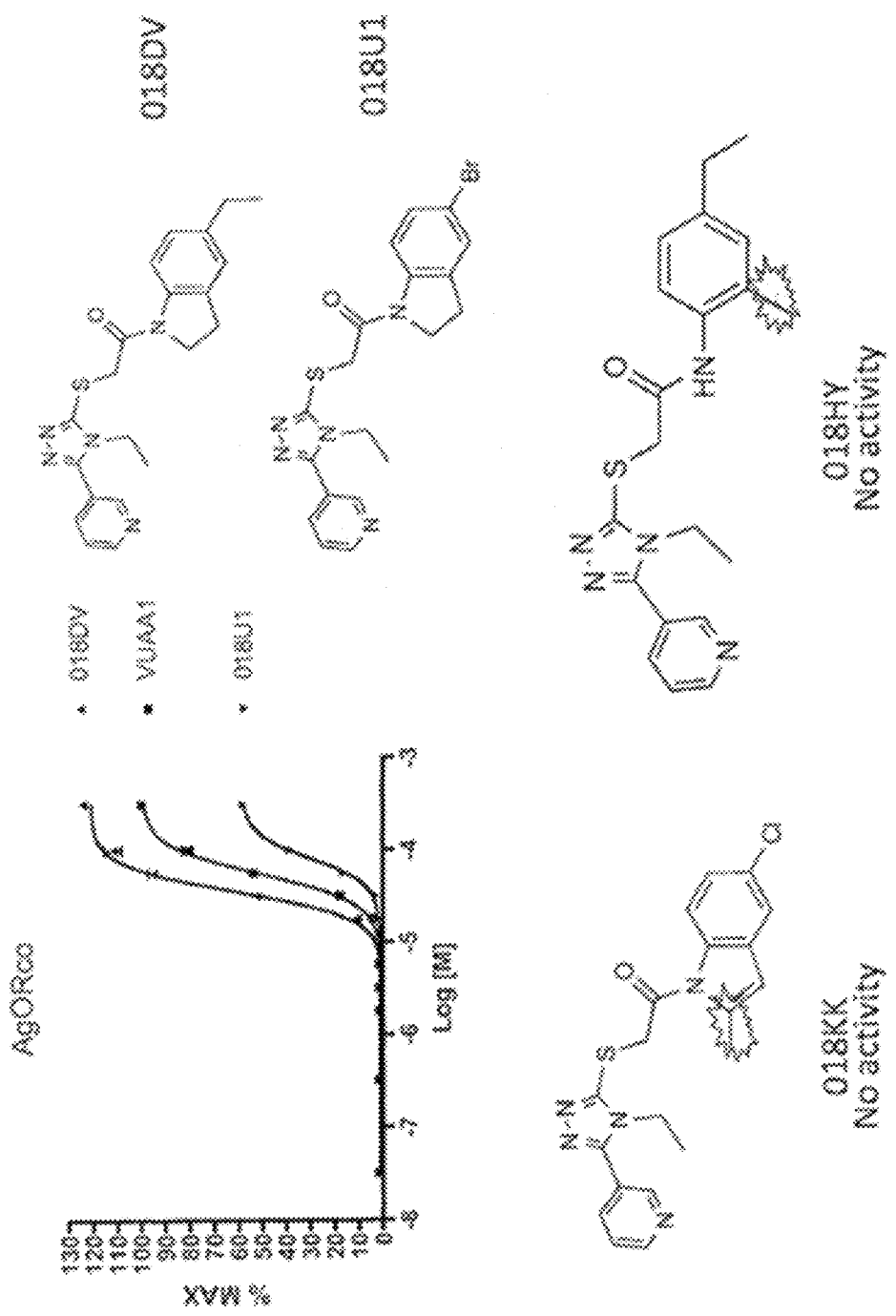
FIG. 16. VUAA1 Indoline Analogs. Composite activity for agonists containing similar indoline moieties, VU0449346 and VU0448094 (top). In contrast, are compounds that are related, but which demonstrate no activity as tested at 10 uM (bottom).
Figure 17:
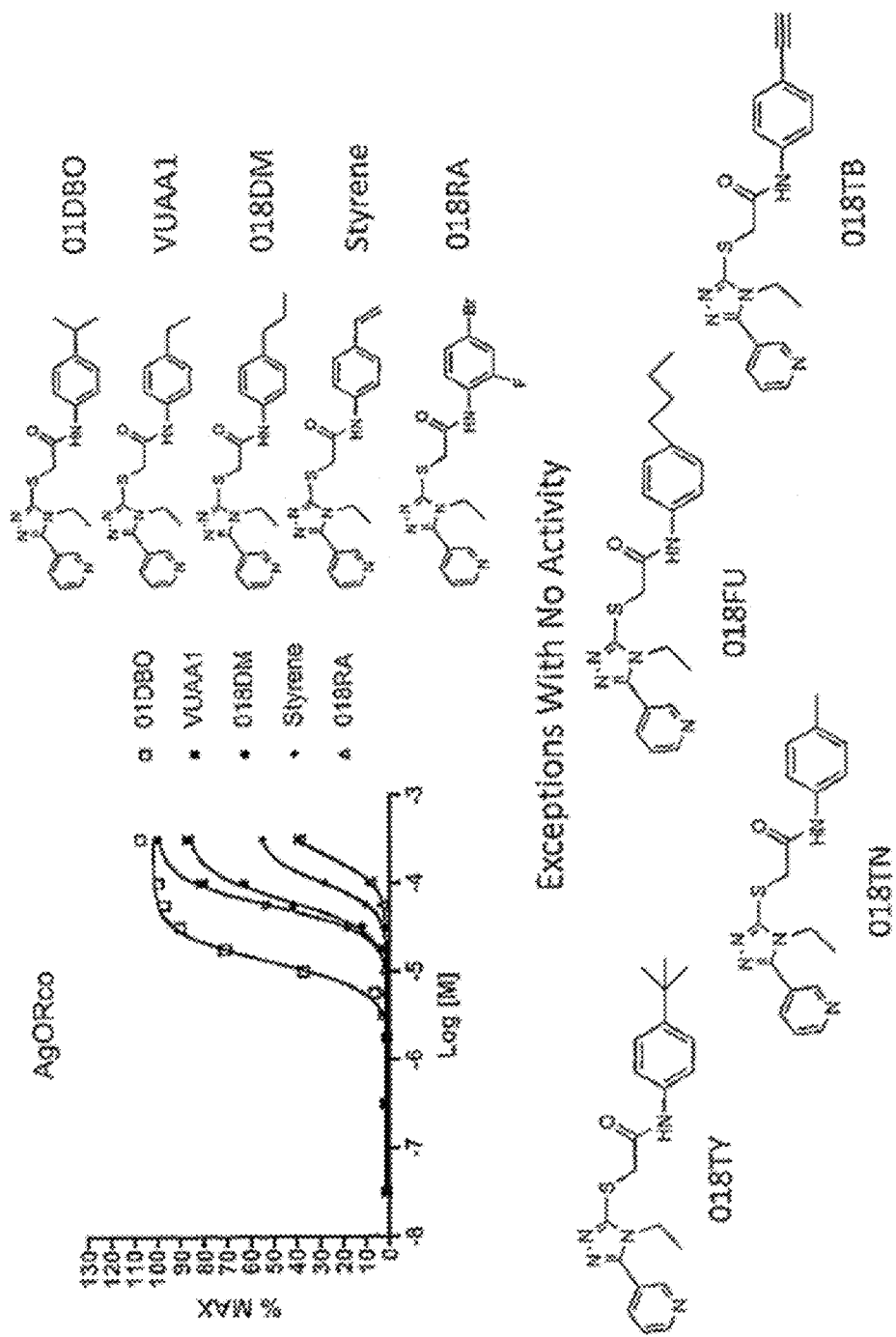
FIG. 17. VUAA1 Aniline Analogs. Composite activity for agonists containing similar aniline moieties. In contrast, (bottom) are compounds that are related, but have no activity as tested at 10 uM.
Figure 18:
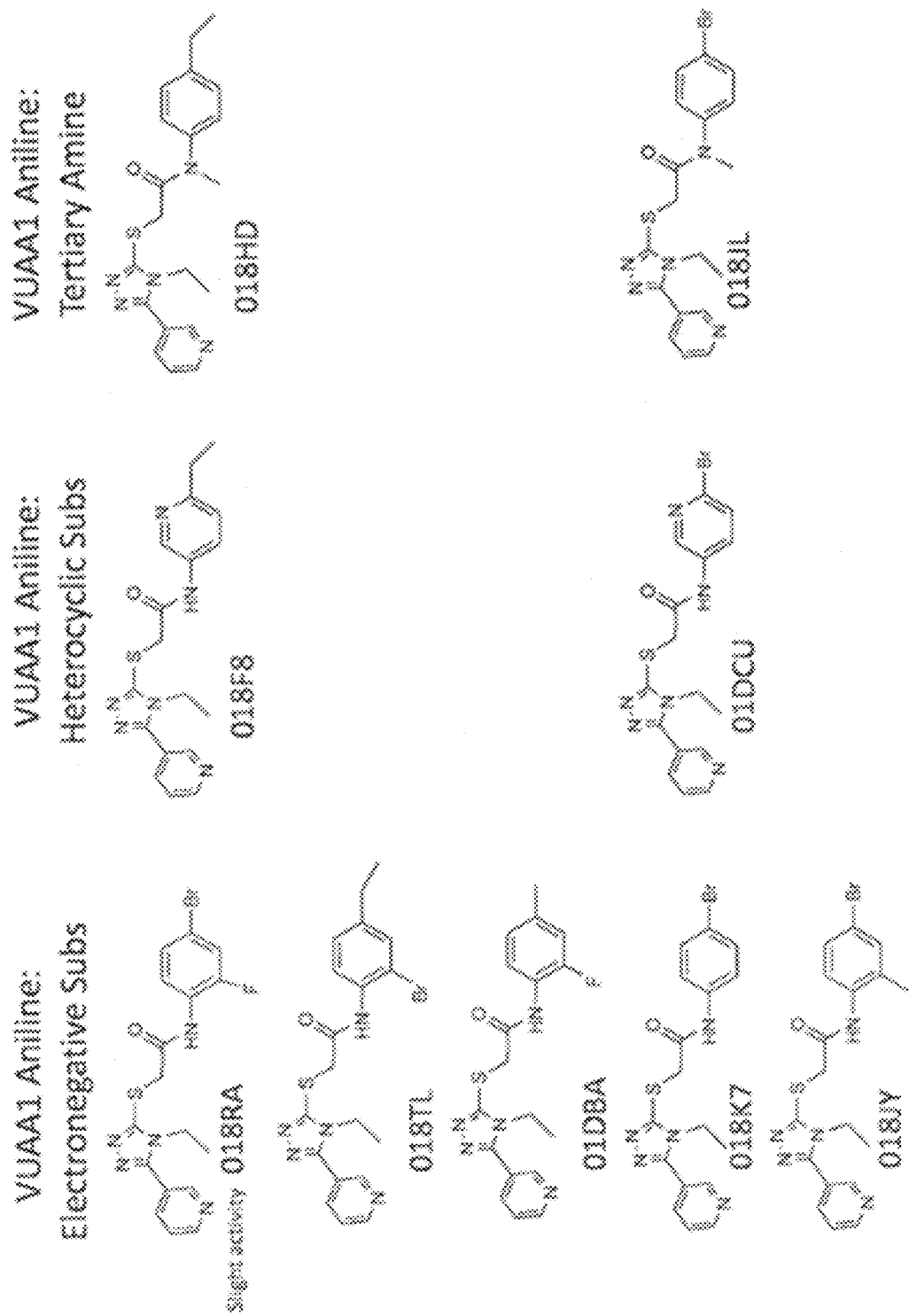
FIG. 18. Aniline Activity "Killers." Composite structures for compounds that demonstrate no activity as tested at 10 uM (with the exception of VU0448095, which has limited activity). (Left column) Compounds with similar electronegative substitutions. (Center column) Compounds with similar substitutions to create heterocyclic ring analogs. (Right column) Compounds with similar substitutions to create analogs containing a tertiary amine.
Figure 19:
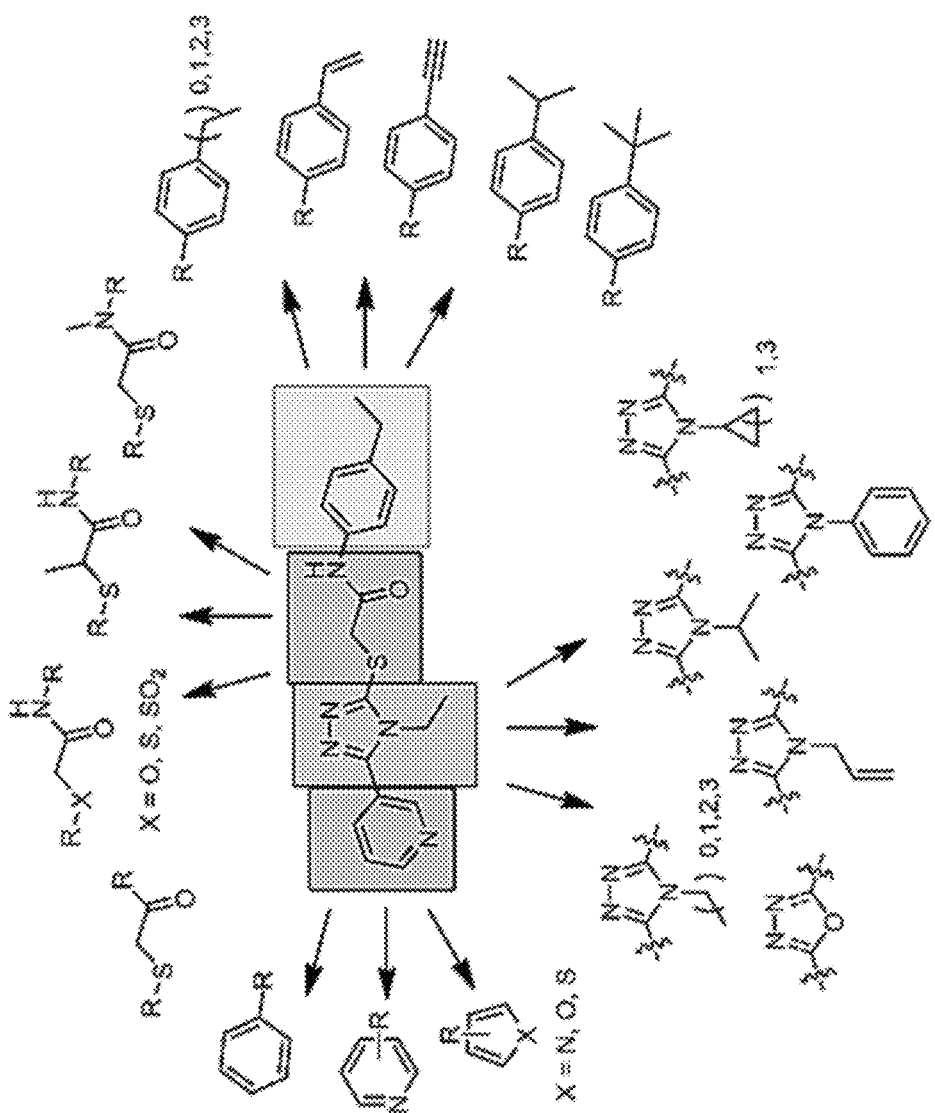
FIG. 19 shows VUAA compounds agonize mosquito odorant receptors (ORs). The structure of VUAA1 was divided into regions based on chemical structure and systematic substitutions were made at each position.
Figure 20:
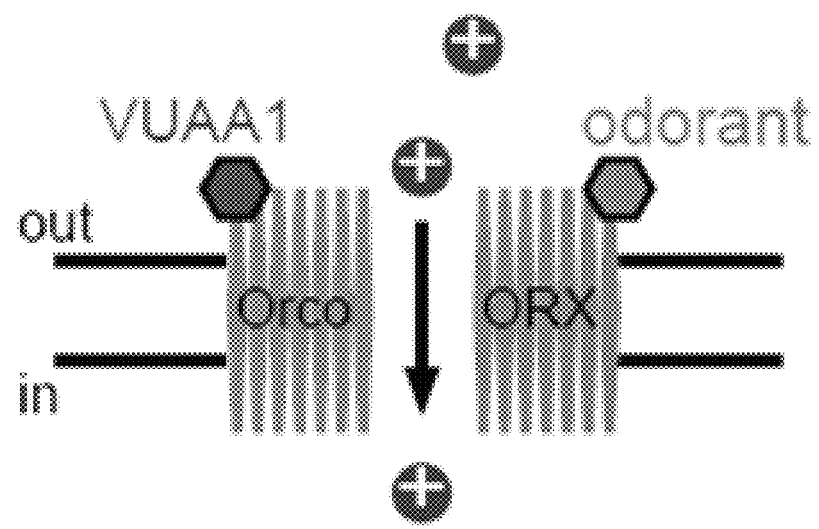
FIG. 20 shows the mechanism of VUAA1.
Figure 21:
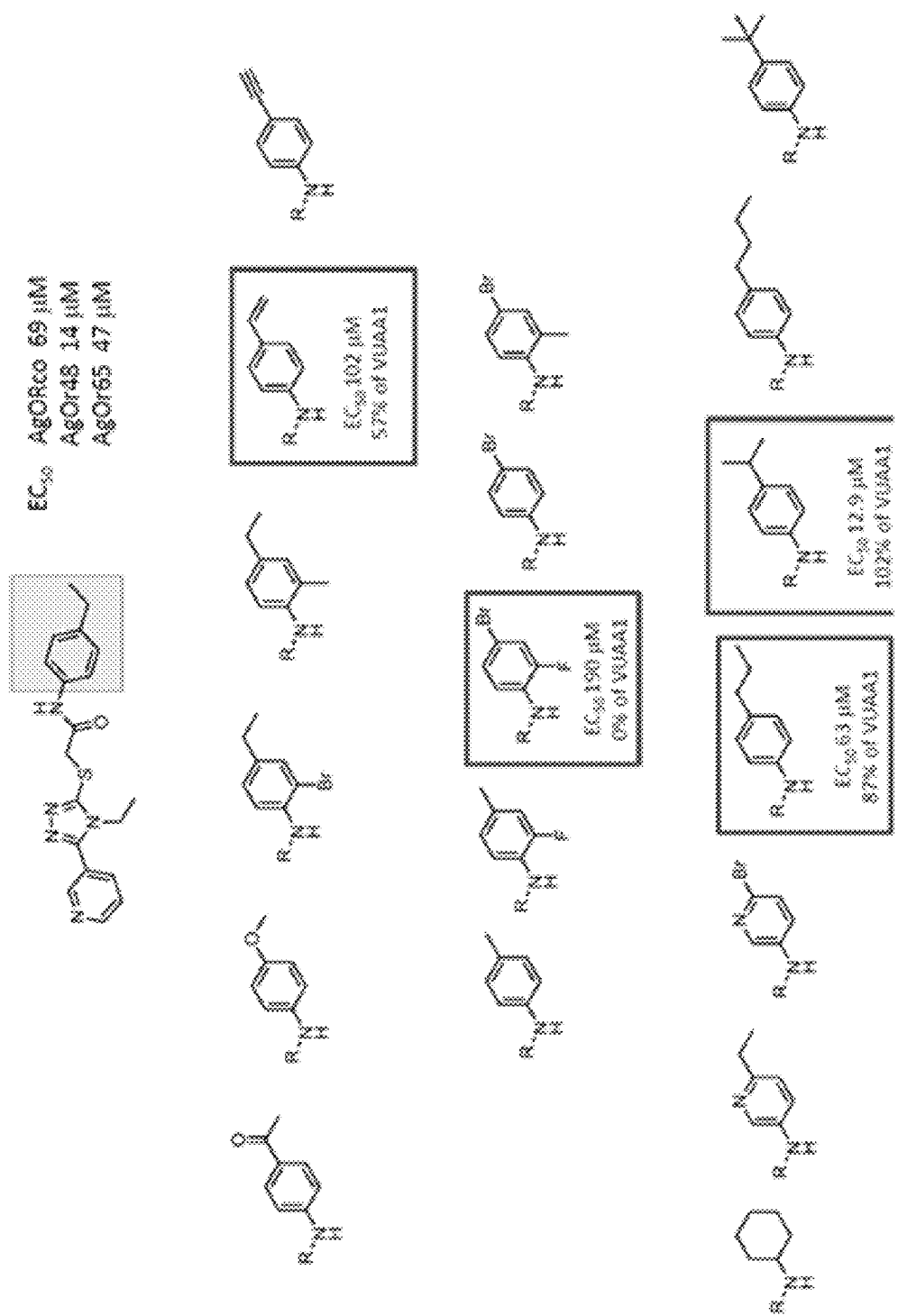
FIG. 21 shows VUAA derivatives and their biological data.
Figure 22:
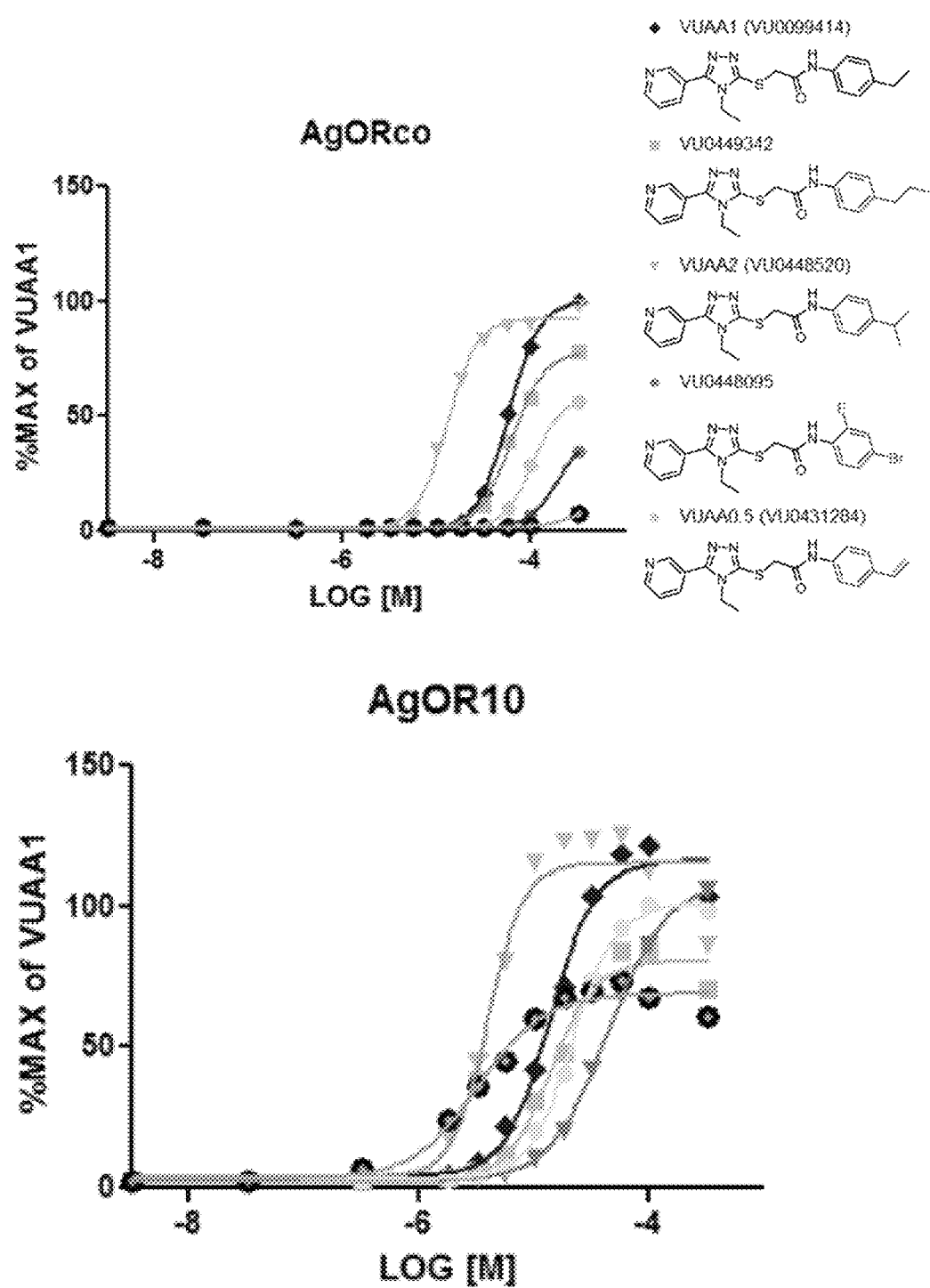
FIG. 22 shows compounds and their ability to agonize mosquito OR receptors.
Figure 23:
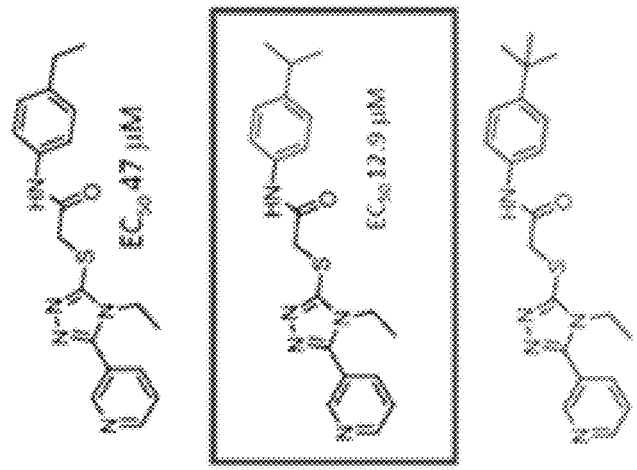
FIG. 23 shows VUAA derivatives and biological data related thereto.
Figure 23:
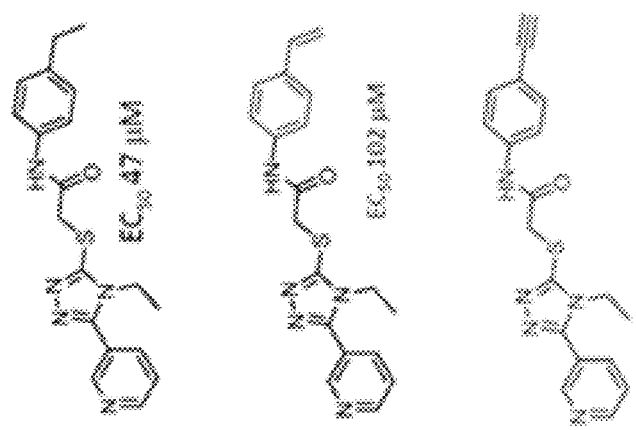
Figure 23:
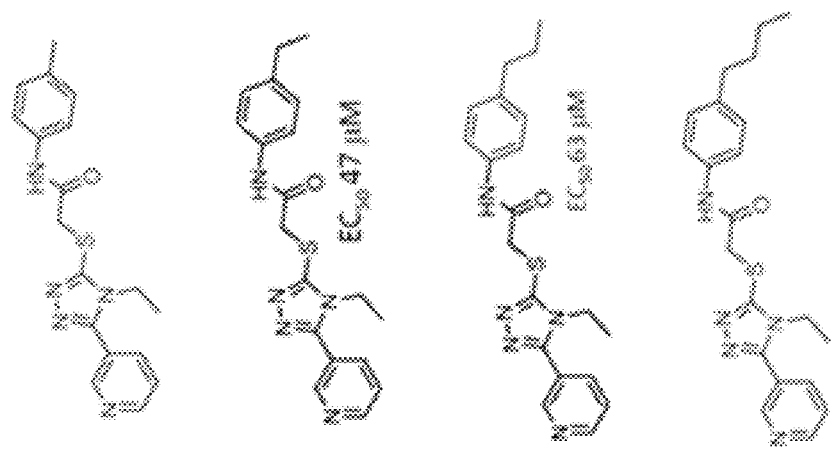
Figure 24:
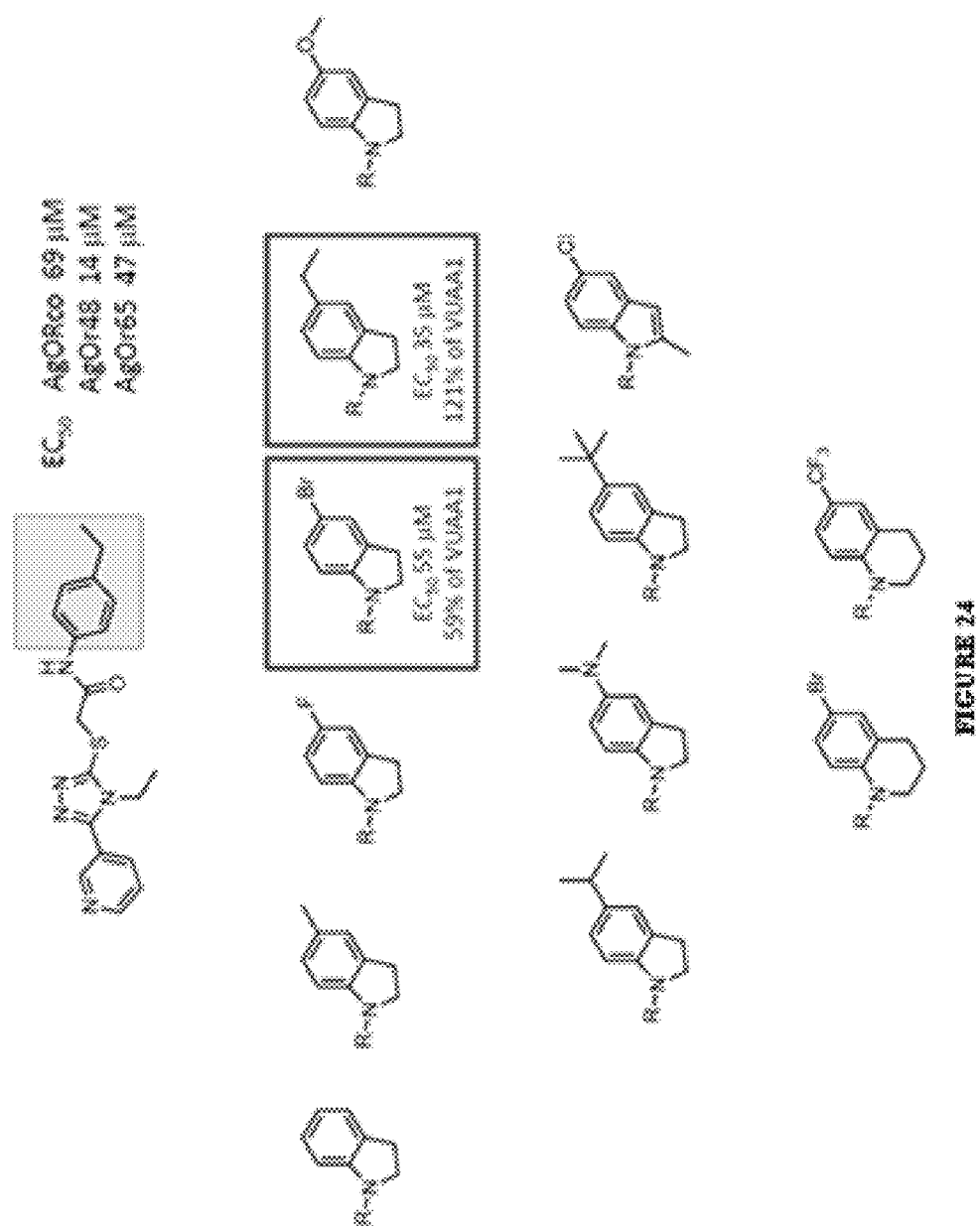
FIG. 24 shows VUAA derivatives and biological data related thereto.
Figure 25:
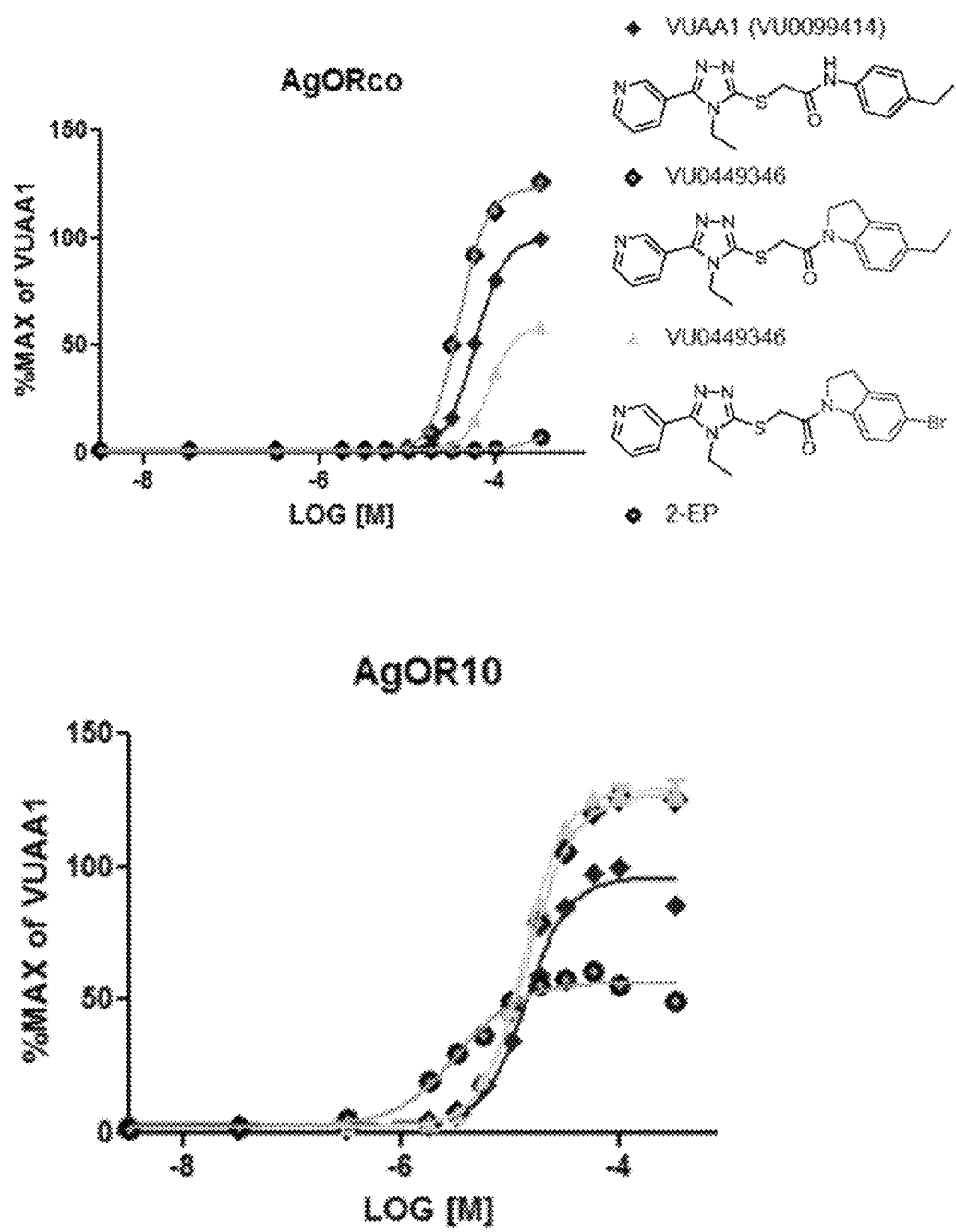
FIG. 25 shows VUAA derivatives and their ability to agonize mosquito ORs.
Figure 26:
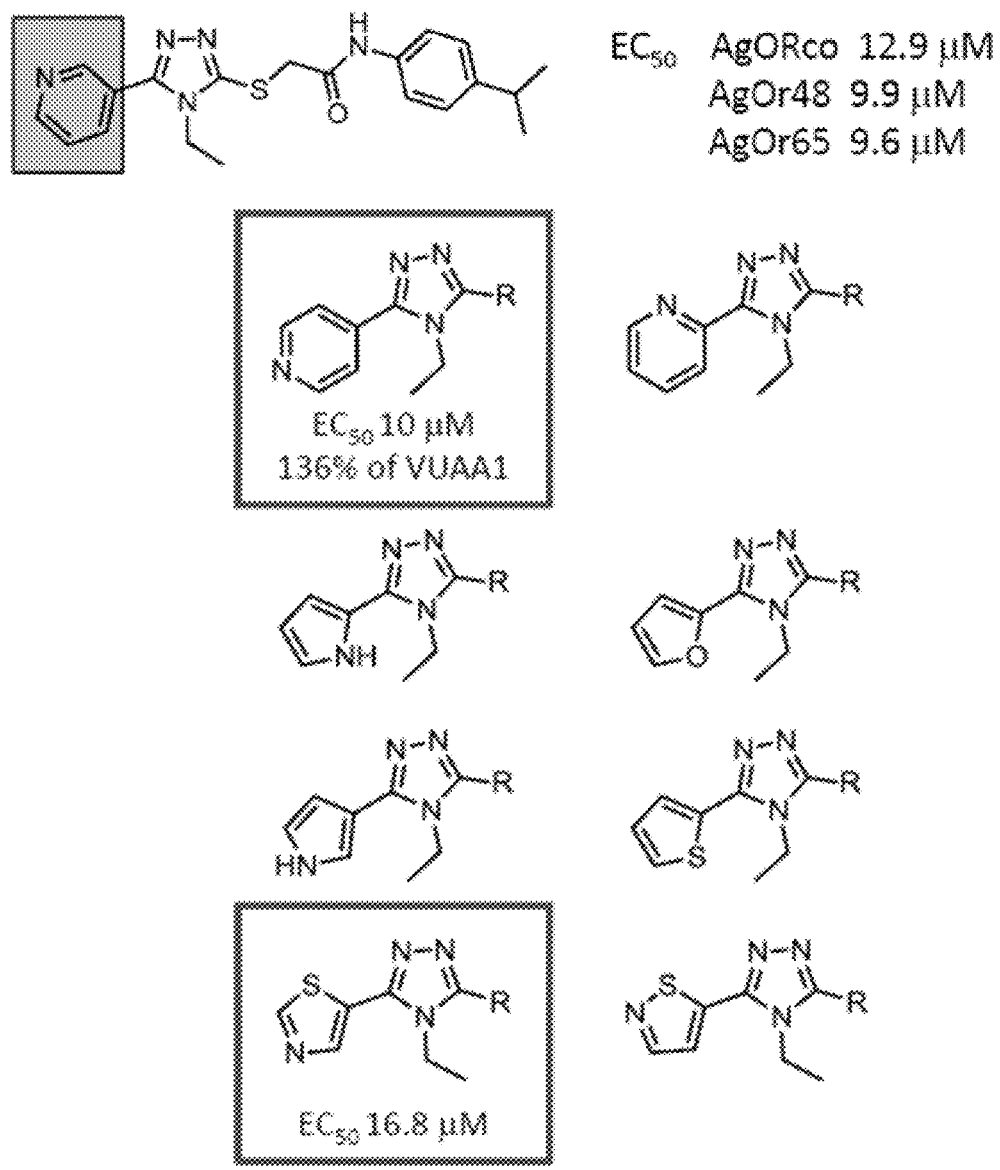
FIG. 26 shows VUAA derivatives and some biological data.
Figure 27:
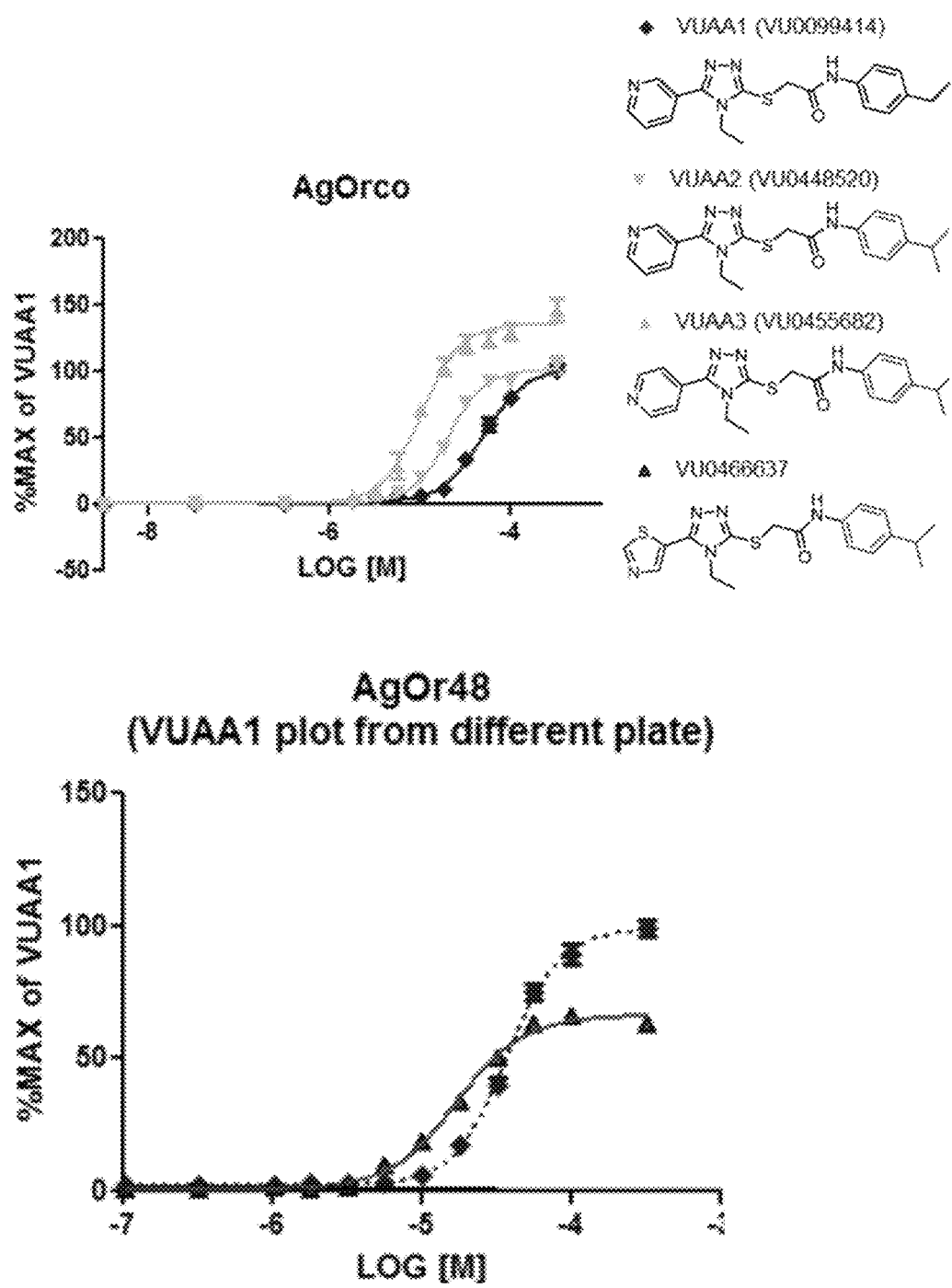
FIG. 27 shows VUAA derivatives and their ability to agonize mosquito ORs.
Figure 28:
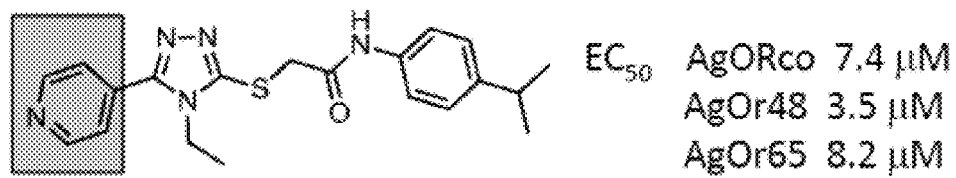
FIG. 28 shows VUAA derivatives and biological data related thereto.
Figure 28:
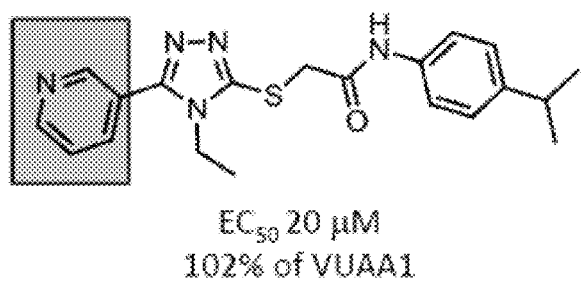
Figure 28:
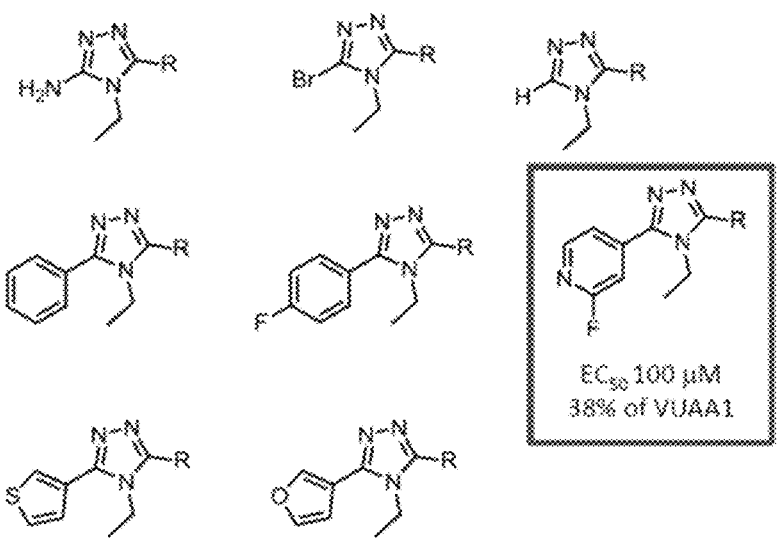
Figure 28:
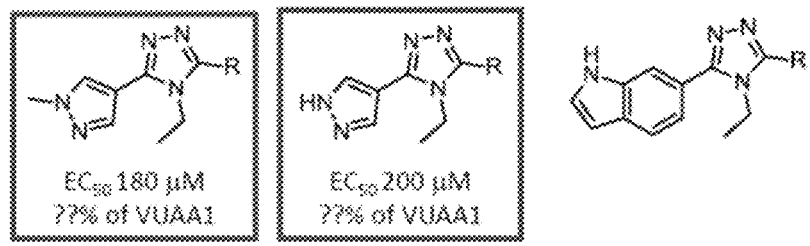
Figure 29:
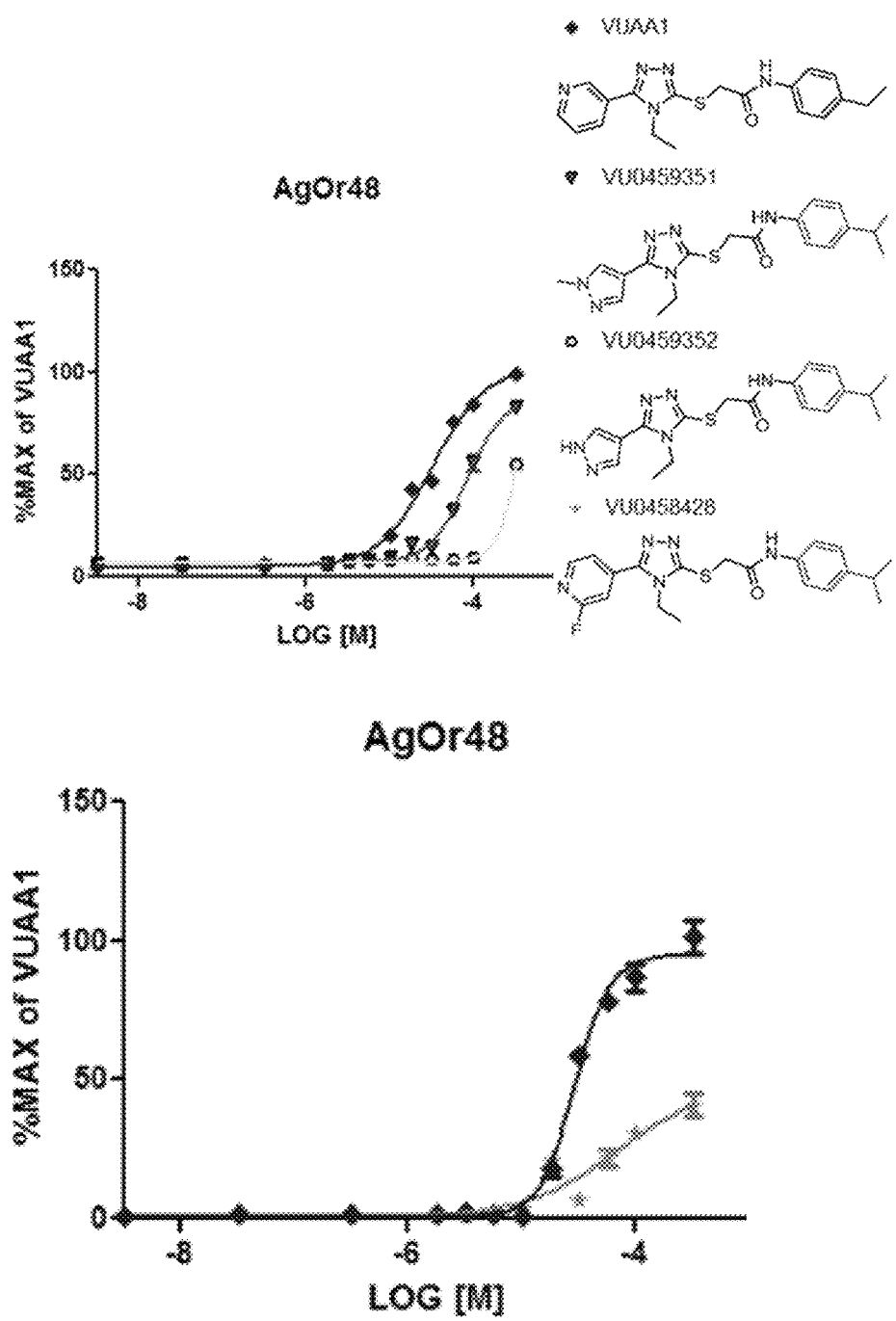
FIG. 29 shows VUAA derivatives and their ability to agonize mosquito ORs.
Figure 30:
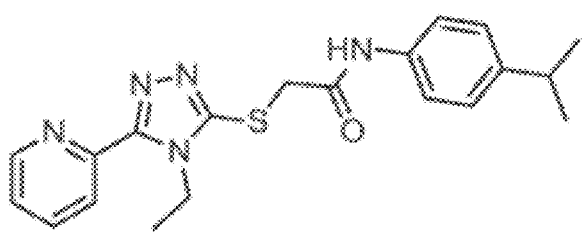
FIG. 30 shows VUAA derivatives and biological data related thereto.
Figure 30:
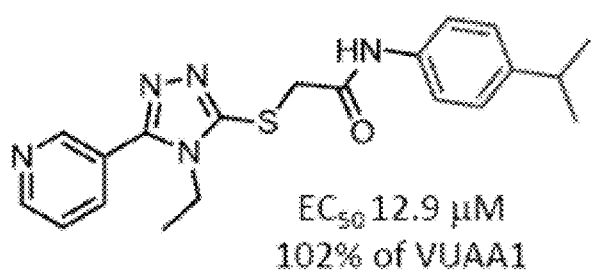
Figure 30:
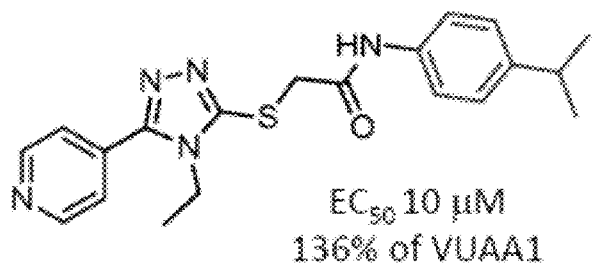
Figure 30:
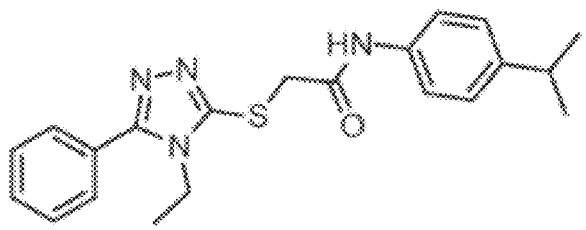
Figure 31:
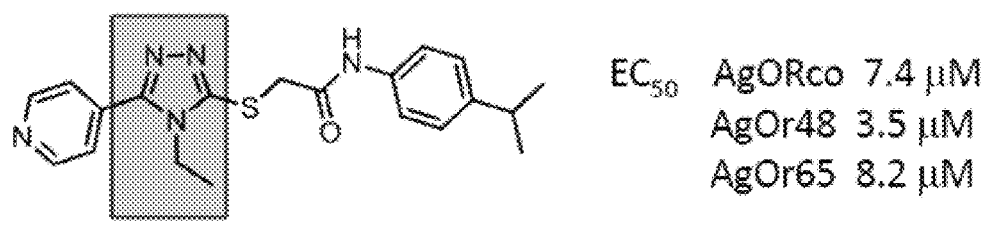
FIG. 31 shows a VUAA derivative and biological data related thereto.
Figure 32:
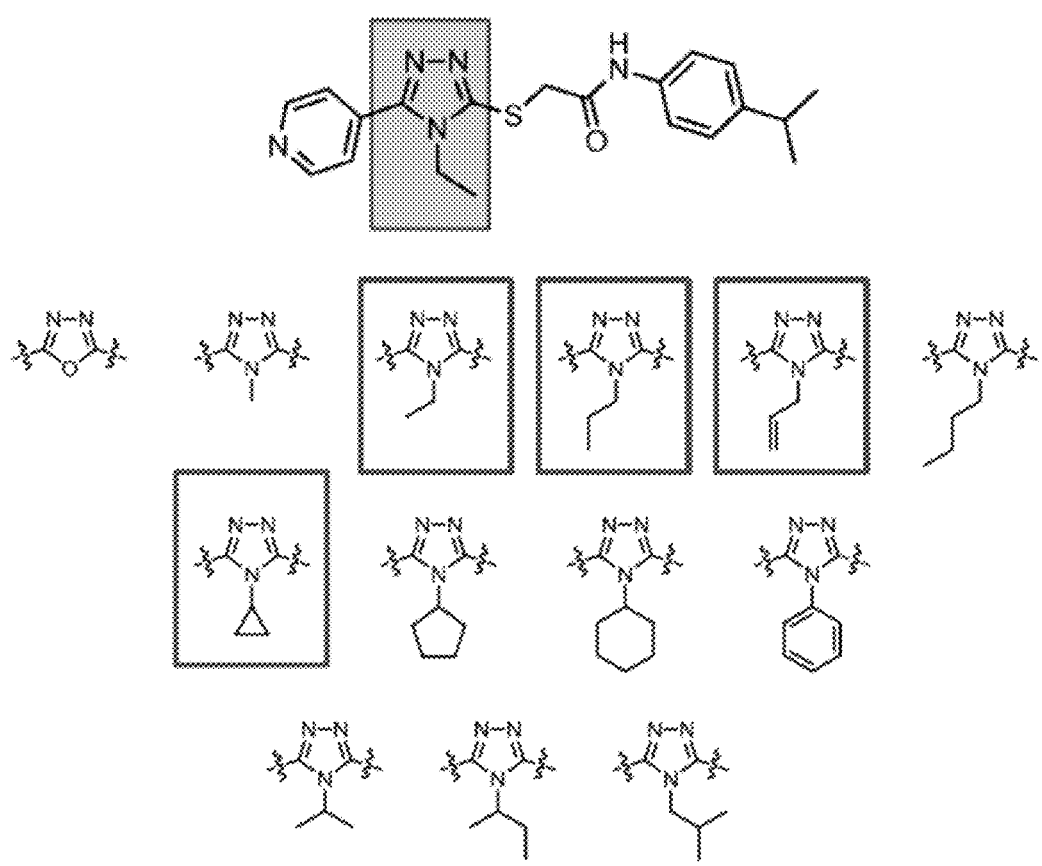
FIG. 32 shows VUAA derivatives.
Figure 33:
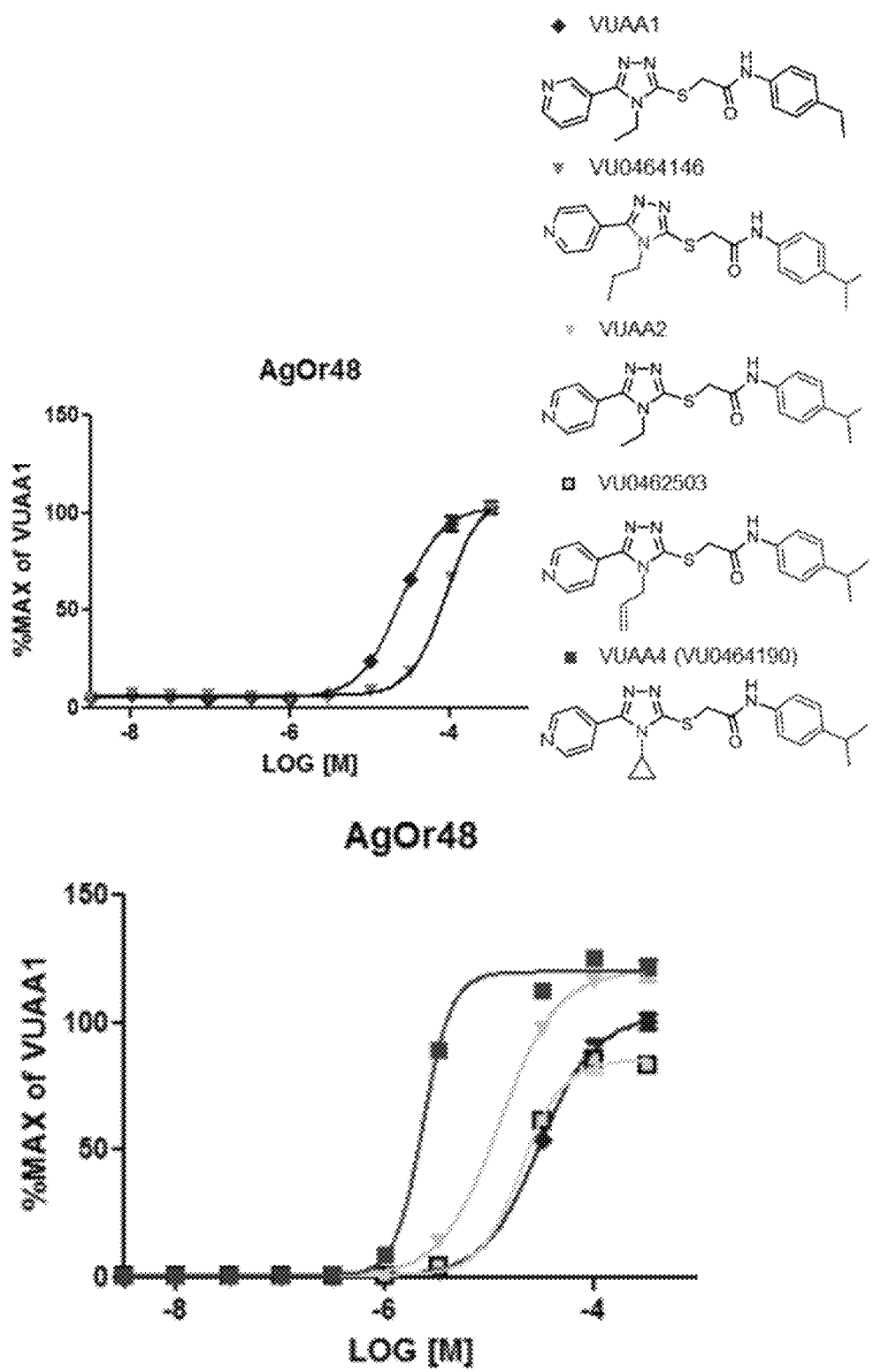
FIG. 33 shows VUAA derivative and their ability to agonize mosquito ORs.
Figure 34:
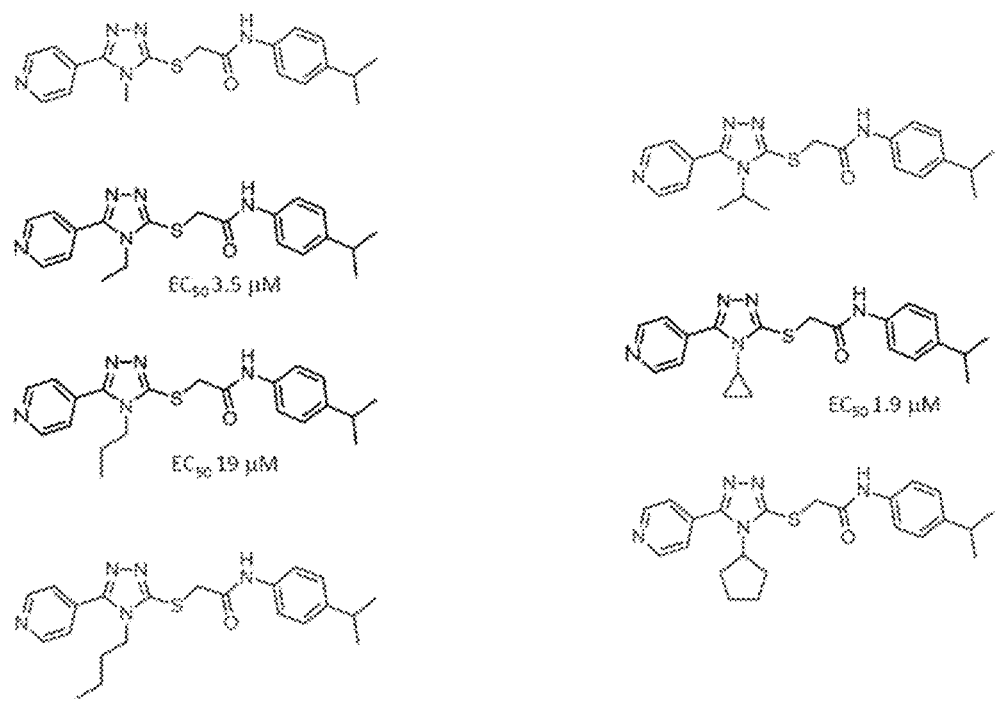
FIG. 34 shows VUAA derivatives and biological data related thereto.
Figure 35:
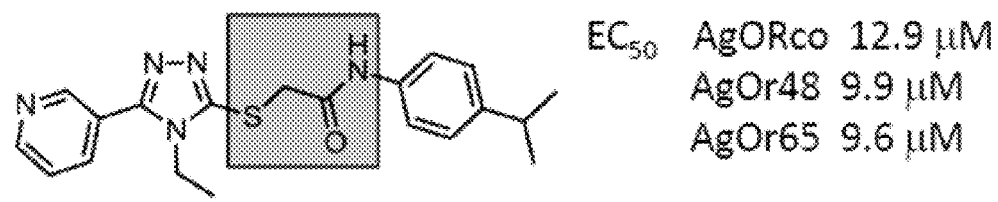
FIG. 35 shows a VUAA derivative and biological data related thereto.
Figure 36:
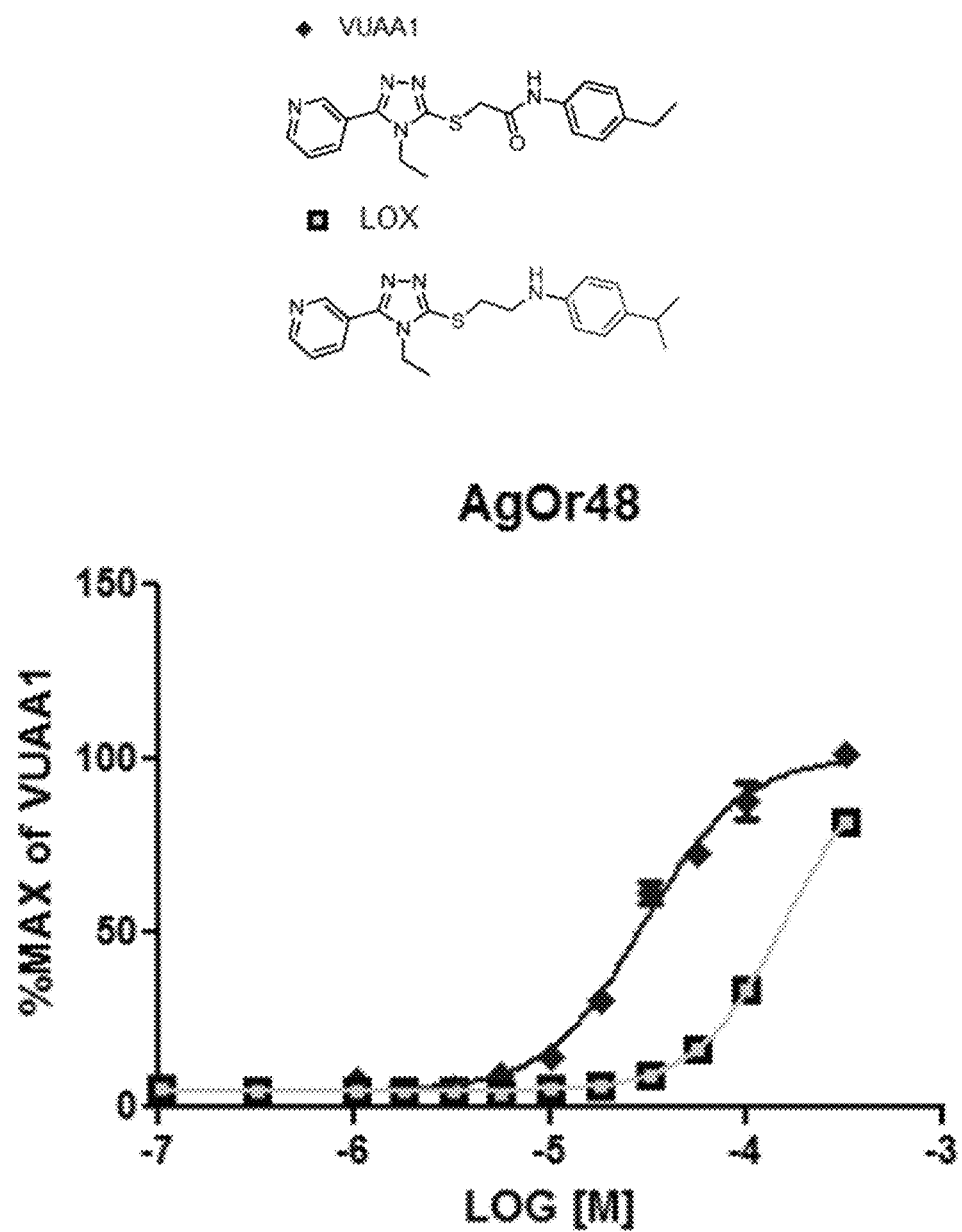
FIG. 36 shows VUAA derivatives and their ability to agonize mosquito ORs.
Figure 37:
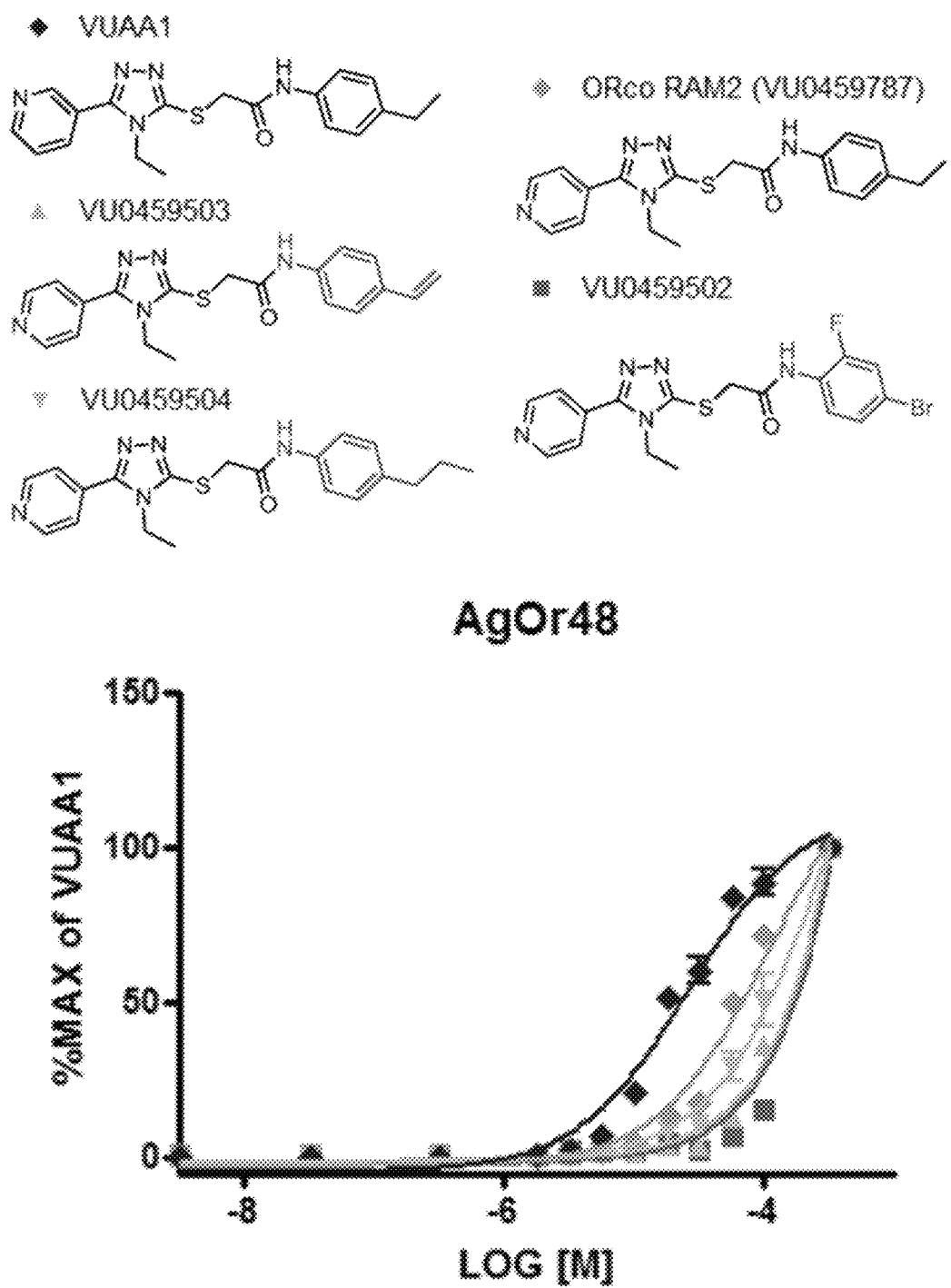
FIG. 37 shows VUAA derivatives and their ability to agonize mosquito ORs.
Figure 38:
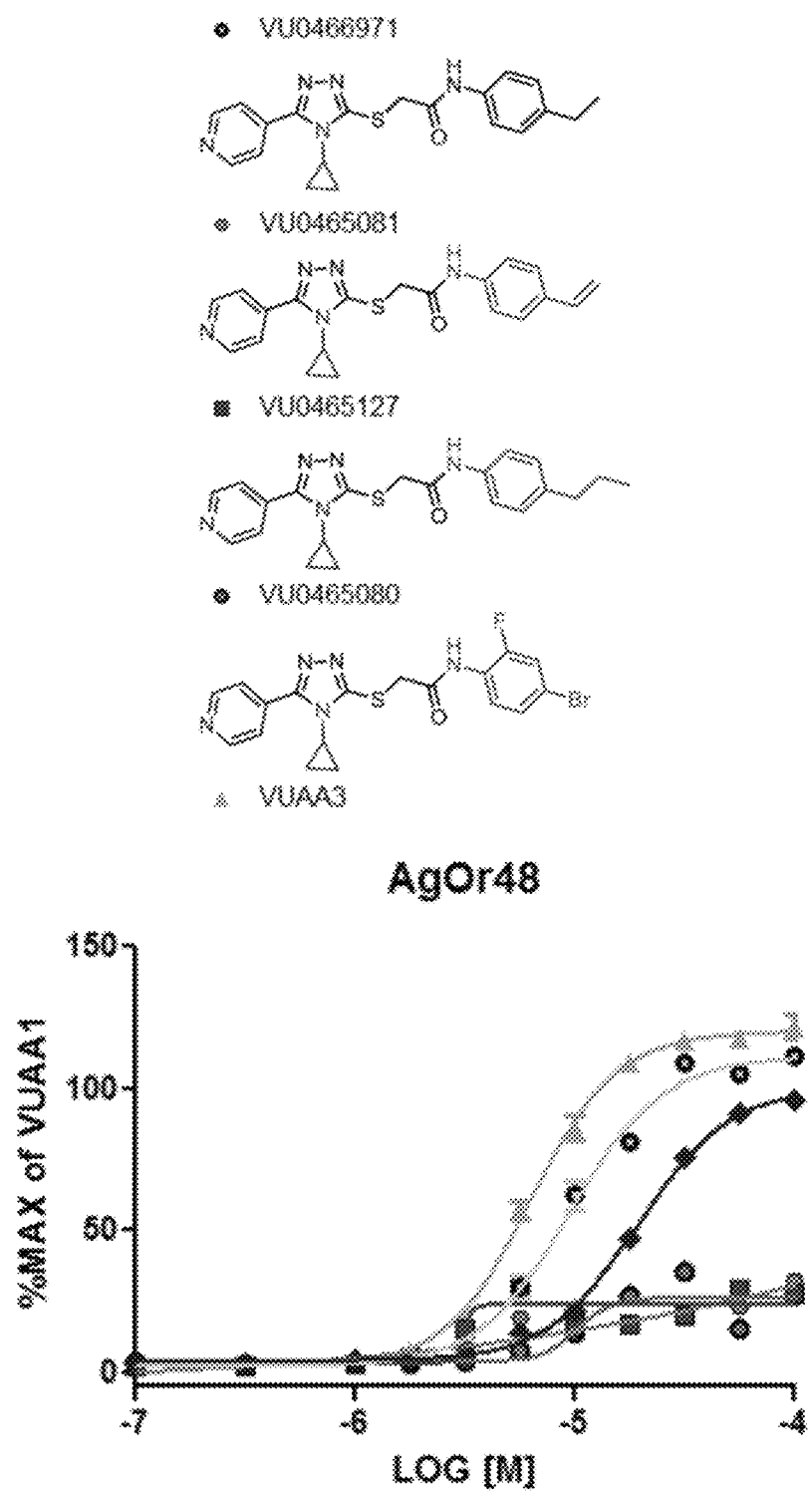
FIG. 38 shows VUAA derivatives and their ability to agonize mosquito ORs.
Figure 39:
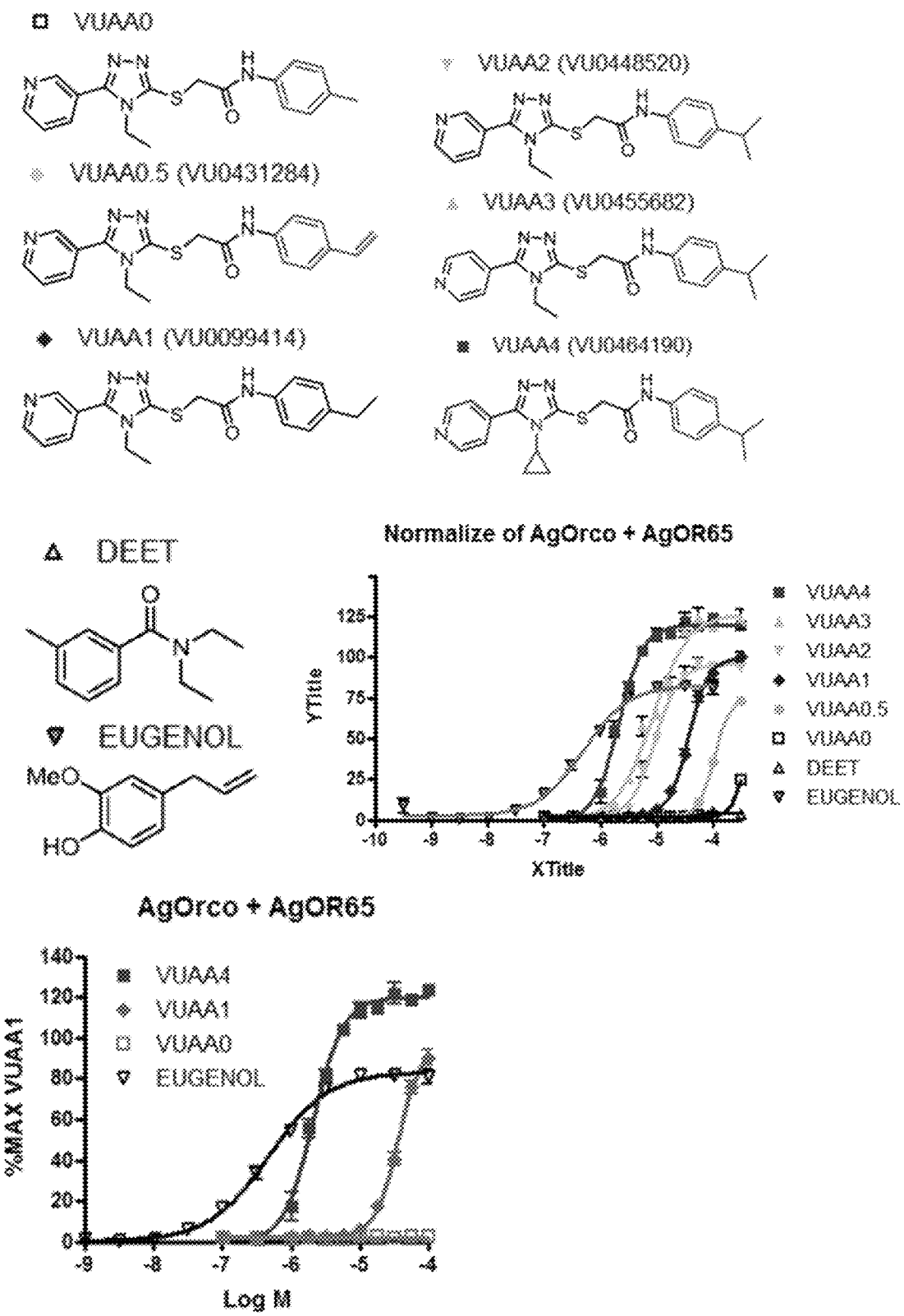
FIG. 39 shows compounds and their ability to agonize mosquito ORs.
Figure 40:
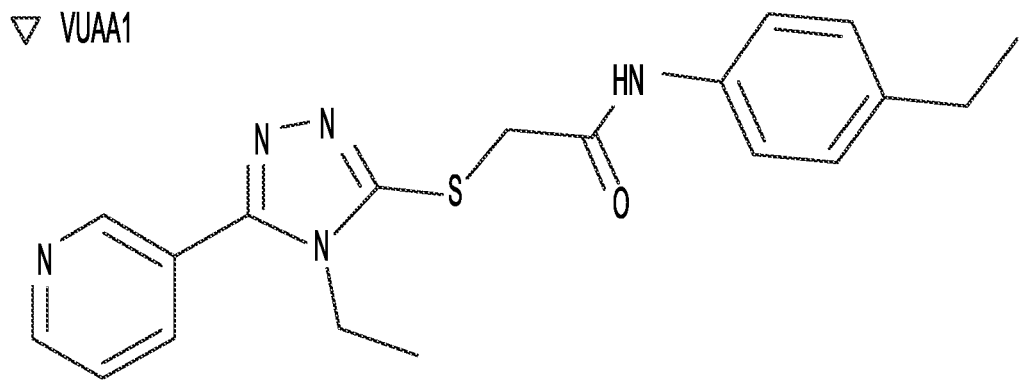
FIG. 40 shows VUAA derivatives and their ability to agonize mosquito ORs.
Figure 40:
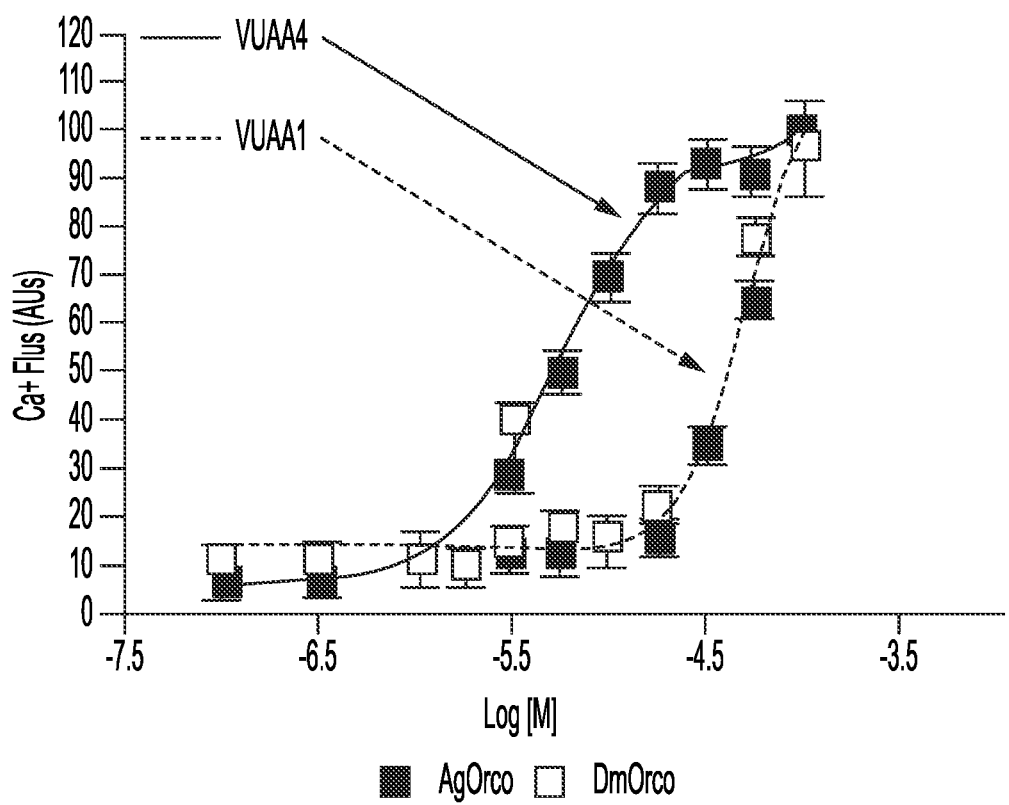
Figure 40:
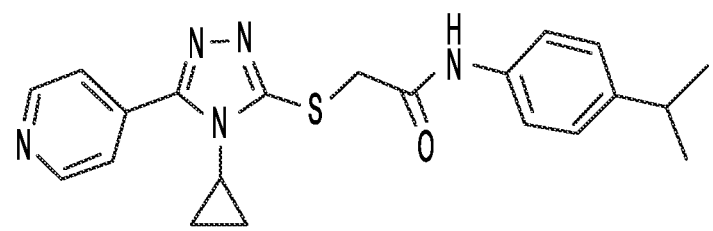
Figure 40:
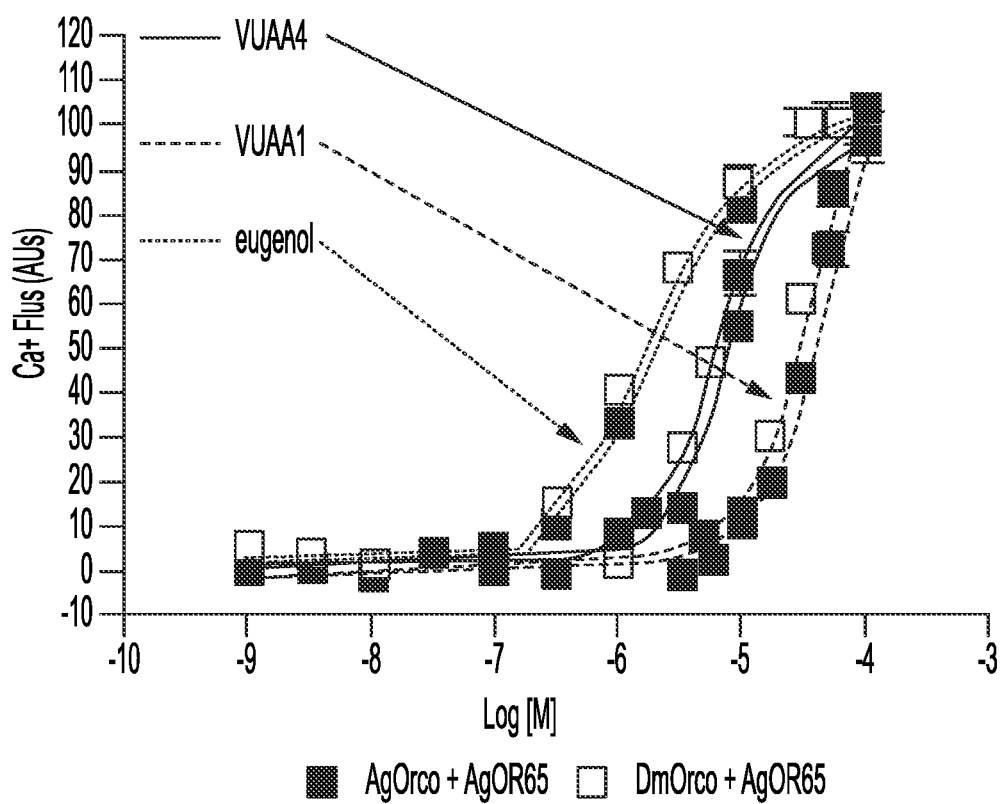
Figure 40:
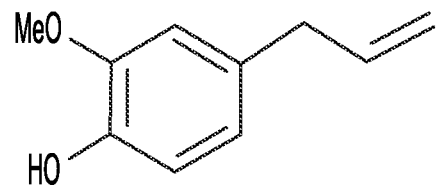
Figure 40:
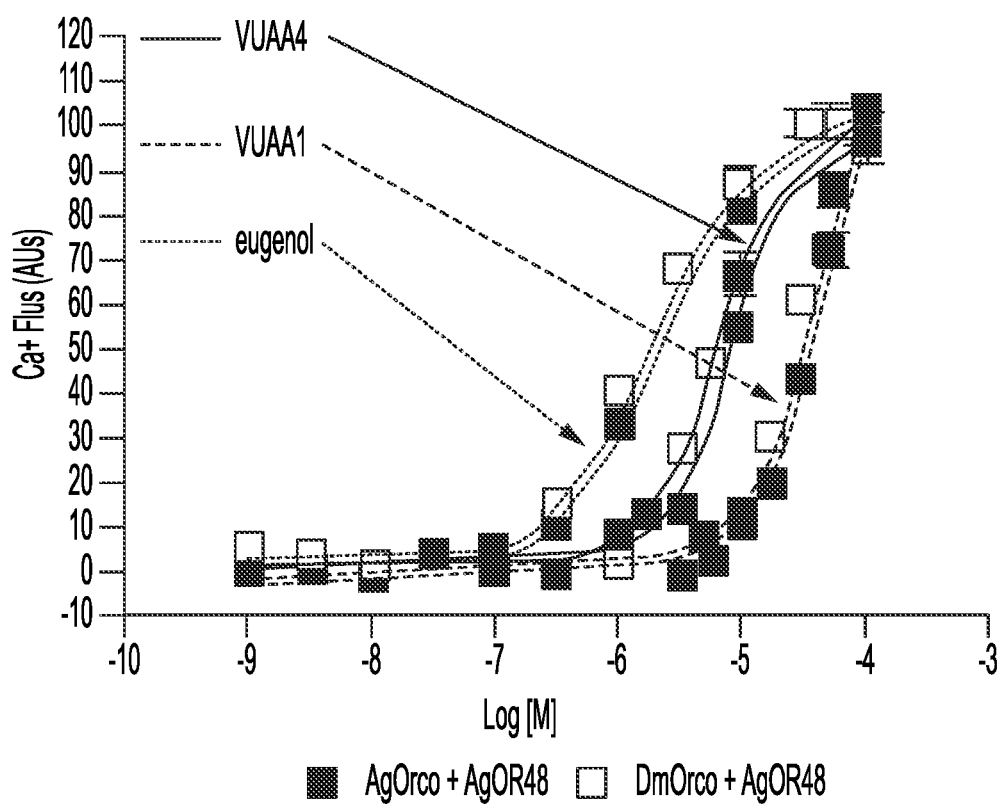
Figure 41:
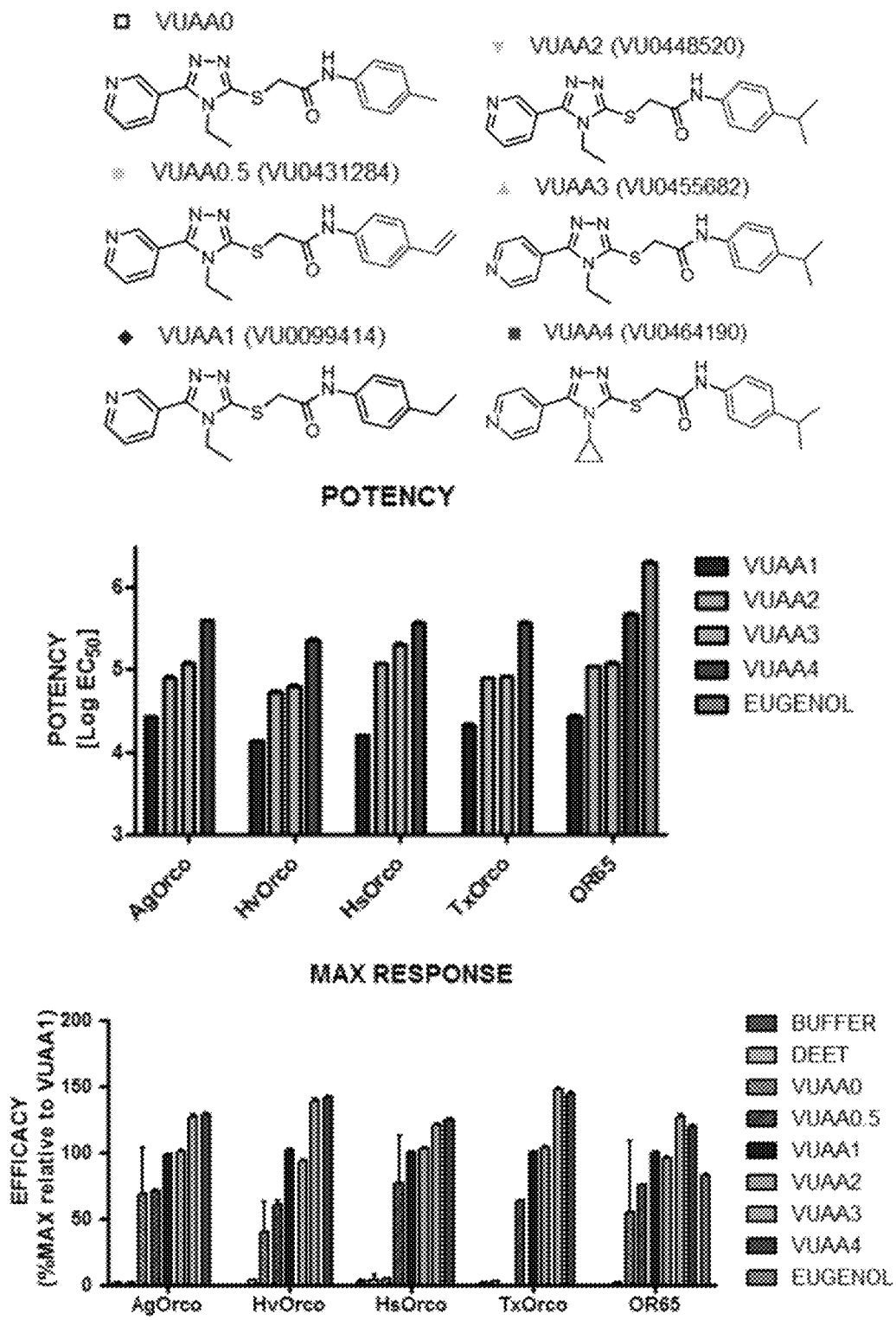
FIG. 41 shows compounds and their potency and efficiency.

Due to its relatively high molecular weight, volatile delivery of VUAA1 was not feasible. As a result, VUAA1 was directly added to each sensillum via the glass-recording electrode where VUAA1 increased the spike frequency of CpB/C neurons in a dose-dependent manner; vehicle alone had no effect (FIGS. 6A, 6B, 6D). Differential CpB/C spike activity was observed immediately after puncturing each sensillum, indicating millisecond compound diffusion rates into the sensillum (FIGS. 6A, 6B, 6D). At the completion of each assay, a $CO_2$ pulse was delivered to the sensillum to test whether VUAA1 affected the CpA neuron; in contrast to the responsiveness of the AgORco-expressing CpB/C neurons, CpA activity was unchanged in the presence of vehicle and/or VUAA1 (FIGS. 6A, 6B, 6D). These data demonstrate that VUAA1 can specifically activate AgORco-expressing neurons in vivo. Moreover, VUAA1's ability to activate AgORco-expressing cells in vivo demonstrates that AgORco is an accessible biological target, which is not directly obscured by other proteins or cofactors involved in olfactory signal transduction. As such, VUAA-mediated modulation serves as a proof-of-concept demonstration that AgORco is a viable target for the development of behaviorally disruptive olfactory compounds (BDOCs) that could foster malaria reduction programs.

While the inventors cannot rule out an eventual identification, there is currently no evidence to support the existence of naturally-occurring AgORco ligands, which indicates that AgORco lacks a typical orthosteric binding site common to other ligand-gated ion channels. Without a more advanced structural analysis of AgORco, it is difficult to postulate as to the mechanism of VUAA1 gating, and whether it is acts in a manner akin to canonical OR-dependent activation of the heteromeric OR complex. However, it is clear that AgORco is ionotropic, ligand-gated ion channel.

FIGS. 9-18 show a series of experiments testing analogs of VUAA1 for activity against the AgORco (shown in these figures as AgORco receptor; see Vosshall and Hansson, 2011).

17. Structure-Activity Relationships (SAR)

a. Aniline Ring Region

For VUAA0, a single methyl from the para position of the aniline ring (compound VUAA0, FIG. 44) in the VUAA1 structure was removed. The removal of this methyl group was observed to result in an almost complete loss of potency when presented to heteromeric OR channels (AgOrco+ AgOR65) (VUAA1 $EC_{50}=3.7\times10^{-5}$M vs VUAA0 $EC_{50}=3.4\times10^{-3}$M). In VUAA0.5, unsaturation was introduced at the para position of the aniline ring (VUAA0.5, FIG. 44). This change was also observed to dramatically reduce potency ($EC_{50}=1.1\times10^{-4}$M, FIG. 44). In VUAA2, the ethyl group of the aniline ring in VUAA1 was replaced with an isopropyl group (VUAA2, FIG. 44). As a result of this change, VUAA2 was observed to have improved potency relative to VUAA1 (VUAA2, FIG. 44; $EC_{50}=9.2\times10^{-6}$M). Moreover, all changes to the amide linker have thus far resulted in near total loss of agonism activity.

b. Western Pyridine Ring Region

Next, the effect of structural changes of the western pyridine ring on Orco agonism was examined. For VUAA3, the nitrogen of the western pyridine ring in VUAA1 was shifted to the para position (VUAA3, FIG. 44). This change was observed to result in an increased potency ($EC_{50}=8.4\times10^{-6}$M) and an increased response relative to both VUAA1 and VUAA2.

c. Triazole Region

In VUAA4, the N-ethyl group of the triazole was changed to a cyclopropyl group (VUAA4, FIG. 44). This change was observed to result in increased potency over previously tested compounds (VUAA4, FIG. 44; $EC_{50}=2.1\times10^{-6}$M). Overall, VUAA4 activity represents a 10-fold improvement in agonist potency and an additional improvement in the maximum response when compared to VUAA1.

When viewed together, this data reveals a narrow series of compounds with only modest substitutions that cover potency ranges from almost undetectable to activity nearly equivalent to the natural volatile agonist, eugenol (FIG. 44). The extremely narrow SAR surrounding the VUAA-based family of Orco agonists indicates that putative binding relationship with ORco targets is complex and generally unforgiving.

18. Activity in Mosquito Odorant Receptors

Figures 45A, 45B:
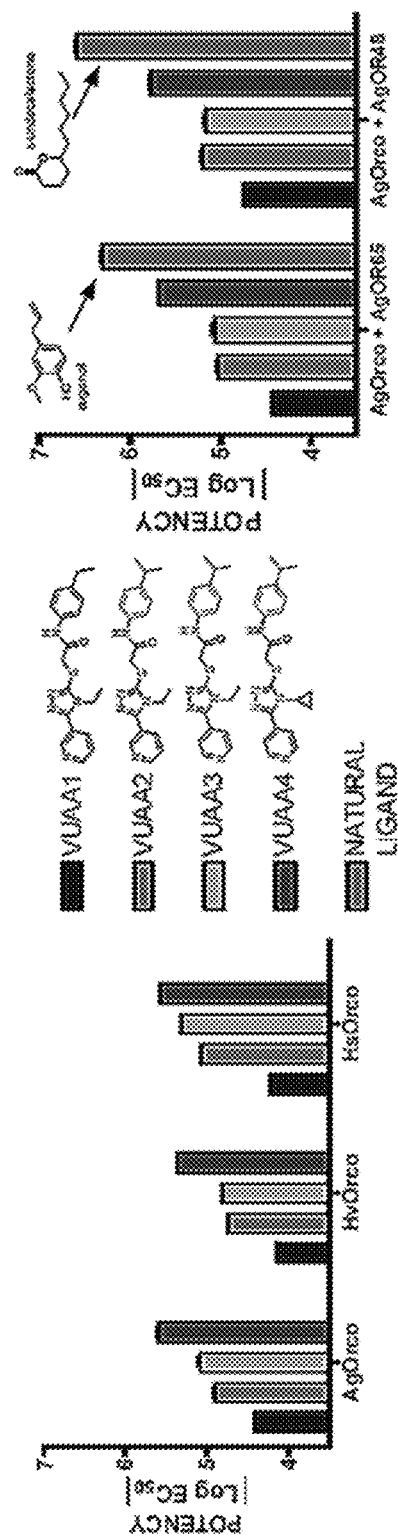
FIG. 45A and FIG. 45B show that VUAA compounds broadly agonize insect odorant receptors (ORs).

The ability of VUAA1 and its analogs to agonize representative ORco proteins from dipteran (*Anopheles gambiae*, AgORco), lepidopteran (*Heliothis virescens*, HvORco) and hymenopteran (*Harpegnathos saltator*, HsORco) orders was tested. In these studies, the relative potency of the VUAA series compounds (VUAA 4>3>2>1) was observed to be consistent regardless of the species-origin of each OR co ion channel (FIG. 45). Furthermore, the hierarchy of VUAA series potency was the same, irrespective of whether AgORco was co-expressed with AgOR65 or AgOR48 tuning ORs (FIG. 45). Without wishing to be bound by a particular theory, odorant ligands are thought to activate the complex via interaction with the tuning ORx and thereby affect ORco/ORx channel properties. Further, in both cases, the potency of VUAA4 is within one order of magnitude of the respective cognate ligand (OR65: VUAA4 $EC_{50}=2.1\times10^{-6}$M, eugenol $EC_{50}=5.0\times10^{-7}$M, OR48: VUAA4 $EC_{50}=1.7\times10^{-6}$M, D-undecalactone $EC_{50}=2.6\times10^{-7}$M). These findings indicate VUAA-class OR co-modulators are viable compounds for further development as broad-spectrum insect control strategies, and VUAA4 can provide an advance in the pharmacological profile of VUAA-based compounds.

19. Larval Mosquito Activity

Figure 42:
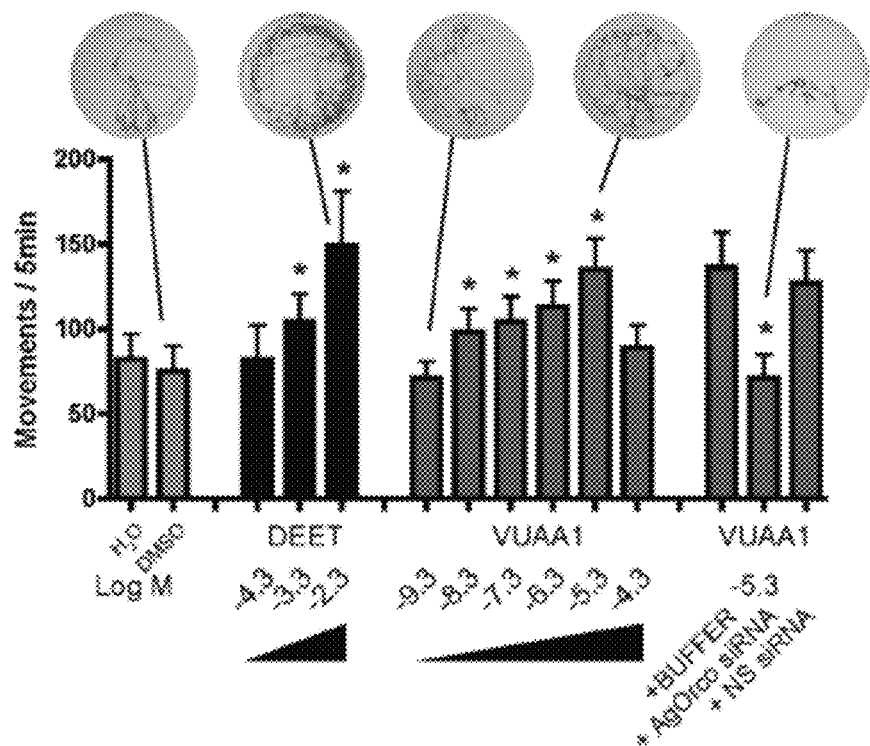
FIG. 42 shows compounds and their ability increase mosquito larvae movement.
Figure 43:
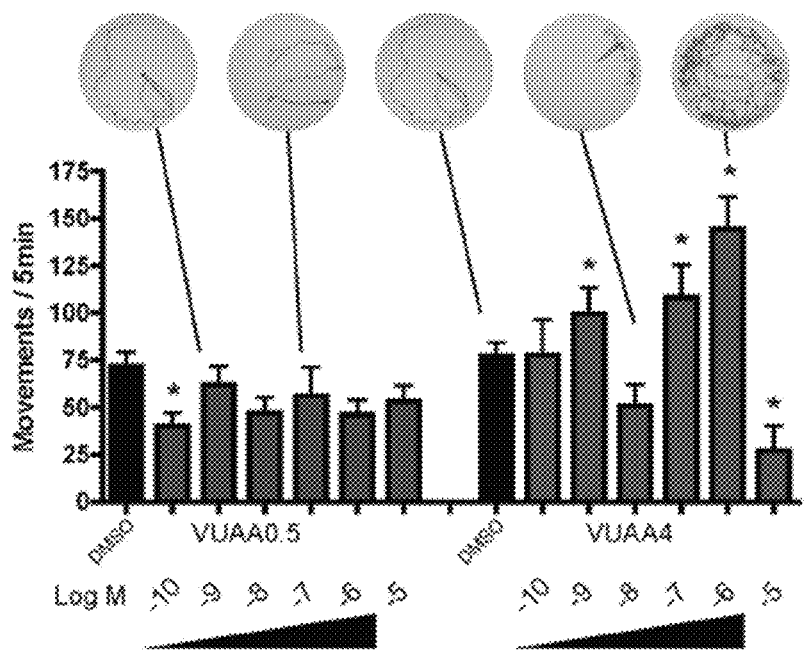
FIG. 43 shows compounds and their ability increase mosquito larvae movement.
Figure 44B:
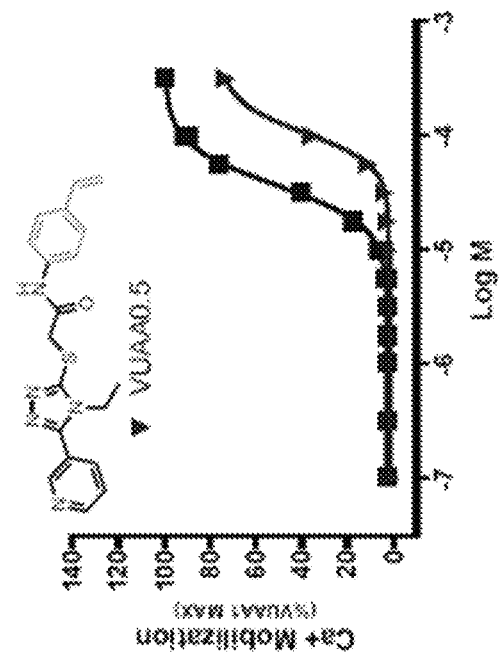
FIG. 44A-F show that VUAA0 and VUAA0.5 (FIG. 44A) have reduced potency while VUAA2 (FIG. 44B), VUAA3 (FIG. 44C) and VUAA4 (FIG. 44D) are increasingly potent. Improvements to VUAA compound activity approach the potency of the odorant eugenol (FIG. 44E).
Figure 44A:
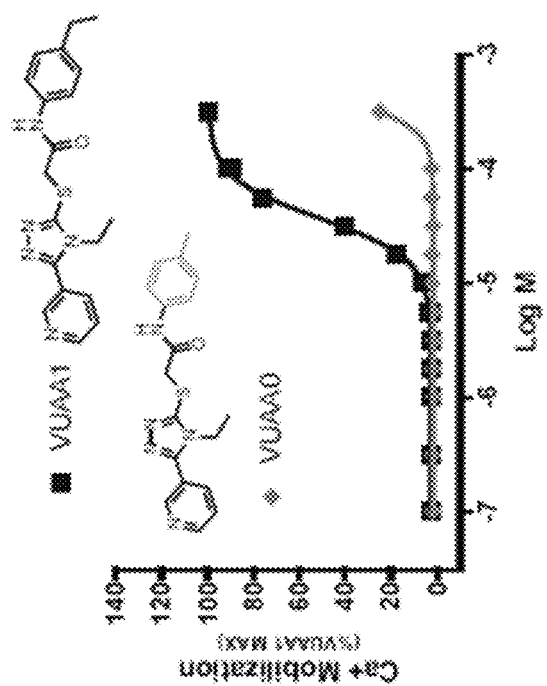
Figure 44C:
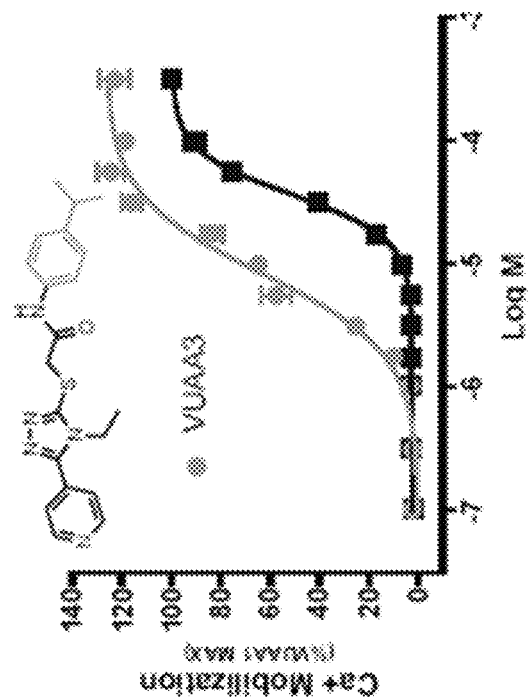
Figure 44D:
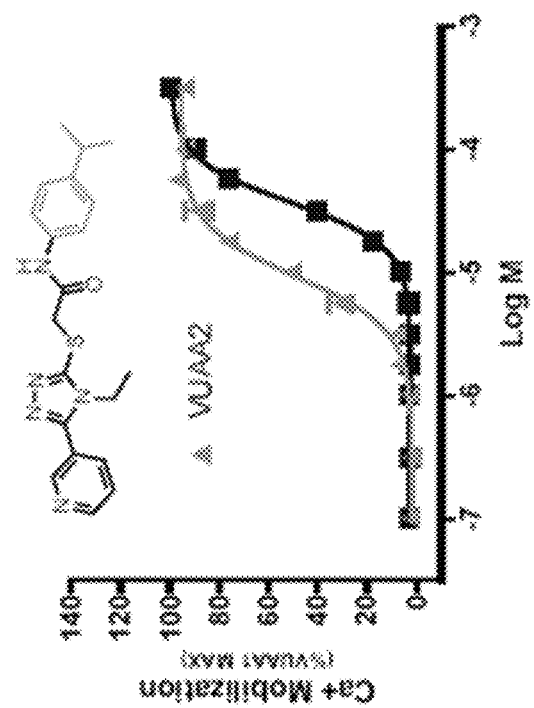
Figure 44F:
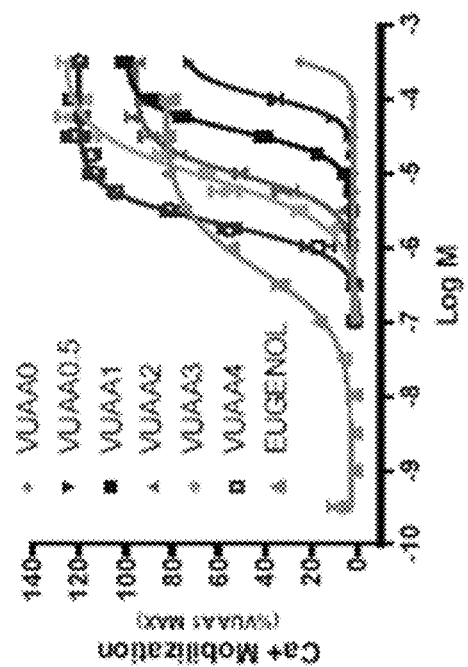
Figure 44E:
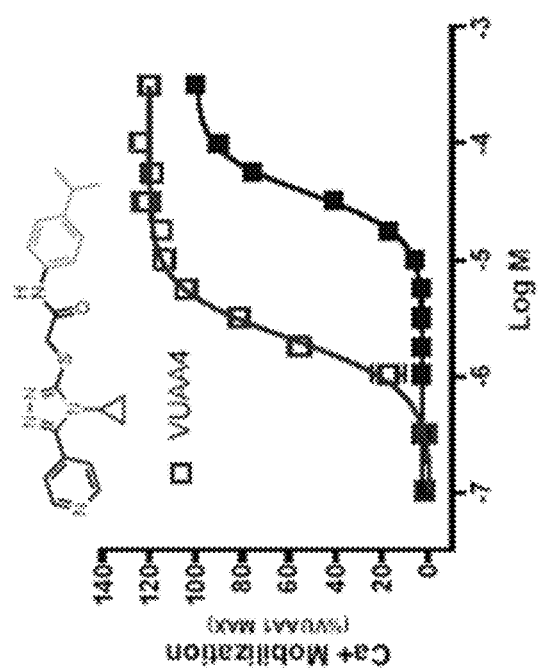

Next, the agonist activity of the VUAA compound class was tested to establish the involvement of AgORs in mediating larval ortho and klinokinesis in response to a series of semiochemicals using larval-stage *An. gambiae* mosquitoes. Mosquito larvae are aquatic, thus compounds can be delivered to individual early $4^{th}$ instar larvae regardless of volatility. The assay currently utilizes 6-well plates and the Daniovision-Ethovision platform (Noldus Inc.) to simultaneously record and analyze 6 larvae, thereby providing modest rates of throughput and a high degree of reproducibility. In these assays, larval movements are automatically quantified over 5-minute period and control larvae consistently move the same number of times in the presence or absence of 0.1% DMSO (p=0.80, n=31) (FIGS. 42-43). Furthermore, the effects of the widely-used synthetic insect repellent N, N-diethyl-meta-toluamide (DEET) was tested and DEET was also observed to increase larval movements at and above a threshold concentration of $5 \times 10^{-4}$M (p=0.013, n=27) (FIGS. 42-43).

Next, VUAA1 effect on larval behavior was evaluated. Over a wide range of concentrations, a significant increase of movement at and above a concentration of $5 \times 10^{-9}$M was observed (p=0.045, n=35) (FIG. 42-43). This data indicates an increase of 5 orders of magnitude over the response threshold of DEET. At higher concentrations of VUAA1 ($5 \times 10^{-5}$M), larval movements were observed to decrease. Without wishing to be bound by a particular theory, this decrease at higher concentrations may reflect non-target effects. To determine the dependence of these larval responses on AgORco agonism, gene silencing studies were carried out against AgOrco mRNAs. Larvae were injected with small interfering RNA (siRNA) oligonucleotides 48 h before evaluation of their behavior in response to VUAA1. In these studies, VUAA1 responses persisted in larvae injected with buffer alone or with a non-target siRNA, while larvae treated with AgOrco siRNAs were no longer responsive to VUAA1 treatment as compared to buffer-injected control (p=0.0025, n=21) (FIGS. 42-43).

To further validate the efficacy of VUAA1 analogs, larvae were exposed to VUAA0, VUAA0.5, VUAA2, VUAA3 and VUAA4. In these studies, *An. gambiae* larvae displayed increases in movement in response to these compounds at almost all tested concentrations. These responses are consistent with efficacy relationships whereby VUAA0<VUAA0.5<VUAA2<VUAA3<VUAA4. In the case of VUAA0 and VUAA0.5, mosquito larvae displayed behavioral responses that were lower and comparable to DMSO controls, respectively. Without wishing to be bound by a particular theory, the reduced larval movement towards VUAA0 may be the result of antagonistic effects on AgO-Rco-ORx complexes. Further, while VUAA2 and VUAA3 display higher efficacy than VUAA1 in HEK cell-based assays, they were not observed to elicit larval responses greater than VUAA1. In contrast, larval movement increases to VUAA4 in a dose-dependent manner with a response-threshold at $10^9$M (p=0.047, n=54). In addition to this 5-fold lower threshold compared to VUAA1, *An. gambiae* larvae displayed higher levels of movement in response to VUAA4. Reduced larval movement was observed in these studies at the highest ($10^{-5}$M) concentrations of VUAA4, which again, may reflect the onset of an off-target response. Surprisingly, a continued absence of response to VUAA4 at $10^{-8}$M was observed.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A compound having a structure represented by a formula:

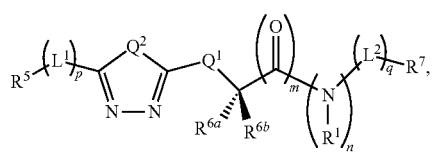

wherein m, n, p, and q are independently 0 or 1;

wherein $L^1$ and $L^2$ are independently divalent organic groups having from 1 to 8 non-hydrogen members;

wherein $Q^1$ is —O—, —S—, —S(O)—, or —SO$_2$—;

wherein $Q^2$ is —O—, —S—, or —NR$^4$;

wherein $R^7$ is optionally substituted and selected from monocyclic aryl, bicyclic aryl, monocyclic heteroaryl, bicyclic heteroaryl, and tricyclic heteroaryl;

wherein $R^1$ is hydrogen, optionally substituted C1-C4 alkyl, optionally substituted phenyl, optionally substituted benzyl, or a structure represented by a formula selected from:

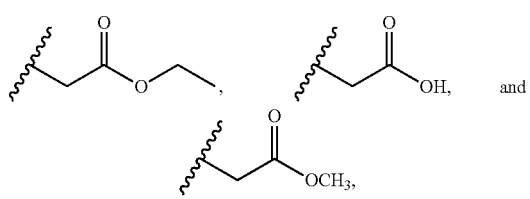

or $R^1$ is taken together with a substituent of $R^7$ to form a five-, six-, or seven-membered heterocycloalkyl ring;

wherein $R^4$ is optionally substituted and selected from (C1-C5) alkyl and (C2-C5) alkenyl; and wherein $R^5$ is optionally substituted aryl or optionally substituted (≤C6) heteroaryl; and wherein $R^{6a}$ and $R^{6b}$ are independently selected from hydrogen, optionally substituted (C1-C5 alkyl), or optionally substituted (C2-C5) alkenyl, or $R^{6a}$ and $R^{6b}$, along with the intermediate carbon, together comprise a C3-C6 cycloalkyl ring or a C2-C5 heterocycloalkyl ring; or salt thereof, wherein the compound is not

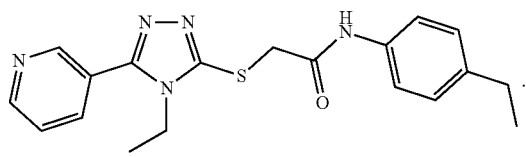 [SMILES: CCc1ccc(NC(=O)CSc2nnc(-c3cccnc3)n2CC)cc1]

2. The compound of claim 1, wherein the compound has a structure represented by a formula:

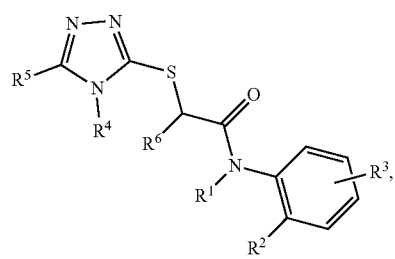

wherein $R^1$ is hydrogen, optionally substituted C1-C4 alkyl, optionally substituted phenyl, optionally substituted benzyl, or a structure represented by a formula selected from:

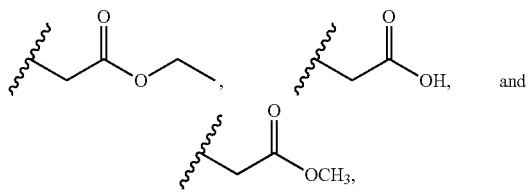

or $R^1$ is taken together with $R^2$ to be optionally substituted (C1-C4) alkanediyl or optionally substituted (C2-C5) alkenediyl, (C1-C4) alkenediyl;

$R^2$ is hydrogen, hydroxy, nitro, halo, optionally substituted (C1-C5) alkyl, or optionally substituted (C2-C5) alkenyl, or $R^2$ is taken together with $R^1$ to be optionally substituted (C1-C4) alkanediyl or optionally substituted (C2-C5) alkenediyl;

$R^3$ is hydrogen, hydroxy, nitro, halo, optionally substituted (C1-C5) alkyl, or optionally substituted (C2-C5) alkenyl;

$R^4$ is optionally substituted and selected from (C1-C5) alkyl and (C2-C5) alkenyl, (C6-C10) aryl;

$R^5$ is optionally substituted aryl or optionally substituted (≤C6) heteroaryl; and $R^6$ is hydrogen, optionally substituted (C1-C5) alkyl, or optionally substituted (C2-C5) alkenyl, wherein when any of the optionally substituted terms is substituted, the substituent is selected from —OH, —F, —Cl, —Br, —I, —NH$_2$, —NO$_2$, —CO$_2$H, —CO$_2$CH$_3$, —CN, —SH, —OCH$_3$, —OCH$_2$CH$_3$, —C(O)CH$_3$, —N(CH$_3$)$_2$, —C(O)NH$_2$, —OC(O)CH$_3$, and —S(O)$_2$NH$_2$.

3. The compound of claim 2, wherein $R^3$ is substituted (C1-C5) alkyl.

4. The compound of claim 3, wherein $R^3$ is (C1-C5) haloalkyl.

5. The compound of claim 4, wherein $R^3$ is —CF$_3$ or —CH$_2$CF$_3$.

6. The compound of claim 3, wherein $R^3$ is C4-5 cycloalkyl.

7. The compound of claim 6, wherein $R^3$ is cyclopropyl or cyclobutyl.

8. The compound of claim 2, wherein the compound is represented by the formula:

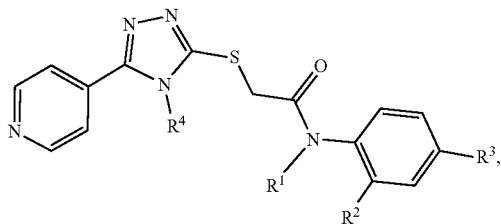

wherein
$R^1$ is hydrogen and $R^2$ is hydrogen,
or $R^1$ is taken together with $R^2$ to be optionally substituted (C1-C4) alkanediyl or optionally substituted (C2-C5) alkenediyl;
$R^3$ is optionally substituted (C1-C5) alkyl; and
$R^4$ is optionally substituted (C1-C5) alkyl.

9. The formulation of claim 8, wherein the compound is represented by a formula selected from:

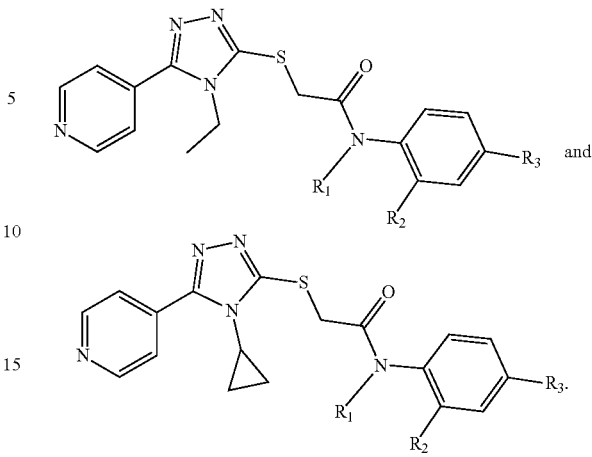

10. The compound of claim 2, wherein the compound is represented by the formula:

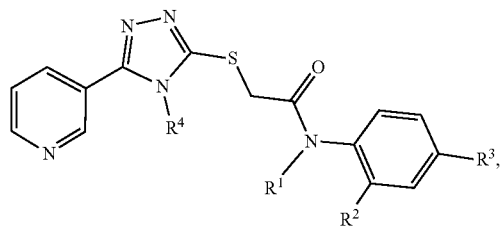

wherein
$R^1$ is hydrogen and $R^2$ is hydrogen,
or $R^1$ is taken together with $R^2$ to be optionally substituted (C1-C4) alkanediyl or optionally substituted (C2-C5) alkenediyl;
$R^3$ is optionally substituted (C1-C5) alkyl; and
$R^4$ is optionally substituted (C1-C5) alkyl.

11. The formulation of claim 10, wherein the compound is represented by a formula selected from:

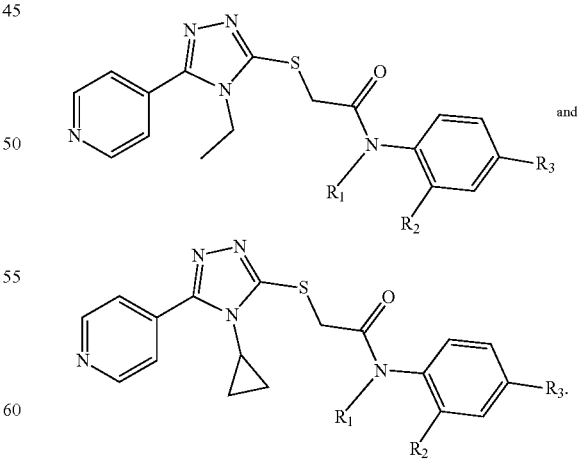

12. The compound of claim 1, wherein $R^4$ is substituted (C1-C5) alkyl.

13. The compound of claim 12, wherein $R^4$ is (C1-C5) haloalkyl.

14. The compound of claim 13, wherein $R^4$ is —$CH_2CF_3$.

15. The compound of claim 12, wherein $R^4$ is C3-5 cycloalkyl.

16. The compound of claim 15, wherein $R^4$ is cyclopropyl or cyclopentyl.

17. The compound of claim 1, wherein $R^5$ is optionally substituted (≤C6) heteroaryl.

18. The compound of claim 17, wherein $R^5$ is selected from furanyl, imidazolyl, indolyl, indazolyl, isoxazolyl, methylpyridinyl, oxazolyl, phenylpyridinyl, pyridinyl, pyrrolyl, pyrimidinyl, pyrazinyl, quinolinyl, quinazolyl, quinoxalinyl, triazinyl, tetraxolyl, thiazolyl, thienyl, and triazolyl, and is optionally substituted.

19. The compound of claim 1, wherein the compound is represented by the formula:

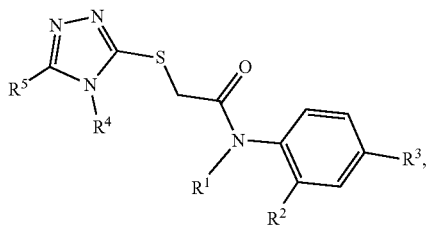

wherein
$R^1$ is hydrogen and $R^2$ is hydrogen,
or $R^1$ is taken together with $R^2$ to be optionally substituted (C1-C4) alkanediyl or optionally substituted (C2-C5) alkenediyl;
$R^3$ is optionally substituted (C1-C5) alkyl;
$R^4$ is optionally substituted (C1-C5) alkyl; and
$R^5$ is optionally substituted (≤C6) heteroaryl.

20. The compound of claim 1, wherein the compound is selected from:

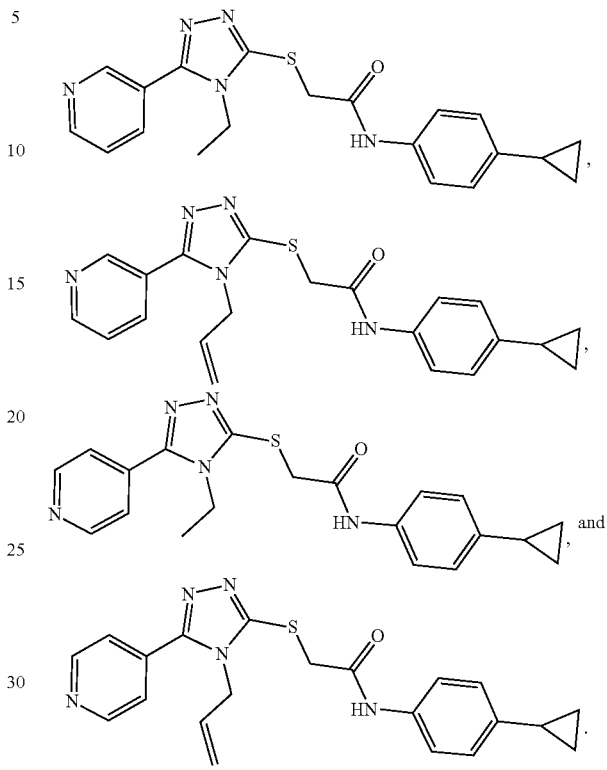

* * * * *

UNITED STATES PATENT AND TRADEMARK OFFICE
CERTIFICATE OF CORRECTION

| | | |
|---|---|---|
| PATENT NO. | : 11,484,032 B2 | Page 1 of 1 |
| APPLICATION NO. | : 16/945369 | |
| DATED | : November 1, 2022 | |
| INVENTOR(S) | : Zwiebel et al. | |

It is certified that error appears in the above-identified patent and that said Letters Patent is hereby corrected as shown below:

In the Claims

In Column 521, Line 41, in Claim 6, "C4-5" should read –C4-C5–

In Column 523, Line 2, in Claim 15, "C3-5" should read –C3-C5–

Signed and Sealed this
Sixteenth Day of May, 2023

Katherine Kelly Vidal
*Director of the United States Patent and Trademark Office*